US012492429B2

(12) United States Patent
Babiarz et al.

(10) Patent No.: US 12,492,429 B2
(45) **Date of Patent: *Dec. 9, 2025**

(54) DETECTING MUTATIONS AND PLOIDY IN CHROMOSOMAL SEGMENTS

(71) Applicant: Natera, Inc., San Carlos, CA (US)

(72) Inventors: Joshua Babiarz, Castro Valley, CA (US); Tudor Pompiliu Constantin, Berkeley, CA (US); Lane A. Eubank, San Carlos, CA (US); George Gemelos, Portland, OR (US); Matthew Micah Hill, Belmont, CA (US); Huseyin Eser Kirkizlar, Los Angeles, CA (US); Matthew Rabinowitz, San Francisco, CA (US); Onur Sakarya, Redwood City, CA (US); Styrmir Sigurjonsson, San Jose, CA (US); Bernhard Zimmermann, Manteca, CA (US)

(73) Assignee: Natera, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/753,991

(22) Filed: Jun. 25, 2024

(65) Prior Publication Data

US 2024/0352513 A1 Oct. 24, 2024

Related U.S. Application Data

(63) Continuation-in-part of application No. 17/692,469, filed on Mar. 11, 2022, and a continuation-in-part of application No. 17/214,403, filed on Mar. 26, 2021, now Pat. No. 12,305,229, which is a continuation of application No. 16/752,339, filed on Jan. 24, 2020, now Pat. No. 11,390,916, which is a continuation of application No. 16/412,301, filed on May 14, 2019, now Pat. No. 10,597,709, said application No. 17/692,469 is a continuation of application No. 15/898,145, filed on Feb. 15, 2018, now Pat. No. 11,319,595, said application No. 16/412,301 is a continuation of application No. 15/336,630, filed on Oct. 27, 2016, now Pat. No. 10,351,906, said application No. 15/898,145 is a continuation of application No. 14/692,703, filed on Apr. 21, 2015, now Pat. No. 10,179,937, said application No. 15/336,630 is a continuation of application No. 14/538,982, filed on Nov. 24, 2014, now Pat. No. 9,677,118.

(60) Provisional application No. 62/148,173, filed on Apr. 15, 2015, provisional application No. 62/147,377, filed on Apr. 14, 2015, provisional application No. 62/146,188, filed on Apr. 10, 2015, provisional application No. 62/066,514, filed on Oct. 21, 2014, provisional application No. 61/994,791, filed on May 16, 2014, provisional application No. 61/987,407, filed on May 1, 2014, provisional application No. 61/982,245, filed on Apr. 21, 2014.

(51) Int. Cl.

| | |
|---|---|
| *C12Q 1/68* | (2018.01) |
| *C12Q 1/6811* | (2018.01) |
| *C12Q 1/6848* | (2018.01) |
| *C12Q 1/686* | (2018.01) |
| *C12Q 1/6874* | (2018.01) |
| *C12Q 1/6883* | (2018.01) |

(52) U.S. Cl.

CPC ............... *C12Q 1/686* (2013.01); *C12Q 1/68* (2013.01); *C12Q 1/6811* (2013.01); *C12Q 1/6848* (2013.01); *C12Q 1/6874* (2013.01); *C12Q 1/6883* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 6,440,706 | B1 | 8/2002 | Vogelstein et al. |
| 6,479,235 | B1 | 11/2002 | Schumm et al. |
| 6,605,451 | B1 | 8/2003 | Marmaro et al. |
| 6,617,137 | B2 | 9/2003 | Dean et al. |
| 6,664,056 | B2 | 12/2003 | Lo et al. |
| 6,720,140 | B1 | 4/2004 | Hartley et al. |
| 6,807,491 | B2 | 10/2004 | Pavlovic et al. |
| 6,852,487 | B1 | 2/2005 | Barany et al. |
| 6,858,412 | B2 | 2/2005 | Willis et al. |
| 6,927,028 | B2 | 8/2005 | Lo et al. |
| 6,964,847 | B1 | 11/2005 | Englert |
| 7,035,739 | B2 | 4/2006 | Schadt et al. |
| 7,058,517 | B1 | 6/2006 | Denton et al. |

(Continued)

FOREIGN PATENT DOCUMENTS

| | | | |
|---|---|---|---|
| CA | 2875281 | A1 | 12/2013 |
| CN | 1650032 | A | 8/2005 |

(Continued)

OTHER PUBLICATIONS

US 8,501,409 B2, 08/2013, Simen et al. (withdrawn)

(Continued)

*Primary Examiner* — Stephanie K Mummert

(57) ABSTRACT

The invention provides methods, systems, and computer readable medium for detecting ploidy of chromosome segments or entire chromosomes, for detecting single nucleotide variants and for detecting both ploidy of chromosome segments and single nucleotide variants. In some aspects, the invention provides methods, systems, and computer readable medium for detecting cancer or a chromosomal abnormality in a gestating fetus.

22 Claims, 105 Drawing Sheets

(56) References Cited

U.S. PATENT DOCUMENTS 7,058,616 B1 6/2006 Larder et al.
7,101,663 B2 9/2006 Godfrey et al.
7,153,656 B2 12/2006 Nolan et al.
7,218,764 B2 5/2007 Vaisberg et al.
7,297,485 B2 11/2007 Bornarth et al.
7,332,277 B2 2/2008 Dhallan
7,410,764 B2 8/2008 Gocke et al.
7,414,118 B1 8/2008 Mullah et al.
7,442,506 B2 10/2008 Dhallan
7,459,273 B2 12/2008 Jones et al.
7,537,897 B2 5/2009 Brenner et al.
7,645,576 B2 1/2010 Lo et al.
7,655,399 B2 2/2010 Cantor et al.
7,700,325 B2 4/2010 Cantor et al.
7,718,367 B2 5/2010 Lo et al.
7,718,370 B2 5/2010 Dhallan
7,727,720 B2 6/2010 Dhallan
7,741,463 B2 6/2010 Gormley et al.
7,785,798 B2 8/2010 Cantor et al.
7,790,393 B2 9/2010 Lyamichev et al.
7,790,418 B2 9/2010 Mayer
7,805,282 B2 9/2010 Casey
7,838,647 B2 11/2010 Hahn et al.
7,888,017 B2 2/2011 Quake
7,981,609 B2 7/2011 Rubin et al.
8,008,018 B2 8/2011 Quake et al.
8,024,128 B2 9/2011 Rabinowitz
8,133,719 B2 3/2012 Drmanac et al.
8,137,912 B2 3/2012 Kapur et al.
8,168,389 B2 5/2012 Shoemaker et al.
8,173,370 B2 5/2012 Oeth et al.
8,195,415 B2 6/2012 Fan et al.
8,236,503 B2 8/2012 Faham et al.
8,296,076 B2 10/2012 Fan et al.
8,304,187 B2 11/2012 Fernando
8,318,430 B2 11/2012 Chuu et al.
8,318,434 B2 11/2012 Cuppens et al.
8,323,897 B2 12/2012 Andersen et al.
8,372,584 B2 2/2013 Shoemaker et al.
8,450,063 B2 5/2013 Dube et al.
8,467,976 B2 6/2013 Lo et al.
8,515,679 B2 8/2013 Rabinowitz et al.
8,532,930 B2 9/2013 Rabinowitz et al.
8,586,310 B2 11/2013 Mitra et al.
8,609,338 B2 12/2013 Mitchell et al.
8,679,741 B2 3/2014 Hoyal-Wrightson et al.
8,682,592 B2 3/2014 Rabinowitz et al.
8,703,652 B2 4/2014 Quake et al.
8,706,422 B2 4/2014 Lo et al.
8,748,103 B2 6/2014 Faham et al.
8,822,153 B2 9/2014 Hayes et al.
8,825,412 B2 9/2014 Rabinowitz et al.
9,051,602 B2 6/2015 Oliphant et al.
9,085,798 B2 7/2015 Chee
9,206,475 B2 12/2015 Gerdes et al.
9,228,234 B2 1/2016 Rabinowitz et al.
9,323,888 B2 4/2016 Rava et al.
9,364,829 B2 6/2016 Heid et al.
9,404,150 B2 8/2016 Lee et al.
9,424,392 B2 8/2016 Rabinowitz et al.
9,447,453 B2 * 9/2016 Rava ...................... G16B 20/00
9,453,257 B2 9/2016 Hoyal-Wrightson et al.
9,476,095 B2 10/2016 Vogelstein et al.
9,487,829 B2 11/2016 Vogelstein et al.
9,493,828 B2 11/2016 Rava et al.
9,506,119 B2 11/2016 Faham et al.
9,598,731 B2 3/2017 Talasaz
9,677,118 B2 6/2017 Zimmermann et al.
9,784,742 B2 10/2017 Benz et al.
9,926,593 B2 3/2018 Ehrich et al.
9,957,558 B2 5/2018 Leamon et al.
10,017,810 B2 7/2018 Iafrate et al.
10,041,127 B2 8/2018 Talasaz
10,061,890 B2 8/2018 Rabinowitz et al.
10,081,839 B2 9/2018 Rabinowitz et al.
10,083,273 B2 9/2018 Rabinowitz et al.
10,174,369 B2 1/2019 Rabinowitz et al.
10,179,937 B2 1/2019 Babiarz et al.
10,227,652 B2 3/2019 Rabinowitz et al.
10,229,244 B2 3/2019 Ghosh
10,240,202 B2 3/2019 Rabinowitz et al.
10,260,096 B2 4/2019 Rabinowitz et al.
10,262,755 B2 4/2019 Babiarz et al.
10,266,893 B2 4/2019 Rabinowitz et al.
10,308,981 B2 6/2019 Sparks et al.
10,316,362 B2 6/2019 Babiarz et al.
10,351,906 B2 7/2019 Zimmermann et al.
10,360,096 B2 7/2019 Morris et al.
10,392,664 B2 8/2019 Rabinowitz et al.
10,450,597 B2 10/2019 Iafrate et al.
10,522,242 B2 12/2019 Rabinowitz et al.
10,526,658 B2 1/2020 Babiarz et al.
10,538,814 B2 1/2020 Babiarz et al.
10,557,172 B2 2/2020 Babiarz et al.
10,597,709 B2 3/2020 Zimmermann et al.
10,640,819 B2 5/2020 Rosenfeld et al.
11,130,995 B2 9/2021 Quake et al.
11,319,596 B2 5/2022 Babiarz et al.
11,332,793 B2 5/2022 Rabinowitz et al.
11,371,100 B2 6/2022 Babiarz et al.
11,519,035 B2 12/2022 Rabinowtiz et al.
2002/0006622 A1 1/2002 Bradley et al.
2002/0107640 A1 8/2002 Ideker et al.
2002/0119478 A1 8/2002 Umansky et al.
2002/0182622 A1 12/2002 Nakamura et al.
2002/0197630 A1 12/2002 Knapp et al.
2003/0044388 A1 3/2003 Lo et al.
2003/0077586 A1 4/2003 Pavlovic et al.
2003/0087276 A1 5/2003 Kopreski et al.
2003/0101000 A1 5/2003 Bader et al.
2003/0108900 A1 6/2003 Oliphant et al.
2003/0119004 A1 6/2003 Wenz et al.
2003/0138780 A1 7/2003 Gill et al.
2003/0148301 A1 8/2003 Aono et al.
2003/0211489 A1 11/2003 Shen et al.
2003/0232348 A1 12/2003 Jones et al.
2003/0232353 A1 12/2003 Kennedy et al.
2003/0235848 A1 12/2003 Neville et al.
2004/0009518 A1 1/2004 Lo et al.
2004/0033596 A1 2/2004 Threadgill et al.
2004/0067493 A1 4/2004 Matsuzaki et al.
2004/0096874 A1 5/2004 Neville et al.
2004/0126760 A1 7/2004 Broude
2004/0137470 A1 7/2004 Dhallan et al.
2004/0146866 A1 7/2004 Fu
2004/0157243 A1 8/2004 Huang et al.
2004/0185495 A1 9/2004 Schueler et al.
2004/0197797 A1 10/2004 Inoko et al.
2004/0209299 A1 10/2004 Pinter et al.
2004/0229231 A1 11/2004 Frudakis et al.
2004/0236518 A1 11/2004 Pavlovic et al.
2005/0043894 A1 2/2005 Fernandez
2005/0049793 A1 3/2005 Paterlini-Brechot
2005/0053950 A1 3/2005 Ubani et al.
2005/0064476 A1 3/2005 Huang et al.
2005/0079521 A1 4/2005 Beaulieu et al.
2005/0123914 A1 6/2005 Katz et al.
2005/0130173 A1 6/2005 Leamon et al.
2005/0142577 A1 6/2005 Jones et al.
2005/0164241 A1 7/2005 Hahn et al.
2005/0164252 A1 7/2005 Yeung
2005/0216207 A1 9/2005 Kermani
2005/0221341 A1 10/2005 Shimkets et al.
2005/0227263 A1 10/2005 Green et al.
2005/0250111 A1 11/2005 Xie et al.
2005/0255508 A1 11/2005 Casey et al.
2005/0282185 A1 12/2005 Lo et al.
2006/0014179 A1 1/2006 Roberts
2006/0019278 A1 1/2006 Lo et al.
2006/0046258 A1 3/2006 Lapidus et al.
2006/0052945 A1 3/2006 Rabinowitz et al.
2006/0057618 A1 3/2006 Piper et al.
2006/0068394 A1 3/2006 Langmore et al.
2006/0088871 A1 4/2006 Finkelstein et al.

(56) References Cited

U.S. PATENT DOCUMENTS

2006/0088912 A1 4/2006 Yan et al.
2006/0094010 A1 5/2006 Giles et al.
2006/0099614 A1 5/2006 Gill et al.
2006/0121452 A1 6/2006 Dhallan
2006/0134662 A1 6/2006 Pratt et al.
2006/0210997 A1 9/2006 Myerson et al.
2006/0216738 A1 9/2006 Wada et al.
2006/0228721 A1 10/2006 Leamon et al.
2006/0229823 A1 10/2006 Liu
2006/0234264 A1 10/2006 Hardenbol
2006/0263789 A1 11/2006 Kincaid
2006/0281105 A1 12/2006 Li et al.
2006/0292599 A1 12/2006 Ritz et al.
2007/0020640 A1* 1/2007 McCloskey ............ C12Q 1/686 435/6.16
2007/0027636 A1 2/2007 Rabinowitz
2007/0031857 A1 2/2007 Makarov et al.
2007/0037166 A1 2/2007 Wohlgemuth et al.
2007/0042384 A1 2/2007 Li et al.
2007/0059700 A1 3/2007 Tao et al.
2007/0059707 A1 3/2007 Cantor et al.
2007/0122805 A1 5/2007 Cantor et al.
2007/0128624 A1 6/2007 Gormley et al.
2007/0134658 A1 6/2007 Bohmer et al.
2007/0178478 A1 8/2007 Dhallan
2007/0178501 A1 8/2007 Rabinowitz et al.
2007/0184467 A1 8/2007 Rabinowitz et al.
2007/0202525 A1 8/2007 Quake et al.
2007/0202536 A1 8/2007 Yamanishi et al.
2007/0207466 A1 9/2007 Cantor et al.
2007/0212689 A1 9/2007 Bianchi et al.
2007/0231823 A1 10/2007 Mckernan et al.
2007/0243549 A1 10/2007 Bischoff
2007/0259351 A1 11/2007 Chinitz
2008/0020390 A1 1/2008 Mitchell
2008/0026390 A1 1/2008 Stoughton et al.
2008/0038733 A1 2/2008 Bischoff et al.
2008/0050739 A1 2/2008 Stoughton et al.
2008/0070792 A1 3/2008 Stoughton
2008/0071076 A1 3/2008 Hahn et al.
2008/0085836 A1 4/2008 Kearns et al.
2008/0090239 A1 4/2008 Shoemaker et al.
2008/0096766 A1 4/2008 Lee
2008/0102455 A1 5/2008 Poetter
2008/0161420 A1 7/2008 Shuber et al.
2008/0193927 A1 8/2008 Mann et al.
2008/0220422 A1 9/2008 Shoemaker et al.
2008/0234142 A1 9/2008 Lietz
2008/0243398 A1 10/2008 Rabinowitz et al.
2008/0280292 A1 11/2008 Wangh et al.
2008/0286783 A1 11/2008 Hosono et al.
2008/0293589 A1 11/2008 Shapero
2008/0299562 A1 12/2008 Oeth et al.
2008/0305473 A1 12/2008 Chowdary et al.
2009/0023190 A1 1/2009 Lao et al.
2009/0029377 A1 1/2009 Lo et al.
2009/0053719 A1 2/2009 Lo et al.
2009/0087847 A1 4/2009 Lo et al.
2009/0099041 A1 4/2009 Church et al.
2009/0105959 A1 4/2009 Braverman et al.
2009/0176662 A1 7/2009 Rigatti et al.
2009/0233802 A1 9/2009 Bignell et al.
2009/0253183 A1 10/2009 Han
2009/0263800 A1 10/2009 Wohlgemuth et al.
2010/0035232 A1 2/2010 Ecker et al.
2010/0041048 A1 2/2010 Diehl et al.
2010/0086914 A1 4/2010 Bentley et al.
2010/0105049 A1 4/2010 Ehrich et al.
2010/0112575 A1 5/2010 Fan et al.
2010/0112586 A1 5/2010 Stoughton et al.
2010/0112590 A1 5/2010 Lo et al.
2010/0120038 A1 5/2010 Mir et al.
2010/0124751 A1 5/2010 Quake et al.
2010/0129792 A1 5/2010 Makrigiorgos et al.
2010/0129874 A1 5/2010 Mitra et al.
2010/0138165 A1 6/2010 Fan et al.
2010/0171954 A1 7/2010 Quake et al.
2010/0173394 A1 7/2010 Colston et al.
2010/0184043 A1 7/2010 Mitchell et al.
2010/0184069 A1 7/2010 Fernando et al.
2010/0184152 A1 7/2010 Sandler
2010/0196892 A1 8/2010 Quake et al.
2010/0203538 A1 8/2010 Dube et al.
2010/0216145 A1 8/2010 Duvdevani
2010/0216151 A1 8/2010 Lapdus et al.
2010/0216153 A1 8/2010 Lapidus et al.
2010/0227329 A1 9/2010 Cuppens
2010/0248231 A1 9/2010 Wei et al.
2010/0255492 A1 10/2010 Quake et al.
2010/0256013 A1 10/2010 Quake et al.
2010/0273159 A1 10/2010 Melo
2010/0273219 A1 10/2010 May et al.
2010/0273678 A1 10/2010 Alexandre et al.
2010/0285478 A1 11/2010 Chen et al.
2010/0285537 A1 11/2010 Zimmermann
2010/0291572 A1 11/2010 Stoughton et al.
2010/0291635 A1 11/2010 Peleg
2010/0323352 A1 12/2010 Lo et al.
2011/0015096 A1 1/2011 Chiu
2011/0033862 A1 2/2011 Rabinowitz et al.
2011/0039724 A1 2/2011 Lo et al.
2011/0045462 A1 2/2011 Fu et al.
2011/0086769 A1 4/2011 Oliphant et al.
2011/0105353 A1 5/2011 Lo et al.
2011/0130558 A1 6/2011 Ritt et al.
2011/0151442 A1 6/2011 Fan et al.
2011/0159499 A1 6/2011 Hindson et al.
2011/0160078 A1 6/2011 Fodor et al.
2011/0178719 A1 7/2011 Rabinowitz et al.
2011/0189677 A1 8/2011 Adli et al.
2011/0201507 A1 8/2011 Rava et al.
2011/0212446 A1 9/2011 Wang et al.
2011/0212846 A1 9/2011 Spier
2011/0224087 A1 9/2011 Quake et al.
2011/0230358 A1 9/2011 Rava
2011/0246083 A1 10/2011 Fan et al.
2011/0288780 A1 11/2011 Rabinowitz et al.
2011/0294699 A1 12/2011 Lee et al.
2011/0300608 A1 12/2011 Ryan et al.
2011/0301854 A1 12/2011 Curry et al.
2011/0312503 A1 12/2011 Chuu et al.
2011/0318734 A1 12/2011 Lo et al.
2012/0003635 A1 1/2012 Lo et al.
2012/0003637 A1 1/2012 Lo et al.
2012/0010085 A1 1/2012 Rava et al.
2012/0028814 A1 2/2012 Toloue et al.
2012/0034603 A1 2/2012 Oliphant et al.
2012/0034685 A1 2/2012 Sparks et al.
2012/0108460 A1 5/2012 Quake et al.
2012/0122701 A1 5/2012 Ryan et al.
2012/0135872 A1 5/2012 Chuu et al.
2012/0165203 A1 6/2012 Quake et al.
2012/0185176 A1 7/2012 Rabinowitz et al.
2012/0190020 A1 7/2012 Oliphant et al.
2012/0190021 A1 7/2012 Oliphant et al.
2012/0190557 A1 7/2012 Oliphant et al.
2012/0191358 A1 7/2012 Oliphant et al.
2012/0196754 A1 8/2012 Quake et al.
2012/0214678 A1 8/2012 Rava et al.
2012/0264121 A1 10/2012 Rava et al.
2012/0264618 A1 10/2012 Nygren
2012/0270212 A1 10/2012 Rabinowitz et al.
2012/0270739 A1 10/2012 Rava et al.
2012/0295810 A1 11/2012 Quake et al.
2012/0295819 A1 11/2012 Leamon et al.
2012/0315633 A1 12/2012 Mantzaris et al.
2013/0005585 A1 1/2013 Anderson et al.
2013/0017549 A1 1/2013 Hong
2013/0022973 A1 1/2013 Hansen et al.
2013/0024127 A1 1/2013 Stuelpnagel
2013/0034546 A1 2/2013 Rava et al.
2013/0040375 A1 2/2013 Sparks et al.
2013/0059733 A1 3/2013 Lo et al.
2013/0060483 A1 3/2013 Struble et al.

(56) References Cited

U.S. PATENT DOCUMENTS

2013/0073214 A1 3/2013 Hyland et al.
2013/0085681 A1 4/2013 Deciu et al.
2013/0090250 A1 4/2013 Sparks et al.
2013/0116130 A1 5/2013 Fu et al.
2013/0123120 A1 5/2013 Zimmermann et al.
2013/0130923 A1 5/2013 Ehrich et al.
2013/0137587 A1 5/2013 Van Eijk et al.
2013/0143219 A1 6/2013 Mitchell et al.
2013/0150253 A1 6/2013 Deciu et al.
2013/0157870 A1 6/2013 Pushkarev et al.
2013/0172211 A1 7/2013 Oliphant et al.
2013/0178373 A1 7/2013 Rabinowitz et al.
2013/0196862 A1 8/2013 Rabinowitz et al.
2013/0210644 A1 8/2013 Stoughton et al.
2013/0225422 A1 8/2013 Rabinowitz et al.
2013/0231252 A1 9/2013 Mitchell et al.
2013/0237431 A1 9/2013 Lo et al.
2013/0252824 A1 9/2013 Rabinowitz
2013/0253369 A1 9/2013 Rabinowitz et al.
2013/0261004 A1 10/2013 Ryan et al.
2013/0274116 A1 10/2013 Rabinowitz et al.
2013/0288252 A1 10/2013 Sparks et al.
2013/0303461 A1 11/2013 Iafrate et al.
2013/0310260 A1 11/2013 Kim et al.
2013/0323727 A1 12/2013 Huang et al.
2013/0323731 A1 12/2013 Lo et al.
2013/0338933 A1 12/2013 Deciu et al.
2013/0344066 A1 12/2013 Faham et al.
2014/0032128 A1 1/2014 Rabinowitz et al.
2014/0038830 A1 2/2014 Srinivasan et al.
2014/0045181 A1 2/2014 Lo et al.
2014/0051585 A1 2/2014 Prosen et al.
2014/0065621 A1 3/2014 Mhatre et al.
2014/0066317 A1 3/2014 Talasaz
2014/0087385 A1 3/2014 Rabinowitz et al.
2014/0094373 A1 4/2014 Zimmermann et al.
2014/0100121 A1* 4/2014 Lo ........................ C12Q 1/6827
702/19
2014/0100126 A1 4/2014 Rabinowitz
2014/0100134 A1 4/2014 Rabinowitz et al.
2014/0106975 A1 4/2014 Stoughton et al.
2014/0141981 A1 5/2014 Zimmermann et al.
2014/0154682 A1 6/2014 Rabinowitz et al.
2014/0162269 A1 6/2014 Rabinowitz
2014/0186827 A1 7/2014 Pieprzyk et al.
2014/0193816 A1 7/2014 Rabinowitz et al.
2014/0206552 A1 7/2014 Rabinowitz et al.
2014/0227691 A1 8/2014 May et al.
2014/0227705 A1 8/2014 Vogelstein et al.
2014/0242588 A1 8/2014 Van Den Boom et al.
2014/0256558 A1 9/2014 Varley et al.
2014/0296081 A1 10/2014 Diehn et al.
2014/0336060 A1 11/2014 Rabinowitz
2015/0051087 A1 2/2015 Rabinowitz et al.
2015/0064695 A1 3/2015 Katz et al.
2015/0086477 A1 3/2015 Mitchell et al.
2015/0087535 A1 3/2015 Patel
2015/0099673 A1 4/2015 Fodor
2015/0147815 A1 5/2015 Babiarz et al.
2015/0167069 A1 6/2015 Schutz et al.
2015/0167077 A1 6/2015 Fehr et al.
2015/0197786 A1 7/2015 Osborne et al.
2015/0211050 A1 7/2015 Iafrate et al.
2015/0218631 A1 8/2015 Chuu et al.
2015/0232938 A1 8/2015 Mhatre et al.
2015/0299812 A1 10/2015 Talasaz
2015/0315657 A1 11/2015 Rhodes et al.
2015/0322507 A1 11/2015 Zimmermann et al.
2016/0024581 A1 1/2016 Sarwal et al.
2016/0032396 A1* 2/2016 Diehn .................. C12Q 1/6886
506/26
2016/0046986 A1 2/2016 Eltoukhy et al.
2016/0053320 A1 2/2016 Schuh et al.
2016/0138112 A1 5/2016 Janne et al.
2016/0201124 A1 7/2016 Donahue et al.
2016/0257993 A1 9/2016 Fu et al.
2016/0289740 A1 10/2016 Fu et al.
2016/0289753 A1 10/2016 Osborne et al.
2016/0369333 A1 12/2016 Babiarz et al.
2017/0011166 A1 1/2017 Rabinowitz et al.
2017/0107576 A1 4/2017 Babiarz et al.
2017/0121716 A1 5/2017 Rodi
2018/0171409 A1 6/2018 Rabinowitz et al.
2018/0298439 A1 10/2018 Ryan et al.
2018/0320239 A1 11/2018 Babiarz et al.
2018/0371531 A1 12/2018 Quake et al.
2019/0211376 A1 7/2019 Quake et al.
2019/0211399 A1 7/2019 Rabinowitz et al.
2019/0316184 A1 10/2019 Zimmermann et al.
2020/0032323 A1 1/2020 Talasaz et al.
2020/0126634 A1 4/2020 Sigurjonsson et al.
2020/0190591 A1 6/2020 Rabinowitz et al.
2020/0232036 A1 7/2020 Rabinowitz et al.
2020/0350034 A1 11/2020 Rabinowitz et al.
2024/0392387 A1 11/2024 Diehn et al.
2025/0027169 A1 1/2025 Babiarz et al.
2025/0027170 A1 1/2025 Babiarz et al.

FOREIGN PATENT DOCUMENTS

CN 102892901 A 1/2013
EP 1325963 B1 9/2006
EP 1524321 B1 7/2009
EP 2551356 A1 1/2013
EP 1524321 B2 7/2014
EP 2902500 A1 8/2015
EP 2315849 B1 11/2017
EP 2877594 B1 12/2019
EP 3760730 A1 1/2021
EP 3760731 A1 1/2021
EP 3760732 A1 1/2021
GB 2488358 8/2012
JP 2002-530121 A 9/2002
JP 2002-300894 A 10/2002
JP 2003/521252 A 7/2003
JP 2004502466 A 1/2004
JP 2004121087 A 4/2004
JP 2005514956 A 5/2005
JP 2005160470 A 6/2005
JP 2006-254912 A 9/2006
JP 2010-509922 A 4/2010
JP 2011/516069 A 5/2011
JP 2012085556 A 5/2012
JP 2013509883 A 3/2013
JP 2015535681 A 12/2015
JP 2016502849 A 2/2016
WO 2001007640 A2 2/2001
WO 01/57269 A2 8/2001
WO 200190419 A2 11/2001
WO 2002004672 A2 1/2002
WO 02/44411 A1 6/2002
WO 02/070751 A1 9/2002
WO 03/000919 A2 1/2003
WO 03/018757 A3 3/2003
WO 03/020974 A3 3/2003
WO 2003031646 A1 4/2003
WO 2003062441 A1 7/2003
WO 2004/051218 A2 6/2004
WO 2004069849 A2 8/2004
WO 2004070005 A2 8/2004
WO 2004070007 A2 8/2004
WO 2004078999 A1 9/2004
WO 2004081183 9/2004
WO 2005003375 A2 1/2005
WO 2005021793 A1 3/2005
WO 2005023091 A2 3/2005
WO 2005035725 A2 4/2005
WO 2005/039389 A3 5/2005
WO WO-2005090607 A1 9/2005
WO 2007145612 A1 6/2006
WO 2006110855 A2 10/2006
WO 2007/052006 A1 5/2007
WO 2007057647 A1 5/2007
WO 2007062164 A3 5/2007

(56) References Cited

FOREIGN PATENT DOCUMENTS

| | | | |
|---|---|---|---|
| WO | 2007/073171 | A2 | 6/2007 |
| WO | 2007075836 | A2 | 7/2007 |
| WO | 2007/092473 | A2 | 8/2007 |
| WO | 2007086935 | A2 | 8/2007 |
| WO | 2007132167 | A2 | 11/2007 |
| WO | 2007/147073 | A2 | 12/2007 |
| WO | 2007/147076 | A2 | 12/2007 |
| WO | 2007140417 | A2 | 12/2007 |
| WO | 2007147074 | A2 | 12/2007 |
| WO | 2007147079 | A2 | 12/2007 |
| WO | 2008024473 | A2 | 2/2008 |
| WO | 2008/061213 | A2 | 5/2008 |
| WO | 2008051928 | A2 | 5/2008 |
| WO | 2008059578 | A1 | 5/2008 |
| WO | 2008079374 | A2 | 7/2008 |
| WO | 2008081451 | A2 | 7/2008 |
| WO | 2008115497 | A2 | 9/2008 |
| WO | 2008118988 | A1 | 10/2008 |
| WO | 2008-263974 | A | 11/2008 |
| WO | 2008/271980 | A | 11/2008 |
| WO | 2008135837 | A2 | 11/2008 |
| WO | 2008157264 | A2 | 12/2008 |
| WO | 2009009769 | A2 | 1/2009 |
| WO | 2009013492 | A1 | 1/2009 |
| WO | 2009013496 | A1 | 1/2009 |
| WO | 2009019215 | A1 | 2/2009 |
| WO | 2009019455 | A2 | 2/2009 |
| WO | 2009/032779 | A2 | 3/2009 |
| WO | 2009/036525 | A2 | 3/2009 |
| WO | 2009030100 | A1 | 3/2009 |
| WO | 2009032781 | A2 | 3/2009 |
| WO | 2009033178 | A1 | 3/2009 |
| WO | 2009049889 | A1 | 4/2009 |
| WO | 2009017784 | A2 | 5/2009 |
| WO | 2009064897 | A2 | 5/2009 |
| WO | 2009091934 | A1 | 7/2009 |
| WO | 2009092035 | A2 | 7/2009 |
| WO | 2009/105531 | A1 | 8/2009 |
| WO | 2009099602 | A1 | 8/2009 |
| WO | 2009100029 | A1 | 8/2009 |
| WO | 2009117122 | A2 | 9/2009 |
| WO | 2009120808 | A2 | 10/2009 |
| WO | 2009145828 | A2 | 12/2009 |
| WO | 2010014920 | A1 | 2/2010 |
| WO | 2010017214 | A1 | 2/2010 |
| WO | WO-2010019588 | A1 | 2/2010 |
| WO | 2010/033639 | A2 | 3/2010 |
| WO | 2010033578 | A2 | 3/2010 |
| WO | 2010042831 | A2 | 4/2010 |
| WO | 2010045617 | A2 | 4/2010 |
| WO | 2010075459 | | 7/2010 |
| WO | 2010/088288 | A2 | 8/2010 |
| WO | 2010115016 | A2 | 10/2010 |
| WO | 2010115154 | A1 | 10/2010 |
| WO | 2010118016 | A2 | 10/2010 |
| WO | 2010/127186 | A1 | 11/2010 |
| WO | 2011015944 | A2 | 2/2011 |
| WO | 2011041485 | A1 | 4/2011 |
| WO | 2011/051283 | A1 | 5/2011 |
| WO | 2011/057061 | A1 | 5/2011 |
| WO | 2011057094 | | 5/2011 |
| WO | 2011/090556 | A1 | 7/2011 |
| WO | 2011087760 | | 7/2011 |
| WO | 2011094646 | A1 | 8/2011 |
| WO | 2011102998 | A2 | 8/2011 |
| WO | 2011/118603 | | 9/2011 |
| WO | 2011109440 | A1 | 9/2011 |
| WO | 2011118603 | A1 | 9/2011 |
| WO | 2011/142836 | A2 | 11/2011 |
| WO | 2011140433 | A2 | 11/2011 |
| WO | 2011146632 | A1 | 11/2011 |
| WO | 2012/019200 | A2 | 2/2012 |
| WO | 2012/028746 | A1 | 3/2012 |
| WO | 2012042374 | A2 | 4/2012 |
| WO | 2012-083189 | A2 | 6/2012 |
| WO | 201283250 | | 6/2012 |
| WO | 2012088456 | A2 | 6/2012 |
| WO | 20120071621 | | 6/2012 |
| WO | 2012092426 | | 7/2012 |
| WO | 2012108920 | A1 | 8/2012 |
| WO | 2012122374 | A2 | 9/2012 |
| WO | WO-2012125848 | A2 | 9/2012 |
| WO | 2012/142531 | A2 | 10/2012 |
| WO | WO-2013030577 | A1 | 3/2013 |
| WO | 2013/049892 | A1 | 4/2013 |
| WO | WO-2013052557 | A2 | 4/2013 |
| WO | WO-2013086464 | A1 | 6/2013 |
| WO | WO-2013123220 | A1 | 8/2013 |
| WO | WO-2013130848 | A1 | 9/2013 |
| WO | WO-2013159035 | A2 | 10/2013 |
| WO | WO-2013169339 | A1 | 11/2013 |
| WO | WO-2013177581 | A2 | 11/2013 |
| WO | WO-2013190441 | A2 | 12/2013 |
| WO | WO-2014004726 | A1 | 1/2014 |
| WO | WO-2014014497 | A1 | 1/2014 |
| WO | WO-2014018080 | A1 | 1/2014 |
| WO | WO-2014026277 | A1 | 2/2014 |
| WO | WO-2014039556 | A1 | 3/2014 |
| WO | WO-2014043763 | A1 | 3/2014 |
| WO | WO-2014053664 | A1 | 4/2014 |
| WO | WO-2014055790 | A2 | 4/2014 |
| WO | WO-2014099919 | A2 | 6/2014 |
| WO | WO-2013138510 | A9 | 7/2014 |
| WO | WO-2014118334 | A1 | 8/2014 |
| WO | WO-2014143989 | A1 | 9/2014 |
| WO | WO-2014149134 | A2 | 9/2014 |
| WO | WO-2014151117 | A1 | 9/2014 |
| WO | WO-2014194113 | A2 | 12/2014 |
| WO | WO-2015006668 | A1 | 1/2015 |
| WO | WO-2015069933 | A1 | 5/2015 |
| WO | WO-2015100427 | A1 | 7/2015 |
| WO | WO-2015134552 | A1 | 9/2015 |
| WO | WO-2015138997 | A1 | 9/2015 |
| WO | WO-2015164432 | A1 | 10/2015 |
| WO | WO-2015169947 | A1 | 11/2015 |
| WO | WO-2015178978 | A2 | 11/2015 |
| WO | WO-2016001411 | A1 | 1/2016 |
| WO | WO-2016009224 | A1 | 1/2016 |
| WO | WO-2016028316 | A1 | 2/2016 |
| WO | WO-2016063122 | A1 | 4/2016 |
| WO | WO-2016077313 | A1 | 5/2016 |
| WO | 2007100911 | A2 | 9/2021 |
| WO | 2011/130751 | | 10/2023 |
| WO | 2011/146942 | | 11/2023 |
| WO | 2011/153254 | A2 | 12/2023 |
| WO | 2024076469 | A1 | 4/2024 |

OTHER PUBLICATIONS

Eeles et al. (Nature Genetics, 2008, 40(3):316-321 and Supplemental documents) (Year: 2008).*

Kukita et al. (PLOS One, 2013, 8(11):e81468, p. 1-10, plus Supplemental content) (Year: 2013).*

Alkan, Can et al., "Personalized Copy Number and Segmental Duplication Maps Using Next-Generation Sequencing", Nature Genetics, 41, 10, 2009, 1061-1068.

Amicucci, P. et al., "Prenatal Diagnosis of Myotonic Dystrophy Using Fetal DNA Obtained from Maternal Plasma", Clinical Chemistry, vol. 46, No. 2, 2000, 301-302.

Andras, S. C. et al., "Strategies for Signal Amplification in Nucleic Acid Detection", Molecular Biotechnology, vol. 19, 2001, 29-44.

Anker, P. et al., "Circulating DNA in Plasma or Serum", Medicina, vol. 60, 2000, 699-702.

Anker, P. et al., "The Second International Symposium on Circulating Nucleic Acids in Plasma and Serum (CNAPS-2) held in conjunction with the 6th Annual Scientific Symposium of the Hong Kong Cancer Institute", Clinical Chemistry, vol. 47, No. 2, 2001, 361-370.

Ansorge, Wilhelm J., "Next-generation DNA Sequencing Techniques", New Biotechnology, vol. 25, No. 4, Feb. 2, 2009, 195-203.

Arandjelovic, M. et al., "Two-Step Multiplex Polymerase Chain Reaction improves the Speed and Accuracy of Genotyping Using

(56) References Cited

OTHER PUBLICATIONS

DNA from Noninvasive and Museum Samples", Molecular Ecology Resources, vol. 9, 2009, pp. 28-36.
Avent, Neil D. et al., "Cell-free Fetal DNA in The Maternal Serum and Plasma: Current and Evolving Applications", Current Opinion in Obstretrics and Gynecology, vol. 21, No. 2, Apr. 1, 2009, 175-179.
Avgidou, K. et al., "Prospective first-trimester screening for trisomy 21 in 30,564 pregnancies", American Journal of Obstetrics and Gynecology, vol. 192, 2005, 1761-1767.
Ayala, et al., "Long-Term Follow-Up of Donor Chimerism Tolerance After Human Liver Transplantation", Liver Transplantation, vol. 15, No. 6, May 28, 2009, 581-591.
Balduini, et al., "Utility of Biochemical Markers in The Follow-up Heart Transplant Recipients", Transplantation Proceedings, vol. 35, No. 8, Dec. 1, 2003, 3075-3078.
Bau, Stephan et al., "Targeted next-generation sequencing by specific capture of multiple genomic loci using low-volume microfluidic DNA arrays", Anal Bioanal Chem, vol. 393, 2009, 171-175.
Bauer, M. et al., "A prospective analysis of cell-free fetal DNA concentration in maternal plasma as an indicator for adverse pregnancy outcome", Prenatal Diagnosis, vol. 26, 2006, 831-836.
Baxter-Lowe, et al., "Tracking Microchimeric DNA in Plasma to Diagnose and Manage Organ Transplant Rejection", Clinical Chemistry, vol. 52, No. 4, Apr. 1, 2006, 559-561.
Beck, et al., "Next Generation Sequencing of Serum Circulating Nucleic Acids from Patients with Invasive Ductal Breast Cancer Reveals Differences to Healthy and Nonmalignant Controls", Molecular Cancer Research, vol. 8, No. 3, Mar. 1, 2010, 335-342.
Beck, J. et al., "Profile of the Circulating DNA in Apparently Healthy Individuals", Clinical Chemistry, vol. 55, No. 4, 2009, 730-738.
Bender, et al., "A Multiplex SNP Typing Approach for The DNA Pyrosequencing Technology", International Congress Series, vol. 1288, Apr. 20, 2006, 73-75.
Bentley, et al., "High-resolution, High-throughput HLA Genotyping by Next-generation Sequencing", Tissue Antigens, vol. 74, No. 5, Nov. 1, 2009, 393-403.
Bergen, A. W. et al., "Effects of DNA mass on multiple displacement whole genome amplification and genotyping performance", BMC Biotechnology, vol. 5, No. 24, Sep. 16, 2005, 11 pgs.
Bianchi, D W. et al., "Insights into Fetal and Neonatal Development Through Analysis of Cell-Free RNA in Body Fluids", Early Human Development, vol. 86, No. 11, Nov. 2010, 747-752.
Bianchi, D. W., "Circulating Fetal DNA: Its Origin and Diagnostic Potential—A Review", Placenta, vol. 25, Supplemental A, May 2004, S93-S101.
Binladen, J. et al., "The Use of Coded PCR Primers Enables High-Throughput Sequencing of Multiple Homolog Amplification Products by 454 Parallel Sequencing", PLOS One, Issue 2, Feb. 2007, 9 pages.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Bisignano, et al., "PGD and Aneuploidy Screening for 24 Chromosomes: Advantages and Disadvantages of Competing Platforms", Reproductive Biomedicine Online, 23, 2011, 677-685.
Bordoni, et al., "Evaluation of Human Gene Variant Detection in Amplicon Pools by the GS-FLX Parallel Pyrosequencer", BMC Genomics, vol. 9, Oct. 8, 2008, 1-8.
Brockman, et al., "Quality Scores and SNP Detection in Sequencing-by-synthesis Systems", Genome Research, vol. 18, No. 5, May 1, 2008, 763-770.
Broude, N E. et al., "High-Level Multiplex DNA Amplification", Antisense & Nucleic Acid Drug Development, vol. 11, 2001, 327-332.
Broude, N. E. et al., "High Multiplexity PCR Based on PCR Suppression", DNA Amplification Current Technologies and Applications, 2004, 61-76.
Broude, N. E. et al., "Multiplex Allele-specific Target Amplification based on PCR Suppression", PNAS, vol. 98, No. 1, Jan. 2, 2001, 206-211.
Bustamante-Aragones, Ana et al., "New Strategy for The Prenatal Detection/Exclusion of Paternal Cystic Fibrosis Mutations in Maternal Plasma", Journal of Cystic Fibrosis, vol. 7, Issue 6, Nov. 1, 2008, 505-510.
Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.
Caliendo, Angela, "Multiplex PCR and Emerging Technologies for the Detection of Respiratory Pathogens", Clinical Infectious Diseases, 52(4), 2011, S326-S330.
Campbell, P. J. et al., "Subclonal phylogenetic structures in cancer revealed by ultra-deep sequencing", PNAS, vol. 105, No. 35, Sep. 2, 2008, 13081-13086.
Casbon, J. A. et al., "A method for counting PCR template molecules with application to next-generation sequencing", Nucleic Acids Research, vol. 39, No. 12, Apr. 13, 2011, 1-8.
Castleberry, et al., "Quantification of Circulating Cell-Free DNA in Pediatric Heart Transplant Recipients", Journal of Heart and Lung Transplantation, Apr. 1, 2011; 30(4): ISSN: 1053-2498, DOI: 10.1016/j.healun.2011.01.415, 2011, S139.
Chan, Allen K. et al., "Cell-free Nucleic Acids in Plasma, Serum and Urine: A New Tool in Molecular Diagnosis", Annals of Clinical Biochemistry, vol. 40, Issue 2, Mar. 1, 2003, 122-130.
Chan, K.C. et al., "Size Distributions of Maternal and Fetal DNA in Maternal Plasma", Clinical Chemistry, vol. 50, No. 1, 2004, 88-92.
Chen, E. et al., "Noninvasive Prenatal Diagnosis of Fetal Trisomy 18 and Trisomy 13 by Maternal Plasma DNA Sequencing", PLoS One, 6(7), e21791, 2011, 7 pgs.
Chen, C. P. et al., "Fetal DNA in maternal plasma: the prenatal detection of a paternally inherited fetal aneuploidy", Prenatal Diagnosis, vol. 20, 2000, 353-357.
Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.
Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K. et al., "Non-Invasive Prenatal Diagnosis by Single Molecule Counting Technologies", Trends in Genetics, 25 (7), 2009, 324-331.
Chiu, Rossa W.K. et al., "Noninvasive Prenatal Diagnosis of Fetal Chromosomal Aneuploidy by Massively Parallel Genomic Sequencing of DNA in Maternal Plasma (with Supporting Information)", PNAS, vol. 105, No. 51, 2008, 20458-20463.
Choi, M. et al., "Genetic diagnosis by whole exome capture and massively parallel DNA sequencing", PNAS, vol. 106, No. 45, Nov. 10, 2009, 19096-19101.
Chu, T. et al., "Statistical Considerations for Digital Approaches to Non- Invasive Fetal Genotyping", Bioinformatics (Advance Access publication), 26 (22), 2010, 2863-2866.
Chu, Tianjiao et al., "Statistical Model for Whole Genome Sequencing and its Application to Minimally Invasive Diagnosis of Fetal Genetic Disease", Bioinformatics, 25(10), 2009, 1244-1250.
Chu, Tianjiao et al., "A Novel Approach Toward the Challenge of Accurately Quantifying Fetal DNA in Maternal Plasma", Prenatal Diagnosis,30, 2010, 1226-1229.
Colella, S. et al., "QuantiSNP: an Objectives Bayes Hidden-Markov Model to Detect and Accurately Map Copy No. Variation Using SNP Genotyping Data", Nucleic Acids Research, 35 (6), 2007, 2013-2025.
Costa, J.-M. et al., "Fetal RHD genotyping in maternal serum during the first trimester of pregnancy", British Journal of Haematology, vol. 119, 2002, 255-260.

(56) References Cited

OTHER PUBLICATIONS

Craig, D. W. et al., "Identification of genetic variants using bar-coded multiplexed sequencing", Nature Methods, vol. 5, Oct. 2008, 887-893.
Crespo-Leiro, et al., "Gene Expression Profiling for Monitoring Graft Rejection in Heart Transplant Recipients", Transplantation Proceedings, vol. 41, No. 6, Jul. 1, 2009, 2240-2243.
Croft, Jr., Daniel et al., "Performance of Whole-Genome Amplified DNA Isolated from Serum and Plasma on High-Density Single Nucleotide Polymorphism Arrays", Journal of Molecular Diagnostics, 10(3), 2008, 249-257.
Cross, Jillian et al., "Resolution of trisomic mosaicism in prenatal diagnosis: estimated performance of a 50K SNP microarray", Prenat Diagn 2007; 27, 2007, 1197-1204.
Dahl, et al., "Multigene Amplification and Massively Parallel Sequencing for Cancer Mutation Discovery", Proceedings of the National Academy of Sciences, vol. 104, No. 22, May 29, 2007, 9387-9392.
Daniels, G. et al., "Fetal blood group genotyping from DNA from maternal plasma: an important advance in the management and prevention of haemolytic disease of the fetus and newborn", Vox Sanguinis, vol. 87, 2004, 223-232.
Daruwala, Raoul-Sam et al., "A Versatile Statistical Analysis Algorithm to Detect Genome Copy Number Variation", PNAS, 101(46), 2004, 16292-16297.
Deutsch, S. et al., "Detection of aneuploidies by paralogous sequence quantification", J Med Genet, vol. 41, 2004, 908-915.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.
Dhallan, Ravinder et al., "A non-invasive test for prenatal diagnosis based on fetal DNA present in maternal blood: a preliminary study", The Lancet, 369, 2007, 474-481.
Diehl, F. et al., "Circulating mutant DNA to assess tumor dynamics", Nature Medicine, vol. 14, No. 9, Jul. 31, 2008, 985-990.
Diehl, F. et al., "Detection and quantification of mutations in the plasma of patients with colorectal tumors", PNAS, vol. 102, No. 45, Nov. 8, 2005, 16368-16373.
Donaghue, C. et al., "Detection of mosaicism for primary trisomies in prenatal samples by QF-PCR and karyotype analysis", Prenatal Diagnosis, vol. 25, 2005, 65-72.
Doostzadeh, et al., "High Throughput Automated Allele Frequency Estimation by Pyrosequencing", PLoS One, vol. 3, No. 7, Jul. 16, 2008, 1-4.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Ellonen, P. et al., "Development of SNP Microarray for Supplementary Paternity Testing", International Congress Series, 1261, 2004, 12-14.
Erlich, R. L. et al., "Next-generation sequencing for HLA typing of class loci", BMC Genomics, vol. 12, No. 42, 2011, 13 pages.
Eronen, L. et al., "HaploRec: efficient and accurate large-scale reconstruction of haplotypes", BMC Bioinformatics, vol. 7, No. 542, Dec. 22, 2006, 18 pages.
European Commission, "The 7th International Conference on Circulating Nucleic Acids in Plasma and Serum (CNAPS VII) in Madrid-Spain", The International Conference on Circulating Nucleic Acids in Plasma and Serum, Oct. 24, 2011, 2 pgs.
Fan, C H. et al., "Detection of Aneuploidy with Digital Polymerase Chain Reaction", Analytical Chemistry, vol. 79, No. 19, Oct. 1, 2007, 7576-7579.
Fan, Christina H et al., "Noninvasive Diagnosis of Fetal Aneuploidy by Shotgun Sequencing DNA from Maternal Blood", PNAS, 105, 42, 2008, 16266-16271.
Fan, H. C. et al., "In Principle Method for Noninvasive Determination of the Fetal Genome", Nat. Prec., 2010, 16 pgs.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Fan, H. Christina et al., "Sensitivity of Noninvasive Prenatal Detection of Fetal Aneuploidy from Maternal Plasma Using Shotgun Sequencing Is Limited Only by Counting Statistics", PLoS One, vol. 5, Issue 5 (e10439), May 3, 2010, 1-6.
Fan, J.-B. et al., "Highly Parallel SNP Genotyping", Cold Spring Harbor Symposia on Quantitative Biology, vol. LXVIII, Feb. 2003, 69-78.
Fan, Jian-Bing et al., "Highly Parallel Genomic Assay", Nature Reviews, 7, 2006, 632-644.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Fredriksson, et al., "Multiplex amplification of all coding sequences within 10 cancer genes by Gene-Collector", Nucleic Acids Research, 2007, vol. 35, No. 7 e47, 1-6.
Fredriksson, M et al., "Assessing Hematopoietic Chimerism After Allogeneic Stem Cell Transplantation by Multiplexed SNP Genotyping Using Microarrays and Quantitive Analysis of SNP Alleles", Leukemia, vol. 18, Issue 2, Dec. 4, 2003, 255-266.
Fu, Yao-Wen et al., "Presence of Donor-and-recipient derived DNA Microchimerism In the Cell-free Blood Samples of Renal Transplantation Recipients Associates with The Acceptance Of Transplanted Kidneys", Asian Journal of Andrology, vol. 8, No. 4, Jul. 1, 2006, 477-482.
Gadi, V. K. et al., "Soluble Donor DNA Concentrations in Recipient Serum Correlate with Pancreas-Kidney Rejection", Clinical Chemistry, vol. 52, No. 3, 2006, 379-382.
Garcia Moreira, V. et al., "Cell-Free DNA as a Noninvasive Acute Rejection Marker in Renal Transplantation", Clinical Chemistry, vol. 55, No. 11, 2009, 1958-1966.
García Moreira, et al., "Cell-free DNA as a noninvasive acute rejection marker in renal transplantation", Clin Chem., Nov. 2009;55(11): doi:10.1373/clinchem.2009.129072. Epub Sep. 3, 2009, 2009, 1958-1966.
Gautier, E. et al., "Fetal RhD genotyping by maternal serum analysis: A two-year experience", American Journal of Obstetrics and Gynecology, vol. 192, 2005, 666-669.
Geifman-Holtzman, et al., "Prenatal Diagnosis: Update on Invasive Versus Noninvasive Fetal Diagnostic Testing from Maternal Blood", Expert Review of Molecular Diagnostics, vol. 8, No. 6, Nov. 1, 2008, 727-751.
Ghanta, Sujana et al., "Non-Invasive Prenatal Detection of Trisomy 21 Using Tandem Single Nucleotide Polymorphisms", PLoS One, 5 (10), 2010, 10 pgs.
Gnirke, A. et al., "Solution hybrid selection with ultra-long oligonucleotides for massively parallel targeted sequencing", Nature Biotechnology, vol. 27, No. 2, Feb. 2009, 182-189.
Go, A. T. et al., "Non-invasive aneuploidy detection using free fetal DNA and RNA in maternal plasma: recent progress and future possibilities", Human Reproduction Update, vol. 17, No. 3, 2011, 372-382.
Goessl, C. et al., "DNA Alterations in Body Fluids as Molecular Tumor Markers for Urological Malignancies", European Urology, vol. 41, 2002, 668-676.
Gormally, et al., "Amount of DNA in plasma and cancer risk: a prospective study", Int J Cancer, Sep. 20, 2004;111(5): doi: 10.1002/ijc.20327, 2004, 746-749.
Gwee, Pai-Chung et al., "Simultaneous Genotyping of Seven Single-nucleotide Polymorphisms in the Mdr1 Gene by Single-tube Multiplex Mini sequencing", Pai-Chung Gwee et al., "Simultaneous Genotyping of Seven Single-nucleotide Polymorphisms in the Mdr1 Gene by Single-tube Multiplex Mini sequencing", Clinical chemistry, Apr. 2003, vol. 49, Issue. 3, pp. 672-676., Apr. 1, 2003, 672-676.
Hall, M., "Panorama Non-Invasive Prenatal Screening for Microdeletion Syndromes", Apr. 1, 2014 (Apr. 1, 2014), XP055157224,

(56) References Cited

OTHER PUBLICATIONS

Retrieved from the Internet: URL:http://www.panoramatest.com/sites/default/files/files/PanoramaMicrodeletionsWhite Paper-2.pdf [retrieved on Dec. 8, 2014].
Handley, D. et al., "Noninvasive prenatal chromosomal aneuploidy detection using plasma cell-free nucleic acid", Expert Rev Obstet. Gynecol, vol. 5, No. 5, 2010, 581-590.
Hardenbol, P., "Multiplexed Genotyping with Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Hayden, et al., "Multiplex-Ready PCR: A new method for multiplexed SSR and SNP genotyping", BMC Genomics 2008, 9(80), 1-12.
Hochberg, et al., "A Novel Rapid Single Nucleotide Polymorphism (SNP)-Based Method for Assessment of Hematopoietic Chimerism After Allogeneic Stem Cell Transplantation", Blood, vol. 101, No. 1, Jan. 1, 2003, 363-369.
Hoffmann, Steven et al., "Donor Genomics Influence Graft Events: The Effect of Donor Polymorphisms on Acute Rejection and Chronic Allograft Nephropathy", Kidney International, vol. 66, No. 4, Oct. 1, 2004, 1686-1693.
Hosono, S. et al., "Unbiased Whole-Genome Amplification Directly from Clinical Samples", Genome Research, vol. 13, 2003, 954-964.
Hu, Dong Gui et al., "Aneuploidy Detection in Single Cells Using DNA Array-Based Comparative Genomic Hybridization", Molecular Human Reproduction, 10(4), 2004, 283-289.
Huang, D. J. et al., "Use of an Automated Method Improves the Yield and Quality of Cell-Free Fetal DNA Extracted from Maternal Plasma", Clinical Chemistry, vol. 51, No. 12, 2005, 2419-2420.
Huang, J. et al., "Whole genome DNA copy number changes identified by high density oligonucleotide arrays", Human Genomics, vol. 1, No. 4, May 2004, 287-299.
Hubacek, et al., "Detection of Donor DNA After Heart Transplantation: How Far Could It Be Affected by Blood Transfusion and Donor Chimerism?", Transplantation Proceedings, vol. 39, Jun. 1, 2007, 1593-1595.
Hung, E.C.W. et al., "Detection of circulating fetal nucleic acids: a review of methods and applications", J. Clin. Pathol., vol. 62, 2009, 308-313.
Ingman, et al., "SNP Frequency Estimation Using Massively Parallel Sequencing of Pooled DNA", European Journal of Human Genetics, vol. 17, No. 3, Oct. 15, 2008, 383-386.
Interewicz, B. et al., "DNA Released from Ischemic and Rejecting Organs as an Indicator of Graft Cellular Damage", Annals of Transplantation, vol. 9, No. 2, May 1, 2004, 42-45.
Ishii, et al., "Optimization of Annealing Temperature to Reduce Bias Caused by a Primer Mismatch in Multitemplate PCR", Applied and Environmental Microbiology, Aug. 2001, p. 3753-3755.
Jarvie, T., "Next generation sequencing technologies", Drug Discovery Today: Technologies, vol. 2, No. 3, 2005, 255-260.
Jen, J. et al., "An Overview on the Isolation and Analysis of Circulating Tumor DNA in Plasma and Serum", Annals New York Academy of Sciences, 2000, 8-12.
Jung, Klaus et al., "Increased cell-free DNA in plasma of patients with metastatic spread in prostate cancer", Cancer Letters, 2004, 173-180.
Kamat, A. A. et al., "Quantification of total plasma cell-free DNA in ovarian cancer using real-time PCR", Ann N Y Acad Sci., vol. 1075, Sep. 2006, 230-234.
Kaper, Fiona et al., "Abstract 1164: Parallel preparation of targeted resequencing libraries from 480 genomic regions using multiplex PCR on the Access Array system", American Association for Cancer Research, 2010, 1-2.
Kaper, Fiona et al., "Parallel Preparation of Targeted Resequencing Libraries from 480 Genomic Regions Using Multiplex PCR on the Access Array System", Fluidigm Poster, 2011, 1.
Kinde, I. et al., "Detection and quantification of rare mutations with massively parallel sequencing", PNAS, vol. 108, No. 23, Jun. 7, 2011, 9530-9535.
Kircher, Martin et al., "Improved Base Calling for the Illumina Genome Analyzer Using Machine Learning Strategies", Genome Biology, vol. 10, Issue 8, Article No. R83, Aug. 14, 2009, 83.2-83.9.
Kittler, R. et al., "A Whole Genome Amplification Method to Generate Long Fragments from Low Quantities of Genomic DNA", Analytical Biochemistry, vol. 300, 2002, 237-244.
Kivioja, T. et al., "Counting absolute number of molecules using unique molecular identifiers", Nature Proceedings, Apr. 14, 2011, 18 pgs.
Koboldt, et al., "VarScan: Variant Detection in Massively Parallel Sequencing of Individual and Pooled Samples", Bioinformatics, vol. 25, No. 17, Jun. 19, 2009, 2283-2285.
Koelman, et al., "Donor-derived Soluble HLA Plasma Levels Can Not Be Used to Monitor Graft Rejection in Heart Transplant Recipients", Transplant Immunology, vol. 8, No. 1, Mar. 1, 2000, 57-64.
Kohler, C. et al., "Levels of plasma circulating cell free nuclear and mitochondrial DNA as potential biomarkers for breast tumors", Molecular Cancer, vol. 8, No. 105, Nov. 17, 2009, 9 pages.
Koide, K. et al., "Fragmentation of cell-free fetal DNA in plasma and urine of pregnant women", Prenatal Diagnosis, vol. 25, 2005, 604-607.
Koldehoff, Michael et al., "Quantitative analysis of chimerism after allogeneic stem cell transplantation by real-time polymerase chain reaction with single nucleotide polymorphisms, standard tandem repeats, and Y-chromosome-specific sequences", American Journal of Hematology, vol. 81, No. 10, Jul. 12, 2006, 735-746.
Korn, et al., "Integrated Genotype Calling and Association Analysis Of SNPS, Common Copy Number Polymorphisms and Rare CNVS", Nature Genetics, vol. 40, No. 10, Oct. 1, 2008, 1253-1260.
Krishnakumar, S. et al., "A comprehensive assay for targeted multiplex amplification of human DNA sequences", PNAS, vol. 105, No. 27, Jul. 8, 2008, 9296-9301.
Krjutskov, K. et al., "Development of a single tube 640-plex genotyping method for detection of nucleic acid variations on microarrays", Nucleic Acids Research, vol. 36, No. 12, May 23, 2008, 7 pages.
Lavebratt, et al., "Single Nucleotide Polymorphism (SNP) Allele Frequency Estimation in DNA Pools Using Pyrosequencing", Nature Protocols, vol. 1, No. 6, Jan. 11, 2007, 2573-2582.
Lavebratt, Catharina et al., "Pyrosequencing-based SNP Allele Frequency Estimation in DNA Pools", Human Mutation, vol. 23, Issue 1, Dec. 19, 2003, 92-97.
Leamon, John H. et al., "A massively parallel PicoTiterPlate based platform for discrete picoliter-scale polymerase chain reactions", Electrophoresis, vol. 24, No. 21, Nov. 1, 2003, 3769-3777.
Leary, R. J. et al., "Development of Personalized Tumor Biomarkers Using Massively Parallel Sequencing", Science Translational Medicine, vol. 2, No. 20, Feb. 24, 2010, 1-8.
Lecomte, et al., "Detection of free-circulating tumor-associated DNA in plasma of colorectal cancer patients and its association with prognosis", Int J Cancer, Aug. 10, 2002;100(5): doi: 10.1002/ijc.10526., 2002, 542-548.
Lee, T. et al., "Down syndrome and cell-free fetal DNA in archived maternal serum", AmJ Obstet Gynecol, vol. 187, No. 5, 1217-1221, Nov. 2002.
Lee, T.H. et al., "Quantitation of genomic DNA in plasma and serum samples: higher concentrations of genomic DNA found in serum than in plasma", Transfusion, vol. 41, Feb. 2001, 276-282.
Lefebure, et al., "Prognostic value of circulating mutant DNA in unresectable metastatic colorectal cancer", Ann Surg., Feb. 2010;251(2): doi: 10.1097/SLA.0b013e3181c35c87, 2010, 275-280.
Li, et al., "Detection of SNPs in the Plasma of Pregnant Women and in the Urine of Kidney Transplant Recipients by Mass Spectrometry", Annals of the New York Academy of Sciences, vol. 1075, Sep. 5, 2006, 144-147.

(56) References Cited

OTHER PUBLICATIONS

Li, R. et al., "SNP detection for massively parallel whole-genome resequencing", Genome Research, vol. 19, 2009, 1124-1132.
Li, Y. et al., "Detection of Paternally Inherited Fetal Point Mutations for b-Thalassemia Using Size-Fractionated Cell-Free DNA in Maternal Plasma", JAMA, vol. 293, No. 7, Apr. 13, 2005, 843-849.
Li, Y. et al., "Non-Invasive Prenatal Diagnosis Using Cell-Free Fetal DNA in Maternal Plasma from PGD Pregnancies", Reproductive Biomedicine Online, 19 (5), 2009, 714-720.
Li, Ying et al., "Biochemical and Clinical Diagnostic Aspects of Circulating Nucleic Acids", Dissertation, 2005, 103 Pages.
Li, Ying et al., "Detection of Donor-specific DNA Polymorphisms in the Urine of Renal Transplant Recipients", Clinical Chemistry, vol. 49, No. 4, Apr. 1, 2003, 655-658.
Li, Ying et al., "Size Separation of Circulatory DNA in Maternal Plasma Permits Ready Detection of Fetal DNA Polymorphisms", Clinical Chemistry, 50, 6, 2004, 1002-1011.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.
Lichtenstein, A. V. et al., "Circulating Nucleic Acids and Apoptosis", Annals New York Academy of Sciences, vol. 945, Aug. 1, 2001, 239-249.
Liew, Michael et al., "Genotyping of Single-Nucleotide Polymorphisms", Clinical Chemistry, 50(7), 2004, 1156-1164.
Liljedahl, Ulrika et al., "Detecting Imbalanced Expression of SNP Alleles by Mini sequencing on Microarrays", BMC Biotechnology, vol. 4, Article No. 24, Oct. 22, 2004, 1-10.
Lindroos, Katatina et al., "Genotyping SNPs by Mini sequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Aug. 7, 2007, 13116-13121.
Lo, et al., "Free Fetal DNA in Maternal Circulation", JAMA, 292(23), (Letters to the Editor), 2004, 2835-2836.
Lo, et al., "Next-generation Sequencing of Plasma/Serum DNA: An Emerging Research and Molecular Diagnostic Tool", Clinical Chemistry, vol. 55, No. 4, Apr. 1, 2009, 607-608.
Lo, et al., "Transplantation monitoring by plasma DNA sequencing", Clin Chem., Jul. 2011;57(7): doi: 10.1373/clinchem.2011.166686. PubMed PMID: 21566070., 2011, 941-942.
Lo, Y M. et al., "Circulating Nucleic Acids in Plasma and Serum: An Overview", Annals of the New York Academy of Sciences, vol. 945, Sep. 1, 2001, 1-7.
Lo, Y., "Noninvasive prenatal detection of fetal chromosomal aneuploidies by maternal plasma nucleic acid analysis: a review of the current state of the art", BJOG An international Journal of Obstetrics and Gynaecology, vol. 116, 2009, 152-157.
Lo, Y.M. Dennis, "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Y.M. Dennis et al., "Maternal Plasma DNA Sequencing Reveals the Genome-Wide Genetic and Mutational Profile of the Fetus", Science Translational Medicine, 2 (61), 2010, 13.
Lo, Y.M. Dennis et al., "Plasma placental RNA allelic ratio permits noninvasive prenatal chromosomal aneuploidy detection", Nature Medicine, 13 (2), 2007, 218-223.
Lo, Y.M.D., "Fetal DNA in Maternal Plasma: Biology and Diagnostic Applications", Clinical Chemistry, vol. 46, No. 12, 2000, 1903-1906.
Lo, Y.M.D. et al., "Prenatal diagnosis: progress through plasma nucleic acids", Nature Reviews, vol. 8, 2007, 71-77.
Lovmar, L. et al., "Quantitative evaluation by Mini sequencing and microarrays reveals accurate multiplexed SNP genotyping of whole genome amplified DN", Nucleic Acids Research, vol. 31, No. 21, 2003, 9 pgs.
Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.
Lui, Yanni Y. et al., "Circulating DNA in Plasma and Serum: Biology, Preanalytical Issues and Diagnostic Applications", Clinical Chemistry and Laboratory Medicine, vol. 40, No. 10, Oct. 29, 2002, 962-968.
Lui, Yanni Y. et al., "Origin of Plasma Cell-Free DNA after Solid Organ Transplantation", Clinical Chemistry, vol. 49, No. 3, Mar. 1, 2003, 495-496.
Lun, Fiona M. et al., "Microfluidics Digital PCR Reveals A Higher Than Expected Fraction Of Fetal DNA In Maternal Plasma", Clinical Chemistry, vol. 54, No. 10, Aug. 14, 2008, 1664-1672.
Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.
Mamanova, L. et al., "Target-enrichment strategies for next-generation sequencing", Nat Methods, vol. 7, No. 2, 2010, 111-118.
Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.
Maron, Jill L. et al., "Cell-free Fetal DNA Plasma Extraction and Real- time Polymerase Chain Reaction Quantification", Methods in Molecular Medicine, vol. 132, Aug. 1, 2007, 51-63.
Matsuzaki, H. et al., "Genotyping over 100,000 SNPs on a pair of oligonucleotide arrays", Nature Methods, vol. 1, No. 2, Nov. 2004, 109-111.
Mcbride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.
Mccloskey, M. L. et al., "Encoding PCR Products with Batch-stamps and Barcodes", Biochem Genet., vol. 45, Oct. 23, 2007, 761-767.
Mertes, F. et al., "Targeted enrichment of genomic DNA regions for next-generation sequencing", Briefings in Functional Genomics, vol. 10, No. 6, Nov. 26, 2011, 374-386.
Meuzelaar, Linda S. et al., "Megaplex PCR: A Strategy for Multiplex Amplification", Nature Methods, vol. 4, 2007, pp. 835-837.
Milani, et al., "Genotyping Single Nucleotide Polymorphisms by Multiplex Mini sequencing Using Tag-arrays", DNA Microarrays for Biomedical Research, vol. 529, Jan. 16, 2009, 215-229.
Miner, B. E. et al., "Molecular barcodes detect redundancy and contamination in hairpin-bisulfite PCR", Nucleic Acids Research, vol. 32, No. 17, 30 Sep. 2004, 1-4.
Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071- 6079.
No Author Listed, "Abstracts for CNAPS III Circulating Nucleic Acids in Plasma and Serum and Serum Proteomics", Clinical Chemistry, vol. 49, No. 11, 2003, 33 pages.
No Author Listed, "Abstracts for CNAPS IV Circulating Nucleic Acids in Plasma/Serum", Fourth International Conference on Circulating Nucleic Acids in Plasma/Serum (CNAPS-IV), 2005, 40 pages.
Owczarzy, Richard et al., "Melting Temperatures of Nucleic Acids: Discrepancies in Analysis", Biophysical Chemistry, vol. 117, 2005, pp. 207-215.
Palomaki, G. E. et al., "DNA sequencing of maternal plasma to detect Down syndrome: An international clinical validation study", Genetics in Medicine, vol. 13, No. 1, Nov. 2011, 913-920.
Palomaki, Glenn E. et al., "DNA Sequencing of Maternal Plasma to Detect Down Syndrome: An International Clinical Validation Study", Genetics in Medicine (pre-print version), 13, 2011, 8 pgs.
Panjkovich, Alejandro et al., "Comparison of Different Melting Temperature Calculation Methods for Short DNA Sequences", Bioinformatics, vol. 21, 2005, pp. 711-722.
Papadopoulou, E. et al., "Cell-Free DNA and RNA in Plasma as a New Molecular Marker for Prostate Cancer", Oncology Research, vol. 14, 2004, 439-445.

(56) References Cited

OTHER PUBLICATIONS

Papageorgiou, Elisavet A. et al., "Fetal-Specific DNA Methylation Ratio Permits Noninvasive Prenatal Diagnosis of Trisomy 21", Nature Medicine (advance online publication), 17, 2011, 5 pgs.
Parameswaran, P. et al., "A pyrosequencing-tailored nucleotide barcode design unveils opportunities for large-scale sample multiplexing", Nucleic Acids Research, vol. 35, No. 19, Oct. 11, 2007, 9 pages.
Pathak, A. et al., "Circulating Cell-Free DNA in Plasma/Serum of Lung Cancer Patients as a Potential Screening and Prognostic Tool", Clinical Chemistry, 52, 2006, 1833-1842.
Peters, David P. et al., "Noninvasive Prenatal Diagnosis of a Fetal Microdeletion Syndrome", New England Journal of Medicine, 365(19), 2011, 1847-1848.
Pinard, et al., "Assessment of Whole Genome Amplification-induced Bias Through High-throughput, Massively Parallel Whole Genome Sequencing", BMC Genomics, vol. 7:216, Aug. 23, 2006, 1-21.
Podder, Mohua et al., "Robust SN P genotyping by multiplex PCR and arrayed primer", BMC Medical Genomics, 1(5), 2008, 1-15.
Pont-Kingdon, G. et al., "Rapid Detection of Aneuploidy (Trisomy 21) by Allele Quantification Combined with Melting Curves Analysis of Single-Nucleotide Polymorphism Loci", Clinical Chemistry, vol. 49, No. 7, 2003, 1087-1094.
Pourmand, et al., "Multiplex Pyrosequencing", Nucleic Acid Research, vol. 30, No. 7, Apr. 1, 2002, 1-5.
Prabhu, et al., "Overlapping Pools for High-throughput Targeted Resequencing", Genome Research, vol. 19, May 15, 2009, 1254-1261.
Puszyk, William, "Epigenetics of cell-free plasma DNA for non-invasive prenatal diagnosis of fetal aneuploidies", Diss. University of Warwick, 2008, 199 pages.
Puszyk, William M. et al., "Noninvasive Prenatal Diagnosis of Aneuploidy Using Cell-free Nucleic Acids In Maternal Blood: Promises And Unanswered Questions", Prenatal Diagnosis, vol. 28, No. 1, Nov. 16, 2007, 1-6.
Roedder, et al., "Biomarkers in solid organ transplantation: establishing personalized transplantation medicine", Genome Med., Jun. 8, 2011;3(6):37, 2011, 12 pages.
Saito, H. et al., "Prenatal DNA diagnosis of a single-gene disorder from maternal plasma", The Lancet, vol. 356, Sep. 30, 2000, 1170.
Samura, O. et al., "Diagnosis of Trisomy 21 in Fetal Nucleated Erythrocytes from Maternal Blood by Use of Short Tandem Repeat Sequences", Clinical Chemistry, vol. 47, No. 9, 2001, 1622-1626.
Schoske, R et al., "Multiplex PCR Design Strategy used for the Simultaneous Amplification of 10 Y Chromosome Short Tandem Repeat (STR) Loci", Analytical and Bioanalytical Chemistry, vol. 375, 2003, 333-343.
Schwarzenbach, H. et al., "Cell~free nucleic acids as biomarkers in cancer patients", Nature Reviews: Cancer, vol. 11, Jun. 2011, 426-437.
Schwarzenbach, H. et al., "Detection and Characterization of Circulating Microsatellite-DNA in Blood of Patients with Breast Cancer", Ann. N.Y. Acad. Sci., vol. 1022, 2004, 25-32.
Schwarzenbach, H. et al., "Evaluation of cell-free tumour DNA and RNA in patients with breast cancer and benign breast disease", Molecular BioSystems, vol. 7, 2011, 2848-2854.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Seppo, A. et al., "Detection of circulating fetal cells utilizing automated microscopy: potential for noninvasive prenatal diagnosis of chromosomal aneuploidies", Prenatal Diagnosis, vol. 28, Jul. 22, 2008, 815-821.
Shen, Zhiyong, "MPprimer: a program for reliable multiplex PCR primer design", BMC Bioinformatics 2010, 11:143, 1-7.
Shendure, J. et al., "Next-generation DNA sequencing", Nature Biotechnology, vol. 26, No. 10, Oct. 2008, 1135-1145.
Smith, et al., "Rapid Whole-genome Mutational Profiling using Next-generation Sequencing Technologies", Genome Research, vol. 18, Sep. 4, 2008, 1638-1642.
Smith, James F. et al., "Cell-free Fetal DNA in Maternal Plasma", Neo Reviews, vol. 9, No. 8, Aug. 1, 2008, e332-e337.
Snyder, et al., "Universal noninvasive detection of solid organ transplant rejection", Proc Natl Acad Sci U S A, Apr. 12, 2011;108(15); doi: 10.1073/pnas.1013924108. Epub Mar. 28, 2011. PubMed PMID: 21444804; PubMed Central PMCID: PMC3076856., 2011, 6229-6234.
Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Sub chromosome Abnormalities via Deep Sequencing of Maternal Plasma", The American Journal of Human Genetics 92, 167-176, Feb. 7, 2013.
Stiller, et al., "Direct Multiplex Sequencing (DMPS)—A Novel Method for Targeted High-throughput Sequencing of Ancient And Highly Degraded DNA", Genome Research, vol. 19, No. 10, Jul. 27, 2009, 1843-1848.
Swarup, V. et al., "Circulating (cell-free) nucleic acids—A promising, non-invasive tool for early detection of several human diseases", FEBS Letters, vol. 581, 2007, 795-799.
Swinkels, D. W. et al., "Effects of Blood-Processing Protocols on Cell-free DNA Quantification in Plasma", Clinical Chemistry, vol. 49, No. 3, 2003, 525-526.
Taback, B. et al., "Quantification of Circulating DNA in the Plasma and Serum of Cancer Patients", Ann. N.Y. Acad. Sci, vol. 1022, 2004, 17-24.
Tamkovich, et al., "Circulating nucleic acids in blood of healthy male and female donors", Clin Chem., Jul. 2005; 51(7): PubMed PMID: 15976134., 2005, 1317-1319.
Ten Bosch, J., "Keeping Up with the Next Generation Massively Parallel Sequencing in Clinical Diagnostics", Journal of Molecular Diagnostics, vol. 10, No. 6, 2008, 484-492.
Tewhey, R. et al., "Microdroplet-based PCR enrichment for large-scale targeted sequencing", Nature Biotechnology, vol. 27, No. 11, Nov. 2009, 1025-1031.
Tewhey, R. et al., "The importance of phase information for human genomics", Nature Reviews Genetics, vol. 12, No. 3, Mar. 1, 2011, 215-223.
Tong, et al., "Diagnostic developments involving cell-free (circulating) nucleic acids", Clin Chim Acta., Jan. 2006;363(1-2): Epub Aug. 26, 2005. Review. PubMed PMID: 16126188, 2005, 187-196.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Toshikazu, et al., "Estimation of Haplotype Frequencies, Linkage-disequilibrium Measures, And Combination of Haplotype Copies in Each Pool By Use Of Pooled DNA Data", American Journal of Human Genetics, vol. 72, Jan. 17, 2003, 384-398.
Tounta, G et al., "Non-invasive prenatal diagnosis using cell-free fetal nucleic acids in maternal plasma: Progress overview beyond predictive and personalized diagnosis", EPMA Journal, vol. 2, Issue 2, 2011, 163-171.
Tounta, G. et al., "A Multiplex PCR for Non-invasive Fetal RHD Genotyping Using Cell-free Fetal DNA", in vivo, vol. 25, 2011, 411-418.
Tsang, Jason C. et al., "Circulating Nucleic Acids in Plasma/Serum", Pathology, vol. 39, No. 2, Apr. 1, 2007, 197-207.
Tufan, N L. et al., "Analysis of Cell-Free Fetal DNA from Maternal Plasma and Serum Using a Conventional Multiplex PCR: Factors Influencing Success", The Turkish Journal of Medical Sciences, vol. 35, 2005, 85-92.
Tungwiwat, et al., "Non-invasive fetal sex determination using a conventional nested PCR analysis of fetal DNA in maternal plasma", Clinica Chimica Acta, vol. 334, No. 1-2, 2003, 173-177.

(56) References Cited

OTHER PUBLICATIONS

Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.
Tzimagiorgis, G. et al., "Recovering circulating extracellular or cell-free RNA from bodily fluids", Cancer Epidemiology, vol. 35, 2011, 580- 589.
Urbanova, M. et al., "Circulating Nucleic Acids as a New Diagnostic Tool", Cellular & Molecular Biology Letters, vol. 15, 2010, 242-259.
Vallone, Peter M. et al., "Demonstration of Rapid Multiplex PCR Amplification Involving 16 Genetic Loci", Forensic Science International: Genetics, vol. 3, 2008, pp. 42-45.
Varley, Katherine Elena et al., "Nested Patch PCR Enables Highly Multiplexed Mutation Discovery in Candidate Genes", Genome Res., 18(11), 2008, 1844-1850.
Veseloskva, "The use of cell-free nucleic acids in maternal plasma for non-invasive prenatal diagnosis of monogenic diseases, placental insufficiency-related complications and Down syndrome", Thesis from Charles University in Prague, 2011, 2011, 104 pages.
Wagner, F. F. et al., "RHD gene deletion occurred in the Rhesus box", Blood, vol. 95, No. 12, 2000, 3662-3668.
Wagner, Jasenka et al., "Non-Invasive Prenatal Paternity Testing from Maternal Blood", Int. J. Legal Med., 123, 2009, 75-79.
Wang, Hui-Yun et al., "A genotyping system capable of simultaneously analyzing >1000 single nucleotide polymorphisms in a haploid genome", Genome Res., 15, 2005, 276-283.
Wang, W.-P. et al., "Multiplex single nucleotide polymorphism genotyping by adapter ligation-mediated allele-specific amplification", Analytical Biochemistry, vol. 355, May 5, 2006, 240-248.
Wang, Yuker et al., "Allele quantification using molecular inversion probes (MIP)", Nucleic Acids Research, vol. 33, No. 21, Nov. 28, 2005, 14 pgs.
Wapner, R. et al., "First-Trimester Screening for Trisomies 21 and 18", The New England Journal of Medicine, vol. 349, No. 15, Oct. 9, 2003, 1405-1413.
Wasson, Jon et al., "Assessing Allele Frequencies of Single Nucleotide Polymorphisms in DNA Pools by Pyrosequencing Technology", Biotechniques, vol. 32, No. 5, May 1, 2002, 1144-1152.
Wei, C. et al., "Detection and Quantification by Homogeneous PCR of Cell-free Fetal DNA in Maternal Plasma", Clinical Chemistry, vol. 47, No. 2, 2001, 336-338.
Wilkening, Stefan et al., "Determination of Allele Frequency in Pooled DNA: Comparison of Three PCR-based Methods", Bio Techniques, vol. 39, No. 6, May 30, 2005, 853-857.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Wright, C. et al., "The use of cell-free fetal nucleic acids in maternal blood for non-invasive prenatal diagnosis", Human Reproduction Update, vol. 15, No. 1, 2009, 139-151.
Wright, C. F. et al., "Cell-free fetal DNA and RNA in maternal blood: implications for safer antenatal testing", BMJ, vol. 39, Jul. 18, 2009, 161-165.
Wright, Caroline et al., "Cell-free Fetal Nucleic Acids for Noninvasive Prenatal Diagnosis", PHG Foundation, Jan. 1, 2009, 1-64.
Wu, T.L. et al., "Cell-free DNA: measurement in various carcinomas and establishment of normal reference range", Clinica Chimica Acta, vol. 321, 2002, 77-87.
Xia, et al., "Simultaneous Quantitative Assessment of Circulating Cell- free Mitochondrial And Nuclear DNA By Multiplex Real-time PCR", Genetics and Molecular Biology, vol. 32, No. 1, Mar. 1, 2009, 20-24.
Xian, et al., "Advances on Circulating Fetal DNA In Maternal Plasma", Chinese Medical Journal, vol. 120, No. 14, Jul. 2, 2007, 1256-1259.
Xie, et al., "CNV-SEQ, A New Method to Detect Copy Number Variation Using High throughput Sequencing", BMC Bioinformatics, vol. 10:80, Mar. 6, 2009, 1-9.
Xue, et al., "Optimizing the Yield and Utility Of Circulating Cell-free DNA From Plasma And Serum", Clinica Chimica Acta, vol. 404, No. 2, Jun. 27, 2009, 100-104.
Zachariah, R. et al., "Circulating cell-free DNA as a potential biomarker for minimal and mild endometriosis", Reproductive Biomedicine Online, vol. 18, No. 3, Jan. 27, 2009, 4007-411.
Zhang, et al., "Diagnosis of Acute Rejection by Analysis of Urinary DNA of Donor Origin in Renal Transplant Recipients", Transplantation Proceedings, vol. 33, No. 1-2, Feb. 2001, 380-381.
Zhang, et al., "Use of PCR And PCR-SSP For Detection Of Urinary Donor-Origin DNA In Renal Transplant Recipients With Acute Rejection", Chinese Medical Journal, vol. 116, No. 2, Feb. 2003, 191-194.
Zhao, Xiaojun et al., "An Integrated View of Copy Number and Allelic Alterations in the Cancer Genome Using Single Nucleotide Polymorphism Arrays", Cancer Research, 64, 2004, 3060-3071.
Zheng, S. et al., "Whole Genome Amplification Increases the Efficiency and Validity of Buccal Cell Genotyping in Pediatric Populations1", Cancer Epidemiology, Biomarkers & Prevention, vol. 10, Jun. 2001, 697-700.
Zhong, X Y. et al., "Detection of Fetal Rhesus D And Sex Using Fetal DNA from Maternal Plasma by Multiplex Polymerase Chain Reaction", British Journal of Obstetrics and Gynecology, vol. 107, Jun. 2000, 766-769.
Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.
Zhong, Xiao Y. et al., "Cell-free DNA In Urine: A Marker for Kidney Graft Rejection, but Not for Prenatal Diagnosis?", Annals of the New York Academy of Sciences, vol. 945, Sep. 1, 2001, 250-257.
Zimmermann, B. et al., "Digital PCR: a powerful new tool for noninvasive prenatal diagnosis?", Prenatal Diagnosis, vol. 28, Nov. 10, 2008, 1087-1093.
Zimmermann, B. et al., "Novel Real-Time Quantitative PCR Test for Trisomy 21", Clinical Chemistry, vol. 48, No. 2, 2002, 362-363.
Zimmermann, B. et al., "Optimized Real-Time Quantitative PCR Measurement of Male Fetal DNA in Maternal Plasma", Clinical Chemistry, vol. 51, No. 9, 2005, 1598-1604.
Zimmermann, B. et al., "Real-Time Quantitative Polymerase Chain Reaction Measurement of Male Fetal DNA in Maternal Plasma", Methods in Molecular Medicine, vol. 132, 2007, 43-49.
Zimmermann, B. et al., "Use of Real-Time Polymerase Chain Reaction for the Detection of Fetal Aneuploidies", Methods in Molecular Biology, vol. 336, Feb. 2006, 83-100.
Cummings, N., et al., "Combining Target Enrichment with Barcode Multiplexing for High-throughput SNP Discovery," BMC Genomics 2010, vol. 11(641), pp. 1-8.
Maughan, P., et al., "SNP Discovery via Genomic Education, Barcoding, and Pyrosequencing in Amaranth," The Plant Genome, 2009, vol. 2(3), pp. 1.
Ashoor G., et al., "Chromosome-selective Sequencing of Maternal Plasma Cell-free DNA for First-trimester Detection of Trisomy 21 and Trisomy 18," American Journal of Obstetrics & Gynecology, Apr. 2012, vol. 206, pp. 322.e1-322.e5.
Ashoor G., et al., "Fetal Fraction in Maternal Plasma Cell-Free DNA at 11-13 Weeks' Gestation: Effect of Maternal and Fetal Factors," Fetal Diagnosis and Therapy, 2012, pp. 1-7, Published Online May 4, 2012.
Ashoor G., et al., "Fetal Fraction in Maternal Plasma Cell-free DNA at 11-13 Weeks' Gestation: Relation to Maternal and Fetal Characteristics," Ultrasound in Obstetrics and Gynecology, 2013, vol. 41, pp. 26-32.
Beck J., et al., "Digital Droplet PCR for Rapid Quantification of Donor DNA in the Circulation of Transplant Recipients as a Potential Universal Biomarker of Graft Injury," Clinical Chemistry, Dec. 2013, vol. 59, No. 12, pp. 1732-1741, DOI: 10.1373/clinchem.2013.210328, EPublished Sep. 23, 2013.

(56) References Cited

OTHER PUBLICATIONS

Benesova L., et al., "Mutation-based Detection and Monitoring of Cell-free Tumor DNA in Peripheral Blood of Cancer Patients," Analytical Biochemistry, 2013, vol. 433, pp. 227-234.

Benn P., et al., "Non-Invasive Prenatal Diagnosis for Down Syndrome: The Paradigm Will Shift, but Slowly," Ultrasound in Obstetrics & Gynecology, 2012, vol. 39, pp. 127-130.

Benn P., et al., "Non-Invasive Prenatal Testing for Aneuploidy: Current Status and Future Prospects," Ultrasound in Obstetrics & Gynecology, 2013, vol. 42, pp. 15-33.

Bianchi D.W., et al., "Genome-Wide Fetal Aneuploidy Detection by Maternal Plasma DNA Sequencing," Obstetrics & Gynecology, May 2012, vol. 119, No. 5. pp. 890-901.

Bianchi D.W., et al., "Noninvasive Prenatal Testing and Incidental Detection of Occult Maternal Malignancies," JAMA the Journal of the American Medical Association, Jul. 14, 2015, vol. 314, No. 2, pp. 162-169.

Blomquist T.M., et al., "Targeted RNA-Sequencing with Competitive Multiplex-PCR Amplicon Libraries," Plos One, Nov. 13, 2013, vol. 8, Issue 11(e79120), 14 Pages.

Canick J.A., et al., "The Impact of Maternal Plasma DNA Fetal Fraction on Next Generation Sequencing Tests for Common Fetal Aneuploidies," Prenatal Diagnosis, 2013, vol. 33, pp. 667-674.

Chan K.C.A., "Scanning for Cancer Genomic Changes in Plasma: Toward an Era of Personalized Blood-Based Tumor Markers," Clinical Chemistry, 2013, vol. 59, No. 11, pp. 1553-1555.

Chan K.C.A., et al., "Cancer Genome Scanning in Plasma: Detection of Tumor-Associated Copy Number Aberrations, Single-Nucleotide Variants, and Tumoral Heterogeneity by Massively Parallel Sequencing," Clinical Chemistry, 2013, vol. 59, No. 1, pp. 211-224.

Chen J.J., et al., "Non-Invasive Prenatal Diagnosis using Fetal DNA in Maternal Plasma: A Preliminary Study for Identification of Paternally-Inherited Alleles using Single Nucleotide Polymorphisms," BMJ Open, Jul. 22, 2015, vol. 5, No. 7 (e007648), 8 Pages, DOI: 10.1136/bmjopen-2015-007648.

Chetty S., et al., "Uptake of Noninvasive Prenatal Testing (NIPT) in Women Following Positive Aneuploidy Screening," Prenatal Diagnosis, 2013, vol. 33, pp. 542-546.

Chitty L.S., et al., "Noninvasive Prenatal Screening for Genetic Diseases Using Massively Parallel Sequencing of Maternal Plasma DNA," Cold Spring Harbor Perspectives in Medicine, 2015, vol. 5, No. 9(a023085), 20 Pages.

Courad S., et al., "Supplementary Data for Noninvasive Diagnosis of Actionable Mutations by Deep Sequencing of Circulating Free DNA in lung Cancer from Never-Smokers: A Proof-of-Concept Study from BioCAST/IFCT-1002," American Association for Cancer Research, Clinical Cancer Research, Sep. 1, 2014, vol. 20, No. 17, 13 Pages.

Couraud S., et al., "Noninvasive Diagnosis of Actionable Mutations by Deep Sequencing of Circulating Free DNA in lung Cancer from Never-Smokers: A Proof-of-Concept Study from BioCAST / IFCT-1002," Clinical Cancer Research, Sep. 1, 2014, vol. 20, No. 17, pp. 4613-4624, 13 Pages, Jul. 10, 2014.

Dawson S-J., et al., "Analysis of Circulating Tumor DNA to Monitor Metastatic Breast Cancer," The New England Journal of Medicine, Mar. 28, 2013, vol. 368, No. 13, pp. 1199-1209.

De Vlaminck I., et al., "Circulating Cell-Free DNA Enables Noninvasive Diagnosis of Heart Transplant Rejection," Science Translational Medicine, Jun. 18, 2014, vol. 6, No. 241, 26 Pages.

Delgado P.O., et al., "Characterization of Cell-Free Circulating DNA in Plasma in Patients with Prostate Cancer," Tumor Biology, Apr. 2013, vol. 34, No. 2, pp. 983-986, DOI: 10.1007/s13277-012-0634-6, Epub Dec. 27, 2012.

Diaz L.A., Jr., et al., "Liquid Biopsies: Genotyping Circulating Tumor DNA," Journal of Clinical Oncology, Feb. 20, 2014, vol. 32, No. 6, pp. 579-586.

Diehl F., et al., "Detection and Quantification of Mutations in the Plasma of Patients with Colorectal Tumors," Proceedings of the National Academy of Sciences, Nov. 8, 2005, vol. 102, No. 45, pp. 16368-16373.

Fan C.H., et al., "Non-Invasive Prenatal Measurement of the Fetal Genome," Nature, 2012, 26 Pages, DOI:10.1038/nature11251.

Forshew T., et al., "Supplementary Materials for Noninvasive Identification and Monitoring of Cancer Mutations by Targeted Deep Sequencing of Plasma DNA," Science Translational Medicine, May 30, 2012, vol. 4(136ra68), 20 Pages.

Genovese G., et al., "Hematopoiesis and Blood-Cancer Risk Inferred from Blood DNA Sequence," The New England Journal Of Medicine, Dec. 2014, vol. 371(26), pp. 2477-2487.

Gielis E.M., et al., "Cell-Free DNA: An Upcoming Biomarker in Transplantation," American Journal of Transplantation, 2015, vol. 15, pp. 2541-2551, 12 Pages.

Goessl C., "Diagnostic Potential of Circulating Nucleic Acids for Oncology," Expert Review of Molecular Diagnostics, 2003, vol. 3(4), pp. 431-432.

Gu H., et al., "Diagnostic Role of MicroRNA Expression Profile in the Serum of Pregnant Women with Fetuses with Neural Tube Defects," Journal of Neurochemistry, 2012, vol. 122, pp. 641-649.

Heidary M., et al., "The Dynamic Range of Circulating Tumor DNA in Metastatic Breast Cancer," Breast Cancer Research, Aug. 9, 2014, vol. 16, No. 421, 10 Pages.

Hidestrand M., et al., "Highly Sensitive Noninvasive Cardiac Transplant Rejection Monitoring Using Targeted Quantification of Donor-Specific Cell-Free Deoxyribonucleic Acid," Journal of the American College of Cardiology, 2014, vol. 63, No. 12, 1224-1226.

Hodgkinson C.L., et al., "Tumorigenicity and Genetic Profiling of Circulating Tumor Cells in Small-Cell Lung Cancer," Nature Medicine, Aug. 2014, vol. 20, No. 8, pp. 897-905.

Imielinski M., et al., "Mapping the Hallmarks of Lung Adenocarcinoma with Massively Parallel Sequencing," Cell, Sep. 14, 2012, vol. 150, pp. 1107-1120, Published Sep. 13, 2012.

Jamal-Hanjani M., et al., "Tracking Genomic Cancer Evolution for Precision Medicine: The Lung TRACERx Study," PLOS Biology, Jul. 2014, vol. 12, No. 7, pp. 1-7.

Kennedy S.R., et al., "Detecting Ultralow-Frequency Mutations by Duplex Sequencing," Nature Protocols, 2014, vol. 9, No. 11, pp. 2586-2606, 22 Pages.

Khater N., et al., "Pseudorejection and True Rejection after Kidney Transplantation: Classification and Clinical Significance," Urologia Internationalis, 2013, vol. 90, No. 4, pp. 373-380, 2012.

Kinnings S.L., et al., "Factors Affecting Levels of Circulating Cell-Free Fetal DNA in Maternal Plasma and Their Implications for Noninvasive Prenatal Testing," Prenatal Diagnosis, 2015, vol. 35, pp. 816-822.

Kivioja T., et al., "Counting Absolute Numbers of Molecules Using Unique Molecular Identifiers," Nature Methods, Advance Online Publication, Nov. 20, 2011, pp. 1-5 (18 Pages).

Kivioja T., et al., "Counting Absolute Numbers of Molecules using Unique Molecular Identifiers," Nature Methods, Jan. 2012, vol. 9, No. 1, pp. 72-76.

Lanman R.B., et al., "Analytical and Clinical Validation of a Digital Sequencing Panel for Quantitative, Highly Accurate Evaluation of Cell-Free Circulating Tumor DNA," Plos One, Oct. 16, 2015, vol. 10, No. 10, e0140712, pp. 1-27, DOI: 10.1371/journal.pone.0140712.

Leary R.J., et al., "Detection of Chromosomal Alterations in the Circulation of Cancer Patients with Whole-Genome Sequencing," Science Translational Medicine, Nov. 28, 2012, vol. 4, No. 162(162ra154), 14 Pages, DOI: 10.1126/scitranslmed.3004742.

Li C., et al., "Highly Multiplexed Amplicon Preparation for Targeted Re-Sequencing of Sample Limited Specimens Using the Ion AmpliSeq™ Technology and Semiconductor Sequencing," Proceedings of the Annual Meeting of the American Society of Human Genetics, 2012, 1 Pages, [Retrieved on Oct. 30, 2012], Retrieved from URL: http://www.ashg.org/2012meeting/abstracts/fulltext/f120121811.html.

Lo Y.M.D., et al., "Fetal Nucleic Acids in Maternal Blood: The Promises," Clinical Chemistry and Laboratory Medicine, 2012, vol. 50, No. 6, pp. 995-998 (5 Pages).

(56) References Cited

OTHER PUBLICATIONS

Lo Y.M.D., et al., "Non-Invasive Prenatal Diagnosis by Massively Parallel Sequencing of Maternal Plasma DNA," Open Biology, 2012, vol. 2, Article 120086, pp. 1-5.
Mersy E., et al., "Noninvasive Detection of Fetal Trisomy 21: Systematic Review and Report of Quality and Outcomes of Diagnostic Accuracy Studies Performed Between 1997 and 2012," Human Reproduction Update, 2013, vol. 19, No. 4, pp. 318-329.
Murtaza M., et al., "Non-Invasive Analysis of Acquired Resistance to Cancer Therapy by Sequencing of Plasma DNA," Nature, May 2, 2013, vol. 497, 6 Pages, DOI:10.1038/nature12065).
Narayan A., et al., "Ultrasensitive Measurement of Hotspot Mutations in Tumor DNA in Blood using Error-Suppressed Multiplexed Deep Sequencing," Cancer Research, Jul. 15, 2012, vol. 72, No. 14, pp. 3492-3498 (8 Pages).
Newman, A., et al., "An Ultrasensitive Method for Quantitating Circulating Tumor DNA With Broad Patient Coverage," Nature Medicine, May 2014, vol. 20 (5), pp. 1-166.
Nguyen-Dumont T., et al., "A High-Plex PCR Approach for Massively Parallel Sequencing," BioTechniques, Aug. 2013, vol. 55, No. 2, pp. 69-74 (5 Pages).
Nicolaides K.H., et al., "Noninvasive Prenatal Testing for Fetal Trisomies in a Routinely Screened First-Trimester Population," American Journal of Obstetrics and Gynecology, (Article in Press), 2012, vol. 207, pp. 1.e1-1.e6.
Nicolaides K.H., et al., "Prenatal Detection of Fetal Triploidy from Cell-Free DNA Testing in Maternal Blood," Fetal Diagnosis and Therapy, Oct. 10, 2013, pp. 1-6.
Nicolaides K.H., et al., "Validation of Targeted Sequencing of Single-Nucleotide Polymorphisms for Non-Invasive Prenatal Detection of Aneuploidy of Chromosomes 13, 18, 21, X, and Y," Prenatal Diagnosis, Jun. 2013, vol. 33, No. 6, pp. 575-579.
Palomaki G., et al., "DNA Sequencing of Maternal Plasma Reliably Identifies Trisomy 18 and Trisomy 13 as Well as Down Syndrome: an International Collaborative Study," Genetics in Medicine, Mar. 2012, vol. 14, No. 3, 10 Pages.
Peng Q., et al., "Reducing Amplification Artifacts in High Multiplex Amplicon Sequencing by using Molecular Barcodes," BMC Genomics, Aug. 7, 2015, vol. 16, No. 1, 589, 12 Pages, DOI: 10.1186/s12864-015-1806-8.
Pergament E., et al., "Single-Nucleotide Polymorphism-Based Noninvasive Prenatal Screening in a High-Risk and Low-Risk Cohort," Obstetrics & Gynecology, Aug. 2014, vol. 124, No. 2, Part 1, pp. 210-218 (26 Pages), Appendix.
Perkel J.M., "Overcoming the Challenges of Multiplex PCR," Biocompare Editorial Article, Oct. 23, 2012, pp. 1-5.
Rabinowitz M., et al., "Non-Invasive Prenatal Aneuploidy Testing of Chromosomes 13, 18, 21, X, and Y Using Targeted Sequencing of Polymorphic Loci," The American Society of Human Genetics, Meeting poster, 2012, 1 Page.
Rabinowitz M., et al., "Origins and Rates of Aneuploidy in Human Blastomeres," Fertility and Sterility, Elsevier Science Inc, New York, NY, USA, Feb. 2012, vol. 97, No. 2, pp. 395-401, DOI: 10.1016/J.FERTNSTERT.2011.11.034, ISSN: 0015-0282, XP028453561, [Retrieved on Nov. 30, 2011], Nov. 24, 2011.
Rava R.P., et al., "Circulating Fetal Cell-Free DNA Fractions Differ in Autosomal Aneuploidies and Monosomy X," Clinical Chemistry, (Papers in Press), 2014, vol. 60, No. 1, 8 Pages, Published as Sep. 17, 2013.
Ryan A., et al., "Informatics-Based, Highly Accurate, Noninvasive Prenatal Paternity Testing," Genetics in Medicine, (Advance Online Publication), 2012, 5 Pages.
Samango-Sprouse C., et al., "SNP-Based Non-Invasive Prenatal Testing Detects Sex Chromosome Aneuploidies With High Accuracy," Prenatal Diagnosis, 2013, vol. 33, 643-649.
Schmitt M.W., "Detection of Ultra-Rare Mutations by the Next Generation Sequencing," Proceedings of the National Academy of Sciences of the United States of America, Sep. 4, 2012, vol. 109, No. 36, pp. 14508-14513 (9 Pages), Supporting Information.
Shiroguchi K., et al., "Digital RNA Sequencing Minimizes Sequence-Dependent Bias and Amplification Noise with Optimized Single-Molecule Barcodes," PNAS, Jan. 24, 2012, vol. 109, No. 4, pp. 1347-1352.
Shokralla S., et al., "Next-generation DNA Barcoding: Using Next-Generation Sequencing to Enhance and Accelerate DNA Barcode Capture from Single Specimens," Molecular Ecology Resources, 2014, vol. 14, pp. 892-901.
Sint D., et al., "Advances in Multiplex PCR: Balancing Primer Efficiencies and Improving Detection Success," Methods in Ecology and Evolution, 2012, vol. 3, pp. 898-905.
Sparks A.B., et al., "Selective Analysis of Cell-free DNA in Maternal Blood for Evaluation of Fetal Trisomy," Prenatal Diagnosis, 2012, vol. 32, No. (1-7), pp. 3-9 (7 Pages), Epublished on Jan. 6, 2012.
Sparks A.B., et al., "Non-invasive Prenatal Detection and Selective Analysis of Cell-free DNA Obtained From Maternal Blood: Evaluation for Trisomy 21 and Trisomy 18," American Journal of Obstetrics & Gynecology, Apr. 2012, vol. 206, pp. 319.e1-319.e9.
Spindler K-L G., et al., "Cell-Free DNA in Healthy Individuals, Noncancerous Disease and Strong Prognostic Value in Colorectal Cancer," International Journal of Cancer, Dec. 15, 2014, vol. 135, No. 12, pp. 2984-2991, DOI: 10.1002/ijc.28946, Epub Jun. 17, 2014.
Tie J., et al., "Circulating Tumor DNA as an Early Marker of Therapeutic Response in Patients with Metastatic Colorectal Cancer," Annals of Oncology, 2015, vol. 26, No. 8, pp. 1715-1722.
Tu J., et al., "Pair-barcode High-throughput Sequencing for Large-scale Multiplexed Sample Analysis," BMC Genomics, Jan. 25, 2012, vol. 13, No. 43, pp. 1-9.
Van Den Oever J.M.E., et al., "Single Molecule Sequencing of Free DNA from Maternal Plasma for Noninvasive Trisomy 21 Detection," Clinical Chemistry, 2012, vol. 58, No. 4, pp. 699-706.
Wang E., et al., "Gestational Age and Maternal Weight Effects on Fetal Cell-Free DNA in Maternal Plasma," Prenatal Diagnosis, 2013, vol. 33, pp. 662-666.
Wang WP., et al., "Multiplex Single Nucleotide Polymorphism Genotyping by Adapter Ligation-mediated Allele-specific Amplification," Analytical Biochemistry, Aug. 2006, vol. 355 (2), pp. 240-248.
Wang Y., et al., Molecular Inversion Probes: A Novel Microarray Technology and its Application in Cancer Research, Cancer Genetics, 2012, vol. 205, pp. 341-355.
Wapner R.J., et al., "Expanding the Scope of Noninvasive Prenatal Testing: Detection of Fetal Microdeletion Syndromes," American Journal of Obstetrics and Gynecology, Mar. 2015, vol. 212, No. 3, pp. 332.e1-332.e9, DOI: 10.1016/j.ajog.2014.11.041, Epub Dec. 2, 2014.
Wen D., et al., "Universal Multiplex PCR: A Novel Method of Simultaneous Amplification of Multiple DNA Fragments," Plant Methods, Null, Aug. 15, 2012, vol. 8, No. 32, pp. 1-9.
Wong K.H., et al., "Multiplex Illumina Sequencing Using DNA Barcoding," Current Protocols in Molecular Biology, Jan. 2013, Supplement 101, pp. 7.11.1-7.11.11, 12 Pages.
Xu W., et al., "A Novel Universal Primer-Multiplex-PCR Method with Sequencing Gel Electrophoresis Analysis," PLOS One, Jan. 17, 2012, vol. 7, No. 1, 10 Pages.
Zhang R., "Quantifying RNA Allelic Ratios by Microfluidic Multiplex PCR and Sequencing," Nature Methods, Jan. 2014, vol. 11, No. 1, pp. 51-56.
Zheng C-X., et al., "Whole-exome Sequencing to Identify Novel Somatic Mutations in Squamous Cell Lung Cancers," International Journal of Oncology, 2013, vol. 43, pp. 755-764, 2015.
Zheng Z., et al., "Anchored Multiplex PCR for Targeted Next-generation Sequencing," Nature Medicine, Dec. 2014, vol. 20, No. 12, pp. 1479-1486.
Zimmermann B., et al., "Noninvasive Prenatal Aneuploidy Testing of Chromosomes 13, 18, 21, X, and Y, using Targeted Sequencing of Polymorphic Loci," Prenatal Diagnosis, Dec. 2012, vol. 32, No. 13, pp. 1233-1241, DOI: 10.1002/pd.3993, Epub Oct. 30, 2012.

(56) References Cited

OTHER PUBLICATIONS

Zimmermann B., "Noninvasive Prenatal Aneuploidy Testing of Chromosomes 13, 18, 21, X, and Y, using Targeted Sequencing of Polymorphic Loci, Supplemental Information," Prenatal Diagnosis, 2012, vol. 32, 7 Pages.
Bianchi D.W., et al., "Integration of Noninvasive DNA Testing for Aneuploidy into Prenatal Care: What Has Happened Since the Rubber Met the Road?," Clinical Chemistry, Nov. 2013, vol. 60(1), pp. 78-87.
Ganova-Raeva L.M., "Chapter 6 - Primer Extension Enrichment Rection (PEER) and Other Methods for Difference Screening," Nucleic Acids Hybridization, 2007, pp. 125-165.
Kukita Y., et al., "Quantitative Identification of Mutant Alleles Derived From Lung Cancer in Plasma Cell-free DNA via Anomaly Detection Using Deep Sequencing Data," Plos One, Nov. 2013, vol. 8(11), pp. 1-10.
*Natera Inc.*v. *NeoGenomics Laboratories, Inc., Memorandum Opinion* and Order: Case 1:23-cv-00629-CCE-JLW, United States District Court for the Middle District of North Carolina, Aug. 28, 2025, pp. 1-16.
Shendure J., et al., "The Expanding Scope of DNA Sequencing," Nature Biotechnology, Nov. 2012, vol. 30(11), pp. 1084-1094.
Snyder M.W., et al., "Noninvasive Fetal Genome Sequencing: A Primer," Prenatal Diagnosis, 2013, vol. 33, pp. 1-8.
Wang S., et al., "Self-Formed Adaptor PCR: a Simple and Efficient Method for Chromosome Walking," Applied and Environmental Microbiology, May 2007, vol. 73(15), p. 50485051.

* cited by examiner

| Syndrome | Sensitivity | Specificity |
|---|---|---|
| 22q11.2 Deletion/ DiGeorge | 97.8% (45/46) [CI: 88.5 – 99.95%] | 99.2% (392/395) [CI: 97.8 - 99.8%] |
| Angelman | 100% (21/21) [CI: 83.9 – 100%] | 100% (418/418) [CI: 99.1 – 100%] |
| Cri du chat | 100% (24/24) [CI: 85.7 – 100%] | 99.8% (415/416) [CI: 98.7 – 99.99%] |
| Monosomy 1p36 | 100% (1/1) [CI: 2.5 – 100%] | 100% (438/438) [CI: 99.2 – 100%] |
| Prader-Willi | 100% (15/15) [CI: 78.2 – 100%] | 100% (424/424) [CI: 99.1 – 100%] |
| Wolf-Hirschhorn | 100% (2/2) [CI: 15.8 – 100%] | 99.8% (437/438) [CI: 98.7 – 100%] |

FIG. 14

With Haplotypes

Without Haplotypes

With Haplotypes

Without Haplotypes

With Haplotypes

Without Haplotypes

| | S=1000,D=1000 | S=500,D=1000 | S=1000,D=500 | S=500,D=500 |
|---|---|---|---|---|
| With Phase | 1.50% | 8.80% | 10.20% | 22.30% |
| Without Phase | 10.60% | 10.80% | 17.90% | 20.80% |

FIG. 26

| | S=1000,D=1000 | S=500,D=1000 | S=1000,D=500 | S=500,D=500 |
|---|---|---|---|---|
| $\rho$ =1%,WithPhase | 0.00% | 0.10% | 3.00% | 9.70% |
| $\rho$ =1%,WithoutPhase | 74.20% | 73.70% | 74.60% | 76.00% |
| $\rho$ =2%,WithPhase | 0.00% | 0.00% | 0.00% | 0.00% |
| $\rho$ =2%,WithoutPhase | 13.90% | 14.80% | 41.00% | 42.70% |
| $\rho$ =3%,WithPhase | 0.00% | 0.00% | 0.00% | 0.00% |
| $\rho$ =3%,WithoutPhase | 0.00% | 0.00% | 5.70% | 5.00% |
| $\rho$ =4%,WithPhase | 0.00% | 0.00% | 0.00% | 0.00% |
| $\rho$ =4%,WithoutPhase | 0.00% | 0.00% | 0.00% | 0.00% |
| $\rho$ =5%,WithPhase | 0.00% | 0.00% | 0.00% | 0.00% |
| $\rho$ =5%,WithoutPhase | 0.00% | 0.00% | 0.00% | 0.00% |

FIG. 27

Genomics

Single Cell

| | gDNA | Single Cell |
|---|---|---|
| Count | 75 | 510 |
| Mean | 0.15 % | 0.51 % |
| Median | 0.09 % | 0.33 % |
| Max | 1.03 % | 10 % |
| Standard Deviation | 0.16% | 0.79 % |
| 95th percentile | 0.43 % | 1.22 % |
| 90th percentile | 0.37 % | 0.92 % |

| | | SNVs Only | | Combined SNVs & CNVs | | |
|---|---|---|---|---|---|---|
| Cancer Type | Total # of Positives | Detected | % | Detected w/ low Depth of Read | % | Expected Diagnostic Load Based on TCGA and COMSIC Datasets |
| Breast | 41 | 29 | 71% | 34 | 83% | >97% |
| Lung | 24 | 17 | 71% | 22 | 92% | >98% |

| Stage | Positive Samples, N | Detected, N | % Detected |
|---|---|---|---|
| I | 10 | 6 | 60% |
| II | 25 | 22 | 88% |
| III | 6 | 6 | 100% |

LOQ for SNVs= 0.2% ctDNA
LOQ for CNVs= 0.45% ctDNA

| Stage | Positive Samples, N | Detected, N | % Detected |
|---|---|---|---|
| I | 10 | 6 | 60% |
| II | 5 | 5 | 100% |
| IIA | 10 | 9 | 90% |
| IIB | 10 | 8 | 80% |
| III | 3 | 3 | 100% |
| IIIA | 2 | 2 | 100% |
| IIIB | 1 | 1 | 100% |

LOQ for SNVs= 0.2% ctDNA

LOQ for CNVs= 0.45% ctDNA

| Stage | Positive Samples, N | Detected, N | % Detected |
|---|---|---|---|
| I | 17 | 15 | 88% |
| II | 5 | 5 | 100% |
| III | 2 | 2 | 100% |

LOQ for SNVs= 0.2% ctDNA
LOQ for CNVs= 0.45% ctDNA

| Stage | Positive Samples, N | Detected, N | % Detected |
|---|---|---|---|
| IA | 6 | 6 | 100% |
| IB | 11 | 9 | 82% |
| IIB | 5 | 5 | 100% |
| IIIA | 2 | 2 | 100% |

LOQ for SNVs= 0.2% ctDNA
LOQ for CNVs= 0.45% ctDNA

| | Histology | Stage | Age | Dia (mm) | Smoker (Pack Years) | |
|---|---|---|---|---|---|---|
| L12 | SSC | IB | 69 | 40 | Yes (?) | 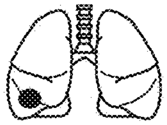 |
| L13 | SSC | IA | 68 | 30 | Yes (100) | 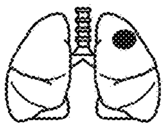 |
| L15 | SSC | IB | 68 | 50 | Yes (50) | 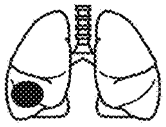 |
| L17 | Adeno | IIB | 61 | 20 | Yes (48) | 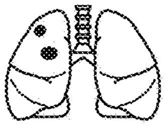 |
FIG. 51A

| Sample | Gene | Chr | ChrStart | VAF R1 | VAF R2 | VAF R3 |
|---|---|---|---|---|---|---|
| L12 | BRIP1 | chr17 | 59924572 | 14 | 6 | 8 |
| L12 | CARS | chr11 | 3062181 | 22 | 11 | 16 |
| L12 | CIC | chr19 | 42797381 | 0 | 0 | 7 |
| L12 | CYFIP1 | chr15 | 22940733 | 0 | 6 | 0 |
| L12 | FAT1 | chr4 | 187519147 | 8 | 4 | 0 |
| L12 | KDM6A | chrX | 44921898 | 10 | 5 | 0 |
| L12 | MLLT4 | chr6 | 168347475 | 9 | 3 | 0 |
| L12 | NFE2L2 | chr2 | 178098801 | 69 | 31 | 50 |
| L12 | RASA1 | chr5 | 86642517 | 7 | 0 | 0 |
| L12 | TP53 | chr17 | 7578406 | 23 | 9 | 17 |
| L12 | TP53 | chr17 | 7578190 | 22 | 8 | 16 |
| | | | | | | |
| L13 | EGFR | chr7 | 55241708 | 21 | 25 | 55 |
| L13 | EGFR | chr7 | 55242511 | 20 | 17 | 48 |
| L13 | HERC4 | chr10 | 69793756 | 0 | 3 | 6 |
| L13 | JAK2 | chr9 | 5022084 | 0 | 11 | 7 |
| L13 | KMT2C | chr7 | 151947008 | 0 | 0 | 4 |
| L13 | MSH2 | chr2 | 47693816 | 5 | 0 | 11 |
| L13 | MTOR | chr1 | 11292495 | 2 | 0 | 3 |
| L13 | PLCG2 | chr16 | 81942036 | 5 | 0 | 6 |
| L13 | TP53 | chr17 | 7579509 | 7 | 4 | 16 |
| | | | | | | |
| L15 | ALK | chr2 | 29940530 | 6 | 2 | |
| L15 | GABRG1 | chr4 | 46060315 | 13 | 0 | |
| L15 | KDM6A | chrX | 44922755 | 18 | 6 | |
| L15 | MLL2 | chr12 | 49443815 | 5 | 0 | |
| L15 | ROS1 | chr6 | 117687379 | 10 | 3 | |
| L15 | SLC39A4 | chr8 | 145638322 | 14 | 0 | |
| L15 | TP53 | chr17 | 7578254 | 19 | 3 | |
| L15 | ZFHX4 | chr8 | 77776735 | 13 | 5 | |
| L15 | ZMYM4 | chr1 | 35827319 | 14 | 2 | |
| | | | | | | |
| L17 | BRCA2 | chr13 | 32914959 | 16 | 28 | 0 |
| L17 | KRAS | chr12 | 25398284 | 13 | 22 | 0 |
| L17 | NF1 | chr17 | 29653134 | 20 | 25 | 0 |
| L17 | NF1 | chr17 | 29528088 | 0 | 0 | 20 |
| L17 | PAX8 | chr2 | 113984793 | 9 | 0 | 0 |
| L17 | TP53 | chr17 | 7577610 | 0 | 0 | 16 |
| L17 | TP53 | chr17 | 7577079 | 20 | 35 | 0 |
| L17 | TRIM67 | chr1 | 231299607 | 0 | 50 | 0 |
| L17 | TRIP11 | chr14 | 92471631 | 7 | 0 | 0 |

FIG. 51B

| Sample | Gene | Chrom | ChromStart | Swanton | | |
|---|---|---|---|---|---|---|
| | | | | VAF R1 | VAF R2 | VAF R3 |
| L12 | BRIP1 | chr17 | 59924572 | 14 | 6 | 8 |
| L12 | CARS | chr11 | 3062181 | 22 | 11 | 16 |
| L12 | CIC | chr19 | 42797381 | 0 | 0 | 7 |
| L12 | CYFIP1 | chr15 | 22940733 | 0 | 6 | 0 |
| L12 | FAT1 | chr4 | 187519147 | 8 | 4 | 0 |
| L12 | KDM6A | chrX | 44921898 | 10 | 5 | 0 |
| L12 | MLLT4 | chr6 | 168347475 | 9 | 3 | 0 |
| L12 | NFE2L2 | chr2 | 178098801 | 69 | 31 | 50 |
| L12 | RASA1 | chr5 | 86642517 | 7 | 0 | 0 |
| L12 | TP53 | chr17 | 7578406 | 23 | 9 | 17 |
| L12 | TP53 | chr17 | 7578190 | 22 | 8 | 16 |
| L13 | EGFR | chr7 | 55241708 | 21 | 25 | 55 |
| L13 | EGFR | chr7 | 55242511 | 20 | 17 | 48 |
| L13 | HERC4 | chr10 | 69793756 | 0 | 3 | 6 |
| L13 | JAK2 | chr9 | 5022084 | 0 | 11 | 7 |
| L13 | KMT2C | chr7 | 151947008 | 0 | 0 | 4 |
| L13 | MSH2 | chr2 | 47693816 | 5 | 0 | 11 |
| L13 | MTOR | chr1 | 11292495 | 2 | 0 | 3 |
| L13 | PLCG2 | chr16 | 81942036 | 5 | 0 | 6 |
| L13 | TP53 | chr17 | 7579509 | 7 | 4 | 16 |
| L15 | ALK | chr2 | 29940530 | 6 | 2 | |
| L15 | GABRG1 | chr4 | 46060315 | 13 | 0 | |
| L15 | KDM6A | chrX | 44922755 | 18 | 6 | |
| L15 | MLL2 | chr12 | 49443815 | 5 | 0 | |
| L15 | ROS1 | chr6 | 117687379 | 10 | 3 | |
| L15 | SLC39A4 | chr8 | 145638322 | 14 | 0 | |
| L15 | TP53 | chr17 | 7578254 | 19 | 3 | |
| L15 | ZFHX4 | chr8 | 77776735 | 13 | 5 | |
| L15 | ZMYM4 | chr1 | 35827319 | 14 | 2 | |
| L17 | BRCA2 | chr13 | 32914959 | 16 | 28 | |
| L17 | KRAS | chr12 | 25398284 | 13 | 22 | |
| L17 | NF1 | chr17 | 29653134 | 20 | 25 | |
| L17 | NF1 | chr17 | 29528088 | 0 | 0 | 20 |
| L17 | PAX8 | chr2 | 113984793 | 9 | 0 | 0 |
| L17 | TP53 | chr17 | 7577610 | 0 | 0 | 16 |
| L17 | TP53 | chr17 | 7577079 | 20 | 35 | 0 |
| L17 | TRIM67 | chr1 | 231299607 | 0 | 50 | 0 |
| L17 | TRIP11 | chr14 | 92471631 | 7 | 0 | 0 |

[hatched box] = Ampliseq

FIG. 53A

| Sample | Gene | Chrom | ChromStart | Natera | | | |
|---|---|---|---|---|---|---|---|
| | | | | VAF R1 | VAF R2 | VAF R3 | VAF Plasma |
| L12 | BRIP1 | chr17 | 59924572 | 22.6 | 7.74 | 10.07 | 3.71 |
| L12 | CARS | chr11 | 3062181 | 22.39 | 10.47 | 18.21 | 5.02 |
| L12 | CIC | chr19 | 42797381 | 0 | 0 | 8.17 | 1.71 |
| L12 | CYFIP1 | chr15 | 22940733 | 0 | 0 | 0 | 0 |
| L12 | FAT1 | chr4 | 187519147 | 9.81 | 4.26 | 0.77 | 0.57 |
| L12 | KDM6A | chrX | 44921898 | 6.33 | 3.54 | 0 | 0.28 |
| L12 | MLLT4 | chr6 | 168347475 | 9.04 | 4.26 | 0.73 | 0.95 |
| L12 | NFE2L2 | chr2 | 178098801 | 73.12 | 39.92 | 53.94 | 23.25 |
| L12 | RASA1 | chr5 | 86642517 | 7.37 | 0 | 0.35 | 0 |
| L12 | TP53 | chr17 | 7578406 | 22.93 | 9.17 | 16.97 | 4.89 |
| L12 | TP53 | chr17 | 7578190 | 21.48 | 8.67 | 22.09 | 5.77 |
| L13 | EGFR | chr7 | 55241708 | 27.06 | 23.14 | 60.79 | 1.16 |
| L13 | EGFR | chr7 | 55242511 | 23.93 | 18.01 | 56.31 | 1.09 |
| L13 | HERC4 | chr10 | 69793756 | 0.16 | 1.92 | 5.72 | 0 |
| L13 | JAK2 | chr9 | 5022084 | 0.27 | 2.79 | 6.09 | 0 |
| L13 | KMT2C | chr7 | 151947008 | 0 | 0 | 6.69 | 0 |
| L13 | MSH2 | chr2 | 47693816 | 5.04 | 3.33 | 12.67 | 0 |
| L13 | MTOR | chr1 | 11292495 | 2.4 | 1.38 | 6.01 | 0 |
| L13 | PLCG2 | chr16 | 81942036 | 2.8 | 1.7 | 6.89 | 0 |
| L13 | TP53 | chr17 | 7579509 | 6.11 | 3.76 | 15.4 | 0.4 |
| L15 | ALK | chr2 | 29940530 | 7.2 | 1.39 | | 0 |
| L15 | GABRG1 | chr4 | 46060315 | 11.84 | 2.04 | | 0 |
| L15 | KDM6A | chrX | 44922755 | 6.54 | 0.91 | | 0.17 |
| L15 | MLL2 | chr12 | 49443815 | 12.41 | 0 | | |
| L15 | ROS1 | chr6 | 117687379 | 10.82 | 2.94 | | 0.15 |
| L15 | SLC39A4 | chr8 | 145638322 | 18.59 | 0 | | 0 |
| L15 | TP53 | chr17 | 7578254 | 12.6 | 2.5 | | 0 |
| L15 | ZFHX4 | chr8 | 77776735 | 10.26 | 2.3 | | 0 |
| L15 | ZMYM4 | chr1 | 35827319 | 12.84 | 3.46 | | 0 |
| L17 | BRCA2 | chr13 | 32914959 | 15.03 | 27 | | 0 |
| L17 | KRAS | chr12 | 25398284 | 14.22 | 23.79 | | 0 |
| L17 | NF1 | chr17 | 29653134 | 18.6 | 23.1 | | 0 |
| L17 | NF1 | chr17 | 29528088 | 0 | 0 | 17.79 | 0.37 |
| L17 | PAX8 | chr2 | 113984793 | 6.6 | 0 | | 0 |
| L17 | TP53 | chr17 | 7577610 | 0 | 0 | 18.97 | 0 |
| L17 | TP53 | chr17 | 7577079 | 15.36 | 33.7 | | 0 |
| L17 | TRIM67 | chr1 | 231299607 | 18.38 | 30.95 | | 0.57 |
| L17 | RIP11 | chr14 | 92471631 | 6.44 | 0 | | 0 |

[hatched box] = mmPCR-NGS

FIG. 53B

- 28K-plex PCR
- > 85% mapped reads
- 4.7M reads (~167 reads per target)
- Mosaicism observed among cells

| Chr No.:Position_Mutation | Chr No.:Position_Mutation | Chr No.:Position_Mutation |
|---|---|---|
| 9:163985-163985_T>C | 9:5050714-5050714_T>C | 17:7577587-7577587_A>T |
| 1:17275337-17275337_C>T | 9:21971111-21971111_C>T | 17:7577590-7577590_A>T |
| 1:23689289-23689289_T>G | 9:32632175-32632175_C>T | 17:7577592-7577592_C>A |
| 1:26774085-26774085_G>A | 9:108097968-108097968_G>A | 17:7577598-7577598_A>G |
| 1:36226206-36226206_A>G | 9:130931780-130931780_C>T | 17:7577599-7577599_G>C |
| 1:43032078-43032078_C>T | 9:141071078-141071078_A>G | 17:7577604-7577604_G>T |
| 1:43912067-43912067_G>A | 10:37486216-37486216_C>G | 17:7578177-7578177_G>C |
| 1:64515405-64515405_C>T | 10:46254776-46254776_A>C | 17:7578183-7578183_G>T |
| 1:99771528-99771528_G>A | 10:47207813-47207813_A>G | 17:7578188-7578188_G>T |
| 1:110173662-110173662_G>A | 10:50678650-50678650_A>T | 17:7578190-7578190_A>G |
| 1:115256528-115256528_A>C | 10:51853633-51853633_C>T | 17:7578191-7578191_T>C |
| 1:115256529-115256529_A>G | 10:72358324-72358324_C>T | 17:7578196-7578196_T>A |
| 1:120458147-120458147_C>T | 10:81058322-81058322_C>G | 17:7578202-7578202_T>A |
| 1:145323656-145323656_A>T | 10:89624275-89624275_C>T | 17:7578203-7578203_G>T |
| 1:148343792-148343792_G>T | 10:89624305-89624305_T>G | 17:7578204-7578204_T>G |
| 1:151149263-151149263_A>G | 10:89692790-89692790_G>A | 17:7578206-7578206_A>G |
| 1:152186837-152186837_G>A | 10:89692794-89692794_A>T | 17:7578207-7578207_T>C |
| 1:152189016-152189016_C>T | 10:89692835-89692835_G>A | 17:7578208-7578208_A>G |
| 1:152328936-152328936_C>G | 10:89692839-89692839_T>G | 17:7578212-7578212_C>T |
| 1:157805906-157805906_G>A | 10:89692883-89692883_C>G | 17:7578215-7578215_T>A |
| 1:158609792-158609792_A>T | 10:89692893-89692893_C>A | 17:7578216-7578216_T>C |
| 1:186276240-186276240_T>C | 10:89692900-89692900_G>C | 17:7578224-7578224_A>T |
| 1:198675866-198675866_A>C | 10:89692905-89692905_G>A | 17:7578225-7578225_C>A |
| 1:202699028-202699028_A>G | 10:89692923-89692923_G>A | 17:7578235-7578235_A>G |
| 1:225306960-225306960_T>G | 10:89692980-89692980_A>G | 17:7578236-7578236_T>G |
| 1:227288919-227288919_C>T | 10:89692998-89692998_G>T | 17:7578239-7578239_G>T |

FIG. 67A

| Chr No.:Position_Mutation | Chr No.:Position_Mutation | Chr No.:Position_Mutation |
|---|---|---|
| 1:228560700-228560700_T>C | 10:123258034-123258034_T>A | 17:7578244-7578244_G>C |
| 1:235884036-235884036_A>G | 10:127548395-127548395_C>G | 17:7578245-7578245_C>A |
| 1:247614573-247614573_C>T | 11:534288-534288_G>A | 17:7578253-7578253_G>T |
| 1:248402566-248402566_T>A | 11:1093430-1093430_C>A | 17:7578254-7578254_G>A |
| 2:32820108-32820108_A>C | 11:1643049-1643049_T>G | 17:7578257-7578257_G>T |
| 2:61719472-61719472_G>A | 11:1651157-1651157_A>G | 17:7578259-7578259_T>G |
| 2:107049425-107049425_T>G | 11:48171648-48171648_A>T | 17:7578260-7578260_G>T |
| 2:107460402-107460402_G>A | 11:49854989-49854989_G>A | 17:7578262-7578262_G>C |
| 2:118715997-118715997_C>G | 11:55541605-55541605_G>A | 17:7578263-7578263_C>T |
| 2:119752091-119752091_G>A | 11:55861593-55861593_G>A | 17:7578265-7578265_T>C |
| 2:129075877-129075877_C>A | 11:60666746-60666746_A>C | 17:7578266-7578266_A>T |
| 2:165986535-165986535_A>G | 11:64544046-64544046_A>G | 17:7578268-7578268_T>C |
| 2:178098803-178098803_G>A | 11:66335548-66335548_T>C | 17:7578269-7578269_C>T |
| 2:179434772-179434772_C>T | 11:71932638-71932638_C>T | 17:7578271-7578271_A>G |
| 2:179635206-179635206_C>G | 11:94204875-94204875_T>G | 17:7578272-7578272_C>T |
| 2:197641324-197641324_C>G | 11:103182692-103182692_G>A | 17:7578275-7578275_C>T |
| 2:198266834-198266834_A>G | 11:108117798-108117798_C>T | 17:7578280-7578280_C>T |
| 2:198363501-198363501_G>A | 11:108175462-108175462_G>A | 17:7578281-7578281_C>T |
| 2:209113113-209113113_C>T | 11:108200961-108200961_G>A | 17:7578284-7578284_G>T |
| 2:238672328-238672328_C>T | 12:4627253-4627253_G>A | 17:7578371-7578371_G>A |
| 3:1269641-1269641_A>G | 12:9453702-9453702_C>T | 17:7578374-7578374_G>C |
| 3:19924193-19924193_G>A | 12:9574020-9574020_A>G | 17:7578375-7578375_C>G |
| 3:25832827-25832827_T>A | 12:9583286-9583286_T>C | 17:7578380-7578380_G>A |
| 3:38104250-38104250_C>G | 12:12630318-12630318_C>T | 17:7578382-7578382_C>T |
| 3:41266100-41266100_T>A | 12:21953991-21953991_G>A | 17:7578388-7578388_G>C |
| 3:41266101-41266101_C>G | 12:22677465-22677465_G>A | 17:7578389-7578389_C>T |

FIG. 67B

| Chr No.:Position_Mutation | Chr No.:Position_Mutation | Chr No.:Position_Mutation |
|---|---|---|
| 3:41266104-41266104_G>T | 12:25380275-25380275_A>T | 17:7578392-7578392_G>C |
| 3:41266113-41266113_C>A | 12:25380276-25380276_A>T | 17:7578393-7578393_T>A |
| 3:41266124-41266124_A>G | 12:25380277-25380277_C>A | 17:7578394-7578394_A>G |
| 3:44612650-44612650_G>T | 12:25398281-25398281_G>A | 17:7578395-7578395_C>A |
| 3:58191274-58191274_G>C | 12:25398282-25398282_G>T | 17:7578400-7578400_C>G |
| 3:108788596-108788596_C>T | 12:25398284-25398284_G>A | 17:7578402-7578402_C>A |
| 3:138022433-138022433_C>T | 12:25398285-25398285_G>C | 17:7578403-7578403_G>A |
| 3:149245633-149245633_T>G | 12:30888067-30888067_G>A | 17:7578404-7578404_T>A |
| 3:172533490-172533490_A>C | 12:31231425-31231425_T>G | 17:7578406-7578406_G>A |
| 3:178916854-178916854_G>A | 12:31242869-31242869_G>A | 17:7578407-7578407_C>A |
| 3:178916876-178916876_G>A | 12:50745677-50745677_A>T | 17:7578409-7578409_G>A |
| 3:178916936-178916936_G>A | 12:50746243-50746243_A>C | 17:7578410-7578410_A>T |
| 3:178916941-178916941_G>A | 12:52385715-52385715_C>T | 17:7578413-7578413_G>T |
| 3:178916944-178916944_A>G | 12:56482341-56482341_G>T | 17:7578415-7578415_T>A |
| 3:178916946-178916946_G>C | 12:91502039-91502039_G>A | 17:7578416-7578416_G>A |
| 3:178917478-178917478_G>A | 12:101745882-101745882_A>T | 17:7578419-7578419_G>A |
| 3:178921548-178921548_G>A | 13:28919595-28919595_G>A | 17:7578420-7578420_G>A |
| 3:178921552-178921552_A>T | 13:32968854-32968854_C>A | 17:7578423-7578423_G>A |
| 3:178921553-178921553_T>A | 13:36700097-36700097_C>T | 17:7578428-7578428_C>T |
| 3:178927974-178927974_G>A | 13:48953760-48953760_C>T | 17:7578431-7578431_C>T |
| 3:178927980-178927980_T>C | 13:49033955-49033955_A>T | 17:7578433-7578433_C>G |
| 3:178928079-178928079_G>A | 14:20215706-20215706_G>T | 17:7578437-7578437_C>T |
| 3:178936050-178936050_T>C | 14:21873400-21873400_G>A | 17:7578440-7578440_A>G |
| 3:178936074-178936074_C>G | 14:44973867-44973867_C>T | 17:7578442-7578442_A>C |
| 3:178936082-178936082_G>A | 14:63784405-63784405_C>T | 17:7578443-7578443_T>A |
| 3:178936083-178936083_A>T | 14:102323093-102323093_T>C | 17:7578448-7578448_C>A |

FIG. 67C

| Chr No.:Position_Mutation | Chr No.:Position_Mutation | Chr No.:Position_Mutation |
|---|---|---|
| 3:178936091-178936091_G>A | 14:105246551-105246551_G>A | 17:7578449-7578449_G>A |
| 3:178936092-178936092_A>C | 15:22743235-22743235_A>G | 17:7578452-7578452_A>G |
| 3:178936093-178936093_G>C | 15:33954810-33954810_G>A | 17:7578454-7578454_C>T |
| 3:178936094-178936094_C>A | 15:66774131-66774131_G>A | 17:7578455-7578455_G>C |
| 3:178936095-178936095_A>G | 15:75047325-75047325_G>A | 17:7578457-7578457_G>A |
| 3:178936097-178936097_G>A | 15:83014132-83014132_G>C | 17:7578460-7578460_T>G |
| 3:178937019-178937019_A>G | 15:84909434-84909434_G>A | 17:7578461-7578461_G>T |
| 3:178938860-178938860_A>C | 15:102516424-102516424_G>T | 17:7578463-7578463_G>C |
| 3:178938934-178938934_G>A | 16:1004605-1004605_T>C | 17:7578464-7578464_C>G |
| 3:178947827-178947827_G>T | 16:2049640-2049640_T>C | 17:7578466-7578466_C>T |
| 3:178951957-178951957_G>A | 16:3820773-3820773_C>T | 17:7578467-7578467_A>C |
| 3:178951964-178951964_G>C | 16:4432029-4432029_A>C | 17:7578469-7578469_G>A |
| 3:178952004-178952004_C>T | 16:28507445-28507445_G>C | 17:7578471-7578471_C>T |
| 3:178952013-178952013_G>T | 16:29110458-29110458_T>C | 17:7578472-7578472_C>T |
| 3:178952018-178952018_A>K | 16:56782199-56782199_G>A | 17:7578475-7578475_C>T |
| 3:178952019-178952019_C>T | 16:68772218-68772218_C>T | 17:7578476-7578476_C>T |
| 3:178952020-178952020_C>T | 16:68844139-68844139_G>A | 17:7578478-7578478_C>A |
| 3:178952030-178952030_G>C | 17:7573982-7573982_G>T | 17:7578479-7578479_C>T |
| 3:178952072-178952072_A>G | 17:7574002-7574002_G>C | 17:7578490-7578490_T>A |
| 3:178952074-178952074_G>C | 17:7574003-7574003_C>T | 17:7578492-7578492_G>A |
| 3:178952075-178952075_A>T | 17:7574012-7574012_G>T | 17:7578493-7578493_G>A |
| 3:178952077-178952077_T>A | 17:7574017-7574017_G>T | 17:7578496-7578496_T>A |
| 3:178952081-178952081_G>A | 17:7574018-7574018_C>T | 17:7578498-7578498_G>T |
| 3:178952082-178952082_C>T | 17:7576855-7576855_C>T | 17:7578499-7578499_A>C |
| 3:178952084-178952084_C>T | 17:7576857-7576857_T>G | 17:7578500-7578500_C>T |
| 3:178952085-178952085_A>G | 17:7576883-7576883_A>G | 17:7578502-7578502_T>C |

FIG. 67D

| Chr No.:Position_Mutation | Chr No.:Position_Mutation | Chr No.:Position_Mutation |
|---|---|---|
| 3:178952088-178952088_A>G | 17:7576897-7576897_C>T | 17:7578506-7578506_C>A |
| 3:178952090-178952090_G>C | 17:7577022-7577022_C>T | 17:7578507-7578507_C>A |
| 3:178952091-178952091_G>C | 17:7577036-7577036_C>A | 17:7578508-7578508_G>A |
| 3:178952100-178952100_C>A | 17:7577046-7577046_G>T | 17:7578509-7578509_T>C |
| 3:192516720-192516720_C>G | 17:7577052-7577052_C>A | 17:7578513-7578513_G>A |
| 3:195452649-195452649_C>T | 17:7577058-7577058_G>T | 17:7578514-7578514_A>G |
| 3:195505836-195505836_C>G | 17:7577069-7577069_G>A | 17:7578517-7578517_C>T |
| 3:195506597-195506597_C>T | 17:7577079-7577079_G>T | 17:7578518-7578518_G>A |
| 3:195506940-195506940_C>G | 17:7577081-7577081_A>C | 17:7578524-7578524_C>T |
| 3:195511945-195511945_C>T | 17:7577082-7577082_G>C | 17:7578525-7578525_C>G |
| 4:11400898-11400898_G>A | 17:7577085-7577085_G>A | 17:7578526-7578526_G>A |
| 4:15443812-15443812_C>A | 17:7577088-7577088_A>C | 17:7578527-7578527_T>G |
| 4:40356408-40356408_C>A | 17:7577090-7577090_G>C | 17:7578528-7578528_T>G |
| 4:46930361-46930361_A>C | 17:7577091-7577091_C>T | 17:7578529-7578529_T>G |
| 4:48597671-48597671_G>A | 17:7577093-7577093_G>A | 17:7578530-7578530_T>C |
| 4:55593613-55593613_T>A | 17:7577094-7577094_C>T | 17:7578532-7578532_T>A |
| 4:55593661-55593661_T>C | 17:7577095-7577095_C>A | 17:7578534-7578534_G>T |
| 4:55594212-55594212_T>C | 17:7577096-7577096_A>G | 17:7578535-7578535_A>G |
| 4:55594221-55594221_A>G | 17:7577097-7577097_G>A | 17:7578536-7578536_A>G |
| 4:55599320-55599320_G>C | 17:7577099-7577099_G>A | 17:7578541-7578541_T>G |
| 4:71469002-71469002_C>G | 17:7577100-7577100_A>T | 17:7578542-7578542_C>T |
| 4:83778206-83778206_C>T | 17:7577102-7577102_G>A | 17:7578548-7578548_C>T |
| 4:88537243-88537243_C>A | 17:7577105-7577105_C>G | 17:7578550-7578550_C>G |
| 4:88537249-88537249_T>C | 17:7577106-7577106_C>A | 17:7578551-7578551_T>A |
| 4:107845202-107845202_G>A | 17:7577107-7577107_T>G | 17:7578553-7578553_A>G |
| 4:144336805-144336805_A>G | 17:7577108-7577108_G>T | 17:7578554-7578554_T>G |

FIG. 67E

| Chr No.:Position_Mutation | Chr No.:Position_Mutation | Chr No.:Position_Mutation |
|---|---|---|
| 4:153245446-153245446_C>T | 17:7577111-7577111_C>T | 17:7579312-7579312_G>C |
| 4:153247168-153247168_A>G | 17:7577112-7577112_G>C | 17:7579313-7579313_C>G |
| 4:153247288-153247288_G>H | 17:7577113-7577113_T>G | 17:7579329-7579329_A>G |
| 4:153247366-153247366_G>T | 17:7577114-7577114_G>T | 17:7579349-7579349_T>G |
| 4:153249456-153249456_G>T | 17:7577115-7577115_T>G | 17:7579355-7579355_T>C |
| 4:164507069-164507069_C>T | 17:7577117-7577117_T>C | 17:7579358-7579358_G>C |
| 4:170321765-170321765_C>T | 17:7577118-7577118_G>T | 17:7579366-7579366_C>G |
| 4:175896768-175896768_C>T | 17:7577120-7577120_G>A | 17:7579377-7579377_C>T |
| 5:13762932-13762932_G>A | 17:7577121-7577121_C>T | 17:7579378-7579378_C>A |
| 5:26906161-26906161_G>A | 17:7577123-7577123_T>C | 17:7579414-7579414_G>A |
| 5:67591128-67591128_G>C | 17:7577124-7577124_G>T | 17:7579503-7579503_G>T |
| 5:112173917-112173917_C>T | 17:7577127-7577127_G>T | 17:7579521-7579521_G>A |
| 5:112175118-112175118_C>T | 17:7577129-7577129_T>G | 17:7579547-7579547_C>T |
| 5:112175219-112175219_A>T | 17:7577130-7577130_T>C | 17:7579882-7579882_G>C |
| 5:112175681-112175681_G>T | 17:7577138-7577138_G>A | 17:11554600-11554600_G>T |
| 5:112175786-112175786_G>T | 17:7577141-7577141_G>A | 17:11998898-11998898_C>T |
| 5:112176020-112176020_G>T | 17:7577142-7577142_G>T | 17:12011144-12011144_C>T |
| 5:126791225-126791225_C>T | 17:7577144-7577144_T>C | 17:37868208-37868208_C>T |
| 5:129030517-129030517_C>T | 17:7577148-7577148_C>G | 17:37880220-37880220_T>C |
| 5:131931452-131931452_A>T | 17:7577501-7577501_C>T | 17:37880261-37880261_G>T |
| 5:135394826-135394826_G>A | 17:7577505-7577505_A>T | 17:37881000-37881000_G>C |
| 5:140683389-140683389_C>T | 17:7577506-7577506_G>T | 17:37881332-37881332_G>A |
| 5:170239186-170239186_A>G | 17:7577508-7577508_A>G | 17:39240627-39240627_T>C |
| 5:180335598-180335598_T>G | 17:7577509-7577509_G>A | 17:39274087-39274087_C>G |
| 6:10756728-10756728_C>T | 17:7577511-7577511_T>A | 17:39274157-39274157_C>T |
| 6:26032069-26032069_G>A | 17:7577517-7577517_T>C | 17:39305800-39305800_A>T |

FIG. 67F

| Chr No.:Position_Mutation | Chr No.:Position_Mutation | Chr No.:Position_Mutation |
|---|---|---|
| 6:28497279-28497279_G>A | 17:7577518-7577518_A>T | 17:39595484-39595484_C>T |
| 6:29910622-29910622_C>T | 17:7577520-7577520_T>C | 17:39673185-39673185_G>A |
| 6:93956553-93956553_C>G | 17:7577521-7577521_A>G | 17:41245274-41245274_G>C |
| 6:112452259-112452259_G>A | 17:7577524-7577524_A>C | 17:45219311-45219311_A>G |
| 6:130497111-130497111_C>T | 17:7577526-7577526_T>C | 17:48777241-48777241_T>A |
| 6:150001395-150001395_C>T | 17:7577529-7577529_T>A | 17:58288421-58288421_G>A |
| 6:170871013-170871013_A>G | 17:7577532-7577532_C>A | 17:61958402-61958402_C>T |
| 7:2577781-2577781_A>G | 17:7577533-7577533_C>G | 18:29470816-29470816_G>A |
| 7:6426892-6426892_C>T | 17:7577534-7577534_G>A | 18:45368211-45368211_C>G |
| 7:27832791-27832791_A>G | 17:7577535-7577535_G>C | 18:48575671-48575671_C>G |
| 7:43591930-43591930_G>A | 17:7577536-7577536_A>T | 18:48604754-48604754_G>T |
| 7:55259482-55259482_C>A | 17:7577538-7577538_G>A | 19:1223125-1223125_C>G |
| 7:55259515-55259515_T>G | 17:7577539-7577539_C>T | 19:22836805-22836805_G>A |
| 7:77379331-77379331_T>G | 17:7577541-7577541_A>T | 19:40383905-40383905_C>T |
| 7:100643088-100643088_A>G | 17:7577543-7577543_G>A | 19:49926533-49926533_C>G |
| 7:100677279-100677279_G>C | 17:7577544-7577544_T>G | 19:51274851-51274851_A>C |
| 7:138268672-138268672_C>T | 17:7577545-7577545_A>G | 19:56369444-56369444_G>A |
| 7:140453136-140453136_T>A | 17:7577547-7577547_G>T | 20:3209652-3209652_T>G |
| 7:140453137-140453137_G>A | 17:7577548-7577548_G>A | 20:6751034-6751034_A>G |
| 7:140481411-140481411_G>T | 17:7577549-7577549_C>G | 20:29623210-29623210_C>T |
| 7:140481412-140481412_G>C | 17:7577550-7577550_G>T | 20:29623224-29623224_C>A |
| 7:140481417-140481417_G>T | 17:7577551-7577551_G>C | 20:29628236-29628236_G>C |
| 7:140500165-140500165_T>C | 17:7577552-7577552_G>C | 20:29628263-29628263_A>G |
| 7:151970859-151970859_G>A | 17:7577554-7577554_A>T | 20:29632643-29632643_T>C |
| 7:151970951-151970951_G>A | 17:7577555-7577555_C>A | 20:31671497-31671497_C>T |
| 8:2796250-2796250_C>T | 17:7577556-7577556_G>A | 20:34242060-34242060_G>A |

FIG. 67G

| Chr No.:Position_Mutation | Chr No.:Position_Mutation | Chr No.:Position_Mutation |
|---|---|---|
| 8:2855562-2855562_A>G | 17:7577557-7577557_T>A | 20:57484420-57484420_C>T |
| 8:3009020-3009020_C>G | 17:7577559-7577559_C>A | 20:57484421-57484421_G>A |
| 8:3205603-3205603_G>A | 17:7577565-7577565_A>C | 21:10951281-10951281_G>A |
| 8:3245034-3245034_G>T | 17:7577566-7577566_A>G | 21:32127654-32127654_G>A |
| 8:10467948-10467948_C>T | 17:7577568-7577568_G>A | 22:16449539-16449539_T>C |
| 8:77768353-77768353_C>T | 17:7577569-7577569_T>A | 22:22899234-22899234_T>C |
| 8:89086854-89086854_G>A | 17:7577570-7577570_G>A | 22:29092948-29092948_C>T |
| 8:101083610-101083610_T>C | 17:7577571-7577571_T>A | 22:30398972-30398972_G>C |
| 8:109796543-109796543_G>A | 17:7577574-7577574_A>G | 23:15821891-15821891_C>G |
| 8:116426722-116426722_G>T | 17:7577575-7577575_T>A | 23:66765161-66765161_A>T |
| 8:121344960-121344960_G>A | 17:7577577-7577577_A>G | 23:78011285-78011285_G>A |
| 8:144940290-144940290_G>C | 17:7577580-7577580_A>G | 23:105153675-105153675_C>A |
| 8:144940331-144940331_G>A | 17:7577581-7577581_T>A | 17:7577586-7577586_T>G |

FIG. 67H

DETECTING MUTATIONS AND PLOIDY IN CHROMOSOMAL SEGMENTS

CROSS-REFERENCE TO RELATED APPLICATIONS

This application is a continuation-in-part of U.S. Utility application Ser. No. 17/214,403, filed Mar. 26, 2021. U.S. Utility application Ser. No. 17/214,403 is a continuation of U.S. Utility application Ser. No. 16/752,339, filed Jan. 24, 2020 (now U.S. Pat. No. 11,390,916). U.S. Utility application Ser. No. 16/752,339 is a continuation of U.S. Utility application Ser. No. 16/412,301, filed May 14, 2019 (now U.S. Pat. No. 10,597,709). U.S. Utility application Ser. No. 16/412,301 is a continuation of U.S. Utility application Ser. No. 15/336,630, filed Oct. 27, 2016 (now U.S. Pat. No. 10,351,906). U.S. Utility application Ser. No. 15/336,630 is a continuation of U.S. Utility application Ser. No. 14/538,982 filed Nov. 24, 2014 (now U.S. Pat. No. 9,677,118). U.S. Utility application Ser. No. 14/538,982 claims the benefit of and priority to U.S. Provisional Application Ser. No. 61/982,245, filed Apr. 21, 2014; U.S. Provisional Application Ser. No. 61/987,407, filed May 1, 2014; U.S. Provisional Application Ser. No. 61/994,791, filed May 16, 2014; and U.S. Provisional Application Ser. No. 62/066,514 filed Oct. 21, 2014. This application is also a continuation-in-part of U.S. Utility application Ser. No. 17/692,469, filed Mar. 11, 2022. U.S. Utility application Ser. No. 17/692,469 is a continuation of U.S. Utility application Ser. No. 15/898,145, filed Feb. 15, 2018 (now U.S. Pat. No. 11,319,595). U.S. Utility application Ser. No. 15/898,145 is a continuation of U.S. Utility application Ser. No. 14/692,703, filed Apr. 21, 2015 (now U.S. Pat. No. 10,179,937). U.S. Utility application Ser. No. 14/692,703 claims the benefit of and priority to U.S. Provisional Application Ser. No. 61/982,245, filed Apr. 21, 2014; U.S. Provisional Application Ser. No. 61/987,407, filed May 1, 2014; U.S. Provisional Application Ser. No. 61/994,791, filed May 16, 2014; U.S. Provisional Application Ser. No. 62/066,514, filed Oct. 21, 2014; U.S. Provisional Application Ser. No. 62/146,188, filed Apr. 10, 2015; U.S. Provisional Application Ser. No. 62/147,377, filed Apr. 14, 2015; U.S. Provisional Application Ser. No. 62/148,173, filed Apr. 15, 2015. The entirety of these applications are hereby incorporated herein by reference for the teachings therein.

FIELD OF THE INVENTION

The present invention generally relates to methods and systems for detecting ploidy of a chromosome segment, and methods and systems for detecting a single nucleotide variant.

BACKGROUND OF THE INVENTION

Copy number variation (CNV) has been identified as a major cause of structural variation in the genome, involving both duplications and deletions of sequences that typically range in length from 1,000 base pairs (1 kb) to 20 megabases (mb). Deletions and duplications of chromosome segments or entire chromosomes are associated with a variety of conditions, such as susceptibility or resistance to disease.

CNVs are often assigned to one of two main categories, based on the length of the affected sequence. The first category includes copy number polymorphisms (CNPs), which are common in the general population, occurring with an overall frequency of greater than 1%. CNPs are typically small (most are less than 10 kilobases in length), and they are often enriched for genes that encode proteins important in drug detoxification and immunity. A subset of these CNPs is highly variable with respect to copy number. As a result, different human chromosomes can have a wide range of copy numbers (e.g., 2, 3, 4, 5, etc.) for a particular set of genes. CNPs associated with immune response genes have recently been associated with susceptibility to complex genetic diseases, including psoriasis, Crohn's disease, and glomerulonephritis.

The second class of CNVs includes relatively rare variants that are much longer than CNPs, ranging in size from hundreds of thousands of base pairs to over 1 million base pairs in length. In some cases, these CNVs may have arisen during production of the sperm or egg that gave rise to a particular individual, or they may have been passed down for only a few generations within a family. These large and rare structural variants have been observed disproportionately in subjects with mental retardation, developmental delay, schizophrenia, and autism. Their appearance in such subjects has led to speculation that large and rare CNVs may be more important in neurocognitive diseases than other forms of inherited mutations, including single nucleotide substitutions.

Gene copy number can be altered in cancer cells. For instance, duplication of Chr1p is common in breast cancer, and the EGFR copy number can be higher than normal in non-small cell lung cancer. Cancer is one of the leading causes of death; thus, early diagnosis and treatment of cancer is important, since it can improve the patient's outcome (such as by increasing the probability of remission and the duration of remission). Early diagnosis can also allow the patient to undergo fewer or less drastic treatment alternatives. Many of the current treatments that destroy cancerous cells also affect normal cells, resulting in a variety of possible side-effects, such as nausea, vomiting, low blood cell counts, increased risk of infection, hair loss, and ulcers in mucous membranes. Thus, early detection of cancer is desirable since it can reduce the amount and/or number of treatments (such as chemotherapeutic agents or radiation) needed to eliminate the cancer.

Copy number variation has also been associated with severe mental and physical handicaps, and idiopathic learning disability. Non-invasive prenatal testing (NIPT) using cell-free DNA (cfDNA) can be used to detect abnormalities, such as fetal trisomies 13, 18, and 21, triploidy, and sex chromosome aneuploidies. Subchromosomal microdeletions, which can also result in severe mental and physical handicaps, are more challenging to detect due to their smaller size. Eight of the microdeletion syndromes have an aggregate incidence of more than 1 in 1000, making them nearly as common as fetal autosomal trisomies.

In addition, a higher copy number of CCL3L1 has been associated with lower susceptibility to HIV infection, and a low copy number of FCGR3B (the CD16 cell surface immunoglobulin receptor) can increase susceptibility to systemic lupus erythematosus and similar inflammatory autoimmune disorders.

Thus, improved methods are needed to detect deletions and duplications of chromosome segments or entire chromosomes. Preferably, these methods can be used to more accurately diagnose disease or an increased risk of disease, such as cancer or CNVs in a gestating fetus.

SUMMARY OF THE INVENTION

In illustrative embodiments, provided herein is a method for determining ploidy of a chromosomal segment in a sample of an individual. The method includes the following steps:

a. receiving allele frequency data comprising the amount of each allele present in the sample at each loci in a set of polymorphic loci on the chromosomal segment;
b. generating phased allelic information for the set of polymorphic loci by estimating the phase of the allele frequency data;
c. generating individual probabilities of allele frequencies for the polymorphic loci for different ploidy states using the allele frequency data;
d. generating joint probabilities for the set of polymorphic loci using the individual probabilities and the phased allelic information; and
e. selecting, based on the joint probabilities, a best fit model indicative of chromosomal ploidy, thereby determining ploidy of the chromosomal segment.

In one illustrative embodiment of the method for determining ploidy, the data is generated using nucleic acid sequence data, especially high throughput nucleic acid sequence data. In certain illustrative examples of the method for determining ploidy, the allele frequency data is corrected for errors before it is used to generate individual probabilities. In specific illustrative embodiments, the errors that are corrected include allele amplification efficiency bias. In other embodiments, the errors that are corrected include ambient contamination and genotype contamination. In some embodiments, errors that are corrected include allele amplification bias, ambient contamination and genotype contamination.

In certain embodiments of the method for determining ploidy, the individual probabilities are generated using a set of models of both different ploidy states and allelic imbalance fractions for the set of polymorphic loci. In these embodiments, and other embodiments, the joint probabilities are generated by considering the linkage between polymorphic loci on the chromosome segment.

Accordingly, in one illustrative embodiment that combines some of these embodiments, provided herein is a method for detecting chromosomal ploidy in a sample of an individual, that includes the following steps:

a. receiving nucleic acid sequence data for alleles at a set of polymorphic loci on a chromosome segment in the individual;
b. detecting allele frequencies at the set of loci using the nucleic acid sequence data;
c. correcting for allele amplification efficiency bias in the detected allele frequencies to generate corrected allele frequencies for the set of polymorphic loci;
d. generating phased allelic information for the set of polymorphic loci by estimating the phase of the nucleic acid sequence data;
e. generating individual probabilities of allele frequencies for the polymorphic loci for different ploidy states by comparing the corrected allele frequencies to a set of models of different ploidy states and allelic imbalance fractions of the set of polymorphic loci;
f. generating joint probabilities for the set of polymorphic loci by combining the individual probabilities considering the linkage between polymorphic loci on the chromosome segment; and
g. selecting, based on the joint probabilities, the best fit model indicative of chromosomal aneuploidy.

In another aspect, provided herein is a system for detecting chromosomal ploidy in a sample of an individual, the system comprising:

a. an input processor configured to receive allelic frequency data comprising the amount of each allele present in the sample at each loci in a set of polymorphic loci on the chromosomal segment;
b. a modeler configured to:
   i. generate phased allelic information for the set of polymorphic loci by estimating the phase of the allele frequency data; and
   ii. generate individual probabilities of allele frequencies for the polymorphic loci for different ploidy states using the allele frequency data; and
   iii. generate joint probabilities for the set of polymorphic loci using the individual probabilities and the phased allelic information; and
c. a hypothesis manager configured to select, based on the joint probabilities, a best fit model indicative of chromosomal ploidy, thereby determining ploidy of the chromosomal segment.

In certain embodiments of this system embodiment, the allele frequency data is data generated by a nucleic acid sequencing system. In certain embodiments, the system further comprises an error correction unit configured to correct for errors in the allele frequency data, wherein the corrected allele frequency data is used by the modeler for to generate individual probabilities. In certain embodiments the error correction unit corrects for allele amplification efficiency bias. In certain embodiments, the modeler generates the individual probabilities using a set of models of both different ploidy states and allelic imbalance fractions for the set of polymorphic loci. The modeler, in certain exemplary embodiments generates the joint probabilities by considering the linkage between polymorphic loci on the chromosome segment.

In one illustrative embodiment, provided herein is a system for detecting chromosomal ploidy in a sample of an individual, that includes the following:

a. an input processor configured to receive nucleic acid sequence data for alleles at a set of polymorphic loci on a chromosome segment in the individual and detect allele frequencies at the set of loci using the nucleic acid sequence data;
b. an error correction unit configured to correct for errors in the detected allele frequencies and generate corrected allele frequencies for the set of polymorphic loci;
c. a modeler configured to:
   i. generate phased allelic information for the set of polymorphic loci by estimating the phase of the nucleic acid sequence data;
   ii. generate individual probabilities of allele frequencies for the polymorphic loci for different ploidy states by comparing the phased allelic information to a set of models of different ploidy states and allelic imbalance fractions of the set of polymorphic loci; and
   iii. generate joint probabilities for the set of polymorphic loci by combining the individual probabilities considering the relative distance between polymorphic loci on the chromosome segment; and
d. a hypothesis manager configured to select, based on the joint probabilities, a best fit model indicative of chromosomal aneuploidy.

In certain aspects, the present invention provides a method for determining whether circulating tumor nucleic acids are present in a sample in an individual, comprising a. analyzing the sample to determine a ploidy at a set of polymorphic loci on a chromosome segment in the individual; and b. determining the level of allelic imbalance present at the polymorphic loci based on the ploidy determination, wherein an allelic imbalance equal to or greater than 0.4%, 0.45%, or 0.5% is indicative of the presence of circulating tumor nucleic acids in the sample.

In certain embodiments the method for determining whether circulating tumor nucleic acids are present, further comprises detecting a single nucleotide variant at a single nucleotide variance site in a set of single nucleotide variance locations, wherein detecting either an allelic imbalance equal to or greater than 45% or detecting the single nucleotide variant, or both, is indicative of the presence of circulating tumor nucleic acids in the sample.

In certain embodiments analyzing step in the method for determining whether circulating tumor nucleic acids are present, includes analyzing a set of chromosome segments known to exhibit aneuploidy in cancer. In certain embodiments analyzing step in the method for determining whether circulating tumor nucleic acids are present, includes analyzing between 1,000 and 50,000 or between 100 and 1000, polymorphic loci for ploidy.

In certain aspects, provided herein are methods for detecting single nucleotide variants in a sample. Accordingly, provided herein is a method for determining whether a single nucleotide variant is present at a set of genomic positions in a sample from an individual, the method comprising:

a. for each genomic position, generating an estimate of efficiency and a per cycle error rate for an amplicon spanning that genomic position, using a training data set;
b. receiving observed nucleotide identity information for each genomic position in the sample;
c. determining a set of probabilities of single nucleotide variant percentage resulting from one or more real mutations at each genomic position, by comparing the observed nucleotide identity information at each genomic position to a model of different variant percentages using the estimated amplification efficiency and the per cycle error rate for each genomic position independently; and
d. determining the most-likely real variant percentage and confidence from the set of probabilities for each genomic position.

In illustrative embodiments of the method for determining whether a single nucleotide variant is present, the estimate of efficiency and the per cycle error rate is generated for a set of amplicons that span the genomic position. For example, 2, 3, 4, 5, 10, 15, 20, 25, 50, 100 or more amplicons can be included that span the genomic position. In certain embodiments of this method for detecting one or more SNVs the limit of detection is 0.015%, 0.017%, or 0.02%.

In illustrative embodiments of the method for determining whether a single nucleotide variant is present, the observed nucleotide identity information comprises an observed number of total reads for each genomic position and an observed number of variant allele reads for each genomic position.

In illustrative embodiments of the method for determining whether a single nucleotide variant is present, the sample is a plasma sample and the single nucleotide variant is present in circulating tumor DNA of the sample.

In another embodiment, provided herein is a method for detecting one or more single nucleotide variants in a test sample from an individual. The method according to this embodiment, includes the following steps:

a. determining a median variant allele frequency for a plurality of control samples from each of a plurality of normal individuals, for each single nucleotide variant position in a set of single nucleotide variance positions based on results generated in a sequencing run, to identify selected single nucleotide variant positions having variant median allele frequencies in normal samples below a threshold value and to determine background error for each of the single nucleotide variant positions after removing outlier samples for each of the single nucleotide variant positions;
b. determining an observed depth of read weighted mean and variance for the selected single nucleotide variant positions for the test sample based on data generated in the sequencing run for the test sample; and
c. identifying using a computer, one or more single nucleotide variant positions with a statistically significant depth of read weighted mean compared to the background error for that position, thereby detecting the one or more single nucleotide variants.

In certain embodiments of this method for detecting one or more SNVs the sample is a plasma sample, the control samples are plasma samples, and the detected one or more single nucleotide variants detected is present in circulating tumor DNA of the sample. In certain embodiments of this method for detecting one or more SNVs the plurality of control samples comprises at least 25 samples. In certain embodiments of this method for detecting one or more SNVs, outliers are removed from the data generated in the high throughput sequencing run to calculate the observed depth of read weighted mean and observed variance are determined. In certain embodiments of this method for detecting one or more SNVs the depth of read for each single nucleotide variant position for the test sample is at least 100 reads.

In certain embodiments of this method for detecting one or more SNVs the sequencing run comprises a multiplex amplification reaction performed under limited primer reaction conditions. In certain embodiments of this method for detecting one or more SNVs the limit of detection is 0.015%, 0.017%, or 0.02%.

In one aspect, the invention features a method of determining if there is an overrepresentation of the number of copies of a first homologous chromosome segment as compared to a second homologous chromosome segment in the genome of one or more cells from an individual. In some embodiments, the method includes obtaining phased genetic data for the first homologous chromosome segment comprising, the identity of the allele present at that locus on the first homologous chromosome segment for each locus in a set of polymorphic loci on the first homologous chromosome segment, obtaining phased genetic data for the second homologous chromosome segment comprising the identity of the allele present at that locus on the second homologous chromosome segment for each locus in the set of polymorphic loci on the second homologous chromosome segment, and obtaining measured genetic allelic data comprising the amount of each allele present in a sample of DNA or RNA from one or more cells from the individual, for each of the alleles at each of the loci in the set of polymorphic loci. In some embodiments, the method includes enumerating a set of one or more hypotheses specifying the degree of overrepresentation of the first homologous chromosome segment in the genome of one or more cells from the individual, calculating (such as calculating on a computer) a likelihood of one or more of the hypotheses based on the obtained genetic data of the sample and the obtained phased genetic data, and selecting the hypothesis with the greatest likelihood, thereby determining the degree of overrepresentation of the number of copies of the first homologous chromosome segment in the genome of one or more cells from the individual. In some embodiments, the phased data includes inferred phased data using population based haplotype frequencies and/or measured phased data (e.g., phased data obtained by measuring a sample containing DNA or RNA from the individual or a relative of the individual).

In one aspect, the invention provides a method for determining if there is an overrepresentation of the number of copies of a first homologous chromosome segment as compared to a second homologous chromosome segment in the genome of one or more cells from an individual. In some embodiments, the method includes obtaining phased genetic data for the first homologous chromosome segment comprising the identity of the allele present at that locus on the first homologous chromosome segment for each locus in a set of polymorphic loci on the first homologous chromosome segment, obtaining phased genetic data for the second homologous chromosome segment comprising the identity of the allele present at that locus on the second homologous chromosome segment for each locus in the set of polymorphic loci on the second homologous chromosome segment, and obtaining measured genetic allelic data comprising the amount of each allele present in a sample of DNA or RNA from one or more cells from the individual for each of the alleles at each of the loci in the set of polymorphic loci. In some embodiments, the method includes enumerating a set of one or more hypotheses specifying the degree of overrepresentation of the first homologous chromosome segment; calculating, for each of the hypotheses, expected genetic data for the plurality of loci in the sample from the obtained phased genetic data; calculating (such as calculating on a computer) the data fit between the obtained genetic data of the sample and the expected genetic data for the sample; ranking one or more of the hypotheses according to the data fit; and selecting the hypothesis that is ranked the highest, thereby determining the degree of overrepresentation of the number of copies of the first homologous chromosome segment in the genome of one or more cells from the individual.

In one aspect, the invention features a method for determining if there is an overrepresentation of the number of copies of a first homologous chromosome segment as compared to a second homologous chromosome segment in the genome of one or more cells from an individual. In some embodiments, the method includes obtaining phased genetic data for the first homologous chromosome segment comprising the identity of the allele present at that locus on the first homologous chromosome segment for each locus in a set of polymorphic loci on the first homologous chromosome segment, obtaining phased genetic data for the second homologous chromosome segment comprising the identity of the allele present at that locus on the second homologous chromosome segment for each locus in the set of polymorphic loci on the second homologous chromosome segment, and obtaining measured genetic allelic data comprising, for each of the alleles at each of the loci in the set of polymorphic loci, the amount of each allele present in a sample of DNA or RNA from one or more target cells and one or more non-target cells from the individual. In some embodiments, the method includes enumerating a set of one or more hypotheses specifying the degree of overrepresentation of the first homologous chromosome segment; calculating (such as calculating on a computer), for each of the hypotheses, expected genetic data for the plurality of loci in the sample from the obtained phased genetic data for one or more possible ratios of DNA or RNA from the one or more target cells to the total DNA or RNA in the sample; calculating (such as calculating on a computer) for each possible ratio of DNA or RNA and for each hypothesis, the data fit between the obtained genetic data of the sample and the expected genetic data for the sample for that possible ratio of DNA or RNA and for that hypothesis; ranking one or more of the hypotheses according to the data fit; and selecting the hypothesis that is ranked the highest, thereby determining the degree of overrepresentation of the number of copies of the first homologous chromosome segment in the genome of one or more cells from the individual.

In one aspect, the invention features a method for determining if there is an overrepresentation of the number of copies of a first homologous chromosome segment as compared to a second homologous chromosome segment in the genome of one or more cells from an individual. In some embodiments, the method includes obtaining phased genetic data for the first homologous chromosome segment comprising the identity of the allele present at that locus on the first homologous chromosome segment for each locus in a set of polymorphic loci on the first homologous chromosome segment, obtaining phased genetic data for the second homologous chromosome segment comprising the identity of the allele present at that locus on the second homologous chromosome segment for each locus in the set of polymorphic loci on the second homologous chromosome segment, and obtaining measured genetic allelic data comprising the amount of each allele present in a sample of DNA or RNA from one or more target cells and one or more non-target cells from the individual for each of the alleles at each of the loci in the set of polymorphic loci. In some embodiments, the method includes enumerating a set of one or more hypotheses specifying the degree of overrepresentation of the first homologous chromosome segment; calculating (such as calculating on a computer), for each of the hypotheses, expected genetic data for the plurality of loci in the sample from the obtained phased genetic data for one or more possible ratios of DNA or RNA from the one or more target cells to the total DNA or RNA in the sample; calculating (such as calculating on a computer) for each locus in the plurality of loci, each possible ratio of DNA or RNA, and each hypothesis, the likelihood that the hypothesis is correct by comparing the obtained genetic data of the sample for that locus and the expected genetic data for that locus for that possible ratio of DNA or RNA and for that hypothesis; determining the combined probability for each hypothesis by combining the probabilities of that hypothesis for each locus and each possible ratio; and selecting the hypothesis with the greatest combined probability, thereby determining the degree of overrepresentation of the number of copies of the first homologous chromosome segment. In some embodiments, all of the loci are considered at once to calculate the probability of a particular hypothesis, and the hypothesis with the greatest probability is selected.

In one aspect, the invention features a method for determining a number of copies of a chromosome segment of interest in the genome of a fetus. In some embodiments, the method includes obtaining phased genetic data for at least one biological parent of the fetus, wherein the phased genetic data comprises the identity of the allele present for each locus in a set of polymorphic loci on a first homologous chromosome segment and a second homologous chromosome segment in a pair of homologous chromosome segments that comprises the chromosome segment of interest. In some embodiments, the method includes obtaining genetic data at the set of polymorphic loci on the chromosome segment of interest in a mixed sample of DNA or RNA comprising fetal DNA or RNA and maternal DNA or RNA from the mother of the fetus by measuring the quantity of each allele at each locus. In some embodiments, the method includes enumerating a set of one or more hypotheses specifying the number of copies of the chromosome segment of interest present in the genome of the fetus. In some embodiments, the method includes enumerating a set of one or more hypotheses specifying, for one or both parents, the number of copies of the first homologous chromosome segment or portion thereof from the parent in the genome of the fetus, the number of copies of the second homologous chromosome segment or portion thereof from the parent in the genome of the fetus, and the total number of copies of the chromosome segment of interest present in the genome of the fetus. In some embodiments, the method includes calculating (such as calculating on a computer), for each of the hypotheses, expected genetic data for the plurality of loci in the mixed sample from the obtained phased genetic data from the parent(s); calculating (such as calculating on a computer) the data fit between the obtained genetic data of the mixed sample and the expected genetic data for the mixed sample; ranking one or more of the hypotheses according to the data fit; and selecting the hypothesis that is ranked the highest, thereby determining the number of copies of the chromosome segment of interest in the genome of the fetus.

In one aspect, the invention features a method for determining a number of copies of a chromosome or chromosome segment of interest in the genome of a fetus. In some embodiments, the method includes obtaining phased genetic data for at least one biological parent of the fetus, wherein the phased genetic data comprises the identity of the allele present for each locus in a set of polymorphic loci on a first homologous chromosome segment and a second homologous chromosome segment in the parent. In some embodiments, the method includes obtaining genetic data at the set of polymorphic loci on the chromosome or chromosome segment in a mixed sample of DNA or RNA comprising fetal DNA or RNA and maternal DNA or RNA from the mother of the fetus by measuring the quantity of each allele at each locus. In some embodiments, the method includes enumerating a set of one or more hypotheses specifying the number of copies of the chromosome or chromosome segment of interest present in the genome of the fetus. In some embodiments, the method includes creating (such as creating on a computer) for each of the hypotheses, a probability distribution of the expected quantity of each allele at each of the plurality of loci in mixed sample from the (i) the obtained phased genetic data from the parent(s) and (ii) optionally the probability of one or more crossovers that may have occurred during the formation of a gamete that contributed a copy of the chromosome or chromosome segment of interest to the fetus; calculating (such as calculating on a computer) a fit, for each of the hypotheses, between (1) the obtained genetic data of the mixed sample and (2) the probability distribution of the expected quantity of each allele at each of the plurality of loci in mixed sample for that hypothesis; ranking one or more of the hypotheses according to the data fit; and selecting the hypothesis that is ranked the highest, thereby determining the number of copies of the chromosome segment of interest in the genome of the fetus.

In some embodiments, the method includes obtaining phased genetic data for the mother of the fetus. In some embodiments, the method includes enumerating a set of one or more hypotheses specifying the number of copies of the first homologous chromosome segment or portion thereof from the mother in the genome of the fetus, the number of copies of the second homologous chromosome segment or portion thereof from the mother in the genome of the fetus, and the total number of copies of the chromosome segment of interest present in the genome of the fetus. In some embodiments, the method includes calculating, for each of the hypotheses, expected genetic data for the plurality of loci in the mixed sample from the obtained phased genetic data from the mother.

In some embodiments, the expected genetic data for each of the hypotheses comprises the identity and an amount of one or more alleles at each locus in the plurality of loci from the maternal DNA or RNA and fetal DNA or RNA in the mixed sample. In some embodiments, the method includes calculating (such as calculating on a computer) expected genetic data by determining a fraction of fetal DNA or RNA and a fraction of maternal DNA or RNA in the mixed sample. In some embodiments, the method includes calculating, for each locus in the plurality of loci, the expected amount of one or more of the alleles for that locus in the maternal DNA or RNA in the mixed sample using the identity of the allele(s) present at that locus in the obtained phased genetic data of the mother and the fraction of maternal DNA or RNA in the mixed sample. In some embodiments, the method includes calculating (such as calculating on a computer), for each locus in the plurality of loci for each hypothesis, the expected amount of one or more of the alleles for that locus in the fetal DNA or RNA inherited from the mother in the mixed sample using the identity of the allele present at that locus in the first or second homologous chromosome segment from the mother that is specified by the hypothesis to have been inherited by the fetus, the number of copies of the first or second homologous chromosome segment from the mother that is specified by the hypothesis to have been inherited by the fetus, and the fraction of fetal DNA or RNA in the mixed sample.

In some embodiments, the expected genetic data for each of the hypotheses comprises the identity and an amount of one or more alleles at each locus in the plurality of loci from the maternal DNA or RNA and fetal DNA or RNA in the mixed sample. In some embodiments, the method includes calculating expected genetic data by determining a fraction of fetal DNA or RNA and a fraction of maternal DNA or RNA in the mixed sample. In some embodiments, the method includes calculating (such as calculating on a computer), for each locus in the plurality of loci, the expected amount of one or more of the alleles for that locus in the maternal DNA or RNA in the mixed sample using the identity of the allele(s) present at that locus in the obtained phased genetic data of the mother and the fraction of maternal DNA or RNA in the mixed sample. In some embodiments, the method includes calculating (such as calculating on a computer), for each locus in the plurality of loci for each hypothesis, the expected amount of one or more of the alleles for that locus in the fetal DNA or RNA inherited from the mother in the mixed sample using the identity of the allele present at that locus in the first or second homologous chromosome segment from the mother that is specified by the hypothesis to have been inherited by the fetus, the number of copies of the first or second homologous chromosome segment from the mother that is specified by the hypothesis to have been inherited by the fetus, the identity of one or more possible alleles at that locus in the first or second homologous chromosome segment from the father that is specified by the hypothesis to have been inherited by the fetus, the number of copies of the first or second homologous chromosome segment from the father that is specified by the hypothesis to have been inherited by the fetus, and the fraction of fetal DNA or RNA in the mixed sample. In some embodiments, population frequencies are used to predict the identity of the alleles in the first or second homologous chromosome segment from the father. In some embodiments, the probability for each of the possible alleles at each locus in the first or second homologous chromosome segment from the father are considered to be the same.

In some embodiments, the method includes obtaining phased genetic data for both the mother and father of the fetus. In some embodiments, the method includes enumerating a set of one or more hypotheses specifying the number of copies of the first homologous chromosome segment or portion thereof from the mother in the genome of the fetus, the number of copies of the second homologous chromosome segment or portion thereof from the mother in the genome of the fetus, the number of copies of the first homologous chromosome segment or portion thereof from the father in the genome of the fetus, the number of copies of the second homologous chromosome segment or portion thereof from the father in the genome of the fetus, and the total number of copies of the chromosome segment of interest present in the genome of the fetus. In some embodiments, the method includes calculating (such as calculating on a computer), for each of the hypotheses, expected genetic data for the plurality of loci in the mixed sample from the obtained phased genetic data from the mother and obtained phased genetic data from the father.

In some embodiments, the expected genetic data for each of the hypotheses comprises the identity and an amount of one or more alleles at each locus in the plurality of loci from the maternal DNA or RNA and fetal DNA or RNA in the mixed sample. In some embodiments, the method includes calculating expected genetic data by determining a fraction of fetal DNA or RNA and a fraction of maternal DNA or RNA in the mixed sample. In some embodiments, the method includes calculating (such as calculating on a computer), for each locus in the plurality of loci, the expected amount of one or more of the alleles for that locus in the maternal DNA or RNA in the mixed sample using the identity of the allele(s) present at that locus in the obtained phased genetic data of the mother and the fraction of maternal DNA or RNA in the mixed sample. In some embodiments, the method includes calculating (such as calculating on a computer), for each locus in the plurality of loci for each hypothesis, the expected amount of one or more of the alleles for that locus in the fetal DNA or RNA in the mixed sample using the identity of the allele present at that locus in the first or second homologous chromosome segment from the mother that is specified by the hypothesis to have been inherited by the fetus, the number of copies of the first or second homologous chromosome segment from the mother that is specified by the hypothesis to have been inherited by the fetus, the identity of the allele present at that locus in the first or second homologous chromosome segment from the father that is specified by the hypothesis to have been inherited by the fetus, the number of copies of the first or second homologous chromosome segment from the father that is specified by the hypothesis to have been inherited by the fetus, and the fraction of fetal DNA or RNA in the mixed sample.

In some embodiments, the method includes calculating (such as calculating on a computer), for each of the hypotheses, a probability distribution of expected genetic data for the plurality of loci in the mixed sample from the obtained phased genetic data from the parent(s). In some embodiments, the method includes increasing the probability in the probability distribution of an a particular allele being present at a first locus in the mixed sample if that particular allele is present in the first homologous segment in the parent and an allele at a nearby locus in the first homologous segment in the parent is observed in the obtained genetic data of the mixed sample; or decreasing the probability in the probability distribution of an a particular allele being present at a first locus in the mixed sample if that particular allele is present in the first homologous segment in the parent and an allele at a nearby locus in the first homologous segment in the parent is not observed in the obtained genetic data of the mixed sample. In some embodiments, the method includes increasing the probability in the probability distribution of an a particular allele being present at a second locus in the mixed sample if that particular allele is present in the second homologous segment in the parent and an allele at a nearby locus in the second homologous segment in the parent is observed in the obtained genetic data of the mixed sample; or decreasing the probability in the probability distribution of an a particular allele being present at a second locus in the mixed sample if that particular allele is present in the second homologous segment in the parent and an allele at a nearby locus in the second homologous segment in the parent is not observed in the obtained genetic data of the mixed sample.

In some embodiments, the method includes obtaining phased genetic data for both the mother and father of the fetus. In some embodiments, the method includes enumerating a set of one or more hypotheses specifying the number of copies of the first homologous chromosome segment or portion thereof from the mother in the genome of the fetus, the number of copies of the second homologous chromosome segment or portion thereof from the mother in the genome of the fetus, the number of copies of the first homologous chromosome segment or portion thereof from the father in the genome of the fetus, the number of copies of the second homologous chromosome segment or portion thereof from the father in the genome of the fetus, and the total number of copies of the chromosome segment of interest present in the genome of the fetus. In some embodiments, the method includes calculating (such as calculating on a computer), for each of the hypotheses, a probability distribution of expected genetic data for the plurality of loci in the mixed sample from the obtained phased genetic data from the mother and father. In some embodiments, the method includes increasing the probability in the probability distribution of an a particular allele being present at a first locus in the mixed sample if that particular allele is present in the first homologous segment in the mother or father and an allele at a nearby locus in the first homologous segment in that parent is observed in the obtained genetic data of the mixed sample; or decreasing the probability in the probability distribution of an a particular allele being present at a first locus in the mixed sample if that particular allele is present in the first homologous segment in the mother or father and an allele at a nearby locus in the first homologous segment in that parent is not observed in the obtained genetic data of the mixed sample. In some embodiments, the method includes increasing the probability in the probability distribution of an a particular allele being present at a second locus in the mixed sample if that particular allele is present in the second homologous segment in the mother or father and an allele at a nearby locus in the second homologous segment in that parent is observed in the obtained genetic data of the mixed sample; or decreasing the probability in the probability distribution of an a particular allele being present at a second locus in the mixed sample if that particular allele is present in the second homologous segment in the mother or father and an allele at a nearby locus in the second homologous segment in that parent is not observed in the obtained genetic data of the mixed sample.

In some embodiments, the first locus and the locus that is nearby to the first locus co-segregate. In some embodiments, the second locus and the locus that is nearby to the second locus co-segregate. In some embodiments, no crossovers are expected to occur between the first locus and the locus that is nearby to the first locus. In some embodiments, no crossovers are expected to occur between the second locus and the locus that is nearby to the second locus. In some embodiments, the distance between the first locus and the locus that is nearby to the first locus is less than 5 mb, 1 mb, 100 kb, 10 kb, 1 kb, 0.1 kb, or 0.01 kb. In some embodiments, the distance between the second locus and the locus that is nearby to the second locus is less than 5 mb, 1 mb, 100 kb, 10 kb, 1 kb, 0.1 kb, or 0.01 kb.

In some embodiments, one or more crossovers occurs during the formation of a gamete that contributed a copy of the chromosome segment of interest to the fetus; and the crossover produces a chromosome segment of interest in the genome of the fetus that comprises a portion of the first homologous segment and a portion of the second homologous segment from the parent. In some embodiments, the set of hypothesis comprises one or more hypotheses specifying the number of copies of the chromosome segment of interest in the genome of the fetus that comprises a portion of the first homologous segment and a portion of the second homologous segment from the parent.

In some embodiments, the expected genetic data of the mixed sample comprises the expected amount of one or more of the alleles at each locus in the plurality of loci in the mixed sample for each of the hypotheses.

In one aspect, the invention features a method of determining if there is an overrepresentation of the number of copies of a first homologous chromosome segment as compared to a second homologous chromosome segment in the genome of an individual (such as in the genome of one or more cells, cfDNA, cfRNA, an individual suspected of having cancer, a fetus, or an embryo) using phased genetic data. In some embodiments, the method involves simultaneously or sequentially in any order (i) obtaining phased genetic data for the first homologous chromosome segment comprising the identity of the allele present at that locus on the first homologous chromosome segment for each locus in a set of polymorphic loci on the first homologous chromosome segment, (ii) obtaining phased genetic data for the second homologous chromosome segment comprising the identity of the allele present at that locus on the second homologous chromosome segment for each locus in the set of polymorphic loci on the second homologous chromosome segment, and (iii) obtaining measured genetic allelic data comprising the amount of each allele at each of the loci in the set of polymorphic loci in a sample of DNA or RNA from one or more cells from the individual or in a mixed sample of cell-free DNA or RNA from two or more genetically different cells from the individual. In some embodiments, the method involves calculating allele ratios for one or more loci in the set of polymorphic loci that are heterozygous in at least one cell from which the sample was derived. In some embodiments, the calculated allele ratio for a particular locus is the measured quantity of one of the alleles divided by the total measured quantity of all the alleles for the locus. In some embodiments, the method involves determining if there is an overrepresentation of the number of copies of the first homologous chromosome segment by comparing one or more calculated allele ratios for a locus to an expected allele ratio, such as a ratio that is expected for that locus if the first and second homologous chromosome segments are present in equal proportions. In some embodiments, the expected ratio is 0.5 for biallelic loci.

In some embodiments for prenatal testing, the method involves simultaneously or sequentially in any order (i) obtaining phased genetic data for the first homologous chromosome segment in the genome of a fetus (such as a fetus gestating in a pregnant mother) comprising the identity of the allele present at that locus on the first homologous chromosome segment for each locus in a set of polymorphic loci on the first homologous chromosome segment, (ii) obtaining phased genetic data for the second homologous chromosome segment in the genome of the fetus comprising the identity of the allele present at that locus on the second homologous chromosome segment for each locus in the set of polymorphic loci on the second homologous chromosome segment, and (iii) obtaining measured genetic allelic data comprising the amount of each allele at each of the loci in the set of polymorphic loci in a mixed sample of DNA or RNA from the mother of the fetus that includes fetal DNA or RNA and maternal DNA or RNA (such as a mixed sample of cell-free DNA or RNA originating from a blood sample from the mother that includes fetal cell-free DNA or RNA and maternal cell-free DNA or RNA). In some embodiments, the method involves calculating allele ratios for one or more loci in the set of polymorphic loci that are heterozygous in the fetus and/or heterozygous in the mother. In some embodiments, the calculated allele ratio for a particular locus is the measured quantity of one of the alleles divided by the total measured quantity of all the alleles for the locus. In some embodiments, the method involves determining if there is an overrepresentation of the number of copies of the first homologous chromosome segment by comparing one or more calculated allele ratios for a locus to an expected allele ratio, such as a ratio that is expected for that locus if the first and second homologous chromosome segments are present in equal proportions.

In some embodiments, a calculated allele ratio is indicative of an overrepresentation of the number of copies of the first homologous chromosome segment if either (i) the allele ratio for the measured quantity of the allele present at that locus on the first homologous chromosome divided by the total measured quantity of all the alleles for the locus is greater than the expected allele ratio for that locus, or (ii) the allele ratio for the measured quantity of the allele present at that locus on the second homologous chromosome divided by the total measured quantity of all the alleles for the locus is less than the expected allele ratio for that locus. In some embodiments, a calculated allele ratio is indicative of no overrepresentation of the number of copies of the first homologous chromosome segment if either (i) the allele ratio for the measured quantity of the allele present at that locus on the first homologous chromosome divided by the total measured quantity of all the alleles for the locus is less than or equal to the expected allele ratio for that locus, or (ii) the allele ratio for the measured quantity of the allele present at that locus on the second homologous chromosome divided by the total measured quantity of all the alleles for the locus is greater than or equal to the expected allele ratio for that locus.

In some embodiments, determining if there is an overrepresentation of the number of copies of the first homologous chromosome segment includes enumerating a set of one or more hypotheses specifying the degree of overrepresentation of the first homologous chromosome segment. In some embodiments, predicted allele ratios for the loci that are heterozygous in at least one cell (such as the loci that are heterozygous in the fetus and/or heterozygous in the mother) are estimated for each hypothesis given the degree of overrepresentation specified by that hypothesis. In some embodiments, the likelihood that the hypothesis is correct is calculated by comparing the calculated allele ratios to the predicted allele ratios, and the hypothesis with the greatest likelihood is selected. In some embodiments, an expected distribution of a test statistic is calculated using the predicted allele ratios for each hypothesis. In some embodiments, the likelihood that the hypothesis is correct is calculated by comparing a test statistic that is calculated using the calculated allele ratios to the expected distribution of the test statistic that is calculated using the predicted allele ratios, and the hypothesis with the greatest likelihood is selected. In some embodiments, predicted allele ratios for the loci that are heterozygous in at least one cell (such as the loci that are heterozygous in the fetus and/or heterozygous in the mother) are estimated given the phased genetic data for the first homologous chromosome segment, the phased genetic data for the second homologous chromosome segment, and the degree of overrepresentation specified by that hypothesis. In some embodiments, the likelihood that the hypothesis is correct is calculated by comparing the calculated allele ratios to the predicted allele ratios; and the hypothesis with the greatest likelihood is selected.

In some embodiments, the ratio of DNA (or RNA) from one or more target cells to the total DNA (or RNA) in the sample is calculated. An exemplary ratio is the ratio of fetal DNA (or RNA) to the total DNA (or RNA) in the sample. In some embodiments, the ratio of fetal DNA to total DNA in the sample is determined by measuring the amount of an allele at one or more loci in which the fetus has the allele and the mother does not have the allele. In some embodiments, the ratio of fetal DNA to total DNA in the sample is determined by measuring the difference in methylation between one or more maternal and fetal alleles. In some embodiments, a set of one or more hypotheses specifying the degree of overrepresentation of the first homologous chromosome segment are enumerated. In some embodiments, predicted allele ratios for the loci that are heterozygous in at least one cell (such as the loci that are heterozygous in the fetus and/or heterozygous in the mother) are estimated given the calculated ratio of DNA or RNA and the degree of overrepresentation specified by that hypothesis are estimated for each hypothesis. In some embodiments, the likelihood that the hypothesis is correct is calculated by comparing the calculated allele ratios to the predicted allele ratios, and the hypothesis with the greatest likelihood is selected. In some embodiments, an expected distribution of a test statistic calculated using the predicted allele ratios and the calculated ratio of DNA or RNA is estimated for each hypothesis. In some embodiments, the likelihood that the hypothesis is correct is determined by comparing a test statistic calculated using the calculated allele ratios and the calculated ratio of DNA or RNA to the expected distribution of the test statistic calculated using the predicted allele ratios and the calculated ratio of DNA or RNA, and the hypothesis with the greatest likelihood is selected.

In some embodiments, the method includes enumerating a set of one or more hypotheses specifying the degree of overrepresentation of the first homologous chromosome segment. In some embodiments, the method includes estimating, for each hypothesis, either (i) predicted allele ratios for the loci that are heterozygous in at least one cell (such as the loci that are heterozygous in the fetus and/or heterozygous in the mother) given the degree of overrepresentation specified by that hypothesis or (ii) for one or more possible ratios of DNA or RNA (such as ratios of fetal DNA or RNA to the total DNA or RNA in the sample), an expected distribution of a test statistic calculated using the predicted allele ratios and the possible ratio of DNA or RNA from the one or more target cells (such as fetal cells) to the total DNA or RNA in the sample. In some embodiments, a data fit is calculated by comparing either (i) the calculated allele ratios to the predicted allele ratios, or (ii) a test statistic calculated using the calculated allele ratios and the possible ratio of DNA or RNA to the expected distribution of the test statistic calculated using the predicted allele ratios and the possible ratio of DNA or RNA. In some embodiments, one or more of the hypotheses are ranked according to the data fit, and the hypothesis that is ranked the highest is selected. In some embodiments, a technique or algorithm, such as a search algorithm, is used for one or more of the following steps: calculating the data fit, ranking the hypotheses, or selecting the hypothesis that is ranked the highest. In some embodiments, the data fit is a fit to a beta-binomial distribution or a fit to a binomial distribution. In some embodiments, the technique or algorithm is selected from the group consisting of maximum likelihood estimation, maximum a-posteriori estimation, Bayesian estimation, dynamic estimation (such as dynamic Bayesian estimation), and expectation-maximization estimation. In some embodiments, the method includes applying the technique or algorithm to the obtained genetic data and the expected genetic data.

In some embodiments, the method includes creating a partition of possible ratios (such as ratios of fetal DNA or RNA to the total DNA or RNA in the sample) that range from a lower limit to an upper limit for the ratio of DNA or RNA from the one or more target cells to the total DNA or RNA in the sample. In some embodiments, a set of one or more hypotheses specifying the degree of overrepresentation of the first homologous chromosome segment are enumerated. In some embodiments, the method includes estimating, for each of the possible ratios of DNA or RNA in the partition and for each hypothesis, either (i) predicted allele ratios for the loci that are heterozygous in at least one cell (such as the loci that are heterozygous in the fetus and/or heterozygous in the mother) given the possible ratio of DNA or RNA and the degree of overrepresentation specified by that hypothesis or (ii) an expected distribution of a test statistic calculated using the predicted allele ratios and the possible ratio of DNA or RNA. In some embodiments, the method includes calculating, for each of the possible ratios of DNA or RNA in the partition and for each hypothesis, the likelihood that the hypothesis is correct by comparing either (i) the calculated allele ratios to the predicted allele ratios, or (ii) a test statistic calculated using the calculated allele ratios and the possible ratio of DNA or RNA to the expected distribution of the test statistic calculated using the predicted allele ratios and the possible ratio of DNA or RNA. In some embodiments, the combined probability for each hypothesis is determined by combining the probabilities of that hypothesis for each of the possible ratios in the partition; and the hypothesis with the greatest combined probability is selected. In some embodiments, the combined probability for each hypothesis is determining by weighting the probability of a hypothesis for a particular possible ratio based on the likelihood that the possible ratio is the correct ratio.

In one aspect, the invention features a method for determining a number of copies of a chromosome or chromosome segment in the genome of one or more cells from an individual using phased or unphased genetic data. In some embodiments, the method involves obtaining genetic data at a set of polymorphic loci on the chromosome or chromosome segment in a sample by measuring the quantity of each allele at each locus. In some embodiments, the sample is a sample of DNA or RNA from one or more cells from the individual or a mixed sample of cell-free DNA from the individual that includes cell-free DNA from two or more genetically different cells. In some embodiments, allele ratios are calculated for the loci that are heterozygous in at least one cell from which the sample was derived. In some embodiments, the calculated allele ratio for a particular locus is the measured quantity of one of the alleles divided by the total measured quantity of all the alleles for the locus. In some embodiments, the calculated allele ratio for a particular locus is the measured quantity of one of the alleles (such as the allele on the first homologous chromosome segment) divided by the measured quantity of one or more other alleles (such as the allele on the second homologous chromosome segment) for the locus. In some embodiments, a set of one or more hypotheses specifying the number of copies of the chromosome or chromosome segment in the genome of one or more of the cells are enumerated. In some embodiments, the hypothesis that is most likely based on the test statistic is selected, thereby determining the number of copies of the chromosome or chromosome segment in the genome of one or more of the cells.

In one aspect, the invention features a method for determining a number of copies of a chromosome or chromosome segment in the genome of a fetus (such as a fetus that is gestating in a pregnant mother) using phased or unphased genetic data. In some embodiments, the method involves obtaining genetic data at a set of polymorphic loci on the chromosome or chromosome segment in a sample by measuring the quantity of each allele at each locus. In some embodiments, the sample is a mixed sample of DNA comprising fetal DNA or RNA and maternal DNA or RNA from the mother of the fetus (such as a mixed sample of cell-free DNA or RNA originating from a blood sample from the mother that includes fetal cell-free DNA or RNA and maternal cell-free DNA or RNA). In some embodiments, allele ratios are calculated for the loci that are heterozygous in the fetus and/or heterozygous in the mother. In some embodiments, the calculated allele ratio for a particular locus is the measured quantity of one of the alleles divided by the total measured quantity of all the alleles for the locus. In some embodiments, the calculated allele ratio for a particular locus is the measured quantity of one of the alleles (such as the allele on the first homologous chromosome segment) divided by the measured quantity of one or more other alleles (such as the allele on the second homologous chromosome segment) for the locus. In some embodiments, a set of one or more hypotheses specifying the number of copies of the chromosome or chromosome segment in the genome of fetus are enumerated. In some embodiments, the hypothesis that is most likely based on the test statistic is selected, thereby determining the number of copies of the chromosome or chromosome segment in the genome of the fetus.

In some embodiments, a hypotheses is selected if the probability that the test statistic belongs to a distribution of the test statistic for that hypothesis is above an upper threshold; one or more of the hypotheses is rejected if the probability that the test statistic belongs to the distribution of the test statistic for that hypothesis is below an lower threshold; or a hypothesis is neither selected nor rejected if the probability that the test statistic belongs to the distribution of the test statistic for that hypothesis is between the lower threshold and the upper threshold, or if the probability is not determined with sufficiently high confidence. In some embodiments, the overrepresentation of the number of copies of the first homologous chromosome segment is due to a duplication of the first homologous chromosome segment or a deletion of the second homologous chromosome segment. In some embodiments, the total measured quantity of all the alleles for one or more of the loci is compared to a reference amount to determine whether the overrepresentation of the number of copies of the first homologous chromosome segment is due to a duplication of the first homologous chromosome segment or a deletion of the second homologous chromosome segment. In some embodiments, the magnitude of the difference between the calculated allele ratio and the expected allele ratio for one or more loci is used to determine whether the overrepresentation of the number of copies of the first homologous chromosome segment is due to a duplication of the first homologous chromosome segment or a deletion of the second homologous chromosome segment. In some embodiments, the first and second homologous chromosome segments are determined to be present in equal proportions if there is not an overrepresentation of the number of copies of the first homologous chromosome segment, and there is not an overrepresentation of the second homologous chromosome segment (such as in the genome of the cells, cfDNA, cfRNA, individual, fetus, or embryo).

In some embodiments, the ratio of DNA from the one or more target cells to the total DNA in the sample is determined based on the total or relative amount of one or more alleles at one or more loci for which the genotype of the target cells differs from the genotype of the non-target cells and for which the target cells and non-target cells are expected to be disomic. In some embodiments, this ratio is used to determine whether the overrepresentation of the number of copies of the first homologous chromosome segment is due to a duplication of the first homologous chromosome segment or a deletion of the second homologous chromosome segment. In some embodiments, the ratio is used to determine the number of extra copies of a chromosome segment or chromosome that is duplicated. In some embodiments, the phased genetic data includes probabilistic data. In some embodiments, obtaining the phased genetic data for the first homologous chromosome segment and/or the second homologous chromosome segment in the genome of the fetus includes obtaining phased genetic data for the first homologous chromosome segment and/or the second homologous chromosome segment in the genome of one or both biological parents of the fetus, and inferring which homologous chromosome segment the fetus inherited from one or both biological parents. In some embodiments, the probability of one or more crossovers (such as 1, 2, 3, or 4 crossovers) that may have occurred during the formation of a gamete that contributed a copy of the first homologous chromosome segment or the second homologous chromosome segment to the fetus individual is used to infer which homologous chromosome segment(s) the fetus inherited from one or both biological parents. In some embodiments, phased genetic data for the mother and/or father of the fetus is obtained using a technique selected from the group consisting of digital PCR, inferring a haplotype using population based haplotype frequencies, haplotyping using a haploid cell such as a sperm or egg, haplotyping using genetic data from one or more first degree relatives, and combinations thereof. In some embodiments, the phased genetic data for the individual is obtained by phasing a portion or all of region corresponding to a deletion or duplication in a sample from the individual. In some embodiments, the phased genetic data for a fetus is obtained by phasing a portion or all of region corresponding to a deletion or duplication in a sample from the fetus or the mother of the fetus. In some embodiments, obtaining phased genetic data for the first and second homologous chromosome segments includes determining the identity of alleles present in one of the chromosome segments and determining the identity of alleles present in the other chromosome segment by inference. In some embodiments, alleles from unphased genetic data that are not present in the first homologous chromosome segment are assigned to the second homologous chromosome segment. For example, if the genotype of the individual is (AB, AB) and the phased data for the individual indicates that the first haplotype is (A,A); then, the other haplotype can be inferred to be (B,B). In some embodiments, if only one allele is measured at a locus then that allele is determined to be part of both the first and second homologous chromosome segments (e.g., if the genotype is AA at a locus than both haplotypes have the A allele). In some embodiments, the phased genetic data for the individual comprises determining whether or not one or more possible chromosome crossovers occurred, such as by determining the sequence of a recombination hotspot and optionally of a region flanking a recombination hotspot. In some embodiments, any of the primer libraries of the invention are used to detect a recombination event to determine what haplotype blocks are present in the genome of an individual.

In some embodiments, the method includes using a joint distribution model (such as a joint distribution model that takes into account the linkage between loci), performing a linkage analysis, using a binomial distribution model, using a beta-binomial distribution model, and/or using the likelihood of crossovers having occurred during the meiosis that gave rise to the gametes that formed the embryo that grew into the fetus (such as using the probability of chromosomes crossing over at different locations in a chromosome to model dependence between polymorphic alleles on the chromosome or chromosome segment of interest).

In some embodiments, one or more of the calculated allele ratios for the cfDNA or cfRNA are indicative of the corresponding allele ratios for DNA or RNA in the cells from which the cfDNA or cfRNA was derived. In some embodiments, one or more of the calculated allele ratios for the cfDNA or cfRNA are indicative of the corresponding allele ratios in the genome of the individual. In some embodiments, an allele ratio is only calculated or is only compared to an expected allele ratio if the measured genetic data indicate that more than one different allele is present for that locus in the sample (such as in a cfDNA or cfRNA sample). In some embodiments, an allele ratio is only calculated or is only compared to an expected allele ratio if the locus is heterozygous in at least one of the cells from which the sample was derived (such as a locus that is heterozygous in the fetus and/or heterozygous in the mother). In some embodiments, an allele ratio is only calculated or is only compared to an expected allele ratio if the locus is heterozygous in the fetus. In some embodiments, an allele ratio is calculated and compared to an expected allele ratio for a homozygous locus. For example, allele ratios for loci that are predicted to be homozygous for a particular individual being tested (or for both a fetus and pregnant mother) may be analyzed to determine the level of noise or error in the system.

In some embodiments, at least 10; 50; 100; 200; 300; 500; 750; 1,000; 2,000; 3,000; 4,000, or more loci (such as SNPs) are analyzed for a chromosome or chromosome segment of interest. In some embodiments, the average number of loci (such as SNPs) per mb in a chromosome or chromosome segment of interest is at least 1; 10; 25; 50; 100; 150; 200; 300; 500; 750; 1,000; or more loci per mb. In some embodiments, the average number of loci (such as SNPs) per mb in a chromosome or chromosome segment of interest is between 1 and 500 loci per mb, such as between 1 and 50, 50 and 100, 100 and 200, 200 and 400, 200 and 300, or 300 and 400 loci per mb, inclusive. In some embodiments, loci in multiple portions of a potential deletion or duplication are analyzed to increase the sensitivity and/or specificity of the CNV determination compared to only analyzing 1 loci or only analyzing a few loci that are near each other. In some embodiments, only the two most common alleles at each locus are measured or are used to determine the calculated allele ratio. In some embodiments, the amplification of loci is performed using a polymerase (e.g., a DNA polymerase, RNA polymerase, or reverse transcriptase) with low 5'→3' exonuclease and/or low strand displacement activity. In some embodiments, the measured genetic allelic data is obtained by (i) sequencing the DNA or RNA in the sample, (ii) amplifying DNA or RNA in the sample and then sequencing the amplified DNA, or (ii) amplifying the DNA or RNA in the sample, ligating PCR products, and then sequencing the ligated products. In some embodiments, measured genetic allelic data is obtained by dividing the DNA or RNA from the sample into a plurality of fractions, adding a different barcode to the DNA or RNA in each fraction (e.g., such that all the DNA or RNA in a particular fraction has the same barcode), optionally amplifying the barcoded DNA or RNA, combining the fractions, and then sequencing the barcoded DNA or RNA in the combined fractions. In some embodiments, alleles of the polymorphic loci (such as SNPs) are identified using one or more of the following methods: sequencing (such as nanopore sequencing or Halcyon Molecular sequencing), SNP array, real time PCR, TaqMan, Nanostring nCounter® Analysis System, Illumina GoldenGate Genotyping Assay that uses a discriminatory DNA polymerase and ligase, ligation-mediated PCR, or Linked Inverted Probes (LIPs; which can also be called pre-circularized probes, pre-circularizing probes, circularizing probes, Padlock Probes, or Molecular Inversion Probes (MIPs)). In some embodiments, two or more (such as 3 or 4) target amplicons are ligated together and then the ligated products are sequenced. In some embodiments, measurements for different alleles for the same locus are adjusted for differences in metabolism, apoptosis, histones, inactivation, and/or amplification between the alleles (such as differences in amplification efficiency between different alleles of the same locus). In some embodiments, this adjustment is performed prior to calculating allele ratios for the obtained genetic data or prior to comparing the measured genetic data to the expected genetic data.

In some embodiments, the method also includes determining the presence or absence of one or more risk factors for a disease or disorder. In some embodiments, the method also includes determining the presence or absence of one or more polymorphisms or mutations associated with the disease or disorder or an increased risk for a disease or disorder. In some embodiments, the method also includes determining the total level of cfDNA cf mDNA, cf nDNA, cfRNA, miRNA, or any combination thereof. In some embodiments, the method includes determining the level of one or more cfDNA cf mDNA, cf nDNA, cfRNA, and/or miRNA molecules of interest, such as molecules with a polymorphism or mutation associated with a disease or disorder or an increased risk for a disease or disorder. In some embodiments, the fraction of tumor DNA out of total DNA (such as the fraction of tumor cfDNA out of total cfDNA or the fraction of tumor cfDNA with a particular mutation out of total cfDNA) is determined. In some embodiments, this tumor fraction is used to determine the stage of a cancer (since higher tumor fractions can be associated with more advanced stages of cancer). In some embodiments, the method also includes determining the total level of DNA or RNA level. In some embodiments, the method includes determining the methylation level of one or more DNA or RNA molecules of interest, such as molecules with a polymorphism or mutation associated with a disease or disorder or an increased risk for a disease or disorder. In some embodiments, the method includes determining the presence or absence of a change in DNA integrity. In some embodiments, the method also includes determining the total level of mRNA splicing. In some embodiments, the method includes determining the level of mRNA splicing or detecting alternative mRNA splicing for one or RNA molecules of interest, such as molecules with a polymorphism or mutation associated with a disease or disorder or an increased risk for a disease or disorder.

In some embodiments, the invention features a method for detecting a cancer phenotype in an individual, wherein the cancer phenotype is defined by the presence of at least one of a set of mutations. In some embodiments, the method includes obtaining DNA or RNA measurements for a sample of DNA or RNA from one or more cells from the individual, wherein one or more of the cells is suspected of having the cancer phenotype; and analyzing the DNA or RNA measurements to determine, for each of the mutations in the set of mutations, the likelihood that at least one of the cells has that mutation. In some embodiments, the method includes determining that the individual has the cancer phenotype if either (i) for at least one of the mutations, the likelihood that at least one of the cells contains that mutations is greater than a threshold, or (ii) for at least one of the mutations, the likelihood that at least one of the cells has that mutations is less than the threshold, and for a plurality of the mutations, the combined likelihood that at least one of the cells has at least one of the mutations is greater than the threshold. In some embodiments, one or more cells have a subset or all of the mutations in the set of mutations. In some embodiments, the subset of mutations is associated with cancer or an increased risk for cancer. In some embodiments, the sample includes cell-free DNA or RNA. In some embodiments, the DNA or RNA measurements include measurements (such as the quantity of each allele at each locus) at a set of polymorphic loci on one or more chromosomes or chromosome segments of interest.

In one aspect, the invention features methods for selecting a therapy for the treatment, stabilization, or prevention of a disease or disorder in a mammal. In some embodiments, the method includes determining if there is an overrepresentation of the number of copies of a first homologous chromosome segment as compared to a second homologous chromosome segment using any of the methods described herein. In some embodiments, a therapy is selected for the mammal (such as a therapy for a disease or disorder associated with the overrepresentation of the first homologous chromosome segment).

In one aspect, the invention features methods for preventing, delaying, stabilizing, or treating a disease or disorder in a mammal. In some embodiments, the method includes determining if there is an overrepresentation of the number of copies of a first homologous chromosome segment as compared to a second homologous chromosome segment using any of the methods described herein. In some embodiments, a therapy is selected for the mammal (such as a therapy for a disease or disorder associated with the overrepresentation of the first homologous chromosome segment) and then the therapy is administered to the mammal.

In some embodiments, treating, stabilizing, or preventing a disease or disorder includes preventing or delaying an initial or subsequent occurrence of a disease or disorder, increasing the disease-free survival time between the disappearance of a condition and its reoccurrence, stabilizing or reducing an adverse symptom associated with a condition, or inhibiting or stabilizing the progression of a condition. In some embodiments, at least 20, 40, 60, 80, 90, or 95% of the treated subjects have a complete remission in which all evidence of the condition disappears. In some embodiments, the length of time a subject survives after being diagnosed with a condition and treated is at least 20, 40, 60, 80, 100, 200, or even 500% greater than (i) the average amount of time an untreated subject survives or (ii) the average amount of time a subject treated with another therapy survives.

In some embodiments, treating, stabilizing, or preventing cancer includes reducing or stabilizing the size of a tumor (e.g., a benign or malignant tumor), slowing or preventing an increase in the size of a tumor, reducing or stabilizing the number of tumor cells, increasing the disease-free survival time between the disappearance of a tumor and its reappearance, preventing an initial or subsequent occurrence of a tumor, or reducing or stabilizing an adverse symptom associated with a tumor. In one embodiment, the number of cancerous cells surviving the treatment is at least 10, 20, 40, 60, 80, or 100% lower than the initial number of cancerous cells, as measured using any standard assay. In some embodiments, the decrease in the number of cancerous cells induced by administration of a therapy of the invention is at least 2, 5, 10, 20, or 50-fold greater than the decrease in the number of non-cancerous cells. In some embodiments, the number of cancerous cells present after administration of a therapy is at least 2, 5, 10, 20, or 50-fold lower than the number of cancerous cells present after administration of a control (such as administration of saline or a buffer). In some embodiments, the methods of the present invention result in a decrease of 10, 20, 40, 60, 80, or 100% in the size of a tumor as determined using standard methods. In some embodiments, at least 10, 20, 40, 60, 80, 90, or 95% of the treated subjects have a complete remission in which there are no detectable cancerous cells. In some embodiments, the cancer does not reappear, or reappears after at least 2, 5, 10, 15, or 20 years. In some embodiments, the length of time a subject survives after being diagnosed with cancer and treated with a therapy of the invention is at least 10, 20, 40, 60, 80, 100, 200, or even 500% greater than (i) the average amount of time an untreated subject survives or (ii) the average amount of time a subject treated with another therapy survives.

In one aspect, the invention features methods for stratification of subjects involved in a clinical trial for the treatment, stabilization, or prevention of a disease or disorder in a mammal. In some embodiments, the method includes determining if there is an overrepresentation of the number of copies of a first homologous chromosome segment as compared to a second homologous chromosome segment using any of the methods described herein before, during, or after the clinical trial. In some embodiments, the presence or absence of the overrepresentation of the first homologous chromosome segment in the genome of the subject places the subject into a subgroup for the clinical trial.

In some embodiments, the disease or disorder is selected from the group consisting of cancer, mental handicap, learning disability (e.g., idiopathic learning disability), mental retardation, developmental delay, autism, neurodegenerative disease or disorder, schizophrenia, physical handicap, autoimmune disease or disorder, systemic lupus erythematosus, psoriasis, Crohn's disease, glomerulonephritis, HIV infection, AIDS, and combinations thereof. In some embodiments, the disease or disorder is selected from the group consisting of DiGeorge syndrome, DiGeorge 2 syndrome, DiGeorge/VCFS syndrome, Prader-Willi syndrome, Angelman syndrome, Beckwith-Wiedemann syndrome, 1p36 deletion syndrome, 2q37 deletion syndrome, 3929 deletion syndrome, 9q34 deletion syndrome, 17q21.31 deletion syndrome, Cri-du-chat syndrome, Jacobsen syndrome, Miller Dieker syndrome, Phelan-McDermid syndrome, Smith-Magenis syndrome, WAGR syndrome, Wolf-Hirschhorn syndrome, Williams syndrome, Williams-Beuren syndrome, Miller-Dieker syndrome, Phelan-McDermid syndrome, Smith-Magenis syndrome, Down syndrome, Edward syndrome, Patau syndrome, Klinefelter syndrome, Turner syndrome, 47,XXX syndrome, 47,XYY syndrome, Sotos syndrome, and combinations thereof. In some embodiments, the method determines the presence or absence of one or more of the following chromosomal abnormalities: nullsomy, monosomy, uniparental disomy, trisomy, matched trisomy, unmatched trisomy, maternal trisomy, paternal trisomy, triploidy, mosaicism tetrasomy, matched tetrasomy, unmatched tetrasomy, other aneuploidies, unbalanced translocations, balanced translocations, insertions, deletions, recombinations, and combinations thereof. In some embodiments, the chromosomal abnormality is any deviation in the copy number of a specific chromosome or chromosome segment from the most common number of copies of that segment or chromosome, for example in a human somatic cell, any deviation from 2 copies can be regarded as a chromosomal abnormality. In some embodiments, the method determines the presence or absence of a euploidy. In some embodiments, the copy number hypotheses include one or more copy number hypotheses for a singleton pregnancy. In some embodiments, the copy number hypotheses include one or more copy number hypotheses for a multiple pregnancy, such as a twin pregnancy (e.g., identical or fraternal twins or a vanishing twin). In some embodiments, the copy number hypotheses include all fetuses in a multiple pregnancy being euploid, all fetuses in a multiple pregnancy being aneuploid (such as any of the aneuploidies disclosed herein), and/or one or more fetuses in a multiple pregnancy being euploid and one or more fetuses in a multiple pregnancy being aneuploidy. In some embodiments, the copy number hypotheses include identical twins (also referred to as monozygotic twins) or fraternal twins (also referred to as dizygotic twins). In some embodiments, the copy number hypotheses include a molar pregnancy, such as a complete or partial molar pregnancy. In some embodiments, the chromosome segment of interest is an entire chromosome. In some embodiments, the chromosome or chromosome segment is selected from the group consisting of chromosome 13, chromosome 18, chromosome 21, the X chromosome, the Y chromosome, segments thereof, and combinations thereof. In some embodiments, the first homologous chromosome segment and second homologous chromosome segment are a pair of homologous chromosome segments that comprises the chromosome segment of interest. In some embodiments, the first homologous chromosome segment and second homologous chromosome segment are a pair of homologous chromosomes of interest. In some embodiments, a confidence is computed for the CNV determination or the diagnosis of the disease or disorder.

In some embodiments, the deletion is a deletion of at least 0.01 kb, 0.1 kb, 1 kb, 10 kb, 100 kb, 1 mb, 2 mb, 3 mb, 5 mb, 10 mb, 15 mb, 20 mb, 30 mb, or 40 mb. In some embodiments, the deletion is a deletion of between 1 kb to 40 mb, such as between 1 kb to 100 kb, 100 kb to 1 mb, 1 to 5 mb, 5 to 10 mb, 10 to 15 mb, 15 to 20 mb, 20 to 25 mb, 25 to 30 mb, or 30 to 40 mb, inclusive. In some embodiments, one copy of the chromosome segment is deleted and one copy is present. In some embodiments, two copies of the chromosome segment are deleted. In some embodiments, an entire chromosome is deleted.

In some embodiments, the duplication is a duplication of at least 0.01 kb, 0.1 kb, 1 kb, 10 kb, 100 kb, 1 mb, 2 mb, 3 mb, 5 mb, 10 mb, 15 mb, 20 mb, 30 mb, or 40 mb. In some embodiments, the duplication is a duplication of between 1 kb to 40 mb, such as between 1 kb to 100 kb, 100 kb to 1 mb, 1 to 5 mb, 5 to 10 mb, 10 to 15 mb, 15 to 20 mb, 20 to 25 mb, 25 to 30 mb, or 30 to 40 mb, inclusive. In some embodiments, the chromosome segment is duplicated one time. In some embodiments, the chromosome segment is duplicated more than one time, such as 2, 3, 4, or 5 times. In some embodiments, an entire chromosome is duplicated. In some embodiments, a region in a first homologous segment is deleted, and the same region or another region in the second homologous segment is duplicated. In some embodiments, at least 50, 60, 70, 80, 90, 95, 96, 98, 99, or 100% of the SNVs tested for are transversion mutations rather than transition mutations.

In some embodiments, the sample comprises DNA and/or RNA from (i) one or more target cells or (ii) one or more non-target cells. In some embodiments, the sample is a mixed sample with DNA and/or RNA from one or more target cells and one or more non-target cells. In some embodiments, the target cells are cells that have a CNV, such as a deletion or duplication of interest, and the non-target cells are cells that do not have the copy number variation of interest. In some embodiments in which the one or more target cells are cancer cell(s) and the one or more non-target cells are non-cancerous cell(s), the method includes determining if there is an overrepresentation of the number of copies of the first homologous chromosome segment in the genome of one or more of the cancer cells. In some embodiments in which the one or more target cells are genetically identical cancer cell(s) and the one or more non-target cells are non-cancerous cell(s), the method includes determining if there is an overrepresentation of the number of copies of the first homologous chromosome segment in the genome of the cancer cell(s). In some embodiments in which the one or more target cells are genetically non-identical cancer cell(s) and the one or more non-target cells are non-cancerous cell(s), the method includes determining if there is an overrepresentation of the number of copies of the first homologous chromosome segment in the genome of one or more of the genetically non-identical cancer cells. In some embodiments in which the sample comprises cell-free DNA from a mixture of one or more cancer cells and one or more non-cancerous cells, the method includes determining if there is an overrepresentation of the number of copies of the first homologous chromosome segment in the genome of one or more of the cancer cells. In some embodiments in which the one or more target cells are genetically identical fetal cell(s) and the one or more non-target cells are maternal cell(s), the method includes determining if there is an overrepresentation of the number of copies of the first homologous chromosome segment in the genome of the fetal cell(s). In some embodiments in which the one or more target cells are genetically non-identical fetal cell(s) and the one or more non-target cells are maternal cell(s), the method includes determining if there is an overrepresentation of the number of copies of the first homologous chromosome segment in the genome of one or more of the genetically non-identical fetal cells. As the cells of most individuals contain a nearly identical set of nuclear DNA, the term "target cell" may be used interchangeably with the term "individual" in some embodiments. Cancerous cells have genotypes that are distinct from the host individual. In this case, the cancer itself may be considered an individual. Moreover, many cancers are heterogeneous meaning that different cells in a tumor are genetically distinct from other cells in the same tumor. In this case, the different genetically identical regions can be considered different individuals. Alternately, the cancer may be considered a single individual with a mixture of cells with distinct genomes. Typically, non-target cells are euploid, though this is not necessarily the case.

In some embodiments, the sample is obtained from a maternal whole blood sample or fraction thereof, cells isolated from a maternal blood sample, an amniocentesis sample, a products of conception sample, a placental tissue sample, a chorionic villus sample, a placental membrane sample, a cervical mucus sample, or a sample from a fetus. In some embodiments, the sample comprises cell-free DNA obtained from a blood sample or fraction thereof from the mother. In some embodiments, the sample comprises nuclear DNA obtained from a mixture of fetal cells and maternal cells. In some embodiments, the sample is obtained from a fraction of maternal blood containing nucleated cells that has been enriched for fetal cells. In some embodiments, a sample is divided into multiple fractions (such as 2, 3, 4 5, or more fractions) that are each analyzed using a method of the invention. If each fraction produces the same results (such as the presence or absence of one or more CNVs of interest), the confidence in the results increases. In different fractions produce different results, the sample could be re-analyzed or another sample could be collected from the same subject and analyzed.

Exemplary subjects include mammals, such as humans and mammals of veterinary interest. In some embodiments, the mammal is a primate (e.g., a human, a monkey, a gorilla, an ape, a lemur, etc.), a bovine, an equine, a porcine, a canine, or a feline.

In some embodiments, any of the methods include generating a report (such as a written or electronic report) disclosing a result of the method of the invention (such as the presence or absence of a deletion or duplication).

In some embodiments, any of the methods include taking a clinical action based on a result of a method of the invention (such as the presence or absence of a deletion or duplication). In some embodiments in which an embryo or fetus has one or more polymorphisms or mutations of interest (such as a CNV) based on a result of a method of the invention, the clinical action includes performing additional testing (such as testing to confirm the presence of the polymorphism or mutation), not implanting the embryo for IVF, implanting a different embryo for IVF, terminating a pregnancy, preparing for a special needs child, or undergoing an intervention designed to decrease the severity of the phenotypic presentation of a genetic disorder. In some embodiments, the clinical action is selected from the group consisting of performing an ultrasound, amniocentesis on the fetus, amniocentesis on a subsequent fetus that inherits genetic material from the mother and/or father, chorion villus biopsy on the fetus, chorion villus biopsy on a subsequent fetus that inherits genetic material from the mother and/or father, in vitro fertilization, preimplantation genetic diagnosis on one or more embryos that inherited genetic material from the mother and/or father, karyotyping on the mother, karyotyping on the father, fetal echocardiogram (such as an echocardiogram of a fetus with trisomy 21, 18, or 13, monosomy X, or a microdeletion) and combinations thereof. In some embodiments, the clinical action is selected from the group consisting of administering growth hormone to a born child with monosomy X (such as administration starting at ~9 months), administering calcium to a born child with a 22q deletion (such as DiGeorge syndrome), administering an androgen such as testosterone to a born child with 47,XXY (such as one injection per month for 3 months of 25 mg testosterone enanthate to an infant or toddler), performing a test for cancer on a woman with a complete or partial molar pregnancy (such as a triploid fetus), administering a therapy for cancer such as a chemotherapeutic agent to a woman with a complete or partial molar pregnancy (such as a triploid fetus), screening a fetus determined to be male (such as a fetus determined to be male using a method of the invention) for one or more X-linked genetic disorders such as Duchenne muscular dystrophy (DMD), adrenoleukodystrophy, or hemophilia, performing amniocentesis on a male fetus at risk for an X-linked disorder, administering dexamethasone to a women with a female fetus (such as a fetus determined to be female using a method of the invention) at risk for congenital adrenal hyperplasia, performing amniocentesis on a female fetus at risk for congenital adrenal hyperplasia, administering killed vaccines (instead of live vaccines) or not administering certain vaccines to a born child that is (or is suspected of being) immune deficient from a 22q11.2 deletion, performing occupational and/or physical therapy, performing early intervention in education, delivering the baby at a tertiary care center with a NICU and/or having pediatric specialists available at delivery, behavioral intervention for born child (such as a child with XXX, XXY, or XYY), and combinations thereof.

In some embodiments, ultrasound or another screening test is performed on a women determined to have multiple pregnancies (such as twins) to determine whether or not two or more of the fetus are monochorionic. Monozygotic twins result from ovulation and fertilization of a single oocyte, with subsequent division of the zygote; placentation may be dichorionic or monochorionic. Dizygotic twins occur from ovulation and fertilization of two oocytes, which usually results in dichorionic placentation. Monochorionic twins have a risk of twin-to-twin transfusion syndrome, which may cause unequal distribution of blood between fetuses that results in differences in their growth and development, sometimes resulting in stillbirth. Thus, twins determined to be monozygotic twins using a method of the invention are desirably tested (such as by ultrasound) to determine if they are monochorionic twins, and if so, these twins can be monitored (such as bi-weekly ultrasounds from 16 weeks) for signs of win-to-twin transfusion syndrome.

In some embodiments in which an embryo or fetus does not have one or more one or more polymorphisms or mutations of interest (such as a CNV) based on a result of a method of the invention, the clinical action includes implanting the embryo for IVF or continuing a pregnancy. In some embodiments, the clinical action is additional testing to confirm the absence of the polymorphism or mutation selected from the group consisting of performing an ultrasound, amniocentesis, chorion villus biopsy, and combinations thereof.

In some embodiments in which an individual has one or more one or more polymorphisms or mutations (such as a polymorphism or mutation associated with a disease or disorder such as cancer or an increased risk for a disease or disorder such as cancer) based on a result of a method of the invention, the clinical action includes performing additional testing or administering one or more therapies for a disease or disorder (such as a therapy for cancer, a therapy for the specific type of cancer or type of mutation the individual is diagnosed with, or any of the therapies disclosed herein). In some embodiments, the clinical action is additional testing to confirm the presence or absence of a polymorphism or mutation selected from the group consisting of biopsy, surgery, medical imaging (such as a mammogram or an ultrasound), and combinations thereof.

In some embodiments, the additional testing includes performing the same or a different method (such as any of the methods described herein) to confirm the presence or absence of the polymorphism or mutation (such as a CNV), such as testing either a second fraction of the same sample that was tested or a different sample from the same individual (such as the same pregnant mother, fetus, embryo, or individual at increased risk for cancer). In some embodiments, the additional testing is performed for an individual for whom the probability of a polymorphism or mutation (such as a CNV) is above a threshold value (such as additional testing to confirm the presence of a likely polymorphism or mutation). In some embodiments, the additional testing is performed for an individual for whom the confidence or z-score for the determination of a polymorphism or mutation (such as a CNV) is above a threshold value (such as additional testing to confirm the presence of a likely polymorphism or mutation). In some embodiments, the additional testing is performed for an individual for whom the confidence or z-score for the determination of a polymorphism or mutation (such as a CNV) is between minimum and maximum threshold values (such as additional testing to increase the confidence that the initial result is correct). In some embodiments, the additional testing is performed for an individual for whom the confidence for the determination of the presence or absence of a polymorphism or mutation (such as a CNV) is below a threshold value (such as a "no call" result due to not being able to determine the presence or absence of the CNV with sufficient confidence). An exemplary Z core is calculated in Chiu et al. BMJ 2011; 342: c7401 (which is hereby incorporated by reference in its entirety) in which chromosome 21 is used as an example and can be replaced with any other chromosome or chromosome segment in the test sample.

Z score for percentage chromosome 21 in test case=((percentage chromosome 21 in test case)−(mean percentage chromosome 21 in reference controls))/(standard deviation of percentage chromosome 21 in reference controls).

In some embodiments, the additional testing is performed for an individual for whom the initial sample did not meet quality control guidelines or had a fetal fraction or a tumor fraction below a threshold value. In some embodiments, the method includes selecting an individual for additional testing based on the result of a method of the invention, the probability of the result, the confidence of the result, or the z-score; and performing the additional testing on the individual (such as on the same or a different sample). In some embodiments, a subject diagnosed with a disease or disorder (such as cancer) undergoes repeat testing using a method of the invention or known testing for the disease or disorder at multiple time points to monitor the progression of the disease or disorder or the remission or reoccurrence of the disease or disorder.

In one aspect, the invention features a report (such as a written or electronic report) with a result from a method of the invention (such as the presence or absence of a deletion or duplication).

In various embodiments, the primer extension reaction or the polymerase chain reaction includes the addition of one or more nucleotides by a polymerase. In some embodiments, the primers are in solution. In some embodiments, the primers are in solution and are not immobilized on a solid support. In some embodiments, the primers are not part of a microarray. In various embodiments, the primer extension reaction or the polymerase chain reaction does not include ligation-mediated PCR. In various embodiments, the primer extension reaction or the polymerase chain reaction does not include the joining of two primers by a ligase. In various embodiments, the primers do not include Linked Inverted Probes (LIPs), which can also be called pre-circularized probes, pre-circularizing probes, circularizing probes, Padlock Probes, or Molecular Inversion Probes (MIPs).

It is understood that aspects and embodiments of the invention described herein include combinations of any two or more of the aspects or embodiments of the invention.

Definitions

Single Nucleotide Polymorphism (SNP) refers to a single nucleotide that may differ between the genomes of two members of the same species. The usage of the term should not imply any limit on the frequency with which each variant occurs.

Sequence refers to a DNA sequence or a genetic sequence. It may refer to the primary, physical structure of the DNA molecule or strand in an individual. It may refer to the sequence of nucleotides found in that DNA molecule, or the complementary strand to the DNA molecule. It may refer to the information contained in the DNA molecule as its representation in silico.

Locus refers to a particular region of interest on the DNA of an individual, which may refer to a SNP, the site of a possible insertion or deletion, or the site of some other relevant genetic variation. Disease-linked SNPs may also refer to disease-linked loci.

Polymorphic Allele, also "Polymorphic Locus," refers to an allele or locus where the genotype varies between individuals within a given species. Some examples of polymorphic alleles include single nucleotide polymorphisms, short tandem repeats, deletions, duplications, and inversions.

Polymorphic Site refers to the specific nucleotides found in a polymorphic region that vary between individuals.

Mutation refers to an alteration in a naturally-occurring or reference nucleic acid sequence, such as an insertion, deletion, duplication, translocation, substitution, frameshift mutation, silent mutation, nonsense mutation, missense mutation, point mutation, transition mutation, transversion mutation, reverse mutation, or microsatellite alteration. In some embodiments, the amino acid sequence encoded by the nucleic acid sequence has at least one amino acid alteration from a naturally-occurring sequence.

Allele refers to the genes that occupy a particular locus.

Genetic Data also "Genotypic Data" refers to the data describing aspects of the genome of one or more individuals. It may refer to one or a set of loci, partial or entire sequences, partial or entire chromosomes, or the entire genome. It may refer to the identity of one or a plurality of nucleotides; it may refer to a set of sequential nucleotides, or nucleotides from different locations in the genome, or a combination thereof. Genotypic data is typically in silico, however, it is also possible to consider physical nucleotides in a sequence as chemically encoded genetic data. Genotypic Data may be said to be "on," "of," "at," "from" or "on" the individual(s). Genotypic Data may refer to output measurements from a genotyping platform where those measurements are made on genetic material.

Genetic Material also "Genetic Sample" refers to physical matter, such as tissue or blood, from one or more individuals comprising DNA or RNA.

Confidence refers to the statistical likelihood that the called SNP, allele, set of alleles, determined number of copies of a chromosome or chromosome segment, or diagnosis of the presence or absence of a disease correctly represents the real genetic state of the individual.

Ploidy Calling, also "Chromosome Copy Number Calling," or "Copy Number Calling" (CNC), may refer to the act of determining the quantity and/or chromosomal identity of one or more chromosomes or chromosome segments present in a cell.

Aneuploidy refers to the state where the wrong number of chromosomes (e.g., the wrong number of full chromosomes or the wrong number of chromosome segments, such as the presence of deletions or duplications of a chromosome segment) is present in a cell. In the case of a somatic human cell it may refer to the case where a cell does not contain 22 pairs of autosomal chromosomes and one pair of sex chromosomes. In the case of a human gamete, it may refer to the case where a cell does not contain one of each of the 23 chromosomes. In the case of a single chromosome type, it may refer to the case where more or less than two homologous but non-identical chromosome copies are present, or where there are two chromosome copies present that originate from the same parent. In some embodiments, the deletion of a chromosome segment is a microdeletion.

Ploidy State refers to the quantity and/or chromosomal identity of one or more chromosomes or chromosome segments in a cell.

Chromosome may refer to a single chromosome copy, meaning a single molecule of DNA of which there are 46 in a normal somatic cell; an example is 'the maternally derived chromosome 18'. Chromosome may also refer to a chromosome type, of which there are 23 in a normal human somatic cell; an example is 'chromosome 18'.

Chromosomal Identity may refer to the referent chromosome number, i.e. the chromosome type. Normal humans have 22 types of numbered autosomal chromosome types, and two types of sex chromosomes. It may also refer to the parental origin of the chromosome. It may also refer to a specific chromosome inherited from the parent. It may also refer to other identifying features of a chromosome.

Allelic Data refers to a set of genotypic data concerning a set of one or more alleles. It may refer to the phased, haplotypic data. It may refer to SNP identities, and it may refer to the sequence data of the DNA, including insertions, deletions, repeats and mutations. It may include the parental origin of each allele.

Allelic State refers to the actual state of the genes in a set of one or more alleles. It may refer to the actual state of the genes described by the allelic data.

Allele Count refers to the number of sequences that map to a particular locus, and if that locus is polymorphic, it refers to the number of sequences that map to each of the alleles. If each allele is counted in a binary fashion, then the allele count will be whole number. If the alleles are counted probabilistically, then the allele count can be a fractional number.

Allele Count Probability refers to the number of sequences that are likely to map to a particular locus or a set of alleles at a polymorphic locus, combined with the probability of the mapping. Note that allele counts are equivalent to allele count probabilities where the probability of the mapping for each counted sequence is binary (zero or one). In some embodiments, the allele count probabilities may be binary. In some embodiments, the allele count probabilities may be set to be equal to the DNA measurements.

Allelic Distribution, or "allele count distribution" refers to the relative amount of each allele that is present for each locus in a set of loci. An allelic distribution can refer to an individual, to a sample, or to a set of measurements made on a sample. In the context of digital allele measurements such as sequencing, the allelic distribution refers to the number or probable number of reads that map to a particular allele for each allele in a set of polymorphic loci. In the context of analog allele measurements such as SNP arrays, the allelic distribution refers to allele intensities and/or allele ratios. The allele measurements may be treated probabilistically, that is, the likelihood that a given allele is present for a give sequence read is a fraction between 0 and 1, or they may be treated in a binary fashion, that is, any given read is considered to be exactly zero or one copies of a particular allele.

Allelic Distribution Pattern refers to a set of different allele distributions for different contexts, such as different parental contexts. Certain allelic distribution patterns may be indicative of certain ploidy states.

Allelic Bias refers to the degree to which the measured ratio of alleles at a heterozygous locus is different to the ratio that was present in the original sample of DNA or RNA. The degree of allelic bias at a particular locus is equal to the observed allelic ratio at that locus, as measured, divided by the ratio of alleles in the original DNA or RNA sample at that locus. Allelic bias maybe due to amplification bias, purification bias, or some other phenomenon that affects different alleles differently.

Allelic imbalance refers for SNVs, to the proportion of abnormal DNA is typically measured using mutant allele frequency (number of mutant alleles at a locus/total number of alleles at that locus). Since the difference between the amounts of two homologs in tumours is analogous, we measure the proportion of abnormal DNA for a CNV by the average allelic imbalance (AAI), defined as $|(H1-H2)|/(H1+H2)$, where Hi is the average number of copies of homolog i in the sample and $Hi/(H1+H2)$ is the fractional abundance, or homolog ratio, of homolog i. The maximum homolog ratio is the homolog ratio of the more abundant homolog.

Assay drop-out rate is the percentage of SNPs with no reads, estimated using all SNPs.

Single allele drop-out (ADO) rate is the percentage of SNPs with only one allele present, estimated using only heterozygous SNPs.

Primer, also "PCR probe" refers to a single nucleic acid molecule (such as a DNA molecule or a DNA oligomer) or a collection of nucleic acid molecules (such as DNA molecules or DNA oligomers) where the molecules are identical, or nearly so, and wherein the primer contains a region that is designed to hybridize to a targeted locus (e.g., a targeted polymorphic locus or a non-polymorphic locus) or to a universal priming sequence, and may contain a priming sequence designed to allow PCR amplification. A primer may also contain a molecular barcode. A primer may contain a random region that differs for each individual molecule.

Library of primers refers to a population of two or more primers. In various embodiments, the library includes at least 100; 200; 500; 750; 1,000; 2,000; 5,000; 7,500; 10,000; 20,000; 25,000; 30,000; 40,000; 50,000; 75,000; or 100,000 different primers. In various embodiments, the library includes at least 100; 200; 500; 750; 1,000; 2,000; 5,000; 7,500; 10,000; 20,000; 25,000; 30,000; 40,000; 50,000; 75,000; or 100,000 different primer pairs, wherein each pair of primers includes a forward test primer and a reverse test primer where each pair of test primers hybridize to a target locus. In some embodiments, the library of primers includes at least 100; 200; 500; 750; 1,000; 2,000; 5,000; 7,500; 10,000; 20,000; 25,000; 30,000; 40,000; 50,000; 75,000; or 100,000 different individual primers that each hybridize to a different target locus, wherein the individual primers are not part of primer pairs. In some embodiments, the library has both (i) primer pairs and (ii) individual primers (such as universal primers) that are not part of primer pairs.

Different primers refers to non-identical primers.

Different pools refers to non-identical pools.

Different target loci refers to non-identical target loci.

Different amplicons refers to non-identical amplicons.

Hybrid Capture Probe refers to any nucleic acid sequence, possibly modified, that is generated by various methods such as PCR or direct synthesis and intended to be complementary to one strand of a specific target DNA sequence in a sample. The exogenous hybrid capture probes may be added to a prepared sample and hybridized through a denature-reannealing process to form duplexes of exogenous-endogenous fragments. These duplexes may then be physically separated from the sample by various means.

Sequence Read refers to data representing a sequence of nucleotide bases that were measured, e.g., using a clonal sequencing method. Clonal sequencing may produce sequence data representing single, or clones, or clusters of one original DNA molecule. A sequence read may also have associated quality score at each base position of the sequence indicating the probability that nucleotide has been called correctly.

Mapping a sequence read is the process of determining a sequence read's location of origin in the genome sequence of a particular organism. The location of origin of sequence reads is based on similarity of nucleotide sequence of the read and the genome sequence.

Matched Copy Error, also "Matching Chromosome Aneuploidy" (MCA), refers to a state of aneuploidy where one cell contains two identical or nearly identical chromosomes. This type of aneuploidy may arise during the formation of the gametes in meiosis, and may be referred to as a meiotic non-disjunction error. This type of error may arise in mitosis. Matching trisomy may refer to the case where three copies of a given chromosome are present in an individual and two of the copies are identical.

Unmatched Copy Error, also "Unique Chromosome Aneuploidy" (UCA), refers to a state of aneuploidy where one cell contains two chromosomes that are from the same parent, and that may be homologous but not identical. This type of aneuploidy may arise during meiosis, and may be referred to as a meiotic error. Unmatching trisomy may refer to the case where three copies of a given chromosome are present in an individual and two of the copies are from the same parent, and are homologous, but are not identical. Note that unmatching trisomy may refer to the case where two homologous chromosomes from one parent are present, and where some segments of the chromosomes are identical while other segments are merely homologous.

Homologous Chromosomes refers to chromosome copies that contain the same set of genes that normally pair up during meiosis.

Identical Chromosomes refers to chromosome copies that contain the same set of genes, and for each gene they have the same set of alleles that are identical, or nearly identical.

Allele Drop Out (ADO) refers to the situation where at least one of the base pairs in a set of base pairs from homologous chromosomes at a given allele is not detected.

Locus Drop Out (LDO) refers to the situation where both base pairs in a set of base pairs from homologous chromosomes at a given allele are not detected.

Homozygous refers to having similar alleles as corresponding chromosomal loci.

Heterozygous refers to having dissimilar alleles as corresponding chromosomal loci.

Heterozygosity Rate refers to the rate of individuals in the population having heterozygous alleles at a given locus. The heterozygosity rate may also refer to the expected or measured ratio of alleles, at a given locus in an individual, or a sample of DNA or RNA.

Chromosomal Region refers to a segment of a chromosome, or a full chromosome.

Segment of a Chromosome refers to a section of a chromosome that can range in size from one base pair to the entire chromosome.

Chromosome refers to either a full chromosome, or a segment or section of a chromosome.

Copies refers to the number of copies of a chromosome segment. It may refer to identical copies, or to non-identical, homologous copies of a chromosome segment wherein the different copies of the chromosome segment contain a substantially similar set of loci, and where one or more of the alleles are different. Note that in some cases of aneuploidy, such as the M2 copy error, it is possible to have some copies of the given chromosome segment that are identical as well as some copies of the same chromosome segment that are not identical.

Haplotype refers to a combination of alleles at multiple loci that are typically inherited together on the same chromosome. Haplotype may refer to as few as two loci or to an entire chromosome depending on the number of recombination events that have occurred between a given set of loci. Haplotype can also refer to a set of SNPs on a single chromatid that are statistically associated.

Haplotypic Data, also "Phased Data" or "Ordered Genetic Data," refers to data from a single chromosome or chromosome segment in a diploid or polyploid genome, e.g., either the segregated maternal or paternal copy of a chromosome in a diploid genome.

Phasing refers to the act of determining the haplotypic genetic data of an individual given unordered, diploid (or polyploidy) genetic data. It may refer to the act of determining which of two genes at an allele, for a set of alleles found on one chromosome, are associated with each of the two homologous chromosomes in an individual.

Phased Data refers to genetic data where one or more haplotypes have been determined.

Hypothesis refers to a possible state, such as a possible degree of overrepresentation of the number of copies of a first homologous chromosome or chromosome segment as compared to a second homologous chromosome or chromosome segment, a possible deletion, a possible duplication, a possible ploidy state at a given set of one or more chromosomes or chromosome segments, a possible allelic state at a given set of one or more loci, a possible paternity relationship, or a possible DNA, RNA, fetal fraction at a given set of one or more chromosomes or chromosome segment, or a set of quantities of genetic material from a set of loci. The genetic states can optionally be linked with probabilities indicating the relative likelihood of each of the elements in the hypothesis being true in relation to other elements in the hypothesis, or the relative likelihood of the hypothesis as a whole being true. The set of possibilities may comprise one or more elements.

Copy Number Hypothesis, also "Ploidy State Hypothesis," refers to a hypothesis concerning the number of copies of a chromosome or chromosome segment in an individual. It may also refer to a hypothesis concerning the identity of each of the chromosomes, including the parent of origin of each chromosome, and which of the parent's two chromosomes are present in the individual. It may also refer to a hypothesis concerning which chromosomes, or chromosome segments, if any, from a related individual correspond genetically to a given chromosome from an individual.

Related Individual refers to any individual who is genetically related to, and thus shares haplotype blocks with, the target individual. In one context, the related individual may be a genetic parent of the target individual, or any genetic material derived from a parent, such as a sperm, a polar body, an embryo, a fetus, or a child. It may also refer to a sibling, parent, or grandparent.

Sibling refers to any individual whose genetic parents are the same as the individual in question. In some embodiments, it may refer to a born child, an embryo, or a fetus, or one or more cells originating from a born child, an embryo, or a fetus. A sibling may also refer to a haploid individual that originates from one of the parents, such as a sperm, a polar body, or any other set of haplotypic genetic matter. An individual may be considered to be a sibling of itself.

Child may refer to an embryo, a blastomere, or a fetus. Note that in the presently disclosed embodiments, the concepts described apply equally well to individuals who are a born child, a fetus, an embryo, or a set of cells therefrom. The use of the term child may simply be meant to connote that the individual referred to as the child is the genetic offspring of the parents.

Fetal refers to "of the fetus," or "of the region of the placenta that is genetically similar to the fetus". In a pregnant woman, some portion of the placenta is genetically similar to the fetus, and the free floating fetal DNA found in maternal blood may have originated from the portion of the placenta with a genotype that matches the fetus. Note that the genetic information in half of the chromosomes in a fetus is inherited from the mother of the fetus. In some embodiments, the DNA from these maternally inherited chromosomes that came from a fetal cell is considered to be "of fetal origin," not "of maternal origin."

DNA of Fetal Origin refers to DNA that was originally part of a cell whose genotype was essentially equivalent to that of the fetus.

DNA of Maternal Origin refers to DNA that was originally part of a cell whose genotype was essentially equivalent to that of the mother.

Parent refers to the genetic mother or father of an individual. An individual typically has two parents, a mother and a father, though this may not necessarily be the case such as in genetic or chromosomal chimerism. A parent may be considered to be an individual.

Parental Context refers to the genetic state of a given SNP, on each of the two relevant chromosomes for one or both of the two parents of the target.

Maternal Plasma refers to the plasma portion of the blood from a female who is pregnant.

Clinical Decision refers to any decision to take or not take an action that has an outcome that affects the health or survival of an individual. A clinical decision may also refer to a decision to conduct further testing, to abort or maintain a pregnancy, to take actions to mitigate an undesirable phenotype, or to take actions to prepare for a phenotype.

Diagnostic Box refers to one or a combination of machines designed to perform one or a plurality of aspects of the methods disclosed herein. In an embodiment, the diagnostic box may be placed at a point of patient care. In an embodiment, the diagnostic box may perform targeted amplification followed by sequencing. In an embodiment the diagnostic box may function alone or with the help of a technician.

Informatics Based Method refers to a method that relies heavily on statistics to make sense of a large amount of data. In the context of prenatal diagnosis, it refers to a method designed to determine the ploidy state at one or more chromosomes or chromosome segments, the allelic state at one or more alleles, or paternity by statistically inferring the most likely state, rather than by directly physically measuring the state, given a large amount of genetic data, for example from a molecular array or sequencing. In an embodiment of the present disclosure, the informatics based technique may be one disclosed in this patent application. In an embodiment of the present disclosure it may be PARENTAL SUPPORT.

Primary Genetic Data refers to the analog intensity signals that are output by a genotyping platform. In the context of SNP arrays, primary genetic data refers to the intensity signals before any genotype calling has been done. In the context of sequencing, primary genetic data refers to the analog measurements, analogous to the chromatogram, that comes off the sequencer before the identity of any base pairs have been determined, and before the sequence has been mapped to the genome.

Secondary Genetic Data refers to processed genetic data that are output by a genotyping platform. In the context of a SNP array, the secondary genetic data refers to the allele calls made by software associated with the SNP array reader, wherein the software has made a call whether a given allele is present or not present in the sample. In the context of sequencing, the secondary genetic data refers to the base pair identities of the sequences have been determined, and possibly also where the sequences have been mapped to the genome.

Preferential Enrichment of DNA that corresponds to a locus, or preferential enrichment of DNA at a locus, refers to any method that results in the percentage of molecules of DNA in a post-enrichment DNA mixture that correspond to the locus being higher than the percentage of molecules of DNA in the pre-enrichment DNA mixture that correspond to the locus. The method may involve selective amplification of DNA molecules that correspond to a locus. The method may involve removing DNA molecules that do not correspond to the locus. The method may involve a combination of methods. The degree of enrichment is defined as the percentage of molecules of DNA in the post-enrichment mixture that correspond to the locus divided by the percentage of molecules of DNA in the pre-enrichment mixture that correspond to the locus. Preferential enrichment may be carried out at a plurality of loci. In some embodiments of the present disclosure, the degree of enrichment is greater than 20, 200, or 2,000. When preferential enrichment is carried out at a plurality of loci, the degree of enrichment may refer to the average degree of enrichment of all of the loci in the set of loci.

Amplification refers to a method that increases the number of copies of a molecule of DNA or RNA.

Selective Amplification may refer to a method that increases the number of copies of a particular molecule of DNA (or RNA), or molecules of DNA (or RNA) that correspond to a particular region of DNA (or RNA). It may also refer to a method that increases the number of copies of a particular targeted molecule of DNA (or RNA), or targeted region of DNA (or RNA) more than it increases non-targeted molecules or regions of DNA (or RNA). Selective amplification may be a method of preferential enrichment.

Universal Priming Sequence refers to a DNA (or RNA) sequence that may be appended to a population of target DNA (or RNA) molecules, for example by ligation, PCR, or ligation mediated PCR. Once added to the population of target molecules, primers specific to the universal priming sequences can be used to amplify the target population using a single pair of amplification primers. Universal priming sequences are typically not related to the target sequences.

Universal Adapters, or "ligation adaptors" or "library tags" are nucleic acid molecules containing a universal priming sequence that can be covalently linked to the 5-prime and 3-prime end of a population of target double stranded nucleic acid molecules. The addition of the adapters provides universal priming sequences to the 5-prime and 3-prime end of the target population from which PCR amplification can take place, amplifying all molecules from the target population, using a single pair of amplification primers.

Targeting refers to a method used to selectively amplify or otherwise preferentially enrich those molecules of DNA (or RNA) that correspond to a set of loci in a mixture of DNA (or RNA).

Joint Distribution Model refers to a model that defines the probability of events defined in terms of multiple random variables, given a plurality of random variables defined on the same probability space, where the probabilities of the variable are linked. In some embodiments, the degenerate case where the probabilities of the variables are not linked may be used.

Cancer-related gene refers to a gene associated with an altered risk for a cancer or an altered prognosis for a cancer. Exemplary cancer-related genes that promote cancer include oncogenes; genes that enhance cell proliferation, invasion, or metastasis; genes that inhibit apoptosis; and pro-angiogenesis genes. Cancer-related genes that inhibit cancer include, but are not limited to, tumor suppressor genes; genes that inhibit cell proliferation, invasion, or metastasis; genes that promote apoptosis; and anti-angiogenesis genes.

Estrogen-related cancer refers to a cancer that is modulated by estrogen. Examples of estrogen-related cancers include, without limitation, breast cancer and ovarian cancer. Her2 is overexpressed in many estrogen-related cancers (U.S. Pat. No. 6,165,464, which is hereby incorporated by reference in its entirety).

Androgen-related cancer refers to a cancer that is modulated by androgen. An example of androgen-related cancers is prostate cancer.

Higher than normal expression level refers to expression of an mRNA or protein at a level that is higher than the average expression level of the corresponding molecule in control subjects (such as subjects without a disease or disorder such as cancer). In various embodiments, the expression level is at least 20, 40, 50, 75, 90, 100, 200, 500, or even 1000% higher than the level in control subjects.

Lower than normal expression level refers to expression of an mRNA or protein at a level that is lower than the average expression level of the corresponding molecule in control subjects (such as subjects without a disease or disorder such as cancer). In various embodiments, the expression level is at least 20, 40, 50, 75, 90, 95, or 100% lower than the level in control subjects. In some embodiments, the expression of the mRNA or protein is not detectable.

Modulate expression or activity refers to either increasing or decreasing expression or activity, for example, of a protein or nucleic acid sequence, relative to control conditions. In some embodiments, the modulation in expression or activity is an increase or decrease of at least 10, 20, 40, 50, 75, 90, 100, 200, 500, or even 1000%. In various embodiments, transcription, translation, mRNA or protein stability, or the binding of the mRNA or protein to other molecules in vivo is modulated by the therapy. In some embodiments, the level of mRNA is determined by standard Northern blot analysis, and the level of protein is determined by standard Western blot analysis, such as the analyses described herein or those described by, for example, Ausubel et al. (Current Protocols in Molecular Biology, John Wiley & Sons, New York, Jul. 11, 2013, which is hereby incorporated by reference in its entirety). In one embodiment, the level of a protein is determined by measuring the level of enzymatic activity, using standard methods. In another preferred embodiment, the level of mRNA, protein, or enzymatic activity is equal to or less than 20, 10, 5, or 2-fold above the corresponding level in control cells that do not express a functional form of the protein, such as cells homozygous for a nonsense mutation. In yet another embodiment, the level of mRNA, protein, or enzymatic activity is equal to or less than 20, 10, 5, or 2-fold above the corresponding basal level in control cells, such as non-cancerous cells, cells that have not been exposed to conditions that induce abnormal cell proliferation or that inhibit apoptosis, or cells from a subject without the disease or disorder of interest.

Dosage sufficient to modulate mRNA or protein expression or activity refers to an amount of a therapy that increases or decreases mRNA or protein expression or activity when administered to a subject. In some embodiments, for a compound that decreases expression or activity, the modulation is a decrease in expression or activity that is at least 10%, 30%, 40%, 50%, 75%, or 90% lower in a treated subject than in the same subject prior to the administration of the inhibitor or than in an untreated, control subject. In addition, In some embodiments, for a compound that increases expression or activity, the amount of expression or activity of the mRNA or protein is at least 1.5-, 2-, 3—, 5-, 10-, or 20-fold greater in a treated subject than in the same subject prior to the administration of the modulator or than in an untreated, control subject.

In some embodiments, compounds may directly or indirectly modulate the expression or activity of the mRNA or protein. For example, a compound may indirectly modulate the expression or activity of an mRNA or protein of interest by modulating the expression or activity of a molecule (e.g., a nucleic acid, protein, signaling molecule, growth factor, cytokine, or chemokine) that directly or indirectly affects the expression or activity of the mRNA or protein of interest. In some embodiments, the compounds inhibit cell division or induce apoptosis. These compounds in the therapy may include, for example, unpurified or purified proteins, antibodies, synthetic organic molecules, naturally-occurring organic molecules, nucleic acid molecules, and components thereof. The compounds in a combination therapy may be administered simultaneously or sequentially. Exemplary compounds include signal transduction inhibitors.

Purified refers to being separated from other components that naturally accompany it. Typically, a factor is substantially pure when it is at least 50%, by weight, free from proteins, antibodies, and naturally-occurring organic molecules with which it is naturally associated. In some embodiments, the factor is at least 75%, 90%, or 99%, by weight, pure. A substantially pure factor may be obtained by chemical synthesis, separation of the factor from natural sources, or production of the factor in a recombinant host cell that does not naturally produce the factor. Proteins and small molecules may be purified by one skilled in the art using standard techniques such as those described by Ausubel et al. (Current Protocols in Molecular Biology, John Wiley & Sons, New York, Jul. 11, 2013, which is hereby incorporated by reference in its entirety). In some embodiments the factor is at least 2, 5, or 10 times as pure as the starting material, as measured using polyacrylamide gel electrophoresis, column chromatography, optical density, HPLC analysis, or western analysis (Ausubel et al., supra). Exemplary methods of purification include immunoprecipitation, column chromatography such as immunoaffinity chromatography, magnetic bead immunoaffinity purification, and panning with a plate-bound antibody.

Other features and advantages of the invention will be apparent from the following detailed description and from the claims.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A: 100 SNPs, FIG. 1B: 333 SNPs, FIG. 1C: 667 SNPs, FIG. 1D: 1000 SNPs.

FIG. 2A: 100 SNPs, FIG. 2B: 333 SNPs, FIG. 2C: 667 SNPs, FIG. 2D: 1000 SNPs.

FIG. 3A: 100 SNPs, FIG. 3B: 333 SNPs, FIG. 3C: 667 SNPs, FIG. 3D: 1000 SNPs.

FIG. 4A: 100 SNPs, FIG. 4B: 333 SNPs, FIG. 4C: 667 SNPs, FIG. 4D: 1000 SNPs.

FIG. 5A: 100 SNPs, FIG. 5B: 333 SNPs, FIG. 5C: 667 SNPs, FIG. 5D: 1000 SNPs.

FIG. 6A: 100 SNPs, FIG. 6B: 333 SNPs, FIG. 6C: 667 SNPs, FIG. 6D: 1000 SNPs.

FIG. 7A: 100 SNPs, FIG. 7B: 333 SNPs, FIG. 7C: 667 SNPs, FIG. 7D: 1000 SNPs.

FIG. 8A: 100 SNPs, FIG. 8B: 333 SNPs, FIG. 8C: 667 SNPs, FIG. 8D: 1000 SNPs.

FIG. 9A: 100 SNPs, FIG. 9B: 333 SNPs, FIG. 9C: 667 SNPs, FIG. 9D: 1000 SNPs.

FIG. 10A: 100 SNPs, FIG. 10B: 333 SNPs, FIG. 10C: 667 SNPs, FIG. 10D: 1000 SNPs.

FIG. 11A: 100 SNPs, FIG. 11B: 333 SNPs, FIG. 11C: 667 SNPs, FIG. 11D: 1000 SNPs.

FIG. 12A: 100 SNPs, FIG. 12B: 333 SNPs, FIG. 12C: 667 SNPs, FIG. 12D: 1000 SNPs.

FIG. 13A: 100 SNPs, FIG. 13B: 333 SNPs, FIG. 13C: 667 SNPs, FIG. 13D: 1000 SNPs.

FIG. 14 is a table indicating the sensitivity and specificity for detecting six microdeletion syndromes.

FIG. 16A is for maternal 22q11.2 deletion carrier (as indicated by the absence of the open triangles indicating AB SNPs). FIG. 16B is for a paternally inherited 22q11 deletion in a fetus (as indicated by the presence of solid circle and solid square peripheral bands). The x-axis represents the linear position of the SNPs, and the y-axis indicates the fraction of A allele reads out of the total reads. Each individual circle, triangle or square represents a single SNP locus.

FIG. 26 is a table of false positive rates for the first simulation.

FIG. 27 is a table of false negative rates for the first simulation.

FIG. 33 is an enlarged version of the graph in FIG. 32A for the low tumor fraction sample.

FIG. 41A: Correlation between CONVERGe-calculated AAI and actual input fraction in PlasmArt samples with DNA from a 22q11.2 deletion and matched normal cell lines. FIG. 41B: Correlation between calculated AAI and actual tumour DNA input in PlasmArt samples with DNA from HCC2218 breast cancer cells with chromosome 2p and 2q CNVs and matched normal HCC2218BL cells, containing 0-9.09% tumour DNA fractions. FIG. 41C: Correlation between calculated AAI and actual tumour DNA input in PlasmArt samples with DNA from HCC1954 breast cancer cells with chromosome 1p and 1q CNVs and matched normal HCC1954BL cells, containing 0-5.66% tumour DNA fractions. FIG. 41D: Allele frequency plot for HCC1954 cells used in FIG. C. In FIGS. 41A-C, data points and error bars indicate the mean and standard deviation (SD), respectively, of 3-8 replicates.

FIG. 42A illustrates a son's plasma with a 22q11 deletion spiked into the father's plasma. Focal CNV: 3 MB. FIG. 42B illustrates Chromosomes 1 and 2: cancer cell lines into normal cell line of same individual. CNVs on chromosome arms 1p, 1q, 2p, 2q. FIGS. 42A and 42B are graphs showing fragment size distributions of an exemplary Plasmart standard.

FIG. 43A is a graph showing the maximum likelihood of tumor. FIG. 43B is an estimate of DNA fraction results as an odds ratio plot. FIG. 43C is a plot for the detection of transversion events. FIG. 43D is a plot for the detection of Transition events.

FIG. 51A represents the histological finding/history for primary lung tumors analyzed for clonal and subclonal tumor heterogeneity. FIG. 51B is a table of the VAF identities of the biopsied lung tumors by whole genome sequencing and assaying by AmpliSEQ.

FIG. 53A is a table comparing VAF calls by AmpliSeq. FIG. 53B is a table comparing VAF calls by mmPCR-NGS. A comparison of the two tables for detection of SNVs in primary tumor indicate that SNVs were missed by AmpliSeq and SNV mutations were identified in ctDNA from plasma with mmPCR-NGS.

FIG. 64A is a FF breast tissue control sample analyzed by CONVERGe. FIG. 64B is a FFPE breast tissue control sample analyzed by CONVERGe. FIG. 64C is a FF breast tumour tissue sample analyzed by CONVERGe. FIG. 64D is a FFPE breast tumour tissue sample analyzed by CONVERGe. FIG. 64E is a FF breast tumour tissue sample analyzed by CytoSNP-12. FIG. 64F is a FFPE breast tumour tissue sample analyzed by CytoSNP-12. FIG. 64G compares the CONVERGe assay to a microarray assay on breast cancer cell lines and FIG. 64H compares the CONVERGe assay to the OneScan assay on breast cancer cell lines.

FIG. 65A is the analysis of 1/3 breast cancer single cell replicates. FIG. 65B is the analysis of 2/3 breast cancer single cell replicates. FIG. 65C is the analysis of 3/3 breast cancer single cell replicates. FIG. 65D is the analysis of a B-lymphocyte cell line lacking CNVs in the target regions.

FIG. 66A is a stage II breast cancer plasma cfDNA sample and its matched tumor biopsy gDNA. FIG. 66B is a late stage ovarian cancer plasma cfDNA sample and its matched tumor biopsy gDNA. FIG. 66C is a chart illustrating tumor heterogeneity as determined by CNV detection in five late stage ovarian cancer plasma and matched tissue samples.

FIGS. 67A-H lists the chromosome positions, SNVs and mutation change in breast cancer.

Figure 1A:
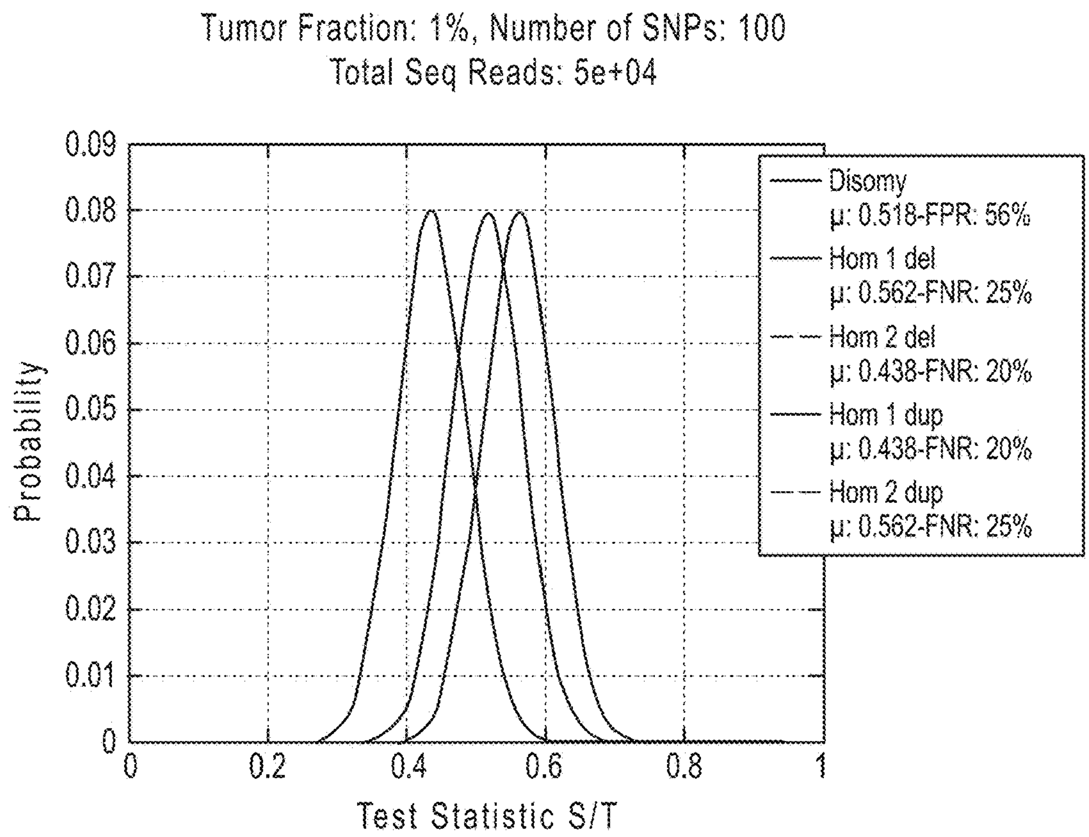
FIGS. 1A-1D are graphs showing the distribution of the test statistic S divided by T (the number of SNPs) ("S/T") for various copy number hypotheses for a depth of read (DOR) of 500 and a tumor fraction of 1% for an increasing number of SNPs.
Figure 1B:
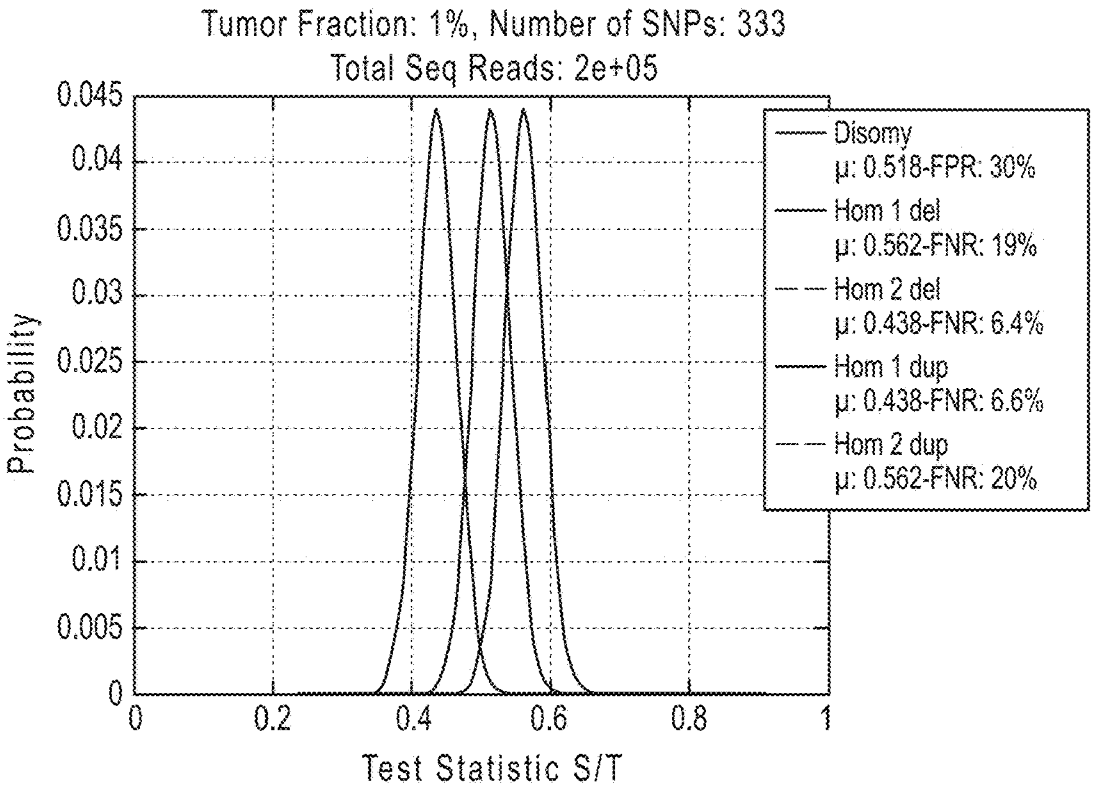
Figure 1C:
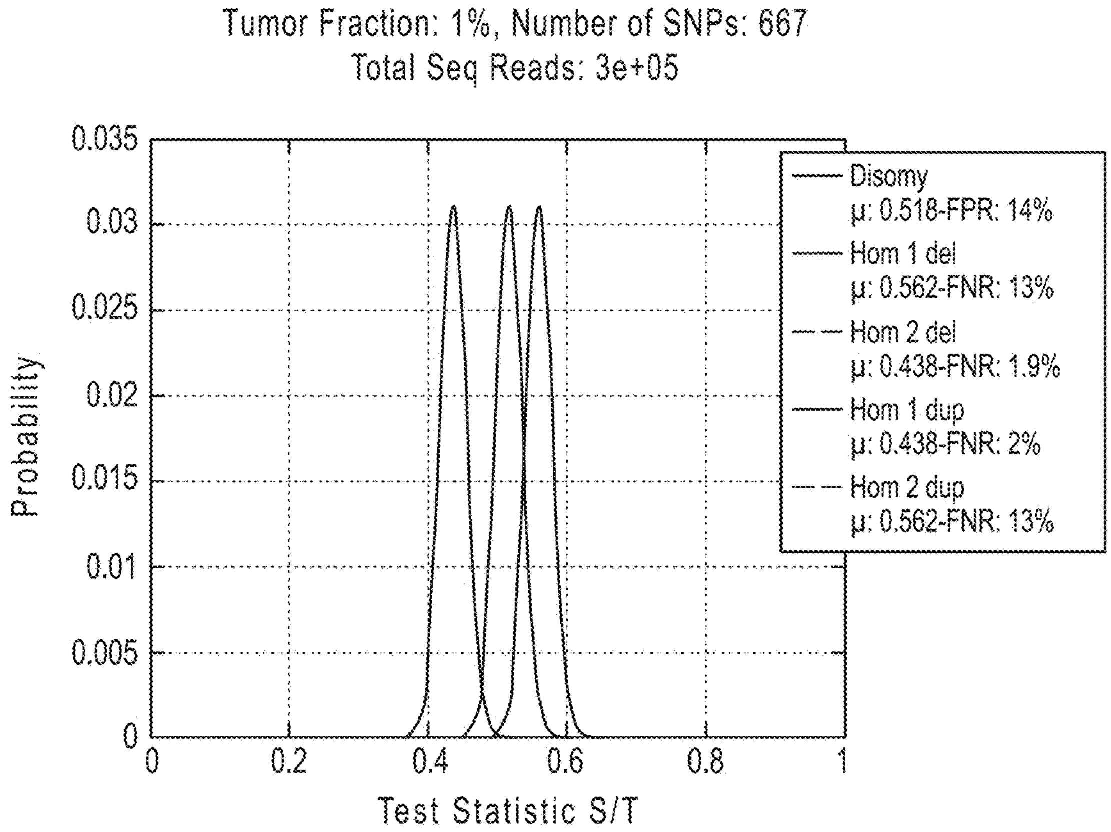
Figure 1D:
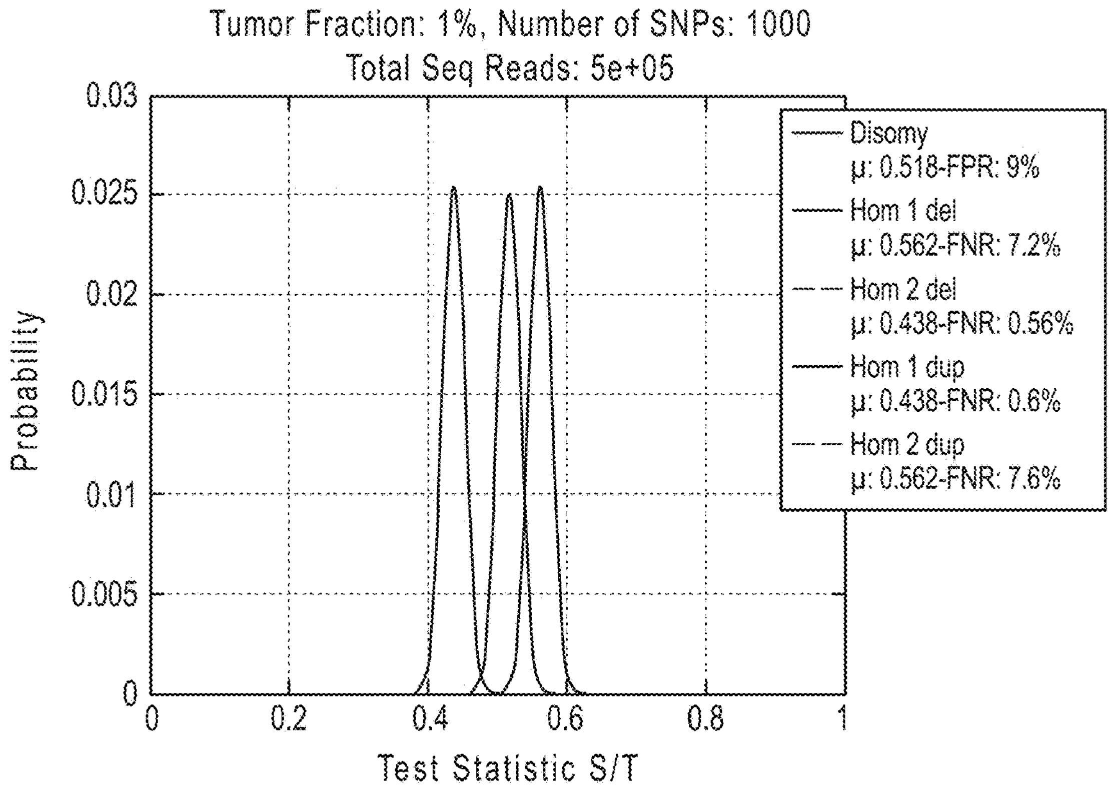
Figure 2A:
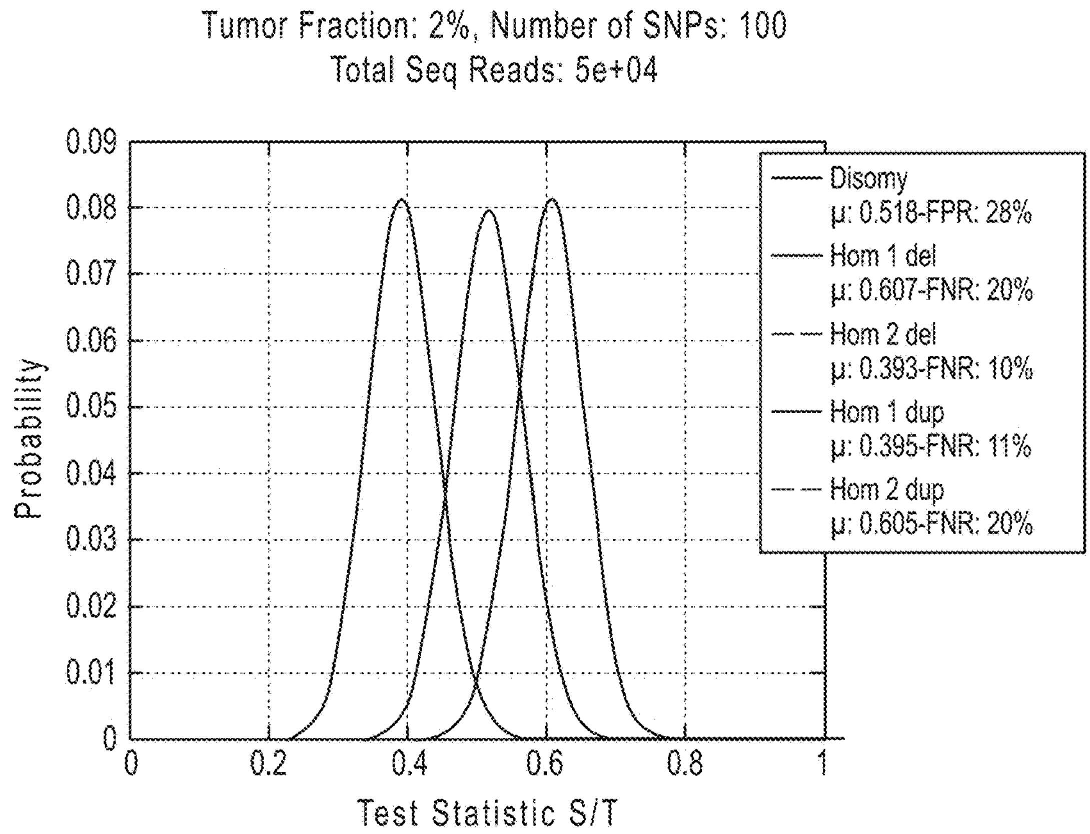
FIGS. 2A-2D are graphs showing the distribution of S/T for various copy number hypotheses for a DOR of 500 and tumor fraction of 2% for an increasing number of SNPs.
Figure 2B:
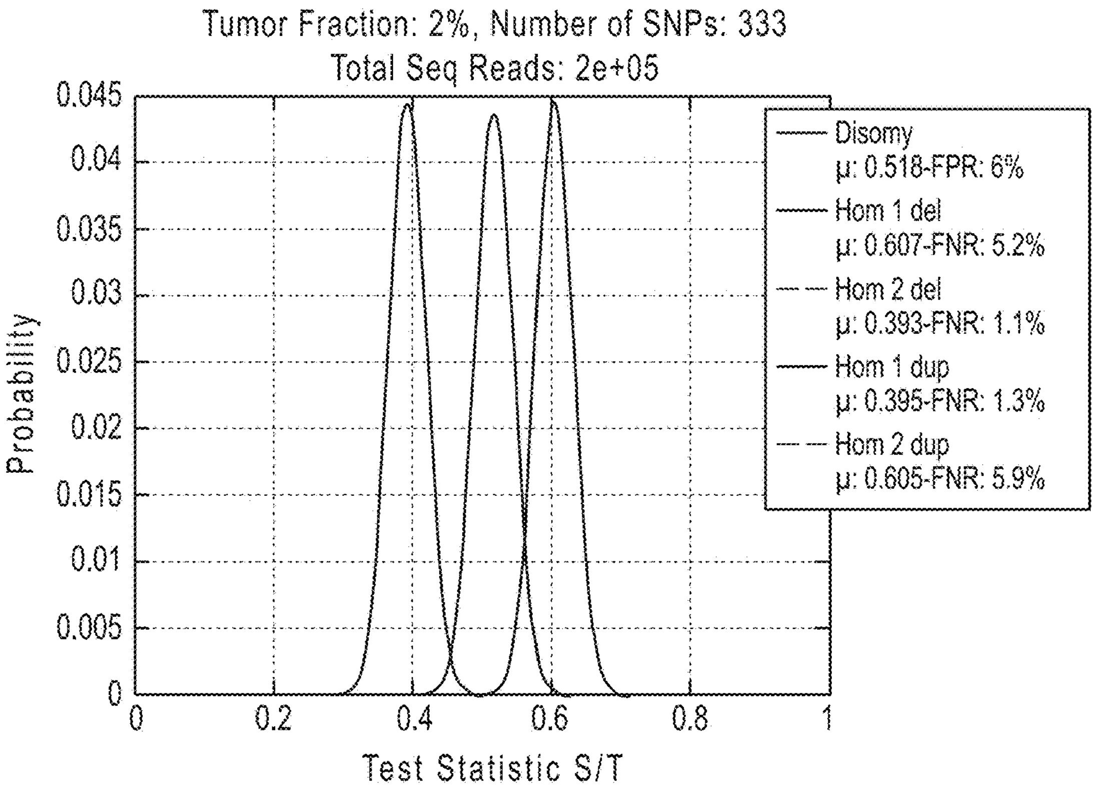
Figure 2C:
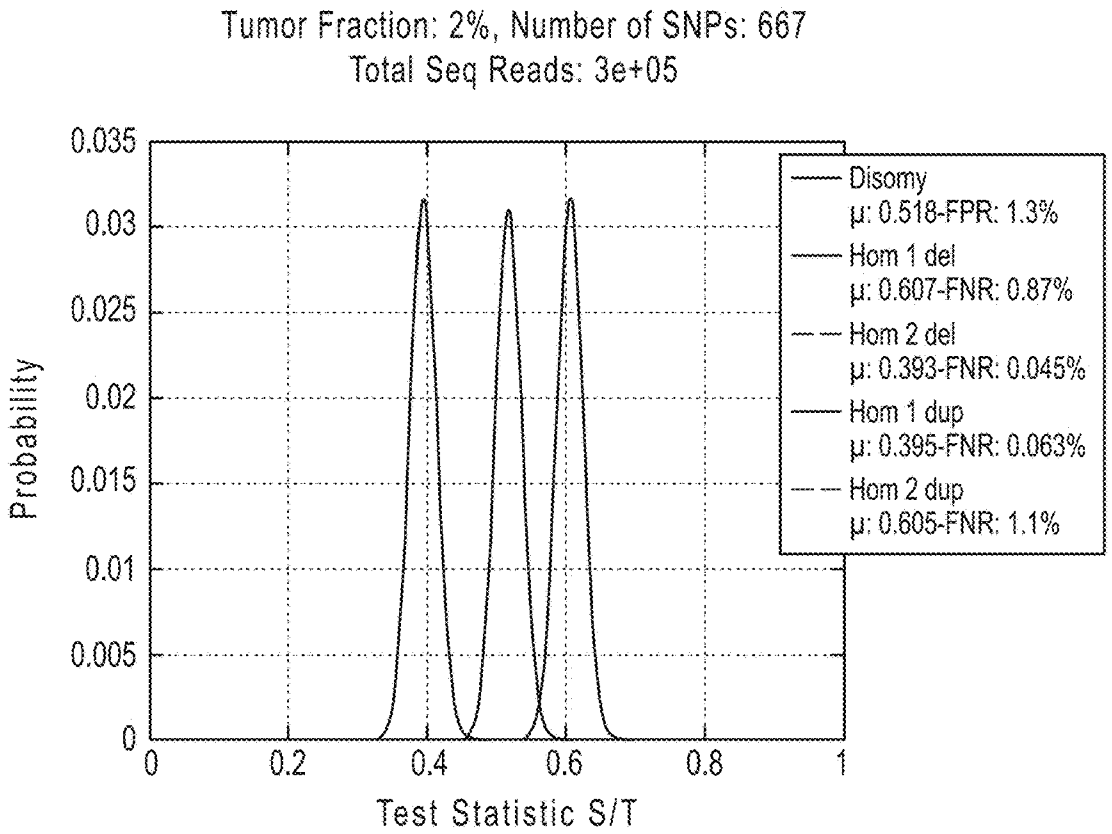
Figure 2D:
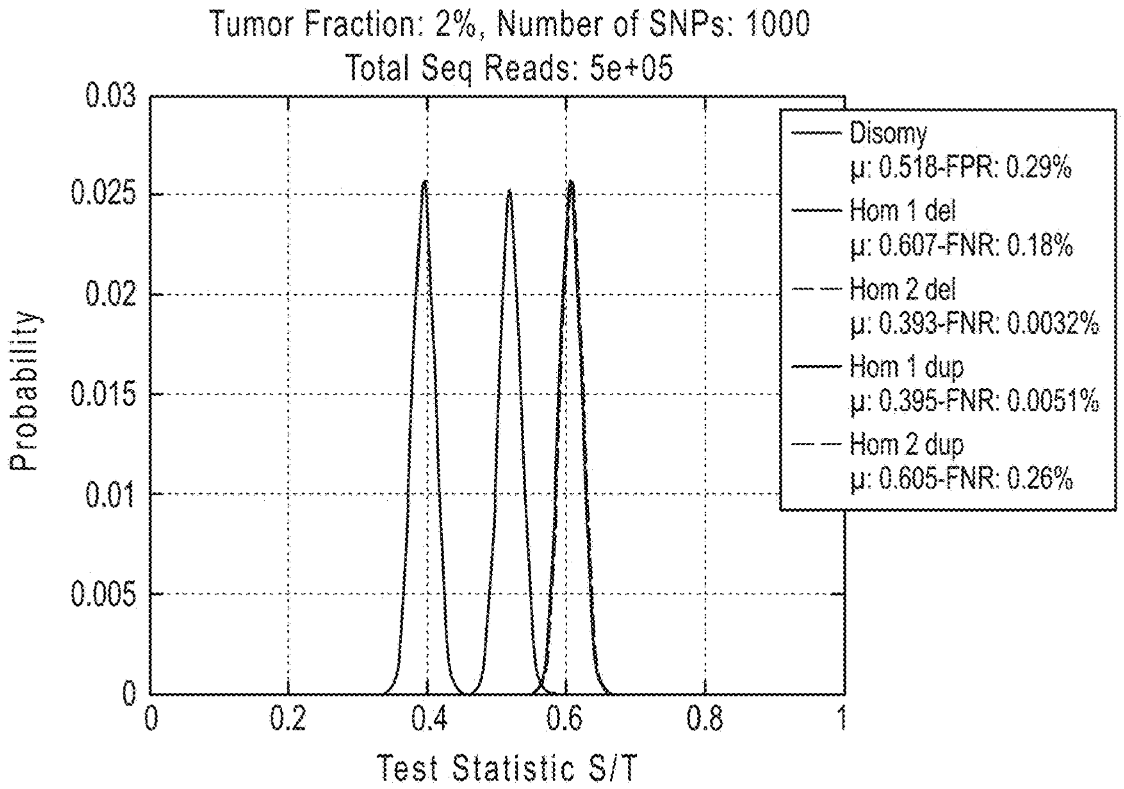
Figure 3A:
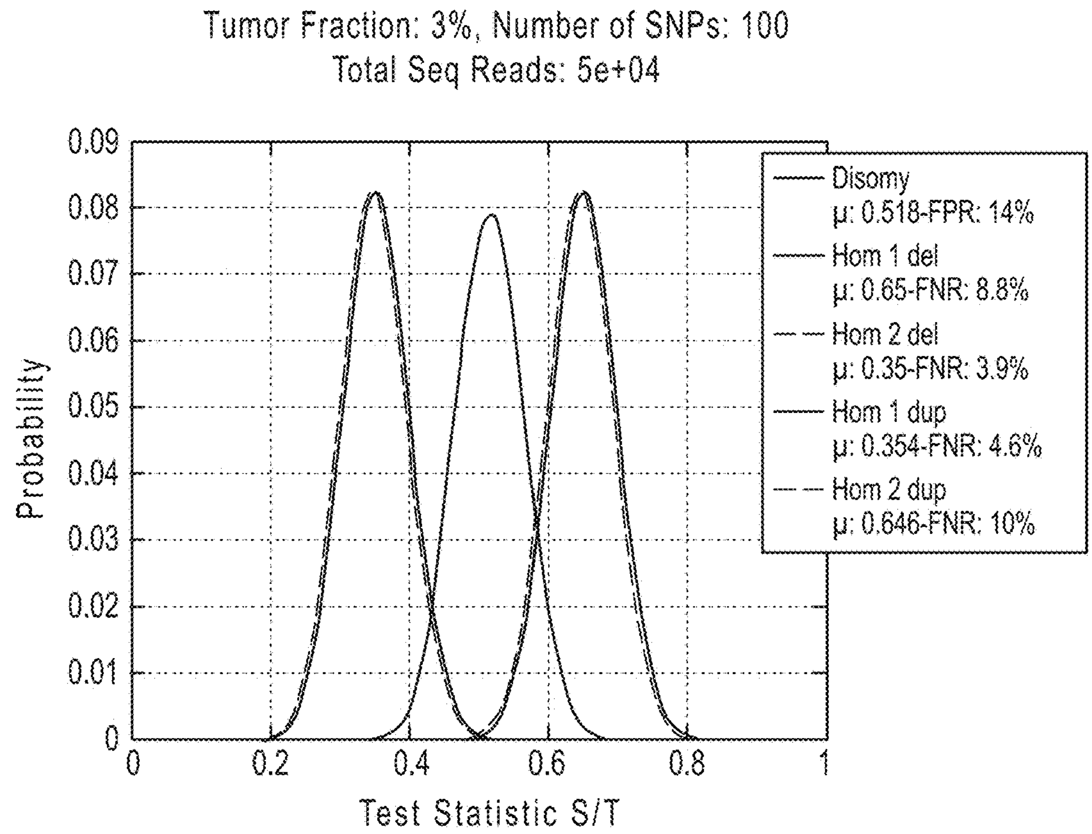
FIGS. 3A-3D are graphs showing the distribution of S/T for various copy number hypotheses for a DOR of 500 and tumor fraction of 3% for an increasing number of SNPs.
Figure 3B:
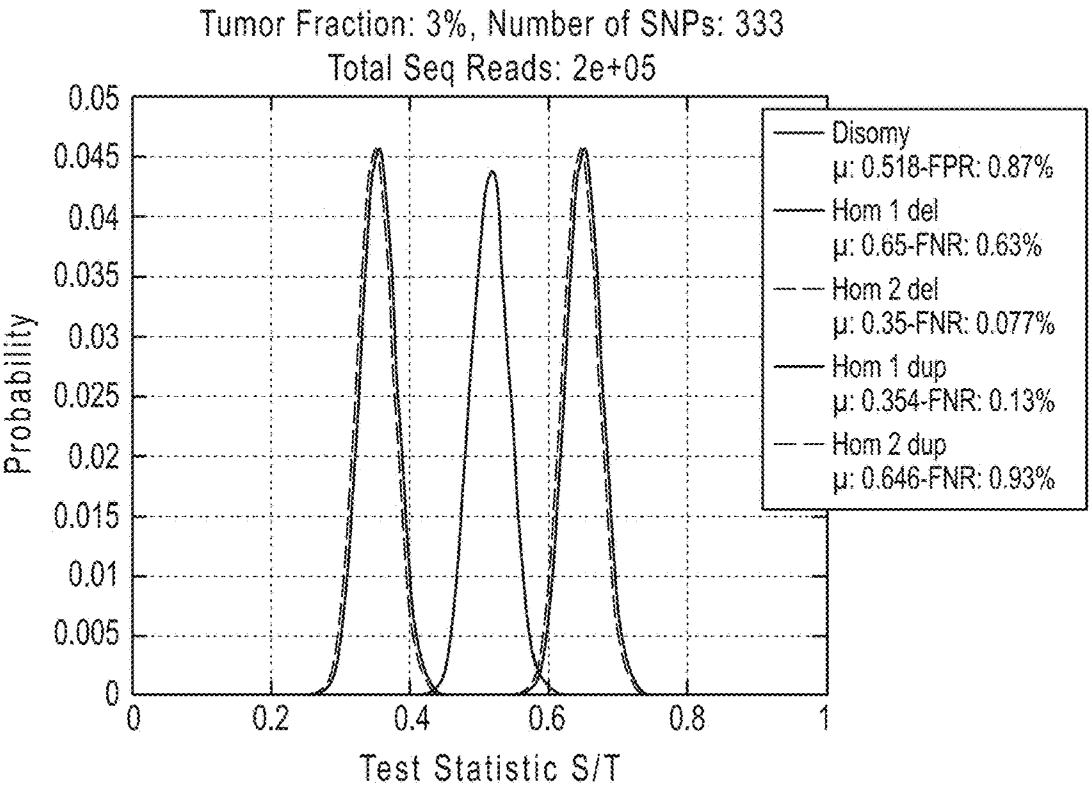
Figure 3C:
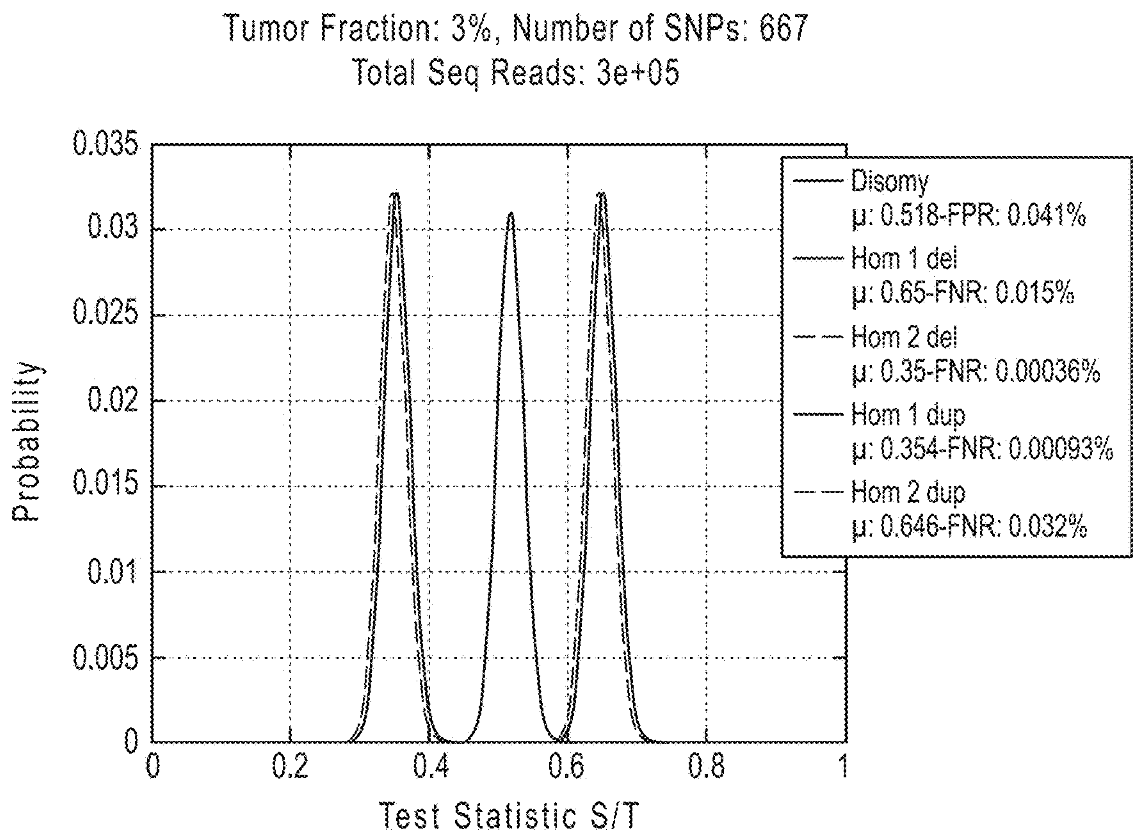
Figure 3D:
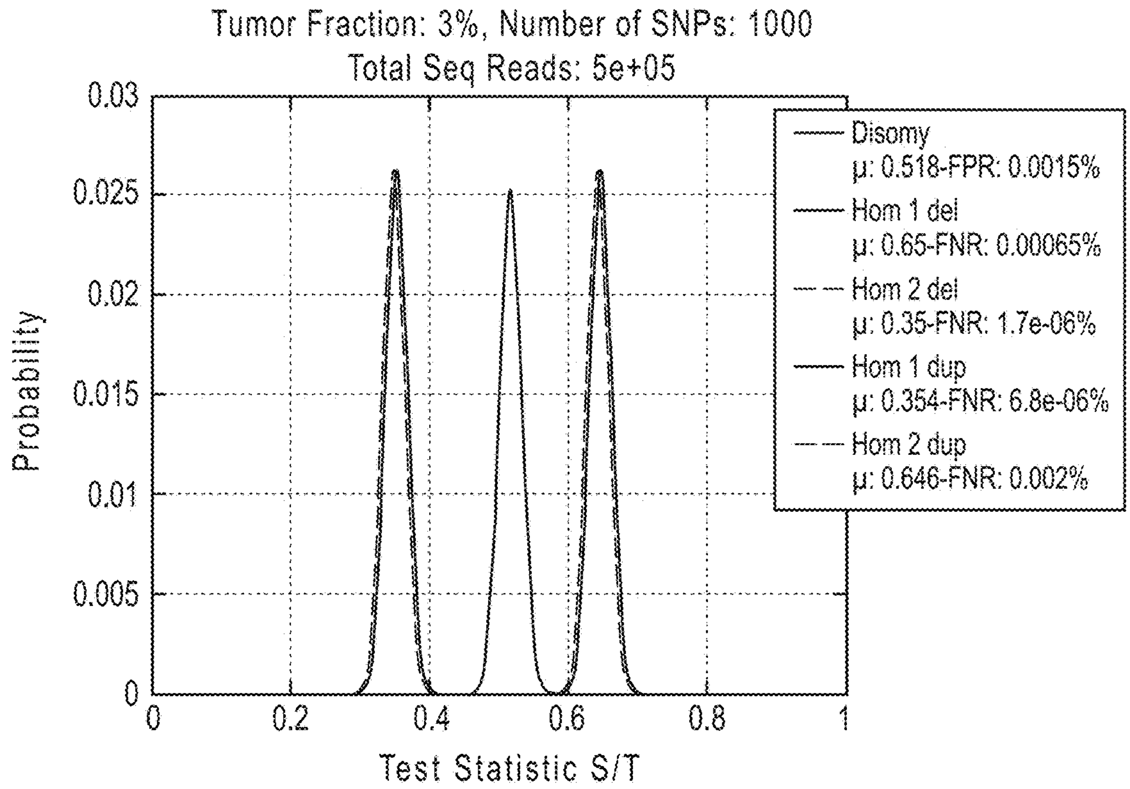
Figure 4A:
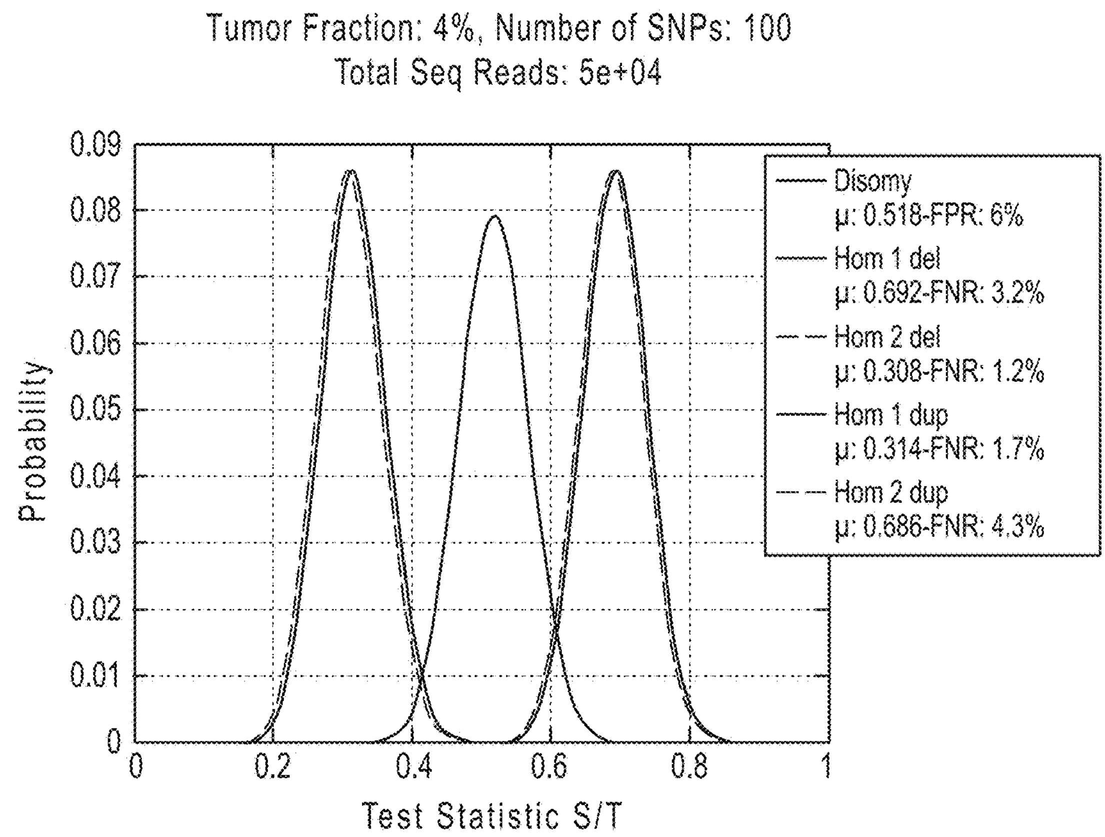
FIGS. 4A-4D are graphs showing the distribution of S/T for various copy number hypotheses for a DOR of 500 and tumor fraction of 4% for an increasing number of SNPs.
Figure 4B:
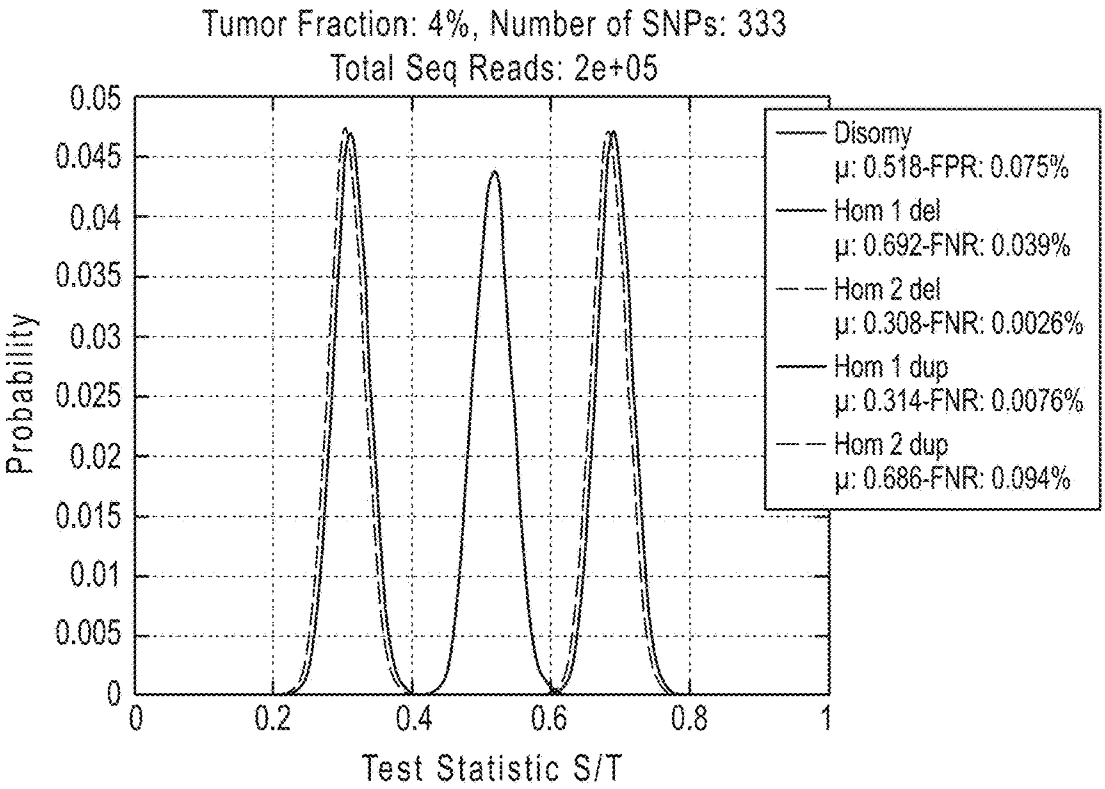
Figure 4C:
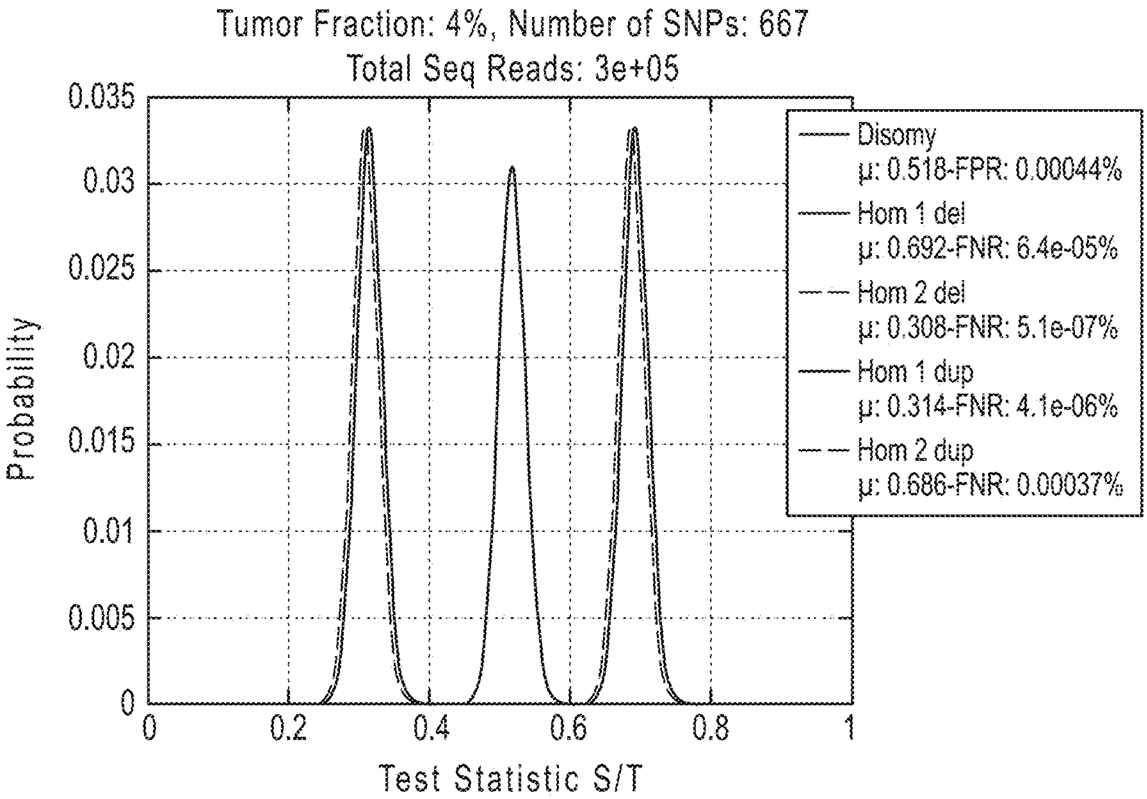
Figure 4D:
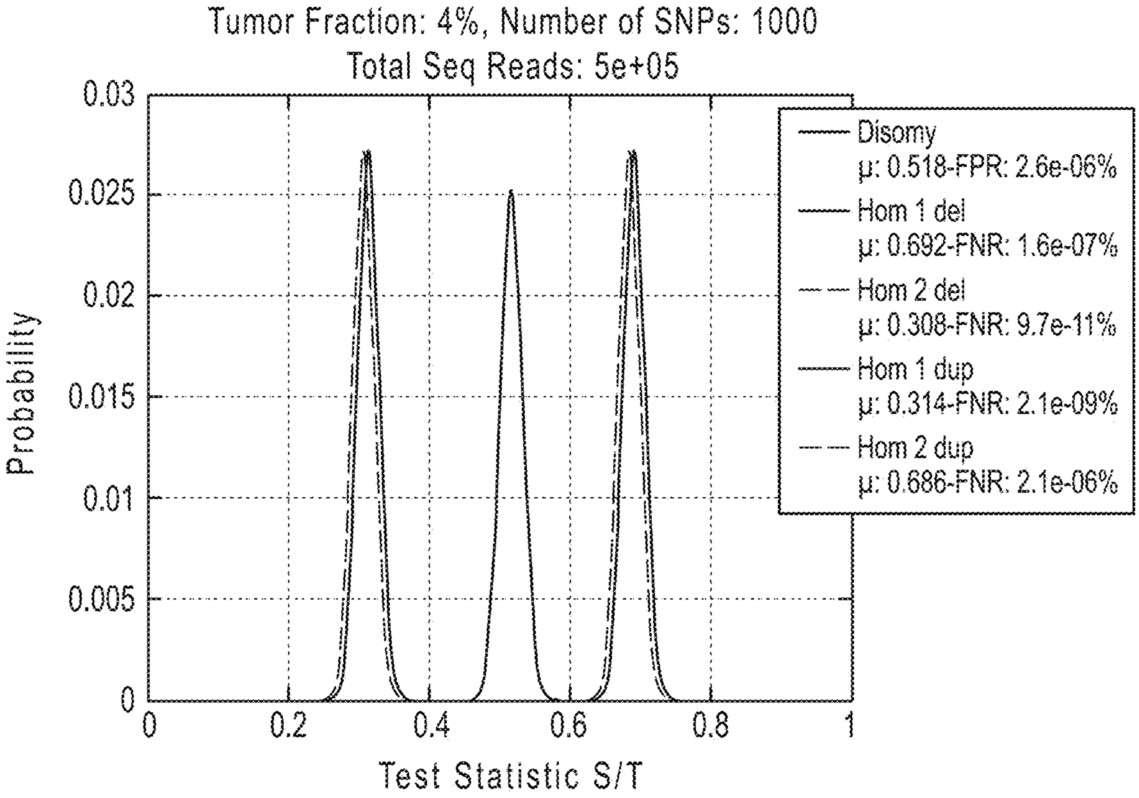
Figure 5A:
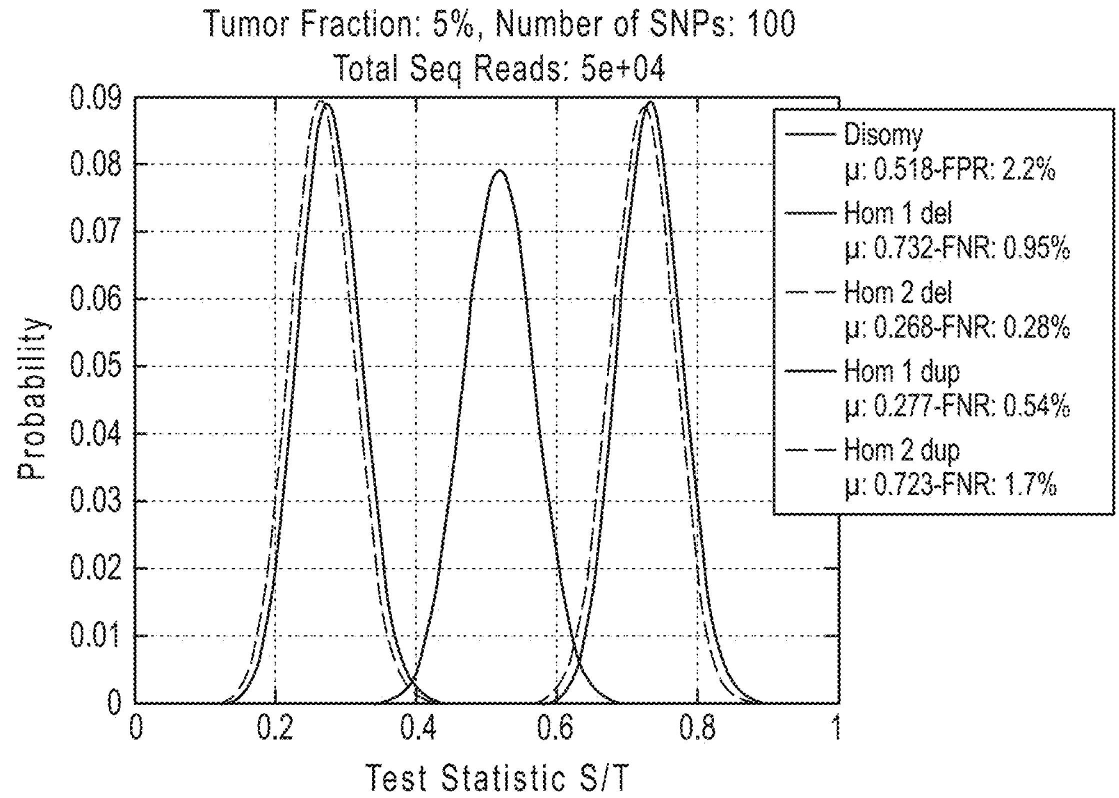
FIGS. 5A-5D are graphs showing the distribution of S/T for various copy number hypotheses for a DOR of 500 and tumor fraction of 5% for an increasing number of SNPs.
Figure 5B:
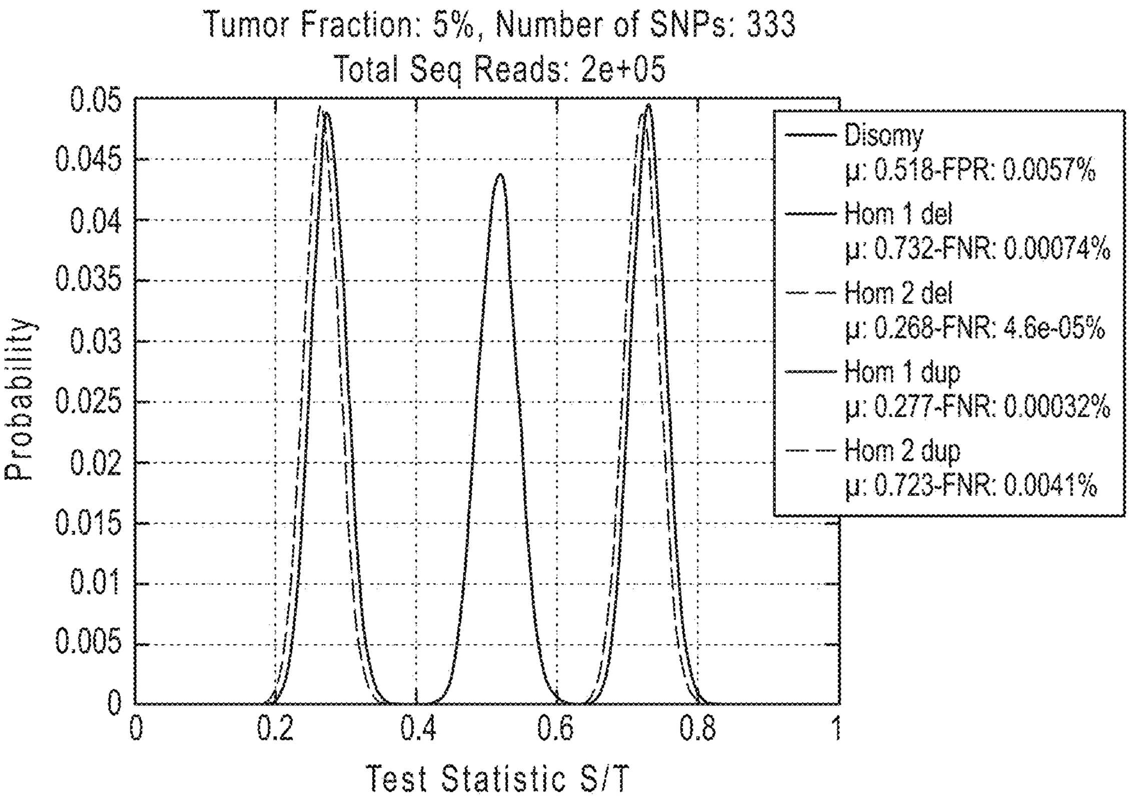
Figure 5C:
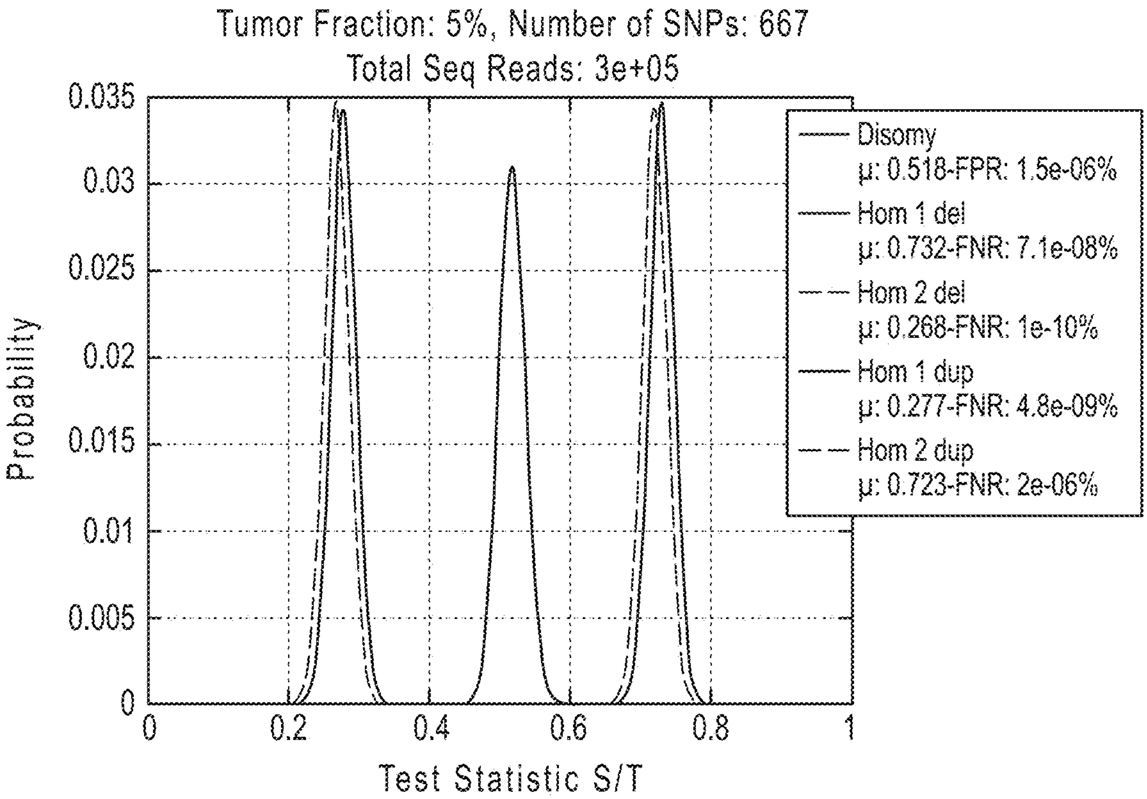
Figure 5D:
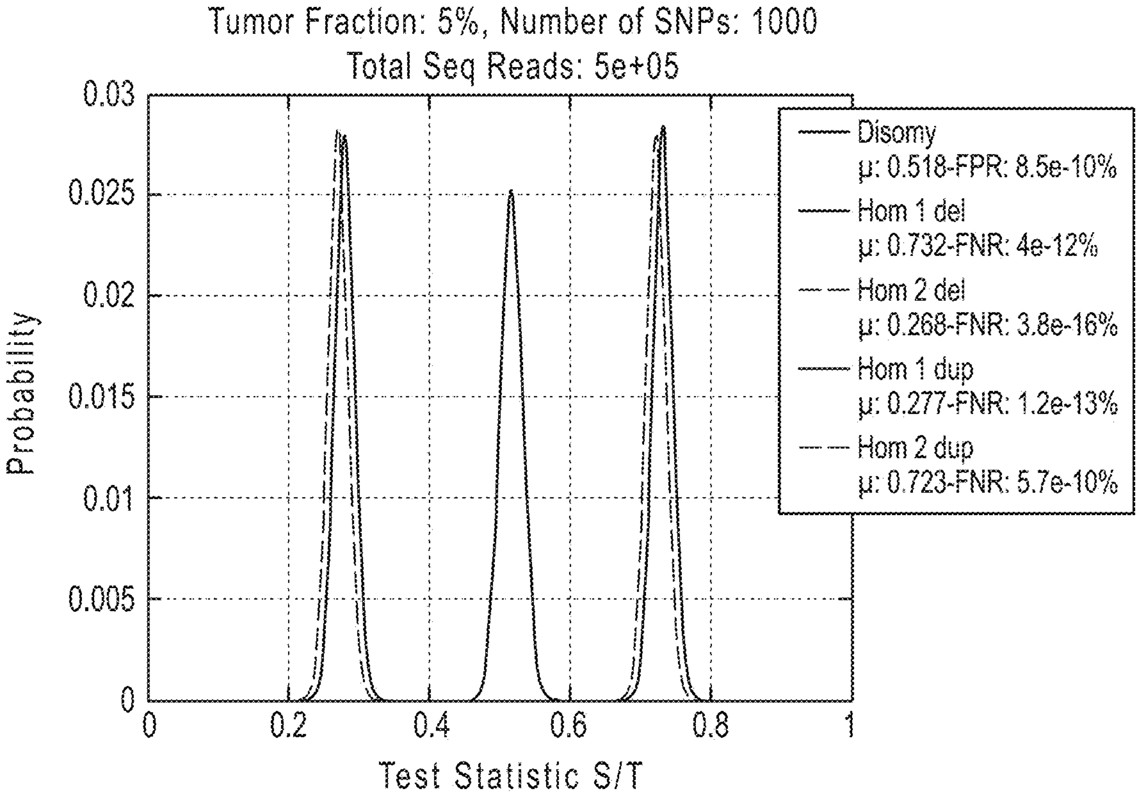
Figure 6A:
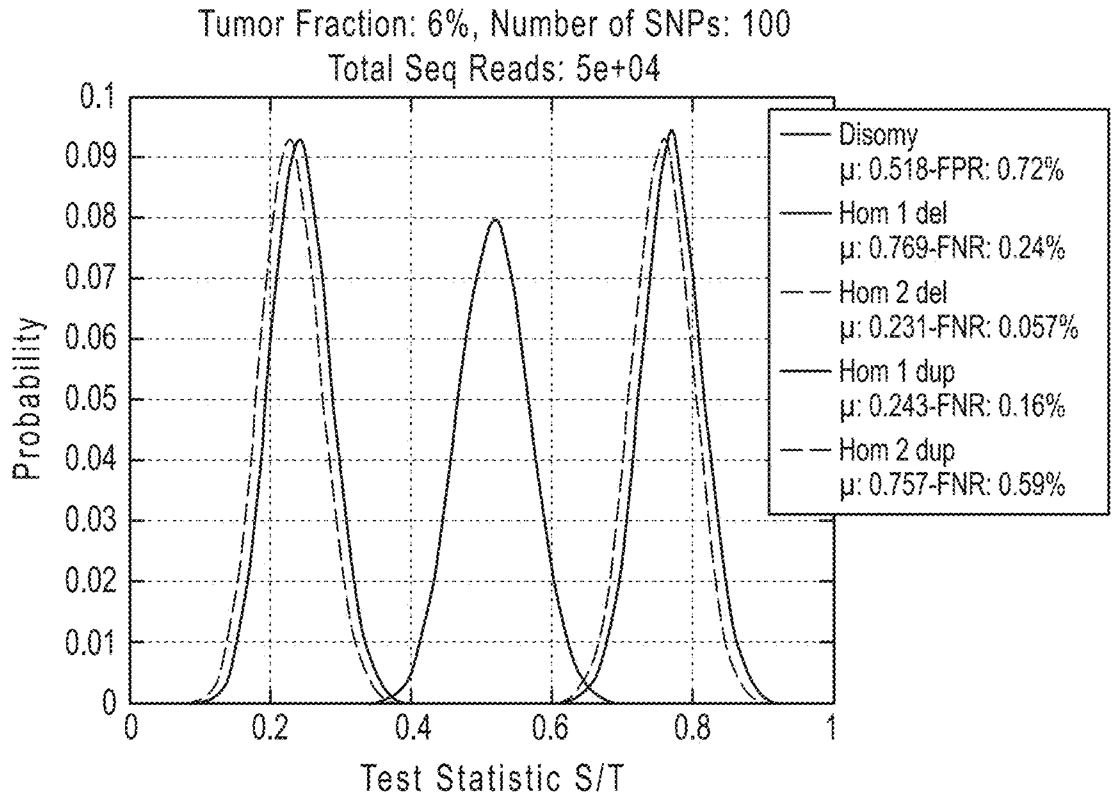
FIGS. 6A-6D are graphs showing the distribution of S/T for various copy number hypotheses for a DOR of 500 and tumor fraction of 6% for an increasing number of SNPs.
Figure 6B:
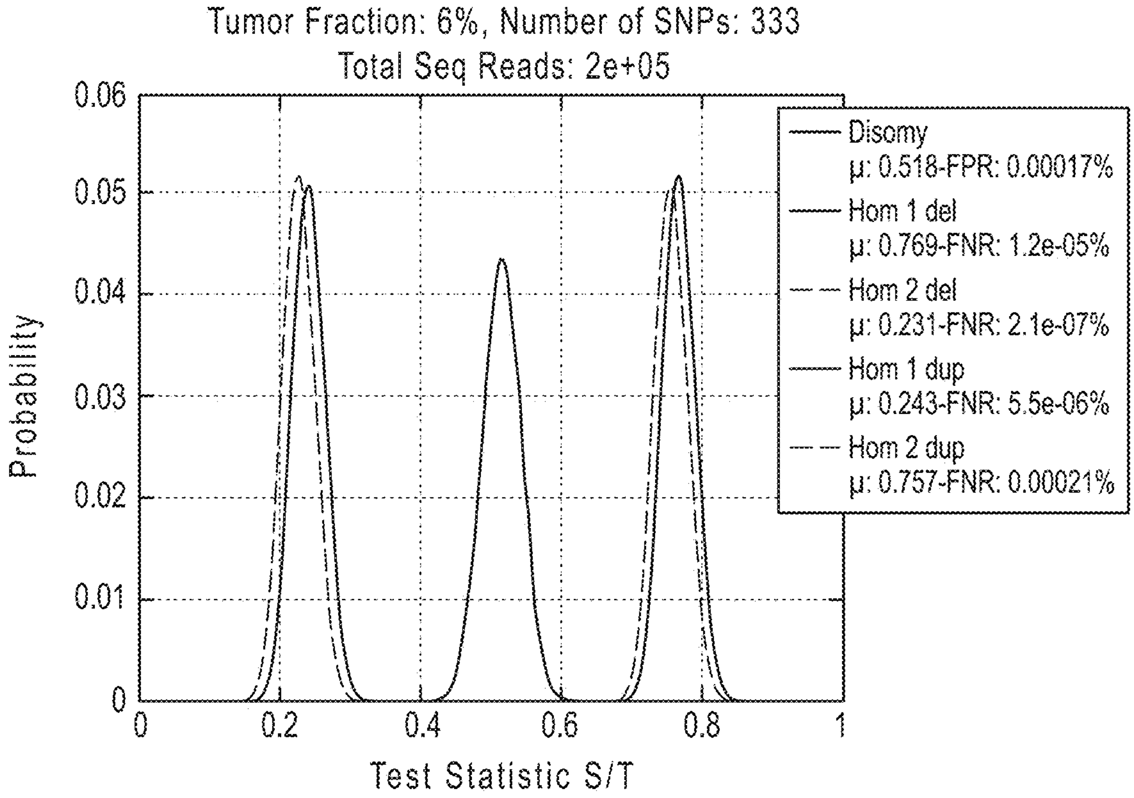
Figure 6C:
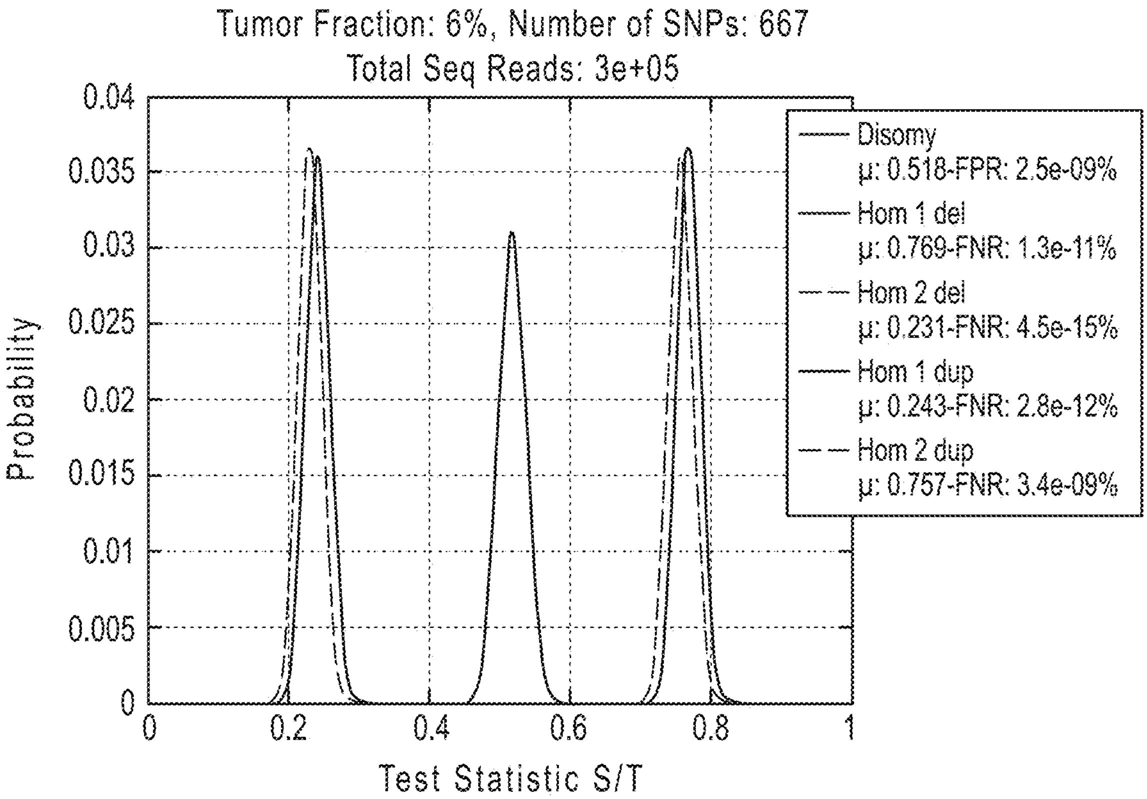
Figure 6D:
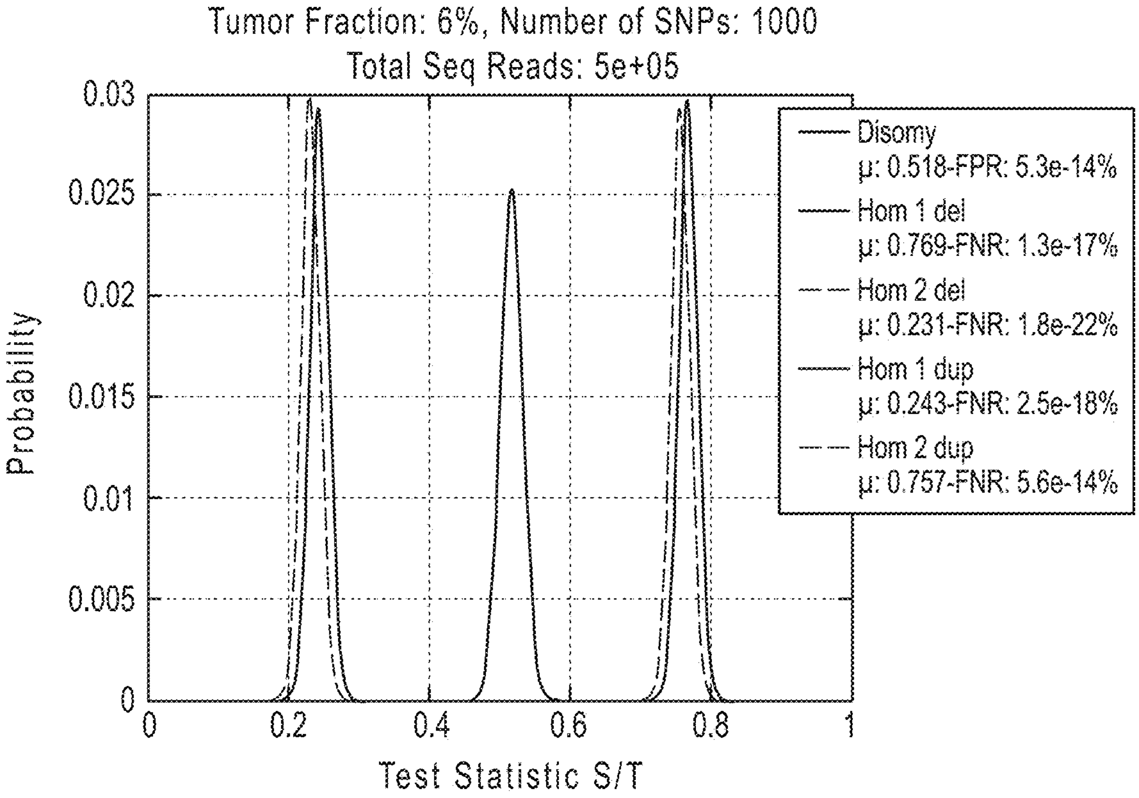
Figure 7A:
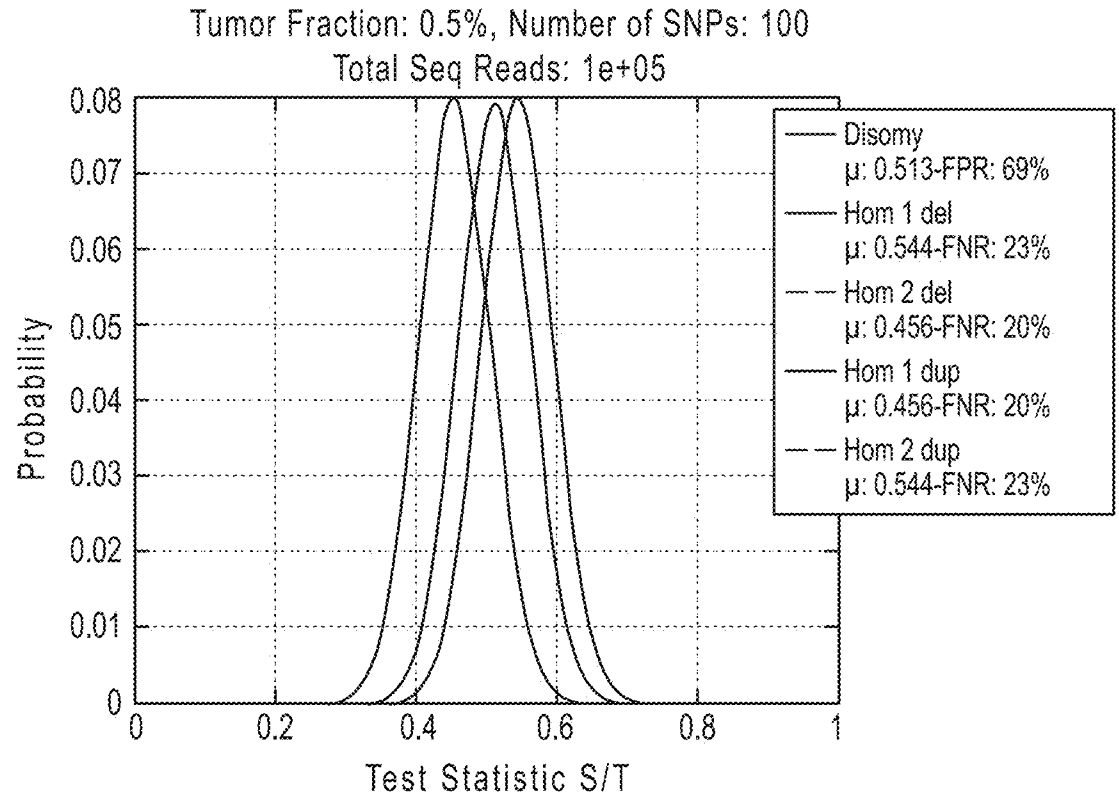
FIGS. 7A-7D are graphs showing the distribution of S/T for various copy number hypotheses for a DOR of 1000 and tumor fraction of 0.5% for an increasing number of SNPs.
Figure 7B:
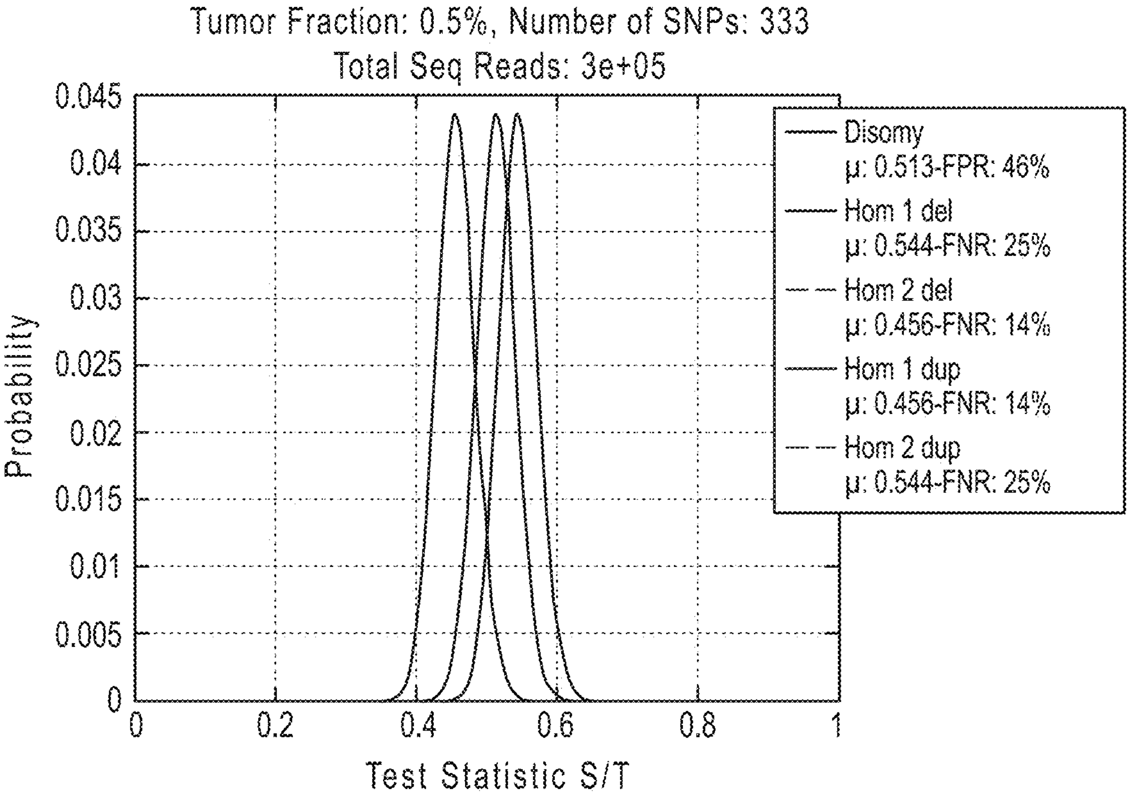
Figure 7C:
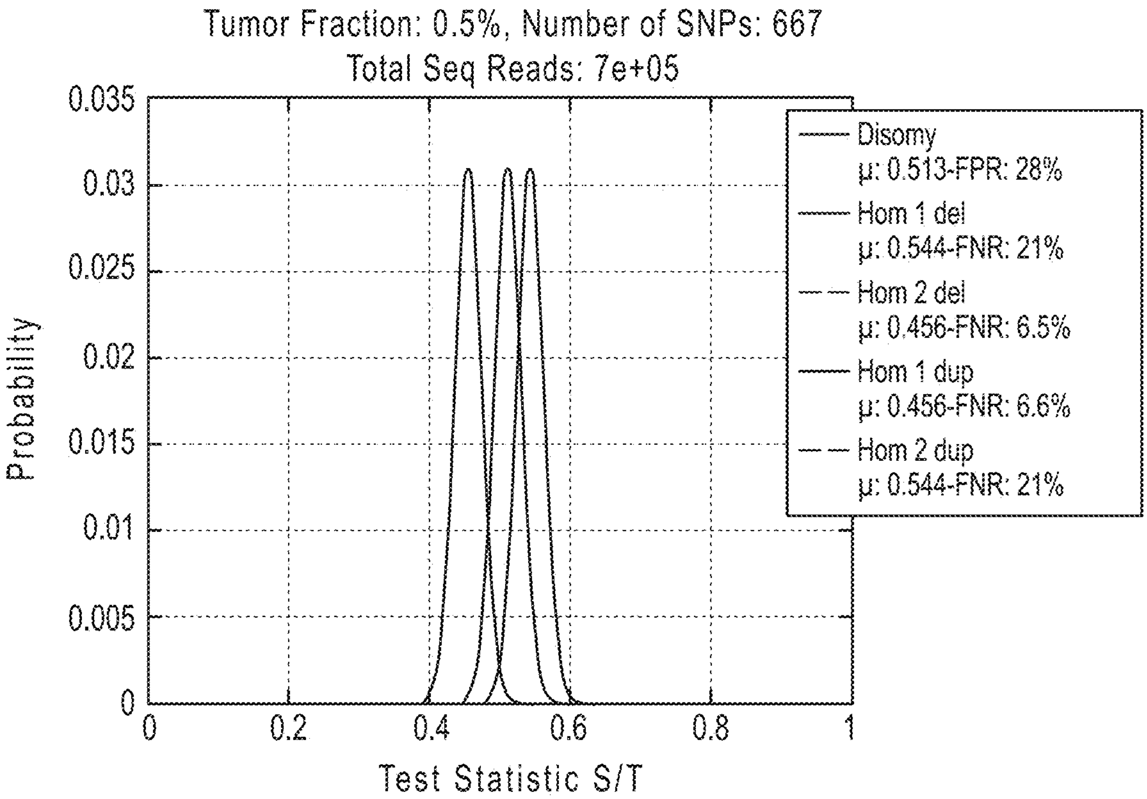
Figure 7D:
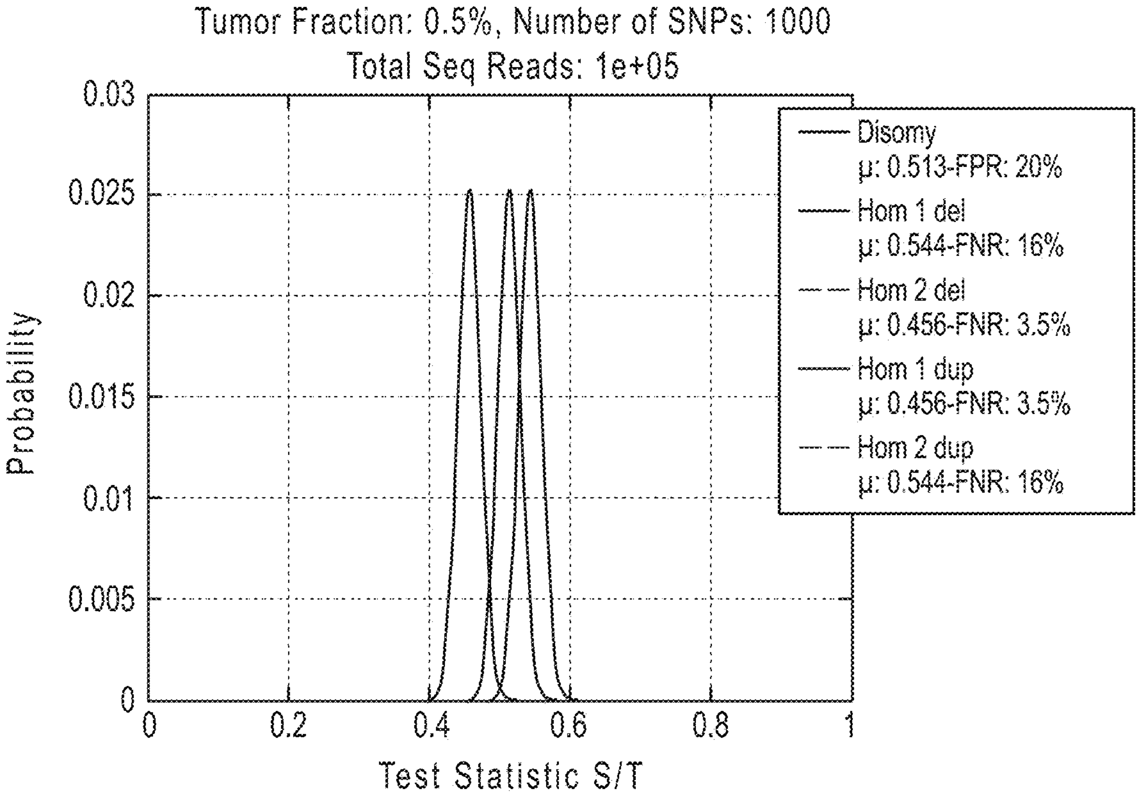
Figure 8A:
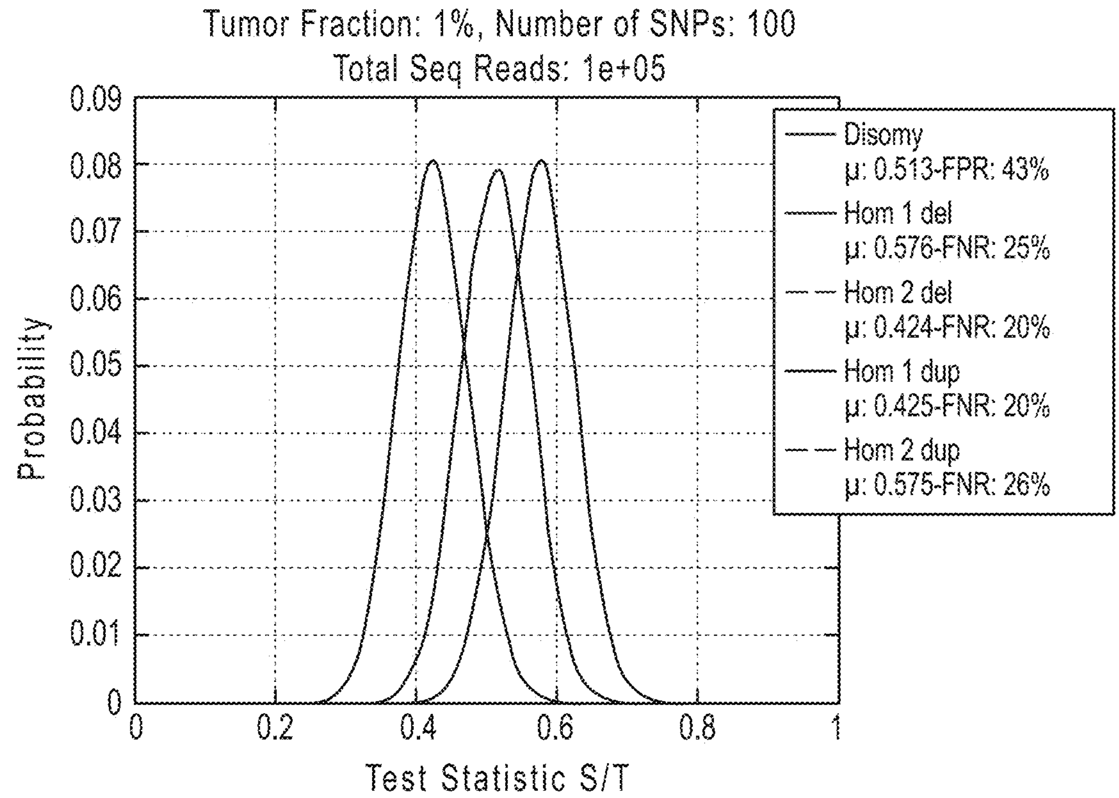
FIGS. 8A-8D are graphs showing the distribution of S/T for various copy number hypotheses for a DOR of 1000 and tumor fraction of 1% for an increasing number of SNPs.
Figure 8B:
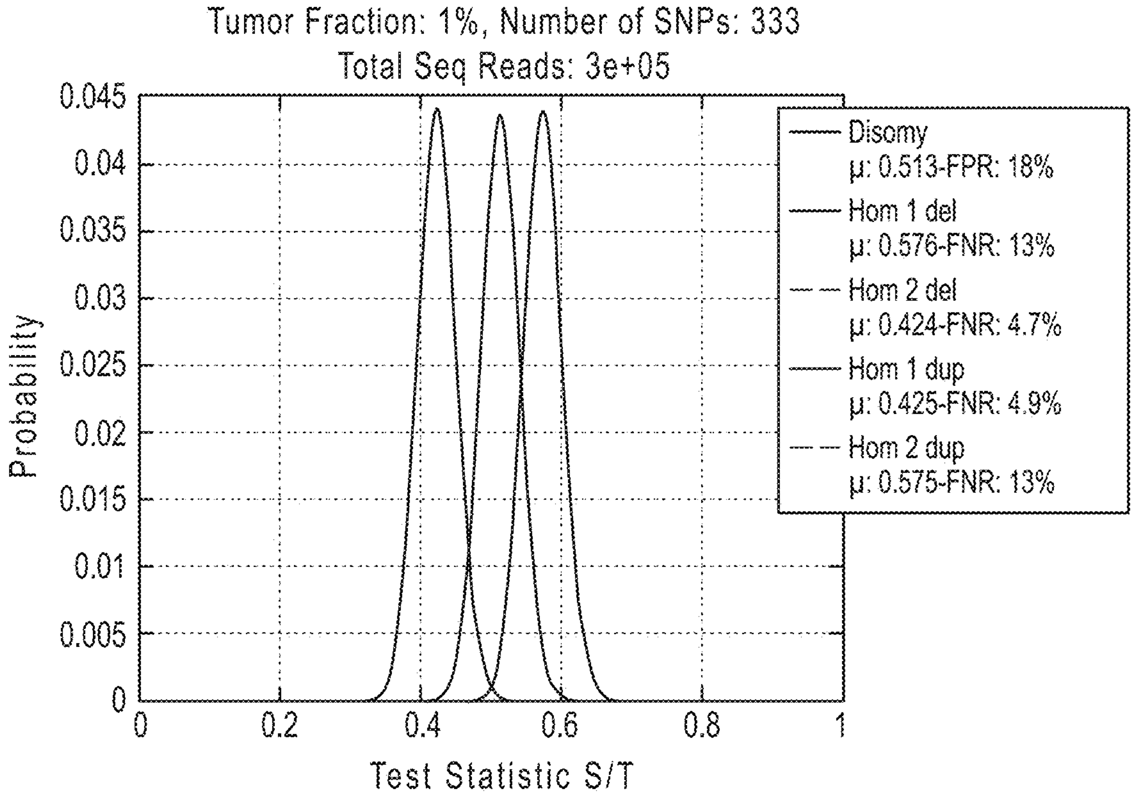
Figure 8C:
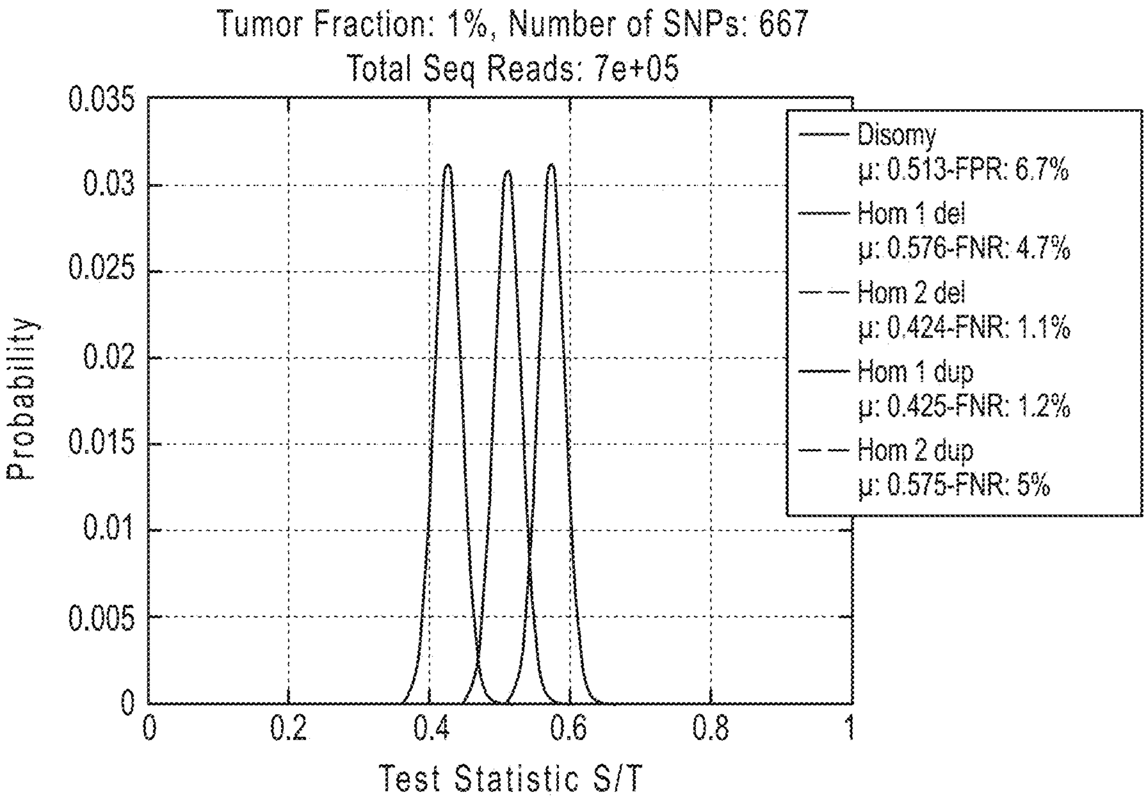
Figure 8D:
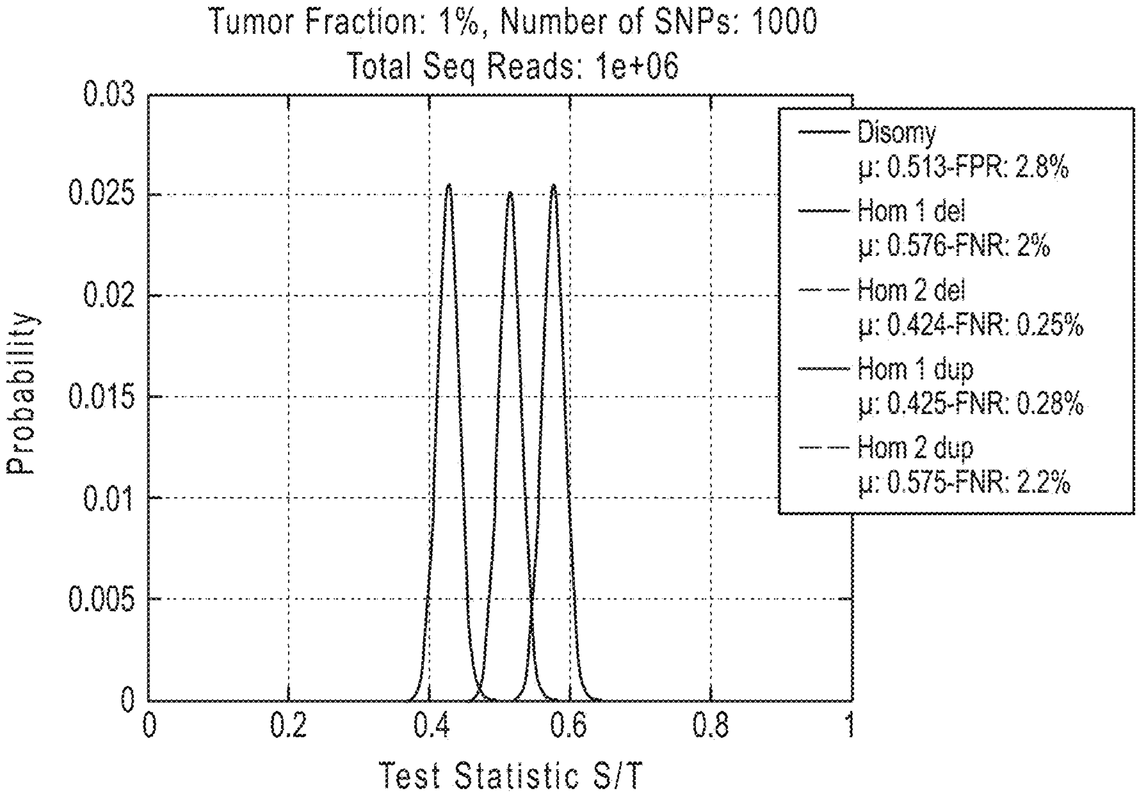
Figure 9A:
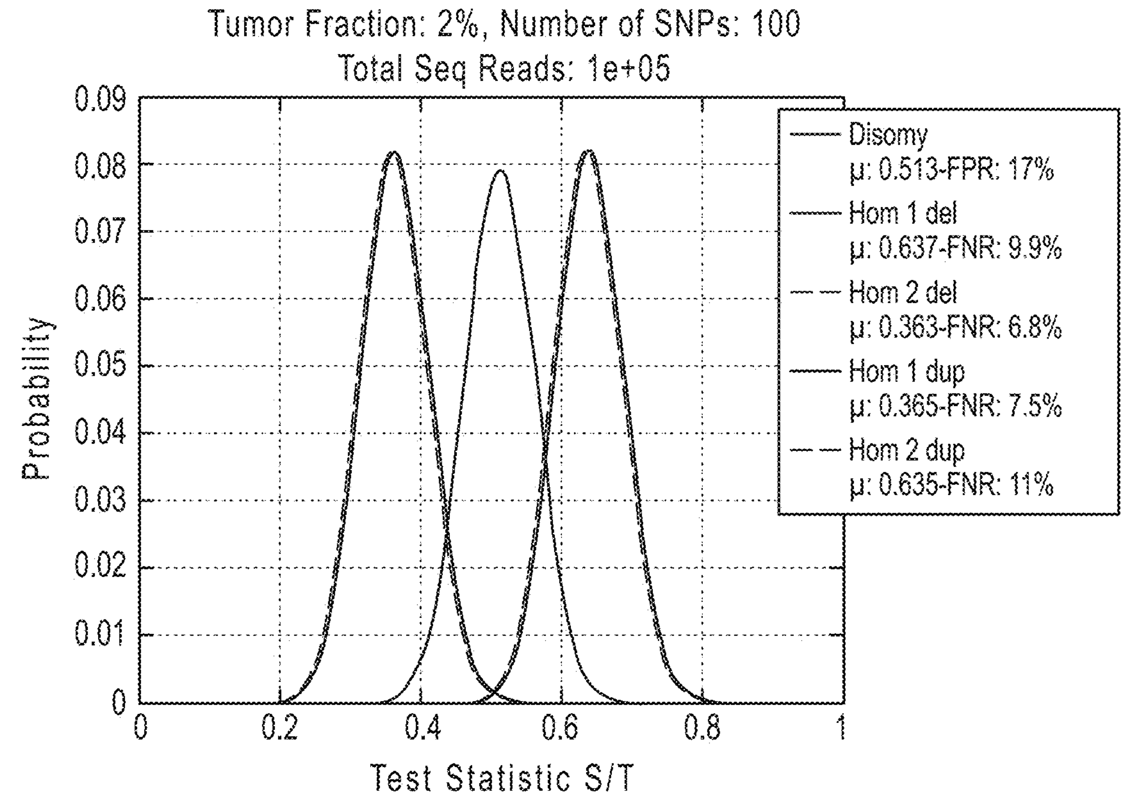
FIGS. 9A-9D are graphs showing the distribution of S/T for various copy number hypotheses for a DOR of 1000 and tumor fraction of 2% for an increasing number of SNPs.
Figure 9B:
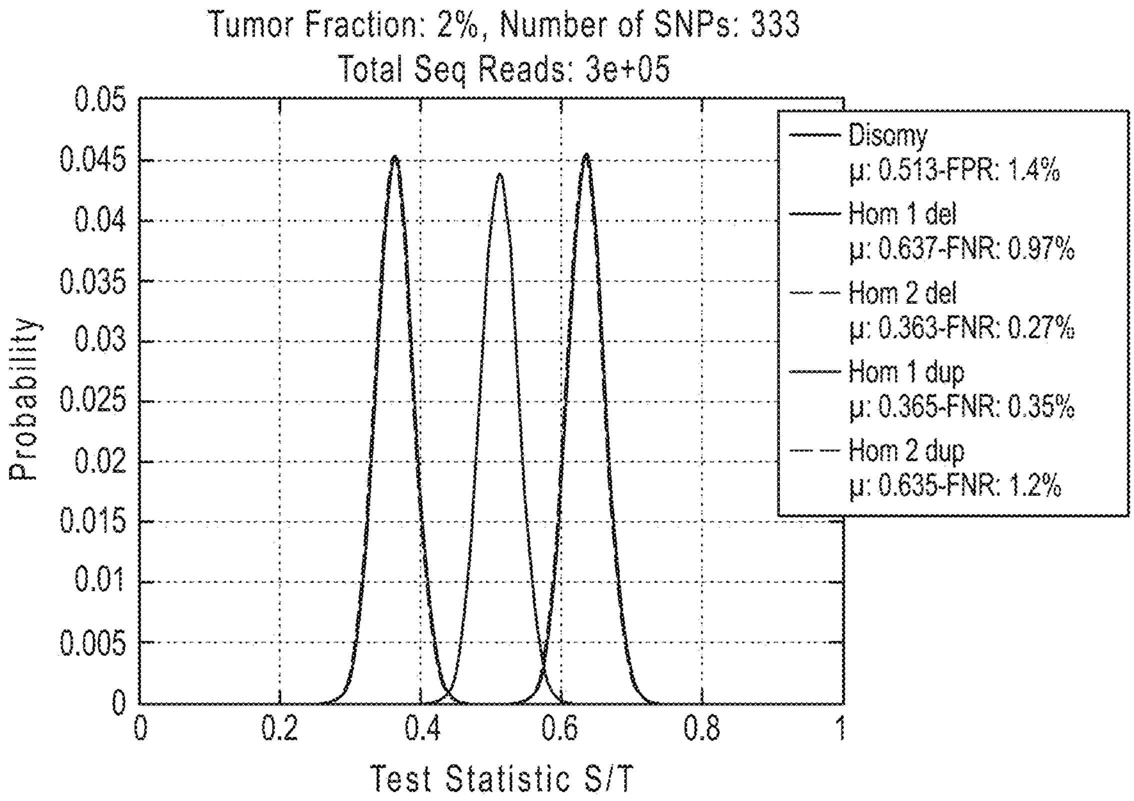
Figure 9C:
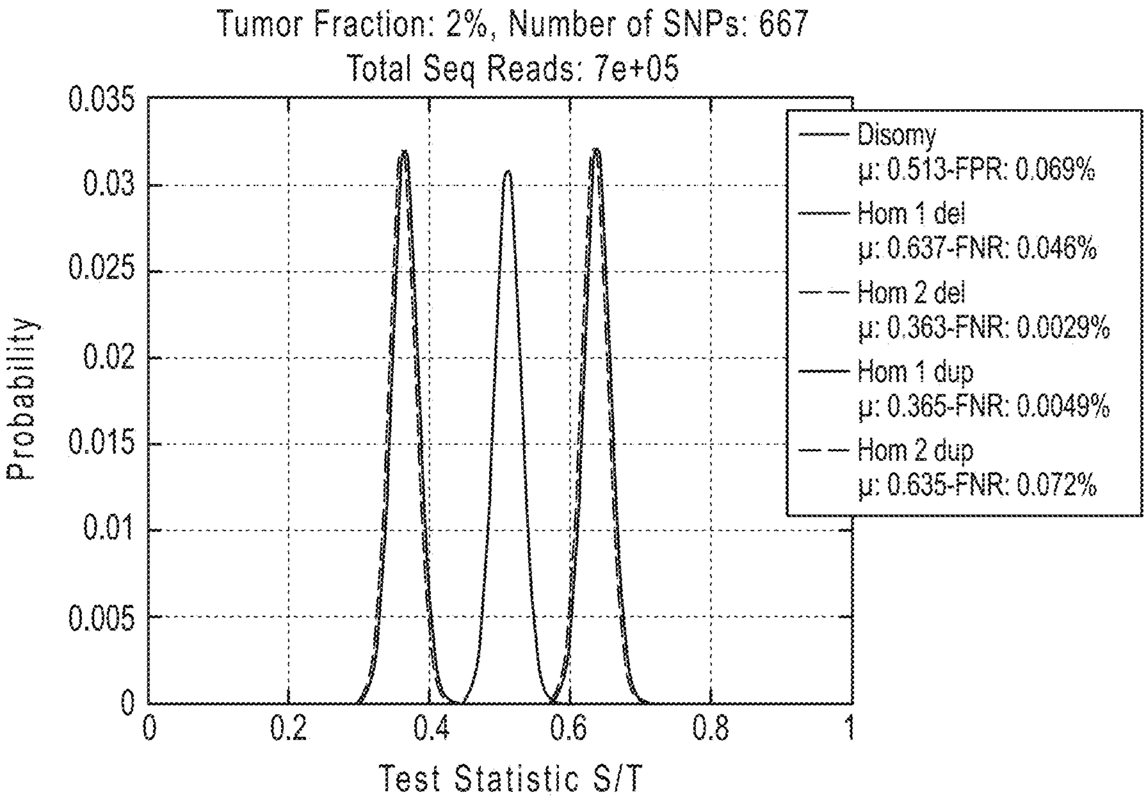
Figure 9D:
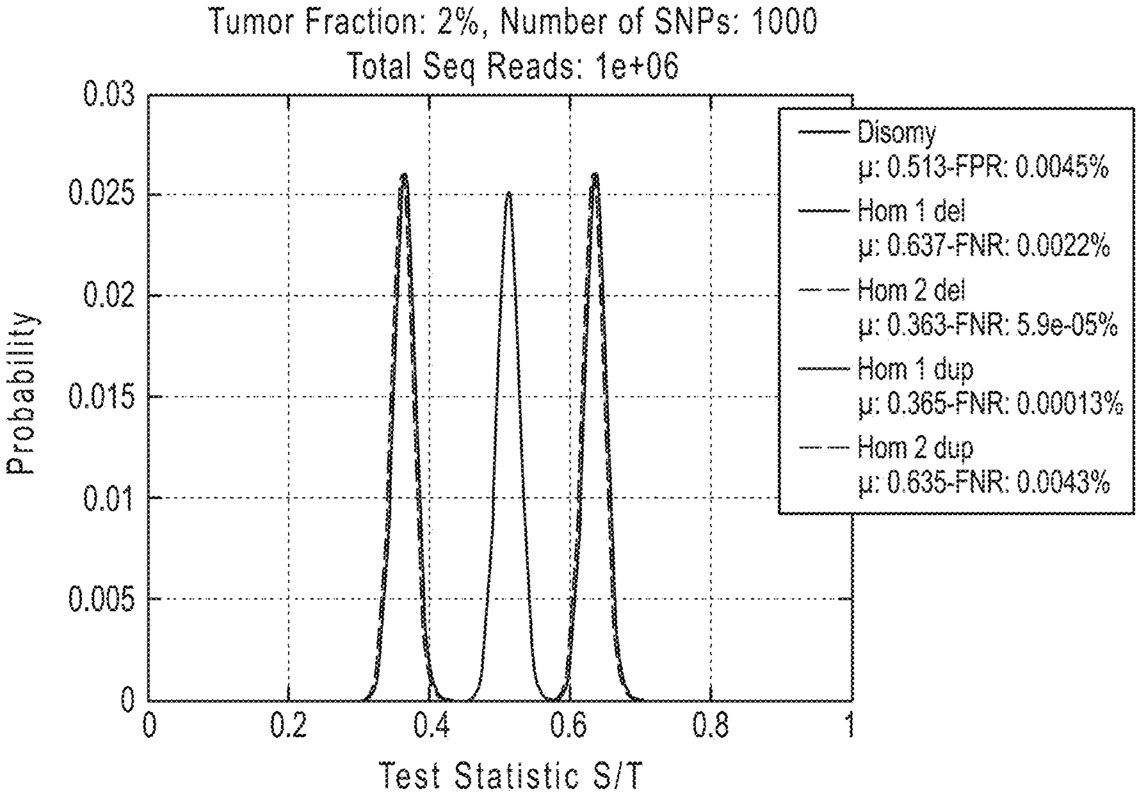
Figure 10A:
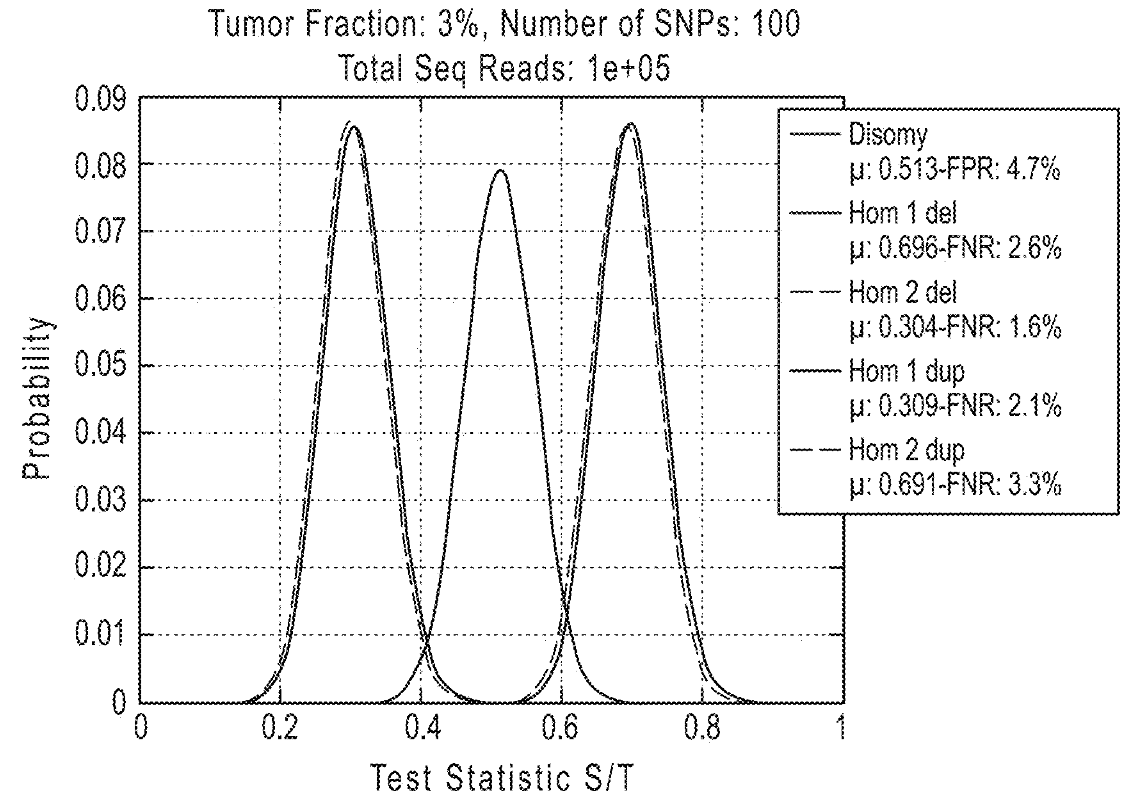
FIGS. 10A-10D are graphs showing the distribution of S/T for various copy number hypotheses for a DOR of 1000 and tumor fraction of 3% for an increasing number of SNPs.
Figure 10B:
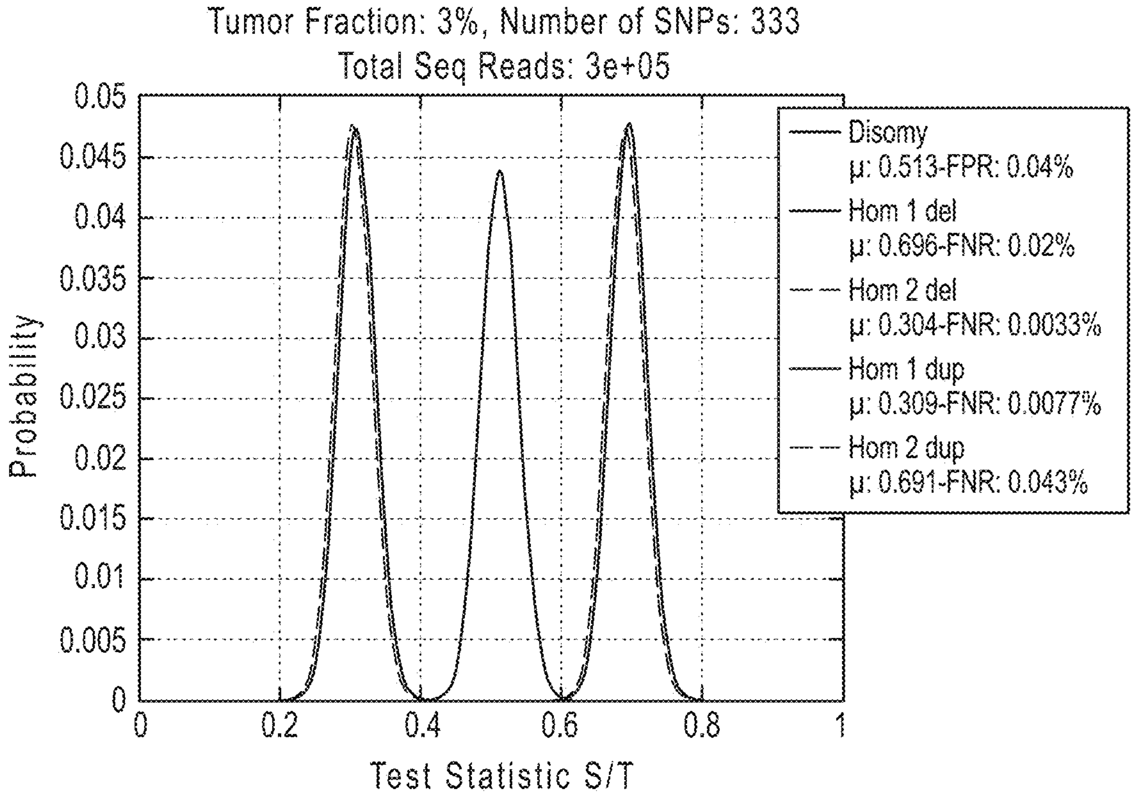
Figure 10C:
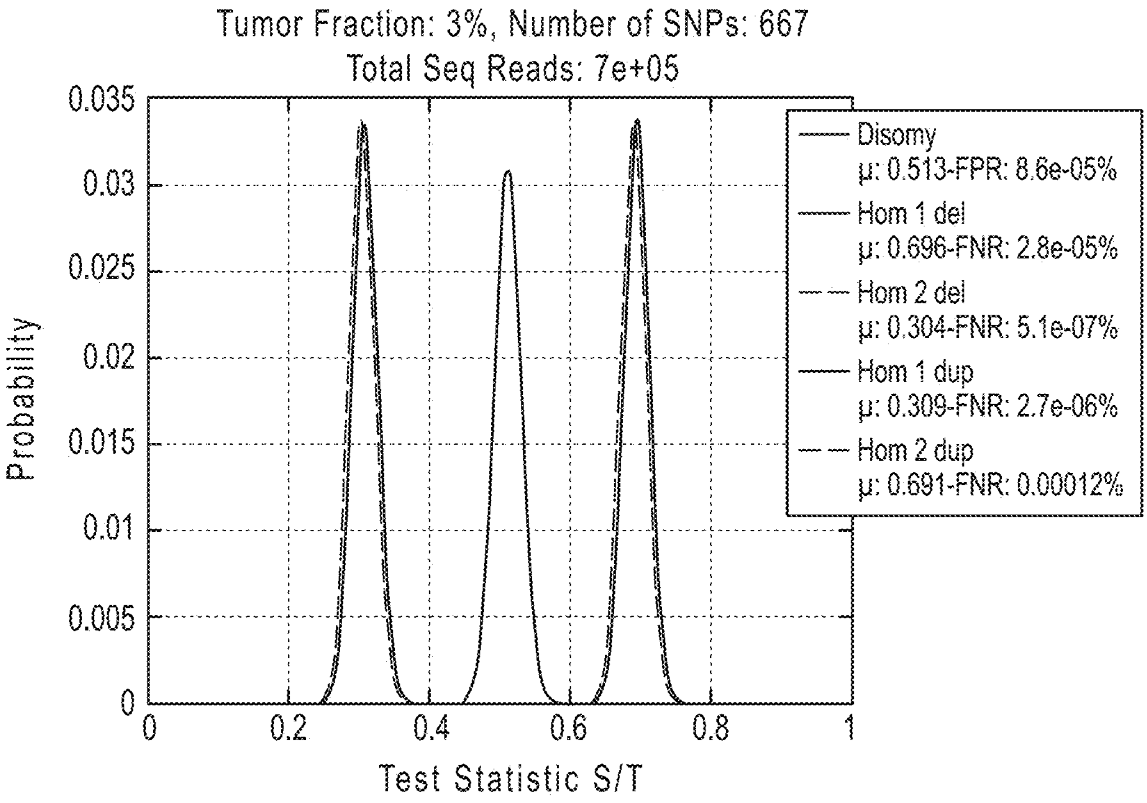
Figure 10D:
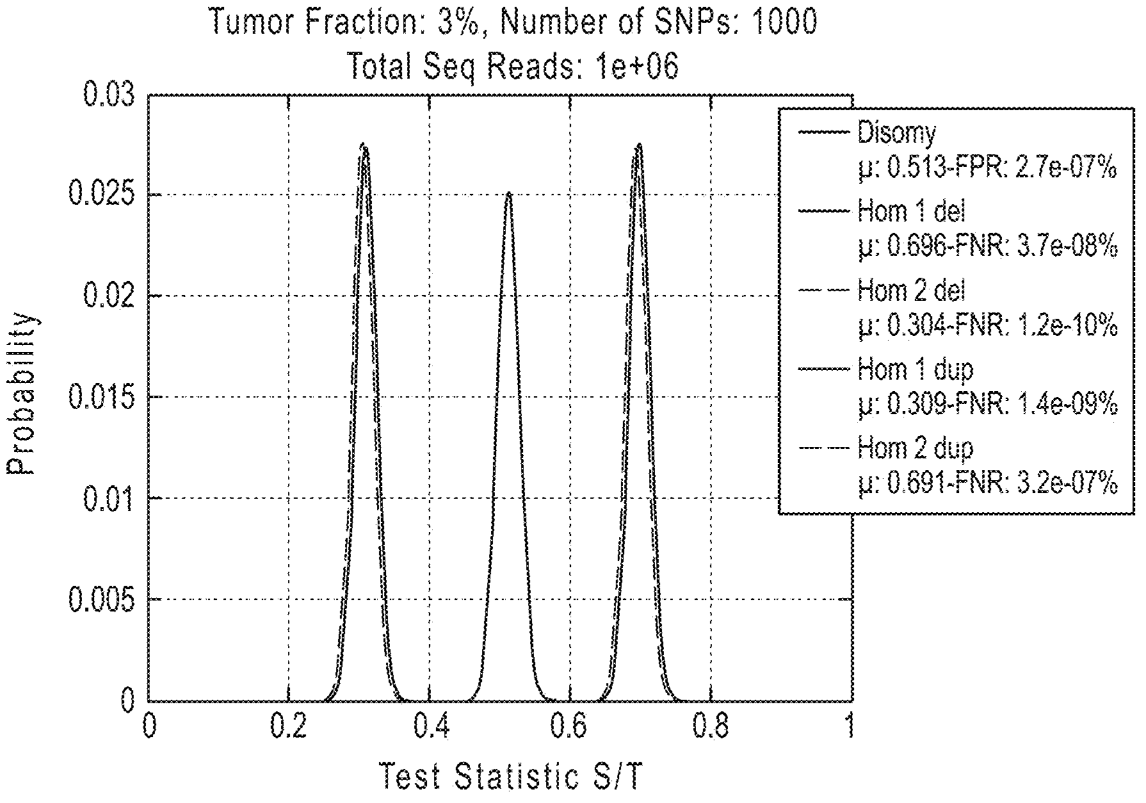
Figure 11A:
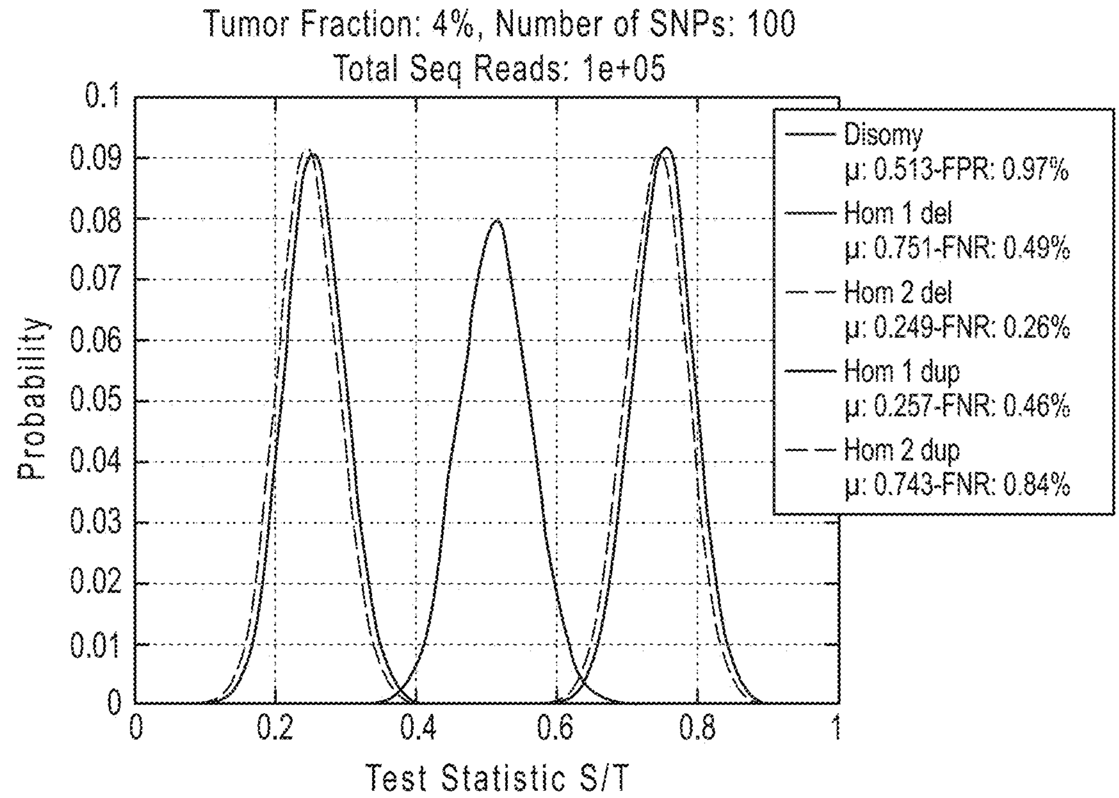
FIGS. 11A-11D are graphs showing the distribution of S/T for various copy number hypotheses for a DOR of 1000 and tumor fraction of 4% for an increasing number of SNPs.
Figure 11B:
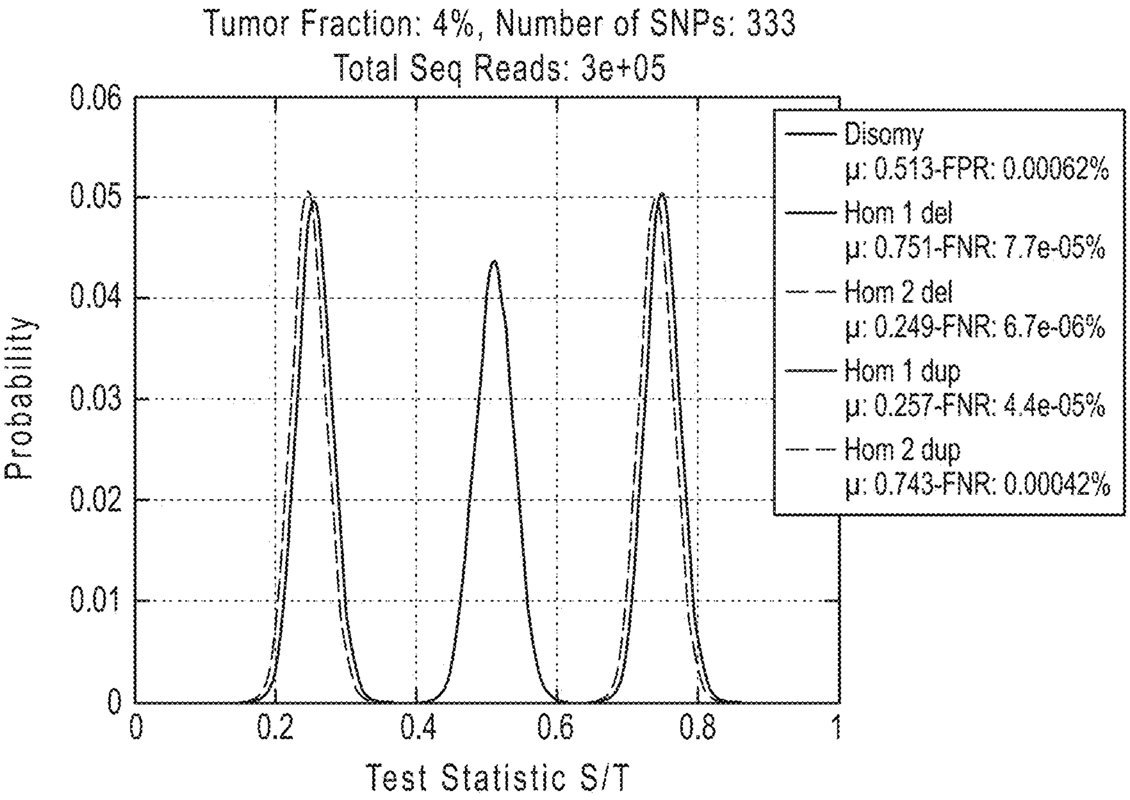
Figure 11C:
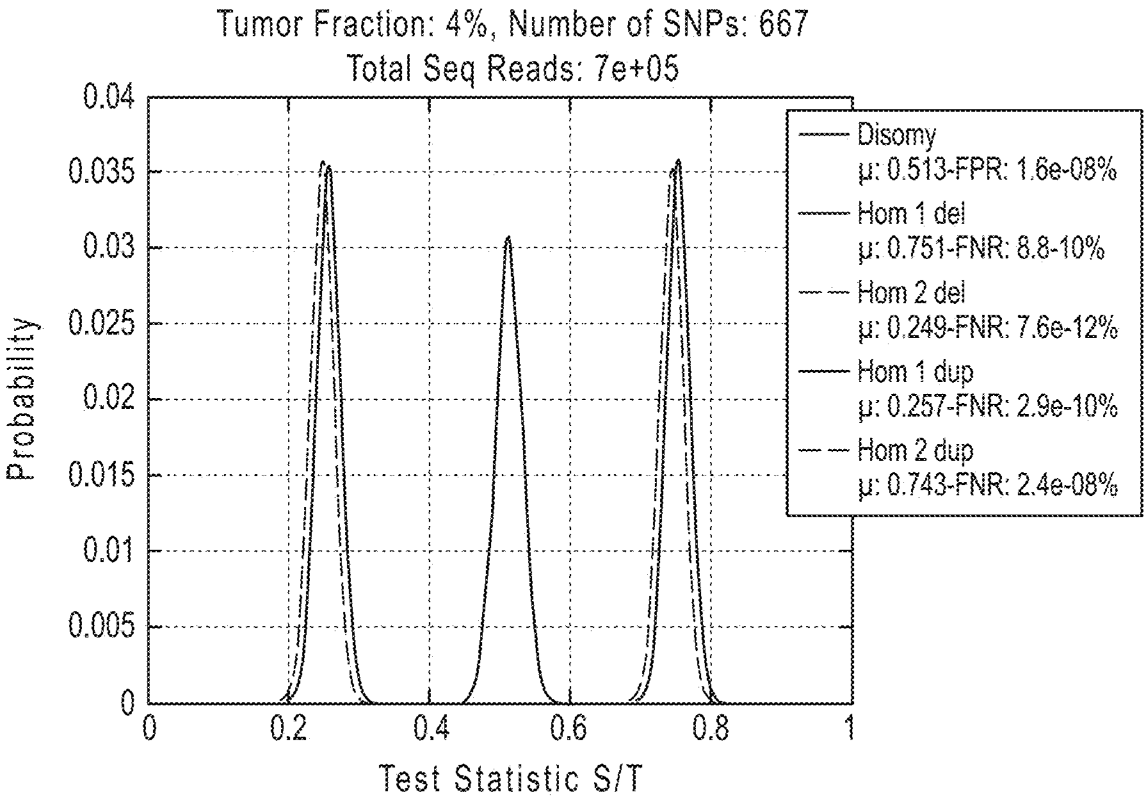
Figure 11D:
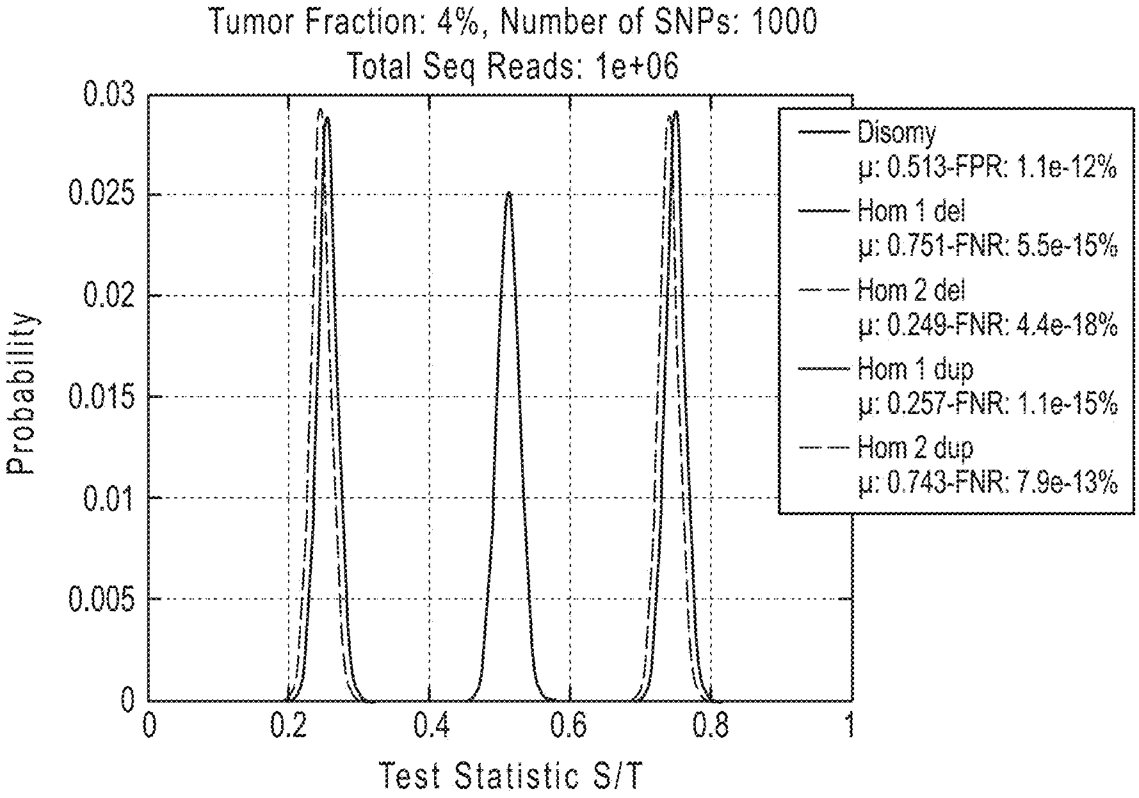
Figure 12A:
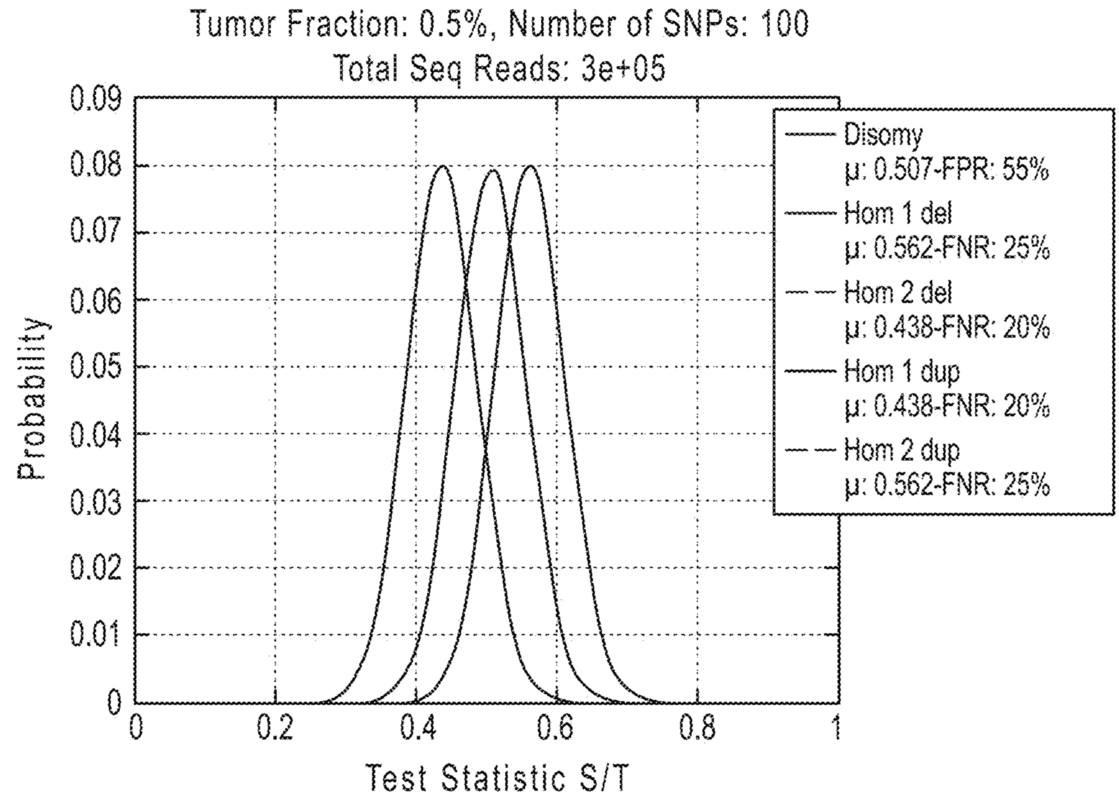
FIGS. 12A-12D are graphs showing the distribution of S/T for various copy number hypotheses for a DOR of 3000 and tumor fraction of 0.5% for an increasing number of SNPs.
Figure 12B:
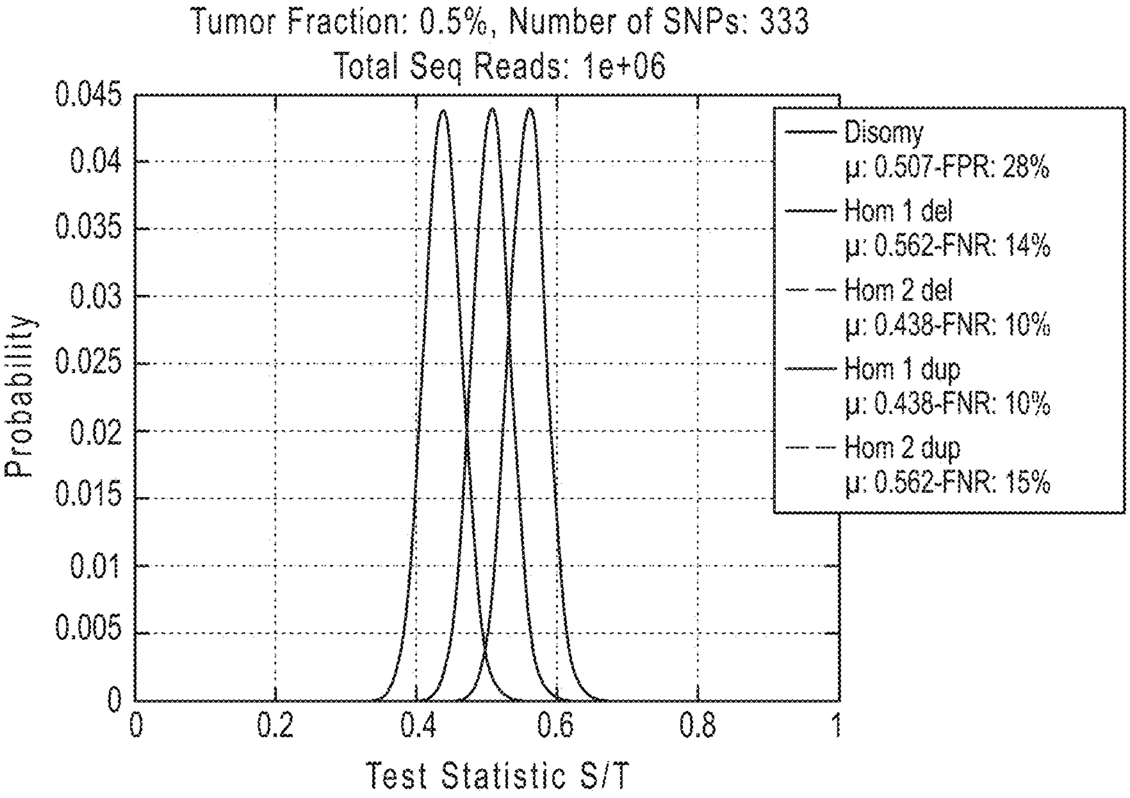
Figure 12C:
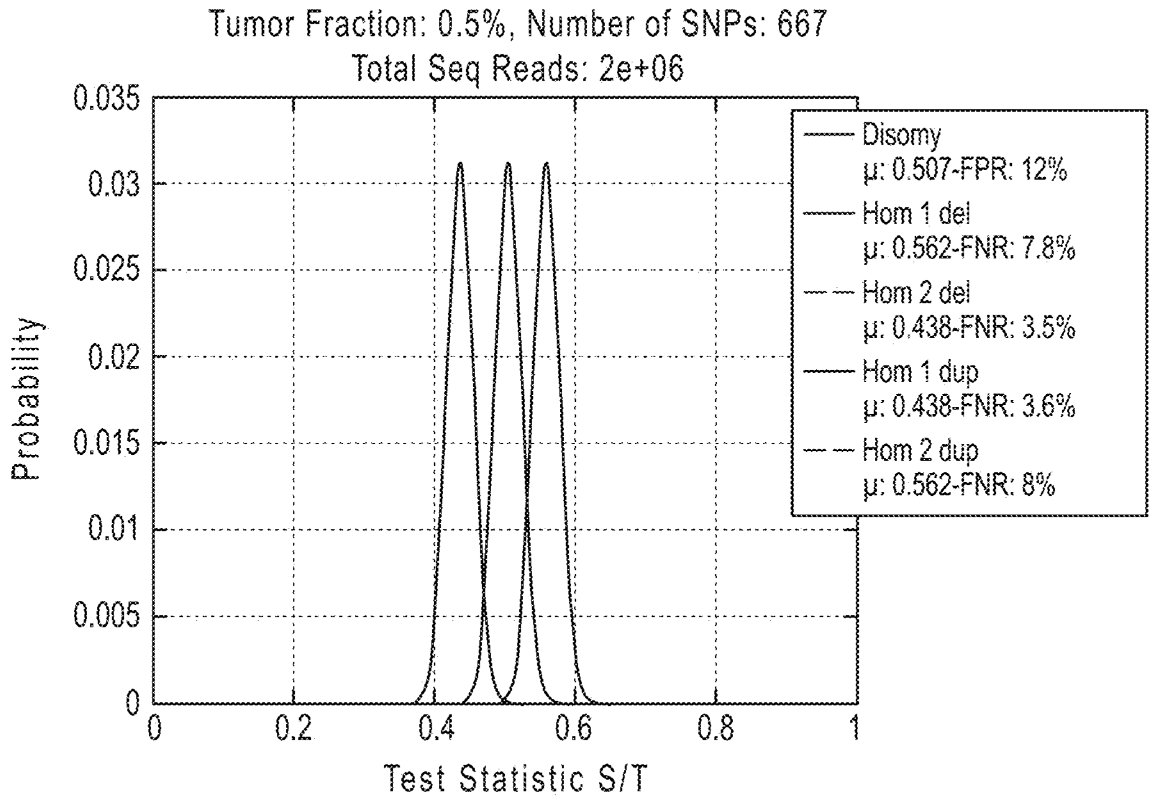
Figure 12D:
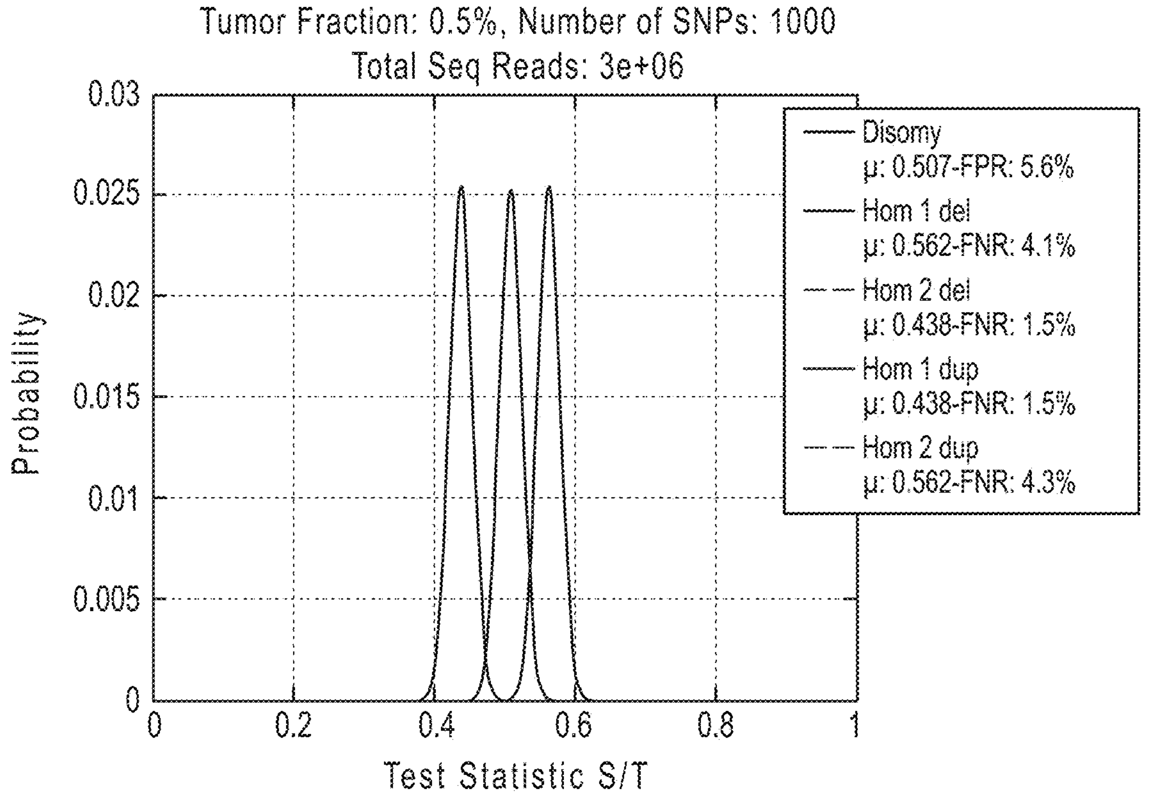
Figure 13A:
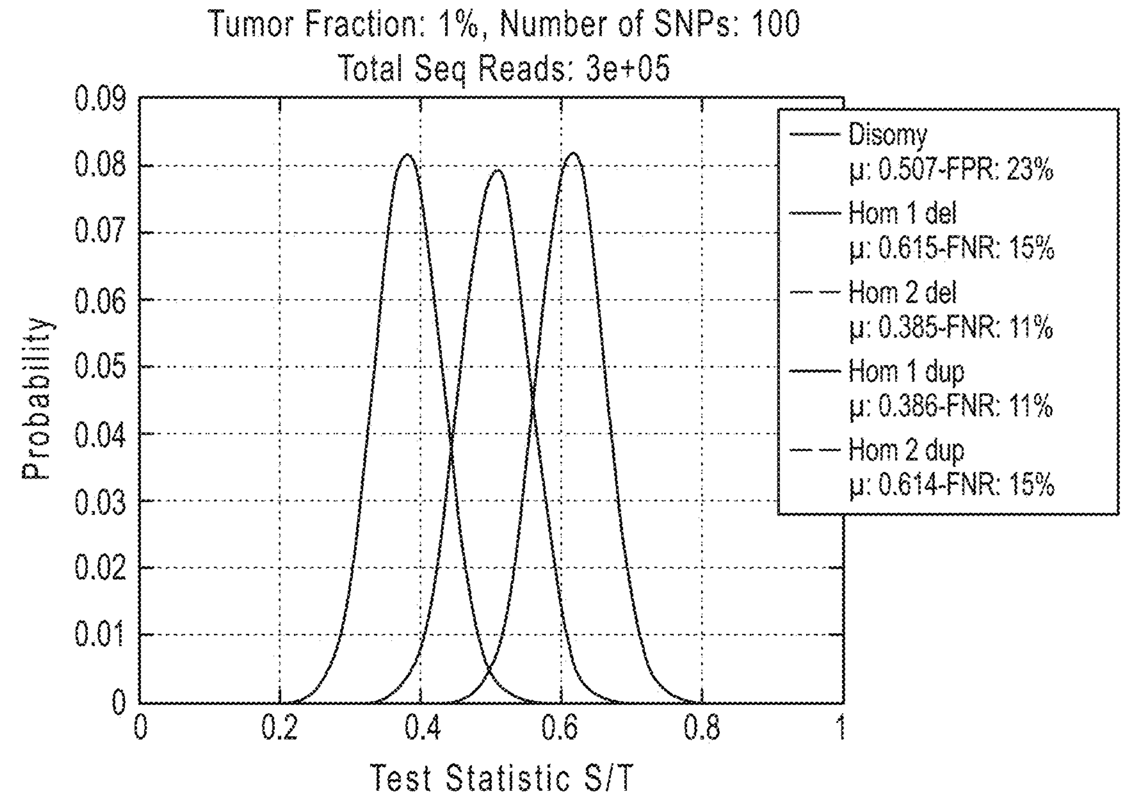
FIGS. 13A-13D are graphs showing the distribution of S/T for various copy number hypotheses for a DOR of 3000 and tumor fraction of 1% for an increasing number of SNPs.
Figure 13B:
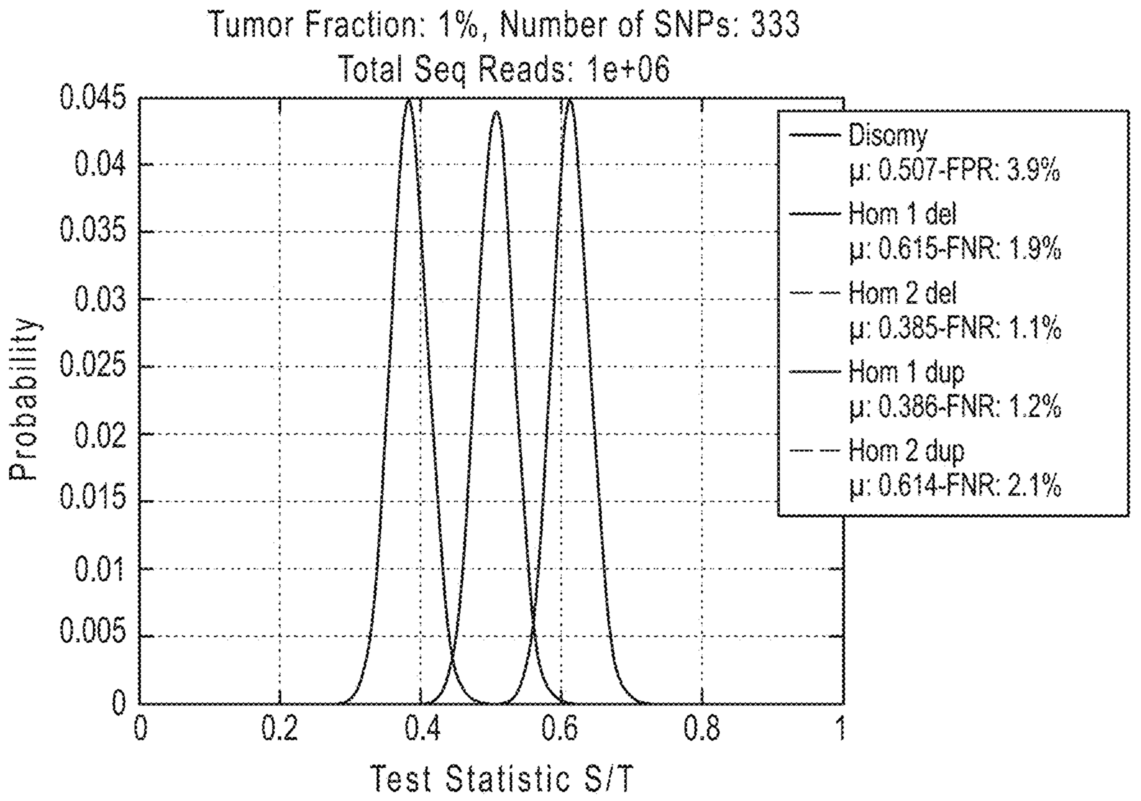
Figure 13C:
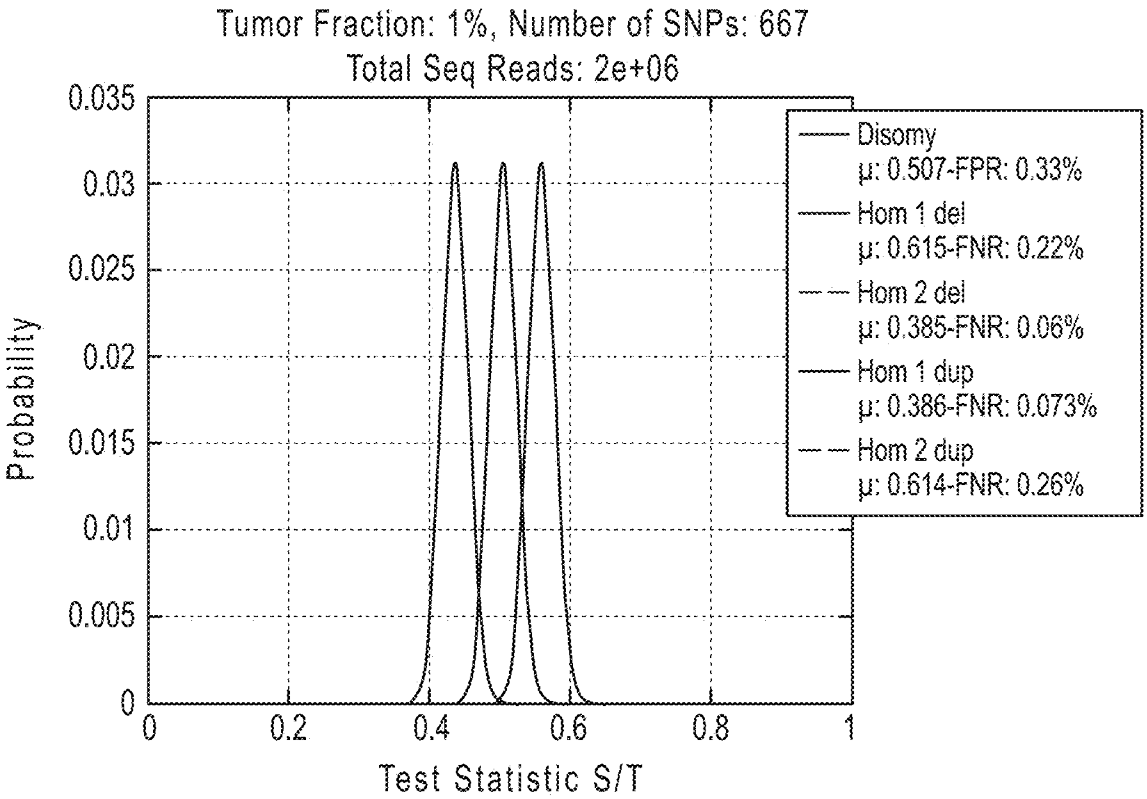
Figure 13D:
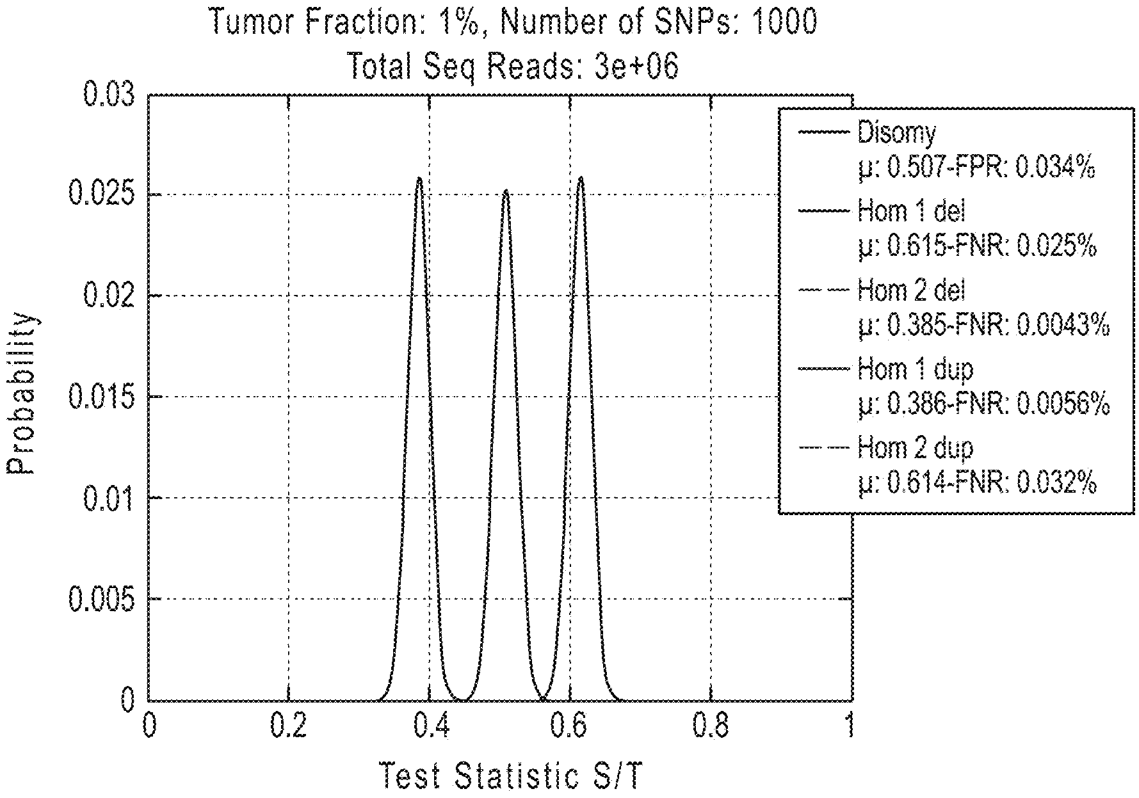
Figure 15:
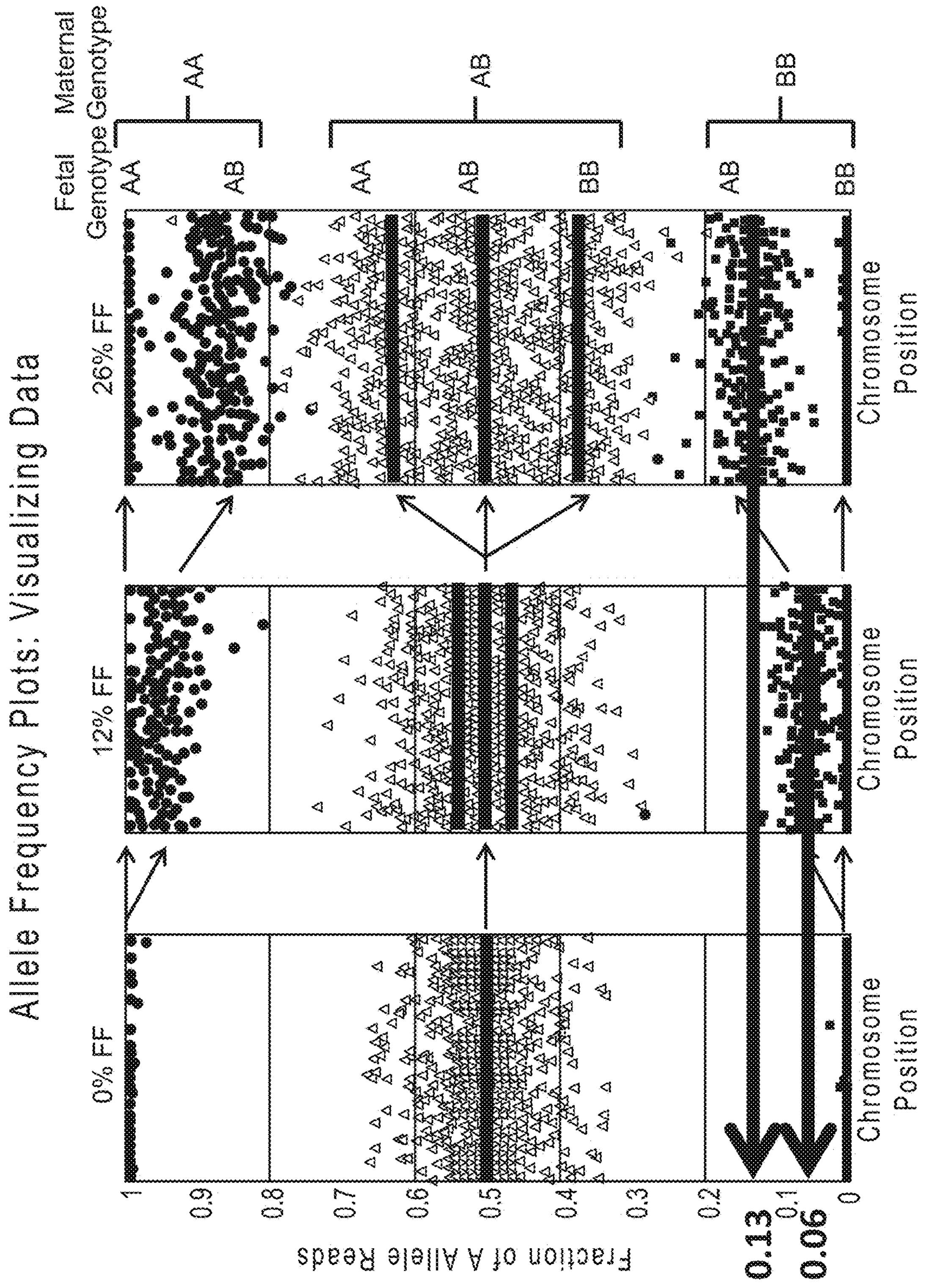
FIG. 15 is a graphical representation of euploidy. The x-axis represents the linear position of the individual polymorphic loci along the chromosome, and the y-axis represents the number of A allele reads as a fraction of the total (A+B) allele reads. Maternal and fetal genotypes are indicated to the right of the plots. The plots are symbol-coded according to maternal genotype, such that solid circles indicate a maternal genotype of AA, solid squares indicate a maternal genotype of BB, and open triangles indicate a maternal genotype of AB. The left plot is a plot of when two chromosomes are present, and the fetal cfDNA fraction is 0%. This plot is from a non-pregnant woman, and thus represents the pattern when the genotype is entirely maternal. Allele clusters are thus centered around 1 (AA alleles), 0.5 (AB alleles), and 0 (BB alleles). The center plot is a plot of when two chromosomes are present, and the fetal fraction is 12%. The contribution of fetal alleles to the fraction of A allele reads shifts the position of some allele spots up or down along the y-axis. The right plot is a plot of when two chromosomes are present, and the fetal fraction is 26%. The pattern, including two solid circle and two solid square peripheral bands and a trio of central open triangles, is readily apparent.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

In one aspect, the present invention generally relates, at least in part, to improved methods of determining the presence or absence of copy number variations, such as deletions or duplications of chromosome segments or entire chromosomes. The methods are particularly useful for detecting small deletions or duplications, which can be difficult to detect with high specificity and sensitivity using prior methods due to the small amount of data available from the relevant chromosome segment. The methods include improved analytical methods, improved bioassay methods, and combinations of improved analytical and bioassay methods. Methods of the invention can also be used to detect deletions or duplications that are only present in a small percentage of the cells or nucleic acid molecules that are tested. This allows deletions or duplications to be detected prior to the occurrence of disease (such as at a precancerous stage) or in the early stages of disease, such as before a large number of diseased cells (such as cancer cells) with the deletion or duplication accumulate. The more accurate detection of deletions or duplications associated with a disease or disorder enable improved methods for diagnosing, prognosticating, preventing, delaying, stabilizing, or treating the disease or disorder. Several deletions or duplications are known to be associated with cancer or with severe mental or physical handicaps.

In another aspect, the present invention generally relates, at least in part, to improved methods of detecting single nucleotide variations (SNVs). These improved methods include improved analytical methods, improved bioassay methods, and improved methods that use a combination of improved analytical and bioassay methods. The methods in certain illustrative embodiments are used to detect, diagnose, monitor, or stage cancer, for example in samples where the SNV is present at very low concentrations, for example less than 10%, 5%, 4%, 3%, 2.5%, 2%, 1%, 0.5%, 0.25%, or 0.1% relative to the total number of normal copies of the SNV locus, such as circulating free DNA samples. That is, these methods in certain illustrative embodiments are particularly well suited for samples where there is a relatively low percentage of a mutation or variant relative to the normal polymorphic alleles present for that genetic loci. Finally, provided herein are methods that combine the improved methods for detecting copy number variations with the improved methods for detecting single nucleotide variations.

Successful treatment of a disease such as cancer often relies on early diagnosis, correct staging of the disease, selection of an effective therapeutic regimen, and close monitoring to prevent or detect relapse. For cancer diagnosis, histological evaluation of tumor material obtained from tissue biopsy is often considered the most reliable method. However, the invasive nature of biopsy-based sampling has rendered it impractical for mass screening and regular follow up. Therefore, the present methods have the advantage of being able to be performed non-invasively if desired for relatively low cost with fast turnaround time. The targeted sequencing that may be used by the methods of the invention requires less reads than shotgun sequencing, such as a few million reads instead of 40 million reads, thereby decreasing cost. The multiplex PCR and next generation sequencing that may be used increase throughput and reduces costs.

In some embodiments, the methods are used to detect a deletion, duplication, or single nucleotide variant in an individual. A sample from the individual that contains cells or nucleic acids suspected of having a deletion, duplication, or single nucleotide variant may be analyzed. In some embodiments, the sample is from a tissue or organ suspected of having a deletion, duplication, or single nucleotide variant, such as cells or a mass suspected of being cancerous. The methods of the invention can be used to detect deletion, duplication, or single nucleotide variant that are only present in one cell or a small number of cells in a mixture containing cells with the deletion, duplication, or single nucleotide variant and cells without the deletion, duplication, or single nucleotide variant. In some embodiments, cfDNA or cfRNA from a blood sample from the individual is analyzed. In some embodiments, cfDNA or cfRNA is secreted by cells, such as cancer cells. In some embodiments, cfDNA or cfRNA is released by cells undergoing necrosis or apoptosis, such as cancer cells. The methods of the invention can be used to detect deletion, duplication, or single nucleotide variant that are only present in a small percentage of the cfDNA or cfRNA. In some embodiments, one or more cells from an embryo are tested.

In some embodiments, the methods are used for non-invasive or invasive prenatal testing of a fetus. These methods can be used to determine the presence or absence of deletions or duplications of a chromosome segment or an entire chromosome, such as deletions or duplications known to be associated severe mental or physical handicaps, learning disabilities, or cancer. In some embodiments for non-invasive prenatal testing (NIPT), cells, cfDNA or cfRNA from a blood sample from the pregnant mother is tested. The methods allow the detection of a deletion or duplication in the cells, cfDNA, or cfRNA from the fetus despite the large amount of cells, cfDNA, or cfRNA from the mother that is also present. In some embodiments for invasive prenatal testing, DNA or RNA from a sample from the fetus is tested (such as a CVS or amniocentesis sample). Even if the sample is contaminated with DNA or RNA from the pregnant mother, the methods can be used to detect a deletion or duplication in the fetal DNA or RNA.

In addition to determining the presence or absence of copy number variation, one or more other factors can be analyzed if desired. These factors can be used to increase the accuracy of the diagnosis (such as determining the presence or absence of cancer or an increased risk for cancer, classifying the cancer, or staging the cancer) or prognosis. These factors can also be used to select a particular therapy or treatment regimen that is likely to be effective in the subject. Exemplary factors include the presence or absence of polymorphisms or mutation; altered (increased or decreased) levels of total or particular cfDNA, cfRNA, microRNA (miRNA); altered (increased or decreased) tumor fraction; altered (increased or decreased) methylation levels, altered (increased or decreased) DNA integrity, altered (increased or decreased) or alternative mRNA splicing.

The following sections describe methods for detecting deletions or duplications using phased data (such as inferred or measured phased data) or unphased data; samples that can be tested; methods for sample preparation, amplification, and quantification; methods for phasing genetic data; polymorphisms, mutations, nucleic acid alterations, mRNA splicing alterations, and changes in nucleic acid levels that can be detected; databases with results from the methods, other risk factors and screening methods; cancers that can be diagnosed or treated; cancer treatments; cancer models for testing treatments; and methods for formulating and administering treatments.

Exemplary Methods for Determining Ploidy Using Phased Data

Some of the methods of the invention are based in part on the discovery that using phased data for detecting CNVs decreases the false negative and false positive rates compared to using unphased data (FIGS. 20A-27). This improvement is greatest for samples with CNVs present in low levels. Thus, phase data increases the accuracy of CNV detection compared to using unphased data (such as methods that calculate allele ratios at one or more loci or aggregate allele ratios to give an aggregated value (such as an average value) over a chromosome or chromosome segment without considering whether the allele ratios at different loci indicate that the same or different haplotypes appear to be present in an abnormal amount). Using phased data allows a more accurate determination to be made of whether differences between measured and expected allele ratios are due to noise or due to the presence of a CNV. For example, if the differences between measured and expected allele ratios at most or all of the loci in a region indicate that the same haplotype is overrepresented, then a CNV is more likely to be present. Using linkage between alleles in a haplotype allows one to determine whether the measured genetic data is consistent with the same haplotype being overrepresented (rather than random noise). In contrast, if the differences between measured and expected allele ratios are only due to noise (such as experimental error), then in some embodiments, about half the time the first haplotype appears to be overrepresented and about the other half of the time, the second haplotype appears to be overrepresented.

Accuracy can be increased by taking into account the linkage between SNPs, and the likelihood of crossovers having occurred during the meiosis that gave rise to the gametes that formed the embryo that grew into the fetus. Using linkage when creating the expected distribution of allele measurements for one or more hypotheses allows the creation of expected allele measurements distributions that correspond to reality considerably better than when linkage is not used. For example, imagine that there are two SNPs, 1 and 2 located nearby one another, and the mother is A at SNP 1 and A at SNP 2 on one homolog, and B at SNP 1 and B at SNP 2 on homolog two. If the father is A for both SNPs on both homologs, and a B is measured for the fetus SNP 1, this indicates that homolog two has been inherited by the fetus, and therefore that there is a much higher likelihood of a B being present in the fetus at SNP 2. A model that takes into account linkage can predict this, while a model that does not take linkage into account cannot. Alternately, if a mother is AB at SNP 1 and AB at nearby SNP 2, then two hypotheses corresponding to maternal trisomy at that location can be used-one involving a matching copy error (nondisjunction in meiosis II or mitosis in early fetal development), and one involving an unmatching copy error (nondisjunction in meiosis I). In the case of a matching copy error trisomy, if the fetus inherited an AA from the mother at SNP 1, then the fetus is much more likely to inherit either an AA or BB from the mother at SNP 2, but not AB. In the case of an unmatching copy error, the fetus inherits an AB from the mother at both SNPs. The allele distribution hypotheses made by a CNV calling method that takes into account linkage can make these predictions, and therefore correspond to the actual allele measurements to a considerably greater extent than a CNV calling method that does not take into account linkage.

In some embodiments, phased genetic data is used to determine if there is an overrepresentation of the number of copies of a first homologous chromosome segment as compared to a second homologous chromosome segment in the genome of an individual (such as in the genome of one or more cells or in cfDNA or cfRNA). Exemplary overrepresentations include the duplication of the first homologous chromosome segment or the deletion of the second homologous chromosome segment. In some embodiments, there is not an overrepresentation since the first and homologous chromosome segments are present in equal proportions (such as one copy of each segment in a diploid sample). In some embodiments, calculated allele ratios in a nucleic acid sample are compared to expected allele ratios to determine if there is an overrepresentation as described further below. In this specification the phrase "a first homologous chromosome segment as compared to a second homologous chromosome segment" means a first homolog of a chromosome segment and a second homolog of the chromosome segment.

In some embodiments, the method includes obtaining phased genetic data for the first homologous chromosome segment comprising the identity of the allele present at that locus on the first homologous chromosome segment for each locus in a set of polymorphic loci on the first homologous chromosome segment, obtaining phased genetic data for the second homologous chromosome segment comprising the identity of the allele present at that locus on the second homologous chromosome segment for each locus in the set of polymorphic loci on the second homologous chromosome segment, and obtaining measured genetic allelic data comprising, for each of the alleles at each of the loci in the set of polymorphic loci, the amount of each allele present in a sample of DNA or RNA from one or more target cells and one or more non-target cells from the individual. In some embodiments, the method includes enumerating a set of one or more hypotheses specifying the degree of overrepresentation of the first homologous chromosome segment; calculating, for each of the hypotheses, expected genetic data for the plurality of loci in the sample from the obtained phased genetic data for one or more possible ratios of DNA or RNA from the one or more target cells to the total DNA or RNA in the sample; calculating (such as calculating on a computer) for each possible ratio of DNA or RNA and for each hypothesis, the data fit between the obtained genetic data of the sample and the expected genetic data for the sample for that possible ratio of DNA or RNA and for that hypothesis; ranking one or more of the hypotheses according to the data fit; and selecting the hypothesis that is ranked the highest, thereby determining the degree of overrepresentation of the number of copies of the first homologous chromosome segment in the genome of one or more cells from the individual.

In one aspect, the invention features a method for determining a number of copies of a chromosome or chromosome segment of interest in the genome of a fetus. In some embodiments, the method includes obtaining phased genetic data for at least one biological parent of the fetus, wherein the phased genetic data comprises the identity of the allele present for each locus in a set of polymorphic loci on a first homologous chromosome segment and a second homologous chromosome segment in the parent. In some embodiments, the method includes obtaining genetic data at the set of polymorphic loci on the chromosome or chromosome segment in a mixed sample of DNA or RNA comprising fetal DNA or RNA and maternal DNA or RNA from the mother of the fetus by measuring the quantity of each allele at each locus. In some embodiments, the method includes enumerating a set of one or more hypotheses specifying the number of copies of the chromosome or chromosome segment of interest present in the genome of the fetus. In some embodiments, the method includes creating (such as creating on a computer) for each of the hypotheses, a probability distribution of the expected quantity of each allele at each of the plurality of loci in mixed sample from the (i) the obtained phased genetic data from the parent(s) and optionally (ii) the probability of one or more crossovers that may have occurred during the formation of a gamete that contributed a copy of the chromosome or chromosome segment of interest to the fetus; calculating (such as calculating on a computer) a fit, for each of the hypotheses, between (1) the obtained genetic data of the mixed sample and (2) the probability distribution of the expected quantity of each allele at each of the plurality of loci in mixed sample for that hypothesis; ranking one or more of the hypotheses according to the data fit; and selecting the hypothesis that is ranked the highest, thereby determining the number of copies of the chromosome segment of interest in the genome of the fetus.

In some embodiments, the method involves obtaining phased genetic data using any of the methods described herein or any known method. In some embodiments, the method involves simultaneously or sequentially in any order (i) obtaining phased genetic data for the first homologous chromosome segment comprising the identity of the allele present at that locus on the first homologous chromosome segment for each locus in a set of polymorphic loci on the first homologous chromosome segment, (ii) obtaining phased genetic data for the second homologous chromosome segment comprising the identity of the allele present at that locus on the second homologous chromosome segment for each locus in the set of polymorphic loci on the second homologous chromosome segment, and (iii) obtaining measured genetic allelic data comprising the amount of each allele at each of the loci in the set of polymorphic loci in a sample of DNA from one or more cells from the individual.

In some embodiments, the method involves calculating allele ratios for one or more loci in the set of polymorphic loci that are heterozygous in at least one cell from which the sample was derived (such as the loci that are heterozygous in the fetus and/or heterozygous in the mother). In some embodiments, the calculated allele ratio for a particular locus is the measured quantity of one of the alleles divided by the total measured quantity of all the alleles for the locus. In some embodiments, the calculated allele ratio for a particular locus is the measured quantity of one of the alleles (such as the allele on the first homologous chromosome segment) divided by the measured quantity of one or more other alleles (such as the allele on the second homologous chromosome segment) for the locus. The calculated allele ratios may be calculated using any of the methods described herein or any standard method (such as any mathematical transformation of the calculated allele ratios described herein).

In some embodiments, the method involves determining if there is an overrepresentation of the number of copies of the first homologous chromosome segment by comparing one or more calculated allele ratios for a locus to an allele ratio that is expected for that locus if the first and second homologous chromosome segments are present in equal proportions. In some embodiments, the expected allele ratio assumes the possible alleles for a locus have an equal likelihood of being present. In some embodiments in which the calculated allele ratio for a particular locus is the measured quantity of one of the alleles divided by the total measured quantity of all the alleles for the locus, the corresponding expected allele ratio is 0.5 for a biallelic locus, or 1/3 for a triallelic locus. In some embodiments, the expected allele ratio is the same for all the loci, such as 0.5 for all loci. In some embodiments, the expected allele ratio assumes that the possible alleles for a locus can have a different likelihood of being present, such as the likelihood based on the frequency of each of the alleles in a particular population that the subject belongs in, such as a population based on the ancestry of the subject. Such allele frequencies are publicly available (see, e.g., HapMap Project; Perlegen Human Haplotype Project; web at ncbi.nlm.nih.gov/projects/SNP/; Sherry S T, Ward M H, Kholodov M, et al. dbSNP: the NCBI database of genetic variation. Nucleic Acids Res. 2001 Jan. 1;29 (1): 308-11, which are each incorporated by reference in its entirety). In some embodiments, the expected allele ratio is the allele ratio that is expected for the particular individual being tested for a particular hypothesis specifying the degree of overrepresentation of the first homologous chromosome segment. For example, the expected allele ratio for a particular individual may be determined based on phased or unphased genetic data from the individual (such as from a sample from the individual that is unlikely to have a deletion or duplication such as a noncancerous sample) or data from one or more relatives from the individual. In some embodiments for prenatal testing, the expected allele ratio is the allele ratio that is expected for a mixed sample that includes DNA or RNA from the pregnant mother and the fetus (such as a maternal plasma or serum sample that includes cfDNA from the mother and cfDNA from the fetus) for a particular hypothesis specifying the degree of overrepresentation of the first homologous chromosome segment. For example, the expected allele ratio for the mixed sample may be determined based on genetic data from the mother and predicted genetic data for the fetus (such as predictions for alleles that the fetus may have inherited from the mother and/or father). In some embodiments, phased or unphased genetic data from a sample of DNA or RNA from only the mother (such as the buffy coat from a maternal blood sample) is to determine the alleles from the maternal DNA or RNA in the mixed sample as well as alleles that the fetus may have been inherited from the mother (and thus may be present in the fetal DNA or RNA in the mixed sample). In some embodiments, phased or unphased genetic data from a sample of DNA or RNA from only the father is used to determine the alleles that the fetus may have been inherited from the father (and thus may be present in the fetal DNA or RNA in the mixed sample). The expected allele ratios may be calculated using any of the methods described herein or any standard method (such as any mathematical transformation of the expected allele ratios described herein) (U.S. Publication No 2012/0270212, filed Nov. 18, 2011, which is hereby incorporated by reference in its entirety).

In some embodiments, a calculated allele ratio is indicative of an overrepresentation of the number of copies of the first homologous chromosome segment if either (i) the allele ratio for the measured quantity of the allele present at that locus on the first homologous chromosome divided by the total measured quantity of all the alleles for the locus is greater than the expected allele ratio for that locus, or (ii) the allele ratio for the measured quantity of the allele present at that locus on the second homologous chromosome divided by the total measured quantity of all the alleles for the locus is less than the expected allele ratio for that locus. In some embodiments, a calculated allele ratio is only considered indicative of overrepresentation if it is significantly greater or lower than the expected ratio for that locus. In some embodiments, a calculated allele ratio is indicative of no overrepresentation of the number of copies of the first homologous chromosome segment if either (i) the allele ratio for the measured quantity of the allele present at that locus on the first homologous chromosome divided by the total measured quantity of all the alleles for the locus is less than or equal to the expected allele ratio for that locus, or (ii) the allele ratio for the measured quantity of the allele present at that locus on the second homologous chromosome divided by the total measured quantity of all the alleles for the locus is greater than or equal to the expected allele ratio for that locus. In some embodiments, calculated ratios equal to the corresponding expected ratio are ignored (since they are indicative of no overrepresentation).

In various embodiments, one or more of the following methods is used to compare one or more of the calculated allele ratios to the corresponding expected allele ratio(s). In some embodiments, one determines whether the calculated allele ratio is above or below the expected allele ratio for a particular locus irrespective of the magnitude of the difference. In some embodiments, one determines the magnitude of the difference between the calculated allele ratio and the expected allele ratio for a particular locus irrespective of whether the calculated allele ratio is above or below the expected allele ratio. In some embodiments, one determines whether the calculated allele ratio is above or below the expected allele ratio and the magnitude of the difference for a particular locus. In some embodiments, one determines whether the average or weighted average value of the calculated allele ratios is above or below the average or weighted average value of the expected allele ratios irrespective of the magnitude of the difference. In some embodiments, one determines the magnitude of the difference between the average or weighted average value of the calculated allele ratios and the average or weighted average value of the expected allele ratios irrespective of whether the average or weighted average of the calculated allele ratio is above or below the average or weighted average value of the expected allele ratio. In some embodiments, one determines whether the average or weighted average value of the calculated allele ratios is above or below the average or weighted average value of the expected allele ratios and the magnitude of the difference. In some embodiments, one determines an average or weighted average value of the magnitude of the difference between the calculated allele ratios and the expected allele ratios.

In some embodiments, the magnitude of the difference between the calculated allele ratio and the expected allele ratio for one or more loci is used to determine whether the overrepresentation of the number of copies of the first homologous chromosome segment is due to a duplication of the first homologous chromosome segment or a deletion of the second homologous chromosome segment in the genome of one or more of the cells.

In some embodiments, an overrepresentation of the number of copies of the first homologous chromosome segment is determined to be present if one or more of following conditions is met. In some embodiments, the number of calculated allele ratios that are indicative of an overrepresentation of the number of copies of the first homologous chromosome segment is above a threshold value. In some embodiments, the number of calculated allele ratios that are indicative of no overrepresentation of the number of copies of the first homologous chromosome segment is below a threshold value. In some embodiments, the magnitude of the difference between the calculated allele ratios that are indicative of an overrepresentation of the number of copies of the first homologous chromosome segment and the corresponding expected allele ratios is above a threshold value. In some embodiments, for all calculated allele ratios that are indicative of overrepresentation, the sum of the magnitude of the difference between a calculated allele ratio and the corresponding expected allele ratio is above a threshold value. In some embodiments, the magnitude of the difference between the calculated allele ratios that are indicative of no overrepresentation of the number of copies of the first homologous chromosome segment and the corresponding expected allele ratios is below a threshold value. In some embodiments, the average or weighted average value of the calculated allele ratios for the measured quantity of the allele present on the first homologous chromosome divided by the total measured quantity of all the alleles for the locus is greater than the average or weighted average value of the expected allele ratios by at least a threshold value. In some embodiments, the average or weighted average value of the calculated allele ratios for the measured quantity of the allele present on the second homologous chromosome divided by the total measured quantity of all the alleles for the locus is less than the average or weighted average value of the expected allele ratios by at least a threshold value. In some embodiments, the data fit between the calculated allele ratios and allele ratios that are predicted for an overrepresentation of the number of copies of the first homologous chromosome segment is below a threshold value (indicative of a good data fit). In some embodiments, the data fit between the calculated allele ratios and allele ratios that are predicted for no overrepresentation of the number of copies of the first homologous chromosome segment is above a threshold value (indicative of a poor data fit).

In some embodiments, an overrepresentation of the number of copies of the first homologous chromosome segment is determined to be absent if one or more of following conditions is met. In some embodiments, the number of calculated allele ratios that are indicative of an overrepresentation of the number of copies of the first homologous chromosome segment is below a threshold value. In some embodiments, the number of calculated allele ratios that are indicative of no overrepresentation of the number of copies of the first homologous chromosome segment is above a threshold value. In some embodiments, the magnitude of the difference between the calculated allele ratios that are indicative of an overrepresentation of the number of copies of the first homologous chromosome segment and the corresponding expected allele ratios is below a threshold value. In some embodiments, the magnitude of the difference between the calculated allele ratios that are indicative of no overrepresentation of the number of copies of the first homologous chromosome segment and the corresponding expected allele ratios is above a threshold value. In some embodiments, the average or weighted average value of the calculated allele ratios for the measured quantity of the allele present on the first homologous chromosome divided by the total measured quantity of all the alleles for the locus minus the average or weighted average value of the expected allele ratios is less than a threshold value. In some embodiments, the average or weighted average value of the expected allele ratios minus the average or weighted average value of the calculated allele ratios for the measured quantity of the allele present on the second homologous chromosome divided by the total measured quantity of all the alleles for the locus is less than a threshold value. In some embodiments, the data fit between the calculated allele ratios and allele ratios that are predicted for an overrepresentation of the number of copies of the first homologous chromosome segment is above a threshold value. In some embodiments, the data fit between the calculated allele ratios and allele ratios that are predicted for no overrepresentation of the number of copies of the first homologous chromosome segment is below a threshold value. In some embodiments, the threshold is determined from empirical testing of samples known to have a CNV of interest and/or samples known to lack the CNV.

In some embodiments, determining if there is an overrepresentation of the number of copies of the first homologous chromosome segment includes enumerating a set of one or more hypotheses specifying the degree of overrepresentation of the first homologous chromosome segment. On exemplary hypothesis is the absence of an overrepresentation since the first and homologous chromosome segments are present in equal proportions (such as one copy of each segment in a diploid sample). Other exemplary hypotheses include the first homologous chromosome segment being duplicated one or more times (such as 1, 2, 3, 4, 5, or more extra copies of the first homologous chromosome compared to the number of copies of the second homologous chromosome segment). Another exemplary hypothesis includes the deletion of the second homologous chromosome segment. Yet another exemplary hypothesis is the deletion of both the first and the second homologous chromosome segments. In some embodiments, predicted allele ratios for the loci that are heterozygous in at least one cell (such as the loci that are heterozygous in the fetus and/or heterozygous in the mother) are estimated for each hypothesis given the degree of overrepresentation specified by that hypothesis. In some embodiments, the likelihood that the hypothesis is correct is calculated by comparing the calculated allele ratios to the predicted allele ratios, and the hypothesis with the greatest likelihood is selected.

In some embodiments, an expected distribution of a test statistic is calculated using the predicted allele ratios for each hypothesis. In some embodiments, the likelihood that the hypothesis is correct is calculated by comparing a test statistic that is calculated using the calculated allele ratios to the expected distribution of the test statistic that is calculated using the predicted allele ratios, and the hypothesis with the greatest likelihood is selected.

In some embodiments, predicted allele ratios for the loci that are heterozygous in at least one cell (such as the loci that are heterozygous in the fetus and/or heterozygous in the mother) are estimated given the phased genetic data for the first homologous chromosome segment, the phased genetic data for the second homologous chromosome segment, and the degree of overrepresentation specified by that hypothesis. In some embodiments, the likelihood that the hypothesis is correct is calculated by comparing the calculated allele ratios to the predicted allele ratios; and the hypothesis with the greatest likelihood is selected.

Use of Mixed Samples

It will be understood that for many embodiments, the sample is a mixed sample with DNA or RNA from one or more target cells and one or more non-target cells. In some embodiments, the target cells are cells that have a CNV, such as a deletion or duplication of interest, and the non-target cells are cells that do not have the copy number variation of interest (such as a mixture of cells with the deletion or duplication of interest and cells without any of the deletions or duplications being tested). In some embodiments, the target cells are cells that are associated with a disease or disorder or an increased risk for disease or disorder (such as cancer cells), and the non-target cells are cells that are not associated with a disease or disorder or an increased risk for disease or disorder (such as noncancerous cells). In some embodiments, the target cells all have the same CNV. In some embodiments, two or more target cells have different CNVs. In some embodiments, one or more of the target cells has a CNV, polymorphism, or mutation associated with the disease or disorder or an increased risk for disease or disorder that is not found it at least one other target cell. In some such embodiments, the fraction of the cells that are associated with the disease or disorder or an increased risk for disease or disorder out of the total cells from a sample is assumed to be greater than or equal to the fraction of the most frequent of these CNVs, polymorphisms, or mutations in the sample. For example if 6% of the cells have a K-ras mutation, and 8% of the cells have a BRAF mutation, at least 8% of the cells are assumed to be cancerous.

In some embodiments, the ratio of DNA (or RNA) from the one or more target cells to the total DNA (or RNA) in the sample is calculated. In some embodiments, a set of one or more hypotheses specifying the degree of overrepresentation of the first homologous chromosome segment are enumerated. In some embodiments, predicted allele ratios for the loci that are heterozygous in at least one cell (such as the loci that are heterozygous in the fetus and/or heterozygous in the mother) are estimated given the calculated ratio of DNA or RNA and the degree of overrepresentation specified by that hypothesis are estimated for each hypothesis. In some embodiments, the likelihood that the hypothesis is correct is calculated by comparing the calculated allele ratios to the predicted allele ratios, and the hypothesis with the greatest likelihood is selected.

In some embodiments, an expected distribution of a test statistic calculated using the predicted allele ratios and the calculated ratio of DNA or RNA is estimated for each hypothesis. In some embodiments, the likelihood that the hypothesis is correct is determined by comparing a test statistic calculated using the calculated allele ratios and the calculated ratio of DNA or RNA to the expected distribution of the test statistic calculated using the predicted allele ratios and the calculated ratio of DNA or RNA, and the hypothesis with the greatest likelihood is selected.

In some embodiments, the method includes enumerating a set of one or more hypotheses specifying the degree of overrepresentation of the first homologous chromosome segment. In some embodiments, the method includes estimating, for each hypothesis, either (i) predicted allele ratios for the loci that are heterozygous in at least one cell (such as the loci that are heterozygous in the fetus and/or heterozygous in the mother) given the degree of overrepresentation specified by that hypothesis or (ii) for one or more possible ratios of DNA or RNA, an expected distribution of a test statistic calculated using the predicted allele ratios and the possible ratio of DNA or RNA from the one or more target cells to the total DNA or RNA in the sample. In some embodiments, a data fit is calculated by comparing either (i) the calculated allele ratios to the predicted allele ratios, or (ii) a test statistic calculated using the calculated allele ratios and the possible ratio of DNA or RNA to the expected distribution of the test statistic calculated using the predicted allele ratios and the possible ratio of DNA or RNA. In some embodiments, one or more of the hypotheses are ranked according to the data fit, and the hypothesis that is ranked the highest is selected. In some embodiments, a technique or algorithm, such as a search algorithm, is used for one or more of the following steps: calculating the data fit, ranking the hypotheses, or selecting the hypothesis that is ranked the highest. In some embodiments, the data fit is a fit to a beta-binomial distribution or a fit to a binomial distribution. In some embodiments, the technique or algorithm is selected from the group consisting of maximum likelihood estimation, maximum a-posteriori estimation, Bayesian estimation, dynamic estimation (such as dynamic Bayesian estimation), and expectation-maximization estimation. In some embodiments, the method includes applying the technique or algorithm to the obtained genetic data and the expected genetic data.

In some embodiments, the method includes creating a partition of possible ratios that range from a lower limit to an upper limit for the ratio of DNA or RNA from the one or more target cells to the total DNA or RNA in the sample. In some embodiments, a set of one or more hypotheses specifying the degree of overrepresentation of the first homologous chromosome segment are enumerated. In some embodiments, the method includes estimating, for each of the possible ratios of DNA or RNA in the partition and for each hypothesis, either (i) predicted allele ratios for the loci that are heterozygous in at least one cell (such as the loci that are heterozygous in the fetus and/or heterozygous in the mother) given the possible ratio of DNA or RNA and the degree of overrepresentation specified by that hypothesis or (ii) an expected distribution of a test statistic calculated using the predicted allele ratios and the possible ratio of DNA or RNA. In some embodiments, the method includes calculating, for each of the possible ratios of DNA or RNA in the partition and for each hypothesis, the likelihood that the hypothesis is correct by comparing either (i) the calculated allele ratios to the predicted allele ratios, or (ii) a test statistic calculated using the calculated allele ratios and the possible ratio of DNA or RNA to the expected distribution of the test statistic calculated using the predicted allele ratios and the possible ratio of DNA or RNA. In some embodiments, the combined probability for each hypothesis is determined by combining the probabilities of that hypothesis for each of the possible ratios in the partition; and the hypothesis with the greatest combined probability is selected. In some embodiments, the combined probability for each hypothesis is determining by weighting the probability of a hypothesis for a particular possible ratio based on the likelihood that the possible ratio is the correct ratio.

In some embodiments, a technique selected from the group consisting of maximum likelihood estimation, maximum a-posteriori estimation, Bayesian estimation, dynamic estimation (such as dynamic Bayesian estimation), and expectation-maximization estimation is used to estimate the ratio of DNA or RNA from the one or more target cells to the total DNA or RNA in the sample. In some embodiments, the ratio of DNA or RNA from the one or more target cells to the total DNA or RNA in the sample is assumed to be the same for two or more (or all) of the CNVs of interest. In some embodiments, the ratio of DNA or RNA from the one or more target cells to the total DNA or RNA in the sample is calculated for each CNV of interest.

Exemplary Methods for Using Imperfectly Phased Data

It will be understood that for many embodiments, imperfectly phased data is used. For example, it may not be known with 100% certainty which allele is present for one or more of the loci on the first and/or second homologous chromosome segment. In some embodiments, the priors for possible haplotypes of the individual (such as haplotypes based on population based haplotype frequencies) are used in calculating the probability of each hypothesis. In some embodiments, the priors for possible haplotypes are adjusted by either using another method to phase the genetic data or by using phased data from other subjects (such as prior subjects) to refine population data used for informatics based phasing of the individual.

In some embodiments, the phased genetic data comprises probabilistic data for two or more possible sets of phased genetic data, wherein each possible set of phased data comprises a possible identity of the allele present at each locus in the set of polymorphic loci on the first homologous chromosome segment and a possible identity of the allele present at each locus in the set of polymorphic loci on the second homologous chromosome segment. In some embodiments, the probability for at least one of the hypotheses is determined for each of the possible sets of phased genetic data. In some embodiments, the combined probability for the hypothesis is determined by combining the probabilities of the hypothesis for each of the possible sets of phased genetic data; and the hypothesis with the greatest combined probability is selected.

Any of the methods disclosed herein or any known method may be used to generate imperfectly phased data (such as using population based haplotype frequencies to infer the most likely phase) for use in the claimed methods. In some embodiments, phased data is obtained by probabilistically combining haplotypes of smaller segments. For example, possible haplotypes can be determined based on possible combinations of one haplotype from a first region with another haplotype from another region from the same chromosome. The probability that particular haplotypes from different regions are part of the same, larger haplotype block on the same chromosome can be determined using, e.g., population based haplotype frequencies and/or known recombination rates between the different regions.

In some embodiments, a single hypothesis rejection test is used for the null hypothesis of disomy. In some embodiments, the probability of the disomy hypothesis is calculated, and the hypothesis of disomy is rejected if the probability is below a given threshold value (such as less than 1 in 1,000). If the null hypothesis is rejected, this could be due to errors in the imperfectly phased data or due to the presence of a CNV. In some embodiments, more accurate phased data is obtained (such as phased data from any of the molecular phasing methods disclosed herein to obtain actual phased data rather than bioinformatics-based inferred phased data). In some embodiments, the probability of the disomy hypothesis is recalculated using the more accurate phased data to determine if the disomy hypothesis should still be rejected. Rejection of this hypothesis indicates that a duplication or deletion of the chromosome segment is present. If desired, the false positive rate can be altered by adjusting the threshold value.

Further Exemplary Embodiments for Determining Ploidy Using Phased Data

In illustrative embodiments, provided herein is a method for determining ploidy of a chromosomal segment in a sample of an individual. The method includes the following steps:

a. receiving allele frequency data comprising the amount of each allele present in the sample at each loci in a set of polymorphic loci on the chromosomal segment;
b. generating phased allelic information for the set of polymorphic loci by estimating the phase of the allele frequency data;
c. generating individual probabilities of allele frequencies for the polymorphic loci for different ploidy states using the allele frequency data;
d. generating joint probabilities for the set of polymorphic loci using the individual probabilities and the phased allelic information; and
e. selecting, based on the joint probabilities, a best fit model indicative of chromosomal ploidy, thereby determining ploidy of the chromosomal segment.

As disclosed herein, the allele frequency data (also referred to herein as measured genetic allelic data) can be generated by methods known in the art. For example, the data can be generated using qPCR or microarrays. In one illustrative embodiment, the data is generated using nucleic acid sequence data, especially high throughput nucleic acid sequence data.

In certain illustrative examples, the allele frequency data is corrected for errors before it is used to generate individual probabilities. In specific illustrative embodiments, the errors that are corrected include allele amplification efficiency bias. In other embodiments, the errors that are corrected include ambient contamination and genotype contamination. In some embodiments, errors that are corrected include allele amplification bias, ambient contamination and genotype contamination.

In certain embodiments, the individual probabilities are generated using a set of models of both different ploidy states and allelic imbalance fractions for the set of polymorphic loci. In these embodiments, and other embodiments, the joint probabilities are generated by considering the linkage between polymorphic loci on the chromosome segment.

Accordingly, in one illustrative embodiment that combines some of these embodiments, provided herein is a method for detecting chromosomal ploidy in a sample of an individual, that includes the following steps:

a. receiving nucleic acid sequence data for alleles at a set of polymorphic loci on a chromosome segment in the individual;
b. detecting allele frequencies at the set of loci using the nucleic acid sequence data;
c. correcting for allele amplification efficiency bias in the detected allele frequencies to generate corrected allele frequencies for the set of polymorphic loci;
d. generating phased allelic information for the set of polymorphic loci by estimating the phase of the nucleic acid sequence data;
e. generating individual probabilities of allele frequencies for the polymorphic loci for different ploidy states by comparing the corrected allele frequencies to a set of models of different ploidy states and allelic imbalance fractions of the set of polymorphic loci;
f. generating joint probabilities for the set of polymorphic loci by combining the individual probabilities considering the linkage between polymorphic loci on the chromosome segment; and
g. selecting, based on the joint probabilities, the best fit model indicative of chromosomal aneuploidy.

As disclosed herein, the individual probabilities can be generated using a set of models or hypothesis of both different ploidy states and average allelic imbalance fractions for the set of polymorphic loci. For example, in a particularly illustrative example, individual probabilities are generated by modeling ploidy states of a first homolog of the chromosome segment and a second homolog of the chromosome segment. The ploidy states that are modeled include the following:

(1) all cells have no deletion or amplification of the first homolog or the second homolog of the chromosome segment;
(2) at least some cells have a deletion of the first homolog or an amplification of the second homolog of the chromosome segment; and
(3) at least some cells have a deletion of the second homolog or an amplification of the first homolog of the chromosome segment.

It will be understood that the above models can also be referred to as hypothesis that are used to constrain a model. Therefore, demonstrated above are 3 hypothesis that can be used.

The average allelic imbalance fractions modeled can include any range of average allelic imbalance that includes the actual average allelic imbalance of the chromosomal segment. For example, in certain illustrative embodiments, the range of average allelic imbalance that is modeled can be between 0, 0.1, 0.2, 0.25, 0.3, 0.4, 0.5, 0.6, 0.75, 1, 2, 2.5, 3, 4, and 5% on the low end, and 1, 2, 2.5, 3, 4, 5, 10, 15, 20, 25, 30, 40, 50, 60, 70 80 90, 95, and 99% on the high end.

The intervals for the modeling with the range can be any interval depending on the computing power used and the time allowed for the analysis. For example, 0.01, 0.05, 0.02, or 0.1 intervals can be modeled.

In certain illustrative embodiments, the sample has an average allelic imbalance for the chromosomal segment of between 0.4% and 5%. In certain embodiments, the average allelic imbalance is low. In these embodiments, average allelic imbalance is typically less than 10%. In certain illustrative embodiments, the allelic imbalance is between 0.25, 0.3, 0.4, 0.5, 0.6, 0.75, 1, 2, 2.5, 3, 4, and 5% on the low end, and 1, 2, 2.5, 3, 4, and 5% on the high end. In other exemplary embodiments, the average allelic imbalance is between 0.4, 0.45, 0.5, 0.6, 0.7, 0.8, 0.9, or 1.0? on the low end and 0.5, 0.6, 0.7, 0.8, 0.9, 1.0, 1.5, 2.0, 3.0, 4.0, or 5.0? on the high end. For example, the average allelic imbalance of the sample in an illustrative example is between 0.45 and 2.5%. In another example, the average allelic imbalance is detected with a sensitivity of 0.45, 0.5, 0.6, 0.8, 0.8, 0.9, or 1.0. In An exemplary sample with low allelic imbalance in methods of the present invention include plasma samples from individuals with cancer having circulating tumor DNA or plasma samples from pregnant females having circulating fetal DNA.

It will be understood that for SNVs, the proportion of abnormal DNA is typically measured using mutant allele frequency (number of mutant alleles at a locus/total number of alleles at that locus). Since the difference between the amounts of two homologs in tumours is analogous, we measure the proportion of abnormal DNA for a CNV by the average allelic imbalance (AAI), defined as |(H1-H2)|/(H1+H2), where Hi is the average number of copies of homolog i in the sample and Hi/(H1+H2) is the fractional abundance, or homolog ratio, of homolog i. The maximum homolog ratio is the homolog ratio of the more abundant homolog.

Assay drop-out rate is the percentage of SNPs with no reads, estimated using all SNPs. Single allele drop-out (ADO) rate is the percentage of SNPs with only one allele present, estimated using only heterozygous SNPs. Genotype confidence can be determined by fitting a binomial distribution to the number of reads at each SNP that were B-allele reads, and using the ploidy status of the focal region of the SNP to estimate the probability of each genotype.

For tumor tissue samples, chromosomal aneuploidy (exemplified in this paragraph by CNVs) can be delineated by transitions between allele frequency distributions. In plasma samples, CNVs can be identified by a maximum likelihood algorithm that searches for plasma CNVs in regions where the tumor sample from the same individual also has CNVs, using haplotype information deduced from the tumor sample. This algorithm can model expected allelic frequencies across all allelic imbalance ratios at 0.025% intervals for three sets of hypotheses: (1) all cells are normal (no allelic imbalance), (2) some/all cells have a homolog 1 deletion or homolog 2 amplification, or (3) some/all cells have a homolog 2 deletion or homolog 1 amplification. The likelihood of each hypothesis can be determined at each SNP using a Bayesian classifier based on a beta binomial model of expected and observed allele frequencies at all heterozygous SNPs, and then the joint likelihood across multiple SNPs can be calculated, in certain illustrative embodiments taking linkage of the SNP loci into consideration, as exemplified herein. The maximum likelihood hypothesis can then be selected.

Consider a chromosomal region with an average of N copies in the tumor, and let c denote the fraction of DNA in plasma derived from the mixture of normal and tumour cells in a disomic region. AAI is calculated as:

$$AAI = \frac{c\,|N-2|}{2 + c\,(N-2)}$$

In certain illustrative examples, the allele frequency data is corrected for errors before it is used to generate individual probabilities. Different types of error and/or bias correction are disclosed herein. In specific illustrative embodiments, the errors that are corrected are allele amplification efficiency bias. In other embodiments, the errors that are corrected include ambient contamination and genotype contamination. In some embodiments, errors that are corrected include allele amplification bias, ambient contamination and genotype contamination.

It will be understood that allele amplification efficiency bias can be determined for an allele as part of an experiment or laboratory determination that includes an on test sample, or it can be determined at a different time using a set of samples that include the allele whose efficiency is being calculated. Ambient contamination and genotype contamination are typically determined on the same run as the on-test sample analysis.

In certain embodiments, ambient contamination and genotype contamination are determined for homozygous alleles in the sample. It will be understood that for any given sample from an individual some loci in the sample, will be heterozygous and others will be homozygous, even if a locus is selected for analysis because it has a relatively high heterozygosity in the population. It is advantageous in some embodiments, although ploidy of a chromosomal segment may be determined using heterozygous loci for an individual, homozygous loci can be used to calculate ambient and genotype contamination.

In certain illustrative examples, the selecting is performed by analyzing a magnitude of a difference between the phased allelic information and estimated allelic frequencies generated for the models.

In illustrative examples, the individual probabilities of allele frequencies are generated based on a beta binomial model of expected and observed allele frequencies at the set of polymorphic loci. In illustrative examples, the individual probabilities are generated using a Bayesian classifier.

In certain illustrative embodiments, the nucleic acid sequence data is generated by performing high throughput DNA sequencing of a plurality of copies of a series of amplicons generated using a multiplex amplification reaction, wherein each amplicon of the series of amplicons spans at least one polymorphic loci of the set of polymorphic loci and wherein each of the polymeric loci of the set is amplified. In certain embodiments, the multiplex amplification reaction is performed under limiting primer conditions for at least ½ of the reactions. In some embodiments, limiting primer concentrations are used in 1/10, 1/5, 1/4, 1/3, 1/2, or all of the reactions of the multiplex reaction. Provided herein are factors to consider to achieve limiting primer conditions in an amplification reaction such as PCR.

In certain embodiments, methods provided herein detect ploidy for multiple chromosomal segments across multiple chromosomes. Accordingly, the chromosomal ploidy in these embodiments is determined for a set of chromosome segments in the sample. For these embodiments, higher multiplex amplification reactions are needed. Accordingly, for these embodiments the multiplex amplification reaction can include, for example, between 2,500 and 50,000 multiplex reactions. In certain embodiments, the following ranges of multiplex reactions are performed: between 100, 200, 250, 500, 1000, 2500, 5000, 10,000, 20,000, 25000, 50000 on the low end of the range and between 200, 250, 500, 1000, 2500, 5000, 10,000, 20,000, 25000, 50000, and 100,000 on the high end of the range.

In illustrative embodiments, the set of polymorphic loci is a set of loci that are known to exhibit high heterozygosity. However, it is expected that for any given individual, some of those loci will be homozygous. In certain illustrative embodiments, methods of the invention utilize nucleic acid sequence information for both homozygous and heterozygous loci for an individual. The homozygous loci of an individual are used, for example, for error correction, whereas heterozygous loci are used for the determination of allelic imbalance of the sample. In certain embodiments, at least 10% of the polymorphic loci are heterozygous loci for the individual.

As disclosed herein, preference is given for analyzing target SNP loci that are known to be heterozygous in the population. Accordingly, in certain embodiments, polymorphic loci are chosen wherein at least 10, 20, 25, 50, 75, 80, 90, 95, 99, or 100% of the polymorphic loci are known to be heterozygous in the population.

As disclosed herein, in certain embodiments the sample is a plasma sample from a pregnant female.

In some examples, the method further comprises performing the method on a control sample with a known average allelic imbalance ratio. The control can have an average allelic imbalance ratio for a particular allelic state indicative of aneuploidy of the chromosome segment, of between 0.4 and 10% to mimic an average allelic imbalance of an allele in a sample that is present in low concentrations, such as would be expected for a circulating free DNA from a fetus or from a tumor.

In some embodiments, PlasmArt controls, as disclosed herein, are used as the controls. Accordingly, in certain aspects the is a sample generated by a method comprising fragmenting a nucleic acid sample known to exhibit a chromosomal aneuploidy into fragments that mimic the size of fragments of DNA circulating in plasma of the individual. In certain aspects a control is used that has no aneuploidy for the chromosome segment.

In illustrative embodiments, data from one or more controls can be analyzed in the method along with a test sample. The controls for example, can include a different sample from the individual that is not suspected of containing Chromosomal aneuploidy, or a sample that is suspected of containing CNV or a chromosomal aneuploidy. For example, where a test sample is a plasma sample suspected of containing circulating free tumor DNA, the method can be also be performed for a control sample from a tumor from the subject along with the plasma sample. As disclosed herein, the control sample can be prepared by fragmenting a DNA sample known to exhibit a chromosomal aneuploidy. Such fragmenting can result in a DNA sample that mimics the DNA composition of an apoptotic cell, especially when the sample is from an individual afflicted with cancer. Data from the control sample will increase the confidence of the detection of Chromosomal aneuploidy.

In certain embodiments of the methods of determining ploidy, the sample is a plasma sample from an individual suspected of having cancer. In these embodiments, the method further comprises determining based on the selecting whether copy number variation is present in cells of a tumor of the individual. For these embodiments, the sample can be a plasma sample from an individual. For these embodiments, the method can further include determining, based on the selecting, whether cancer is present in the individual.

These embodiments for determining ploidy of a chromosomal segment, can further include detecting a single nucleotide variant at a single nucleotide variance location in a set of single nucleotide variance locations, wherein detecting either a chromosomal aneuploidy or the single nucleotide variant or both, indicates the presence of circulating tumor nucleic acids in the sample.

These embodiments can further include receiving haplotype information of the chromosome segment for a tumor of the individual and using the haplotype information to generate the set of models of different ploidy states and allelic imbalance fractions of the set of polymorphic loci.

As disclosed herein, certain embodiments of the methods of determining ploidy can further include removing outliers from the initial or corrected allele frequency data before comparing the initial or the corrected allele frequencies to the set of models. For example, in certain embodiments, loci allele frequencies that are at least 2 or 3 standard deviations above or below the mean value for other loci on the chromosome segment, are removed from the data before being used for the modeling.

As mentioned herein, it will be understood that for many of the embodiments provided herein, including those for determining ploidy of a chromosomal segment, imperfectly or perfectly phased data is preferably used. It will also be understood, that provided herein are a number of features that provide improvements over prior methods for detecting ploidy, and that many different combinations of these features could be used.

Figure 69:
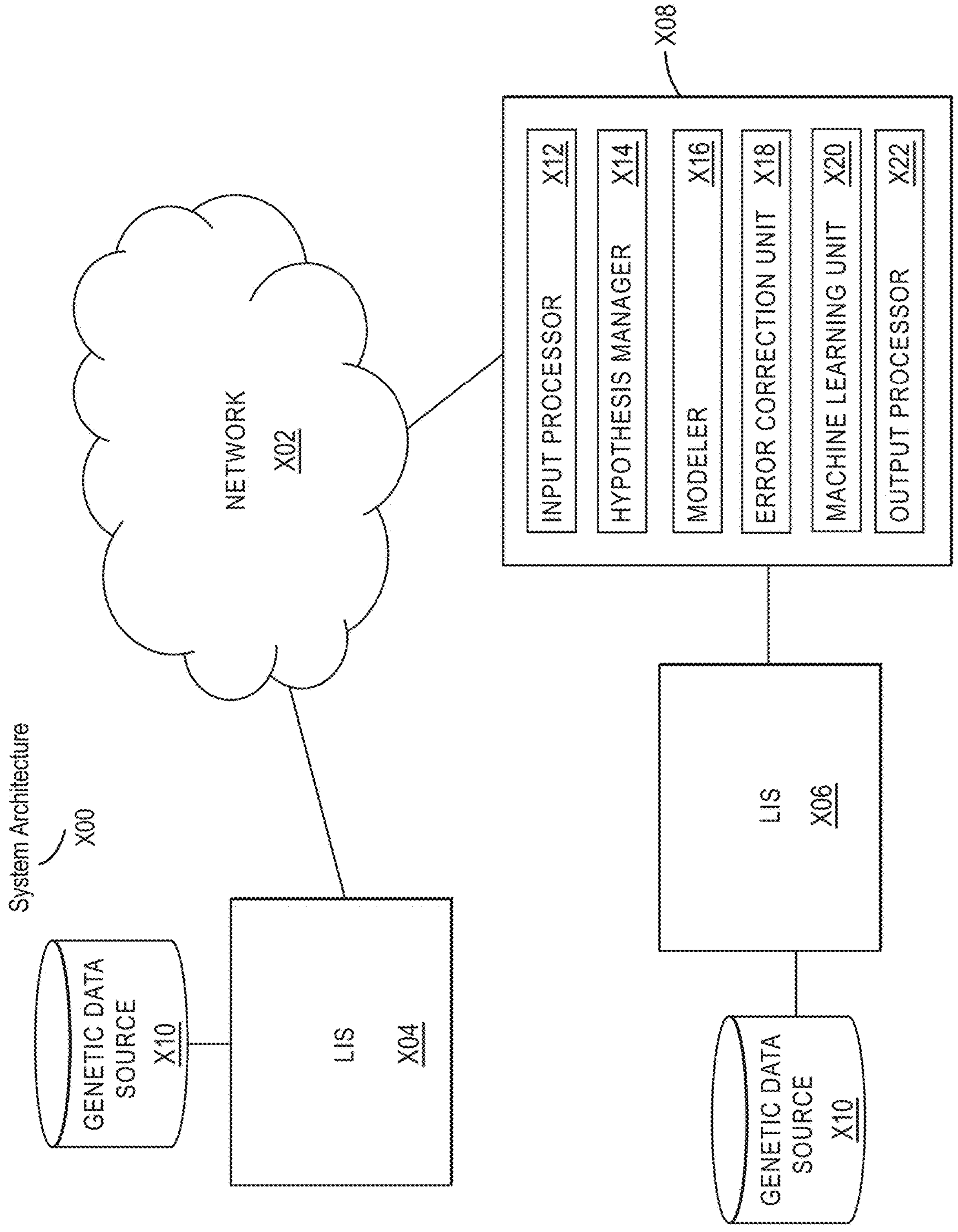
FIG. 69 shows an example system architecture X00 useful for performing embodiments of the present invention. System architecture X00 includes an analysis platform X08 and a laboratory information systems ("LISs") X04. X04 can be connected to Genetic Data Source X10. X08 may be connected to LIS X04 over a network X02. Analysis platform X08 may alternatively or additionally be connected directly to LIS X06. LIS X06 can be connected to Genetic Data Source X10. Analysis platform X08 includes one or more of an input processor X12, a hypothesis manager X14, a modeler X16, an error correction unit X18, a machine learning unit X20, and an output processor X22.
Figure 70:
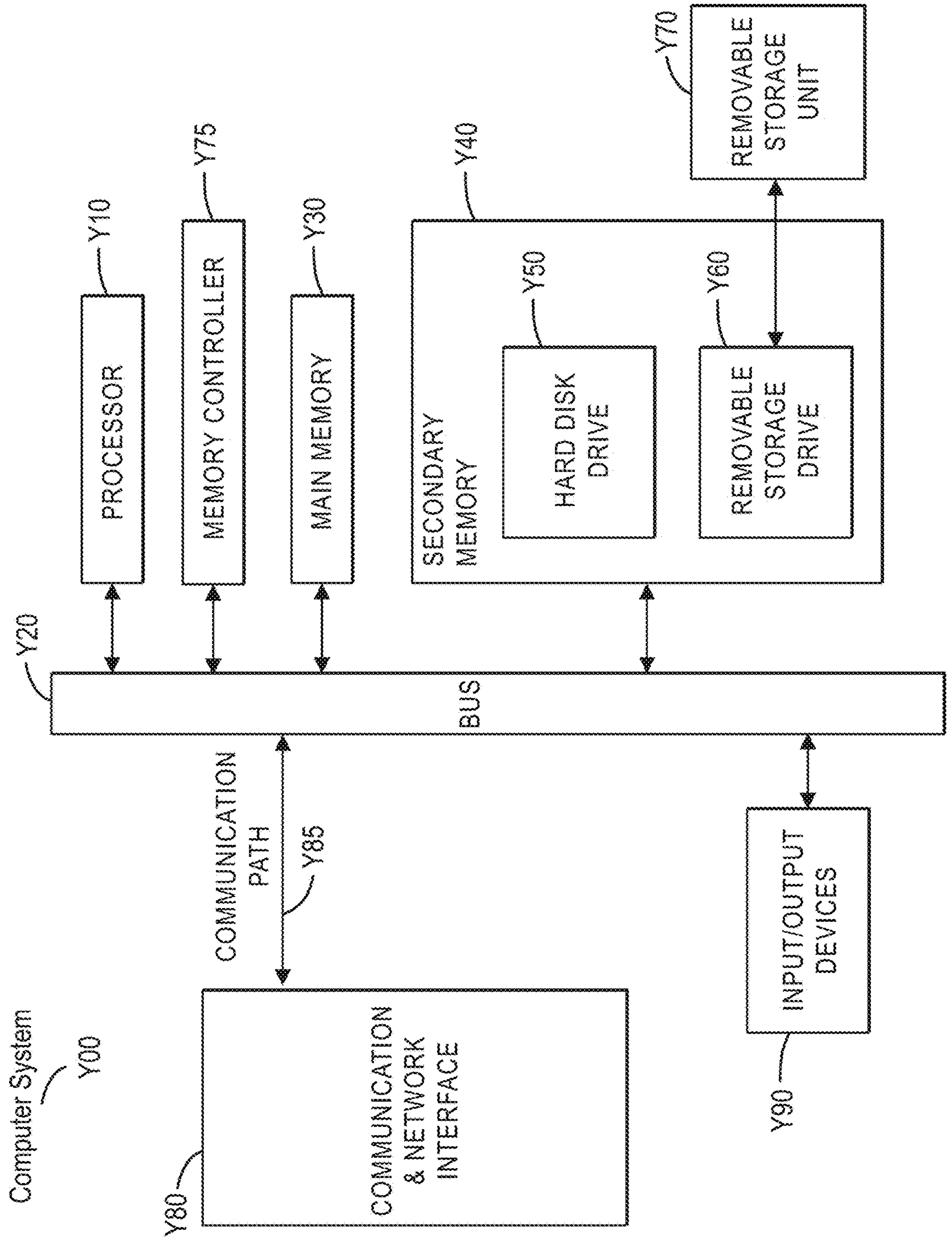
FIG. 70 illustrates an example computer system Y00 for performing embodiments of the present invention. System architecture Y00 includes one or more processors Y10, a BUS Y20, a main memory Y30, a memory controller Y75, a communications and network interface Y80, a communication path Y85, an input/output/display devices Y90, and may also include a secondary memory Y40. Y40 may include a hard disk drive Y50 and a removable storage drive Y60. Y60 can write to a removable storage unit Y70.

In certain embodiments, as illustrated in FIGS. 69-70, provided herein are computer systems and computer readable media to perform any methods of the present invention. These include systems and computer readable media for performing methods of determining ploidy. Accordingly, and as non-limiting examples of system embodiments, to demonstrate that any of the methods provided herein can be performed using a system and a computer readable medium using the disclosure herein, in another aspect, provided herein is a system for detecting chromosomal ploidy in a sample of an individual, the system comprising:

a. an input processor configured to receive allelic frequency data comprising the amount of each allele present in the sample at each loci in a set of polymorphic loci on the chromosomal segment;
b. a modeler configured to:
   i. generate phased allelic information for the set of polymorphic loci by estimating the phase of the allele frequency data; and
   ii. generate individual probabilities of allele frequencies for the polymorphic loci for different ploidy states using the allele frequency data; and
   iii. generate joint probabilities for the set of polymorphic loci using the individual probabilities and the phased allelic information; and
c. a hypothesis manager configured to select, based on the joint probabilities, a best fit model indicative of chromosomal ploidy, thereby determining ploidy of the chromosomal segment.

In certain embodiments of this system embodiment, the allele frequency data is data generated by a nucleic acid sequencing system. In certain embodiments, the system further comprises an error correction unit configured to correct for errors in the allele frequency data, wherein the corrected allele frequency data is used by the modeler for to generate individual probabilities. In certain embodiments the error correction unit corrects for allele amplification efficiency bias. In certain embodiments, the modeler generates the individual probabilities using a set of models of both different ploidy states and allelic imbalance fractions for the set of polymorphic loci. The modeler, in certain exemplary embodiments generates the joint probabilities by considering the linkage between polymorphic loci on the chromosome segment.

In one illustrative embodiment, provided herein is a system for detecting chromosomal ploidy in a sample of an individual, that includes the following:

a. an input processor configured to receive nucleic acid sequence data for alleles at a set of polymorphic loci on a chromosome segment in the individual and detect allele frequencies at the set of loci using the nucleic acid sequence data;

b. an error correction unit configured to correct for errors in the detected allele frequencies and generate corrected allele frequencies for the set of polymorphic loci;

c. a modeler configured to:

i. generate phased allelic information for the set of polymorphic loci by estimating the phase of the nucleic acid sequence data;

ii. generate individual probabilities of allele frequencies for the polymorphic loci for different ploidy states by comparing the phased allelic information to a set of models of different ploidy states and allelic imbalance fractions of the set of polymorphic loci; and iii. generate joint probabilities for the set of polymorphic loci by combining the individual probabilities considering the relative distance between polymorphic loci on the chromosome segment; and d. a hypothesis manager configured to select, based on the joint probabilities, a best fit model indicative of chromosomal aneuploidy.

In certain exemplary system embodiments provided herein the set of polymorphic loci comprises between 1000 and 50,000 polymorphic loci. In certain exemplary system embodiments provided herein the set of polymorphic loci comprises 100 known heterozygosity hot spot loci. In certain exemplary system embodiments provided herein the set of polymorphic loci comprise 100 loci that are at or within 0.5 kb of a recombination hot spot.

In certain exemplary system embodiments provided herein the best fit model analyzes the following ploidy states of a first homolog of the chromosome segment and a second homolog of the chromosome segment:

(1) all cells have no deletion or amplification of the first homolog or the second homolog of the chromosome segment;

(2) some or all cells have a deletion of the first homolog or an amplification of the second homolog of the chromosome segment; and (3) some or all cells have a deletion of the second homolog or an amplification of the first homolog of the chromosome segment.

In certain exemplary system embodiments provided herein the errors that are corrected comprise allelic amplification efficiency bias, contamination, and/or sequencing errors. In certain exemplary system embodiments provided herein the contamination comprises ambient contamination and genotype contamination. In certain exemplary system embodiments provided herein the ambient contamination and genotype contamination is determined for homozygous alleles.

In certain exemplary system embodiments provided herein the hypothesis manager is configured to analyze a magnitude of a difference between the phased allelic information and estimated allelic frequencies generated for the models. In certain exemplary system embodiments provided herein the modeler generates individual probabilities of allele frequencies based on a beta binomial model of expected and observed allele frequencies at the set of polymorphic loci. In certain exemplary system embodiments provided herein the modeler generates individual probabilities using a Bayesian classifier.

In certain exemplary system embodiments provided herein the nucleic acid sequence data is generated by performing high throughput DNA sequencing of a plurality of copies of a series of amplicons generated using a multiplex amplification reaction, wherein each amplicon of the series of amplicons spans at least one polymorphic loci of the set of polymorphic loci and wherein each of the polymeric loci of the set is amplified. In certain exemplary system embodiments provided herein, wherein the multiplex amplification reaction is performed under limiting primer conditions for at least ½ of the reactions. In certain exemplary system embodiments provided herein, wherein the sample has an average allelic imbalance of between 0.4% and 5%.

In certain exemplary system embodiments provided herein, the sample is a plasma sample from an individual suspected of having cancer, and the hypothesis manager is further configured to determine, based on the best fit model, whether copy number variation is present in cells of a tumor of the individual.

In certain exemplary system embodiments provided herein the sample is a plasma sample from an individual and the hypothesis manager is further configured to determine, based on the best fit model, that cancer is present in the individual. In these embodiments, the hypothesis manager can be further configured to detect a single nucleotide variant at a single nucleotide variance location in a set of single nucleotide variance locations, wherein detecting either a chromosomal aneuploidy or the single nucleotide variant or both, indicates the presence of circulating tumor nucleic acids in the sample.

In certain exemplary system embodiments provided herein, the input processor is further configured to receiving haplotype information of the chromosome segment for a tumor of the individual, and the modeler is configured to use the haplotype information to generate the set of models of different ploidy states and allelic imbalance fractions of the set of polymorphic loci.

In certain exemplary system embodiments provided herein, the modeler generates the models over allelic imbalance fractions ranging from 0% to 25%.

It will be understood that any of the methods provided herein can be executed by computer readable code that is stored on nontransitory computer readable medium. Accordingly, provided herein in one embodiment, is a nontransitory computer readable medium for detecting chromosomal ploidy in a sample of an individual, comprising computer readable code that, when executed by a processing device, causes the processing device to:

a. receive allele frequency data comprising the amount of each allele present in the sample at each loci in a set of polymorphic loci on the chromosomal segment;

b. generate phased allelic information for the set of polymorphic loci by estimating the phase of the allele frequency data;
c. generate individual probabilities of allele frequencies for the polymorphic loci for different ploidy states using the allele frequency data;
d. generate joint probabilities for the set of polymorphic loci using the individual probabilities and the phased allelic information; and
e. select, based on the joint probabilities, a best fit model indicative of chromosomal ploidy, thereby determining ploidy of the chromosomal segment.

In certain computer readable medium embodiments, the allele frequency data is generated from nucleic acid sequence data. certain computer readable medium embodiments further comprise correcting for errors in the allele frequency data and using the corrected allele frequency data for the generating individual probabilities step. In certain computer readable medium embodiments the errors that are corrected are allele amplification efficiency bias. In certain computer readable medium embodiments the individual probabilities are generated using a set of models of both different ploidy states and allelic imbalance fractions for the set of polymorphic loci. In certain computer readable medium embodiments the joint probabilities are generated by considering the linkage between polymorphic loci on the chromosome segment.

In one particular embodiment, provided herein is a nontransitory computer readable medium for detecting chromosomal ploidy in a sample of an individual, comprising computer readable code that, when executed by a processing device, causes the processing device to:

a. receive nucleic acid sequence data for alleles at a set of polymorphic loci on a chromosome segment in the individual;
b. detect allele frequencies at the set of loci using the nucleic acid sequence data;
c. correcting for allele amplification efficiency bias in the detected allele frequencies to generate corrected allele frequencies for the set of polymorphic loci;
d. generate phased allelic information for the set of polymorphic loci by estimating the phase of the nucleic acid sequence data;
e. generate individual probabilities of allele frequencies for the polymorphic loci for different ploidy states by comparing the corrected allele frequencies to a set of models of different ploidy states and allelic imbalance fractions of the set of polymorphic loci;
f. generate joint probabilities for the set of polymorphic loci by combining the individual probabilities considering the linkage between polymorphic loci on the chromosome segment; and
g. select, based on the joint probabilities, the best fit model indicative of chromosomal aneuploidy.

In certain illustrative computer readable medium embodiments, the selecting is performed by analyzing a magnitude of a difference between the phased allelic information and estimated allelic frequencies generated for the models.

In certain illustrative computer readable medium embodiments the individual probabilities of allele frequencies are generated based on a beta binomial model of expected and observed allele frequencies at the set of polymorphic loci.

It will be understood that any of the method embodiments provided herein can be performed by executing code stored on nontransitory computer readable medium.

Exemplary Embodiments for Detecting Cancer

In certain aspects, the present invention provides a method for detecting cancer. The sample, it will be understood can be a tumor sample or a liquid sample, such as plasma, from an individual suspected of having cancer. The methods are especially effective at detecting genetic mutations such as single nucleotide alterations such as SNVs, or copy number alterations, such as CNVs in samples with low levels of these genetic alterations as a fraction of the total DNA in a sample. Thus the sensitivity for detecting DNA or RNA from a cancer in samples is exceptional. The methods can combine any or all of the improvements provided herein for detecting CNV and SNV to achieve this exceptional sensitivity.

Accordingly, in certain embodiments provided herein, is a method for determining whether circulating tumor nucleic acids are present in a sample in an individual, and a nontransitory computer readable medium comprising computer readable code that, when executed by a processing device, causes the processing device to carry out the method. The method includes the following steps:

c. analyzing the sample to determine a ploidy at a set of polymorphic loci on a chromosome segment in the individual; and
d. determining the level of average allelic imbalance present at the polymorphic loci based on the ploidy determination, wherein an average allelic imbalance equal to or greater than 0.4%, 0.45%, 0.5%, 0.6%, 0.7%, 0.75%, 0.8%, 0.9%, or 1% is indicative of the presence of circulating tumor nucleic acids, such as ctDNA, in the sample.

In certain illustrative examples, an average allelic imbalance greater than 0.4, 0.45, or 0.5% is indicative the presence of ctDNA. In certain embodiments the method for determining whether circulating tumor nucleic acids are present, further comprises detecting a single nucleotide variant at a single nucleotide variance site in a set of single nucleotide variance locations, wherein detecting either an allelic imbalance equal to or greater than 0.5% or detecting the single nucleotide variant, or both, is indicative of the presence of circulating tumor nucleic acids in the sample. It will be understood that any of the methods provided for detecting chromosomal ploidy or CNV can be used to determine the level of allelic imbalance, typically expressed as average allelic imbalance. It will be understood that any of the methods provided herein for detecting an SNV can be used to detect the single nucleotide for this aspect of the present invention.

In certain embodiments the method for determining whether circulating tumor nucleic acids are present, further comprises performing the method on a control sample with a known average allelic imbalance ratio. The control, for example, can be a sample from the tumor of the individual. In some embodiments, the control has an average allelic imbalance expected for the sample under analysis. For example, an AAI between 0.5% and 0.5% or an average allelic imbalance ratio of 0.5%.

In certain embodiments analyzing step in the method for determining whether circulating tumor nucleic acids are present, includes analyzing a set of chromosome segments known to exhibit aneuploidy in cancer. In certain embodiments analyzing step in the method for determining whether circulating tumor nucleic acids are present, includes analyzing between 1,000 and 50,000 or between 100 and 1000, polymorphic loci for ploidy. In certain embodiments analyzing step in the method for determining whether circulating tumor nucleic acids are present, includes analyzing between 100 and 1000 single nucleotide variant sites. For example, in these embodiments the analyzing step can include performing a multiplex PCR to amplify amplicons across the 1000 to 50,000 polymeric loci and the 100 to 1000 single nucleotide variant sites. This multiplex reaction can be set up as a single reaction or as pools of different subset multiplex reactions. The multiplex reaction methods provided herein, such as the massive multiplex PCR disclosed herein provide an exemplary process for carrying out the amplification reaction to help attain improved multiplexing and therefore, sensitivity levels.

In certain embodiments, the multiplex PCR reaction is carried out under limiting primer conditions for at least 10%, 20%, 25%, 50%, 75%, 90%, 95%, 98%, 99%, or 100% of the reactions. Improved conditions for performing the massive multiplex reaction provided herein can be used.

In certain aspects, the above method for determining whether circulating tumor nucleic acids are present in a sample in an individual, and all embodiments thereof, can be carried out with a system. The disclosure provides teachings regarding specific functional and structural features to carry out the methods. As a non-limiting example, the system includes the following:

a. An input processor configured to analyze data from the sample to determine a ploidy at a set of polymorphic loci on a chromosome segment in the individual; and
b. A modeler configured to determine the level of allelic imbalance present at the polymorphic loci based on the ploidy determination, wherein an allelic imbalance equal to or greater than 0.5% is indicative of the presence of circulating.

Exemplary Embodiments for Detecting Single Nucleotide Variants

In certain aspects, provided herein are methods for detecting single nucleotide variants in a sample. The improved methods provided herein can achieve limits of detection of 0.015, 0.017, 0.02, 0.05, 0.1, 0.2, 0.3, 0.4 or 0.5 percent SNV in a sample. All the embodiments for detecting SNVs can be carried out with a system. The disclosure provides teachings regarding specific functional and structural features to carry out the methods. Furthermore, provided herein are embodiments comprising a nontransitory computer readable medium comprising computer readable code that, when executed by a processing device, causes the processing device to carry out the methods for detecting SNVs provided herein.

Accordingly, provided herein in one embodiment, is a method for determining whether a single nucleotide variant is present at a set of genomic positions in a sample from an individual, the method comprising:

a. for each genomic position, generating an estimate of efficiency and a per cycle error rate for an amplicon spanning that genomic position, using a training data set;
b. receiving observed nucleotide identity information for each genomic position in the sample;
c. determining a set of probabilities of single nucleotide variant percentage resulting from one or more real mutations at each genomic position, by comparing the observed nucleotide identity information at each genomic position to a model of different variant percentages using the estimated amplification efficiency and the per cycle error rate for each genomic position independently; and
d. determining the most-likely real variant percentage and confidence from the set of probabilities for each genomic position.

In illustrative embodiments of the method for determining whether a single nucleotide variant is present, the estimate of efficiency and the per cycle error rate is generated for a set of amplicons that span the genomic position. For example, 2, 3, 4, 5, 10, 15, 20, 25, 50, 100 or more amplicons can be included that span the genomic position.

In illustrative embodiments of the method for determining whether a single nucleotide variant is present, the observed nucleotide identity information comprises an observed number of total reads for each genomic position and an observed number of variant allele reads for each genomic position.

In illustrative embodiments of the method for determining whether a single nucleotide variant is present, the sample is a plasma sample and the single nucleotide variant is present in circulating tumor DNA of the sample.

In another embodiment provided herein is a method for estimating the percent of single nucleotide variants that are present in a sample from an individual. The method includes the following steps:

a. at a set of genomic positions, generating an estimate of efficiency and a per cycle error rate for one or more amplicon spanning those genomic positions, using a training data set;
b. receiving observed nucleotide identity information for each genomic position in the sample;
c. generating an estimated mean and variance for the total number of molecules, background error molecules and real mutation molecules for a search space comprising an initial percentage of real mutation molecules using the amplification efficiency and the per cycle error rate of the amplicons; and
d. determining the percentage of single nucleotide variants present in the sample resulting from real mutations by determining a most-likely real single nucleotide variant percentage by fitting a distribution using the estimated means and variances to an observed nucleotide identity information in the sample.

In illustrative examples of this method for estimating the percent of single nucleotide variants that are present in a sample, the sample is a plasma sample and the single nucleotide variant is present in circulating tumor DNA of the sample.

The training data set for this embodiment of the invention typically includes samples from one or preferably a group of healthy individuals. In certain illustrative embodiments, the training data set is analyzed on the same day or even on the same run as one or more on-test samples. For example, samples from a group of 2, 3, 4, 5, 10, 15, 20, 25, 30, 36, 48, 96, 100, 192, 200, 250, 500, 1000 or more healthy individuals can be used to generate the training data set. Where data is available for larger number of healthy individuals, e.g. 96 or more, confidence increases for amplification efficiency estimates even if runs are performed in advance of performing the method for on-test samples. The PCR error rate can use nucleic acid sequence information generated not only for the SNV base location, but for the entire amplified region around the SNV, since the error rate is per amplicon. For example, using samples from 50 individuals and sequencing a 20 base pair amplicon around the SNV, error frequency data from 1000 base reads can be used to determine error frequency rate.

Typically the amplification efficiency is estimating by estimating a mean and standard deviation for amplification efficiency for an amplified segment and then fitting that to a distribution model, such as a binomial distribution or a beta binomial distribution. Error rates are determined for a PCR reaction with a known number of cycles and then a per cycle error rate is estimated.

In certain illustrative embodiments, estimating the starting molecules of the test data set further includes updating the estimate of the efficiency for the testing data set using the starting number of molecules estimated in step (b) if the observed number of reads is significantly different than the estimated number of reads. Then the estimate can be updated for a new efficiency and/or starting molecules.

The search space used for estimating the total number of molecules, background error molecules and real mutation molecules can include a search space from 0.1%, 0.2%, 0.25%, 0.5%, 1%, 2.5%, 5%, 10%, 15%, 20%, or 25% on the low end and 1%, 2%, 2.5%, 5%, 10%, 12.5%, 15%, 20%, 25%, 50%, 75%, 90%, or 95% on the high end copies of a base at an SNV position being the SNV base. Lower ranges, 0.1%, 0.2%, 0.25%, 0.5%, or 1% on the low end and 1%, 2%, 2.5%, 5%, 10%, 12.5%, or 15% on the high end can be used in illustrative examples for plasma samples where the method is detecting circulating tumor DNA. Higher ranges are used for tumor samples.

A distribution is fit to the number of total error molecules (background error and real mutation) in the total molecules to calculate the likelihood or probability for each possible real mutation in the search space. This distribution could be a binomial distribution or a beta binomial distribution.

The most likely real mutation is determined by determining the most likely real mutation percentage and calculating the confidence using the data from fitting the distribution. As an illustrative example and not intended to limit the clinical interpretation of the methods provided herein, if the mean mutation rate is high then the percent confidence needed to make a positive determination of an SNV is lower. For example, if the mean mutation rate for an SNV in a sample using the most likely hypothesis is 5% and the percent confidence is 99%, then a positive SNV call would be made. On the other hand for this illustrative example, if the mean mutation rate for an SNV in a sample using the most likely hypothesis is 1% and the percent confidence is 50%, then in certain situations a positive SNV call would not be made. It will be understood that clinical interpretation of the data would be a function of sensitivity, specificity, prevalence rate, and alternative product availability.

In one illustrative embodiment, the sample is a circulating DNA sample, such as a circulating tumor DNA sample.

In another embodiment, provided herein is a method for detecting one or more single nucleotide variants in a test sample from an individual. The method according to this embodiment, includes the following steps:

d. determining a median variant allele frequency for a plurality of control samples from each of a plurality of normal individuals, for each single nucleotide variant position in a set of single nucleotide variance positions based on results generated in a sequencing run, to identify selected single nucleotide variant positions having variant median allele frequencies in normal samples below a threshold value and to determine background error for each of the single nucleotide variant positions after removing outlier samples for each of the single nucleotide variant positions;
e. determining an observed depth of read weighted mean and variance for the selected single nucleotide variant positions for the test sample based on data generated in the sequencing run for the test sample; and
f. identifying using a computer, one or more single nucleotide variant positions with a statistically significant depth of read weighted mean compared to the background error for that position, thereby detecting the one or more single nucleotide variants.

In certain embodiments of this method for detecting one or more SNVs the sample is a plasma sample, the control samples are plasma samples, and the detected one or more single nucleotide variants detected is present in circulating tumor DNA of the sample. In certain embodiments of this method for detecting one or more SNVs the plurality of control samples comprises at least 25 samples. In certain illustrative embodiments, the plurality of control samples is at least 5, 10, 15, 20, 25, 50, 75, 100, 200, or 250 samples on the low end and 10, 15, 20, 25, 50, 75, 100, 200, 250, 500, and 1000 samples on the high end.

In certain embodiments of this method for detecting one or more SNVs, outliers are removed from the data generated in the high throughput sequencing run to calculate the observed depth of read weighted mean and observed variance are determined. In certain embodiments of this method for detecting one or more SNVs the depth of read for each single nucleotide variant position for the test sample is at least 100 reads.

In certain embodiments of this method for detecting one or more SNVs the sequencing run comprises a multiplex amplification reaction performed under limited primer reaction conditions. Improved methods for performing multiplex amplification reactions provided herein, are used to perform these embodiments in illustrative examples.

Not to be limited by theory, methods of the present embodiment utilize a background error model using normal plasma samples, that are sequenced on the same sequencing run as an on-test sample, to account for run-specific artifacts. Noisy positions with normal median variant allele frequencies above a threshold, for example >0.1%, 0.2%, 0.25%, 0.5% 0.75%, and 1.0%, are removed.

Outlier samples are iteratively removed from the model to account for noise and contamination. For each base substitution of every genomic loci, the depth of read weighted mean and standard deviation of the error are calculated. In certain illustrative embodiments, samples, such as tumor or cell-free plasma samples, with single nucleotide variant positions with at least a threshold number of reads, for example, at least 2, 3, 4, 5, 6, 7, 8, 9, 10, 15, 20, 25, 50, 100, 250, 500, or 1000 variant reads and al Z-score greater than 2.5, 5, 7.5 or 10 against the background error model in certain embodiments, are counted as a candidate mutation.

In certain embodiments, a depth of read of greater than 100, 250, 500, 1,000, 2000, 2500, 5000, 10,000, 20,000, 25,000, 50,000, or 100,000 on the low end of the range and 2000, 2500, 5,000, 7,500, 10,000, 25,000, 50,000, 100,000, 250,000 or 500,000 reads on the high end, is attained in the sequencing run for each single nucleotide variant position in the set of single nucleotide variant positions. Typically, the sequencing run is a high throughput sequencing run. The mean or median values generated for the on-test samples, in illustrative embodiments are weighted by depth of reads. Therefore, the likelihood that a variant allele determination is real in a sample with 1 variant allele detected in 1000 reads is weighed higher than a sample with 1 variant allele detected in 10,000 reads. Since determinations of a variant allele (i.e. mutation) are not made with 100% confidence, the identified single nucleotide variant can be considered a candidate variant or a candidate mutations.

Exemplary Test Statistic for Analysis of Phased Data

An exemplary test statistic is described below for analysis of phased data from a sample known or suspected of being a mixed sample containing DNA or RNA that originated from two or more cells that are not genetically identical. Let f denote the fraction of DNA or RNA of interest, for example the fraction of DNA or RNA with a CNV of interest, or the fraction of DNA or RNA from cells of interest, such as cancer cells. In some embodiments for prenatal testing, f denotes the fraction of fetal DNA, RNA, or cells in a mixture of fetal and maternal DNA, RNA, or cells. Note that this refers to the fraction of DNA from cells of interest assuming two copies of DNA are given by each cell of interest. This differs from the DNA fraction from cells of interest at a segment that is deleted or duplicated.

The possible allelic values of each SNP are denoted A and B. AA, AB, BA, and BB are used to denote all possible ordered allele pairs. In some embodiments, SNPs with ordered alleles AB or BA are analyzed. Let $N_i$ denote the number of sequence reads of the ith SNP, and $A_i$ and $B_i$ denote the number of reads of the ith SNP that indicate allele A and B, respectively. It is assumed:

$$N_i = A_i + B_i.$$

The allele ratio $R_i$ is defined:

$$R_i \triangleq \frac{A_i}{N_i}.$$

Let T denote the number of SNPs targeted.

Without loss of generality, some embodiments focus on a single chromosome segment. As a matter of further clarity, in this specification the phrase "a first homologous chromosome segment as compared to a second homologous chromosome segment" means a first homolog of a chromosome segment and a second homolog of the chromosome segment. In some such embodiments, all of the target SNPs are contained in the segment chromosome of interest. In other embodiments, multiple chromosome segments are analyzed for possible copy number variations.

MAP Estimation

This method leverages the knowledge of phasing via ordered alleles to detect the deletion or duplication of the target segment. For each SNP i, define $$X_i \triangleq \begin{cases} 1 & R_i < 0.5 \text{ and } SNP\ i\ AB \\ 0 & R_i \geq 0.5 \text{ and } SNP\ i\ AB \\ 0 & R_i < 0.5 \text{ and } SNP\ i\ BA \\ 1 & R_i \geq 0.5 \text{ and } SNP\ i\ BA \end{cases}$$

Then define $$S \triangleq \sum_{All\ SNPs} X_i.$$

The distributions of the $X_i$ and S under various copy number hypotheses (such as hypotheses for disomy, deletion of the first or second homolog, or duplication of the first or second homolog) are described below.

Disomy Hypothesis

Under the hypothesis that the target segment is not deleted or duplicated, $$X_i = \begin{cases} 0 & wp\ 1 - p\left(\frac{1}{2}, N_i\right) \\ 1 & wp\ p\left(\frac{1}{2}, N_i\right) \end{cases}$$

where $$p(b, n) \triangleq Pr\left\{X \sim Bino(b, n) \geq \frac{n}{2}\right\}.$$

If we assume a constant depth of read N, this gives us a Binomial distribution S with parameters $$p\left(\frac{1}{2}, N\right) \text{ and } T.$$

Deletion Hypotheses

Under the hypothesis that the first homolog is deleted (i.e., an AB SNP becomes B, and a BA SNP becomes A), then $R_i$ has a Binomial distribution with parameters $$1 - \frac{1}{2-f}$$

and T for AB SNPs, and $$\frac{1}{2-f}$$

and T for BA SNPs. Therefore, $$X_i = \begin{cases} 0 & wp\ 1 - p\left(\frac{1}{2-f}, N_i\right) \\ 1 & wp\ p\left(\frac{1}{2-f}, N_i\right) \end{cases}$$

If we assume a constant depth of read N, this gives a Binomial distribution S with parameters $$p\left(\frac{1}{2-f}, N\right) \text{ and } T.$$

Under the hypothesis that the second homolog is deleted (i.e., an AB SNP becomes A, and a BA SNP becomes B), then $R_i$ has a Binomial distribution with parameters $$\frac{1}{2-f}$$

and T for AB SNPs, and $$1 - \frac{1}{2-f}$$

and T for BA SNPs. Therefore, $$X_i = \begin{cases} 0 & wp\ p\left(\frac{1}{2-f}, N_i\right) \\ 1 & wp\ 1 - p\left(\frac{1}{2-f}, N_i\right) \end{cases}$$

If we assume a constant depth of read N, this gives a Binomial distribution S with parameters $$1 - p\left(\frac{1}{2-f}, N\right) \text{ and } T.$$

Duplication Hypotheses

Under the hypothesis that the first homolog is duplicated (i.e., an AB SNP becomes AAB, and a BA SNP becomes BBA), then $R_i$ has a Binomial distribution with parameters $$\frac{1+f}{2+f}$$

and T for AB SNPs, and $$1 - \frac{1+f}{2+f}$$

and T for BA SNPs. Therefore, $$X_i = \begin{cases} 0 & wp\ p\left(\frac{1+f}{2+f}, N_i\right) \\ 1 & wp\ 1 - p\left(\frac{1+f}{2+f}, N_i\right) \end{cases}$$

If we assume a constant depth of read N, this gives us a Binomial distribution S with parameters $$1 - p\left(\frac{1+f}{2+f}, N\right) \text{ and } T.$$

Under the hypothesis that the second homolog is duplicated (i.e., an AB SNP becomes ABB, and a BA SNP becomes BAA), then $R_i$ has a Binomial distribution with parameters $$1 - \frac{1+f}{2+f}$$

and T for AB SNPs, and $$\frac{1+f}{2+f}$$

and T for BA SNPs. Therefore, $$X_i = \begin{cases} 0 & wp\ 1 - p\left(\frac{1+f}{2+f}, N_i\right) \\ 1 & wp\ p\left(\frac{1+f}{2+f}, N_i\right) \end{cases}$$

If we assume a constant depth of read N, this gives a Binomial distribution S with parameters $$p\left(\frac{1+f}{2+f}, N\right) \text{ and } T.$$

Classification

As demonstrated in the sections above, $X_i$ is a binary random variable with $$Pr\{X_1 = 1\} = \begin{cases} p\left(\frac{1}{2}, N_1\right) & \text{given disomy} \\ p\left(\frac{1}{2-f}, N_i\right) & \text{homolog 1 deletion} \\ 1 - p\left(\frac{1}{2-f}, N_i\right) & \text{homolog 2 deletion} \\ 1 - p\left(\frac{1+f}{2+f}, N_i\right) & \text{homolog 1 duplication} \\ p\left(\frac{1+f}{2+f}, N_i\right) & \text{homolog 2 duplication} \end{cases}$$

This allows one to calculate the probability of the test statistic S under each hypothesis. The probability of each hypothesis given the measured data can be calculated. In some embodiments, the hypothesis with the greatest probability is selected. If desired, the distribution on S can be simplified by either approximating each $N_i$ with a constant depth of reach N or by truncating the depth of reads to a constant N. This simplification gives $$S \sim \begin{cases} Bino\left(p\left(\frac{1}{2}, N\right), T\right) & \text{given disomy} \\ Bino\left(p\left(\frac{1}{2-f}, N\right), T\right) & \text{homolog 1 deletion} \\ Bino\left(1 - p\left(\frac{1}{2-f}, N\right), T\right) & \text{homolog 2 deletion} \\ Bino\left(1 - p\left(\frac{1+f}{2+f}, N\right), T\right) & \text{homolog 1 duplication} \\ Bino\left(p\left(\frac{1+f}{2+f}, N\right), T\right) & \text{homolog 2 duplication} \end{cases}$$

The value for f can be estimate by selecting the most likely value of f given the measured data, such as the value of f that generates the best data fit using an algorithm (e.g., a search algorithm) such as maximum likelihood estimation, maximum a-posteriori estimation, or Bayesian estimation. In some embodiments, multiple chromosome segments are analyzed and a value for f is estimated based on the data for each segment. If all the target cells have these duplications or deletions, the estimated values for f based on data for these different segments are similar. In some embodiments, f is experimentally measured such as by determining the fraction of DNA or RNA from cancer cells based on methylation differences (hypomethylation or hypermethylation) between cancer and non-cancerous DNA or RNA.

In some embodiments for mixed samples of fetal and maternal nucleic acids, the value of f is the fetal fraction, that is the fraction of fetal DNA (or RNA) out of the total amount of DNA (or RNA) in the sample. In some embodiments, the fetal fraction is determined by obtaining genotypic data from a maternal blood sample (or fraction thereof) for a set of polymorphic loci on at least one chromosome that is expected to be disomic in both the mother and the fetus; creating a plurality of hypotheses each corresponding to different possible fetal fractions at the chromosome; building a model for the expected allele measurements in the blood sample at the set of polymorphic loci on the chromosome for possible fetal fractions; calculating a relative probability of each of the fetal fractions hypotheses using the model and the allele measurements from the blood sample or fraction thereof; and determining the fetal fraction in the blood sample by selecting the fetal fraction corresponding to the hypothesis with the greatest probability. In some embodiments, the fetal fraction is determined by identifying those polymorphic loci where the mother is homozygous for a first allele at the polymorphic locus, and the father is (i) heterozygous for the first allele and a second allele or (ii) homozygous for a second allele at the polymorphic locus; and using the amount of the second allele detected in the blood sample for each of the identified polymorphic loci to determine the fetal fraction in the blood sample (see, e.g., US Publ. No. 2012/0185176, filed Mar. 29, 2012, and US Pub. No. 2014/0065621, filed Mar. 13, 2013 which are each incorporated herein by reference in their entirety).

Another method for determining fetal fraction includes using a high throughput DNA sequencer to count alleles at a large number of polymorphic (such as SNP) genetic loci and modeling the likely fetal fraction (see, for example, US Publ. No. 2012/0264121, which is incorporated herein by reference in its entirety). Another method for calculating fetal fraction can be found in Sparks et al.," Noninvasive prenatal detection and selective analysis of cell-free DNA obtained from maternal blood: evaluation for trisomy 21 and trisomy 18," Am J Obstet Gynecol 2012; 206:319.e1-9, which is incorporated herein by reference in its entirety. In some embodiments, fetal fraction is determined using a methylation assay (see, e.g., U.S. Pat. Nos. 7,754,428; 7,901,884; and 8,166,382, which are each incorporated herein by reference in their entirety) that assumes certain loci are methylated or preferentially methylated in the fetus, and those same loci are unmethylated or preferentially unmethylated in the mother.

FIGS. 1A-13D are graphs showing the distribution of the test statistic S divided by T (the number of SNPs) ("S/T") for various copy number hypotheses for various depth of reads and tumor fractions (where f is the fraction of tumor DNA out of total DNA) for an increasing number of SNPs.

Single Hypothesis Rejection

The distribution of S for the disomy hypothesis does not depend on f. Thus, the probability of the measured data can be calculated for the disomy hypothesis without calculating f. A single hypothesis rejection test can be used for the null hypothesis of disomy. In some embodiments, the probability of S under the disomy hypothesis is calculated, and the hypothesis of disomy is rejected if the probability is below a given threshold value (such as less than 1 in 1,000). This indicates that a duplication or deletion of the chromosome segment is present. If desired, the false positive rate can be altered by adjusting the threshold value.

Exemplary Methods for Analysis of Phased Data:

Exemplary methods are described below for analysis of data from a sample known or suspected of being a mixed sample containing DNA or RNA that originated from two or more cells that are not genetically identical. In some embodiments, phased data is used. In some embodiments, the method involves determining, for each calculated allele ratio, whether the calculated allele ratio is above or below the expected allele ratio and the magnitude of the difference for a particular locus. In some embodiments, a likelihood distribution is determined for the allele ratio at a locus for a particular hypothesis and the closer the calculated allele ratio is to the center of the likelihood distribution, the more likely the hypothesis is correct. In some embodiments, the method involves determining the likelihood that a hypothesis is correct for each locus. In some embodiments, the method involves determining the likelihood that a hypothesis is correct for each locus, and combining the probabilities of that hypothesis for each locus, and the hypothesis with the greatest combined probability is selected. In some embodiments, the method involves determining the likelihood that a hypothesis is correct for each locus and for each possible ratio of DNA or RNA from the one or more target cells to the total DNA or RNA in the sample. In some embodiments, a combined probability for each hypothesis is determined by combining the probabilities of that hypothesis for each locus and each possible ratio, and the hypothesis with the greatest combined probability is selected.

In one embodiment, the following hypotheses are considered: $H_{11}$ (all cells are normal), $H_{10}$ (presence of cells with only homolog 1, hence homolog 2 deletion), $H_{01}$ (presence of cells with only homolog 2, hence homolog 1 deletion), $H_{21}$ (presence of cells with homolog 1 duplication), $H_{12}$ (presence of cells with homolog 2 duplication). For a fraction f of target cells such as cancer cells or mosaic cells (or the fraction of DNA or RNA from the target cells), the expected allele ratio for heterozygous (AB or BA) SNPs can be found as follows:

$$r(AB, H_{11}) = r(BA, H_{11}) = 0.5, \qquad \text{Equation (1)}$$

$$r(AB, H_{10}) = r(BA, H_{01}) = \frac{1}{2-f},$$

$$r(AB, H_{01}) = r(BA, H_{10}) = \frac{1-f}{2-f},$$

$$r(AB, H_{21}) = r(BA, H_{12}) = \frac{1+f}{2+f},$$

$$r(AB, H_{12}) = r(BA, H_{21}) = \frac{1}{2+f}.$$

Bias, Contamination, and Sequencing Error Correction:

The observation $D_s$ at the SNP consists of the number of original mapped reads with each allele present, $n_A^0$ and $n_B^0$. Then, we can find the corrected reads $n_A$ and $n_B$ using the expected bias in the amplification of A and B alleles.

Let $c_a$ to denote the ambient contamination (such as contamination from DNA in the air or environment) and $r(c_a)$ to denote the allele ratio for the ambient contaminant (which is taken to be 0.5 initially). Moreover, $c_g$ denotes the genotyped contamination rate (such as the contamination from another sample), and $r(c_g)$ is the allele ratio for the contaminant. Let $s_e(A,B)$ and $s_e(B,A)$ denote the sequencing errors for calling one allele a different allele (such as by erroneously detecting an A allele when a B allele is present).

One can find the observed allele ratio $q(r, c_a, r(c_a), c_g, r(c_g), s_e(A,B), s_e(B,A))$ for a given expected allele ratio r by correcting for ambient contamination, genotyped contamination, and sequencing error.

Since the contaminant genotypes are unknown, population frequencies can be used to find $P(r(c_g))$. More specifically, let p be the population frequency for one of the alleles (which may be referred to as a reference allele). Then, we have $P(r(c_g)=0)=(1-p)^2$, $P(r(c_g)=0)=2p(1-p)$, and $P(r(c_g)=0)=p^2$. The conditional expectation over $r(c_g)$ can be used to determine the $E[q(r, c_a, r(c_a), c_g, r(c_g), s_e(A,B), s_e(B,A)]$. Note that the ambient and genotyped contamination are determined using the homozygous SNPs, hence they are not affected by the absence or presence of deletions or duplications. Moreover, it is possible to measure the ambient and genotyped contamination using a reference chromosome if desired.

Likelihood at each SNP:

The equation below gives the probability of observing $n_A$ and $n_B$ given an allele ratio r:

$$P(n_A, n_B \mid r) = p_{bino}(n_A; n_A + n_B, r) = \binom{n_A+n_B}{n_A} r^{n_A}(1-r)^{n_B}. \quad \text{Equation (2)}$$

Let $D_s$ denote the data for SNP s. For each hypothesis h $\in \{H_{11}, H_{01}, H_{10}, H_{21}, H_{12}\}$, one can let r=r(AB,h) or r=r(BA,h) in the equation (1) and find the conditional expectation over $r(c_g)$ to determine the observed allele ratio $E[q(r, c_a, r(c_a), c_g, r(c_g)]$. Then, letting $r=E[q(r, c_a, r(c_a), c_g, r(c_g), s_e(A,B), s_e(B,A))]$ in equation (2) one can determine $P(D_s|h,f)$.

Search Algorithm:

In some embodiments, SNPs with allele ratios that seem to be outliers are ignored (such as by ignoring or eliminating SNPs with allele ratios that are at least 2 or 3 standard deviations above or below the mean value). Note that an advantage identified for this approach is that in the presence of higher mosaicism percentage, the variability in the allele ratios may be high, hence this ensures that SNPs will not be trimmed due to mosaicism.

Let $F=\{f1, \ldots, f_N\}$ denote the search space for the mosaicism percentage (such as the tumor fraction). One can determine $P(D_s|h,f)$ at each SNP s and $f \in F$, and combine the likelihood over all SNPs.

The algorithm goes over each f for each hypothesis. Using a search method, one concludes that mosaicism exists if there is a range F* of f where the confidence of the deletion or duplication hypothesis is higher than the confidence of the no deletion and no duplication hypotheses. In some embodiments, the maximum likelihood estimate for $P(D_s|h,f)$ in F* is determined. If desired, the conditional expectation over f $\in$ F* may be determined. If desired, the confidence for each hypothesis can be determined.

Additional Embodiments

In some embodiments, a beta binomial distribution is used instead of binomial distribution. In some embodiments, a reference chromosome or chromosome segment is used to determine the sample specific parameters of beta binomial.

Theoretical Performance using Simulations:

If desired, one can evaluate the theoretical performance of the algorithm by randomly assigning number of reference reads to a SNP with given depth of read (DOR). For the normal case, use p=0.5 for the binomial probability parameter, and for deletions or duplications, p is revised accordingly. Exemplary input parameters for each simulation are as follows: (1) number of SNPs S (2) constant DOR D per SNP, (3) p, and (4) number of experiments.

First Simulation Experiment:

This experiment focused on S $\in$ {500, 1000}, D $\in$ {500, 1000} and p $\in$ {0%, 1%, 2%, 3%, 4%, 5%}. We performed 1,000 simulation experiments in each setting (hence 24,000 experiments with phase, and 24,000 without phase). We simulated the number of reads from a binomial distribution (if desired, other distributions can be used). The false positive rate (in the case of p=0%) and false negative rate (in the case of p>0%) were determined both with or without phase information. False positive rates are listed in FIG. 26. Note that phase information is very helpful, especially for S=1000, D=1000. Although for S=500, D=500, the algorithm has the highest false positive rates with or without phase out of the conditions tested. False negative rates are listed in FIG. 27.

Phase information is particularly useful for low mosaicism percentages (≤3%). Without phase information, a high level of false negatives were observed for p=1% because the confidence on deletion is determined by assigning equal chance to $H_{10}$ and $H_{01}$, and a small deviation in favor of one hypothesis is not sufficient to compensate for the low likelihood from the other hypothesis. This applies to duplications as well. Note also that the algorithm seems to be more sensitive to depth of read compared to number of SNPs. For the results with phase information, we assume that perfect phase information is available for a high number of consecutive heterozygous SNPs. If desired, haplotype information can be obtained by probabilistically combining haplotypes on smaller segments.

Figure 20A:
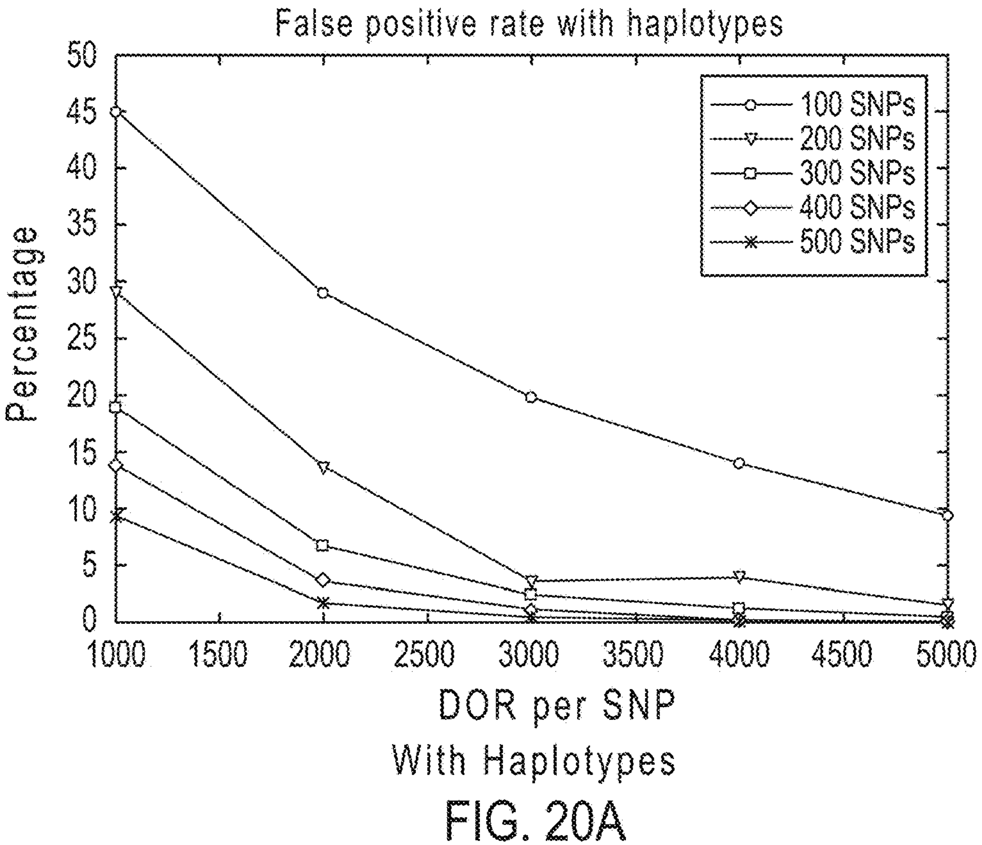
FIGS. 20A and 20B are graphs of the false negative rate using haplotype data (FIG. 20A) and without haplotype data (FIG. 20B).
Figure 20B:
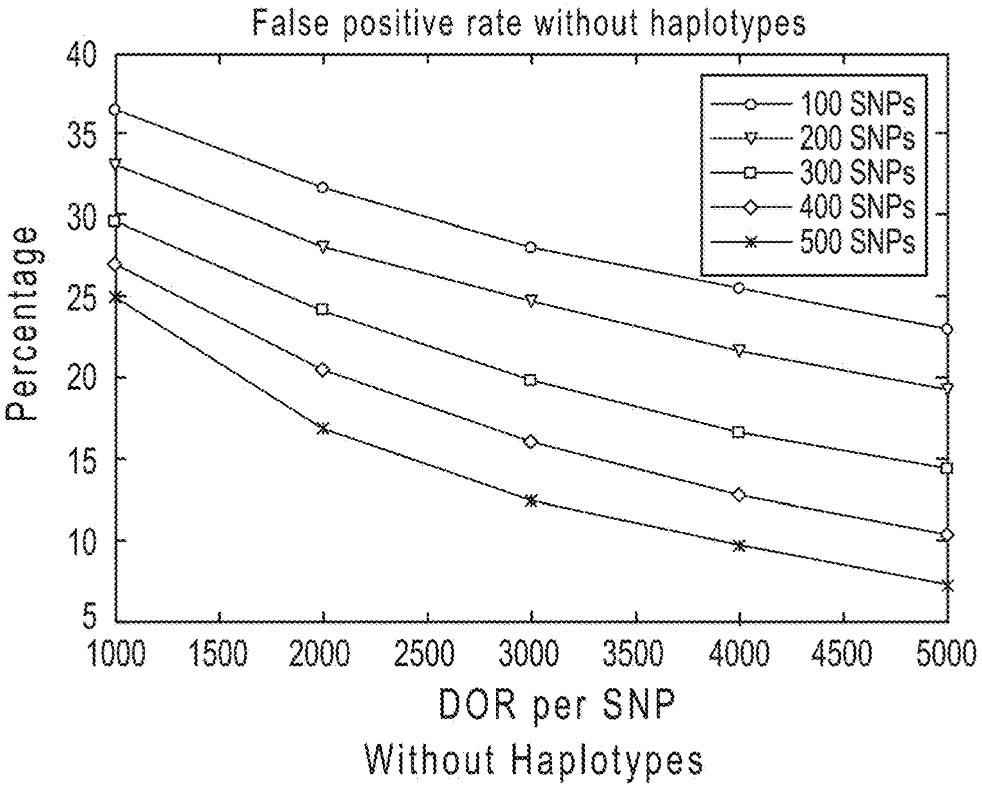
Figure 21A:
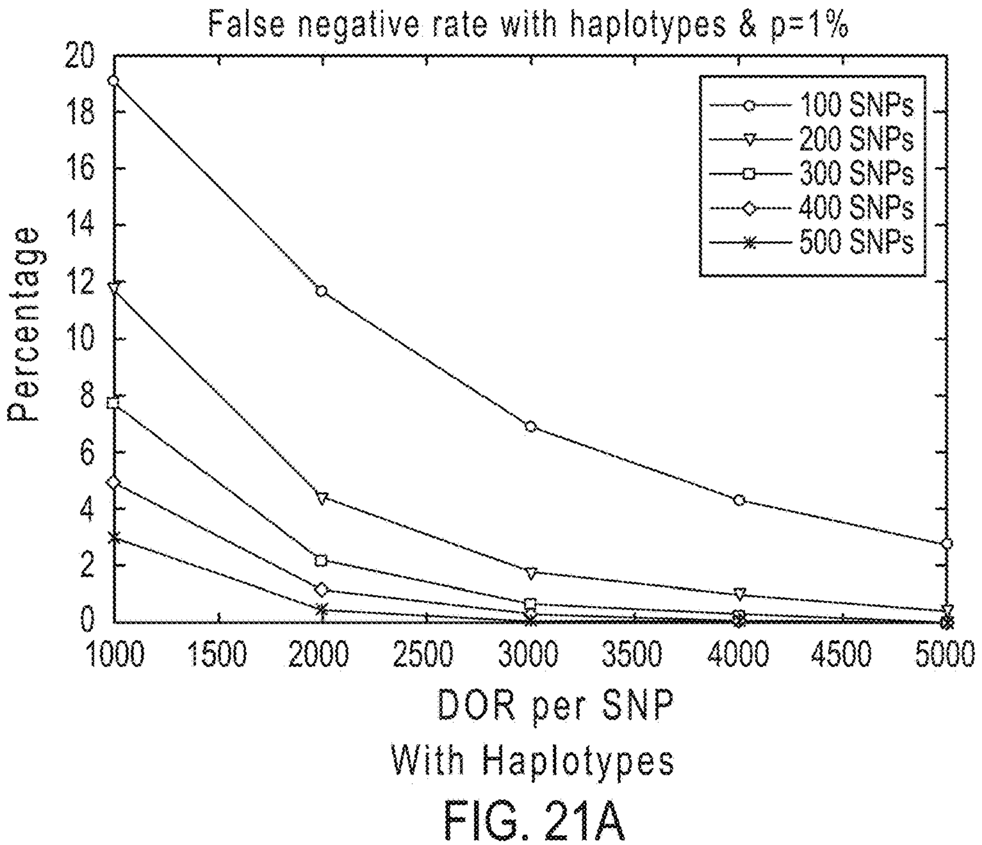
FIGS. 21A and 21B are graphs of the false positive rate for p=1% using haplotype data (FIG. 21A) and without haplotype data (FIG. 21B).
Figure 21B:
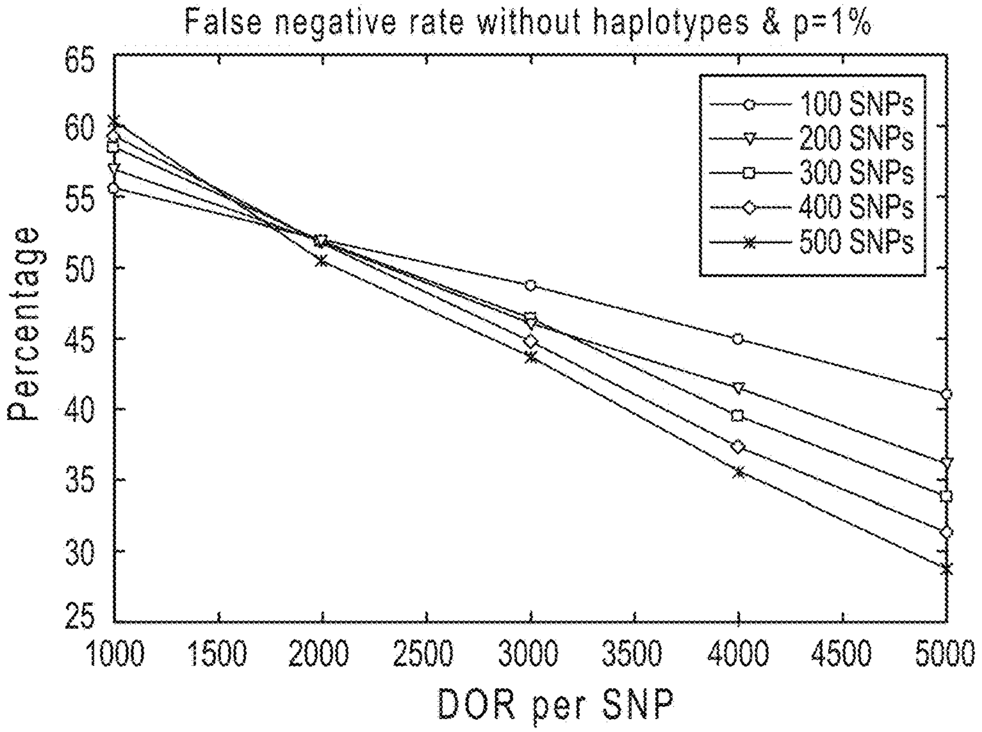
Figure 22A:
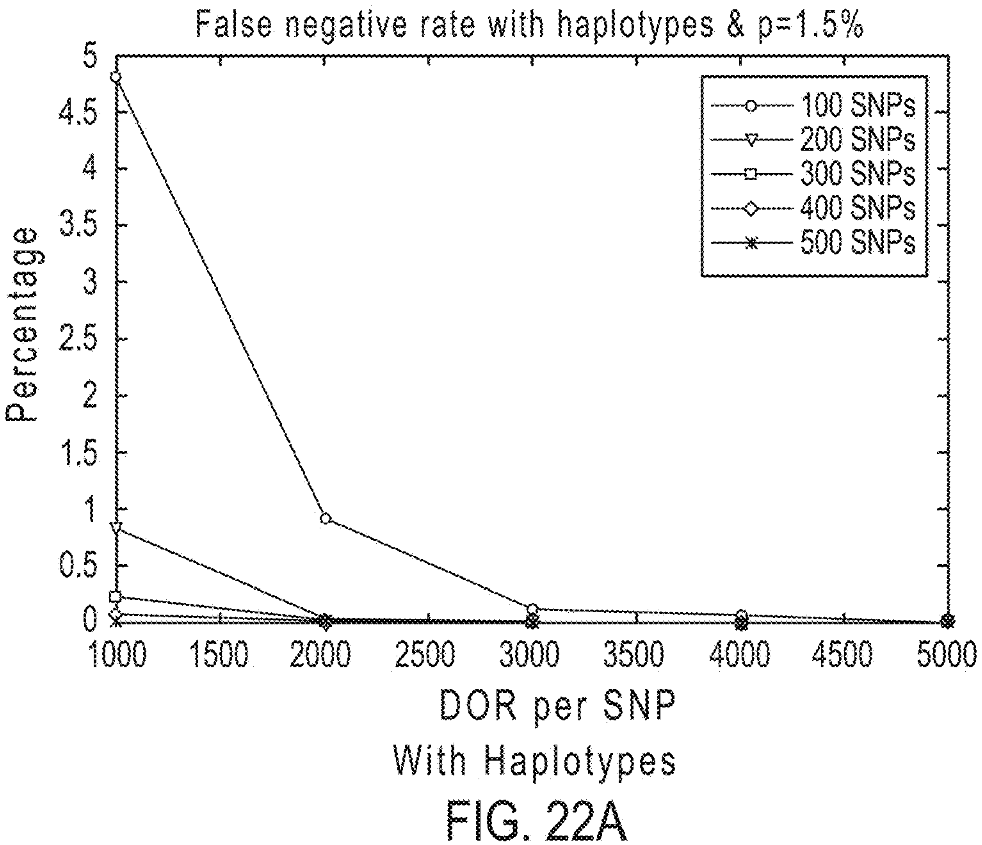
FIGS. 22A and 22B are graphs of the false positive rate for p=1.5% using haplotype data (FIG. 22A) and without haplotype data (FIG. 22B).
Figure 22B:
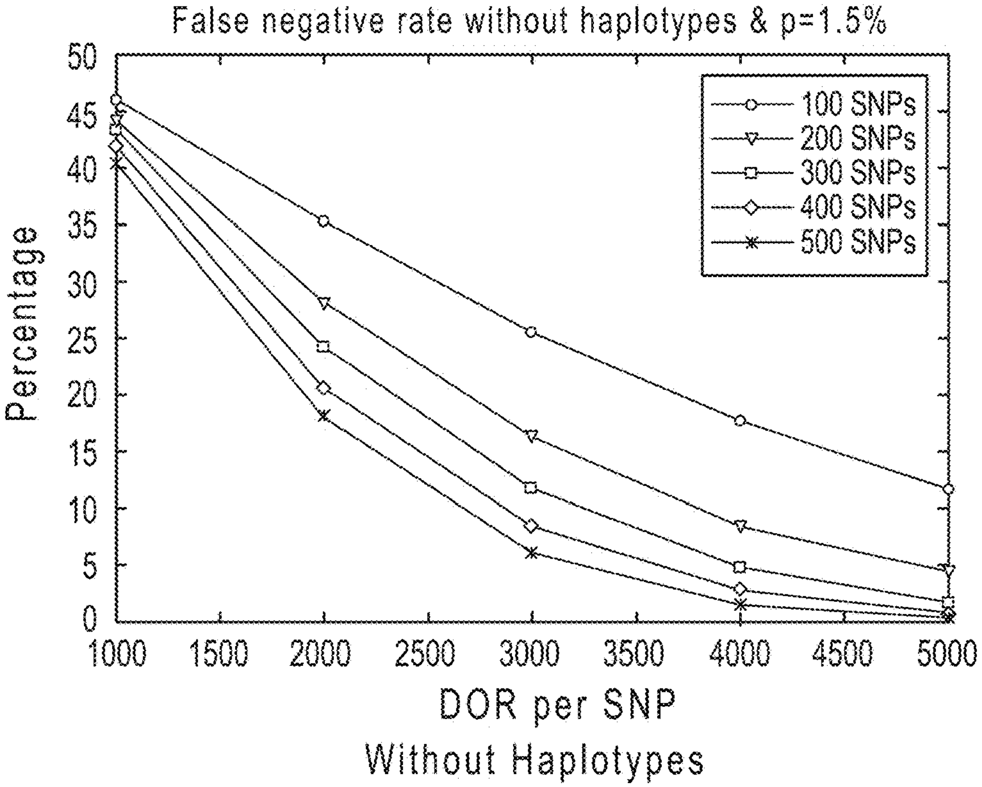
Figure 23A:
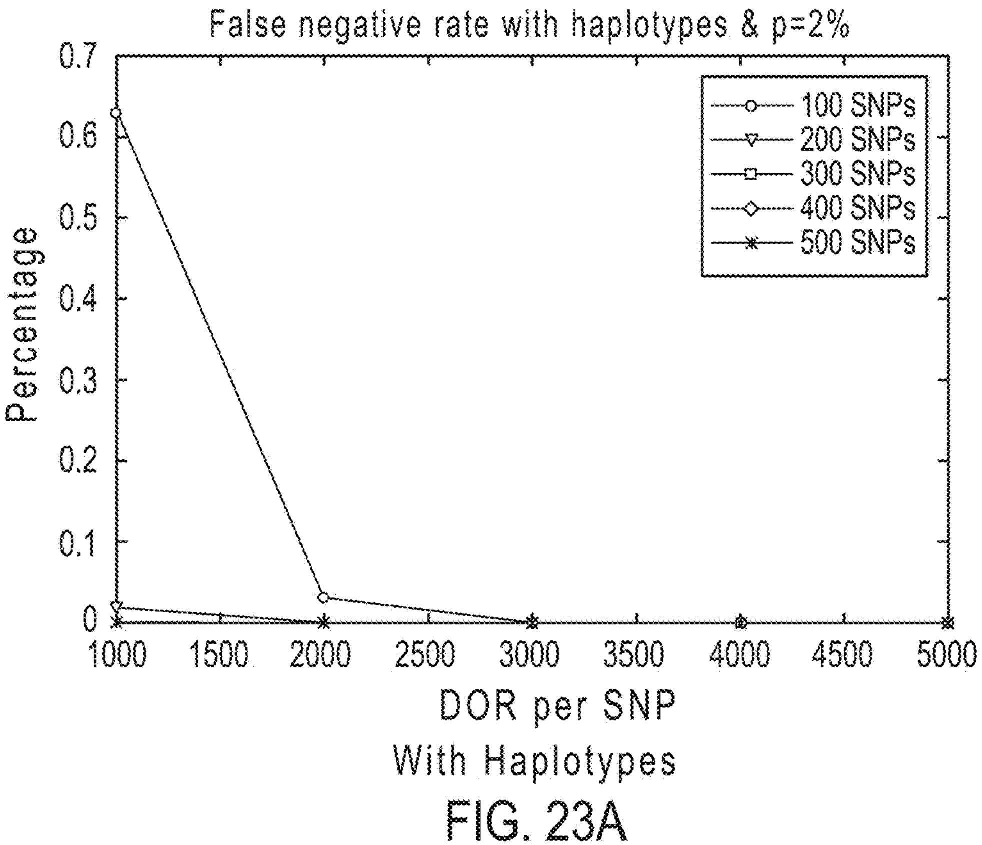
FIGS. 23A and 23B are graphs of the false positive rate for p=2% using haplotype data (FIG. 23A) and without haplotype data (FIG. 23B).
Figure 23B:
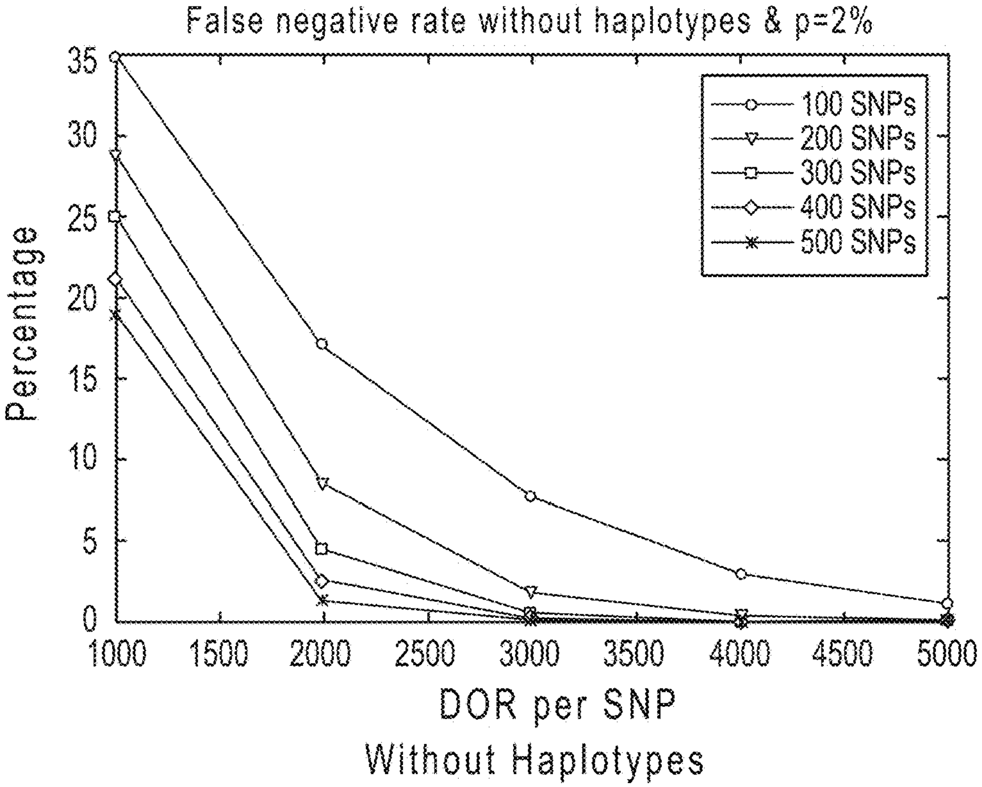
Figure 24A:
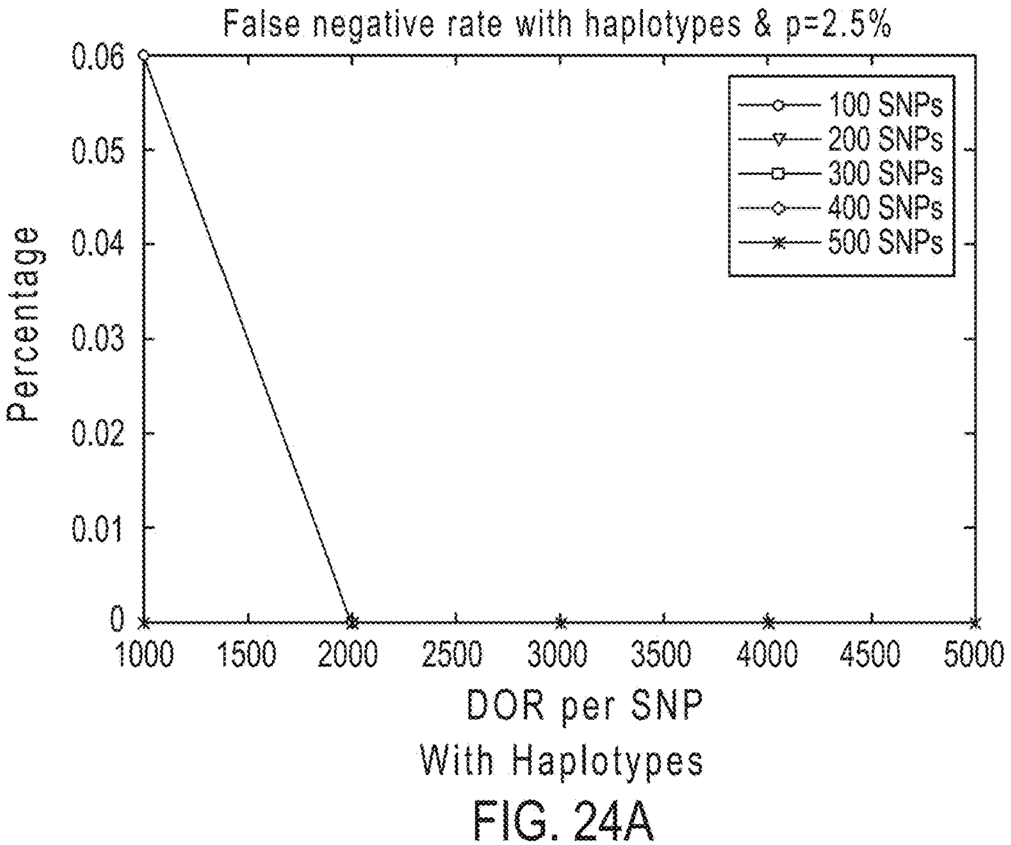
FIGS. 24A and 24B are graphs of the false positive rate for p=2.5% using haplotype data (FIG. 24A) and without haplotype data (FIG. 24B).
Figure 24B:
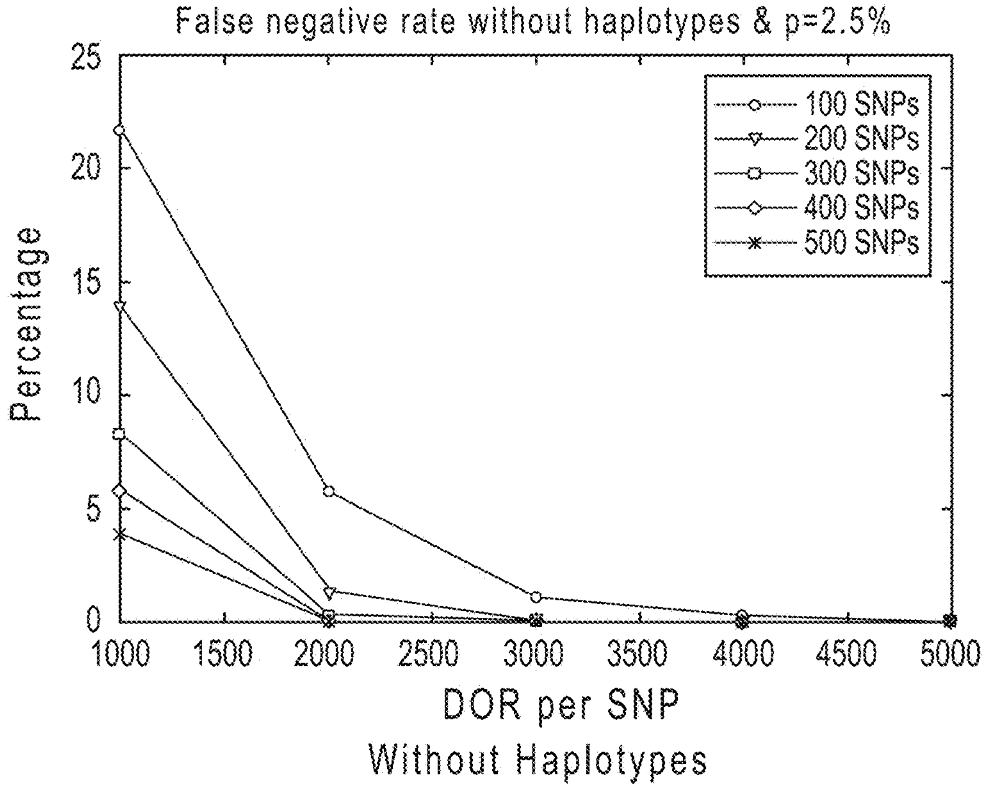
Figure 25A:
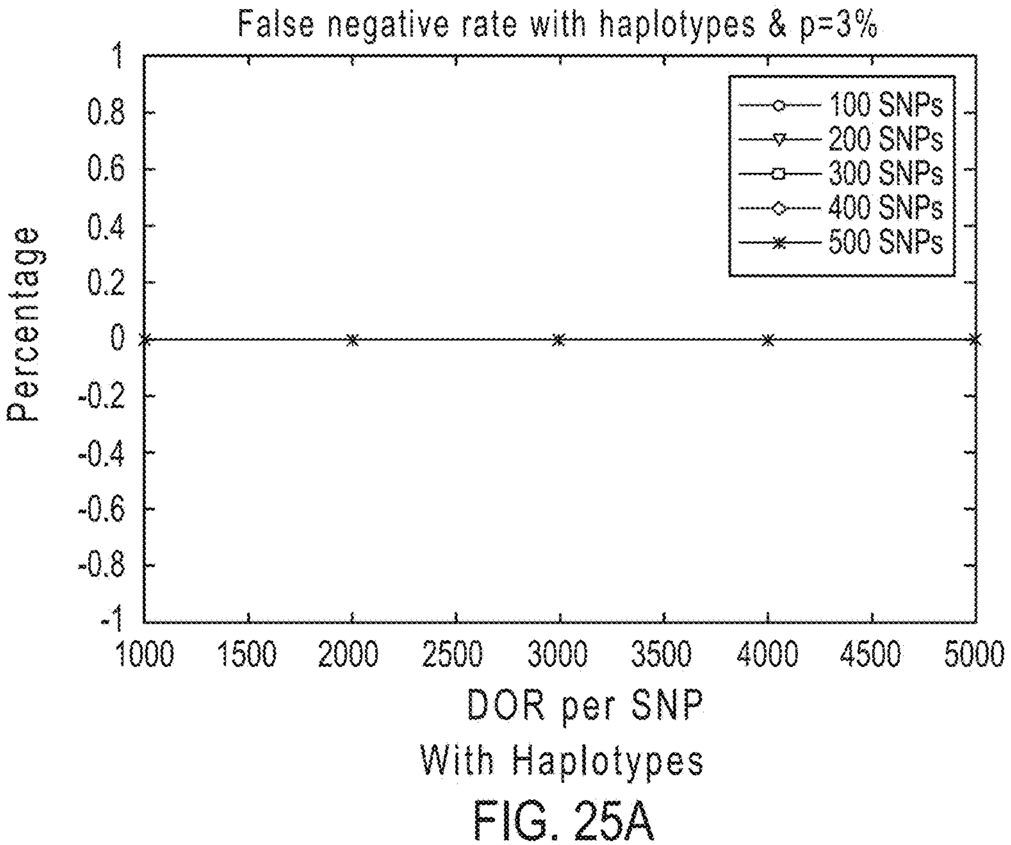
FIGS. 25A and 25B are graphs of the false positive rate for p=3% using haplotype data (FIG. 25A) and without haplotype data (FIG. 25B).
Figure 25B:
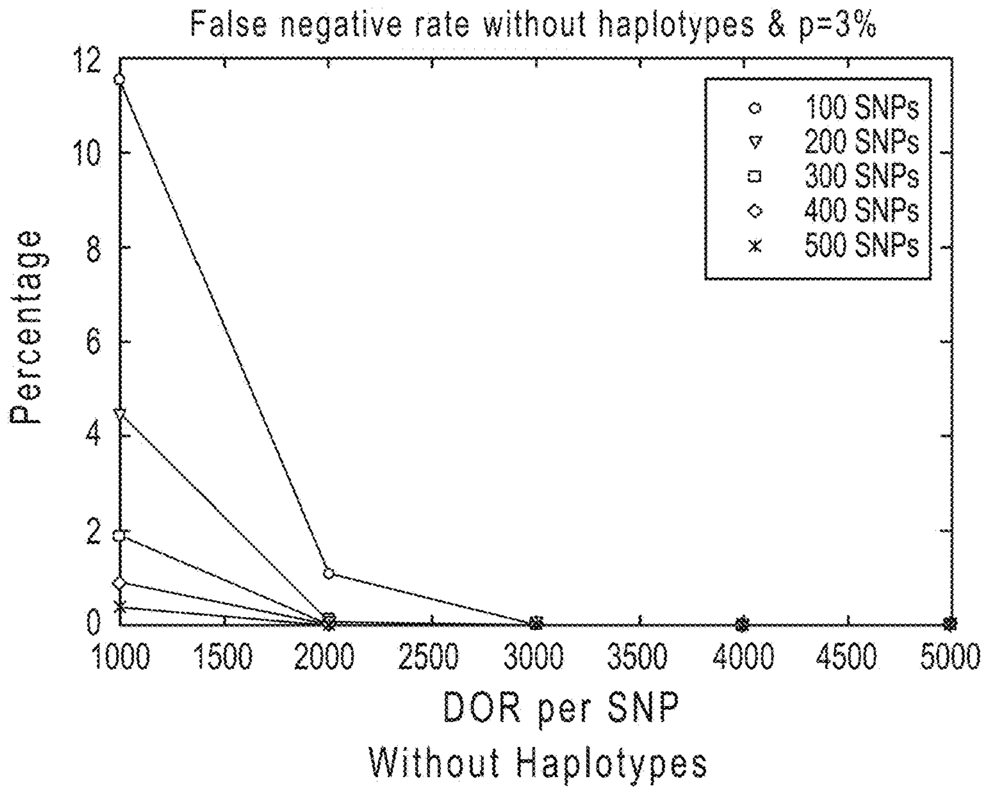

Second Simulation Experiment:

This experiment focused on S $\in$ {100, 200, 300, 400, 500}, D $\in$ {1000, 2000, 3000, 4000, 5000} and p $\in$ {0%, 1%,1.5%, 2%, 2.5%, 3%} and 10000 random experiments at each setting. The false positive rate (in the case of p=0%) and false negative rate (in the case of p>0%) were determined both with or without phase information. The false negative rate is below 10% for D≥3000 and N≥200 using haplotype information, whereas the same performance is reached for D=5000 and N≥400 (FIGS. 20A and 20B). The difference between the false negative rate was particularly stark for small mosaicism percentages (FIGS. 21A-25B). For example, when p=1%, a less than 20% false negative rate is never reached without haplotype data, whereas it is close to 0% for N ≥300 and D ≥3000. For p=3%, a 0% false negative rate is observed with haplotype data, while N>300 and D ≥3000 is needed to reach the same performance without haplotype data.

Exemplary Methods for Detecting Deletions and Duplications Without Phased Data

In some embodiments, unphased genetic data is used to determine if there is an overrepresentation of the number of copies of a first homologous chromosome segment as compared to a second homologous chromosome segment in the genome of an individual (such as in the genome of one or more cells or in cfDNA or cfRNA). In some embodiments, phased genetic data is used but the phasing is ignored. In some embodiments, the sample of DNA or RNA is a mixed sample of cfDNA or cfRNA from the individual that includes cfDNA or cfRNA from two or more genetically different cells. In some embodiments, the method utilizes the magnitude of the difference between the calculated allele ratio and the expected allele ratio for each of the loci.

In some embodiments, the method involves obtaining genetic data at a set of polymorphic loci on the chromosome or chromosome segment in a sample of DNA or RNA from one or more cells from the individual by measuring the quantity of each allele at each locus. In some embodiments, allele ratios are calculated for the loci that are heterozygous in at least one cell from which the sample was derived (such as the loci that are heterozygous in the fetus and/or heterozygous in the mother). In some embodiments, the calculated allele ratio for a particular locus is the measured quantity of one of the alleles divided by the total measured quantity of all the alleles for the locus. In some embodiments, the calculated allele ratio for a particular locus is the measured quantity of one of the alleles (such as the allele on the first homologous chromosome segment) divided by the measured quantity of one or more other alleles (such as the allele on the second homologous chromosome segment) for the locus. The calculated allele ratios and expected allele ratios may be calculated using any of the methods described herein or any standard method (such as any mathematical transformation of the calculated allele ratios or expected allele ratios described herein).

In some embodiments, a test statistic is calculated based on the magnitude of the difference between the calculated allele ratio and the expected allele ratio for each of the loci. In some embodiments, the test statistic Δ is calculated using the following formula $$\Delta = \frac{\sum_{All\ Loci}(\delta_i - \mu_i)}{\sqrt{\sum_{All\ Loci}\sigma_i^2}}$$

wherein $\delta_i$ is the magnitude of the difference between the calculated allele ratio and the expected allele ratio for the ith loci;

wherein $\mu_i$ is the mean value of $\delta_i$; and wherein $\sigma_i^2$ is the standard deviation of $\delta_i$.

For example, we can define $\delta_i$ as follows when the expected allele ratio is 0.5:

$$\delta_i \triangleq \left|\frac{1}{2} - R_i\right|.$$

Values for $\mu_i$ and $\sigma_i$ can be computed using the fact that $R_i$ is a Binomial random variable. In some embodiments, the standard deviation is assumed to be the same for all the loci. In some embodiments, the average or weighted average value of the standard deviation or an estimate of the standard deviation is used for the value of $\sigma_i^2$. In some embodiments, the test statistic is assumed to have a normal distribution. For example, the central limit theorem implies that the distribution of Δ converges to a standard normal as the number of loci (such as the number of SNPs T) grows large.

In some embodiments, a set of one or more hypotheses specifying the number of copies of the chromosome or chromosome segment in the genome of one or more of the cells are enumerated. In some embodiments, the hypothesis that is most likely based on the test statistic is selected, thereby determining the number of copies of the chromosome or chromosome segment in the genome of one or more of the cells. In some embodiments, a hypotheses is selected if the probability that the test statistic belongs to a distribution of the test statistic for that hypothesis is above an upper threshold; one or more of the hypotheses is rejected if the probability that the test statistic belongs to the distribution of the test statistic for that hypothesis is below an lower threshold; or a hypothesis is neither selected nor rejected if the probability that the test statistic belongs to the distribution of the test statistic for that hypothesis is between the lower threshold and the upper threshold, or if the probability is not determined with sufficiently high confidence. In some embodiments, an upper and/or lower threshold is determined from an empirical distribution, such as a distribution from training data (such as samples with a known copy number, such as diploid samples or samples known to have a particular deletion or duplication). Such an empirical distribution can be used to select a threshold for a single hypothesis rejection test.

Note that the test statistic Δ is independent of S and therefore both can be used independently, if desired.

Exemplary Methods for Detecting Deletions and Duplications Using Allele Distributions or Patterns This section includes methods for determining if there is an overrepresentation of the number of copies of a first homologous chromosome segment as compared to a second homologous chromosome segment. In some embodiments, the method involves enumerating (i) a plurality of hypotheses specifying the number of copies of the chromosome or chromosome segment that are present in the genome of one or more cells (such as cancer cells) of the individual or (ii) a plurality of hypotheses specifying the degree of overrepresentation of the number of copies of a first homologous chromosome segment as compared to a second homologous chromosome segment in the genome of one or more cells of the individual. In some embodiments, the method involves obtaining genetic data from the individual at a plurality of polymorphic loci (such as SNP loci) on the chromosome or chromosome segment. In some embodiments, a probability distribution of the expected genotypes of the individual for each of the hypotheses is created. In some embodiments, a data fit between the obtained genetic data of the individual and the probability distribution of the expected genotypes of the individual is calculated. In some embodiments, one or more hypotheses are ranked according to the data fit, and the hypothesis that is ranked the highest is selected. In some embodiments, a technique or algorithm, such as a search algorithm, is used for one or more of the following steps: calculating the data fit, ranking the hypotheses, or selecting the hypothesis that is ranked the highest. In some embodiments, the data fit is a fit to a beta-binomial distribution or a fit to a binomial distribution. In some embodiments, the technique or algorithm is selected from the group consisting of maximum likelihood estimation, maximum a-posteriori estimation, Bayesian estimation, dynamic estimation (such as dynamic Bayesian estimation), and expectation-maximization estimation. In some embodiments, the method includes applying the technique or algorithm to the obtained genetic data and the expected genetic data.

In some embodiments, the method involves enumerating (i) a plurality of hypotheses specifying the number of copies of the chromosome or chromosome segment that are present in the genome of one or more cells (such as cancer cells) of the individual or (ii) a plurality of hypotheses specifying the degree of overrepresentation of the number of copies of a first homologous chromosome segment as compared to a second homologous chromosome segment in the genome of one or more cells of the individual. In some embodiments, the method involves obtaining genetic data from the individual at a plurality of polymorphic loci (such as SNP loci) on the chromosome or chromosome segment. In some embodiments, the genetic data includes allele counts for the plurality of polymorphic loci. In some embodiments, a joint distribution model is created for the expected allele counts at the plurality of polymorphic loci on the chromosome or chromosome segment for each hypothesis. In some embodiments, a relative probability for one or more of the hypotheses is determined using the joint distribution model and the allele counts measured on the sample, and the hypothesis with the greatest probability is selected.

In some embodiments, the distribution or pattern of alleles (such as the pattern of calculated allele ratios) is used to determine the presence or absence of a CNV, such as a deletion or duplication. If desired the parental origin of the CNV can be determined based on this pattern. A maternally inherited duplication is an extra copy of a chromosome segment from the mother, and maternally inherited deletion is the absence of the copy of a chromosome segment from the mother such that the only copy of the chromosome segment that is present is from the father. Exemplary patterns are illustrated in FIGS. 15A-19D and are described further below.

To determine the presence or absence of a deletion of a chromosome segment of interest, the algorithm considers the distribution of sequence counts from each of two possible alleles at large number of SNPs per chromosome. It is important to note that some embodiments of the algorithm use an approach that does not lend itself to visualization. Thus, for the purposes of illustration, the data is displayed in FIGS. 15A-18 in a simplified fashion as ratios of the two most likely alleles, labeled as A and B, so that the relevant trends can be more readily visualized. This simplified illustration does not take into account some of the possible features of the algorithm. For example, two embodiments for the algorithm that are not possible to illustrate with a method of visualization that displays allele ratios are: 1) the ability to leverage linkage disequilibrium, i.e. the influence that a measurement at one SNP has on the likely identity of a neighboring SNP, and 2) the use of non-Gaussian data models that describe the expected distribution of allele measurements at a SNP given platform characteristics and amplification biases. Also note that a simplified version of the algorithm only considers the two most common alleles at each SNP, ignoring other possible alleles.

Deletions of interest were detected in genomic and maternal blood samples. In some embodiments, the genomic and maternal plasma samples are analyzed using the multiplex-PCR and sequencing method of Example 1. The genomic DNA syndrome samples tested lacked heterozygous SNPs in the targeted regions, confirming the ability of the assays to distinguish monosomy (affected) from disomy (unaffected). Analysis of cfDNA from a maternal blood sample was able to detect 22q11.2 deletion syndrome, Cri-du-Chat deletion syndrome, and Wolf-Hirschhorn deletion syndrome, as well as the other deletion syndromes in FIG. 14 in the fetus.

FIGS. 15A-15C depict data that indicate the presence of two chromosomes when the sample is entirely maternal (no fetal cfDNA present, FIG. 15A), contains a moderate fetal cfDNA fraction of 12% (FIG. 15B), or contains a high fetal cfDNA fraction of 26% (FIG. 15C). The x-axis represents the linear position of the individual polymorphic loci along the chromosome, and the y-axis represents the number of A allele reads as a fraction of the total (A+B) allele reads. Maternal and fetal genotypes are indicated to the right of the plots. The plots are color-coded according to maternal genotype, such that red indicates a maternal genotype of AA, blue indicates a maternal genotype of BB, and green indicates a maternal genotype of AB. Note that the measurements are made on total cfDNA isolated from maternal blood, and the cfDNA includes both maternal and fetal cfDNA; thus, each spot represents the combination of the fetal and maternal DNA contribution for that SNP. Therefore, increasing the proportion of maternal cfDNA from 0% to 100% will gradually shift some spots up or down within the plots, depending on the maternal and fetal genotype.

In all cases, SNPs that are homozygous for the A allele (AA) in both the mother and the fetus are found tightly associated with the upper limit of the plots, as the fraction of A allele reads is high because there should be no B alleles present. Conversely, SNPs that are homozygous for the B allele in both the mother and the fetus are found tightly associated with the lower limit of the plots, as the fraction of A allele reads is low because there should be only B alleles. The spots that are not tightly associated with the upper and lower limits of the plots represent SNPs for which the mother, the fetus, or both are heterozygous; these spots are useful for identifying fetal deletions or duplications, but can also be informative for determining paternal versus maternal inheritance. These spots segregate based on both maternal and fetal genotypes and fetal fraction, and as such the precise position of each individual spot along the y-axis depends on both stoichiometry and fetal fraction. For example, loci where the mother is AA and the fetus is AB are expected to have a different fraction of A allele reads, and thus different positioning along the y-axis, depending on the fetal fraction.

FIG. 15A has data for a non-pregnant woman, and thus represents the pattern when the genotype is entirely maternal. This pattern includes "clusters" of spots: a red cluster tightly associated with the top of the plot (SNPs where the maternal genotype is AA), a blue cluster tightly associated with the bottom of the plot (SNPs where the maternal genotype is BB), and a single, centered green cluster (SNPs where the maternal genotype is AB). For FIG. 15B, the contribution of fetal alleles to the fraction of A allele reads shifts the position of some allele spots up or down along the y-axis. For FIG. 15C, the pattern, including two red and two blue peripheral bands and a trio of central green bands, is readily apparent. The three central green bands correspond to SNPs that are heterozygous in the mother, and two "peripheral" bands each at both the top (red) and bottom (blue) of the plots correspond to SNPs that are homozygous in the mother.

Figure 16A:
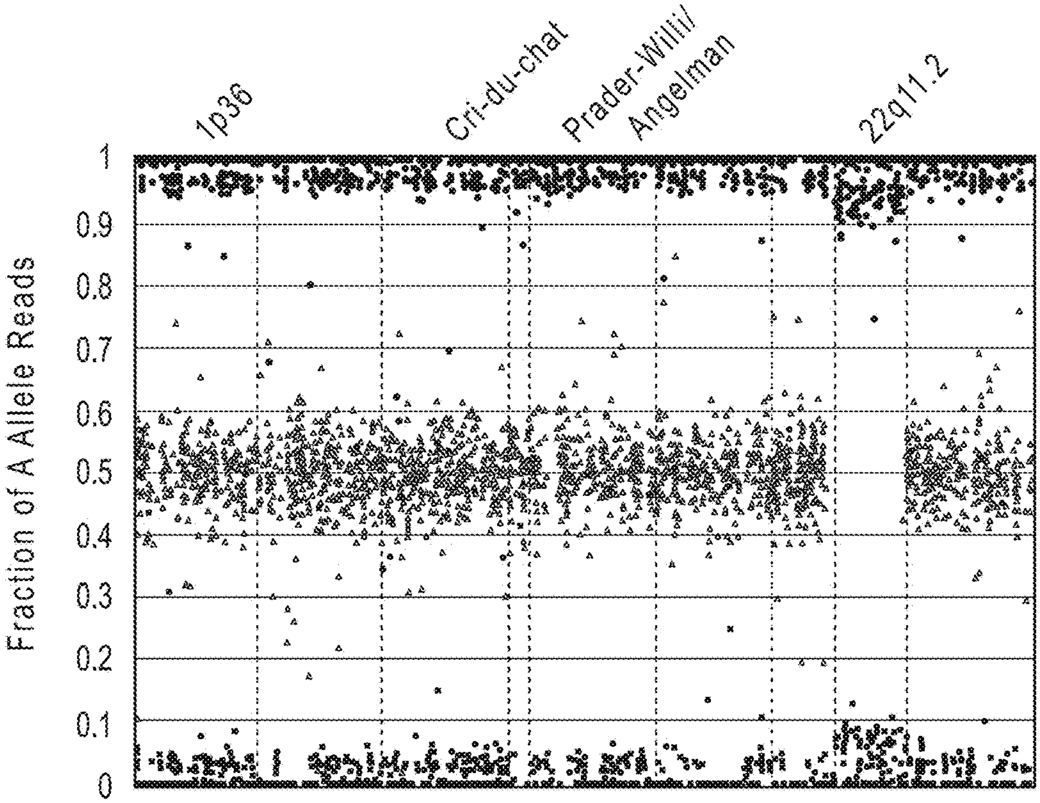
FIGS. 16A and 16B are graphical representations of 22q11.2 deletion syndrome.
Figure 16B:
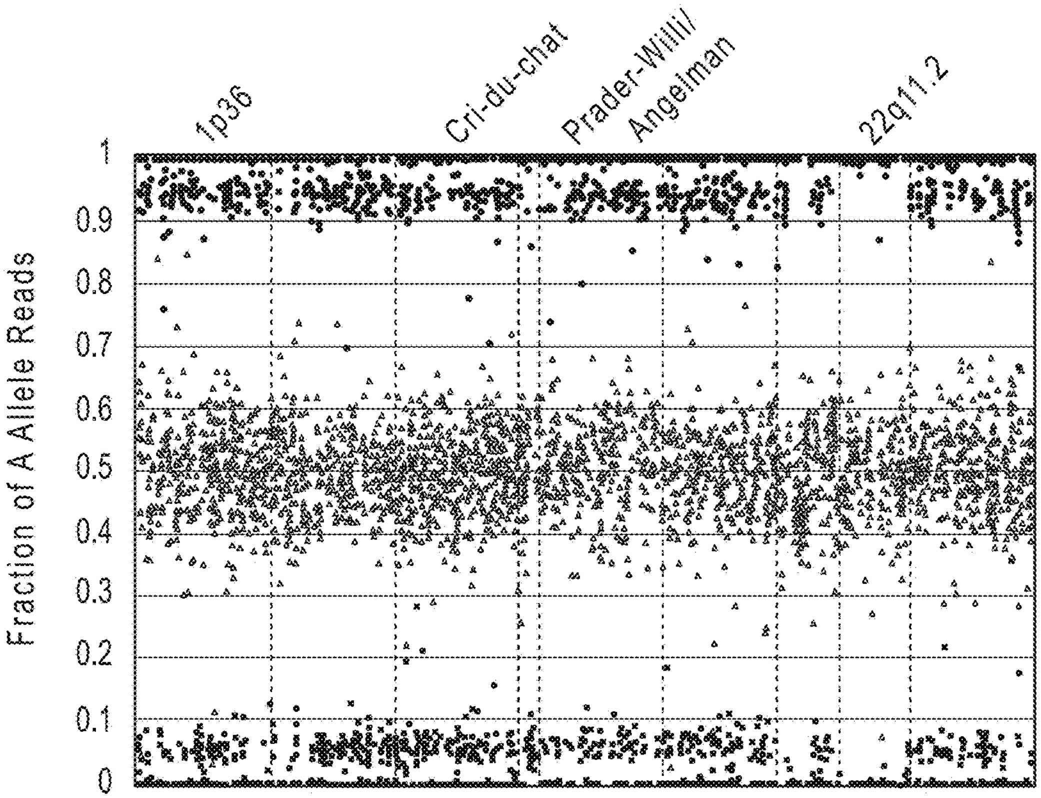

Analysis of a 22q11.2 deletion carrier (a mother with this deletion) is shown in FIG. 16A. The deletion carrier does not have heterozygous SNPs in this region since the carrier only has one copy of this region. Thus, this deletion is indicated by the absence of the green AB SNPs. The analysis of a paternally inherited 22q11 deletion in a fetus is shown in FIG. 16B. When the fetus only inherits a single copy of a chromosome segment (in the case of a paternally inherited deletion, the copy present in the fetus comes from the mother), and thus only inherits a single allele for each locus in this segment, heterozygosity of the fetus is not possible. As such, the only possible fetal SNP identities are A or B. Note the absence of internal peripheral bands. For a paternally inherited deletion, the characteristic pattern includes two central green bands that represent SNPs for which the mother is heterozygous, and only has single peripheral red and blue bands that represent SNPs for which the mother is homozygous, and which remain tightly associated with the upper and lower limits of the plots (1 and 0), respectively.

Figure 17:
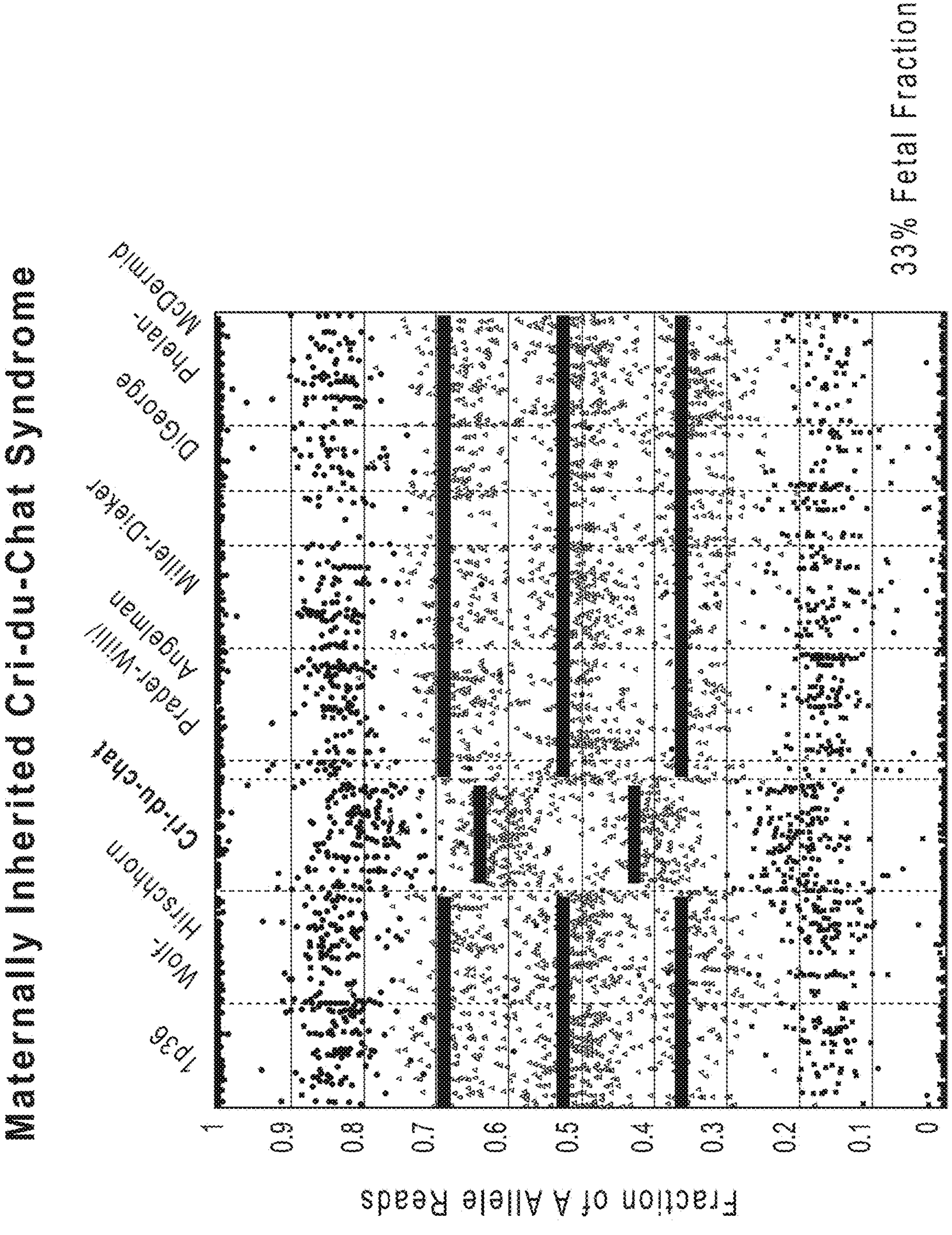
FIG. 17 is a graphical representation of maternally inherited Cri-du-Chat deletion syndrome (as indicated by the presence of two central open triangle shape bands instead of three open triangle shape bands). The x-axis represents the linear position of the SNPs, and the y-axis indicates the fraction of A allele reads out of the total reads. Each individual circle, triangle or square represents a single SNP locus.

Analysis of a maternally inherited Cri-du-Chat deletion syndrome is shown in FIG. 17. There are two central green bands instead of three green bands, and there are two red and two blue peripheral bands. A maternally inherited deletion (such as a maternal carrier of Duchenne's muscular dystrophy) can also be detected based on the small amount of signal in that region of the deletion in a mixed sample of maternal and fetal DNA (such as a plasma sample) due to both the mother and the fetus having the deletion.

Figure 18:
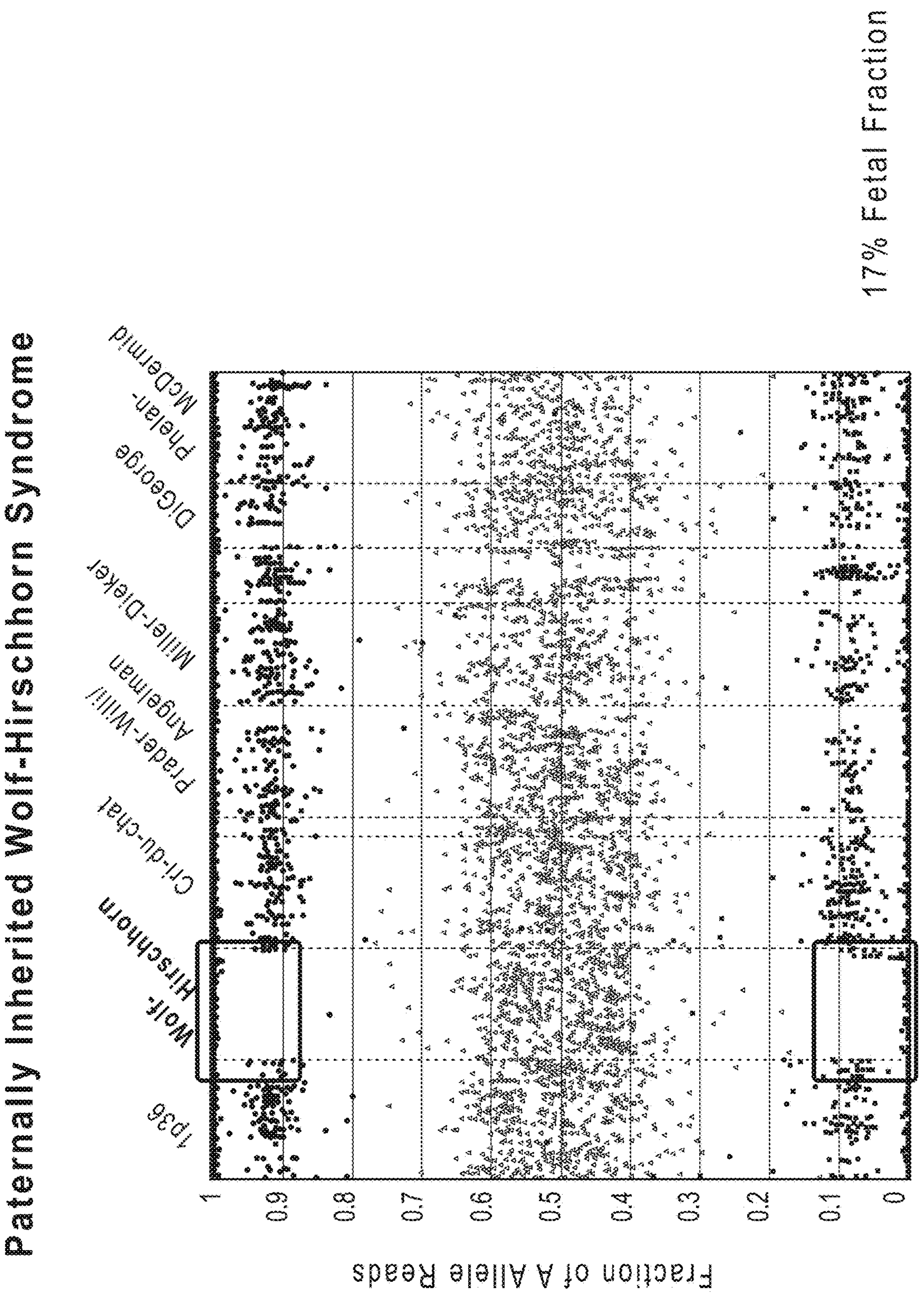
FIG. 18 is a graphical representation of paternally inherited Wolf-Hirschhorn deletion syndrome (as indicated by the presence of solid circle and solid square peripheral bands). The x-axis represents the linear position of the SNPs, and the y-axis indicates the fraction of A allele reads out of the total reads. Each individual circle, triangle or square represents a single SNP locus.
Figure 19A:
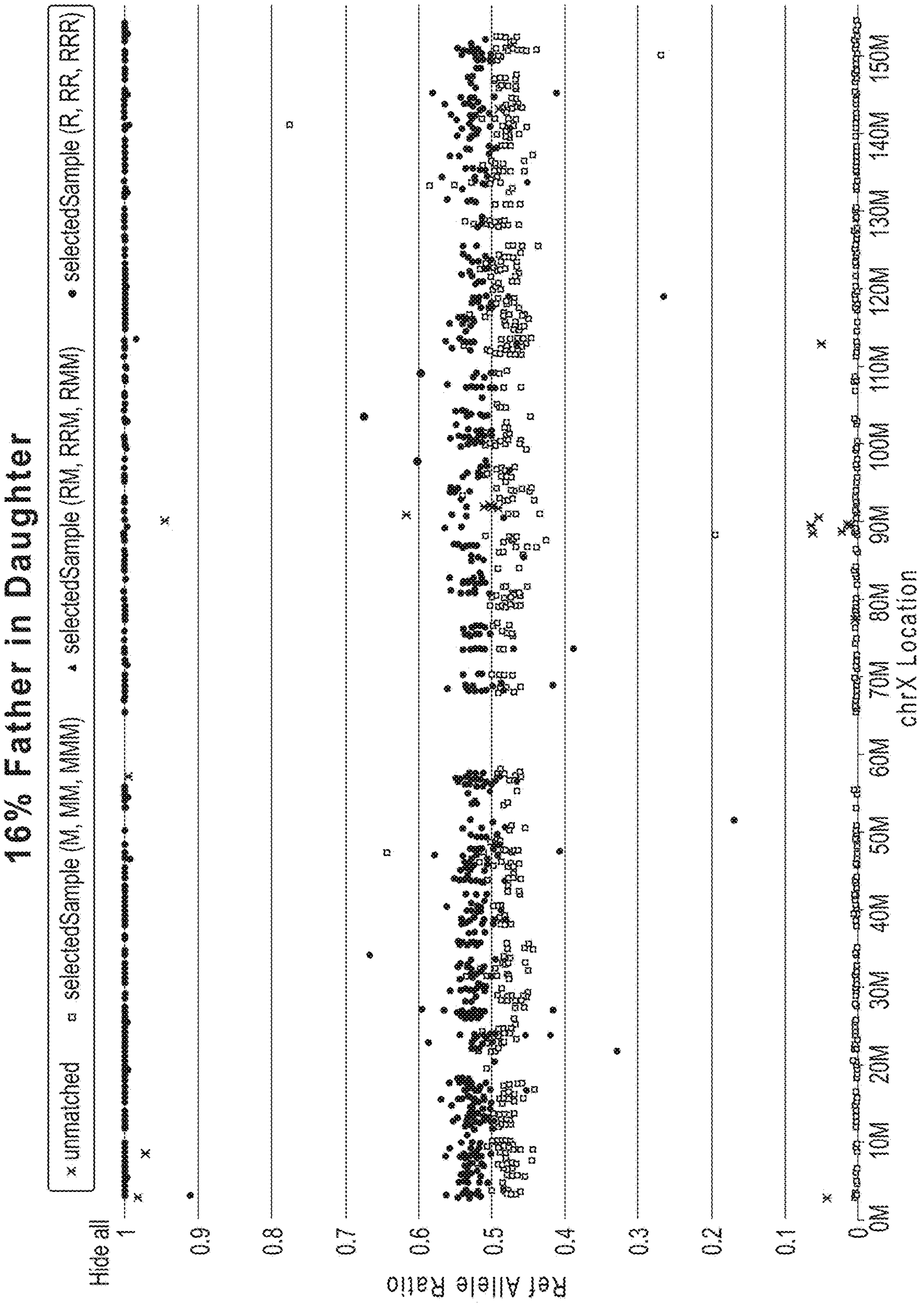
FIGS. 19A-19D are graphical representations of X chromosome spike-in experiments to represent an extra copy of a chromosome or chromosome segment. The plots show different amounts of DNA from a father mixed with DNA from the daughter: 16% father DNA (FIG. 19A), 10% father DNA (FIG. 19B), 1% father DNA (FIG. 19C), and 0.1% father DNA (FIG. 19D). The x-axis represents the linear position of the SNPs on the X chromosome, and the y-axis indicates the fraction of M allele reads out of the total reads (M+R). Each individual criss-cross, circle, triangle or square represents a single SNP locus with allele M or R.
Figure 19B:
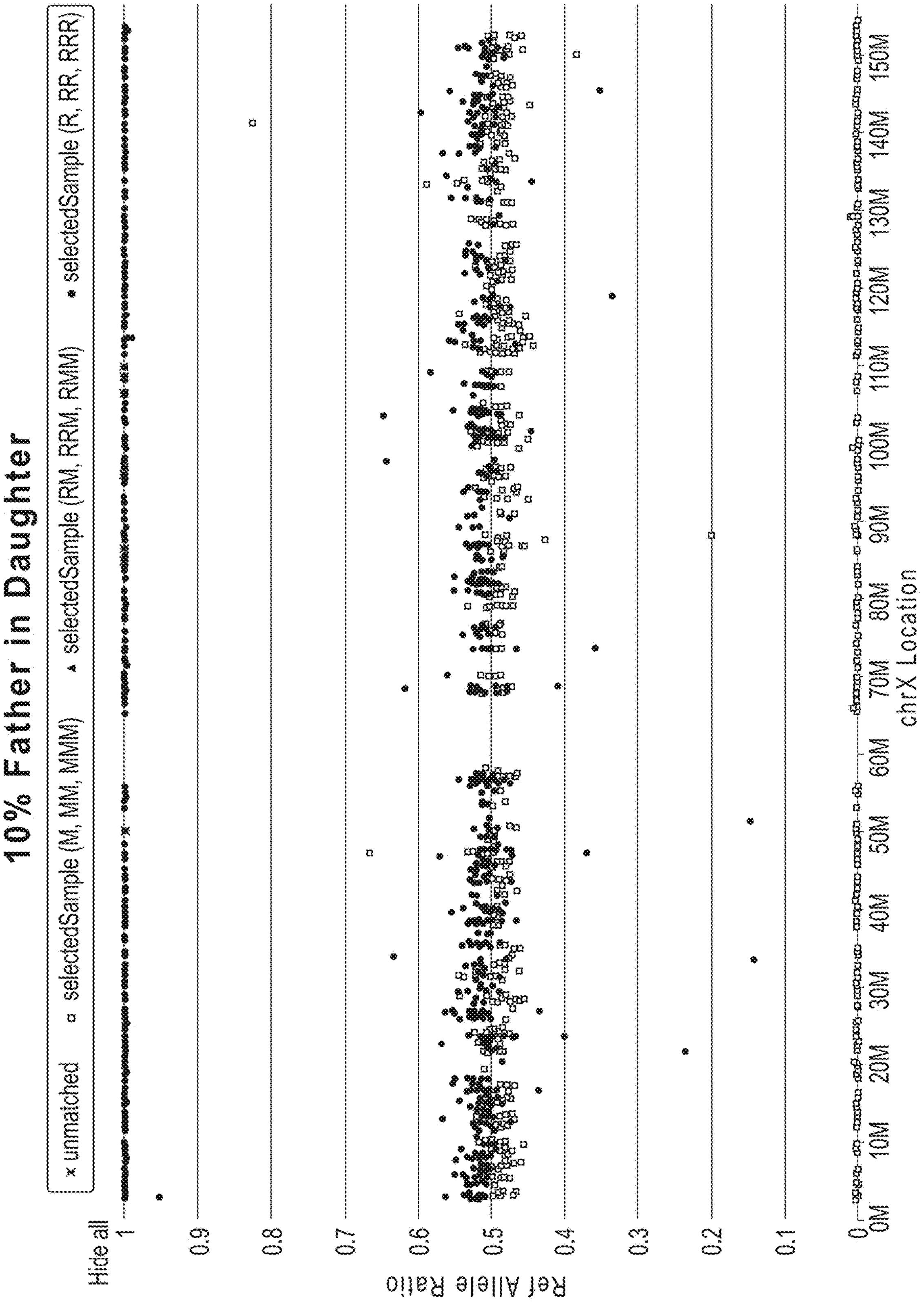
Figure 19C:
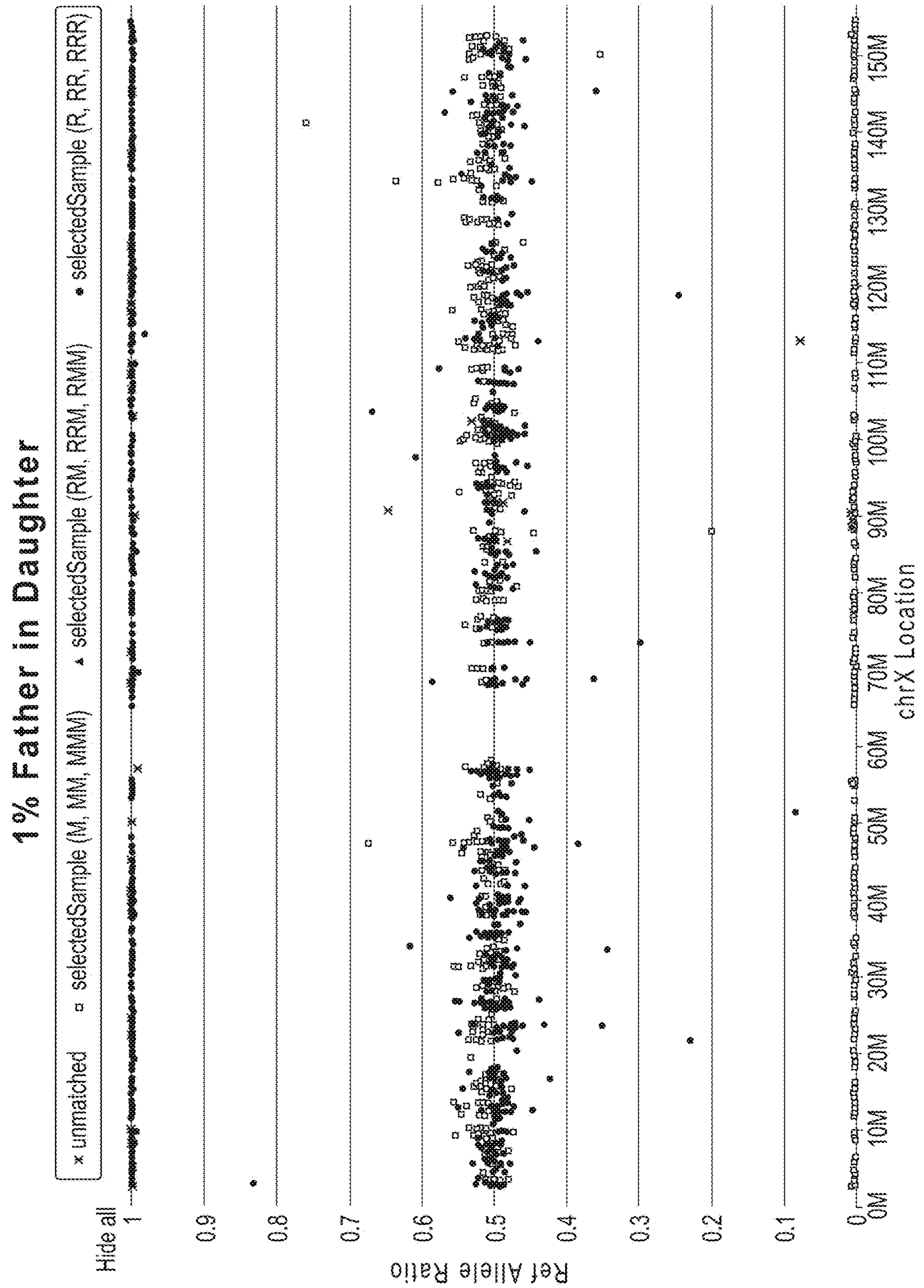
Figure 19D:
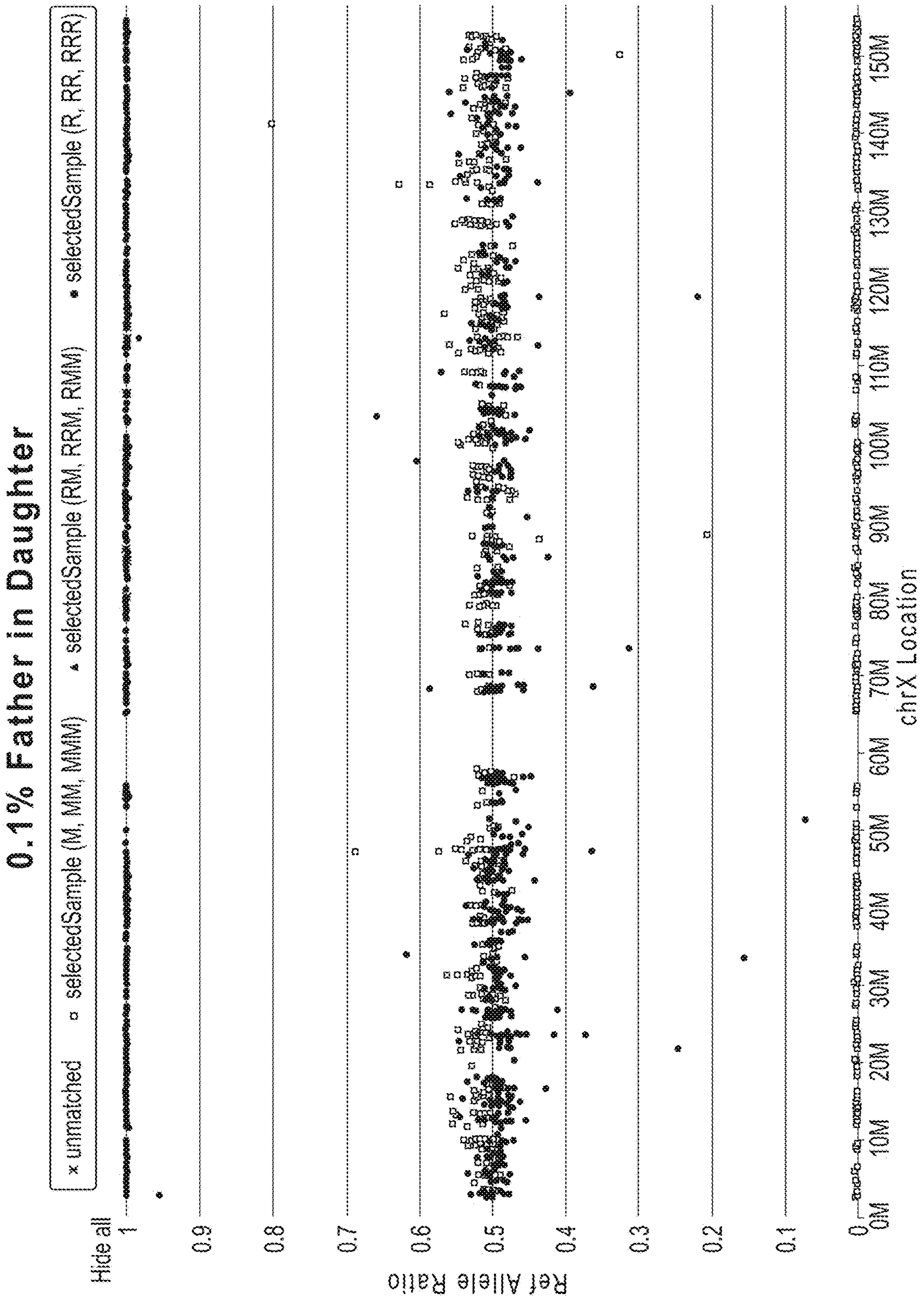

FIG. 18 is a plot of a paternally inherited Wolf-Hirschhorn deletion syndrome, as indicated by the presence of one red and one blue peripheral band.

If desired, similar plots can be generated for a sample from an individual suspected of having a deletion or duplication, such as a CNV associated with cancer. In such plots, the following color coding can be used based on the genotype of cells without the CNV: red indicates a genotype of AA, blue indicates a genotype of BB, and green indicates a genotype of AB. In some embodiments for a deletion, the pattern includes two central green bands that represent SNPs for which the individual is heterozygous (top green band represents AB from cells without the deletion and A from cells with the deletion, and bottom green band represents AB from cells without the deletion and B from cells with the deletion), and only has single peripheral red and blue bands that represent SNPs for which the individual is homozygous, and which remain tightly associated with the upper and lower limits of the plots (1 and 0), respectively. In some embodiments, the separation of the two green bands increases as the fraction of cells, DNA, or RNA with the deletion increases.

Exemplary Methods for Identifying and Analyzing Multiple Pregnancies

In some embodiments, any of the methods of the present invention are used to detect the presence of a multiple pregnancy, such as a twin pregnancy, where at least one of the fetuses is genetically different from at least one other fetus. In some embodiments, fraternal twins are identified based on the presence of two fetus with different allele, different allele ratios, or different allele distributions at some (or all) of the tested loci. In some embodiments, fraternal twins are identified by determining the expected allele ratio at each locus (such as SNP loci) for two fetuses that may have the same or different fetal fractions in the sample (such as a plasma sample). In some embodiments, the likelihood of a particular pair of fetal fractions (where f1 is the fetal fraction for fetus 1, and f2 is the fetal fraction for fetus 2) is calculated by considering some or all of the possible genotypes of the two fetuses, conditioned on the mother's genotype and genotype population frequencies. The mixture of two fetal and one maternal genotype, combined with the fetal fractions, determine the expected allele ratio at a SNP. For example, if the mother is AA, fetus 1 is AA, and fetus 2 is AB, the overall fraction of B allele at the SNP is one-half of f2. The likelihood calculation asks how well all of the SNPs together match the expected allele ratios based on all of the possible combinations of fetal genotypes. The fetal fraction pair (f1, f2) that best matches the data is selected. It is not necessary to calculated specific genotypes of the fetuses; instead, one can, for example, considered all of the possible genotypes in a statistical combination. In some embodiments, if the method does not distinguish between singleton and identical twins, an ultrasound can be performed to determine whether there is a singleton or identical twin pregnancy. If the ultrasound detects a twin pregnancy it can be assumed that the pregnancy is an identical twin pregnancy because a fraternal twin pregnancy would have been detected based on the SNP analysis discussed above.

In some embodiments, a pregnant mother is known to have a multiple pregnancy (such as a twin pregnancy) based on prior testing, such as an ultrasound. Any of the methods of the present invention can be used to determine whether the multiple pregnancy includes identical or fraternal twins. For example, the measured allele ratios can be compared to what would be expected for identical twins (the same allele ratios as a singleton pregnancy) or for fraternal twins (such as the calculation of allele ratios as described above). Some identical twins are monochorionic twins, which have a risk of twin-to-twin transfusion syndrome. Thus, twins determined to be identical twins using a method of the invention are desirably tested (such as by ultrasound) to determine if they are monochorionic twins, and if so, these twins can be monitored (such as bi-weekly ultrasounds from 16 weeks) for signs of win-to-twin transfusion syndrome.

In some embodiments, any of the methods of the present invention are used to determine whether any of the fetuses in a multiple pregnancy, such as a twin pregnancy, are aneuploid. Aneuploidy testing for twins begins with the fetal fraction estimate. In some embodiments, the fetal fraction pair (f1, f2) that best matches the data is selected as described above. In some embodiments, a maximum likelihood estimate is performed for the parameter pair (f1, f2) over the range of possible fetal fractions. In some embodiments, the range of f2 is from 0 to f1 because f2 is defined as the smaller fetal fraction. Given a pair (f1, f2), data likelihood is calculated from the allele ratios observed at a set of loci such as SNP loci. In some embodiments, the data likelihood reflects the genotypes of the mother, the father if available, population frequencies, and the resulting probabilities of fetal genotypes. In some embodiments, SNPs are assumed independent. The estimated fetal fraction pair is the one that produces the highest data likelihood. If f2 is 0 then the data is best explained by only one set of fetal genotypes, indicating identical twins, where f1 is the combined fetal fraction. Otherwise f1 and f2 are the estimates of the individual twin fetal fractions. Having established the best estimate of (f1, f2), one can predict the overall fraction of B allele in the plasma for any combination of maternal and fetal genotypes, if desired. It is not necessary to assign individual sequence reads to the individual fetuses. Ploidy testing is performed using another maximum likelihood estimate which compares the data likelihood of two hypotheses. In some embodiments for identical twins, one consider the hypotheses (i) both twins are euploid, and (ii) both twins are trisomic. In some embodiments for fraternal twins, one considers the hypotheses (i) both twins are euploid and (ii) at least one twin is trisomic. The trisomy hypotheses for fraternal twins are based on the lower fetal fraction, since a trisomy in the twin with a higher fetal fraction would also be detected. Ploidy likelihoods are calculated using a method which predicts the expected number of reads at each targeted genome locus conditioned on either the disomy or trisomy hypothesis. There is no requirement for a disomy reference chromosome. The variance model for the expected number of reads takes into account the performance of individual target loci as well as the correlation between loci (see, for example, U.S. Ser. No. 62/008,235, filed Jun. 5, 2014, and U.S. Ser. No. 62/032,785, filed Aug. 4, 2014, which are each hereby incorporated by reference in its entirety). If the smaller twin has fetal fraction f1, our ability to detect a trisomy in that twin is equivalent to our ability to detect a trisomy in a singleton pregnancy at the same fetal fraction. This is because the part of the method that detects the trisomy in some embodiments does not depend on genotypes and does not distinguish between multiple or singleton pregnancy. It simply looks for an increased number of reads in accordance with the determined fetal fraction.

In some embodiments, the method includes detecting the presence of twins based on SNP loci (such as described above). If twins are detected, SPNs are used to determine the fetal fraction of each fetus (f1, f2) such as described above. In some embodiments, samples that have high confidence disomy calls are used to determine the amplification bias on a per-SNP basis. In some embodiments, these samples with high confidence disomy calls are analyzed in the same run as one or more samples of interest. In some embodiments, the amplification bias on a per-SNP basis is used to model the distribution of reads for one or more chromosomes or chromosome segments of interest such as chromosome 21 that are expected or the disomy hypothesis and the trisomy hypothesis given the lower of the two twin fetal fraction. The likelihood or probability of disomy or trisomy is calculated given the two models and the measured quantity of the chromosome or chromosome segment of interest.

In some embodiments, the threshold for a positive aneuploidy call (such as a trisomy call) is set based on the twin with the lower fetal fraction. This way, if the other twin is positive, or if both are positive, the total chromosome representation is definitely above the threshold.

Exemplary Counting Methods/Quantitative Methods

In some embodiments, one or more counting methods (also referred to as quantitative methods) are used to detect one or more CNS, such as deletions or duplications of chromosome segments or entire chromosomes. In some embodiments, one or more counting methods are used to determine whether the overrepresentation of the number of copies of the first homologous chromosome segment is due to a duplication of the first homologous chromosome segment or a deletion of the second homologous chromosome segment. In some embodiments, one or more counting methods are used to determine the number of extra copies of a chromosome segment or chromosome that is duplicated (such as whether there are 1, 2, 3, 4, or more extra copies). In some embodiments, one or more counting methods are used to differentiate a sample has many duplications and a smaller tumor fraction from a sample with fewer duplications and a larger tumor fraction. For example, one or more counting methods may be used to differentiate a sample with four extra chromosome copies and a tumor fraction of 10% from a sample with two extra chromosome copies and a tumor fraction of 20%. Exemplary methods are disclosed, e.g. U.S. Publication Nos. 2007/0184467; 2013/0172211; and 2012/0003637; U.S. Pat. Nos. 8,467,976; 7,888,017; 8,008,018; 8,296,076; and 8,195,415; U.S. Ser. No. 62/008,235, filed Jun. 5, 2014, and U.S. Ser. No. 62/032,785, filed Aug. 4, 2014, which are each hereby incorporated by reference in its entirety.

In some embodiment, the counting method includes counting the number of DNA sequence-based reads that map to one or more given chromosomes or chromosome segments. Some such methods involve creation of a reference value (cut-off value) for the number of DNA sequence reads mapping to a specific chromosome or chromosome segment, wherein a number of reads in excess of the value is indicative of a specific genetic abnormality.

In some embodiments, the total measured quantity of all the alleles for one or more loci (such as the total amount of a polymorphic or non-polymorphic locus) is compared to a reference amount. In some embodiments, the reference amount is (i) a threshold value or (ii) an expected amount for a particular copy number hypothesis. In some embodiments, the reference amount (for the absence of a CNV) is the total measured quantity of all the alleles for one or more loci for one or more chromosomes or chromosomes segments known or expected to not have a deletion or duplication. In some embodiments, the reference amount (for the presence of a CNV) is the total measured quantity of all the alleles for one or more loci for one or more chromosomes or chromosomes segments known or expected to have a deletion or duplication. In some embodiments, the reference amount is the total measured quantity of all the alleles for one or more loci for one or more reference chromosomes or chromosome segments. In some embodiments, the reference amount is the mean or median of the values determined for two or more different chromosomes, chromosome segments, or different samples. In some embodiments, random (e.g., massively parallel shotgun sequencing) or targeted sequencing is used to determine the amount of one or more polymorphic or non-polymorphic loci.

In some embodiments utilizing a reference amount, the method includes (a) measuring the amount of genetic material on a chromosome or chromosome segment of interest; (b) comparing the amount from step (a) to a reference amount; and (c) identifying the presence or absence of a deletion or duplication based on the comparison.

In some embodiments utilizing a reference chromosome or chromosome segment, the method includes sequencing DNA or RNA from a sample to obtain a plurality of sequence tags aligning to target loci. In some embodiments, the sequence tags are of sufficient length to be assigned to a specific target locus (e.g., 15-100 nucleotides in length); the target loci are from a plurality of different chromosomes or chromosome segments that include at least one first chromosome or chromosome segment suspected of having an abnormal distribution in the sample and at least one second chromosome or chromosome segment presumed to be normally distributed in the sample. In some embodiments, the plurality of sequence tags are assigned to their corresponding target loci. In some embodiments, the number of sequence tags aligning to the target loci of the first chromosome or chromosome segment and the number of sequence tags aligning to the target loci of the second chromosome or chromosome segment are determined. In some embodiments, these numbers are compared to determine the presence or absence of an abnormal distribution (such as a deletion or duplication) of the first chromosome or chromosome segment.

In some embodiments, the value of f (such as the fetal fraction or tumor fraction) is used in the CNV determination, such as to compare the observed difference between the amount of two chromosomes or chromosome segments to the difference that would be expected for a particular type of CNV given the value of f (see, e.g., US Publication No 2012/0190020; US Publication No 2012/0190021; US Publication No 2012/0190557; US Publication No 2012/0191358, which are each hereby incorporated by reference in its entirety). For example, the difference in the amount of a chromosome segment that is duplicated in a fetus compared to a disomic reference chromosome segment in a blood sample from a mother carrying the fetus increases as the fetal fraction increases. Additionally, the difference in the amount of a chromosome segment that is duplicated in a tumor compared to a disomic reference chromosome segment increases as the tumor fraction increases. In some embodiments, the method includes comparing the relative frequency of a chromosome or chromosome segment of interest to a reference chromosomes or chromosome segment (such as a chromosome or chromosome segment expected or known to be disomic) to the value of f to determine the likelihood of the CNV. For example, the difference in amounts between the first chromosomes or chromosome segment to the reference chromosome or chromosome segment can be compared to what would be expected given the value of f for various possible CNVs (such as one or two extra copies of a chromosome segment of interest).

The following prophetic examples illustrate the use of a counting method/quantitative method to differentiate between a duplication of the first homologous chromosome segment and a deletion of the second homologous chromosome segment. If one considers the normal disomic genome of the host to be the baseline, then analysis of a mixture of normal and cancer cells yields the average difference between the baseline and the cancer DNA in the mixture. For example, imagine a case where 10% of the DNA in the sample originated from cells with a deletion over a region of a chromosome that is targeted by the assay. In some embodiments, a quantitative approach shows that the quantity of reads corresponding to that region is expected to be 95% of what is expected for a normal sample. This is because one of the two target chromosomal regions in each of the tumor cells with a deletion of the targeted region is missing, and thus the total amount of DNA mapping to that region is 90% (for the normal cells) plus ½×10% (for the tumor cells) =95%. Alternately in some embodiments, an allelic approach shows that the ratio of alleles at heterozygous loci averaged 19:20. Now imagine a case where 10% of the DNA in the sample originated from cells with a five-fold focal amplification of a region of a chromosome that is targeted by the assay. In some embodiments, a quantitative approach shows that the quantity of reads corresponding to that region is expected to be 125% of what is expected for a normal sample. This is because one of the two target chromosomal regions in each of the tumor cells with a five-fold focal amplification is copied an extra five times over the targeted region, and thus the total amount of DNA mapping to that region is 90% (for the normal cells) plus (2+5)×10%/2 (for the tumor cells)=125%. Alternately in some embodiments, an allelic approach shows that the ratio of alleles at heterozygous loci averaged 25:20. Note that when using an allelic approach alone, a focal amplification of five-fold over a chromosomal region in a sample with 10% cfDNA may appear the same as a deletion over the same region in a sample with 40% cfDNA; in these two cases, the haplotype that is under-represented in the case of the deletion appears to be the haplotype without a CNV in the case with the focal duplication, and the haplotype without a CNV in the case of the deletion appears to be the over-represented haplotype in the case with the focal duplication. Combining the likelihoods produced by this allelic approach with likelihoods produced by a quantitative approach differentiates between the two possibilities.

Exemplary Counting Methods/Quantitative Methods Using Reference Samples

An exemplary quantitative method that uses one or more reference samples is described in U.S. Ser. No. 62/008,235, filed Jun. 5, 2014 and U.S. Ser. No. 62/032,785, filed Aug. 4, 2014, which is hereby incorporated by reference in its entirety. In some embodiments, one or more reference samples most likely to not have any CNVs on one or more chromosomes or chromosomes of interest (e.g., a normal sample) are identified by selecting the samples with the highest fraction of tumor DNA, selecting the samples with the z-score closest to zero, selecting the samples where the data fits the hypothesis corresponding to no CNVs with the highest confidence or likelihood, selecting the samples known to be normal, selecting the samples from individuals with the lowest likelihood of having cancer (e.g., having a low age, being a male when screening for breast cancer, having no family history, etc.), selecting the samples with the highest input amount of DNA, selecting the samples with the highest signal to noise ratio, selecting samples based on other criteria believed to be correlated to the likelihood of having cancer, or selecting samples using some combination of criteria. Once the reference set is chosen, one can make the assumption that these cases are disomic, and then estimate the per-SNP bias, that is, the experiment-specific amplification and other processing bias for each locus. Then, one can use this experiment-specific bias estimate to correct the bias in the measurements of the chromosome of interest, such as chromosome 21 loci, and for the other chromosome loci as appropriate, for the samples that are not part of the subset where disomy is assumed for chromosome 21. Once the biases have been corrected for in these samples of unknown ploidy, the data for these samples can then be analyzed a second time using the same or a different method to determine whether the individuals (such as fetuses) are afflicted with trisomy 21. For example, a quantitative method can be used on the remaining samples of unknown ploidy, and a z-score can be calculated using the corrected measured genetic data on chromosome 21. Alternately, as part of the preliminary estimate of the ploidy state of chromosome 21, a fetal fraction (or tumor fraction for samples from an individual suspected of having cancer) can be calculated. The proportion of corrected reads that are expected in the case of a disomy (the disomy hypothesis), and the proportion of corrected reads that are expected in the case of a trisomy (the trisomy hypothesis) can be calculated for a case with that fetal fraction. Alternately, if the fetal fraction was not measured previously, a set of disomy and trisomy hypotheses can be generated for different fetal fractions. For each case, an expected distribution of the proportion of corrected reads can be calculated given expected statistical variation in the selection and measurement of the various DNA loci. The observed corrected proportion of reads can be compared to the distribution of the expected proportion of corrected reads, and a likelihood ratio can be calculated for the disomy and trisomy hypotheses, for each of the samples of unknown ploidy. The ploidy state associated with the hypothesis with the highest calculated likelihood can be selected as the correct ploidy state.

In some embodiments, a subset of the samples with a sufficiently low likelihood of having cancer may be selected to act as a control set of samples. The subset can be a fixed number, or it can be a variable number that is based on choosing only those samples that fall below a threshold. The quantitative data from the subset of samples may be combined, averaged, or combined using a weighted average where the weighting is based on the likelihood of the sample being normal. The quantitative data may be used to determine the per-locus bias for the amplification the sequencing of samples in the instant batch of control samples. The per-locus bias may also include data from other batches of samples. The per-locus bias may indicate the relative over- or under-amplification that is observed for that locus compared to other loci, making the assumption that the subset of samples do not contain any CNVs, and that any observed over or under-amplification is due to amplification and/or sequencing or other bias. The per-locus bias may take into account the GC content of the amplicon. The loci may be grouped into groups of loci for the purpose of calculating a per-locus bias. Once the per-locus bias has been calculated for each locus in the plurality of loci, the sequencing data for one or more of the samples that are not in the subset of the samples, and optionally one or more of the samples that are in the subset of samples, may be corrected by adjusting the quantitative measurements for each locus to remove the effect of the bias at that locus. For example, if SNP 1 was observed, in the subset of patients, to have a depth of read that is twice as great as the average, the adjustment may involve replacing the number of reads corresponding from SNP 1 with a number that is half as great. If the locus in question is a SNP, the adjustment may involve cutting the number of reads corresponding to each of the alleles at that locus in half. Once the sequencing data for each of the loci in one or more samples has been adjusted, it may be analyzed using a method for the purpose of detecting the presence of a CNV at one or more chromosomal regions.

In an example, sample A is a mixture of amplified DNA originating from a mixture of normal and cancerous cells that is analyzed using a quantitative method. The following illustrates exemplary possible data. A region of the q arm on chromosome 22 is found to only have 90% as much DNA mapping to that region as expected; a focal region corresponding to the HER2 gene is found to have 150% as much DNA mapping to that region as expected; and the p-arm of chromosome 5 is found to have 105% as much DNA mapping to it as expected. A clinician may infer that the sample has a deletion of a region on the q arm on chromosome 22, and a duplication of the HER2 gene. The clinician may infer that since the 22q deletions are common in breast cancer, and that since cells with a deletion of the 22q region on both chromosomes usually do not survive, that approximately 20% of the DNA in the sample came from cells with a 22q deletion on one of the two chromosomes. The clinician may also infer that if the DNA from the mixed sample that originated from tumor cells originated from a set of genetically tumor cells whose HER2 region and 22q regions were homogenous, then the cells contained a five-fold duplication of the HER2 region.

In an example, Sample A is also analyzed using an allelic method. The following illustrates exemplary possible data. The two haplotypes on same region on the q arm on chromosome 22 are present in a ratio of 4:5; the two haplotypes in a focal region corresponding to the HER2 gene are present in ratios of 1:2; and the two haplotypes in the p-arm of chromosome 5 are present in ratios of 20:21. All other assayed regions of the genome have no statistically significant excess of either haplotype. A clinician may infer that the sample contains DNA from a tumor with a CNV in the 22q region, the HER2 region, and the 5p arm. Based on the knowledge that 22q deletions are very common in breast cancer, and/or the quantitative analysis showing an under-representation of the amount of DNA mapping to the 22q region of the genome, the clinician may infer the existence of a tumor with a 22q deletion. Based on the knowledge that HER2 amplifications are very common in breast cancer, and/or the quantitative analysis showing an over-representation of the amount of DNA mapping to the HER2 region of the genome, the clinician may infer the existence of a tumor with a HER2 amplification.

Exemplary Reference Chromosomes or Chromosome Segments

In some embodiments, any of the methods described herein are also performed on one or more reference chromosomes or chromosomes segments and the results are compared to those for one or more chromosomes or chromosome segments of interest.

In some embodiments, the reference chromosome or chromosome segment is used as a control for what would be expected for the absence of a CNV. In some embodiments, the reference is the same chromosome or chromosome segment from one or more different samples known or expected to not have a deletion or duplication in that chromosome or chromosome segment. In some embodiments, the reference is a different chromosome or chromosome segment from the sample being tested that is expected to be disomic. In some embodiments, the reference is a different segment from one of the chromosomes of interest in the same sample that is being tested. For example, the reference may be one or more segments outside of the region of a potential deletion or duplication. Having a reference on the same chromosome that is being tested avoids variability between different chromosomes, such as differences in metabolism, apoptosis, histones, inactivation, and/or amplification between chromosomes. Analyzing segments without a CNV on the same chromosome as the one being tested can also be used to determine differences in metabolism, apoptosis, histones, inactivation, and/or amplification between homologs, allowing the level of variability between homologs in the absence of a CNV to be determined for comparison to the results from a potential CNV. In some embodiments, the magnitude of the difference between the calculated and expected allele ratios for a potential CNV is greater than the corresponding magnitude for the reference, thereby confirming the presence of a CNV.

In some embodiments, the reference chromosome or chromosome segment is used as a control for what would be expected for the presence of a CNV, such as a particular deletion or duplication of interest. In some embodiments, the reference is the same chromosome or chromosome segment from one or more different samples known or expected to have a deletion or duplication in that chromosome or chromosome segment. In some embodiments, the reference is a different chromosome or chromosome segment from the sample being tested that is known or expected to have a CNV. In some embodiments, the magnitude of the difference between the calculated and expected allele ratios for a potential CNV is similar to (such as not significantly different) than the corresponding magnitude for the reference for the CNV, thereby confirming the presence of a CNV. In some embodiments, the magnitude of the difference between the calculated and expected allele ratios for a potential CNV is less than (such as significantly less) than the corresponding magnitude for the reference for the CNV, thereby confirming the absence of a CNV. In some embodiments, one or more loci for which the genotype of a cancer cell (or DNA or RNA from a cancer cell such as cfDNA or cfRNA) differs from the genotype of a noncancerous cell (or DNA or RNA from a noncancerous cell such as cfDNA or cfRNA) is used to determine the tumor fraction. The tumor fraction can be used to determine whether the overrepresentation of the number of copies of the first homologous chromosome segment is due to a duplication of the first homologous chromosome segment or a deletion of the second homologous chromosome segment. The tumor fraction can also be used to determine the number of extra copies of a chromosome segment or chromosome that is duplicated (such as whether there are 1, 2, 3, 4, or more extra copies), such as to differentiate a sample with four extra chromosome copies and a tumor fraction of 10% from a sample with two extra chromosome copies and a tumor fraction of 20%. The tumor fraction can also be used to determine how well the observed data fits the expected data for possible CNVs. In some embodiments, the degree of overrepresentation of a CNV is used to select a particular therapy or therapeutic regimen for the individual. For example, some therapeutic agents are only effective for at least four, six, or more copies of a chromosome segment.

In some embodiments, the one or more loci used to determine the tumor fraction are on a reference chromosome or chromosomes segment, such as a chromosome or chromosome segment known or expected to be disomic, a chromosome or chromosome segment that is rarely duplicated or deleted in cancer cells in general or in a particular type of cancer that an individual is known to have or is at increased risk of having, or a chromosome or chromosome segment that is unlikely to be aneuploid (such segment that is expected to lead to cell death if deleted or duplicated). In some embodiments, any of the methods of the invention are used to confirm that the reference chromosome or chromosome segment is disomic in both the cancer cells and noncancerous cells. In some embodiments, one or more chromosomes or chromosomes segments for which the confidence for a disomy call is high are used.

Exemplary loci that can be used to determine the tumor fraction include polymorphisms or mutations (such as SNPs) in a cancer cell (or DNA or RNA such as cfDNA or cfRNA from a cancer cell) that aren't present in a noncancerous cell (or DNA or RNA from a noncancerous cell) in the individual. In some embodiments, the tumor fraction is determined by identifying those polymorphic loci where a cancer cell (or DNA or RNA from a cancer cell) has an allele that is absent in noncancerous cells (or DNA or RNA from a noncancerous cell) in a sample (such as a plasma sample or tumor biopsy) from an individual; and using the amount of the allele unique to the cancer cell at one or more of the identified polymorphic loci to determine the tumor fraction in the sample. In some embodiments, a noncancerous cell is homozygous for a first allele at the polymorphic locus, and a cancer cell is (i) heterozygous for the first allele and a second allele or (ii) homozygous for a second allele at the polymorphic locus. In some embodiments, a noncancerous cell is heterozygous for a first allele and a second allele at the polymorphic locus, and a cancer cell is (i) has one or two copies of a third allele at the polymorphic locus. In some embodiments, the cancer cells are assumed or known to only have one copy of the allele that is not present in the noncancerous cells. For example, if the genotype of the noncancerous cells is AA and the cancer cells is AB and 5% of the signal at that locus in a sample is from the B allele and 95% is from the A allele, then the tumor fraction of the sample is 10%. In some embodiments, the cancer cells are assumed or known to have two copies of the allele that is not present in the noncancerous cells. For example, if the genotype of the noncancerous cells is AA and the cancer cells is BB and 5% of the signal at that locus in a sample is from the B allele and 95% is from the A allele, the tumor fraction of the sample is 5%. In some embodiments, multiple loci for which the cancer cells have an allele not in the noncancerous cells are analyzed to determine which of the loci in the cancer cells are heterozygous and which are homozygous. For example for loci in which the noncancerous cells are AA, if the signal from the B allele is ~5% at some loci and ~10% at some loci, then the cancer cells are assumed to be heterozygous at loci with ~5% B allele, and homozygous at loci with ~10% B allele (indicating the tumor fraction is ~10%).

Exemplary loci that can be used to determine the tumor fraction include loci for which a cancer cell and noncancerous cell have one allele in common (such as loci in which the cancer cell is AB and the noncancerous cell is BB, or the cancer cell is BB and the noncancerous cell is AB). The amount of A signal, the amount of B signal, or the ratio of A to B signal in a mixed sample (containing DNA or RNA from a cancer cell and a noncancerous cell) is compared to the corresponding value for (i) a sample containing DNA or RNA from only cancer cells or (ii) a sample containing DNA or RNA from only noncancerous cells. The difference in values is used to determine the tumor fraction of the mixed sample.

In some embodiments, loci that can be used to determine the tumor fraction are selected based on the genotype of (i) a sample containing DNA or RNA from only cancer cells, and/or (ii) a sample containing DNA or RNA from only noncancerous cells. In some embodiments, the loci are selected based on analysis of the mixed sample, such as loci for which the absolute or relative amounts of each allele differs from what would be expected if both the cancer and noncancerous cells have the same genotype at a particular locus. For example, if the cancer and noncancerous cells have the same genotype, the loci would be expected to produce 0% B signal if all the cells are AA, 50% B signal if all the cells are AB, or 100% B signal if all the cells are BB. Other values for the B signal indicate that the genotype of the cancer and noncancerous cells are different at that locus and thus that locus can be used to determine the tumor fraction.

In some embodiments, the tumor fraction calculated based on the alleles at one or more loci is compared to the tumor fraction calculated using one or more of the counting methods disclosed herein.

Exemplary Methods for Detecting a Phenotype or Analyzing Multiple Mutations

In some embodiments, the method includes analyzing a sample for a set of mutations associated with a disease or disorder (such as cancer) or an increased risk for a disease or disorder. There are strong correlations between events within classes (such as M or C cancer classes) which can be used to improve the signal to noise ratio of a method and classify tumors into distinct clinical subsets. For example, borderline results for a few mutations (such as a few CNVs) on one or more chromosomes or chromosomes segments considered jointly may be a very strong signal. In some embodiments, determining the presence or absence of multiple polymorphisms or mutations of interest (such as 2, 3, 4, 5, 8, 10, 12, 15, or more) increases the sensitivity and/or specificity of the determination of the presence or absence of a disease or disorder such as cancer, or an increased risk for with a disease or disorder such as cancer. In some embodiments, the correlation between events across multiple chromosomes is used to more powerfully look at a signal compared to looking at each of them individually. The design of the method itself can be optimized to best categorize tumors. This may be incredibly useful for early detection and screening—vis-a-vis recurrence where sensitivity to one particular mutation/CNV may be paramount. In some embodiments, the events are not always correlated but have a probability of being correlated. In some embodiments, a matrix estimation formulation with a noise covariance matrix that has off diagonal terms is used.

In some embodiments, the invention features a method for detecting a phenotype (such as a cancer phenotype) in an individual, wherein the phenotype is defined by the presence of at least one of a set of mutations. In some embodiments, the method includes obtaining DNA or RNA measurements for a sample of DNA or RNA from one or more cells from the individual, wherein one or more of the cells is suspected of having the phenotype; and analyzing the DNA or RNA measurements to determine, for each of the mutations in the set of mutations, the likelihood that at least one of the cells has that mutation. In some embodiments, the method includes determining that the individual has the phenotype if either (i) for at least one of the mutations, the likelihood that at least one of the cells contains that mutations is greater than a threshold, or (ii) for at least one of the mutations, the likelihood that at least one of the cells has that mutations is less than the threshold, and for a plurality of the mutations, the combined likelihood that at least one of the cells has at least one of the mutations is greater than the threshold. In some embodiments, one or more cells have a subset or all of the mutations in the set of mutations. In some embodiments, the subset of mutations is associated with cancer or an increased risk for cancer. In some embodiments, the set of mutations includes a subset or all of the mutations in the M class of cancer mutations (Ciriello, Nat Genet. 45 (10): 1127-1133, 2013, doi: 10.1038/ng.2762, which is hereby incorporated by reference in its entirety). In some embodiments, the set of mutations includes a subset or all of the mutations in the C class of cancer mutations (Ciriello, supra). In some embodiments, the sample includes cell-free DNA or RNA. In some embodiments, the DNA or RNA measurements include measurements (such as the quantity of each allele at each locus) at a set of polymorphic loci on one or more chromosomes or chromosome segments of interest.

Exemplary Methods for Paternity Testing or Genetic Relatedness Testing

The methods of the invention can be used to improve the accuracy of paternity testing or other genetic relatedness testing (see, e.g., U.S. Publication No. 2012/0122701, filed Dec. 22, 2011, which is hereby incorporated by reference in its entirety). For example, the multiplex PCR method can allow thousands of polymorphic loci (such as SNPs) to be analyzed for use in the PARENTAL SUPPORT algorithm described herein to determine whether an alleged father in is the biological father of a fetus. In some embodiments, the invention features a method for establishing whether an alleged father is the biological father of a fetus that is gestating in a pregnant mother. In some embodiments, the method involves obtaining phased genetic data for the alleged father (such as by using another of the methods described herein for phasing genetic data), wherein the phased genetic data comprises the identity of the allele present for each locus in a set of polymorphic loci on a first homologous chromosome segment and a second homologous chromosome segment in the alleged father. In some embodiments, the method involves obtaining genetic data at the set of polymorphic loci on the chromosome or chromosome segment in a mixed sample of DNA comprising fetal DNA and maternal DNA from the mother of the fetus by measuring the quantity of each allele at each locus. In some embodiments, the method involves calculating, on a computer, expected genetic data for the mixed sample of DNA from the phased genetic data for the alleged father; determining, on a computer, the probability that the alleged father is the biological father of the fetus by comparing the obtaining genetic data made on the mixed sample of DNA to the expected genetic data for the mixed sample of DNA; and establishing whether the alleged father is the biological father of the fetus using the determined probability that the alleged father is the biological father of the fetus. In some embodiments, the method involves obtaining phased genetic data for the biological mother of the fetus (such as by using another of the methods described herein for phasing genetic data), wherein the phased genetic data comprises the identity of the allele present for each locus in a set of polymorphic loci on a first homologous chromosome segment and a second homologous chromosome segment in the mother. In some embodiments, the method involves obtaining phased genetic data for the fetus (such as by using another of the methods described herein for phasing genetic data), wherein the phased genetic data comprises the identity of the allele present for each locus in a set of polymorphic loci on a first homologous chromosome segment and a second homologous chromosome segment in the fetus. In some embodiments, the method involves calculating, on a computer, expected genetic data for the mixed sample of DNA using the phased genetic data for the alleged father and using the phased genetic data for the mother and/or the phased genetic data for the fetus.

In some embodiments, the invention features a method for establishing whether an alleged father is the biological father of a fetus that is gestating in a pregnant mother. In some embodiments, the method involves obtaining phased genetic data for the alleged father (such as by using another of the methods described herein for phasing genetic data), wherein the phased genetic data comprises the identity of the allele present for each locus in a set of polymorphic loci on a first homologous chromosome segment and a second homologous chromosome segment in the alleged father. In some embodiments, the method involves obtaining genetic data at the set of polymorphic loci on the chromosome or chromosome segment in a mixed sample of DNA comprising fetal DNA and maternal DNA from the mother of the fetus by measuring the quantity of each allele at each locus. In some embodiments, the method involves identifying (i) alleles that are present in the fetal DNA but are absent in the maternal DNA at polymorphic loci, and/or identifying (i) alleles that are absent in the fetal DNA and the maternal DNA at polymorphic loci. In some embodiments, the method involves determining, on a computer, the probability that the alleged father is the biological father of the fetus; wherein the determination comprises: (1) comparing (i) the alleles that are present in the fetal DNA but are absent in the maternal DNA at polymorphic loci to (ii) the alleles at the corresponding polymorphic loci in the genetic material from the alleged father, and/or (2) comparing (i) the alleles that are absent in the fetal DNA and the maternal DNA at polymorphic loci to (ii) the alleles at the corresponding polymorphic loci in the genetic material from the alleged father; and establishing whether the alleged father is the biological father of the fetus using the determined probability that the alleged father is the biological father of the fetus.

In some embodiments, a method described above for determining whether an alleged father is the biological father of the fetus is used to determine if an alleged relative (such as a grandparent, sibling, aunt, or uncle) of a fetus is an actual biological relative of the fetus (such as by using genetic data of the alleged relative instead of genetic data of the alleged father).

Exemplary Combinations of Methods

To increase the accuracy of the results, two or more methods (such as any of the methods of the invention or any known method) for detecting the presence or absence of a CNV are performed. In some embodiments, one or more methods for analyzing a factor (such as any of the method described herein or any known method) indicative of the presence or absence of a disease or disorder or an increased risk for a disease or disorder are performed.

In some embodiments, standard mathematical techniques are used to calculate the covariance and/or correlation between two or more methods. Standard mathematical techniques may also be used to determine the combined probability of a particular hypothesis based on two or more tests. Exemplary techniques include meta-analysis, Fisher's combined probability test for independent tests, Brown's method for combining dependent p-values with known covariance, and Kost's method for combining dependent p-values with unknown covariance. In cases where the likelihoods are determined by a first method in a way that is orthogonal, or unrelated, to the way in which a likelihood is determined for a second method, combining the likelihoods is straightforward and can be done by multiplication and normalization, or by using a formula such as:

$$R_{comb} = R_1 R_2 / [R_1 R_2 + (1 - R_1)(1 - R_2)]$$

$R_{comb}$ is the combined likelihood, and $R_i$ and $R_2$ are the individual likelihoods. For example, if the likelihood of trisomy from method 1 is 90%, and the likelihood of trisomy from method 2 is 95%, then combining the outputs from the two methods allows the clinician to conclude that the fetus is trisomic with a likelihood of (0.90)(0.95)/[(0.90)(0.95)+(1-0.90)(1-0.95)}=99.42%. In cases where the first and the second methods are not orthogonal, that is, where there is a correlation between the two methods, the likelihoods can still be combined.

Exemplary methods of analyzing multiple factors or variables are disclosed in U.S. Pat. No. 8,024,128 issued on Sep. 20, 2011; U.S. Publication No. 2007/0027636, filed Jul. 31, 2006; and U.S. Publication No. 2007/0178501, filed Dec. 6, 2006, which are each hereby incorporated by reference in its entirety).

In various embodiments, the combined probability of a particular hypothesis or diagnosis is greater than 80, 85, 90, 92, 94, 96, 98, 99, or 99.9%, or is greater than some other threshold value.

Limit of Detection

In some embodiments, a limit of detection of a mutation (such as an SNV or CNV) of a method of the invention is less than or equal to 10, 5, 2, 1, 0.5, 0.1, 0.05, 0.01, or 0.005%. In some embodiments, a limit of detection of a mutation (such as an SNV or CNV) of a method of the invention is between 15 to 0.005%, such as between 10 to 0.005%, 10 to 0.01%, 10 to 0.1%, 5 to 0.005%, 5 to 0.01%, 5 to 0.1%, 1 to 0.005%, 1 to 0.01%, 1 to 0.1%, 0.5 to 0.005%, 0.5 to 0.01%, 0.5 to 0.1%, or 0.1 to 0.01, inclusive. In some embodiments, a limit of detection is such that a mutation (such as an SNV or CNV) that is present in less than or equal to 10, 5, 2, 1, 0.5, 0.1, 0.05, 0.01, or 0.005% of the DNA or RNA molecules with that locus in a sample (such as a sample of cfDNA or cfRNA) is detected (or is capable of being detected). For example, the mutation can be detected even if less than or equal to 10, 5, 2, 1, 0.5, 0.1, 0.05, 0.01, or 0.005% of the DNA or RNA molecules that have that locus have that mutation in the locus (instead of, for example, a wild-type or non-mutated version of the locus or a different mutation at that locus). In some embodiments, a limit of detection is such that a mutation (such as an SNV or CNV) that is present in less than or equal to 10, 5, 2, 1, 0.5, 0.1, 0.05, 0.01, or 0.005% of the DNA or RNA molecules in a sample (such as a sample of cfDNA or cfRNA) is detected (or is capable of being detected). In some embodiments in which the CNV is a deletion, the deletion can be detected even if it is only present in less than or equal to 10, 5, 2, 1, 0.5, 0.1, 0.05, 0.01, or 0.005% of the DNA or RNA molecules that have a region of interest that may or may not contain the deletion in a sample. In some embodiments in which the CNV is a deletion, the deletion can be detected even if it is only present in less than or equal to 10, 5, 2, 1, 0.5, 0.1, 0.05, 0.01, or 0.005% of the DNA or RNA molecules in a sample. In some embodiments in which the CNV is a duplication, the duplication can be detected even if the extra duplicated DNA or RNA that is present is less than or equal to 10, 5, 2, 1, 0.5, 0.1, 0.05, 0.01, or 0.005% of the DNA or RNA molecules that have a region of interest that may or may not be duplicated in a sample in a sample. In some embodiments in which the CNV is a duplication, the duplication can be detected even if the extra duplicated DNA or RNA that is present is less than or equal to 10, 5, 2, 1, 0.5, 0.1, 0.05, 0.01, or 0.005% of the DNA or RNA molecules in a sample. Example 6 provides exemplary methods for calculating the limit of detection. In some embodiments, the "LOD-zs5.0-mr5" method of Example 6 is used.

Exemplary Samples

In some embodiments of any of the aspects of the invention, the sample includes cellular and/or extracellular genetic material from cells suspected of having a deletion or duplication, such as cells suspected of being cancerous. In some embodiments, the sample comprises any tissue or bodily fluid suspected of containing cells, DNA, or RNA having a deletion or duplication, such as cancer cells, DNA, or RNA. The genetic measurements used as part of these methods can be made on any sample comprising DNA or RNA, for example but not limited to, tissue, blood, serum, plasma, urine, hair, tears, saliva, skin, fingernails, feces, bile, lymph, cervical mucus, semen, or other cells or materials comprising nucleic acids. Samples may include any cell type or DNA or RNA from any cell type may be used (such as cells from any organ or tissue suspected of being cancerous, or neurons). In some embodiments, the sample includes nuclear and/or mitochondrial DNA. In some embodiments, the sample is from any of the target individuals disclosed herein. In some embodiments, the target individual is a born individual, a gestating fetus, a non-gestating fetus such as a products of conception sample, an embryo, or any other individual.

Exemplary samples include those containing cfDNA or cfRNA. In some embodiments, cfDNA is available for analysis without requiring the step of lysing cells. Cell-free DNA may be obtained from a variety of tissues, such as tissues that are in liquid form, e.g., blood, plasma, lymph, ascites fluid, or cerebral spinal fluid. In some cases, cfDNA is comprised of DNA derived from fetal cells. In some cases, cfDNA is comprised of DNA derived from both fetal and maternal cells. In some cases, the cfDNA is isolated from plasma that has been isolated from whole blood that has been centrifuged to remove cellular material. The cfDNA may be a mixture of DNA derived from target cells (such as cancer cells) and non-target cells (such as non-cancer cells).

In some embodiments, the sample contains or is suspected to contain a mixture of DNA (or RNA), such as mixture of cancer DNA (or RNA) and noncancerous DNA (or RNA). In some embodiments, at least 0.5, 1, 3, 5, 7, 10, 15, 20, 30, 40, 50, 60, 70, 80, 90, 92, 94, 95, 96, 98, 99, or 100% of the cells in the sample are cancer cells. In some embodiments, at least 0.5, 1, 3, 5, 7, 10, 15, 20, 30, 40, 50, 60, 70, 80, 90, 92, 94, 95, 96, 98, 99, or 100% of the DNA (such as cfDNA) or RNA (such as cfRNA) in the sample is from cancer cell(s). In various embodiments, the percent of cells in the sample that are cancerous cells is between 0.5 to 99%, such as between 1 to 95%, 5 to 95%, 10 to 90%, 5 to 70%, 10 to 70%, 20 to 90%, or 20 to 70%, inclusive. In some embodiments, the sample is enriched for cancer cells or for DNA or RNA from cancer cells. In some embodiments in which the sample is enriched for cancer cells, at least 0.5, 1, 2, 3, 4, 5, 6, 7, 10, 15, 20, 30, 40, 50, 60, 70, 80, 90, 92, 94, 95, 96, 98, 99, or 100% of the cells in the enriched sample are cancer cells. In some embodiments in which the sample is enriched for DNA or RNA from cancer cells, at least 0.5, 1, 2, 3, 4, 5, 6, 7, 10, 15, 20, 30, 40, 50, 60, 70, 80, 90, 92, 94, 95, 96, 98, 99, or 100% of the DNA or RNA in the enriched sample is from cancer cell(s). In some embodiments, cell sorting (such as Fluorescent Activated Cell Sorting (FACS)) is used to enrich for cancer cells (Barteneva et. al., Biochim Biophys Acta., 1836 (1): 105-22, August 2013. doi: 10.1016/j.bbcan.2013.02.004. Epub 2013 Feb. 24, and Ibrahim et al., Adv Biochem Eng Biotechnol. 106:19-39, 2007, which are each hereby incorporated by reference in its entirety).

In some embodiments of any of the aspects of the invention, the sample comprises any tissue suspected of being at least partially of fetal origin. In some embodiments, the sample includes cellular and/or extracellular genetic material from the fetus, contaminating cellular and/or extracellular genetic material (such as genetic material from the mother of the fetus), or combinations thereof. In some embodiments, the sample comprises cellular genetic material from the fetus, contaminating cellular genetic material, or combinations thereof.

In some embodiments, the sample is from a gestating fetus. In some embodiments, the sample is from a non-gestating fetus, such as a products of conception sample or a sample from any fetal tissue after fetal demise. In some embodiments, the sample is a maternal whole blood sample, cells isolated from a maternal blood sample, maternal plasma sample, maternal serum sample, amniocentesis sample, placental tissue sample (e.g., chorionic villus, decidua, or placental membrane), cervical mucus sample, or other sample from a fetus. In some embodiments, at least 3, 5, 7, 10, 15, 20, 30, 40, 50, 60, 70, 80, 90, 92, 94, 95, 96, 98, 99, or 100% of the cells in the sample are maternal cells. In various embodiments, the percent of cells in the sample that are maternal cells is between 5 to 99%, such as between 10 to 95%, 20 to 95%, 30 to 90%, 30 to 70%, 40 to 90%, 40 to 70%, 50 to 90%, or 50 to 80%, inclusive.

In some embodiments, the sample is enriched for fetal cells. In some embodiments in which the sample is enriched for fetal cells, at least 0.5, 1, 2, 3, 4, 5, 6, 7% or more of the cells in the enriched sample are fetal cells. In some embodiments, the percent of cells in the sample that are fetal cells is between 0.5 to 100%, such as between 1 to 99%, 5 to 95%, 10 to 95%, 10 to 95%, 20 to 90%, or 30 to 70%, inclusive. In some embodiments, the sample is enriched for fetal DNA. In some embodiments in which the sample is enriched for fetal DNA, at least 0.5, 1, 2, 3, 4, 5, 6, 7% or more of the DNA in the enriched sample is fetal DNA. In some embodiments, the percent of DNA in the sample that is fetal DNA is between 0.5 to 100%, such as between 1 to 99%, 5 to 95%, 10 to 95%, 10 to 95%, 20 to 90%, or 30 to 70%, inclusive.

In some embodiments, the sample includes a single cell or includes DNA and/or RNA from a single cell. In some embodiments, multiple individual cells (e.g., at least 5, 10, 20, 30, 40, or 50 cells from the same subject or from different subjects) are analyzed in parallel. In some embodiments, cells from multiple samples from the same individual are combined, which reduces the amount of work compared to analyzing the samples separately. Combining multiple samples can also allow multiple tissues to be tested for cancer simultaneously (which can be used to provide or more thorough screening for cancer or to determine whether cancer may have metastasized to other tissues).

In some embodiments, the sample contains a single cell or a small number of cells, such as 2, 3, 5, 6, 7, 8, 9, or 10 cells. In some embodiments, the sample has between 1 to 100, 100 to 500, or 500 to 1,000 cells, inclusive. In some embodiments, the sample contains 1 to 10 picograms, 10 to 100 picograms, 100 picograms to 1 nanogram, 1 to 10 nanograms, 10 to 100 nanograms, or 100 nanograms to 1 microgram of RNA and/or DNA, inclusive.

In some embodiments, the sample is embedded in parafilm. In some embodiments, the sample is preserved with a preservative such as formaldehyde and optionally encased in paraffin, which may cause cross-linking of the DNA such that less of it is available for PCR. In some embodiments, the sample is a formaldehyde fixed-paraffin embedded (FFPE) sample. In some embodiments, the sample is a fresh sample (such as a sample obtained with 1 or 2 days of analysis). In some embodiments, the sample is frozen prior to analysis. In some embodiments, the sample is a historical sample.

These samples can be used in any of the methods of the invention.

Exemplary Sample Preparation Methods

In some embodiments, the method includes isolating or purifying the DNA and/or RNA. There are a number of standard procedures known in the art to accomplish such an end. In some embodiments, the sample may be centrifuged to separate various layers. In some embodiments, the DNA or RNA may be isolated using filtration. In some embodiments, the preparation of the DNA or RNA may involve amplification, separation, purification by chromatography, liquid liquid separation, isolation, preferential enrichment, preferential amplification, targeted amplification, or any of a number of other techniques either known in the art or described herein. In some embodiments for the isolation of DNA, RNase is used to degrade RNA. In some embodiments for the isolation of RNA, DNase (such as DNase I from Invitrogen, Carlsbad, CA, USA) is used to degrade DNA. In some embodiments, an RNeasy mini kit (Qiagen), is used to isolate RNA according to the manufacturer's protocol. In some embodiments, small RNA molecules are isolated using the mirVana PARIS kit (Ambion, Austin, TX, USA) according to the manufacturer's protocol (Gu et al., J. Neurochem. 122:641-649, 2012,, which is hereby incorporated by reference in its entirety). The concentration and purity of RNA may optionally be determined using Nanovue (GE Healthcare, Piscataway, NJ, USA), and RNA integrity may optionally be measured by use of the 2100 Bioanalyzer (Agilent Technologies, Santa Clara, CA, USA) (Gu et al., J. Neurochem. 122:641-649, 2012,, which is hereby incorporated by reference in its entirety). In some embodiments, TRIZOL or RNAlater (Ambion) is used to stabilize RNA during storage.

In some embodiments, universal tagged adaptors are added to make a library. Prior to ligation, sample DNA may be blunt ended, and then a single adenosine base is added to the 3-prime end. Prior to ligation the DNA may be cleaved using a restriction enzyme or some other cleavage method. During ligation the 3-prime adenosine of the sample fragments and the complementary 3-prime tyrosine overhang of adaptor can enhance ligation efficiency. In some embodiments, adaptor ligation is performed using the ligation kit found in the AGILENT SURESELECT kit. In some embodiments, the library is amplified using universal primers. In an embodiment, the amplified library is fractionated by size separation or by using products such as AGENCOURT AMPURE beads or other similar methods. In some embodiments, PCR amplification is used to amplify target loci. In some embodiments, the amplified DNA is sequenced (such as sequencing using an ILLUMINA IIGAX or HiSeq sequencer). In some embodiments, the amplified DNA is sequenced from each end of the amplified DNA to reduce sequencing errors. If there is a sequence error in a particular base when sequencing from one end of the amplified DNA, there is less likely to be a sequence error in the complementary base when sequencing from the other side of the amplified DNA (compared to sequencing multiple times from the same end of the amplified DNA).

In some embodiments, whole genome application (WGA) is used to amplify a nucleic acid sample. There are a number of methods available for WGA: ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. MDA uses the phi-29 polymerase, which is a highly processive and non-specific enzyme that replicates DNA and has been used for single-cell analysis. In some embodiments, WGA is not performed.

In some embodiments, selective amplification or enrichment are used to amplify or enrich target loci. In some embodiments, the amplification and/or selective enrichment technique may involve PCR such as ligation mediated PCR, fragment capture by hybridization, Molecular Inversion Probes, or other circularizing probes. In some embodiments, real-time quantitative PCR (RT-qPCR), digital PCR, or emulsion PCR, single allele base extension reaction followed by mass spectrometry are used (Hung et al., J Clin Pathol 62:308-313, 2009, which is hereby incorporated by reference in its entirety). In some embodiments, capture by hybridization with hybrid capture probes is used to preferentially enrich the DNA. In some embodiments, methods for amplification or selective enrichment may involve using probes where, upon correct hybridization to the target sequence, the 3-prime end or 5-prime end of a nucleotide probe is separated from the polymorphic site of a polymorphic allele by a small number of nucleotides. This separation reduces preferential amplification of one allele, termed allele bias. This is an improvement over methods that involve using probes where the 3-prime end or 5-prime end of a correctly hybridized probe are directly adjacent to or very near to the polymorphic site of an allele. In an embodiment, probes in which the hybridizing region may or certainly contains a polymorphic site are excluded. Polymorphic sites at the site of hybridization can cause unequal hybridization or inhibit hybridization altogether in some alleles, resulting in preferential amplification of certain alleles. These embodiments are improvements over other methods that involve targeted amplification and/or selective enrichment in that they better preserve the original allele frequencies of the sample at each polymorphic locus, whether the sample is pure genomic sample from a single individual or mixture of individuals In some embodiments, PCR (referred to as mini-PCR) is used to generate very short amplicons (U.S. application Ser. No. 13/683,604, filed Nov. 21, 2012, U.S. Publication No. 2013/0123120, U.S. application Ser. No. 13/300,235, filed Nov. 18, 2011, U.S. Publication No 2012/0270212, filed Nov. 18, 2011, and U.S. Ser. No. 61/994,791, filed May 16, 2014, which are each hereby incorporated by reference in its entirety). cfDNA (such as fetal cfDNA in maternal serum or necroptically-or apoptotically-released cancer cfDNA) is highly fragmented. For fetal cfDNA, the fragment sizes are distributed in approximately a Gaussian fashion with a mean of 160 bp, a standard deviation of 15 bp, a minimum size of about 100 bp, and a maximum size of about 220 bp. The polymorphic site of one particular target locus may occupy any position from the start to the end among the various fragments originating from that locus. Because cfDNA fragments are short, the likelihood of both primer sites being present the likelihood of a fragment of length L comprising both the forward and reverse primers sites is the ratio of the length of the amplicon to the length of the fragment. Under ideal conditions, assays in which the amplicon is 45, 50, 55, 60, 65, or 70 bp will successfully amplify from 72%, 69%, 66%, 63%, 59%, or 56%, respectively, of available template fragment molecules. In certain embodiments that relate most preferably to cfDNA from samples of individuals suspected of having cancer, the cfDNA is amplified using primers that yield a maximum amplicon length of 85, 80, 75 or 70 bp, and in certain preferred embodiments 75 bp, and that have a melting temperature between 5° and 65° C., and in certain preferred embodiments, between 54-60.5° C. The amplicon length is the distance between the 5-prime ends of the forward and reverse priming sites. Amplicon length that is shorter than typically used by those known in the art may result in more efficient measurements of the desired polymorphic loci by only requiring short sequence reads. In an embodiment, a substantial fraction of the amplicons are less than 100 bp, less than 90 bp, less than 80 bp, less than 70 bp, less than 65 bp, less than 60 bp, less than 55 bp, less than 50 bp, or less than 45 bp.

In some embodiments, amplification is performed using direct multiplexed PCR, sequential PCR, nested PCR, doubly nested PCR, one-and-a-half sided nested PCR, fully nested PCR, one sided fully nested PCR, one-sided nested PCR, hemi-nested PCR, hemi-nested PCR, triply hemi-nested PCR, semi-nested PCR, one sided semi-nested PCR, reverse semi-nested PCR method, or one-sided PCR, which are described in U.S. application Ser. No. 13/683,604, filed Nov. 21, 2012, U.S. Publication No. 2013/0123120, U.S. application Ser. No. 13/300,235, filed Nov. 18, 2011, U.S. Publication No 2012/0270212, and U.S. Ser. No. 61/994,791, filed May 16, 2014, which are hereby incorporated by reference in their entirety. If desired, any of these methods can be used for mini-PCR.

If desired, the extension step of the PCR amplification may be limited from a time standpoint to reduce amplification from fragments longer than 200 nucleotides, 300 nucleotides, 400 nucleotides, 500 nucleotides or 1,000 nucleotides. This may result in the enrichment of fragmented or shorter DNA (such as fetal DNA or DNA from cancer cells that have undergone apoptosis or necrosis) and improvement of test performance.

In some embodiments, multiplex PCR is used. In some embodiments, the method of amplifying target loci in a nucleic acid sample involves (i) contacting the nucleic acid sample with a library of primers that simultaneously hybridize to least 100; 200; 500; 750; 1,000; 2,000; 5,000; 7,500; 10,000; 20,000; 25,000; 30,000; 40,000; 50,000; 75,000; or 100,000 different target loci to produce a reaction mixture; and (ii) subjecting the reaction mixture to primer extension reaction conditions (such as PCR conditions) to produce amplified products that include target amplicons. In some embodiments, at least 50, 60, 70, 80, 90, 95, 96, 97, 98, 99, or 99.5% of the targeted loci are amplified. In various embodiments, less than 60, 50, 40, 30, 20, 10, 5, 4, 3, 2, 1, 0.5, 0.25, 0.1, or 0.05% of the amplified products are primer dimers. In some embodiments, the primers are in solution (such as being dissolved in the liquid phase rather than in a solid phase). In some embodiments, the primers are in solution and are not immobilized on a solid support. In some embodiments, the primers are not part of a microarray. In some embodiments, the primers do not include molecular inversion probes (MIPs).

In some embodiments, two or more (such as 3 or 4) target amplicons (such as amplicons from the miniPCR method disclosed herein) are ligated together and then the ligated products are sequenced. Combining multiple amplicons into a single ligation product increases the efficiency of the subsequent sequencing step. In some embodiments, the target amplicons are less than 150, 100, 90, 75, or 50 base pairs in length before they are ligated. The selective enrichment and/or amplification may involve tagging each individual molecule with different tags, molecular barcodes, tags for amplification, and/or tags for sequencing. In some embodiments, the amplified products are analyzed by sequencing (such as by high throughput sequencing) or by hybridization to an array, such as a SNP array, the ILLUMINA INFINIUM array, or the AFFYMETRIX gene chip. In some embodiments, nanopore sequencing is used, such as the nanopore sequencing technology developed by Genia (see, for example, the world wide web at geniachip.com/technology, which is hereby incorporated by reference in its entirety). In some embodiments, duplex sequencing is used (Schmitt et al., "Detection of ultra-rare mutations by next-generation sequencing," Proc Natl Acad Sci USA. 109 (36): 14508-14513, 2012, which is hereby incorporated by reference in its entirety). This approach greatly reduces errors by independently tagging and sequencing each of the two strands of a DNA duplex. As the two strands are complementary, true mutations are found at the same position in both strands. In contrast, PCR or sequencing errors result in mutations in only one strand and can thus be discounted as technical error. In some embodiments, the method entails tagging both strands of duplex DNA with a random, yet complementary double-stranded nucleotide sequence, referred to as a Duplex Tag. Double-stranded tag sequences are incorporated into standard sequencing adapters by first introducing a single-stranded randomized nucleotide sequence into one adapter strand and then extending the opposite strand with a DNA polymerase to yield a complementary, double-stranded tag. Following ligation of tagged adapters to sheared DNA, the individually labeled strands are PCR amplified from asymmetric primer sites on the adapter tails and subjected to paired-end sequencing. In some embodiments, a sample (such as a DNA or RNA sample) is divided into multiple fractions, such as different wells (e.g., wells of a WaferGen SmartChip). Dividing the sample into different fractions (such as at least 5, 10, 20, 50, 75, 100, 150, 200, or 300 fractions) can increase the sensitivity of the analysis since the percent of molecules with a mutation are higher in some of the wells than in the overall sample. In some embodiments, each fraction has less than 500, 400, 200, 100, 50, 20, 10, 5, 2, or 1 DNA or RNA molecules. In some embodiments, the molecules in each fraction are sequenced separately. In some embodiments, the same barcode (such as a random or non-human sequence) is added to all the molecules in the same fraction (such as by amplification with a primer containing the barcode or by ligation of a barcode), and different barcodes are added to molecules in different fractions. The barcoded molecules can be pooled and sequenced together. In some embodiments, the molecules are amplified before they are pooled and sequenced, such as by using nested PCR. In some embodiments, one forward and two reverse primers, or two forward and one reverse primers are used.

In some embodiments, a mutation (such as an SNV or CNV) that is present in less than 10, 5, 2, 1, 0.5, 0.1, 0.05, 0.01, or 0.005% of the DNA or RNA molecules in a sample (such as a sample of cfDNA or cfRNA) is detected (or is capable of being detected). In some embodiments, a mutation (such as an SNV or CNV) that is present in less than 1,000, 500, 100, 50, 20, 10, 5, 4, 3, or 2 original DNA or RNA molecules (before amplification) in a sample (such as a sample of cfDNA or cfRNA from, e.g., a blood sample) is detected (or is capable of being detected). In some embodiments, a mutation (such as an SNV or CNV) that is present in only 1 original DNA or RNA molecule (before amplification) in a sample (such as a sample of cfDNA or cfRNA from, e.g., a blood sample) is detected (or is capable of being detected).

For example, if the limit of detection of a mutation (such as a single nucleotide variant (SNV)) is 0.1%, a mutation present at 0.01% can be detected by dividing the fraction into multiple, fractions such as 100 wells. Most of the wells have no copies of the mutation. For the few wells with the mutation, the mutation is at a much higher percentage of the reads. In one example, there are 20,000 initial copies of DNA from the target locus, and two of those copies include a SNV of interest. If the sample is divided into 100 wells, 98 wells have the SNV, and 2 wells have the SNV at 0.5%. The DNA in each well can be barcoded, amplified, pooled with DNA from the other wells, and sequenced. Wells without the SNV can be used to measure the background amplification/sequencing error rate to determine if the signal from the outlier wells is above the background level of noise.

In some embodiments, the amplified products are detected using an array, such as an array especially a microarray with probes to one or more chromosomes of interest (e.g., chromosome 13, 18, 21, X, Y, or any combination thereof). It will be understood for example, that a commercially available SNP detection microarray could be used such as, for example, the Illumina (San Diego, CA) GoldenGate, DASL, Infinium, or CytoSNP-12 genotyping assay, or a SNP detection microarray product from Affymetrix, such as the OncoScan microarray. In some embodiments, phased genetic data for one or both biological parents of the embryo or fetus is used to increase the accuracy of analysis of array data from a single cell.

In some embodiments involving sequencing, the depth of read is the number of sequencing reads that map to a given locus. The depth of read may be normalized over the total number of reads. In some embodiments for depth of read of a sample, the depth of read is the average depth of read over the targeted loci. In some embodiments for the depth of read of a locus, the depth of read is the number of reads measured by the sequencer mapping to that locus. In general, the greater the depth of read of a locus, the closer the ratio of alleles at the locus tend to be to the ratio of alleles in the original sample of DNA. Depth of read can be expressed in variety of different ways, including but not limited to the percentage or proportion. Thus, for example in a highly parallel DNA sequencer such as an Illumina HISEQ, which, e.g., produces a sequence of 1 million clones, the sequencing of one locus 3,000 times results in a depth of read of 3,000 reads at that locus. The proportion of reads at that locus is 3,000 divided by 1 million total reads, or 0.3% of the total reads.

In some embodiments, allelic data is obtained, wherein the allelic data includes quantitative measurement(s) indicative of the number of copies of a specific allele of a polymorphic locus. In some embodiments, the allelic data includes quantitative measurement(s) indicative of the number of copies of each of the alleles observed at a polymorphic locus. Typically, quantitative measurements are obtained for all possible alleles of the polymorphic locus of interest. For example, any of the methods discussed in the preceding paragraphs for determining the allele for a SNP or SNV locus, such as for example, microarrays, qPCR, DNA sequencing, such as high throughput DNA sequencing, can be used to generate quantitative measurements of the number of copies of a specific allele of a polymorphic locus. This quantitative measurement is referred to herein as allelic frequency data or measured genetic allelic data. Methods using allelic data are sometimes referred to as quantitative allelic methods; this is in contrast to quantitative methods which exclusively use quantitative data from non-polymorphic loci, or from polymorphic loci but without regard to allelic identity. When the allelic data is measured using high-throughput sequencing, the allelic data typically include the number of reads of each allele mapping to the locus of interest.

In some embodiments, non-allelic data is obtained, wherein the non-allelic data includes quantitative measurement(s) indicative of the number of copies of a specific locus. The locus may be polymorphic or non-polymorphic. In some embodiments when the locus is non-polymorphic, the non-allelic data does not contain information about the relative or absolute quantity of the individual alleles that may be present at that locus. Methods using non-allelic data only (that is, quantitative data from non-polymorphic alleles, or quantitative data from polymorphic loci but without regard to the allelic identity of each fragment) are referred to as quantitative methods. Typically, quantitative measurements are obtained for all possible alleles of the polymorphic locus of interest, with one value associated with the measured quantity for all of the alleles at that locus, in total. Non-allelic data for a polymorphic locus may be obtained by summing the quantitative allelic for each allele at that locus. When the allelic data is measured using high-throughput sequencing, the non-allelic data typically includes the number of reads of mapping to the locus of interest. The sequencing measurements could indicate the relative and/or absolute number of each of the alleles present at the locus, and the non-allelic data includes the sum of the reads, regardless of the allelic identity, mapping to the locus. In some embodiments the same set of sequencing measurements can be used to yield both allelic data and non-allelic data. In some embodiments, the allelic data is used as part of a method to determine copy number at a chromosome of interest, and the produced non-allelic data can be used as part of a different method to determine copy number at a chromosome of interest. In some embodiments, the two methods are statistically orthogonal, and are combined to give a more accurate determination of the copy number at the chromosome of interest.

In some embodiments obtaining genetic data includes (i) acquiring DNA sequence information by laboratory techniques, e.g., by the use of an automated high throughput DNA sequencer, or (ii) acquiring information that had been previously obtained by laboratory techniques, wherein the information is electronically transmitted, e.g., by a computer over the internet or by electronic transfer from the sequencing device.

Additional exemplary sample preparation, amplification, and quantification methods are described in U.S. application Ser. No. 13/683,604, filed Nov. 21, 2012 (U.S. Publication No. 2013/0123120 and U.S. Ser. No. 61/994,791, filed May 16, 2014, which is hereby incorporated by reference in its entirety). These methods can be used for analysis of any of the samples disclosed herein.

Exemplary Quantification Methods for Cell-free DNA

If desired, that amount or concentration of cfDNA or cfRNA can be measured using standard methods. In some embodiments, the amount or concentration of cell-free mitochondrial DNA (cf mDNA) is determined. In some embodiments, the amount or concentration of cell-free DNA that originated from nuclear DNA (cf nDNA) is determined. In some embodiments, the amount or concentration of cf mDNA and cf nDNA are determined simultaneously.

In some embodiments, qPCR is used to measure cf nDNA and/or cfm DNA (Kohler et al. "Levels of plasma circulating cell free nuclear and mitochondrial DNA as potential biomarkers for breast tumors." Mol Cancer 8:105, 2009, 8: doi: 10.1186/1476-4598-8-105, which is hereby incorporated by reference in its entirety). For example, one or more loci from cf nDNA (such as Glyceraldehyd-3-phosphat-dehydrogenase, GAPDH) and one or more loci from cf mDNA (ATPase 8, MTATP 8) can be measured using multiplex qPCR. In some embodiments, fluorescence-labelled PCR is used to measure cf nDNA and/or cf mDNA (Schwarzenbach et al., "Evaluation of cell-free tumour DNA and RNA in patients with breast cancer and benign breast disease." Mol Biosys 7:2848-2854, 2011, which is hereby incorporated by reference in its entirety). If desired, the normality distribution of the data can be determined using standard methods, such as the Shapiro-Wilk-Test. If desired, cf nDNA and mDNA levels can be compared using standard methods, such as the Mann-Whitney-U-Test. In some embodiments, cf nDNA and/or mDNA levels are compared with other established prognostic factors using standard methods, such as the Mann-Whitney-U-Test or the Kruskal-Wallis-Test.

Exemplary RNA Amplification, Quantification, and Analysis Methods

Any of the following exemplary methods may be used to amplify and optionally quantify RNA, such as such as cfRNA, cellular RNA, cytoplasmic RNA, coding cytoplasmic RNA, non-coding cytoplasmic RNA, mRNA, miRNA, mitochondrial RNA, IRNA, or tRNA. In some embodiments, the miRNA is any of the miRNA molecules listed in the miRBase database available at the world wide web at mirbase.org, which is hereby incorporated by reference in its entirety. Exemplary miRNA molecules include miR-509; miR-21, and miR-146a.

In some embodiments, reverse-transcriptase multiplex ligation-dependent probe amplification (RT-MLPA) is used to amplify RNA. In some embodiments, each set of hybridizing probes consists of two short synthetic oligonucleotides spanning the SNP and one long oligonucleotide (Li et al., Arch Gynecol Obstet. "Development of noninvasive prenatal diagnosis of trisomy 21 by RT-MLPA with a new set of SNP markers," Jul. 5, 2013, DOI 10.1007/s00404-013-2926-5;. Schouten et al. "Relative quantification of 40 nucleic acid sequences by multiplex ligation-dependent probe amplification." Nucleic Acids Res 30: e57, 2002; Deng et al. (2011) "Non-invasive prenatal diagnosis of trisomy 21 by reverse transcriptase multiplex ligation-dependent probe amplification," Clin, Chem. Lab Med. 49:641-646, 2011, which are each hereby incorporated by reference in its entirety).

In some embodiments, RNA is amplified with reverse-transcriptase PCR. In some embodiments, RNA is amplified with real-time reverse-transcriptase PCR, such as one-step real-time reverse-transcriptase PCR with SYBR GREEN I as previously described (Li et al., Arch Gynecol Obstet. "Development of noninvasive prenatal diagnosis of trisomy 21 by RT-MLPA with a new set of SNP markers," Jul. 5, 2013, DOI 10.1007/s00404-013-2926-5; Lo et al., "Plasma placental RNA allelic ratio permits noninvasive prenatal chromosomal aneuploidy detection," Nat Med 13:218-223, 2007; Tsui et al., Systematic micro-array based identification of placental mRNA in maternal plasma: towards non-invasive prenatal gene expression profiling. J Med Genet 41:461-467, 2004; Gu et al., J. Neurochem. 122:641-649, 2012, which are each hereby incorporated by reference in its entirety).

In some embodiments, a microarray is used to detect RNA. For example, a human miRNA microarray from Agilent Technologies can be used according to the manufacturer's protocol. Briefly, isolated RNA is dephosphorylated and ligated with pCp-Cy3. Labeled RNA is purified and hybridized to miRNA arrays containing probes for human mature miRNAs on the basis of Sanger miRBase release 14.0. The arrays is washed and scanned with use of a microarray scanner (G2565BA, Agilent Technologies). The intensity of each hybridization signal is evaluated by Agilent extraction software v9.5.3. The labeling, hybridization, and scanning may be performed according to the protocols in the Agilent miRNA microarray system (Gu et al., J. Neurochem. 122:641-649, 2012, which is hereby incorporated by reference in its entirety).

In some embodiments, a TaqMan assay is used to detect RNA. An exemplary assay is the TaqMan Array Human MicroRNA Panel v1.0 (Early Access) (Applied Biosystems), which contains 157 TaqMan MicroRNA Assays, including the respective reverse-transcription primers, PCR primers, and TaqMan probe (Chim et al., "Detection and characterization of placental microRNAs in maternal plasma," Clin Chem. 54 (3): 482-90, 2008, which is hereby incorporated by reference in its entirety).

If desired, the mRNA splicing pattern of one or more mRNAs can be determined using standard methods (Fackenthall and Godley, Disease Models & Mechanisms 1:37-42, 2008, doi: 10.1242/dmm.000331, which is hereby incorporated by reference in its entirety). For example, high-density microarrays and/or high-throughput DNA sequencing can be used to detect mRNA splice variants.

In some embodiments, whole transcriptome shotgun sequencing or an array is used to measure the transcriptome.

Exemplary Amplification Methods

Improved PCR amplification methods have also been developed that minimize or prevent interference due to the amplification of nearby or adjacent target loci in the same reaction volume (such as part of the sample multiplex PCR reaction that simultaneously amplifies all the target loci). These methods can be used to simultaneously amplify nearby or adjacent target loci, which is faster and cheaper than having to separate nearby target loci into different reaction volumes so that they can be amplified separately to avoid interference.

In some embodiments, the amplification of target loci is performed using a polymerase (e.g., a DNA polymerase, RNA polymerase, or reverse transcriptase) with low 5'→3' exonuclease and/or low strand displacement activity. In some embodiments, the low level of 5'→3' exonuclease reduces or prevents the degradation of a nearby primer (e.g., an unextended primer or a primer that has had one or more nucleotides added to during primer extension). In some embodiments, the low level of strand displacement activity reduces or prevents the displacement of a nearby primer (e.g., an unextended primer or a primer that has had one or more nucleotides added to it during primer extension). In some embodiments, target loci that are adjacent to each other (e.g., no bases between the target loci) or nearby (e.g., loci are within 50, 40, 30, 20, 15, 10, 9, 8, 7, 6, 5, 4, 3, 2, or 1 base) are amplified. In some embodiments, the 3' end of one locus is within 50, 40, 30, 20, 15, 10, 9, 8, 7, 6, 5, 4, 3, 2, or 1 base of the 5' end of next downstream locus.

In some embodiments, at least 100, 200, 500, 750, 1,000; 2,000; 5,000; 7,500; 10,000; 20,000; 25,000; 30,000; 40,000; 50,000; 75,000; or 100,000 different target loci are amplified, such as by the simultaneous amplification in one reaction volume. In some embodiments, at least 50, 60, 70, 80, 90, 95, 96, 97, 98, 99, or 99.5% of the amplified products are target amplicons. In various embodiments, the amount of amplified products that are target amplicons is between 50 to 99.5%, such as between 60 to 99%, 70 to 98%, 80 to 98%, 90 to 99.5%, or 95 to 99.5%, inclusive. In some embodiments, at least 50, 60, 70, 80, 90, 95, 96, 97, 98, 99, or 99.5% of the targeted loci are amplified (e.g., amplified at least 5, 10, 20, 30, 50, or 100-fold compared to the amount prior to amplification), such as by the simultaneous amplification in one reaction volume. In various embodiments, the amount target loci that are amplified (e.g., amplified at least 5, 10, 20, 30, 50, or 100-fold compared to the amount prior to amplification) is between 50 to 99.5%, such as between 60 to 99%, 70 to 98%, 80 to 99%, 90 to 99.5%, 95 to 99.9%, or 98 to 99.99% inclusive. In some embodiments, fewer non-target amplicons are produced, such as fewer amplicons formed from a forward primer from a first primer pair and a reverse primer from a second primer pair. Such undesired non-target amplicons can be produced using prior amplification methods if, e.g., the reverse primer from the first primer pair and/or the forward primer from the second primer pair are degraded and/or displaced.

In some embodiments, these methods allows longer extension times to be used since the polymerase bound to a primer being extended is less likely to degrade and/or displace a nearby primer (such as the next downstream primer) given the low 5'→3' exonuclease and/or low strand displacement activity of the polymerase. In various embodiments, reaction conditions (such as the extension time and temperature) are used such that the extension rate of the polymerase allows the number of nucleotides that are added to a primer being extended to be equal to or greater than 80, 90, 95, 100, 110, 120, 130, 140, 150, 175, or 200% of the number of nucleotides between the 3' end of the primer binding site and the 5' end of the next downstream primer binding site on the same strand.

In some embodiments, a DNA polymerase is used produce DNA amplicons using DNA as a template. In some embodiments, a RNA polymerase is used produce RNA amplicons using DNA as a template. In some embodiments, a reverse transcriptase is used produce cDNA amplicons using RNA as a template.

In some embodiments, the low level of 5'→3' exonuclease of the polymerase is less than 80, 70, 60, 50, 40, 30, 20, 10, 5, 1, or 0.1% of the activity of the same amount of *Thermus aquaticus* polymerase ("Taq" polymerase, which is a commonly used DNA polymerase from a thermophilic bacterium, PDB 1BGX, EC 2.7.7.7, Murali et al., "Crystal structure of Taq DNA polymerase in complex with an inhibitory Fab: the Fab is directed against an intermediate in the helix-coil dynamics of the enzyme," Proc. Natl. Acad. Sci. USA 95:12562-12567, 1998, which is hereby incorporated by reference in its entirety) under the same conditions. In some embodiments, the low level of strand displacement activity of the polymerase is less than 80, 70, 60, 50, 40, 30, 20, 10, 5, 1, or 0.1% of the activity of the same amount of Taq polymerase under the same conditions.

In some embodiments, the polymerase is a PUSHION DNA polymerase, such as PHUSION High Fidelity DNA polymerase (M0530S, New England BioLabs, Inc.) or PHUSION Hot Start Flex DNA polymerase (M0535S, New England BioLabs, Inc.; Frey and Suppman *BioChemica.* 2:34-35, 1995; Chester and Marshak *Analytical Biochemistry.* 209:284-290, 1993, which are each hereby incorporated by reference in its entirety). The PHUSION DNA polymerase is a *Pyrococcus*-like enzyme fused with a processivity-enhancing domain. PHUSION DNA polymerase possesses 5'→3' polymerase activity and 3'→5' exonuclease activity, and generates blunt-ended products. PHUSION DNA polymerase lacks 5'→3' exonuclease activity and strand displacement activity.

In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M0493S, New England BioLabs, Inc.). Q5® High-Fidelity DNA polymerase is a high-fidelity, thermostable, DNA polymerase with 3'→5' exonuclease activity, fused to a processivity-enhancing Sso7d domain. Q5® High-Fidelity DNA polymerase lacks 5'→3' exonuclease activity and strand displacement activity.

In some embodiments, the polymerase is a T4 DNA polymerase (M0203S, New England BioLabs, Inc.; Tabor and Struh. (1989). "DNA-Dependent DNA Polymerases," In Ausebel et al. (Ed.), *Current Protocols in Molecular Biology.* 3.5.10-3.5.12. New York: John Wiley & Sons, Inc., 1989; Sambrook et al. *Molecular Cloning: A Laboratory Manual.* (2nd ed.), 5.44-5.47. Cold Spring Harbor: Cold Spring Harbor Laboratory Press, 1989, which are each hereby incorporated by reference in its entirety). T4 DNA Polymerase catalyzes the synthesis of DNA in the 5' →3' direction and requires the presence of template and primer. This enzyme has a 3'→5' exonuclease activity which is much more active than that found in DNA Polymerase I. T4 DNA polymerase lacks 5'→3' exonuclease activity and strand displacement activity.

In some embodiments, the polymerase is a *Sulfolobus* DNA Polymerase IV (M0327S, New England BioLabs, Inc.; (Boudsocq, et al. (2001). *Nucleic Acids Res.,* 29:4607-4616, 2001; McDonald, et al. (2006). *Nucleic Acids Res.,* 34:1102-1111, 2006, which are each hereby incorporated by reference in its entirety). *Sulfolobus* DNA Polymerase IV is a thermostable Y-family lesion-bypass DNA Polymerase that efficiently synthesizes DNA across a variety of DNA template lesions McDonald, J. P. et al. (2006). *Nucleic Acids Res.,* 34, 1102-1111, which is hereby incorporated by reference in its entirety). *Sulfolobus* DNA Polymerase IV lacks 5'→3' exonuclease activity and strand displacement activity.

In some embodiments, if a primer binds a region with a SNP, the primer may bind and amplify the different alleles with different efficiencies or may only bind and amplify one allele. For subjects who are heterozygous, one of the alleles may not be amplified by the primer. In some embodiments, a primer is designed for each allele. For example, if there are two alleles (e.g., a biallelic SNP), then two primers can be used to bind the same location of a target locus (e.g., a forward primer to bind the "A" allele and a forward primer to bind the "B" allele). Standard methods, such as the dbSNP database, can be used to determine the location of known SNPs, such as SNP hot spots that have a high heterozygosity rate.

In some embodiments, the amplicons are similar in size. In some embodiments, the range of the length of the target amplicons is less than 100, 75, 50, 25, 15, 10, or 5 nucleotides. In some embodiments (such as the amplification of target loci in fragmented DNA or RNA), the length of the target amplicons is between 50 and 100 nucleotides, such as between 60 and 80 nucleotides, or 60 and 75 nucleotides, inclusive. In some embodiments (such as the amplification of multiple target loci throughout an exon or gene), the length of the target amplicons is between 100 and 500 nucleotides, such as between 150 and 450 nucleotides, 200 and 400 nucleotides, 200 and 300 nucleotides, or 300 and 400 nucleotides, inclusive.

In some embodiments, multiple target loci are simultaneously amplified using a primer pair that includes a forward and reverse primer for each target locus to be amplified in that reaction volume. In some embodiments, one round of PCR is performed with a single primer per target locus, and then a second round of PCR is performed with a primer pair per target locus. For example, the first round of PCR may be performed with a single primer per target locus such that all the primers bind the same strand (such as using a forward primer for each target locus). This allows the PCR to amplify in a linear manner and reduces or eliminates amplification bias between amplicons due to sequence or length differences. In some embodiments, the amplicons are then amplified using a forward and reverse primer for each target locus.

Exemplary Primer Design Methods

If desired, multiplex PCR may be performed using primers with a decreased likelihood of forming primer dimers. In particular, highly multiplexed PCR can often result in the production of a very high proportion of product DNA that results from unproductive side reactions such as primer dimer formation. In an embodiment, the particular primers that are most likely to cause unproductive side reactions may be removed from the primer library to give a primer library that will result in a greater proportion of amplified DNA that maps to the genome. The step of removing problematic primers, that is, those primers that are particularly likely to firm dimers has unexpectedly enabled extremely high PCR multiplexing levels for subsequent analysis by sequencing.

There are a number of ways to choose primers for a library where the amount of non-mapping primer dimer or other primer mischief products are minimized. Empirical data indicate that a small number of 'bad' primers are responsible for a large amount of non-mapping primer dimer side reactions. Removing these 'bad' primers can increase the percent of sequence reads that map to targeted loci. One way to identify the 'bad' primers is to look at the sequencing data of DNA that was amplified by targeted amplification; those primer dimers that are seen with greatest frequency can be removed to give a primer library that is significantly less likely to result in side product DNA that does not map to the genome. There are also publicly available programs that can calculate the binding energy of various primer combinations, and removing those with the highest binding energy will also give a primer library that is significantly less likely to result in side product DNA that does not map to the genome.

In some embodiments for selecting primers, an initial library of candidate primers is created by designing one or more primers or primer pairs to candidate target loci. A set of candidate target loci (such as SNPs) can selected based on publicly available information about desired parameters for the target loci, such as frequency of the SNPs within a target population or the heterozygosity rate of the SNPs. In one embodiment, the PCR primers may be designed using the Primer3 program (the worldwide web at primer3.sourceforge.net; libprimer3 release 2.2.3, which is hereby incorporated by reference in its entirety). If desired, the primers can be designed to anneal within a particular annealing temperature range, have a particular range of GC contents, have a particular size range, produce target amplicons in a particular size range, and/or have other parameter characteristics. Starting with multiple primers or primer pairs per candidate target locus increases the likelihood that a primer or prime pair will remain in the library for most or all of the target loci. In one embodiment, the selection criteria may require that at least one primer pair per target locus remains in the library. That way, most or all of the target loci will be amplified when using the final primer library. This is desirable for applications such as screening for deletions or duplications at a large number of locations in the genome or screening for a large number of sequences (such as polymorphisms or other mutations) associated with a disease or an increased risk for a disease. If a primer pair from the library would produces a target amplicon that overlaps with a target amplicon produced by another primer pair, one of the primer pairs may be removed from the library to prevent interference.

In some embodiments, an "undesirability score" (higher score representing least desirability) is calculated (such as calculation on a computer) for most or all of the possible combinations of two primers from a library of candidate primers. In various embodiments, an undesirability score is calculated for at least 80, 90, 95, 98, 99, or 99.5% of the possible combinations of candidate primers in the library. Each undesirability score is based at least in part on the likelihood of dimer formation between the two candidate primers. If desired, the undesirability score may also be based on one or more other parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the target amplicon, GC content of the target amplicon, amplification efficiency of the target amplicon, size of the target amplicon, and distance from the center of a recombination hotspot. In some embodiments, the lower the number of SNPs with the candidate primer (such as 2, 1 or 0 SNPs) the better. In some embodiments, there are no SNPs in the candidate primer. In some embodiments, SNPs (if any) are preferably not in the last 5 nucleotides in the 3' end of the candidate primer. In some embodiments, the target bases (the bases of interest in a target locus) are preferably near an end (the 3' or 5' end) of the amplicon; this may improve the quality of sequencing data (since bases near the end of an amplicon are sequenced more accurately), and/or allow shorter sequencing reads to be performed. In some embodiments, a single amplicon includes 2 or more target loci (such as 2 or more nearby SNPs or variants). In some embodiments, the specificity of the candidate primer for the target locus includes the likelihood that the candidate primer will mis-prime by binding and amplifying a locus other than the target locus it was designed to amplify. In some embodiments, one or more or all the candidate primers that mis-prime are removed from the library. In some embodiments to increase the number of candidate primers to choose from, candidate primers that may mis-prime are not removed from the library. If multiple factors are considered, the undesirability score may be calculated based on a weighted average of the various parameters. The parameters may be assigned different weights based on their importance for the particular application that the primers will be used for. In some embodiments, the primer with the highest undesirability score is removed from the library. If the removed primer is a member of a primer pair that hybridizes to one target locus, then the other member of the primer pair may be removed from the library. The process of removing primers may be repeated as desired. In some embodiments, the selection method is performed until the undesirability scores for the candidate primer combinations remaining in the library are all equal to or below a minimum threshold. In some embodiments, the selection method is performed until the number of candidate primers remaining in the library is reduced to a desired number.

In various embodiments, after the undesirability scores are calculated, the candidate primer that is part of the greatest number of combinations of two candidate primers with an undesirability score above a first minimum threshold is removed from the library. This step ignores interactions equal to or below the first minimum threshold since these interactions are less significant. If the removed primer is a member of a primer pair that hybridizes to one target locus, then the other member of the primer pair may be removed from the library. The process of removing primers may be repeated as desired. In some embodiments, the selection method is performed until the undesirability scores for the candidate primer combinations remaining in the library are all equal to or below the first minimum threshold. If the number of candidate primers remaining in the library is higher than desired, the number of primers may be reduced by decreasing the first minimum threshold to a lower second minimum threshold and repeating the process of removing primers. If the number of candidate primers remaining in the library is lower than desired, the method can be continued by increasing the first minimum threshold to a higher second minimum threshold and repeating the process of removing primers using the original candidate primer library, thereby allowing more of the candidate primers to remain in the library. In some embodiments, the selection method is performed until the undesirability scores for the candidate primer combinations remaining in the library are all equal to or below the second minimum threshold, or until the number of candidate primers remaining in the library is reduced to a desired number., If desired, primer pairs that produce a target amplicon that overlaps with a target amplicon produced by another primer pair can be divided into separate amplification reactions. Multiple PCR amplification reactions may be desirable for applications in which it is desirable to analyze all of the candidate target loci (instead of omitting candidate target loci from the analysis due to overlapping target amplicons).

These selection methods minimize the number of candidate primers that have to be removed from the library to achieve the desired reduction in primer dimers. By removing a smaller number of candidate primers from the library, more (or all) of the target loci can be amplified using the resulting primer library.

Multiplexing large numbers of primers imposes considerable constraint on the assays that can be included. Assays that unintentionally interact result in spurious amplification products. The size constraints of miniPCR may result in further constraints. In an embodiment, it is possible to begin with a very large number of potential SNP targets (between about 500 to greater than 1 million) and attempt to design primers to amplify each SNP. Where primers can be designed it is possible to attempt to identify primer pairs likely to form spurious products by evaluating the likelihood of spurious primer duplex formation between all possible pairs of primers using published thermodynamic parameters for DNA duplex formation. Primer interactions may be ranked by a scoring function related to the interaction and primers with the worst interaction scores are eliminated until the number of primers desired is met. In cases where SNPs likely to be heterozygous are most useful, it is possible to also rank the list of assays and select the most heterozygous compatible assays. Experiments have validated that primers with high interaction scores are most likely to form primer dimers. At high multiplexing it is not possible to eliminate all spurious interactions, but it is essential to remove the primers or pairs of primers with the highest interaction scores in silico as they can dominate an entire reaction, greatly limiting amplification from intended targets. We have performed this procedure to create multiplex primer sets of up to and in some cases more than 10,000 primers. The improvement due to this procedure is substantial, enabling amplification of more than 80%, more than 90%, more than 95%, more than 98%, and even more than 99% on target products as determined by sequencing of all PCR products, as compared to 10% from a reaction in which the worst primers were not removed. When combined with a partial semi-nested approach as previously described, more than 90%, and even more than 95% of amplicons may map to the targeted sequences.

Note that there are other methods for determining which PCR probes are likely to form dimers. In an embodiment, analysis of a pool of DNA that has been amplified using a non-optimized set of primers may be sufficient to determine problematic primers. For example, analysis may be done using sequencing, and those dimers which are present in the greatest number are determined to be those most likely to form dimers, and may be removed. In an embodiment, the method of primer design may be used in combination with the mini-PCR method described herein.

The use of tags on the primers may reduce amplification and sequencing of primer dimer products. In some embodiments, the primer contains an internal region that forms a loop structure with a tag. In particular embodiments, the primers include a 5' region that is specific for a target locus, an internal region that is not specific for the target locus and forms a loop structure, and a 3' region that is specific for the target locus. In some embodiments, the loop region may lie between two binding regions where the two binding regions are designed to bind to contiguous or neighboring regions of template DNA. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the primers include a 5' region that is not specific for a target locus (such as a tag or a universal primer binding site) followed by a region that is specific for a target locus, an internal region that is not specific for the target locus and forms a loop structure, and a 3' region that is specific for the target locus. Tag-primers can be used to shorten necessary target-specific sequences to below 20, below 15, below 12, and even below 10 base pairs. This can be serendipitous with standard primer design when the target sequence is fragmented within the primer binding site or, or it can be designed into the primer design. Advantages of this method include: it increases the number of assays that can be designed for a certain maximal amplicon length, and it shortens the "non-informative" sequencing of primer sequence. It may also be used in combination with internal tagging.

In an embodiment, the relative amount of nonproductive products in the multiplexed targeted PCR amplification can be reduced by raising the annealing temperature. In cases where one is amplifying libraries with the same tag as the target specific primers, the annealing temperature can be increased in comparison to the genomic DNA as the tags will contribute to the primer binding. In some embodiments reduced primer concentrations are used, optionally along with longer annealing times. In some embodiments the annealing times may be longer than 3 minutes, longer than 5 minutes, longer than 8 minutes, longer than 10 minutes, longer than 15 minutes, longer than 20 minutes, longer than 30 minutes, longer than 60 minutes, longer than 120 minutes, longer than 240 minutes, longer than 480 minutes, and even longer than 960 minutes. In certain illustrative embodiments, longer annealing times are used along with reduced primer concentrations. In various embodiments, longer than normal extension times are used, such as greater than 3, 5, 8, 10, or 15 minutes. In some embodiments, the primer concentrations are as low as 50 nM, 20 nM, 10 nM, 5 nM, 1 nM, and lower than 1 nM. This surprisingly results in robust performance for highly multiplexed reactions, for example 1,000-plex reactions, 2,000-plex reactions, 5,000-plex reactions, 10,000-plex reactions, 20,000-plex reactions, 50,000-plex reactions, and even 100,000-plex reactions. In an embodiment, the amplification uses one, two, three, four or five cycles run with long annealing times, followed by PCR cycles with more usual annealing times with tagged primers.

To select target locations, one may start with a pool of candidate primer pair designs and create a thermodynamic model of potentially adverse interactions between primer pairs, and then use the model to eliminate designs that are incompatible with other the designs in the pool.

In an embodiment, the invention features a method of decreasing the number of target loci (such as loci that may contain a polymorphism or mutation associated with a disease or disorder or an increased risk for a disease or disorder such as cancer) and/or increasing the disease load that is detected (e.g., increasing the number of polymorphisms or mutations that are detected). In some embodiments, the method includes ranking (such as ranking from highest to lowest) loci by frequency or reoccurrence of a polymorphism or mutation (such as a single nucleotide variation, insertion, or deletion, or any of the other variations described herein) in each locus among subjects with the disease or disorder such as cancer. In some embodiments, PCR primers are designed to some or all of the loci. During selection of PCR primers for a library of primers, primers to loci that have a higher frequency or reoccurrence (higher ranking loci) are favored over those with a lower frequency or reoccurrence (lower ranking loci). In some embodiments, this parameter is included as one of the parameters in the calculation of the undesirability scores described herein. If desired, primers (such as primers to high ranking loci) that are incompatible with other designs in the library can be included in a different PCR library/pool. In some embodiments, multiple libraries/pools (such as 2, 3, 4, 5 or more) are used in separate PCR reactions to enable amplification of all (or a majority) of the loci represented by all the libraries/pools. In some embodiment, this method is continued until sufficient primers are included in one or more libraries/pools such that the primers, in aggregate, enable the desired disease load to be captured for the disease or disorder (e.g., such as by detection of at least 80, 85, 90, 95, or 99% of the disease load).

Exemplary Primer Libraries

In one aspect, the invention features libraries of primers, such as primers selected from a library of candidate primers using any of the methods of the invention. In some embodiments, the library includes primers that simultaneously hybridize (or are capable of simultaneously hybridizing) to or that simultaneously amplify (or are capable of simultaneously amplifying) at least 100; 200; 500; 750; 1,000;

2,000; 5,000; 7,500; 10,000; 20,000; 25,000; 30,000; 40,000; 50,000; 75,000; or 100,000 different target loci in one reaction volume. In various embodiments, the library includes primers that simultaneously amplify (or are capable of simultaneously amplifying) between 100 to 500; 500 to 1,000; 1,000 to 2,000; 2,000 to 5,000; 5,000 to 7,500; 7,500 to 10,000; 10,000 to 20,000; 20,000 to 25,000; 25,000 to 30,000; 30,000 to 40,000; 40,000 to 50,000; 50,000 to 75,000; or 75,000 to 100,000 different target loci in one reaction volume, inclusive. In various embodiments, the library includes primers that simultaneously amplify (or are capable of simultaneously amplifying) between 1,000 to 100,000 different target loci in one reaction volume, such as between 1,000 to 50,000; 1,000 to 30,000; 1,000 to 20,000; 1,000 to 10,000; 2,000 to 30,000; 2,000 to 20,000; 2,000 to 10,000; 5,000 to 30,000; 5,000 to 20,000; or 5,000 to 10,000 different target loci, inclusive. In some embodiments, the library includes primers that simultaneously amplify (or are capable of simultaneously amplifying) the target loci in one reaction volume such that less than 60, 40, 30, 20, 10, 5, 4, 3, 2, 1, 0.5, 0.25, 0.1, or 0.5% of the amplified products are primer dimers. The various embodiments, the amount of amplified products that are primer dimers is between 0.5 to 60%, such as between 0.1 to 40%, 0.1 to 20%, 0.25 to 20%, 0.25 to 10%, 0.5 to 20%, 0.5 to 10%, 1 to 20%, or 1 to 10%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the amplified products are target amplicons. In various embodiments, the amount of amplified products that are target amplicons is between 50 to 99.5%, such as between 60 to 99%, 70 to 98%, 80 to 98%, 90 to 99.5%, or 95 to 99.5%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the targeted loci are amplified (e.g., amplified at least 5, 10, 20, 30, 50, or 100-fold compared to the amount prior to amplification). In various embodiments, the amount target loci that are amplified (e.g., amplified at least 5, 10, 20, 30, 50, or 100-fold compared to the amount prior to amplification) is between 50 to 99.5%, such as between 60 to 99%, 70 to 98%, 80 to 99%, 90 to 99.5%, 95 to 99.9%, or 98 to 99.99% inclusive. In some embodiments, the library of primers includes at least 100; 200; 500; 750; 1,000; 2,000; 5,000; 7,500; 10,000; 20,000; 25,000; 30,000; 40,000; 50,000; 75,000; or 100,000 primer pairs, wherein each pair of primers includes a forward test primer and a reverse test primer where each pair of test primers hybridize to a target locus. In some embodiments, the library of primers includes at least 100; 200; 500; 750; 1,000; 2,000; 5,000; 7,500; 10,000; 20,000; 25,000; 30,000; 40,000; 50,000; 75,000; or 100,000 individual primers that each hybridize to a different target locus, wherein the individual primers are not part of primer pairs.

In various embodiments, the concentration of each primer is less than 100, 75, 50, 25, 20, 10, 5, 2, or 1 nM, or less than 500, 100, 10, or 1 μM. In various embodiments, the concentration of each primer is between 1 μM to 100 nM, such as between 1 μM to 1 nM, 1 to 75 nM, 2 to 50 nM or 5 to 50 nM, inclusive. In various embodiments, the GC content of the primers is between 30 to 80%, such as between 40 to 70%, or 50 to 60%, inclusive. In some embodiments, the range of GC content of the primers is less than 30, 20, 10, or 5%. In some embodiments, the range of GC content of the primers is between 5 to 30%, such as 5 to 20% or 5 to 10%, inclusive. In some embodiments, the melting temperature (Tm) of the test primers is between 40 to 80° C., such as 50 to 70° C., 55 to 65° C., or 57 to 60.5° C., inclusive. In some embodiments, the $T_m$ is calculated using the Primer3 program (libprimer3 release 2.2.3) using the built-in SantaLucia parameters (the world wide web at primer3.sourceforge.net). In some embodiments, the range of melting temperature of the primers is less than 15, 10, 5, 3, or 1° C. In some embodiments, the range of melting temperature of the primers is between 1 to 15° C., such as between 1 to 10° C., 1 to 5° C., or 1 to 3° C., inclusive. In some embodiments, the length of the primers is between 15 to 100 nucleotides, such as between 15 to 75 nucleotides, 15 to 40 nucleotides, 17 to 35 nucleotides, 18 to 30 nucleotides, or 20 to 65 nucleotides, inclusive. In some embodiments, the range of the length of the primers is less than 50, 40, 30, 20, 10, or 5 nucleotides. In some embodiments, the range of the length of the primers is between 5 to 50 nucleotides, such as 5 to 40 nucleotides, 5 to 20 nucleotides, or 5 to 10 nucleotides, inclusive. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the library does not comprise a microarray. In some embodiments, the library comprises a microarray.

In some embodiments, some (such as at least 80, 90, or 95%) or all of the adaptors or primers include one or more linkages between adjacent nucleotides other than a naturally-occurring phosphodiester linkage. Examples of such linkages include phosphoramide, phosphorothioate, and phosphorodithioate linkages. In some embodiments, some (such as at least 80, 90, or 95%) or all of the adaptors or primers include a thiophosphate (such as a monothiophosphate) between the last 3' nucleotide and the second to last 3' nucleotide. In some embodiments, some (such as at least 80, 90, or 95%) or all of the adaptors or primers include a thiophosphate (such as a monothiophosphate) between the last 2, 3, 4, or 5 nucleotides at the 3' end. In some embodiments, some (such as at least 80, 90, or 95%) or all of the adaptors or primers include a thiophosphate (such as a monothiophosphate) between at least 1, 2, 3, 4, or 5 nucleotides out of the last 10 nucleotides at the 3' end. In some embodiments, such primers are less likely to be cleaved or degraded. In some embodiments, the primers do not contain an enzyme cleavage site (such as a protease cleavage site).

Additional exemplary multiplex PCR methods and libraries are described in U.S. application Ser. No. 13/683,604, filed Nov. 21, 2012 (U.S. Publication No. 2013/0123120) and U.S. Ser. No. 61/994,791, filed May 16, 2014, which are each hereby incorporated by reference in its entirety). These methods and libraries can be used for analysis of any of the samples disclosed herein and for use in any of the methods of the invention.

Exemplary Primer Libraries for Detection of Recombination

In some embodiments, primers in the primer library are designed to determine whether or not recombination occurred at one or more known recombination hotspots (such as crossovers between homologous human chromosomes). Knowing what crossovers occurred between chromosomes allows more accurate phased genetic data to be determined for an individual. Recombination hotspots are local regions of chromosomes in which recombination events tend to be concentrated. Often they are flanked by "coldspots," regions of lower than average frequency of recombination. Recombination hotspots tend to share a similar morphology and are approximately 1 to 2 kb in length. The hotspot distribution is positively correlated with GC content and repetitive element distribution. A partially degenerated 13-mer motif CCNCCNTNNCCNC plays a role in some hotspot activity. It has been shown that the zinc finger protein called PRDM9 binds to this motif and initiates recombination at its location. The average distance between the centers of recombination hot spots is reported to be ~80 kb. In some embodiments, the distance between the centers of recombination hot spots ranges between ~3 kb to ~100 kb. Public databases include a large number of known human recombination hotspots, such as the HUMHOT and International HapMap Project databases (see, for example, Nishant et al., "HUMHOT: a database of human meiotic recombination hot spots," Nucleic Acids Research, 34: D25-D28, 2006, Database issue; Mackiewicz et al., "Distribution of Recombination Hotspots in the Human Genome—A Comparison of Computer Simulations with Real Data" PLOS ONE 8 (6): e65272, doi: 10.1371/journal-.pone.0065272; and the world wide web at hap-map.ncbi.nlm.nih.gov/downloads/index.html.en, which are each hereby incorporated by reference in its entirety).

In some embodiments, primers in the primer library are clustered at or near recombination hotspots (such as known human recombination hotspots). In some embodiments, the corresponding amplicons are used to determine the sequence within or near a recombination hotspot to determine whether or not recombination occurred at that particular hotspot (such as whether the sequence of the amplicon is the sequence expected if a recombination had occurred or the sequence expected if a recombination had not occurred). In some embodiments, primers are designed to amplify part or all of a recombination hotspot (and optionally sequence flanking a recombination hotspot). In some embodiments, long read sequencing (such as sequencing using the Moleculo Technology developed by Illumina to sequence up to ~10 kb) or paired end sequencing is used to sequence part or all of a recombination hotspot. Knowledge of whether or not a recombination event occurred can be used to determine which haplotype blocks flank the hotspot. If desired, the presence of particular haplotype blocks can be confirmed using primers specific to regions within the haplotype blocks. In some embodiments, it is assumed there are no crossovers between known recombination hotspots. In some embodiments, primers in the primer library are clustered at or near the ends of chromosomes. For example, such primers can be used to determine whether or not a particular arm or section at the end of a chromosome is present. In some embodiments, primers in the primer library are clustered at or near recombination hotspots and at or near the ends of chromosomes.

In some embodiments, the primer library includes one or more primers (such as at least 5; 10; 50; 100; 200; 500; 750; 1,000; 2,000; 5,000; 7,500; 10,000; 20,000; 25,000; 30,000; 40,000; or 50,000 different primers or different primer pairs) that are specific for a recombination hotspot (such as a known human recombination hotspot) and/or are specific for a region near a recombination hotspot (such as within 10, 8, 5, 3, 2, 1, or 0.5 kb of the 5' or 3' end of a recombination hotspot). In some embodiments, at least 1, 5, 10, 20, 40, 60, 80, 100, or 150 different primer (or primer pairs) are specific for the same recombination hotspot, or are specific for the same recombination hotspot or a region near the recombination hotspot. In some embodiments, at least 1, 5, 10, 20, 40, 60, 80, 100, or 150 different primer (or primer pairs) are specific for a region between recombination hotspots (such as a region unlikely to have undergone recombination); these primers can be used to confirm the presence of haplotype blocks (such as those that would be expected depending on whether or not recombination has occurred). In some embodiments, at least 10, 20, 30, 40, 50, 60, 70, 80, or 90% of the primers in the primer library are specific for a recombination hotspot and/or are specific for a region near a recombination hotspot (such as within 10, 8, 5, 3, 2, 1, or 0.5 kb of the 5' or 3' end of the recombination hotspot). In some embodiments, the primer library is used to determine whether or not recombination has occurred at greater than or equal to 5; 10; 50; 100; 200; 500; 750; 1,000; 2,000; 5,000; 7,500; 10,000; 20,000; 25,000; 30,000; 40,000; or 50,000 different recombination hotspots (such as known human recombination hotspots). In some embodiments, the regions targeted by primers to a recombination hotspot or nearby region are approximately evenly spread out along that portion of the genome. In some embodiments, at least 1, 5, 10, 20, 40, 60, 80, 100, or 150 different primer (or primer pairs) are specific for the a region at or near the end of a chromosome (such as a region within 20, 10, 5, 1, 0.5, 0.1, 0.01, or 0.001 mb from the end of a chromosome). In some embodiments, at least 10, 20, 30, 40, 50, 60, 70, 80, or 90% of the primers in the primer library are specific for the a region at or near the end of a chromosome (such as a region within 20, 10, 5, 1, 0.5, 0.1, 0.01, or 0.001 mb from the end of a chromosome). In some embodiments, at least 1, 5, 10, 20, 40, 60, 80, 100, or 150 different primer (or primer pairs) are specific for a region within a potential microdeletion in a chromosome. In some embodiments, at least 10, 20, 30, 40, 50, 60, 70, 80, or 90% of the primers in the primer library are specific for a region within a potential microdeletion in a chromosome. In some embodiments, at least 10, 20, 30, 40, 50, 60, 70, 80, or 90% of the primers in the primer library are specific for a recombination hotspot, a region near a recombination hotspot, a region at or near the end of a chromosome, or a region within a potential microdeletion in a chromosome.

Exemplary Kits

In one aspect, the invention features a kit, such as a kit for amplifying target loci in a nucleic acid sample for detecting deletions and/or duplications of chromosome segments or entire chromosomes using any of the methods described herein). In some embodiments, the kit can include any of the primer libraries of the invention. In an embodiment, the kit comprises a plurality of inner forward primers and optionally a plurality of inner reverse primers, and optionally outer forward primers and outer reverse primers, where each of the primers is designed to hybridize to the region of DNA immediately upstream and/or downstream from one of the target sites (e.g., polymorphic sites) on the target chromosome(s) or chromosome segment(s), and optionally additional chromosomes or chromosome segments. In some embodiments, the kit includes instructions for using the primer library to amplify the target loci, such as for detecting one or more deletions and/or duplications of one or more chromosome segments or entire chromosomes using any of the methods described herein.

In certain embodiments, kits of the invention provide primer pairs for detecting chromosomal aneuploidy and CNV determination, such as primer pairs for massively multiplex reactions for detecting chromosomal aneuploidy such as CNV (CONVERGe) (Copy Number Variant Events Revealed Genotypically) and/or SNVs. In these embodiments, the kits can include between at least 100, 200, 250, 300, 500, 1000, 2000, 2500, 3000, 5000, 10,000, 20,000, 25,000, 28,000, 50,000, or 75,000 and at most 200, 250, 300, 500, 1000, 2000, 2500, 3000, 5000, 10,000, 20,000, 25,000, 28,000, 50,000, 75,000, or 100,000 primer pairs that are shipped together. The primer pairs can be contained in a single vessel, such as a single tube or box, or multiple tubes or boxes. In certain embodiments, the primer pairs are pre-qualified by a commercial provider and sold together, and in other embodiments, a customer selects custom gene targets and/or primers and a commercial provider makes and ships the primer pool to the customer neither in one tube or a plurality of tubes. In certain exemplary embodiments, the kits include primers for detecting both CNVs and SNVs, especially CNVs and SNVs known to be correlated to at least one type of cancer.

Kits for circulating DNA detection according to some embodiments of the present invention, include standards and/or controls for circulating DNA detection. For example, in certain embodiments, the standards and/or controls are sold and optionally shipped and packaged together with primers used to perform the amplification reactions provided herein, such as primers for performing CONVERGe. In certain embodiments, the controls include polynucleotides such as DNA, including isolated genomic DNA that exhibits one or more chromosomal aneuploidies such as CNV and/or includes one or more SNVs. In certain embodiments, the standards and/or controls are called PlasmArt standards and include polynucleotides having sequence identity to regions of the genome known to exhibit CNV, especially in certain inherited diseases, and in certain disease states such as cancer, as well as a size distribution that reflects that of cfDNA fragments naturally found in plasma. Exemplary methods for making PlasmArt standards are provided in the examples herein. In general, genomic DNA from a source known to include a chromosomal aneuoploidy is isolated, fragmented, purified and size selected.

Accordingly, artificial cfDNA polynucleotide standards and/or controls can be made by spiking isolated polynucleotide samples prepared as summarized above, into DNA samples known not to exhibit a chromosomal aneuploidy and/or SNVs, at concentrations similar to those observed for cfDNA in vivo, such as between, for example, 0.01% and 20%, 0.1 and 15%, or 0.4 and 10% of DNA in that fluid. These standards/controls can be used as controls for assay design, characterization, development, and/or validation, and as quality control standards during testing, such as cancer testing performed in a CLIA lab and/or as standards included in research use only or diagnostic test kits.

Exemplary Normalization/Correction Methods

In some embodiments, measurements for different loci, chromosome segments, or chromosomes are adjusted for bias, such as bias due to differences in GC content or bias due to other differences in amplification efficiency or adjusted for sequencing errors. In some embodiments, measurements for different alleles for the same locus are adjusted for differences in metabolism, apoptosis, histones, inactivation, and/or amplification between the alleles. In some embodiments, measurements for different alleles for the same locus in RNA are adjusted for differences in transcription rates or stability between different RNA alleles.

Exemplary Methods for Phasing Genetic Data

In some embodiments, genetic data is phased using the methods described herein or any known method for phasing genetic data (see, e.g., PCT Publ. No. WO2009/105531, filed Feb. 9, 2009, and PCT Publ. No. WO2010/017214, filed Aug. 4, 2009; U.S. Publ. No. 2013/0123120, Nov. 21, 2012; U.S. Publ. No. 2011/0033862, filed Oct. 7, 2010; U.S. Publ. No. 2011/0033862, filed Aug. 19, 2010; U.S. Publ. No. 2011/0178719, filed Feb. 3, 2011; U.S. Pat. No. 8,515,679, filed Mar. 17, 2008; U.S. Publ. No. 2007/0184467, filed Nov. 22, 2006; U.S. Publ. No. 2008/0243398, filed Mar. 17, 2008, and U.S. Ser. No. 61/994,791, filed May 16, 2014, which are each hereby incorporated by reference in its entirety). In some embodiments, the phase is determined for one or more regions that are known or suspected to contain a CNV of interest. In some embodiments, the phase is also determined for one or more regions flanking the CNV region(s) and/or for one or more reference regions. In one embodiment, genetic data of an individual (e.g., an individual being tested using the methods of the invention or a relative of a gestating fetus or embryo, such as a parent of the fetus or embryo) is phased by inference by measuring tissue from the individual that is haploid, for example by measuring one or more sperm or eggs. In one embodiment, an individual's genetic data is phased by inference using the measured genotypic data of one or more first degree relatives, such as the individual's parents (e.g., sperm from the individual's father) or siblings.

In one embodiment, an individual's genetic data is phased by dilution where the DNA or RNA is diluted in one or a plurality of wells, such as by using digital PCR. In some embodiments, the DNA or RNA is diluted to the point where there is expected to be no more than approximately one copy of each haplotype in each well, and then the DNA or RNA in the one or more wells is measured. In some embodiments, cells are arrested at phase of mitosis when chromosomes are tight bundles, and microfluidics is used to put separate chromosomes in separate wells. Because the DNA or RNA is diluted, it is unlikely that more than one haplotype is in the same fraction (or tube). Thus, there may be effectively a single molecule of DNA in the tube, which allows the haplotype on a single DNA or RNA molecule to be determined. In some embodiments, the method includes dividing a DNA or RNA sample into a plurality of fractions such that at least one of the fractions includes one chromosome or one chromosome segment from a pair of chromosomes, and genotyping (e.g., determining the presence of two or more polymorphic loci) the DNA or RNA sample in at least one of the fractions, thereby determining a haplotype. In some embodiments, the genotyping involves sequencing (such as shotgun sequencing or single molecule sequencing), a SNP array to detect polymorphic loci, or multiplex PCR. In some embodiments, the genotyping involves use of a SNP array to detect polymorphic loci, such as at least 100; 200; 500; 750; 1,000; 2,000; 5,000; 7,500; 10,000; 20,000; 25,000; 30,000; 40,000; 50,000; 75,000; or 100,000 different polymorphic loci. In some embodiments, the genotyping involves the use of multiplex PCR. In some embodiments, the method involves contacting the sample in a fraction with a library of primers that simultaneously hybridize to at least 100; 200; 500; 750; 1,000; 2,000; 5,000; 7,500; 10,000; 20,000; 25,000; 30,000; 40,000; 50,000; 75,000; or 100,000 different polymorphic loci (such as SNPs) to produce a reaction mixture; and subjecting the reaction mixture to primer extension reaction conditions to produce amplified products that are measured with a high throughput sequencer to produce sequencing data. In some embodiments, RNA (such as mRNA) is sequenced. Since mRNA contains only exons, sequencing mRNA allows alleles to be determined for polymorphic loci (such as SNPs) over a large distance in the genome, such as a few megabases. In some embodiments, a haplotype of an individual is determined by chromosome sorting. An exemplary chromosome sorting method includes arresting cells at phase of mitosis when chromosomes are tight bundles and using microfluidics to put separate chromosomes in separate wells. Another method involves collecting single chromosomes using FACS-mediated single chromosome sorting. Standard methods (such as sequencing or an array) can be used to identify the alleles on a single chromosome to determine a haplotype of the individual.

In some embodiments, a haplotype of an individual is determined by long read sequencing, such as by using the Moleculo Technology developed by Illumina. In some embodiments, the library prep step involves shearing DNA into fragments, such as fragments of ~10 kb size, diluting the fragments and placing them into wells (such that about 3,000 fragments are in a single well), amplifying fragments in each well by long-range PCR and cutting into short fragments and barcoding the fragments, and pooling the barcoded fragments from each well together to sequence them all. After sequencing, the computational steps involve separating the reads from each well based on the attached barcodes and grouping them into fragments, assembling the fragments at their overlapping heterozygous SNVs into haplotype blocks, and phasing the blocks statistically based on a phased reference panel and producing long haplotype contigs.

In some embodiments, a haplotype of the individual is determined using data from a relative of the individual. In some embodiments, a SNP array is used to determine the presence of at least 100; 200; 500; 750; 1,000; 2,000; 5,000; 7,500; 10,000; 20,000; 25,000; 30,000; 40,000; 50,000; 75,000; or 100,000 different polymorphic loci in a DNA or RNA sample from the individual and a relative of the individual. In some embodiments, the method involves contacting a DNA sample from the individual and/or a relative of the individual with a library of primers that simultaneously hybridize to at least 100; 200; 500; 750; 1,000; 2,000; 5,000; 7,500; 10,000; 20,000; 25,000; 30,000; 40,000; 50,000; 75,000; or 100,000 different polymorphic loci (such as SNPs) to produce a reaction mixture; and subjecting the reaction mixture to primer extension reaction conditions to produce amplified products that are measured with a high throughput sequencer to produce sequencing data.

In one embodiment, an individual's genetic data is phased using a computer program that uses population based haplotype frequencies to infer the most likely phase, such as HapMap-based phasing. For example, haploid data sets can be deduced directly from diploid data using statistical methods that utilize known haplotype blocks in the general population (such as those created for the public HapMap Project and for the Perlegen Human Haplotype Project). A haplotype block is essentially a series of correlated alleles that occur repeatedly in a variety of populations. Since these haplotype blocks are often ancient and common, they may be used to predict haplotypes from diploid genotypes. Publicly available algorithms that accomplish this task include an imperfect phylogeny approach, Bayesian approaches based on conjugate priors, and priors from population genetics. Some of these algorithms use a hidden Markov model.

In one embodiment, an individual's genetic data is phased using an algorithm that estimates haplotypes from genotype data, such as an algorithm that uses localized haplotype clustering (see, e.g., Browning and Browning, "Rapid and Accurate Haplotype Phasing and Missing-Data Inference for Whole-Genome Association Studies By Use of Localized Haplotype Clustering" Am J Hum Genet. November 2007; 81 (5): 1084-1097, which is hereby incorporated by reference in its entirety). An exemplary program is Beagle version: 3.3.2 or version 4 (available at the world wide web at hfaculty.washington.edu/browning/beagle/beagle.html, which is hereby incorporated by reference in its entirety).

In one embodiment, an individual's genetic data is phased using an algorithm that estimates haplotypes from genotype data, such as an algorithm that uses the decay of linkage disequilibrium with distance, the order and spacing of genotyped markers, missing-data imputation, recombination rate estimates, or a combination thereof (see, e.g., Stephens and Scheet, "Accounting for Decay of Linkage Disequilibrium in Haplotype Inference and Missing-Data Imputation" Am. J. Hum. Genet. 76:449-462, 2005, which is hereby incorporated by reference in its entirety). An exemplary program is PHASE v.2.1 or v2.1.1. (available at the world wide web at stephenslab.uchicago.edu/software.html, which is hereby incorporated by reference in its entirety).

In one embodiment, an individual's genetic data is phased using an algorithm that estimates haplotypes from population genotype data, such as an algorithm that allows cluster memberships to change continuously along the chromosome according to a hidden Markov model. This approach is flexible, allowing for both "block-like" patterns of linkage disequilibrium and gradual decline in linkage disequilibrium with distance (see, e.g., Scheet and Stephens, "A fast and flexible statistical model for large-scale population genotype data: applications to inferring missing genotypes and haplotypic phase." Am J Hum Genet, 78:629-644, 2006, which is hereby incorporated by reference in its entirety). An exemplary program is fastPHASE (available at the world wide web at stephenslab.uchicago.edu/software.html, which is hereby incorporated by reference in its entirety).

In one embodiment, an individual's genetic data is phased using a genotype imputation method, such as a method that uses one or more of the following reference datasets: HapMap dataset, datasets of controls genotyped on multiple SNP chips, and densely typed samples from the 1,000 Genomes Project. An exemplary approach is a flexible modelling framework that increases accuracy and combines information across multiple reference panels (see, e.g., Howie, Donnelly, and Marchini (2009) "A flexible and accurate genotype imputation method for the next generation of genome-wide association studies." PLOS Genetics 5 (6): e1000529, 2009, which is hereby incorporated by reference in its entirety). Exemplary programs are IMPUTE or IMPUTE version 2 (also known as IMPUTE2) (available at the world wide web at mathgen.stats.ox.ac.uk/impute/impute_v2.html, which is hereby incorporated by reference in its entirety).

In one embodiment, an individual's genetic data is phased using an algorithm that infers haplotypes, such as an algorithm that infers haplotypes under the genetic model of coalescence with recombination, such as that developed by Stephens in PHASE v2.1. The major algorithmic improvements rely on the use of binary trees to represent the sets of candidate haplotypes for each individual. These binary tree representations: (1) speed up the computations of posterior probabilities of the haplotypes by avoiding the redundant operations made in PHASE v2.1, and (2) overcome the exponential aspect of the haplotypes inference problem by the smart exploration of the most plausible pathways (i.e., haplotypes) in the binary trees (see, e.g., Delaneau, Coulonges and Zagury, "Shape-IT: new rapid and accurate algorithm for haplotype inference," BMC Bioinformatics 9:540, 2008 doi: 10.1186/1471-2105-9-540, which is hereby incorporated by reference in its entirety). An exemplary program is SHAPEIT (available at the world wide web at mathgen.stats.ox.ac.uk/genetics_software/shapeit/shapeit.html, which is hereby incorporated by reference in its entirety).

In one embodiment, an individual's genetic data is phased using an algorithm that estimates haplotypes from population genotype data, such as an algorithm that uses haplotype-fragment frequencies to obtain empirically based probabilities for longer haplotypes. In some embodiments, the algorithm reconstructs haplotypes so that they have maximal local coherence (see, e.g., Eronen, Geerts, and Toivonen, "HaploRec: Efficient and accurate large-scale reconstruction of haplotypes," *BMC Bioinformatics* 7:542, 2006, which is hereby incorporated by reference in its entirety). An exemplary program is HaploRec, such as HaploRec version 2.3. (available at the world wide web at cs.helsinki.fi/group/genetics/haplotyping.html, which is hereby incorporated by reference in its entirety).

In one embodiment, an individual's genetic data is phased using an algorithm that estimates haplotypes from population genotype data, such as an algorithm that uses a partition-ligation strategy and an expectation-maximization-based algorithm (see, e.g., Qin, Niu, and Liu, "Partition-Ligation-Expectation-Maximization Algorithm for Haplotype Inference with Single-Nucleotide Polymorphisms," Am J Hum Genet. 71 (5): 1242-1247, 2002, which is hereby incorporated by reference in its entirety). An exemplary program is PL-EM (available at the world wide web at people.fas.harvard.edu/~junliu/plem/click.html, which is hereby incorporated by reference in its entirety).

In one embodiment, an individual's genetic data is phased using an algorithm that estimates haplotypes from population genotype data, such as an algorithm for simultaneously phasing genotypes into haplotypes and block partitioning. In some embodiments, an expectation-maximization algorithm is used (see, e.g., Kimmel and Shamir, "GERBIL: Genotype Resolution and Block Identification Using Likelihood," Proceedings of the National Academy of Sciences of the United States of America (PNAS) 102:158-162, 2005, which is hereby incorporated by reference in its entirety). An exemplary program is GERBIL, which is available as part of the GEVALT version 2 program (available at the world wide web at acgt.cs.tau.ac.il/gevalt/, which is hereby incorporated by reference in its entirety).

In one embodiment, an individual's genetic data is phased using an algorithm that estimates haplotypes from population genotype data, such as an algorithm that uses an EM algorithm to calculate ML estimates of haplotype frequencies given genotype measurements which do not specify phase. The algorithm also allows for some genotype measurements to be missing (due, for example, to PCR failure). It also allows multiple imputation of individual haplotypes (see, e.g., Clayton, D. (2002), "SNPHAP: A Program for Estimating Frequencies of Large Haplotypes of SNPs", which is hereby incorporated by reference in its entirety). An exemplary program is SNPHAP (available at the world wide web at gene.cimr.cam.ac.uk/clayton/software/snphap.txt, which is hereby incorporated by reference in its entirety).

In one embodiment, an individual's genetic data is phased using an algorithm that estimates haplotypes from population genotype data, such as an algorithm for haplotype inference based on genotype statistics collected for pairs of SNPs. This software can be used for comparatively accurate phasing of large number of long genome sequences, e.g. obtained from DNA arrays. An exemplary program takes genotype matrix as an input, and outputs the corresponding haplotype matrix (see, e.g., Brinza and Zelikovsky, "2SNP: scalable phasing based on 2-SNP haplotypes," Bioinformatics.22 (3): 371-3, 2006, which is hereby incorporated by reference in its entirety). An exemplary program is 2SNP (available at the world wide web at alla.cs.gsu.edu/~software/2SNP, which is hereby incorporated by reference in its entirety).

In various embodiments, an individual's genetic data is phased using data about the probability of chromosomes crossing over at different locations in a chromosome or chromosome segment (such as using recombination data such as may be found in the HapMap database to create a recombination risk score for any interval) to model dependence between polymorphic alleles on the chromosome or chromosome segment. In some embodiments, allele counts at the polymorphic loci are calculated on a computer based on sequencing data or SNP array data. In some embodiments, a plurality of hypotheses each pertaining to a different possible state of the chromosome or chromosome segment (such as an overrepresentation of the number of copies of a first homologous chromosome segment as compared to a second homologous chromosome segment in the genome of one or more cells from an individual, a duplication of the first homologous chromosome segment, a deletion of the second homologous chromosome segment, or an equal representation of the first and second homologous chromosome segments) are created (such as creation on a computer); a model (such as a joint distribution model) for the expected allele counts at the polymorphic loci on the chromosome is built (such as building on a computer) for each hypothesis; a relative probability of each of the hypotheses is determined (such as determination on a computer) using the joint distribution model and the allele counts; and the hypothesis with the greatest probability is selected. In some embodiments, building a joint distribution model for allele counts and the step of determining the relative probability of each hypothesis are done using a method that does not require the use of a reference chromosome.

In one embodiment, genetic data of an individual is phased using genetic data of one or more relatives of the individual (such as one or more parents, siblings, children, fetuses, embryos, grandparents, uncles, aunts, or cousins). In one embodiment, genetic data of an individual is phased using genetic data of one or more genetic offspring of the individual (e.g., 1, 2, 3, or more offspring), such as embryos, fetuses, born children, or a sample of a miscarriage. In one embodiment, genetic data of a parent (such as a parent of a gestating fetus or embryo) is phased using phased haplotypic data for the other parent along with unphased genetic data of one or more genetic offspring of the parents.

In some embodiments, a sample (e.g., a biopsy such as a tumor biopsy, blood sample, plasma sample, serum sample, or another sample likely to contain mostly or only cells, DNA, or RNA with a CNV of interest) from the individual (such as an individual suspected of having cancer, a fetus, or an embryo) is analyzed to determine the phase for one or more regions that are known or suspected to contain a CNV of interest (such as a deletion or duplication). In some embodiments, the sample has a high tumor fraction (such as 30, 40, 50, 60, 70, 80, 90, 95, 98, 99, or 100%). In some embodiments, a sample (e.g., a maternal whole blood sample, cells isolated from a maternal blood sample, maternal plasma sample, maternal serum sample, amniocentesis sample, placental tissue sample (e.g., chorionic villus, decidua, or placental membrane), cervical mucus sample, fetal tissue after fetal demise, other sample from a fetus, or another sample likely to contain mostly or only cells, DNA, or RNA with a CNV of interest) from a fetus or the pregnant mother of a fetus is analyzed to determine the phase for one or more regions that are known or suspected to contain a CNV of interest (such as a deletion or duplication). In some embodiments, the sample has a high fetal fraction (such as 25, 30, 40, 50, 60, 70, 80, 90, 95, 98, 99, or 100%).

In some embodiments, the sample has a haplotypic imbalance or any aneuploidy. In some embodiments, the sample includes any mixture of two types of DNA where the two types have different ratios of the two haplotypes, and share at least one haplotype. For example, in the fetal-maternal case, the mother is 1:1 and the fetus is 1:0 (plus a paternal haplotype). For example, in the tumor case, the normal tissue is 1:1, and the tumor tissue is 1:0 or 1:2, 1:3, 1:4, etc. In some embodiments, at least 10; 100; 500; 1,000; 2,000; 3,000; 5,000; 8,000; or 10,000 polymorphic loci are analyzed to determine the phase of alleles at some or all of the loci. In some embodiments, a sample is from a cell or tissue that was treated to become aneuploidy, such as aneuploidy induced by prolonged cell culture.

In some embodiments, a large percent or all of the DNA or RNA in the sample has the CNV of interest. In some embodiments, the ratio of DNA or RNA from the one or more target cells that contain the CNV of interest to the total DNA or RNA in the sample is at least 80, 85, 90, 95, or 100%. For samples with a deletion, only one haplotype is present for the cells (or DNA or RNA) with the deletion. This first haplotype can be determined using standard methods to determine the identity of alleles present in the region of the deletion. In samples that only contain cells (or DNA or RNA) with the deletion, there will only be signal from the first haplotype that is present in those cells. In samples that also contain a small amount of cells (or DNA or RNA) without the deletion (such as a small amount of noncancerous cells), the weak signal from the second haplotype in these cells (or DNA or RNA) can be ignored. The second haplotype that is present in other cells, DNA, or RNA from the individual that lack the deletion can be determined by inference. For example, if the genotype of cells from the individual without the deletion is (AB,AB) and the phased data for the individual indicates that the first haplotype is (A,A); then, the other haplotype can be inferred to be (B,B).

For samples in which both cells (or DNA or RNA) with a deletion and cells (or DNA or RNA) without a deletion are present, the phase can still be determined. For example, plots can be generated similar to FIG. 18 or 29 in which the x-axis represents the linear position of the individual loci along the chromosome, and the y-axis represents the number of A allele reads as a fraction of the total (A+B) allele reads. In some embodiments for a deletion, the pattern includes two central bands that represent SNPs for which the individual is heterozygous (top band represents AB from cells without the deletion and A from cells with the deletion, and bottom band represents AB from cells without the deletion and B from cells with the deletion). In some embodiments, the separation of these two bands increases as the fraction of cells, DNA, or RNA with the deletion increases. Thus, the identity of the A alleles can be used to determine the first haplotype, and the identity of the B alleles can be used to determine the second haplotype.

For samples with a duplication, an extra copy of the haplotype is present for the cells (or DNA or RNA) with duplication. This haplotype of the duplicated region can be determined using standard methods to determine the identity of alleles present at an increased amount in the region of the duplication, or the haplotype of the region that is not duplicated can be determined using standard methods to determine the identity of alleles present at an decreased amount. Once one haplotype is determined, the other haplotype can be determined by inference.

For samples in which both cells (or DNA or RNA) with a duplication and cells (or DNA or RNA) without a duplication are present, the phase can still be determined using a method similar to that described above for deletions. For example, plots can be generated similar to FIG. 18 or 29 in which the x-axis represents the linear position of the individual loci along the chromosome, and the y-axis represents the number of A allele reads as a fraction of the total (A+B) allele reads. In some embodiments for a deletion, the pattern includes two central bands that represent SNPs for which the individual is heterozygous (top band represents AB from cells without the duplication and AAB from cells with the duplication, and bottom band represents AB from cells without the duplication and ABB from cells with the duplication). In some embodiments, the separation of these two bands increases as the fraction of cells, DNA, or RNA with the duplication increases. Thus, the identity of the A alleles can be used to determine the first haplotype, and the identity of the B alleles can be used to determine the second haplotype. In some embodiments, the phase of one or more CNV region(s) (such as the phase of at least 50, 60, 70, 80, 90, 95, or 100% of the polymorphic loci in the region that were measured) is determined for a sample (such as a tumor biopsy or plasma sample) from an individual known to have cancer and is used for analysis of subsequent samples from the same individual to monitor the progression of the cancer (such as monitoring for remission or reoccurrence of the cancer). In some embodiments, a sample with a high tumor fraction (such as a tumor biopsy or a plasma sample from an individual with a high tumor load) is used to obtain phased data that is used for analysis of subsequent samples with a lower tumor fraction (such as a plasma sample from an individual undergoing treatment for cancer or in remission).

In another embodiment for prenatal diagnostics, phased parental haplotypic data is to detect the presence of more than one homolog from the father, implying that the genetic material from more than one fetus is present in a maternal blood sample. By focusing on chromosomes that are expected to be euploid in a fetus, one could rule out the possibility that the fetus was afflicted with a trisomy. Also, it is possible to determine if the fetal DNA is not from the current father.

In some embodiments, two or more of the methods described herein are used to phase genetic data of an individual. In some embodiments, both a bioinformatics method (such as using population based haplotype frequencies to infer the most likely phase) and a molecular biology method (such as any of the molecular phasing methods disclosed herein to obtain actual phased data rather than bioinformatics-based inferred phased data) are used. In some embodiments, phased data from other subjects (such as prior subjects) is used to refine the population data. For example, phased data from other subjects can be added to population data to calculate priors for possible haplotypes for another subject. In some embodiments, phased data from other subjects (such as prior subjects) is used to calculate priors for possible haplotypes for another subject.

In some embodiments, probabilistic data may be used. For example, due to the probabilistic nature of the representation of DNA molecules in a sample, as well as various amplification and measurement biases, the relative number of molecules of DNA measured from two different loci, or from different alleles at a given locus, is not always representative of the relative number of molecules in the mixture, or in the individual. If one were trying to determine the genotype of a normal diploid individual at a given locus on an autosomal chromosome by sequencing DNA from the plasma of the individual, one would expect to either observe only one allele (homozygous) or about equal numbers of two alleles (heterozygous). If, at that allele, ten molecules of the A allele were observed, and two molecules of the B allele were observed, it would not be clear if the individual was homozygous at the locus, and the two molecules of the B allele were due to noise or contamination, or if the individual was heterozygous, and the lower number of molecules of the B allele were due to random, statistical variation in the number of molecules of DNA in the plasma, amplification bias, contamination or any number of other causes. In this case, a probability that the individual was homozygous, and a corresponding probability that the individual was heterozygous could be calculated, and these probabilistic genotypes could be used in further calculations.

Note that for a given allele ratio, the likelihood that the ratio closely represents the ratio of the DNA molecules in the individual is greater the greater the number of molecules that are observed. For example, if one were to measure 100 molecules of A and 100 molecules of B, the likelihood that the actual ratio was 50% is considerably greater than if one were to measure 10 molecules of A and 10 molecules of B. In one embodiment, one uses Bayesian theory combined with a detailed model of the data to determine the likelihood that a particular hypothesis is correct given an observation. For example, if one were considering two hypotheses-one that corresponds to a trisomic individual and one that corresponds to a disomic individual-then the probability of the disomic hypothesis being correct would be considerably higher for the case where 100 molecules of each of the two alleles were observed, as compared to the case where 10 molecules of each of the two alleles were observed. As the data becomes noisier due to bias, contamination or some other source of noise, or as the number of observations at a given locus goes down, the probability of the maximum likelihood hypothesis being true given the observed data drops. In practice, it is possible to aggregate probabilities over many loci to increase the confidence with which the maximum likelihood hypothesis may be determined to be the correct hypothesis. In some embodiments, the probabilities are simply aggregated without regard for recombination. In some embodiments, the calculations take into account cross-overs.

In an embodiment, probabilistically phased data is used in the determination of copy number variation. In some embodiments, the probabilistically phased data is population based haplotype block frequency data from a data source such as the HapMap data base. In some embodiments, the probabilistically phased data is haplotypic data obtained by a molecular method, for example phasing by dilution where individual segments of chromosomes are diluted to a single molecule per reaction, but where, due to stochastic noise the identities of the haplotypes may not be absolutely known. In some embodiments, the probabilistically phased data is haplotypic data obtained by a molecular method, where the identities of the haplotypes may be known with a high degree of certainty.

Imagine a hypothetical case where a doctor wanted to determine whether or not an individual had some cells in their body which had a deletion at a particular chromosomal segment by measuring the plasma DNA from the individual. The doctor could make use of the knowledge that if all of the cells from which the plasma DNA originated were diploid, and of the same genotype, then for heterozygous loci, the relative number of molecules of DNA observed for each of the two alleles would fall into one distribution that was centered at 50% A allele and 50% B allele. However, if a fraction of the cells from which the plasma DNA originated had a deletion at a particular chromosome segment, then for heterozygous loci, one would expect that the relative number of molecules of DNA observed for each of the two alleles would fall into two distributions, one centered at above 50% A allele for the loci where there was a deletion of the chromosome segment containing the B allele, and one centered at below 50% for the loci where there was a deletion of the chromosome segment containing the A allele. The greater the proportion of the cells from which the plasma DNA originated contained the deletion, the further from 50% these two distributions would be.

In this hypothetical case, imagine a clinician who wants to determine if an individual had a deletion of a chromosomal region in a proportion of cells in the individual's body. The clinician may draw blood from the individual into a vacutainer or other type of blood tube, centrifuge the blood, and isolate the plasma layer. The clinician may isolate the DNA from the plasma, enrich the DNA at the targeted loci, possibly through targeted or other amplification, locus capture techniques, size enrichment, or other enrichment techniques. The clinician may analyze such as by measuring the number of alleles at a set of SNPs, in other words generating allele frequency data, the enriched and/or amplified DNA using an assay such as qPCR, sequencing, a microarray, or other techniques that measure the quantity of DNA in a sample. We will consider data analysis for the case where the clinician amplified the cell-free plasma DNA using a targeted amplification technique, and then sequenced the amplified DNA to give the following exemplary possible data at six SNPs found on a chromosome segment that is indicative of cancer, where the individual was heterozygotic at those SNPs:

SNP 1:460 reads A allele; 540 reads B allele (46% A)
SNP 2:530 reads A allele; 470 reads B allele (53% A)
SNP 3:40 reads A allele; 60 reads B allele (40% A)
SNP 4:46 reads A allele; 54 reads B allele (46% A)
SNP 5:520 reads A allele; 480 reads B allele (52% A)
SNP 6:200 reads A allele; 200 reads B allele (50% A)

From this set of data, it may be difficult to differentiate between the case where the individual is normal, with all cells being disomic, or where the individual may have a cancer, with some portion of cells whose DNA contributed towards the cell-free DNA found in the plasma having a deletion or duplication at the chromosome. For example, the two hypotheses with the maximum likelihood may be that the individual has a deletion at this chromosome segment, with a tumor fraction of 6%, and where the deleted segment of the chromosome has the genotype over the six SNPs of (A,B,A,A,B,B) or (A,B,A,A,B,A). In this representation of the individual's genotype over a set of SNPs, the first letter in the parentheses corresponds to the genotype of the haplotype for SNP 1, the second to SNP 2, etc.

If one were to use a method to determine the haplotype of the individual at that chromosome segment, and were to find that the haplotype for one of the two chromosomes was (A,B,A,A,B,B), this would agree with the maximum likelihood hypothesis, and the calculated likelihood that the individual has a deletion at that segment, and therefore may have cancerous or precancerous cells, would be considerably increased. On the other hand, if the individual were found to have the haplotype (A,A,A,A,A,A), then the likelihood that the individual has a deletion at that chromosome segment would be considerably decreased, and perhaps the likelihood of the no-deletion hypothesis would be higher (the actual likelihood values would depend on other parameters such as the measured noise in the system, among others).

There are many ways to determine the haplotype of the individual, many of which are described elsewhere in this document. A partial list is given here, and is not meant to be exhaustive. One method is a biological method where individual DNA molecules are diluted until approximately one molecule from each chromosomal region is in any given reaction volume, and then methods such as sequencing are used to measure the genotype. Another method is informatically based where population data on various haplotypes coupled with their frequency can be used in a probabilistic manner. Another method is to measure the diploid data of the individual, along with one or a plurality of related individuals who are expected to share haplotype blocks with the individual and to infer the haplotype blocks. Another method would be to take a sample of tissue with a high concentration of the deleted or duplicated segment, and determine the haplotype based on allelic imbalance, for example, genotype measurements from a sample of tumor tissue with a deletion can be used to determine the phased data for that deletion region, and this data can then be used to determine if the cancer has regrown post-resection.

In practice, typically more than 20 SNPs, more than 50 SNPs, more than 100 SNPs, more than 500 SNPs, more than 1,000 SNPs, or more than 5,000 SNPs are measured on a given chromosome segment.

Exemplary Methods for Phasing, Predicting Allele Ratios, and Reconstructing Fetal Genetic Data In one aspect, the invention features methods for determining one or more haplotypes of a fetus. In various embodiments, this method allows one to determine which polymorphic loci (such as SNPs) were inherited by the fetus and to reconstruct which homologs (including recombination events) are present in the fetus (and thereby interpolate the sequence between the polymorphic loci). If desired, essentially the entire genome of the fetus can be reconstructed. If there is some remaining ambiguity in the genome of the fetus (such as in intervals with a crossover), this ambiguity can be minimized if desired by analyzing additional polymorphic loci. In various embodiments, the polymorphic loci are chosen to cover one or more of the chromosomes at a density to reduce any ambiguity to a desired level. This method has important applications for the detection of polymorphisms or other mutations of interest (such as deletions or duplications) in a fetus since it enables their detection based on linkage (such as the presence of linked polymorphic loci in the fetal genome) rather than by directing detecting the polymorphism or other mutation of interest in the fetal genome. For example, if a parent is a carrier for a mutation associated with cystic fibrosis (CF), a nucleic acid sample that includes maternal DNA from the mother of the fetus and fetal DNA from the fetus can be analyzed to determine whether the fetal DNA include the haplotype containing the CF mutation. In particular, polymorphic loci can be analyzed to determine whether the fetal DNA includes the haplotype containing the CF mutation without having to detect the CF mutation itself in the fetal DNA. This is useful in screening for one or more mutations, such as disease-linked mutations, without having to directly detect the mutations.

In some embodiments, the method involves determining a parental haplotype (e.g., a haplotype of the mother or father of the fetus), such as by using any of the methods described herein. In some embodiments, this determination is made without using data from a relative of the mother or father. In some embodiments, a parental haplotype is determined using a dilution approach followed by SNP genotyping or sequencing as described herein. In some embodiments, a haplotype of the mother (or father) is determined by any of the methods described herein using data from a relative of the mother (or father). In some embodiments, a haplotype is determined for both the father and the mother.

This parental haplotype data can be used to determine if the fetus inherited the parental haplotype. In some embodiments, a nucleic acid sample that includes maternal DNA from the mother of the fetus and fetal DNA from the fetus is analyzed using a SNP array to detect at least 100; 200; 500; 750; 1,000; 2,000; 5,000; 7,500; 10,000; 20,000; 25,000; 30,000; 40,000; 50,000; 75,000; or 100,000 different polymorphic loci. In some embodiments, a nucleic acid sample that includes maternal DNA from the mother of the fetus and fetal DNA from the fetus is analyzed by contacting the sample with a library of primers that simultaneously hybridize to at least 100; 200; 500; 750; 1,000; 2,000; 5,000; 7,500; 10,000; 20,000; 25,000; 30,000; 40,000; 50,000; 75,000; or 100,000 different polymorphic loci (such as SNPs) to produce a reaction mixture. In some embodiments, the reaction mixture is subjected to primer extension reaction conditions to produce amplified products. In some embodiments, the amplified products are measured with a high throughput sequencer to produce sequencing data.

In various embodiments, a fetal haplotype is determined using data about the probability of chromosomes crossing over at different locations in a chromosome or chromosome segment (such as by using recombination data such as may be found in the HapMap database to create a recombination risk score for any interval) to model dependence between polymorphic alleles on the chromosome or chromosome segment as described above. In some embodiments, the method takes into account physical distance of the SNPs (such as SNPs flanking a gene or mutation of interest) and recombination data from location specific recombination likelihoods and the data observed from the genetic measurements of the maternal plasma to obtain the most likely genotype of the fetus. Then PARENTAL SUPPORT™ may be performed on the targeted sequencing or SPN array data obtained from these SNPs to determine which homologs were inherited by the fetus from both parents (see, e.g., U.S. application Ser. No. 11/603,406 (US Publication No. 20070184467), U.S. application Ser. No. 12/076,348 (US Publication No. 20080243398), U.S. application Ser. No. 13/110,685 (U.S. Publication No. 2011/0288780), PCT Application PCT/US09/52730 (PCT Publication No. WO/2010/017214), and PCT Application No. PCT/US10/050824 (PCT Publication No. WO/2011/041485), U.S. application Ser. No. 13/300,235 (U.S. Publication No. 2012/0270212), U.S. application Ser. No. 13/335,043 (U.S. Publication No. 2012/0122701), U.S. application Ser. No. 13/683,604, and U.S. application Ser. No. 13/780,022, which are each hereby incorporated by reference in its entirety).

Assume a generalized example where the possible alleles at one locus are A and B; assignment of the identity A or B to particular alleles is arbitrary. Parental genotypes for a particular SNP, termed genetic contexts, are expressed as maternal genotype|paternal genotype. Thus, if the mother is homozygous and the father is heterozygous, this would be represented as AA|AB. Similarly, if both parents are homozygous for the same allele, the parental genotypes would be represented as AA|AA. Furthermore, the fetus would never have AB or BB states and the number of sequence reads with the B allele will be low, and thus can be used to determine the noise responses of the assay and genotyping platform, including effects such as low level DNA contamination and sequencing errors; these noise responses are useful for modeling expected genetic data profiles. There are only five possible maternal|paternal genetic contexts: AA|AA, AA|AB, AB|AA, AB|AB, and AA|BB; other contexts are equivalent by symmetry. SNPs where the parents are homozygous for the same allele are only informative for determining noise and contamination levels. SNPs where the parents are not homozygous for the same allele are informative in determining fetal fraction and copy number count.

Let $N_{A,i}$ and $N_{B,i}$ represent the number of reads of each allele at SNP i, and let Ci represent the parental genetic context at that locus. The data set for a particular chromosome is represented by $N_{AB}=\{N_{A,i}, N_{B,i}\}$i=1 . . . N and $C=\{C_i\}$, i=1 . . . N. For reconstructing part or all of the fetal genome, it can optionally be determined if the fetus has an aneuploidy (such as a missing or extra copy of a chromosome or chromosome segment). For each individual chromosome or chromosome under study, let H represent the set of one or more hypotheses for the total number of chromosomes, the parental origin of each chromosome, and the positions on the parent chromosomes where recombination occurred during formation of the gametes that fertilized to create the child. The probability of a hypothesis P(H) can be computed using the data from the HapMap database and prior information related to each of the ploidy states.

Furthermore, let F represent the fetal cfDNA fraction in the sample. Given a set of possible H, C, and F, one can compute the probability of $N_{AB}$, $P(N_{AB}|H,F,C)$ based on modeling the noise sources of the molecular assay and the sequencing platform. The goal is to find the hypothesis H and the fetal fraction F that maximizes $P(H,F|N_{AB})$. Using standard Bayesian statistical techniques, and assuming a uniform probability distribution for F from 0 to 1, this can be recast in terms of maximizing the probability of $P(N_{AB}|H,F,C)\,P(H)$ over H and F, all of which can now be computed. The probability of all hypotheses associated with a particular copy number and fetal fraction, e.g., trisomy and F=10%, but covering all possible parental chromosome origins and crossover locations, are summed. The copy number hypothesis with the highest probability is selected as the test result, the fetal fraction associated with that hypothesis reveals the fetal fraction, and the probability associated with that hypothesis is the calculated accuracy of the result.

In some embodiments, the algorithm uses in silico simulations to generate a very large number of hypothetical sequencing data sets that could result from the possible fetal genetic inheritance patterns, sample parameters, and amplification and measurement artifacts of the method. More specifically, the algorithm first utilizes parental genotypes at a large number of SNPs and crossover frequency data from the HapMap database to predict possible fetal genotypes. It then predicts expected data profiles for the sequencing data that would be measured from mixed samples originating from a mother carrying a fetus with each of the possible fetal genotypes and taking into account a variety of parameters including fetal fraction, expected read depth profile, fetal genome equivalents present in the sample, expected amplification bias at each of the SNPs, and a number of noise parameters. A data model describes how the sequencing or SNP array data is expected to appear for each of these hypotheses given the particular parameter set. The hypothesis with the best data fit between this modeled data and the measured data is selected.

If desired, expected allele ratios can be calculated for DNA or RNA from the fetus using the results of what haplotypes were inherited by the fetus. The expected allele ratios can also be calculated for a mixed sample containing nucleic acids from both the mother and the fetus (these allele ratios indicate what is expected for measurement of the total amount of each allele, including the amount of the allele from both maternal nucleic acids and fetal nucleic acids in the sample). The expected allele ratios can be calculated for different hypotheses specifying the degree of overrepresentation of the first homologous chromosome segment.

In some embodiments, the method involves determining whether the fetus has one or more of the following conditions: cystic fibrosis, Huntington's disease, Fragile X, thalassemia, muscular dystrophy (such as Duchenne's muscular dystrophy), Alzheimer, Fanconi Anemia, Gaucher Disease, Mucolipidosis IV, Niemann-Pick Disease, Tay-Sachs disease, Sickle cell anemia, Parkinson disease, Torsion Dystonia, and cancer. In some embodiments, a fetal haplotype is determined for one or more chromosomes taken from the group consisting of chromosomes 13, 18, 21, X, and Y. In some embodiments, a fetal haplotype is determined for all of the fetal chromosomes. In various embodiments, the method determines essentially the entire genome of the fetus. In some embodiments, the haplotype is determined for at least 30, 40, 50, 60, 70, 80, 90, or 95% of the genome of the fetus. In some embodiments, the haplotype determination of the fetus includes information about which allele is present for at least 100; 200; 500; 750; 1,000; 2,000; 5,000; 7,500; 10,000; 20,000; 25,000; 30,000; 40,000; 50,000; 75,000; or 100,000 different polymorphic loci. In some embodiments, this method is used to determine a haplotype or allele ratios for an embryo.

Exemplary Methods for Predicting Allele Ratios

Exemplary methods are described below for calculating expected allele ratios for a sample. Table 1 shows expected allele ratios for a mixed sample (such as a maternal blood sample) containing nucleic acids from both the mother and the fetus. These expected allele ratios indicate what is expected for measurement of the total amount of each allele, including the amount of the allele from both maternal nucleic acids and fetal nucleic acids in the mixed sample. In an example, the mother is heterozygous at two neighboring loci that are expected to cosegregate (e.g., two loci for which no chromosome crossovers are expected between the loci). Thus, the mother is (AB, AB). Now imagine that the phased data for the mother indicates that for one haplotype she is (A, A); thus, for the other haplotype one can infer that she is (B, B). Table 1 gives the expected allele ratios for different hypotheses where the fetal fraction is 20%. For this example, no knowledge of the paternal data is assumed, and the heterozygosity rate is assumed to be 50%. The expected allele ratios are given in terms of (expected proportion of A reads/total number of reads) for each of the two SNPs. These ratios are calculated both using maternal phased data (the knowledge that one haplotype is (A, A) and one is (B, B)) and without using the maternal phased data. Table 1 includes different hypotheses for the number of copies of the chromosome segment in the fetus from each parent.

TABLE 1

Expected Genetic Data for Mixed Sample of Maternal and Fetal Nucleic Acids

| Copy Number Hypothesis | Expected allele ratios when using maternal phased data | Expected allele ratios when not using maternal phased data |
|---|---|---|
| Monosomy | (0.444; 0.444) | (0.444; 0.444) |
| (maternal | (0.444; 0.555) | (0.444; 0.555) |
| copy missing) | (0.555; 0.444) | (0.555; 0.444) |
| | (0.555; 0.555) | (0.555; 0.555) |

TABLE 1-continued

Expected Genetic Data for Mixed Sample of Maternal and Fetal Nucleic Acids

| Copy Number Hypothesis | Expected allele ratios when using maternal phased data | Expected allele ratios when not using maternal phased data |
|---|---|---|
| Monosomy (paternal copy missing) | (0.444; 0.444) | (0.444; 0.444) |
| | (0.555; 0.555) | (0.444; 0.555) |
| | | (0.555; 0.444) |
| | | (0.555; 0.555) |
| Disomy | (0.40; 0.40) | (0.40; 0.40) |
| | (0.40; 0.50) | (0.40; 0.50) |
| | (0.50; 0.40) | (0.40; 0.60) |
| | (0.50; 0.50) | (0.50; 0.40) |
| | (0.50; 0.60) | (0.50; 0.50) |
| | (0.60; 0.50) | (0.50; 0.60) |
| | (0.60; 0.60) | (0.60; 0.40) |
| | | (0.60; 0.50) |
| | | (0.60; 0.60) |
| Trisomy (extra matching maternal copy) | (0.36; 0.36) | (0.36; 0.36) |
| | (0.36; 0.45) | (0.36; 0.45) |
| | (0.45; 0.36) | (0.36; 0.54) |
| | (0.45; 0.45) | (0.36; 0.63) |
| | (0.54; 0.54) | (0.45; 0.36) |
| | (0.54; 0.63) | (0.45; 0.45) |
| | (0.63; 0.54) | (0.45; 0.54) |
| | (0.63; 0.63) | (0.45; 0.63) |
| | | (0.54; 0.36) |
| | | (0.54; 0.45) |
| | | (0.54; 0.54) |
| | | (0.54; 0.63) |
| | | (0.63; 0.36) |
| | | (0.63; 0.45) |
| | | (0.63; 0.54) |
| | | (0.63; 0.63) |
| Trisomy (extra unmatching maternal copy) | (0.45, 0.45) | (0.36; 0.36) |
| | (0.45; 0.54) | (0.36; 0.45) |
| | (0.54; 0.45) | (0.36; 0.54) |
| | (0.54; 0.54) | (0.36; 0.63) |
| | | (0.45; 0.36) |
| | | (0.45; 0.45) |
| | | (0.45; 0.54) |
| | | (0.45; 0.63) |
| | | (0.54; 0.36) |
| | | (0.54; 0.45) |
| | | (0.54; 0.54) |
| | | (0.54; 0.63) |
| | | (0.63; 0.36) |
| | | (0.63; 0.45) |
| | | (0.63; 0.54) |
| | | (0.63; 0.63) |
| Trisomy (extra matching paternal copy) | (0.36; 0.36) | (0.36; 0.36) |
| | (0.36; 0.54) | (0.36; 0.45) |
| | (0.54; 0.36) | (0.36; 0.54) |
| | (0.54; 0.54) | (0.36; 0.63) |
| | (0.45; 0.45) | (0.45; 0.36) |
| | (0.45; 0.63) | (0.45; 0.45) |
| | (0.63; 0.45) | (0.45; 0.54) |
| | (0.63; 0.63) | (0.45; 0.63) |
| | | (0.54; 0.36) |
| | | (0.54; 0.45) |
| | | (0.54; 0.54) |
| | | (0.54; 0.63) |
| | | (0.63; 0.36) |
| | | (0.63; 0.45) |
| | | (0.63; 0.54) |
| | | (0.63; 0.63) |
| Trisomy (extra unmatching paternal copy) | (0.36; 0.36) | (0.36; 0.36) |
| | (0.36; 0.45) | (0.36; 0.45) |
| | (0.36; 0.54) | (0.36; 0.54) |
| | (0.36; 0.63) | (0.36; 0.63) |
| | (0.45; 0.36) | (0.45; 0.36) |
| | (0.45; 0.45) | (0.45; 0.45) |
| | (0.45; 0.54) | (0.45; 0.54) |
| | (0.45; 0.63) | (0.45; 0.63) |
| | (0.54; 0.36) | (0.54; 0.36) |
| | (0.54; 0.45) | (0.54; 0.45) |
| | (0.54; 0.54) | (0.54; 0.54) |
| | (0.54; 0.63) | (0.54; 0.63) |

TABLE 1-continued

Expected Genetic Data for Mixed Sample of Maternal and Fetal Nucleic Acids

| Copy Number Hypothesis | Expected allele ratios when using maternal phased data | Expected allele ratios when not using maternal phased data |
|---|---|---|
| | (0.63; 0.36) | (0.63; 0.36) |
| | (0.63; 0.45) | (0.63; 0.45) |
| | (0.63; 0.54) | (0.63; 0.54) |
| | (0.63; 0.63) | (0.63; 0.63) |

In addition to the fact that using phased data reduces the number of possible expected allele ratios, it also changes the prior likelihood of each of the expected allele ratios, such that the maximum likelihood result is more likely to be correct. Eliminating expected allele ratios or hypotheses that are not possible increases the likelihood that the correct hypothesis will be chosen. As an example, suppose the measured allele ratios are (0.41, 0.59). Without using phased data, one might assume that the hypothesis with maximum likelihood is a disomy hypothesis (given the similarity of the measured allele ratios to expected allele ratios of (0.40, 0.60) for disomy). However, using phased data, one can exclude (0.40, 0.60) as expected allele ratios for the disomy hypothesis, and one can select a trisomy hypothesis as more likely.

Assume the measured allele ratios are (0.4, 0.4). Without any haplotype information, the probability of a maternal deletion at each SNP would be the 0.5×P(A deleted)+0.5×P(B deleted). Therefore, although it looks like A is deleted (missing in the fetus), the likelihood of deletion would be the average of the two. For high enough fetal fraction, one can still determine the most likely hypothesis. For low enough fetal fraction, averaging may work in disfavor of the deletion hypothesis. However, with haplotype information, the probability of homolog 1 being deleted, P (A deleted), is greater and will fit the measured data better. If desired, crossover probabilities between the two loci can also be considered.

In a further illustrative example of combining likelihoods using phased data, consider two consecutive SNPs s1 and s2, and D1 and D2 denote the allele data in these SNPs. Here we provide an example on how to combine the likelihoods for these two SNPs. Let c denote the probability that two consecutive heterozygous SNPs have the same allele in the same homolog (i.e., both SNPs are AB or both SNPs are BA). Hence 1-c is the probability that one SNP is AB and the other one is BA. For example, consider the hypothesis H10 and allelic imbalance value f. First, assume that all likelihoods are computed assuming that all SNPs are either AB or BA. Then, we can combine the likelihoods in two consecutive SNPs as follows:

$$Lik(D_1, D_2 \mid H_{10}, f) = Lik(D_1 \mid H_{10}, f) \times c \times Lik(D_2 \mid H_{10}, f) + Lik(D_1 \mid H_{10}, f) \times (1-c) \times Lik(D_2 \mid H_{01}, f).$$

We can do this recursively to determine the joint likelihood $Lik(D_1, \ldots, D_N|H_{10}, f)$ for all SNPs.

Exemplary Mutations

Exemplary mutations associated with a disease or disorder such as cancer or an increased risk (such as an above normal level of risk) for a disease or disorder such as cancer include single nucleotide variants (SNVs), multiple nucleotide mutations, deletions (such as deletion of a 2 to 30 million base pair region), duplications, or tandem repeats. In some embodiments, the mutation is in DNA, such as cfDNA, cell-free mitochondrial DNA (cf mDNA), cell-free DNA that originated from nuclear DNA (cf nDNA), cellular DNA, or mitochondrial DNA. In some embodiments, the mutation is in RNA, such as cfRNA, cellular RNA, cytoplasmic RNA, coding cytoplasmic RNA, non-coding cytoplasmic RNA, mRNA, miRNA, mitochondrial RNA, rRNA, or tRNA. In some embodiments, the mutation is present at a higher frequency in subjects with a disease or disorder (such as cancer) than subjects without the disease or disorder (such as cancer). In some embodiments, the mutation is indicative of cancer, such as a causative mutation. In some embodiments, the mutation is a driver mutation that has a causative role in the disease or disorder. In some embodiments, the mutation is not a causative mutation. For example, in some cancers, multiple mutations accumulate but some of them are not causative mutations. Mutations (such as those that are present at a higher frequency in subjects with a disease or disorder than subjects without the disease or disorder) that are not causative can still be useful for diagnosing the disease or disorder. In some embodiments, the mutation is loss-of-heterozygosity (LOH) at one or more microsatellites.

In some embodiments, a subject is screened for one of more polymorphisms or mutations that the subject is known to have (e.g., to test for their presence, a change in the amount of cells, DNA, or RNA with these polymorphisms or mutations, or cancer remission or re-occurrence). In some embodiments, a subject is screened for one of more polymorphisms or mutations that the subject is known to be at risk for (such as a subject who has a relative with the polymorphism or mutation). In some embodiments, a subject is screened for a panel of polymorphisms or mutations associated with a disease or disorder such as cancer (e.g., at least 5, 10, 50, 100, 200, 300, 500, 750, 1,000, 1,500, 2,000, or 5,000 polymorphisms or mutations).

Many coding variants associated with cancer are described in Abaan et al., "The Exomes of the NCI-60 Panel: A Genomic Resource for Cancer Biology and Systems Pharmacology", *Cancer Research*, Jul. 15, 2013, and world wide web at dtp.nci.nih.gov/branches/btb/characterizationNCI60.html, which are each hereby incorporated by reference in its entirety). The NCI-60 human cancer cell line panel consists of 60 different cell lines representing cancers of the lung, colon, brain, ovary, breast, prostate, and kidney, as well as leukemia and melanoma. The genetic variations that were identified in these cell lines consisted of two types: type I variants that are found in the normal population, and type II variants that are cancer-specific.

Exemplary polymorphisms or mutations (such as deletions or duplications) are in one or more of the following genes: TP53, PTEN, PIK3CA, APC, EGFR, NRAS, NF2, FBXW7, ERBBs, ATAD5, KRAS, BRAF, VEGF, EGFR, HER2, ALK, p53, BRCA, BRCA1, BRCA2, SETD2, LRP1B, PBRM, SPTA1, DNMT3A, ARID1A, GRIN2A, TRRAP, STAG2, EPHA3/5/7, POLE, SYNE1, C20orf80, CSMD1, CTNNB1, ERBB2, FBXW7, KIT, MUC4, ATM, CDH1, DDX11, DDX12, DSPP, EPPK1, FAM186A, GNAS, HRNR, KRTAP4-11, MAP2K4, MLL3, NRAS, RB1, SMAD4, TTN, ABCC9, ACVR1B, ADAM29, ADAMTS19, AGAP10, AKT1, AMBN, AMPD2, ANKRD30A, ANKRD40, APOBR, AR, BIRC6, BMP2, BRAT1, BTNL8, C12orf4, C1QTNF7, C20orf186, CAPRIN2, CBWD1, CCDC30, CCDC93, CD5L, CDC27, CDC42BPA, CDH9, CDKN2A, CHD8, CHEK2, CHRNA9, CIZ1, CLSPN, CNTN6, COL14A1, CREBBP, CROCC, CTSF, CYP1A2, DCLK1, DHDDS, DHX32, DKK2, DLEC1, DNAH14, DNAH5, DNAH9, DNASEIL3, DUSP16, DYNC2H1, ECT2, EFHB, RRN3P2, TRIM49B, TUBB8P5, EPHA7, ERBB3, ERCC6, FAM21A, FAM21C, FCGBP, FGFR2, FLG2, FLT1, FOLR2, FRYL, FSCB, GAB1, GABRA4, GABRP, GH2, GOLGA6L1, GPHB5, GPR32, GPX5, GTF3C3, HECW1; HIST1H3B, HLA-A, HRAS, HS3ST1, HS6ST1, HSPD1, IDH1, JAK2, KDM5B, KIAA0528, KRT15, KRT38, KRTAP21-1, KRTAP4-5, KRTAP4-7, KRTAP5-4, KRTAP5-5, LAMA4, LATS1, LMF1, LPAR4, LPPR4, LRRFIP1, LUM, LYST, MAP2K1, MARCH1, MARCO, MB21D2, MEGF10, MMP16, MORC1, MRE11A, MTMR3, MUC12, MUC17, MUC2, MUC20, NBPF10, NBPF20, NEK1, NFE2L2, NLRP4, NOTCH2, NRK, NUP93, OBSCN, OR11H1, OR2B11, OR2M4, OR4Q3, OR5D13, OR812, OXSM, PIK3R1, PPP2R5C, PRAME, PRF1, PRG4, PRPF19, PTH2, PTPRC, PTPRJ, RAC1, RAD50, RBM12, RGPD3, RGS22, ROR1, RP11-671M22.1, RP13-996F3.4, RP1L1, RSBN1L, RYR3, SAMD3, SCN3A, SEC31A, SF1, SF3B1, SLC25A2, SLC44A1, SLC4A11, SMAD2, SPTA1, ST6GAL2, STK11, SZT2, TAF1L, TAXIBP1, TBP, TGFB1, TIF1, TMEM14B, TMEM74, TPTE, TRAPPC8, TRPS1, TXNDC6, USP32, UTP20, VASN, VPS72, WASH3P, WWTR1, XPO1, ZFHX4, ZMIZ1, ZNF167, ZNF436, ZNF492, ZNF598, ZRSR2, ABL1, AKT2, AKT3, ARAF, ARFRP1, ARID2, ASXL1, ATR, ATRX, AURKA, AURKB, AXL, BAP1, BARD1, BCL2, BCL2L2, BCL6, BCOR, BCORL1, BLM, BRIP1, BTK, CARD11, CBFB, CBL, CCND1, CCND2, CCND3, CCNE1, CD79A, CD79B, CDC73, CDK12, CDK4, CDK6, CDK8, CDKN1B, CDKN2B, CDKN2C, CEBPA, CHEK1, CIC, CRKL, CRLF2, CSFIR, CTCF, CTNNA1, DAXX, DDR2, DOT1L, EMSY (C11orf30), EP300, EPHA3, EPHA5, EPHB1, ERBB4, ERG, ESR1, EZH2, FAM123B (WTX), FAM46C, FANCA, FANCC, FANCD2, FANCE, FANCF, FANCG, FANCL, FGF10, FGF14, FGF19, FGF23, FGF3, FGF4, FGF6, FGFR1, FGFR2, FGFR3, FGFR4, FLT3, FLT4, FOXL2, GATA1, GATA2, GATA3, GID4 (C17orf39), GNA11, GNA13, GNAQ, GNAS, GPR124, GSK3B, HGF, IDH1, IDH2, IGF1R, IKBKE, IKZF1, IL7R, INHBA, IRF4, IRS2, JAK1, JAK3, JUN, KAT6A (MYST3), KDM5A, KDM5C, KDM6A, KDR, KEAP1, KLHL6, MAP2K2, MAP2K4, MAP3K1, MCL1, MDM2, MDM4, MED12, MEF2B, MEN1, MET, MITF, MLH1, MLL, MLL2, MPL, MSH2, MSH6, MTOR, MUTYH, MYC, MYCL1, MYCN, MYD88, NF1, NFKB1A, NKX2-1, NOTCH1, NPM1, NRAS, NTRK1, NTRK2, NTRK3, PAK3, PALB2, PAX5, PBRM1, PDGFRA, PDGFRB, PDK1, PIK3CG, $PIK3R_2$, $PPP2R_1A$, PRDM1, PRKAR1A, PRKDC, PTCH1, PTPN11, RAD51, RAF1, RARA, RET, RICTOR, RNF43, RPTOR, RUNX1, SMARCA4, SMARCB1, SMO, SOCS1, SOX10, SOX2, SPEN, SPOP, SRC, STAT4, SUFU, TET2, TGFBR2, TNFAIP3, TNFRSF14, TOP1, TP53, TSC1, TSC2, TSHR, VHL, WISP3, WT1, ZNF217, ZNF703, and combinations thereof (Su et al., J Mol Diagn 2011, 13:74-84; DOI: 10.1016/j.jmoldx.2010.11.010; and Abaan et al., "The Exomes of the NCI-60 Panel: A Genomic Resource for Cancer Biology and Systems Pharmacology", *Cancer Research*, Jul. 15, 2013, which are each hereby incorporated by reference in its entirety). In some embodiments, the duplication is a chromosome 1p ("Chr1p") duplication associated with breast cancer. In some embodiments, one or more polymorphisms or mutations are in BRAF, such as the V600E mutation. In some embodiments, one or more polymorphisms or mutations are in K-ras. In some embodiments, there is a combination of one or more polymorphisms or mutations in K-ras and APC. In some embodiments, there is a combination of one or more polymorphisms or mutations in K-ras and p53. In some embodiments, there is a combination of one or more polymorphisms or mutations in APC and p53. In some embodiments, there is a combination of one or more polymorphisms or mutations in K-ras, APC, and p53. In some embodiments, there is a combination of one or more polymorphisms or mutations in K-ras and EGFR. Exemplary polymorphisms or mutations are in one or more of the following microRNAs: miR-15a, miR-16-1, miR-23a, miR-23b, miR-24-1, miR-24-2, miR-27a, miR-27b, miR-29b-2, miR-29c, miR-146, miR-155, miR-221, miR-222, and miR-223 (Calin et al. "A microRNA signature associated with prognosis and progression in chronic lymphocytic leukemia." N Engl J Med 353:1793-801, 2005, which is hereby incorporated by reference in its entirety).

In some embodiments, the deletion is a deletion of at least 0.01 kb, 0.1 kb, 1 kb, 10 kb, 100 kb, 1 mb, 2 mb, 3 mb, 5 mb, 10 mb, 15 mb, 20 mb, 30 mb, or 40 mb. In some embodiments, the deletion is a deletion of between 1 kb to 40 mb, such as between 1 kb to 100 kb, 100 kb to 1 mb, 1 to 5 mb, 5 to 10 mb, 10 to 15 mb, 15 to 20 mb, 20 to 25 mb, 25 to 30 mb, or 30 to 40 mb, inclusive.

In some embodiments, the duplication is a duplication of at least 0.01 kb, 0.1 kb, 1 kb, 10 kb, 100 kb, 1 mb, 2 mb, 3 mb, 5 mb, 10 mb, 15 mb, 20 mb, 30 mb, or 40 mb. In some embodiments, the duplication is a duplication of between 1 kb to 40 mb, such as between 1 kb to 100 kb, 100 kb to 1 mb, 1 to 5 mb, 5 to 10 mb, 10 to 15 mb, 15 to 20 mb, 20 to 25 mb, 25 to 30 mb, or 30 to 40 mb, inclusive.

In some embodiments, the tandem repeat is a repeat of between 2 and 60 nucleotides, such as 2 to 6, 7 to 10, 10 to 20, 20 to 30, 30 to 40, 40 to 50, or 50 to 60 nucleotides, inclusive. In some embodiments, the tandem repeat is a repeat of 2 nucleotides (dinucleotide repeat). In some embodiments, the tandem repeat is a repeat of 3 nucleotides (trinucleotide repeat).

In some embodiments, the polymorphism or mutation is prognostic. Exemplary prognostic mutations include K-ras mutations, such as K-ras mutations that are indicators of post-operative disease recurrence in colorectal cancer (Ryan et al." A prospective study of circulating mutant KRAS2 in the serum of patients with colorectal neoplasia: strong prognostic indicator in postoperative follow up," Gut 52:101-108, 2003; and Lecomte T et al. Detection of free-circulating tumor-associated DNA in plasma of colorectal cancer patients and its association with prognosis," Int J Cancer 100:542-548, 2002, which are each hereby incorporated by reference in its entirety).

In some embodiments, the polymorphism or mutation is associated with altered response to a particular treatment (such as increased or decreased efficacy or side-effects). Examples include K-ras mutations are associated with decreased response to EGFR-based treatments in non-small cell lung cancer (Wang et al. "Potential clinical significance of a plasma-based KRAS mutation analysis in patients with advanced non-small cell lung cancer," Clin Canc Res16: 1324-1330, 2010, which is hereby incorporated by reference in its entirety).

K-ras is an oncogene that is activated in many cancers. Exemplary K-ras mutations are mutations in codons 12, 13, and 61. K-ras cfDNA mutations have been identified in pancreatic, lung, colorectal, bladder, and gastric cancers (Fleischhacker & Schmidt "Circulating nucleic acids (CNAs) and caner—a survey," Biochim Biophys Acta 1775: 181-232, 2007, which is hereby incorporated by reference in its entirety).

p53 is a tumor suppressor that is mutated in many cancers and contributes to tumor progression (Levine & Oren "The first 30 years of p53: growing ever more complex. Nature Rev Cancer," 9:749-758, 2009, which is hereby incorporated by reference in its entirety). Many different codons can be mutated, such as Ser249. p53 cfDNA mutations have been identified in breast, lung, ovarian, bladder, gastric, pancreatic, colorectal, bowel, and hepatocellular cancers (Fleischhacker & Schmidt "Circulating nucleic acids (CNAs) and caner—a survey," Biochim Biophys Acta 1775:181-232, 2007, which is hereby incorporated by reference in its entirety).

BRAF is an oncogene downstream of Ras. BRAF mutations have been identified in glial neoplasm, melanoma, thyroid, and lung cancers (Dias-Santagata et al. BRAF V600E mutations are common in pleomorphic xanthoastrocytoma: diagnostic and therapeutic implications. PLOS ONE 2011; 6: e17948, 2011; Shinozaki et al. Utility of circulating B-RAF DNA mutation in serum for monitoring melanoma patients receiving biochemotherapy. Clin Canc Res 13:2068-2074, 2007; and Board et al. Detection of BRAF mutations in the tumor and serum of patients enrolled in the AZD6244 (ARRY-142886) advanced melanoma phase II study. Brit J Canc 2009; 101:1724-1730, which are each hereby incorporated by reference in its entirety). The BRAF V600E mutation occurs, e.g., in melanoma tumors, and is more common in advanced stages. The V600E mutation has been detected in cfDNA:

EGFR contributes to cell proliferation and is misregulated in many cancers (Downward J. Targeting RAS signaling pathways in cancer therapy. Nature Rev Cancer 3:11-22, 2003; and Levine & Oren "The first 30 years of p53: growing ever more complex. Nature Rev Cancer," 9:749-758, 2009, which is hereby incorporated by reference in its entirety). Exemplary EGFR mutations include those in exons 18-21, which have been identified in lung cancer patients. EGFR cfDNA mutations have been identified in lung cancer patients (Jia et al. "Prediction of epidermal growth factor receptor mutations in the plasma/pleural effusion to efficacy of gefitinib treatment in advanced non-small cell lung cancer," J Canc Res Clin Oncol 2010; 136:1341-1347, 2010, which is hereby incorporated by reference in its entirety).

Exemplary polymorphisms or mutations associated with breast cancer include LOH at microsatellites (Kohler et al. "Levels of plasma circulating cell free nuclear and mitochondrial DNA as potential biomarkers for breast tumors," Mol Cancer 8: doi: 10.1186/1476-4598-8-105, 2009, which is hereby incorporated by reference in its entirety), p53 mutations (such as mutations in exons 5-8) (Garcia et al." Extracellular tumor DNA in plasma and overall survival in breast cancer patients," Genes, Chromosomes & Cancer 45:692-701, 2006, which is hereby incorporated by reference in its entirety), HER2 (Sorensen et al. "Circulating HER2 DNA after trastuzumab treatment predicts survival and response in breast cancer," Anticancer Res30: 2463-2468, 2010, which is hereby incorporated by reference in its entirety), PIK3CA, MED1, and GAS6 polymorphisms or mutations (Murtaza et al. "Non-invasive analysis of acquired resistance to cancer therapy by sequencing of plasma DNA," Nature 2013;doi: 10.1038/nature12065, 2013, which is hereby incorporated by reference in its entirety).

Increased cfDNA levels and LOH are associated with decreased overall and disease-free survival. p53 mutations (exons 5-8) are associated with decreased overall survival. Decreased circulating HER2 cfDNA levels are associated with a better response to HER2-targeted treatment in HER2-positive breast tumor subjects. An activating mutation in PIK3CA, a truncation of MED1, and a splicing mutation in GAS6 result in resistance to treatment.

Exemplary polymorphisms or mutations associated with colorectal cancer include p53, APC, K-ras, and thymidylate synthase mutations and p16 gene methylation (Wang et al. "Molecular detection of APC, K-ras, and p53 mutations in the serum of colorectal cancer patients as circulating biomarkers," World J Surg 28:721-726, 2004; Ryan et al. "A prospective study of circulating mutant KRAS2 in the serum of patients with colorectal neoplasia: strong prognostic indicator in postoperative follow up," Gut 52:101-108, 2003; Lecomte et al. "Detection of free-circulating tumor-associated DNA in plasma of colorectal cancer patients and its association with prognosis," Int J Cancer 100:542-548, 2002; Schwarzenbach et al. "Molecular analysis of the polymorphisms of thymidylate synthase on cell-free circulating DNA in blood of patients with advanced colorectal carcinoma," Int J Cancer 127:881-888, 2009, which are each hereby incorporated by reference in its entirety). Post-operative detection of K-ras mutations in serum is a strong predictor of disease recurrence. Detection of K-ras mutations and p16 gene methylation are associated with decreased survival and increased disease recurrence. Detection of K-ras, APC, and/or p53 mutations is associated with recurrence and/or metastases. Polymorphisms (including LOH, SNPs, variable number tandem repeats, and deletion) in the thymidylate synthase (the target of fluoropyrimidine-based chemotherapies) gene using cfDNA may be associated with treatment response.

Exemplary polymorphisms or mutations associated with lung cancer (such as non-small cell lung cancer) include K-ras (such as mutations in codon 12) and EGFR mutations. Exemplary prognostic mutations include EGFR mutations (exon 19 deletion or exon 21 mutation) associated with increased overall and progression-free survival and K-ras mutations (in codons 12 and 13) are associated with decreased progression-free survival (Jian et al. "Prediction of epidermal growth factor receptor mutations in the plasma/pleural effusion to efficacy of gefitinib treatment in advanced non-small cell lung cancer," J Canc Res Clin Oncol 136:1341-1347, 2010; Wang et al. "Potential clinical significance of a plasma-based KRAS mutation analysis in patients with advanced non-small cell lung cancer," Clin Canc Res 16:1324-1330, 2010, which are each hereby incorporated by reference in its entirety). Exemplary polymorphisms or mutations indicative of response to treatment include EGFR mutations (exon 19 deletion or exon 21 mutation) that improve response to treatment and K-ras mutations (codons 12 and 13) that decrease the response to treatment. A resistance-conferring mutation in EFGR has been identified (Murtaza et al. "Non-invasive analysis of acquired resistance to cancer therapy by sequencing of plasma DNA," Nature doi: 10.1038/nature12065, 2013, which is hereby incorporated by reference in its entirety).

Exemplary polymorphisms or mutations associated with melanoma (such as uveal melanoma) include those in GNAQ, GNA11, BRAF, and p53. Exemplary GNAQ and GNA11 mutations include R183 and Q209 mutations. Q209 mutations in GNAQ or GNA11 are associated with metastases to bone. BRAF V600E mutations can be detected in patients with metastatic/advanced stage melanoma. BRAF V600E is an indicator of invasive melanoma. The presence of the BRAF V600E mutation after chemotherapy is associated with a non-response to the treatment Exemplary polymorphisms or mutations associated with pancreatic carcinomas include those in K-ras and p53 (such as p53 Ser249). p53 Ser249 is also associated with hepatitis B infection and hepatocellular carcinoma, as well as ovarian cancer, and non-Hodgkin's lymphoma.

Even polymorphisms or mutations that are present in low frequency in a sample can be detected with the methods of the invention. For example, a polymorphism or mutation that is present at a frequency of 1 in a million can be observed 10 times by performing 10 million sequencing reads. If desired, the number of sequencing reads can be altered depending of the level of sensitivity desired. In some embodiments, a sample is re-analyzed or another sample from a subject is analyzed using a greater number of sequencing reads to improve the sensitivity. For example, if no or only a small number (such as 1, 2, 3, 4, or 5) polymorphisms or mutations that are associated with cancer or an increased risk for cancer are detected, the sample is re-analyzed or another sample is tested.

In some embodiments, multiple polymorphisms or mutations are required for cancer or for metastatic cancer. In such cases, screening for multiple polymorphisms or mutations improves the ability to accurately diagnose cancer or metastatic cancer. In some embodiments when a subject has a subset of multiple polymorphisms or mutations that are required for cancer or for metastatic cancer, the subject can be re-screened later to see if the subject acquires additional mutations.

In some embodiments in which multiple polymorphisms or mutations are required for cancer or for metastatic cancer, the frequency of each polymorphism or mutation can be compared to see if they occur at similar frequencies. For example, if two mutations required for cancer (denoted "A" and "B"), some cells will have none, some cells with A, some with B, and some with A and B. If A and B are observed at similar frequencies, the subject is more likely to have some cells with both A and B. If observer A and B at dissimilar frequencies, the subject is more likely to have different cell populations.

In some embodiments in which multiple polymorphisms or mutations are required for cancer or for metastatic cancer, the number or identity of such polymorphisms or mutations that are present in the subject can be used to predict how likely or soon the subject is likely to have the disease or disorder. In some embodiments in which polymorphisms or mutations tend to occur in a certain order, the subject may be periodically tested to see if the subject has acquired the other polymorphisms or mutations.

In some embodiments, determining the presence or absence of multiple polymorphisms or mutations (such as 2, 3, 4, 5, 8, 10, 12, 15, or more) increases the sensitivity and/or specificity of the determination of the presence or absence of a disease or disorder such as cancer, or an increased risk for with a disease or disorder such as cancer.

In some embodiments, the polymorphism(s) or mutation(s) are directly detected. In some embodiments, the polymorphism(s) or mutation(s) are indirectly detected by detection of one or more sequences (e.g., a polymorphic locus such as a SNP) that are linked to the polymorphism or mutation.

Exemplary Nucleic Acid Alterations

In some embodiments, there is a change to the integrity of RNA or DNA (such as a change in the size of fragmented cfRNA or cfDNA or a change in nucleosome composition) that is associated with a disease or disorder such as cancer, or an increased risk for a disease or disorder such as cancer. In some embodiments, there is a change in the methylation pattern RNA or DNA that is associated with a disease or disorder such as cancer, or an increased risk for with a disease or disorder such as cancer (e.g., hypermethylation of tumor suppressor genes). For example, methylation of the CpG islands in the promoter region of tumor-suppressor genes has been suggested to trigger local gene silencing. Aberrant methylation of the p16 tumor suppressor gene occurs in subjects with liver, lung, and breast cancer. Other frequently methylated tumor suppressor genes, including APC, Ras association domain family protein 1A (RASSF1A), glutathione S-transferase P1 (GSTP1), and DAPK, have been detected in various type of cancers, for example nasopharyngeal carcinoma, colorectal cancer, lung cancer, esophageal cancer, prostate cancer, bladder cancer, melanoma, and acute leukemia. Methylation of certain tumor-suppressor genes, such as p16, has been described as an early event in cancer formation, and thus is useful for early cancer screening.

In some embodiments, bisulphite conversion or a non-bisulphite based strategy using methylation sensitive restriction enzyme digestion is used to determine the methylation pattern (Hung et al., J Clin Pathol 62:308-313, 2009, which is hereby incorporated by reference in its entirety). On bisulphite conversion, methylated cytosines remain as cytosines while unmethylated cytosines are converted to uracils. Methylation-sensitive restriction enzymes (e.g., BstUI) cleaves unmethylated DNA sequences at specific recognition sites (e.g., 5'-CG V CG-3' for BstUI), while methylated sequences remain intact. In some embodiments, the intact methylated sequences are detected. In some embodiments, stem-loop primers are used to selectively amplify restriction enzyme-digested unmethylated fragments without co-amplifying the non-enzyme-digested methylated DNA.

Exemplary Changes in mRNA Splicing

In some embodiments, a change in mRNA splicing is associated with a disease or disorder such as cancer, or an increased risk for a disease or disorder such as cancer. In some embodiments, the change in mRNA splicing is in one or more of the following nucleic acids associated with cancer or an increased risk for cancer: DNMT3B, BRCA1, KLF6, Ron, or Gemin5. In some embodiments, the detected mRNA splice variant is associated with a disease or disorder, such as cancer. In some embodiments, multiple mRNA splice variants are produced by healthy cells (such as non-cancerous cells), but a change in the relative amounts of the mRNA splice variants is associated with a disease or disorder, such as cancer. In some embodiments, the change in mRNA splicing is due to a change in the mRNA sequence (such as a mutation in a splice site), a change in splicing factor levels, a change in the amount of available splicing factor (such as a decrease in the amount of available splicing factor due to the binding of a splicing factor to a repeat), altered splicing regulation, or the tumor microenvironment.

The splicing reaction is carried out by a multi-protein/RNA complex called the spliceosome (Fackenthall and Godley, Disease Models & Mechanisms 1:37-42, 2008, doi: 10.1242/dmm.000331, which is hereby incorporated by reference in its entirety). The spliceosome recognizes intron-exon boundaries and removes intervening introns via two transesterification reactions that result in ligation of two adjacent exons. The fidelity of this reaction must be exquisite, because if the ligation occurs incorrectly, normal protein-encoding potential may be compromised. For example, in cases where exon-skipping preserves the reading frame of the triplet codons specifying the identity and order of amino acids during translation, the alternatively spliced mRNA may specify a protein that lacks crucial amino acid residues. More commonly, exon-skipping will disrupt the translational reading frame, resulting in premature stop codons. These mRNAs are typically degraded by at least 90% through a process known as nonsense-mediated mRNA degradation, which reduces the likelihood that such defective messages will accumulate to generate truncated protein products. If mis-spliced mRNAs escape this pathway, then truncated, mutated, or unstable proteins are produced.

Alternative splicing is a means of expressing several or many different transcripts from the same genomic DNA and results from the inclusion of a subset of the available exons for a particular protein. By excluding one or more exons, certain protein domains may be lost from the encoded protein, which can result in protein function loss or gain. Several types of alternative splicing have been described: exon skipping; alternative 5' or 3' splice sites; mutually exclusive exons; and, much more rarely, intron retention. Others have compared the amount of alternative splicing in cancer versus normal cells using a bioinformatic approach and determined that cancers exhibit lower levels of alternative splicing than normal cells. Furthermore, the distribution of the types of alternative splicing events differed in cancer versus normal cells. Cancer cells demonstrated less exon skipping, but more alternative 5' and 3' splice site selection and intron retention than normal cells. When the phenomenon of exonization (the use of sequences as exons that are used predominantly by other tissues as introns) was examined, genes associated with exonization in cancer cells were preferentially associated with mRNA processing, indicating a direct link between cancer cells and the generation of aberrant mRNA splice forms.

Exemplary Changes in DNA or RNA Levels

In some embodiments, there is a change in the total amount or concentration of one or more types of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA). In some embodiments, there is a change in the amount or concentration of one or more specific DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, IRNA, or tRNA) molecules. In some embodiments, one allele is expressed more than another allele of a locus of interest. Exemplary miRNAs are short 20-22 nucleotide RNA molecules that regulate the expression of a gene. In some embodiments, there is a change in the transcriptome, such as a change in the identity or amount of one or more RNA molecules.

In some embodiments, an increase in the total amount or concentration of cfDNA or cfRNA is associated with a disease or disorder such as cancer, or an increased risk for a disease or disorder such as cancer. In some embodiments, the total concentration of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) increases by at least 2, 3, 4, 5, 6, 7, 8, 9, 10-fold, or more compared to the total concentration of that type of DNA or RNA in healthy (such as non-cancerous) subjects. In some embodiments, a total concentration of cfDNA between 75 to 100 ng/mL, 100 to 150 ng/mL, 150 to 200 ng/mL, 200 to 300 ng/mL, 300 to 400 ng/mgL, 400 to 600 ng/mL, 600 to 800 ng/mL, 800 to 1,000 ng/mL, inclusive, or a total concentration of cfDNA of more than 100 ng, mL, such as more than 200, 300, 400, 500, 600, 700, 800, 900, or 1,000 ng/mL is indicative of cancer, an increased risk for cancer, an increased risk of a tumor being malignant rather than benign, a decreased probably of the cancer going into remission, or a worse prognosis for the cancer. In some embodiments, the amount of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) having one or more polymorphisms/mutations (such as deletions or duplications) associated with a disease or disorder such as cancer or an increased risk for a disease or disorder such as cancer is at least 2, 3, 4, 5, 6, 7, 8, 9, 10, 11, 12, 14, 16, 18, 20, or 25% of the total amount of that type of DNA or RNA. In some embodiments, at least 2, 3, 4, 5, 6, 7, 8, 9, 10, 11, 12, 14, 16, 18, 20, or 25% of the total amount of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) has a particular polymorphism or mutation (such as a deletion or duplication) associated with a disease or disorder such as cancer or an increased risk for a disease or disorder such as cancer.

In some embodiments, the cfDNA is encapsulated. In some embodiments, the cfDNA is not encapsulated.

In some embodiments, the fraction of tumor DNA out of total DNA (such as fraction of tumor cfDNA out of total cfDNA or fraction of tumor cfDNA with a particular mutation out of total cfDNA) is determined. In some embodiments, the fraction of tumor DNA may be determined for a plurality of mutations, where the mutations can be single nucleotide variants, copy number variants, differential methylation, or combinations thereof. In some embodiments, the average tumor fraction calculated for one or a set of mutations with the highest calculated tumor fraction is taken as the actual tumor fraction in the sample. In some embodiments, the average tumor fraction calculated for all of the mutations is taken as the actual tumor fraction in the sample. In some embodiments, this tumor fraction is used to stage a cancer (since higher tumor fractions can be associated with more advanced stages of cancer). In some embodiments, the tumor fraction is used to size a cancer, since larger tumors may be correlated with the fraction of tumor DNA in the plasma. In some embodiments, the tumor fraction is used to size the proportion of a tumor that is afflicted with a single or plurality of mutations, since there may be a correlation between the measured tumor fraction in a plasma sample and the size of tissue with a given mutation(s) genotype. For example, the size of tissue with a given mutation(s) genotype may be correlated with the fraction of tumor DNA that may be calculated by focusing on that particular mutation(s).

Exemplary Databases

The invention also features databases containing one or more results from a method of the invention. For example, the database may include records with any of the following information for one or more subjects: any polymorphisms/mutations (such as CNVs) identified, any known association of the polymorphisms/mutations with a disease or disorder or an increased risk for a disease or disorder, effect of the polymorphisms/mutations on the expression or activity level of the encoded mRNA or protein, fraction of DNA, RNA, or cells associated with a disease or disorder (such as DNA, RNA, or cells having polymorphism/mutation associated with a disease or disorder) out of the total DNA, RNA, or cells in sample, source of sample used to identify the polymorphisms/mutations (such as a blood sample or sample from a particular tissue), number of diseased cells, results from later repeating the test (such as repeating the test to monitor the progression or remission of the disease or disorder), results of other tests for the disease or disorder, type of disease or disorder the subject was diagnosed with, treatment(s) administered, response to such treatment(s), side-effects of such treatment(s), symptoms (such as symptoms associated with the disease or disorder), length and number of remissions, length of survival (such as length of time from initial test until death or length of time from diagnosis until death), cause of death, and combinations thereof.

In some embodiments, the database includes records with any of the following information for one or more subjects: any polymorphisms/mutations identified, any known association of the polymorphisms/mutations with cancer or an increased risk for cancer, effect of the polymorphisms/mutations on the expression or activity level of the encoded mRNA or protein, fraction of cancerous DNA, RNA or cells out of the total DNA, RNA, or cells in sample, source of sample used to identify the polymorphisms/mutations (such as a blood sample or sample from a particular tissue), number of cancerous cells, size of tumor(s), results from later repeating the test (such as repeating the test to monitor the progression or remission of the cancer), results of other tests for cancer, type of cancer the subject was diagnosed with, treatment(s) administered, response to such treatment (s), side-effects of such treatment(s), symptoms (such as symptoms associated with cancer), length and number of remissions, length of survival (such as length of time from initial test until death or length of time from cancer diagnosis until death), cause of death, and combinations thereof. In some embodiments, the response to treatment includes any of the following: reducing or stabilizing the size of a tumor (e.g., a benign or cancerous tumor), slowing or preventing an increase in the size of a tumor, reducing or stabilizing the number of tumor cells, increasing the disease-free survival time between the disappearance of a tumor and its reappearance, preventing an initial or subsequent occurrence of a tumor, reducing or stabilizing an adverse symptom associated with a tumor, or combinations thereof. In some embodiments, the results from one or more other tests for a disease or disorder such as cancer are included, such as results from screening tests, medical imaging, or microscopic examination of a tissue sample.

In one such aspect, the invention features an electronic database including at least 5, 10, $10^2$, $\mathbf{10^3}$, $\mathbf{10^4}$, $\mathbf{10^5}$, $\mathbf{10^6}$, $\mathbf{10^7}$, $\mathbf{10^8}$ or more records. In some embodiments, the database has records for at least 5, 10, $10^2$, $\mathbf{10^3}$, $\mathbf{10^4}$, $\mathbf{10^5}$, $\mathbf{10^6}$, $\mathbf{10^7}$, $\mathbf{10^8}$ or more different subjects.

In another aspect, the invention features a computer including a database of the invention and a user interface. In some embodiments, the user interface is capable of displaying a portion or all of the information contained in one or more records. In some embodiments, the user interface is capable of displaying (i) one or more types of cancer that have been identified as containing a polymorphism or mutation whose record is stored in the computer, (ii) one or more polymorphisms or mutations that have been identified in a particular type of cancer whose record is stored in the computer, (iii) prognosis information for a particular type of cancer or a particular a polymorphism or mutation whose record is stored in the computer (iv) one or more compounds or other treatments useful for cancer with a polymorphism or mutation whose record is stored in the computer, (v) one or more compounds that modulate the expression or activity of an mRNA or protein whose record is stored in the computer, and (vi) one or more mRNA molecules or proteins whose expression or activity is modulated by a compound whose record is stored in the computer. The internal components of the computer typically include a processor coupled to a memory. The external components usually include a mass-storage device, e.g., a hard disk drive; user input devices, e.g., a keyboard and a mouse; a display, e.g., a monitor; and optionally, a network link capable of connecting the computer system to other computers to allow sharing of data and processing tasks. Programs may be loaded into the memory of this system during operation.

In another aspect, the invention features a computer-implemented process that includes one or more steps of any of the methods of the invention.

Exemplary Risk Factors

In some embodiments, the subject is also evaluated for one or more risk factors for a disease or disorder, such as cancer. Exemplary risk factors include family history for the disease or disorder, lifestyle (such as smoking and exposure to carcinogens) and the level of one or more hormones or serum proteins (such as alpha-fetoprotein (AFP) in liver cancer, carcinoembryonic antigen (CEA) in colorectal cancer, or prostate-specific antigen (PSA) in prostate cancer). In some embodiments, the size and/or number of tumors is measured and use in determining a subject's prognosis or selecting a treatment for the subject.

Exemplary Screening Methods

If desired, the presence or absence of a disease or disorder such cancer can be confirmed, or the disease or disorder such as cancer can be classified using any standard method. For example, a disease or disorder such as cancer can be detected in a number of ways, including the presence of certain signs and symptoms, tumor biopsy, screening tests, or medical imaging (such as a mammogram or an ultrasound). Once a possible cancer is detected, it may be diagnosed by microscopic examination of a tissue sample. In some embodiments, a subject diagnosed undergoes repeat testing using a method of the invention or known testing for the disease or disorder at multiple time points to monitor the progression of the disease or disorder or the remission or reoccurrence of the disease or disorder.

Exemplary Cancers

Exemplary cancers that can be diagnosed, prognosed, stabilized, treated, or prevented using any of the methods of the invention include solid tumors, carcinomas, sarcomas, lymphomas, leukemias, germ cell tumors, or blastomas. In various embodiments, the cancer is an acute lymphoblastic leukemia, acute myeloid leukemia, adrenocortical carcinoma, AIDS-related cancer, AIDS-related lymphoma, anal cancer, appendix cancer, astrocytoma (such as childhood cerebellar or cerebral astrocytoma), basal-cell carcinoma, bile duct cancer (such as extrahepatic bile duct cancer) bladder cancer, bone tumor (such as osteosarcoma or malignant fibrous histiocytoma), brainstem glioma, brain cancer (such as cerebellar astrocytoma, cerebral astrocytoma/malignant glioma, ependymo, medulloblastoma, supratentorial primitive neuroectodermal tumors, or visual pathway and hypothalamic glioma), glioblastoma, breast cancer, bronchial adenoma or carcinoid, burkitt's lymphoma, carcinoid tumor (such as a childhood or gastrointestinal carcinoid tumor), carcinoma central nervous system lymphoma, cerebellar astrocytoma or malignant glioma (such as childhood cerebellar astrocytoma or malignant glioma), cervical cancer, childhood cancer, chronic lymphocytic leukemia, chronic myelogenous leukemia, chronic myeloproliferative disorders, colon cancer, cutaneous t-cell lymphoma, desmoplastic small round cell tumor, endometrial cancer, ependymoma, esophageal cancer, ewing's sarcoma, tumor in the ewing family of tumors, extracranial germ cell tumor (such as a childhood extracranial germ cell tumor), extragonadal germ cell tumor, eye cancer (such as intraocular melanoma or retinoblastoma eye cancer), gallbladder cancer, gastric cancer, gastrointestinal carcinoid tumor, gastrointestinal stromal tumor, germ cell tumor (such as extracranial, extragonadal, or ovarian germ cell tumor), gestational trophoblastic tumor, glioma (such as brain stem, childhood cerebral astrocytoma, or childhood visual pathway and hypothalamic glioma), gastric carcinoid, hairy cell leukemia, head and neck cancer, heart cancer, hepatocellular (liver) cancer, hodgkin lymphoma, hypopharyngeal cancer, hypothalamic and visual pathway glioma (such as childhood visual pathway glioma), islet cell carcinoma (such as endocrine or pancreas islet cell carcinoma), kaposi sarcoma, kidney cancer, laryngeal cancer, leukemia (such as acute lymphoblastic, acute myeloid, chronic lymphocytic, chronic myelogenous, or hairy cell leukemia), lip or oral cavity cancer, liposarcoma, liver cancer (such as non-small cell or small cell cancer), lung cancer, lymphoma (such as AIDS-related, burkitt, cutaneous T cell, Hodgkin, non-hodgkin, or central nervous system lymphoma), macroglobulinemia (such as waldenström macroglobulinemia, malignant fibrous histiocytoma of bone or osteosarcoma, medulloblastoma (such as childhood medulloblastoma), melanoma, merkel cell carcinoma, mesothelioma (such as adult or childhood mesothelioma), metastatic squamous neck cancer with occult, mouth cancer, multiple endocrine neoplasia syndrome (such as childhood multiple endocrine neoplasia syndrome), multiple myeloma or plasma cell neoplasm. mycosis fungoides, myelodysplastic syndrome, myelodysplastic or myeloproliferative disease, myelogenous leukemia (such as chronic myelogenous leukemia), myeloid leukemia (such as adult acute or childhood acute myeloid leukemia), myeloproliferative disorder (such as chronic myeloproliferative disorder), nasal cavity or paranasal sinus cancer, nasopharyngeal carcinoma, neuroblastoma, oral cancer, oropharyngeal cancer, osteosarcoma or malignant fibrous histiocytoma of bone, ovarian cancer, ovarian epithelial cancer, ovarian germ cell tumor, ovarian low malignant potential tumor, pancreatic cancer (such as islet cell pancreatic cancer), paranasal sinus or nasal cavity cancer, parathyroid cancer, penile cancer, pharyngeal cancer, pheochromocytoma, pineal astrocytoma, pineal germinoma. pineoblastoma or supratentorial primitive neuroectodermal tumor (such as childhood pineoblastoma or supratentorial primitive neuroectodermal tumor), pituitary adenoma, plasma cell neoplasia, pleuropulmonary blastoma, primary central nervous system lymphoma, cancer, rectal cancer, renal cell carcinoma, renal pelvis or ureter cancer (such as renal pelvis or ureter transitional cell cancer, retinoblastoma, rhabdomyosarcoma (such as childhood rhabdomyosarcoma), salivary gland cancer, sarcoma (such as sarcoma in the ewing family of tumors, Kaposi, soft tissue, or uterine sarcoma), sézary syndrome, skin cancer (such as nonmelanoma, melanoma, or merkel cell skin cancer), small intestine cancer, squamous cell carcinoma, supratentorial primitive neuroectodermal tumor (such as childhood supratentorial primitive neuroectodermal tumor), T-cell lymphoma (such as cutaneous T-cell lymphoma), testicular cancer, throat cancer, thymoma (such as childhood thymoma), thymoma or thymic carcinoma, thyroid cancer (such as childhood thyroid cancer), trophoblastic tumor (such as gestational trophoblastic tumor), unknown primary site carcinoma (such as adult or childhood unknown primary site carcinoma), urethral cancer (such as endometrial uterine cancer), uterine sarcoma, vaginal cancer, visual pathway or hypothalamic glioma (such as childhood visual pathway or hypothalamic glioma), vulvar cancer, waldenström macroglobulinemia, or wilms tumor (such as childhood wilms tumor). In various embodiments, the cancer has metastasized or has not metastasized.

The cancer may or may not be a hormone related or dependent cancer (e.g., an estrogen or androgen related cancer). Benign tumors or malignant tumors may be diagnosed, prognosed, stabilized, treated, or prevented using the methods and/or compositions of the present invention.

In some embodiments, the subject has a cancer syndrome. A cancer syndrome is a genetic disorder in which genetic mutations in one or more genes predispose the affected individuals to the development of cancers and may also cause the early onset of these cancers. Cancer syndromes often show not only a high lifetime risk of developing cancer, but also the development of multiple independent primary tumors. Many of these syndromes are caused by mutations in tumor suppressor genes, genes that are involved in protecting the cell from turning cancerous. Other genes that may be affected are DNA repair genes, oncogenes and genes involved in the production of blood vessels (angiogenesis). Common examples of inherited cancer syndromes are hereditary breast-ovarian cancer syndrome and hereditary non-polyposis colon cancer (Lynch syndrome).

In some embodiments, a subject with one or more polymorphisms or mutations n K-ras, p53, BRA, EGFR, or HER2 is administered a treatment that targets K-ras, p53, BRA, EGFR, or HER2, respectively.

The methods of the invention can be generally applied to the treatment of malignant or benign tumors of any cell, tissue, or organ type.

Exemplary Treatments

If desired, any treatment for stabilizing, treating, or preventing a disease or disorder such as cancer or an increased risk for a disease or disorder such as cancer can be administered to a subject (e.g., a subject identified as having cancer or an increased risk for cancer using any of the methods of the invention). In various embodiments, the treatment is a known treatment or combination of treatments for a disease or disorder such as cancer, such as cytotoxic agents, targeted therapy, immunotherapy, hormonal therapy, radiation therapy, surgical removal of cancerous cells or cells likely to become cancerous, stem cell transplantation, bone marrow transplantation, photodynamic therapy, palliative treatment, or a combination thereof. In some embodiments, a treatment (such as a preventative medication) is used to prevent, delay, or reduce the severity of a disease or disorder such as cancer in a subject at increased risk for a disease or disorder such as cancer.

In some embodiments, the targeted therapy is a treatment that targets the cancer's specific genes, proteins, or the tissue environment that contributes to cancer growth and survival. This type of treatment blocks the growth and spread of cancer cells while limiting damage to normal cells, usually leading to fewer side effects than other cancer medications.

One of the more successful approaches has been to target angiogenesis, the new blood vessel growth around a tumor. Targeted therapies such as bevacizumab (Avastin), lenalidomide (Revlimid), sorafenib (Nexavar), sunitinib (Sutent), and thalidomide (Thalomid) interfere with angiogenesis. Another example is the use of a treatment that targets HER2, such as trastuzumab or lapatinib, for cancers that overexpress HER2 (such as some breast cancers). In some embodiments, a monoclonal antibody is used to block a specific target on the outside of cancer cells. Examples include alemtuzumab (Campath-1H), bevacizumab, cetuximab (Erbitux), panitumumab (Vectibix), pertuzumab (Omnitarg), rituximab (Rituxan), and trastuzumab. In some embodiments, the monoclonal antibody tositumomab (Bexxar) is used to deliver radiation to the tumor. In some embodiments, an oral small molecule inhibits a cancer process inside of a cancer cell. Examples include dasatinib (Sprycel), erlotinib (Tarceva), gefitinib (Iressa), imatinib (Gleevec), lapatinib (Tykerb), nilotinib (Tasigna), sorafenib, sunitinib, and temsirolimus (Torisel). In some embodiments, a proteasome inhibitor (such as the multiple myeloma drug, bortezomib (Velcade)) interferes with specialized proteins called enzymes that break down other proteins in the cell.

In some embodiments, immunotherapy is designed to boost the body's natural defenses to fight the cancer. Exemplary types of immunotherapy use materials made either by the body or in a laboratory to bolster, target, or restore immune system function.

In some embodiments, hormonal therapy treats cancer by lowering the amounts of hormones in the body. Several types of cancer, including some breast and prostate cancers, only grow and spread in the presence of natural chemicals in the body called hormones. In various embodiments, hormonal therapy is used to treat cancers of the prostate, breast, thyroid, and reproductive system.

In some embodiments, the treatment includes a stem cell transplant in which diseased bone marrow is replaced by highly specialized cells, called hematopoietic stem cells. Hematopoietic stem cells are found both in the bloodstream and in the bone marrow.

In some embodiments, the treatment includes photodynamic therapy, which uses special drugs, called photosensitizing agents, along with light to kill cancer cells. The drugs work after they have been activated by certain kinds of light.

In some embodiments, the treatment includes surgical removal of cancerous cells or cells likely to become cancerous (such as a lumpectomy or a mastectomy). For example, a woman with a breast cancer susceptibility gene mutation (BRCA1 or BRCA2 gene mutation) may reduce her risk of breast and ovarian cancer with a risk reducing salpingo-oophorectomy (removal of the fallopian tubes and ovaries) and/or a risk reducing bilateral mastectomy (removal of both breasts). Lasers, which are very powerful, precise beams of light, can be used instead of blades (scalpels) for very careful surgical work, including treating some cancers.

In addition to treatment to slow, stop, or eliminate the cancer (also called disease-directed treatment), an important part of cancer care is relieving a subject's symptoms and side effects, such as pain and nausea. It includes supporting the subject with physical, emotional, and social needs, an approach called palliative or supportive care. People often receive disease-directed therapy and treatment to ease symptoms at the same time.

Exemplary treatments include actinomycin D, adcetris, Adriamycin, aldesleukin, alemtuzumab, alimta, amsidine, amsacrine, anastrozole, aredia, arimidex, aromasin, asparaginase, avastin, bevacizumab, bicalutamide, bleomycin, bondronat, bonefos, bortezomib, busilvex, busulphan, campto, capecitabine, carboplatin, carmustine, casodex, cetuximab, chimax, chlorambucil, cimetidine, cisplatin, cladribine, clodronate, clofarabine, crisantaspase, cyclophosphamide, cyproterone acetate, cyprostat, cytarabine, cytoxan, dacarbozine, dactinomycin, dasatinib, daunorubicin, dexamethasone, diethylstilbestrol, docetaxel, doxorubicin, drogenil, emcyt, epirubicin, eposin, Erbitux, erlotinib, estracyte, estramustine, etopophos, etoposide, evoltra, exemestane, fareston, femara, filgrastim, fludara, fludarabine, fluorouracil, flutamide, gefinitib, gemcitabine, gemzar, gleevec, glivec. gonapeptyl depot, goserelin, halaven, herceptin, hycamptin, hydroxycarbamide, ibandronic acid, ibritumomab, idarubicin, ifosfomide, interferon, imatinib mesylate, iressa, irinotecan, jevtana, lanvis, lapatinib, letrozole, leukeran, leuprorelin, leustat, lomustine, mabcampath, mabthera, megace, megestrol, methotrexate, mitozantrone, mitomycin, mutulane, myleran, navelbine, neulasta, neupogen, nexavar, nipent, nolvadex D, novantron, oncovin, paclitaxel, pamidronate, PCV, pemetrexed, pentostatin, perjeta, procarbazine, provenge, prednisolone, prostrap, raltitrexed, rituximab, sprycel, sorafenib, soltamox, streptozocin, stilboestrol, stimuvax, sunitinib, sutent, tabloid, tagamet, tamofen, tamoxifen, tarceva, taxol, taxotere, tegafur with uracil, temodal, temozolomide, thalidomide, thioplex, thiotepa, tioguanine, tomudex, topotecan, toremifene, trastuzumab, tretinoin, treosulfan, triethylenethiophorsphoramide, triptorelin, tyverb, uftoral, velcade, vepesid, vesanoid, vincristine, vinorelbine, xalkori, xeloda, yervoy, zactima, zanosar, zavedos, zevelin, zoladex, zoledronate, zometa zoledronic acid, and zytiga.

For subjects that express both a mutant form (e.g., a cancer-related form) and a wild-type form (e.g., a form not associated with cancer) of an mRNA or protein, the therapy preferably inhibits the expression or activity of the mutant form by at least 2, 5, 10, or 20-fold more than it inhibits the expression or activity of the wild-type form. The simultaneous or sequential use of multiple therapeutic agents may greatly reduce the incidence of cancer and reduce the number of treated cancers that become resistant to therapy. In addition, therapeutic agents that are used as part of a combination therapy may require a lower dose to treat cancer than the corresponding dose required when the therapeutic agents are used individually. The low dose of each compound in the combination therapy reduces the severity of potential adverse side-effects from the compounds.

In some embodiments, a subject identified as having an increased risk of cancer may invention or any standard method), avoid specific risk factors, or make lifestyle changes to reduce any additional risk of cancer.

In some embodiments, the polymorphisms, mutations, risk factors, or any combination thereof are used to select a treatment regimen for the subject. In some embodiments, a larger dose or greater number of treatments is selected for a subject at greater risk of cancer or with a worse prognosis.

Other Compounds for Inclusion in Individual or Combination Therapies

If desired, additional compounds for stabilizing, treating, or preventing a disease or disorder such as cancer or an increased risk for a disease or disorder such as cancer may be identified from large libraries of both natural product or synthetic (or semi-synthetic) extracts or chemical libraries according to methods known in the art. Those skilled in the field or drug discovery and development will understand that the precise source of test extracts or compounds is not critical to the methods of the invention. Accordingly, virtually any number of chemical extracts or compounds can be screened for their effect on cells from a particular type of cancer or from a particular subject or screened for their effect on the activity or expression of cancer related molecules (such as cancer related molecules known to have altered activity or expression in a particular type of cancer). When a crude extract is found to modulate the activity or expression of a cancer related molecule, further fractionation of the positive lead extract may be performed to isolate chemical constituent responsible for the observed effect using methods known in the art.

Exemplary Assays and Animal Models for the Testing of Therapies

If desired, one or more of the treatment disclosed herein can be tested for their effect on a disease or disorder such as cancer using a cell line (such as a cell line with one or more of the mutations identified in the subject who has been diagnosed with cancer or an increased risk of cancer using the methods of the invention) or an animal model of the disease or disorder, such as a SCID mouse model (Jain et al., Tumor Models In Cancer Research, ed. Teicher, Humana Press Inc., Totowa, N.J., pp. 647-671, 2001, which is hereby incorporated by reference in its entirety). Additionally, there are numerous standard assays and animal models that can be used to determine the efficacy of particular therapies for stabilizing, treating, or preventing a disease or disorder such as cancer or an increased risk for a disease or disorder such as cancer. Therapies can also be tested in standard human clinical trials.

For the selection of a preferred therapy for a particular subject, compounds can be tested for their effect on the expression or activity on one or more genes that are mutated in the subject. For example, the ability of a compound to modulate the expression of particular mRNA molecules or proteins can be detected using standard Northern, Western, or microarray analysis. In some embodiments, one or more compounds are selected that (i) inhibit the expression or activity of mRNA molecules or proteins that promote cancer that are expressed at a higher than normal level or have a higher than normal level of activity in the subject (such as in a sample from the subject) or (ii) promote the expression or activity of mRNA molecules or proteins that inhibit cancer that are expressed at a lower than normal level or have a lower than normal level of activity in the subject. An individual or combination therapy that (i) modulates the greatest number of mRNA molecules or proteins that have mutations associated with cancer in the subject and (ii) modulates the least number of mRNA molecules or proteins that do not have mutations associated with cancer in the subject. In some embodiments, the selected individual or combination therapy has high drug efficacy and produces few, if any, adverse side-effects.

As an alternative to the subject-specific analysis described above, DNA chips can be used to compare the expression of mRNA molecules in a particular type of early or late-stage cancer (e.g., breast cancer cells) to the expression in normal tissue (Marrack et al., Current Opinion in Immunology 12, 206-209, 2000; Harkin, Oncologist. 5:501-507, 2000; Pelizzari et al., Nucleic Acids Res. 28 (22): 4577-4581, 2000, which are each hereby incorporated by reference in its entirety). Based on this analysis, an individual or combination therapy for subjects with this type of cancer can be selected to modulate the expression of the mRNA or proteins that have altered expression in this type of cancer.

In addition to being used to select a therapy for a particular subject or group of subjects, expression profiling can be used to monitor the changes in mRNA and/or protein expression that occur during treatment. For example, expression profiling can be used to determine whether the expression of cancer related genes has returned to normal levels. If not, the dose of one or more compounds in the therapy can be altered to either increase or decrease the effect of the therapy on the expression levels of the corresponding cancer related gene(s). In addition, this analysis can be used to determine whether a therapy affects the expression of other genes (e.g., genes that are associated with adverse side-effects). If desired, the dose or composition of the therapy can be altered to prevent or reduce undesired side-effects.

Exemplary Formulations and Methods of Administration

For stabilizing, treating, or preventing a disease or disorder such as cancer or an increased risk for a disease or disorder such as cancer, a composition may be formulated and administered using any method known to those of skill in the art (see, e.g., U.S. Pat. Nos. 8,389,578 and 8,389,557, which are each hereby incorporated by reference in its entirety). General techniques for formulation and administration are found in "Remington: The Science and Practice of Pharmacy," 21 st Edition, Ed. David Troy, 2006, Lippincott Williams & Wilkins, Philadelphia, Pa., which is hereby incorporated by reference in its entirety). Liquids, slurries, tablets, capsules, pills, powders, granules, gels, ointments, suppositories, injections, inhalants, and aerosols are examples of such formulations. By way of example, modified or extended release oral formulation can be prepared using additional methods known in the art. For example, a suitable extended release form of an active ingredient may be a matrix tablet or capsule composition. Suitable matrix forming materials include, for example, waxes (e.g., carnauba, bees wax, paraffin wax, ceresin, shellac wax, fatty acids, and fatty alcohols), oils, hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tableting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Optionally, the finished tablet may be coated or uncoated.

Typical routes of administering such compositions include, without limitation, oral, sublingual, buccal, topical, transdermal, inhalation, parenteral (e.g., subcutaneous, intravenous, intramuscular, intrasternal injection, or infusion techniques), rectal, vaginal, and intranasal. In preferred embodiments, the therapy is administered using an extended release device. Compositions of the invention are formulated so as to allow the active ingredient(s) contained therein to be bioavailable upon administration of the composition. Compositions may take the form of one or more dosage units. Compositions may contain 1, 2, 3, 4, or more active ingredients and may optionally contain 1, 2, 3, 4, or more inactive ingredients.

ALTERNATE EMBODIMENTS

Any of the methods described herein may include the output of data in a physical format, such as on a computer screen, or on a paper printout. Any of the methods of the invention may be combined with the output of the actionable data in a format that can be acted upon by a physician. Some of the embodiments described in the document for determining genetic data pertaining to a target individual may be combined with the notification of a potential chromosomal abnormality (such as a deletion or duplication), or lack thereof, with a medical professional, optionally combined with the decision to abort, or to not abort, a fetus in the context of prenatal diagnosis. Some of the embodiments described herein may be combined with the output of the actionable data, and the execution of a clinical decision that results in a clinical treatment, or the execution of a clinical decision to make no action.

In some embodiments, a method is disclosed herein for generating a report disclosing a result of any method of the invention (such as the presence or absence of a deletion or duplication). A report may be generated with a result from a method of the invention, and it may be sent to a physician electronically, displayed on an output device (such as a digital report), or a written report (such as a printed hard copy of the report) may be delivered to the physician. In addition, the described methods may be combined with the actual execution of a clinical decision that results in a clinical treatment, or the execution of a clinical decision to make no action.

In certain embodiments, the present invention provides reagents, kits, and methods, and computer systems and computer media with encoded instructions for performing such methods, for detecting both CNVs and SNVs from the same sample using the multiplex PCR methods disclosed herein. In certain preferred embodiments the sample is a single cell sample or a plasma sample suspected of containing circulating tumor DNA. These embodiments take advantage of the discovery that by interrogating DNA samples from single cells or plasma for CNVs and SNVs using the highly sensitive multiplex PCR methods disclosed herein, improved cancer detection can be achieved, versus interrogating for either CNVs or SNVs alone, especially for cancers exhibiting CNV such as breast, ovarian, and lung cancer. The methods in certain illustrative embodiments for analyzing CNVs interrogate for between 50 and 100,000 or 50 and 10,000, or 50 and 1,000 SNPs and for SNVs interrogate for between 50 and 1000 SNVs or for between 50 and 500 SNVs or for between 50 and 250 SNVs. The methods provided herein for detecting CNVs and/or SNVs in plasma of subjects suspected of having cancer, including for example, cancers known to exhibit CNVs and SNVs, such as breast, lung, and ovarian cancer, provide the advantage of detecting CNVs and/or SNVs from tumors that often are composed of heterogeneous cancer cell populations in terms of genetic compositions. Thus, traditional methods, which focus on analyzing only certain regions of the tumors can often miss CNVs or SNVs that are present in cells in other regions of the tumor. The plasma samples act as liquid biopsies that can be interrogated to detect any of the CNVs and/or SNVs that are present in only subpopulations of tumor cells.

Example Computer Architecture

FIG. 69 shows an example system architecture X00 useful for performing embodiments of the present invention. System architecture X00 includes an analysis platform X08 connected to one or more laboratory information systems ("LISs") X04. As shown in FIG. 69, analysis platform X08 may be connected to LIS X04 over a network X02. Network X02 may include one or more networks of one or more network types, including any combination of LAN, WAN, the Internet, etc. Network X02 may encompass connections between any or all components in system architecture X00. Analysis platform X08 may alternatively or additionally be connected directly to LIS X06. In an embodiment, analysis platform X08 analyzes genetic data provided by LIS X04 in a software-as-a-service model, where LIS X04 is a third-party LIS, while analysis platform X08 analyzes genetic data provided by LIS X06 in a full-service or in-house model, where LIS X06 and analysis platform X08 are controlled by the same party. In an embodiment where analysis platform X08 is providing information over network X02, analysis platform X08 may be a server.

In an example embodiment, laboratory information system X04 includes one or more public or private institutions that collect, manage, and/or store genetic data. A person having skill in the relevant art(s) would understand that methods and standards for securing genetic data are known and can be implemented using various information security techniques and policies, e.g., username/password, Transport Layer Security (TLS), Secure Sockets Layer (SSL), and/or other cryptographic protocols providing communication security.

In an example embodiment, system architecture X00 operates as a service-oriented architecture and uses a client-server model that would be understood by one of skill in the relevant art(s) to enable various forms of interaction and communication between LIS X04 and analysis platform X08. System architecture X00 may be distributed over various types of networks X02 and/or may operate as cloud computing architecture. Cloud computing architecture may include any type of distributed network architecture. By way of example and not of limitation, cloud computing architecture is useful for providing software as a service (SaaS), infrastructure as a service (IaaS), platform as a service (PaaS), network as a service (NaaS), data as a service (DaaS), database as a service (DBaaS), backend as a service (BaaS), test environment as a service (TEaaS), API as a service (APIaaS), integration platform as a service (IPaaS) etc.

In an example embodiment, LISs X04 and X06 each include a computer, device, interface, etc. or any sub-system thereof. LISs X04 and X06 may include an operating system (OS), applications installed to perform various functions such as, for example, access to and/or navigation of data made accessible locally, in memory, and/or over network X02. In an embodiment, LIS X04 accesses analysis platform X08 through an application programming interface ("API"). LIS X04 may also include one or more native applications that may operate independently of an API.

In an example embodiment, analysis platform X08 includes one or more of an input processor X12, a hypothesis manager X14, a modeler X16, an error correction unit X18, a machine learning unit X20, and an output processor X18. Input processor X12 receives and processes inputs from LISs X04 and/or X06. Processing may include but is not limited to operations such as parsing, transcoding, translating, adapting, or otherwise handling any input received from LISs X04 and/or X06. Inputs may be received via one or more streams, feeds, databases, or other sources of data, such as may be made accessible by LISs X04 and X06. Data errors may be corrected by error correction unit X18 through performance of the error correction mechanisms described above.

In an example embodiment, hypothesis manager X14 is configured to receive the inputs passed from input processor X12 in a form ready to be processed in accordance with hypotheses for genetic analysis that are represented as models and/or algorithms. Such models and/or algorithms may be used by modeler X16 to generate probabilities, for example, based on dynamic, real-time, and/or historical statistics or other indicators. Data used to derive and populate such strategy models and/or algorithms are available to hypothesis manager X14 via, for example, genetic data source X10. Genetic data source X10 may include, for example, a nucleic acid sequencer. Hypothesis manager X14 may be configured to formulate hypotheses based on, for example, the variables required to populate its models and/or algorithms. Models and/or algorithms, once populated, may be used by modeler X16 to generate one or more hypotheses as described above. Hypothesis manager X14 may select a particular value, range of values, or estimate based on a most-likely hypothesis as an output as described above. Modeler X16 may operate in accordance with models and/or algorithms trained by machine learning unit X20. For example, machine learning unit X20 may develop such models and/or algorithms by applying a classification algorithm as described above to a training set database (not shown). In certain embodiments, the machine learning unit analyzes one or more control samples to generate training data sets useful in SNV detections methods provided herein.

Once hypothesis manager X14 has identified a particular output, such output may be returned to the particular LIS 104 or 106 requesting the information by output processor X22.

Various aspects of the disclosure can be implemented on a computing device by software, firmware, hardware, or a combination thereof. FIG. 70 illustrates an example computer system Y00 in which the contemplated embodiments, or portions thereof, can be implemented as computer-readable code. Various embodiments are described in terms of this example computer system Y00.

Processing tasks in the embodiment of FIG. 70 are carried out by one or more processors Y02. However, it should be noted that various types of processing technology may be used here, including programmable logic arrays (PLAs), application-specific integrated circuits (ASICs), multi-core processors, multiple processors, or distributed processors. Additional specialized processing resources such as graphics, multimedia, or mathematical processing capabilities may also be used to aid in certain processing tasks. These processing resources may be hardware, software, or an appropriate combination thereof. For example, one or more of processors Y02 may be a graphics-processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data. Alternatively or in addition, one or more of processors Y02 may be a special parallel processing without the graphics optimization, such parallel processors performing the mathematically intensive functions described herein. One or more of processors Y02 may include a processing accelerator (e.g., DSP or other special-purpose processor).

Computer system Y00 also includes a main memory Y30, and may also include a secondary memory Y40. Main memory Y30 may be a volatile memory or non-volatile memory, and divided into channels. Secondary memory Y40 may include, for example, non-volatile memory such as a hard disk drive Y50, a removable storage drive Y60, and/or a memory stick. Removable storage drive Y60 may comprise a floppy disk drive, a magnetic tape drive, an optical disk drive, a flash memory, or the like. The removable storage drive Y60 reads from and/or writes to a removable storage unit 470 in a well-known manner. Removable storage unit Y70 may comprise a floppy disk, magnetic tape, optical disk, etc. which is read by and written to by removable storage drive Y60. As will be appreciated by persons skilled in the relevant art(s), removable storage unit Y70 includes a computer usable storage medium having stored therein computer software and/or data.

In alternative implementations, secondary memory Y40 may include other similar means for allowing computer programs or other instructions to be loaded into computer system Y00. Such means may include, for example, a removable storage unit Y70 and an interface (not shown). Examples of such means may include a program cartridge and cartridge interface (such as that found in video game devices), a removable memory chip (such as an EPROM, or PROM) and associated socket, and other removable storage units Y70 and interfaces which allow software and data to be transferred from the removable storage unit Y70 to computer system Y00.

Computer system Y00 may also include a memory controller Y75. Memory controller Y75 controls data access to main memory Y30 and secondary memory Y40. In some embodiments, memory controller Y75 may be external to processor Y10, as shown in FIG. 70. In other embodiments, memory controller Y75 may also be directly part of processor Y10. For example, many AMD™ and Intel™ processors use integrated memory controllers that are part of the same chip as processor Y10 (not shown in FIG. 70).

Computer system Y00 may also include a communications and network interface Y80. Communication and network interface Y80 allows software and data to be transferred between computer system Y00 and external devices. Communications and network interface Y80 may include a modem, a communications port, a PCMCIA slot and card, or the like. Software and data transferred via communications and network interface Y80 are in the form of signals which may be electronic, electromagnetic, optical, or other signals capable of being received by communication and network interface Y80. These signals are provided to communication and network interface Y80 via a communication path Y85. Communication path Y85 carries signals and may be implemented using wire or cable, fiber optics, a phone line, a cellular phone link, an RF link or other communications channels.

The communication and network interface Y80 allows the computer system Y00 to communicate over communication networks or mediums such as LANs, WANs the Internet, etc. The communication and network interface Y80 may interface with remote sites or networks via wired or wireless connections.

In this document, the terms "computer program medium," "computer-usable medium" and "non-transitory medium" are used to generally refer to tangible media such as removable storage unit Y70, removable storage drive Y60, and a hard disk installed in hard disk drive Y50. Signals carried over communication path Y85 can also embody the logic described herein. Computer program medium and computer usable medium can also refer to memories, such as main memory Y30 and secondary memory Y40, which can be memory semiconductors (e.g. DRAMs, etc.). These computer program products are means for providing software to computer system Y00.

Computer programs (also called computer control logic) are stored in main memory Y30 and/or secondary memory Y40. Computer programs may also be received via communication and network interface Y80. Such computer programs, when executed, enable computer system Y00 to implement embodiments as discussed herein. In particular, the computer programs, when executed, enable processor Y10 to implement the disclosed processes. Accordingly, such computer programs represent controllers of the computer system Y00. Where the embodiments are implemented using software, the software may be stored in a computer program product and loaded into computer system Y00 using removable storage drive Y60, interfaces, hard drive Y50 or communication and network interface Y80, for example.

The computer system Y00 may also include input/output/display devices Y90, such as keyboards, monitors, pointing devices, touchscreens, etc.

It should be noted that the simulation, synthesis and/or manufacture of various embodiments may be accomplished, in part, through the use of computer readable code, including general programming languages (such as C or C++), hardware description languages (HDL) such as, for example, Verilog HDL, VHDL, Altera HDL (AHDL), or other available programming tools. This computer readable code can be disposed in any known computer-usable medium including a semiconductor, magnetic disk, optical disk (such as CD-ROM, DVD-ROM). As such, the code can be transmitted over communication networks including the Internet.

The embodiments are also directed to computer program products comprising software stored on any computer-usable medium. Such software, when executed in one or more data processing devices, causes a data processing device(s) to operate as described herein. Embodiments employ any computer-usable or-readable medium, and any computer-usable or-readable storage medium known now or in the future. Examples of computer-usable or computer-readable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nano-technological storage devices, etc.), and communication mediums (e.g., wired and wireless communications networks, local area networks, wide area networks, intranets, etc.). Computer-usable or computer-readable mediums can include any form of transitory (which include signals) or non-transitory media (which exclude signals). Non-transitory media comprise, by way of non-limiting example, the aforementioned physical storage devices (e.g., primary and secondary storage devices).

It will be understood that any of the embodiments disclosed herein can be used in combination with any other embodiment disclosed herein.

Experimental Section

The presently disclosed embodiments are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to use the described embodiments, and is not intended to limit the scope of the disclosure nor is it intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by volume, and temperature is in degrees Centigrade. It should be understood that variations in the methods as described may be made without changing the fundamental aspects that the experiments are meant to illustrate.

Example 1

Exemplary sample preparation and amplification methods are described in U.S. application Ser. No. 13/683,604, filed Nov. 21, 2012; U.S. Publication No. 2013/0123120, and U.S. Ser. No. 61/994,791, filed May 16, 2014, which is hereby incorporated by reference in its entirety. These methods can be used for analysis of any of the samples disclosed herein.

In one experiment, plasma samples were prepared and amplified using a hemi-nested 19,488-plex protocol. The samples were prepared in the following way: up to 20 mL of blood were centrifuged to isolate the buffy coat and the plasma. The genomic DNA in the blood sample was prepared from the buffy coat. Genomic DNA can also be prepared from a saliva sample. Cell-free DNA in the plasma was isolated using the QIAGEN CIRCULATING NUCLEIC ACID kit and eluted in 50 uL TE buffer according to manufacturer's instructions. Universal ligation adapters were appended to the end of each molecule of 40 uL of purified plasma DNA and libraries were amplified for 9 cycles using adaptor specific primers. Libraries were purified with AGENCOURT AMPURE beads and eluted in 50 ul DNA suspension buffer.

6 ul of the DNA was amplified with 15 cycles of STAR 1 (95° C. for 10 min for initial polymerase activation, then 15 cycles of 96° C. for 30 s; 65° C. for 1 min; 58° C. for 6 min; 60° C. for 8 min; 65° C. for 4 min and 72° C. for 30s; and a final extension at 72° C. for 2 min) using 7.5 nM primer concentration of 19,488 target-specific tagged reverse primers and one library adaptor specific forward primer at 500 nM.

The hemi-nested PCR protocol involved a second amplification of a dilution of the STAR 1 product for 15 cycles (STAR 2) (95° C. for 10 min for initial polymerase activation, then 15 cycles of 95° C. for 30s; 65° C. for 1 min; 60° C. for 5 min; 65° C. for 5 min and 72° C. for 30s; and a final extension at 72° C. for 2 min) using reverse tag concentration of 1000 nM, and a concentration of 20 nM for each of 19,488 target-specific forward primers.

An aliquot of the STAR 2 products was then amplified by standard PCR for 12 cycles with 1 uM of tag-specific forward and barcoded reverse primers to generate barcoded sequencing libraries. An aliquot of each library was mixed with libraries of different barcodes and purified using a spin column.

In this way, 19,488 primers were used in the single-well reactions; the primers were designed to target SNPs found on chromosomes 1, 2, 13, 18, 21, X and Y. The amplicons were then sequenced using an ILLUMINA GAIIX sequencer. If desired, the number of sequencing reads can be increased to increase the number of targeted SNPs that are amplified and sequenced.

Relevant genomic DNA samples amplified using a semi-nested 19,488 outer forward primers and tagged reverse primers at 7.5 nM in the STAR 1. Thermocycling conditions and composition of STAR 2, and the barcoding PCR were the same as for the hemi-nested protocol.

Example 2

Exemplary primer selection methods are described in U.S. application Ser. No. 13/683,604, filed Nov. 21, 2012 (U.S. Publication No. 2013/0123120) and U.S. Ser. No. 61/994,791, filed May 16, 2014, which is hereby incorporated by reference in its entirety). These methods can be used for analysis of any of the samples disclosed herein.

The following experiment illustrates an exemplary method for designing and selecting a library of primers that can be used in any of the multiplexed PCR methods of the invention. The goal is to select primers from an initial library of candidate primers that can be used to simultaneously amplify a large number of target loci (or a subset of target loci) in a single reaction volume. For an initial set of candidate target loci, primers did not have to be designed or selected for each target locus. Preferably, primers are designed and selected for a large portion of the most desirable target loci.

Step 1

A set of candidate target loci (such as SNPs) were selected based on publicly available information about desired parameters for the target loci, such as frequency of the SNPs within a target population or heterozygosity of the rate SNPs (worldwide web at ncbi.nlm.nih.gov/projects/SNP/; Sherry ST, Ward MH, Kholodov M, et al. dbSNP: the NCBI database of genetic variation. Nucleic Acids Res. 2001 Jan. 1;29 (1): 308-11, which are each incorporated by reference in its entirety). For each candidate locus, one or more PCR primer pairs were designed using the Primer3 program (the worldwide web at primer3.sourceforge.net; libprimer3 release 2.2.3, which is hereby incorporated by reference in its entirety). If there were no feasible designs for PCR primers for a particular target locus, then that target locus was eliminated from further consideration.

If desired, a "target locus score" (higher score representing higher desirability) can be calculated for most or all of the target loci, such as a target locus score calculated based on a weighted average of various desired parameters for the target loci. The parameters may be assigned different weights based on their importance for the particular application that the primers will be used for. Exemplary parameters include the heterozygosity rate of the target locus, the disease prevalence associated with a sequence (e.g., a polymorphism) at the target locus, the disease penetrance associated with a sequence (e.g., a polymorphism) at the target locus, the specificity of the candidate primer(s) used to amplify the target locus, the size of the candidate primer(s) used to amply the target locus, and the size of the target amplicon. In some embodiments, the specificity of the candidate primer for the target locus includes the likelihood that the candidate primer will mis-prime by binding and amplifying a locus other than the target locus it was designed to amplify. In some embodiments, one or more or all the candidate primers that mis-prime are removed from the library.

Step 2

A thermodynamic interaction score was calculated between each primer and all primers for all other target loci from Step 1 (see, e.g., Allawi, H. T. & SantaLucia, J., Jr. (1998), "Thermodynamics of Internal C-T Mismatches in DNA", *Nucleic Acids Res.* 26, 2694-2701; Peyret, N., Seneviratne, P. A., Allawi, H. T. & SantaLucia, J., Jr. (1999), "Nearest-Neighbor Thermodynamics and NMR of DNA Sequences with Internal A-A, C-C, G-G, and T-T Mismatches", *Biochemistry* 38, 3468-3477; Allawi, H. T. & SantaLucia, J., Jr. (1998), "Nearest-Neighbor Thermodynamics of Internal A-C Mismatches in DNA: Sequence Dependence and pH Effects", *Biochemistry* 37, 9435-9444.; Allawi, H. T. & SantaLucia, J., Jr. (1998), "Nearest Neighbor Thermodynamic Parameters for Internal G-A Mismatches in DNA", *Biochemistry* 37, 2170-2179; and Allawi, H. T. & SantaLucia, J., Jr. (1997), "Thermodynamics and NMR of Internal G-T Mismatches in DNA", *Biochemistry* 36, 10581-10594; MultiPLX 2.1 (Kaplinski L, Andreson R, Puurand T, Remm M. MultiPLX: automatic grouping and evaluation of PCR primers. Bioinformatics. 2005 Apr. 15;21 (8): 1701-2, which are each hereby incorporated by reference in its entirety). This step resulted in a 2D matrix of interaction scores. The interaction score predicted the likelihood of primer-dimers involving the two interacting primers. The score was calculated as follows:

$$\text{interaction\_score} = \max(-\text{deltaG\_2},\ 0.8*(-\text{deltaG\_1}))$$

where deltaG_2 = Gibbs energy (energy required to break the dimer) for a dimer that is extensible by *PCR* on both ends, i.e., the 3′ end of each primer anneals to the other primer;

and deltaG_1 = Gibbs energy for a dimer that is extensible by *PCR* on at least one end.

Step 3:

For each target locus, if there was more than one primer-pair design, then one design was selected using the following method:

1 For each primer-pair design for the locus, find the worst-case (highest) interaction score for the two primers in that design and all primers from all designs for all other target loci.
2 Pick the design with the best (lowest) worst-case interaction score.

Step 4

A graph was built such that each node represented one locus and its associated primer-pair design (e.g., a Maximal Clique problem). One edge was created between every pair of nodes. A weight was assigned to each edge equal to the worst-case (highest) interaction score between the primers associated with the two nodes connected by the edge.

Step 5

If desired, for every pair of designs for two different target loci where one of the primers from one design and one of the primers from the other design would anneal to overlapping target regions, an additional edge was added between the nodes for the two design. The weight of these edges was set equal to the highest weight assigned in Step 4. Thus, Step 5 prevents the library from having primers that would anneal to overlapping target regions, and thus interfere with each other during a multiplex PCR reaction.

Step 6

An initial interaction score threshold was calculated as follows:

$$\text{weight\_threshold} = \max(\text{edge\_weight}) - 0.05*(\max(\text{edge\_weight}) - \min(\text{edge\_weight}))$$

where max(edge_weight) is the maximum edge weight in the graph;

and min(edge_weight) is the minimum edge weight in the graph.

The initial bounds for the threshold were set as follows:

$$\text{max\_weight\_threshold} = \max(\text{edge\_weight})$$

$$\text{min\_weight\_threshold} = \min(\text{edge\_weight})$$

Step 7

A new graph was constructed consisting of the same set of nodes as the graph from Step 5, only including edges with weights that exceed weight_threshold. Thus, step ignores interactions with scores equal to or below weight_threshold.

Step 8

Nodes (and all of the edges connected to the removed nodes) were removed from the graph of Step 7 until there were no edges left. Nodes were removed by applying the following procedure repeatedly:

1 Find the node with the highest degree (highest number of edges). If there is more than one then pick one arbitrarily.
2 Define the set of nodes consisting of the node picked above and all of the nodes connected to it, but excluding any nodes that have degree less than the node picked above.
3 Choose the node from the set that has the lowest target locus score (lower score representing lower desirability) from Step 1. Remove that node from the graph.

Step 9

If the number of nodes remaining in the graph satisfies the required number of target loci for the multiplexed PCR pool (within an acceptable tolerance), then the method was continued at Step 10.

If there were too many or too few nodes remaining in the graph, then a binary search was performed to determine what threshold values would result in the desired number of nodes remaining in the graphs. If there were too many nodes in the graph then, the weight threshold bounds were adjusted as follows:

$$\text{max\_weight\_threshold} = \text{weight\_threshold}$$

Otherwise (if there are two few nodes in the graph), then the weight threshold bounds were adjusted as follows:

$$\text{min\_weight\_threshold} = \text{weight\_threshold}$$

Then, the weight threshold was adjusted follows:

$$\text{weight\_threshold} = (\text{max\_weight\_threshold} + \text{min\_weight\_threshold})/2$$

Steps 7-9 were repeated.

Step 10

The primer-pair designs associated with the nodes remaining in the graph were selected for the library of primers. This primer library can be used in any of the methods of the invention.

If desired, this method of designing and selecting primers can be performed for primer libraries in which only one primer (instead of a primer pair) is used for amplification of a target locus. In this case, a node presents one primer per target locus (rather than a primer pair).

Example 3

If desired, methods of the invention can be tested to evaluate their ability to detect a deletion or duplication of a chromosome or chromosome segment. The following experiment was performed to demonstrate the detection of an overrepresentation of the X chromosome or a segment from the X chromosome inherited from the father compared to the X chromosome or X chromosome segment from the mother. This assay is designed to mimic a deletion or duplication of a chromosome or chromosome segment. Different amounts of DNA from a father (with XY sex chromosomes) were mixed with DNA from a daughter (with XX sex chromosomes) of the father for analysis of the extra amount of X chromosome from the father (FIGS. 19A-19D).

DNA from father and daughter cells lines was extracted and quantified using Qubit. Father cell line AG16782, cAG16782-2-F and daughter cell line AG16777, cAG16777-2-P were used. To determine the father's haplotype for the X chromosome, SNPs were detected that are present on the X chromosome but not on the Y chromosome, so there would be a signal from the father's X chromosome but not Y chromosome. The daughter inherited this haplotype from the father. The haplotype from the other X chromosome in the daughter was inherited from her mother. This haplotype from the mother can be determined by assigning the SNPs in the DNA from the daughter cell line that were not inherited from the father to the haplotype from the mother.

To determine whether an overrepresentation of the X chromosome from the father could be detected, different amounts DNA from the father cell line were mixed with DNA from the daughter cell line. The total DNA input was approximately 75 ng (~25k copies) of genomic DNA. Approximately 3,456 SNPs were amplified using direct multiplex PCR for X and Y chromosome assays. The amplified products were sequenced using 50 bp single run sequencing with 7 bp barcodes using the Rapid/HT mode. The number of reads was approximately 10K per SNP.

As shown in FIGS. 19A-19D, mosaicism from the father's DNA could be detected. These figures indicate that chromosomes segments or entire chromosomes that are overrepresented can be detected.

All patents, patent applications, and published references cited herein are hereby incorporated by reference in their entirety. While the methods of the present disclosure have been described in connection with the specific embodiments thereof, it will be understood that it is capable of further modification. Furthermore, this application is intended to cover any variations, uses, or adaptations of the methods of the present disclosure, including such departures from the present disclosure as come within known or customary practice in the art to which the methods of the present disclosure pertain, and as fall within the scope of the appended claims. Any of the embodiments of the invention can be performed by analyzing the DNA and/or RNA in a sample. For example, any of the methods disclosed herein for DNA can be readily adapted for RNA, for example, by including a reverse transcription step to convert the RNA into DNA.

Example 4

Figure 29:
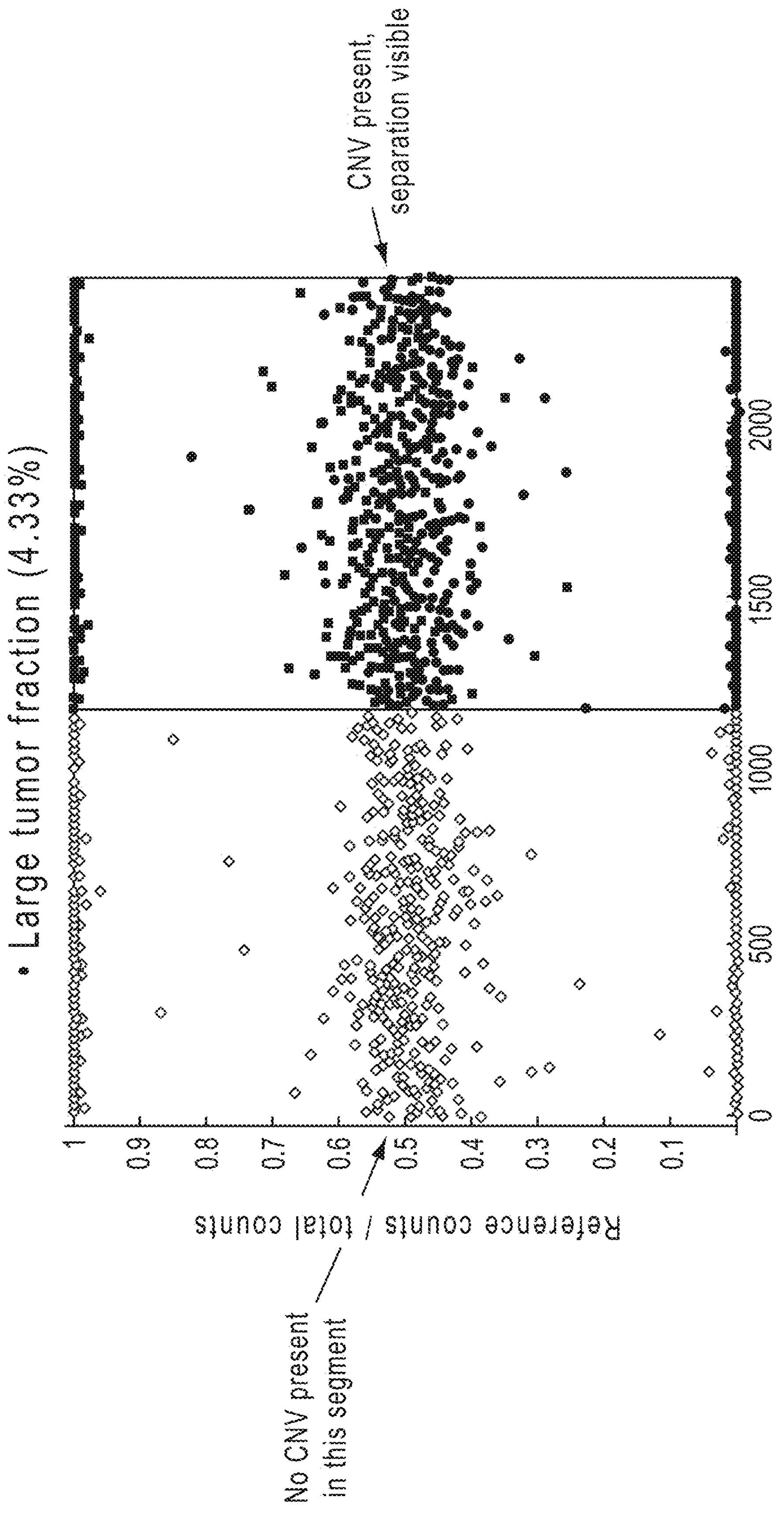
FIG. 29 is a graph of reference counts divided by total counts for a plasma sample from a patient with stage IIa breast cancer with a tumor fraction estimated to be 4.33% (in which 4.33% of the DNA is from tumor cells). The diamond portion of the graph represents a region in which no CNV is present. The portion of the graph with solid circles and squares represents a region in which a CNV is present and there is a visible separation of the measured allele ratios from the expected allele ratio of 0.5. The solid square indicates one haplotype, and the solid circle indicates the other haplotype. Approximately 636 heterozygous SNPs were analyzed in the region of the CNV.
Figure 30:
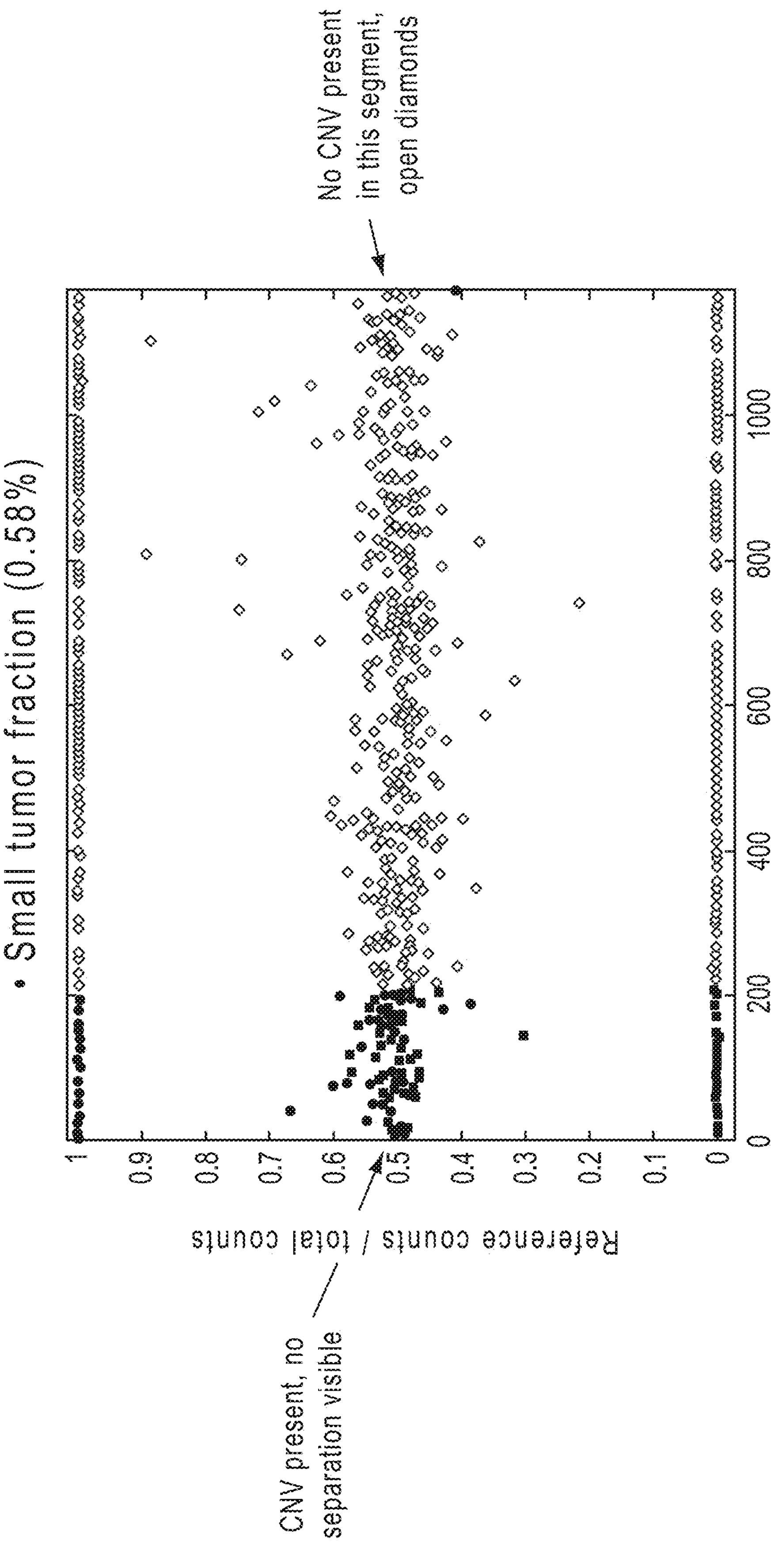
FIG. 30 is a graph of reference counts divided by total counts for a plasma sample from a patient with stage IIb breast cancer with a tumor fraction estimated to be 0.58%. The open diamonds of the graph represents a region in which no CNV is present. The portion of the graph with solid circles and squares represents a region in which a CNV is present but there is no clearly visible separation of the measured allele ratios from the expected allele ratio of 0.5. For this analysis, 86 heterozygous SNPs were analyzed in the region of the CNV.
Figure 31A:
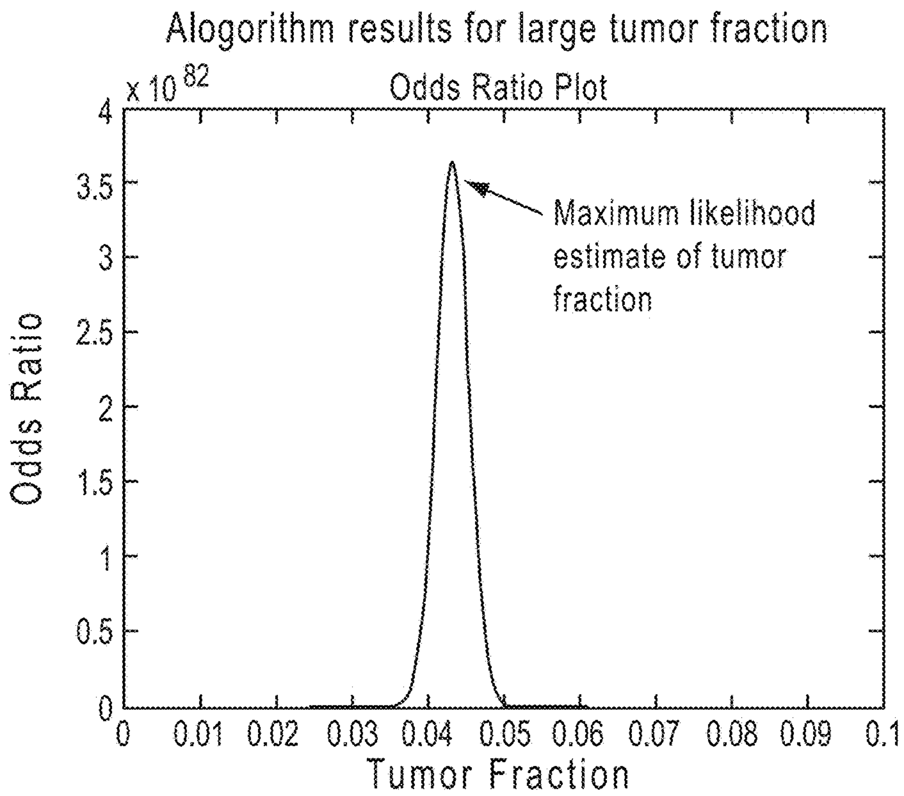
FIGS. 31A and 31B are graphs showing the maximum likelihood estimation of the tumor fraction. The maximum likelihood estimate is indicated by the peak of the graph and is 4.33% for FIG. 31A and 0.58% for FIG. 31B.
Figure 31B:
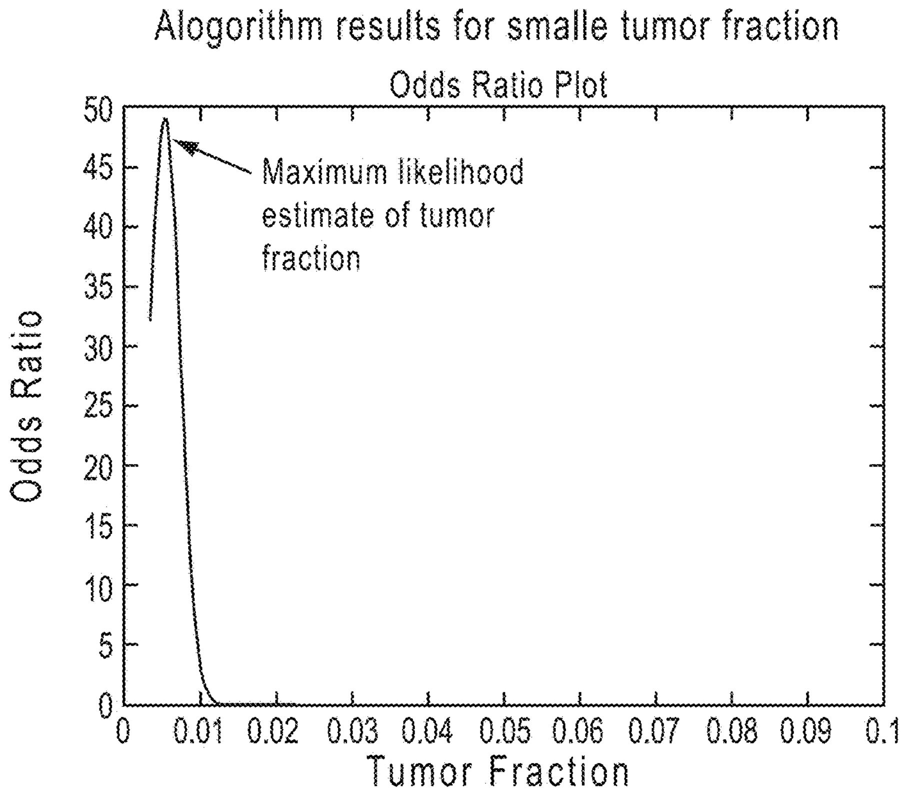
Figure 32A:
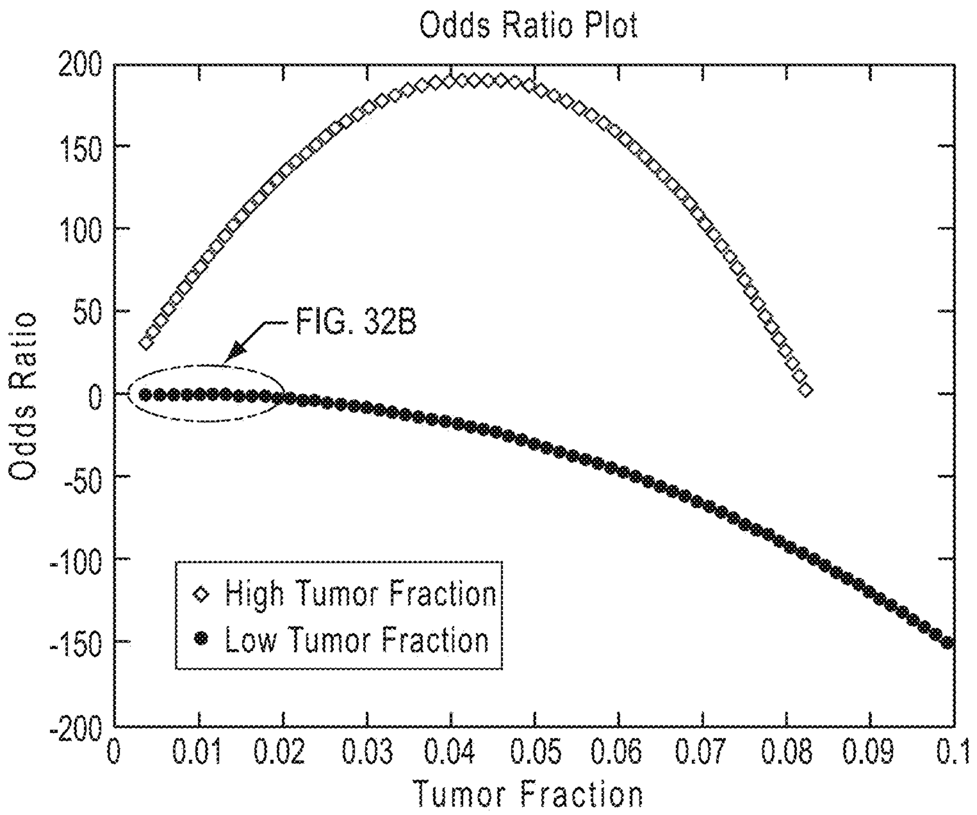
FIG. 32A is a comparison of the graphs of the log of the odds ratio for various possible tumor fractions for the high tumor fraction sample (4.33%) and the low tumor fraction sample (0.58%). If the log odds ratio is less than 0, the euploid hypothesis is more likely. If the log odds ratio is greater than 0, the presence of a CNV is more likely.
Figure 32B:
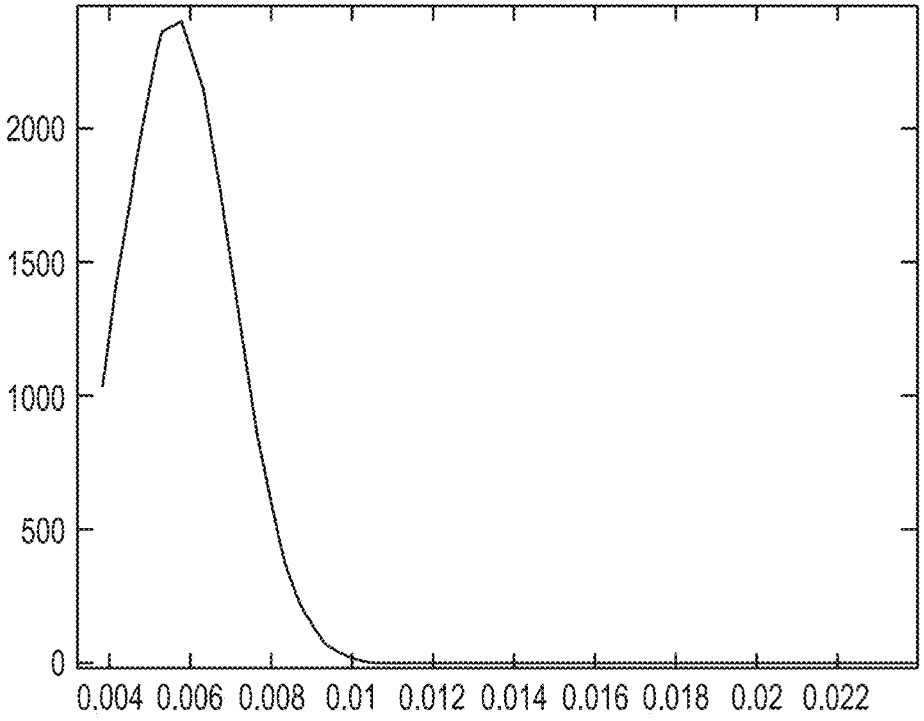
FIG. 32B is a graph of small tumor results plotted in probability space. The graph depicts the probability of a deletion divided by the probability of no deletion for various possible tumor fractions for the low tumor fraction sample (0.58%).
Figure 33:
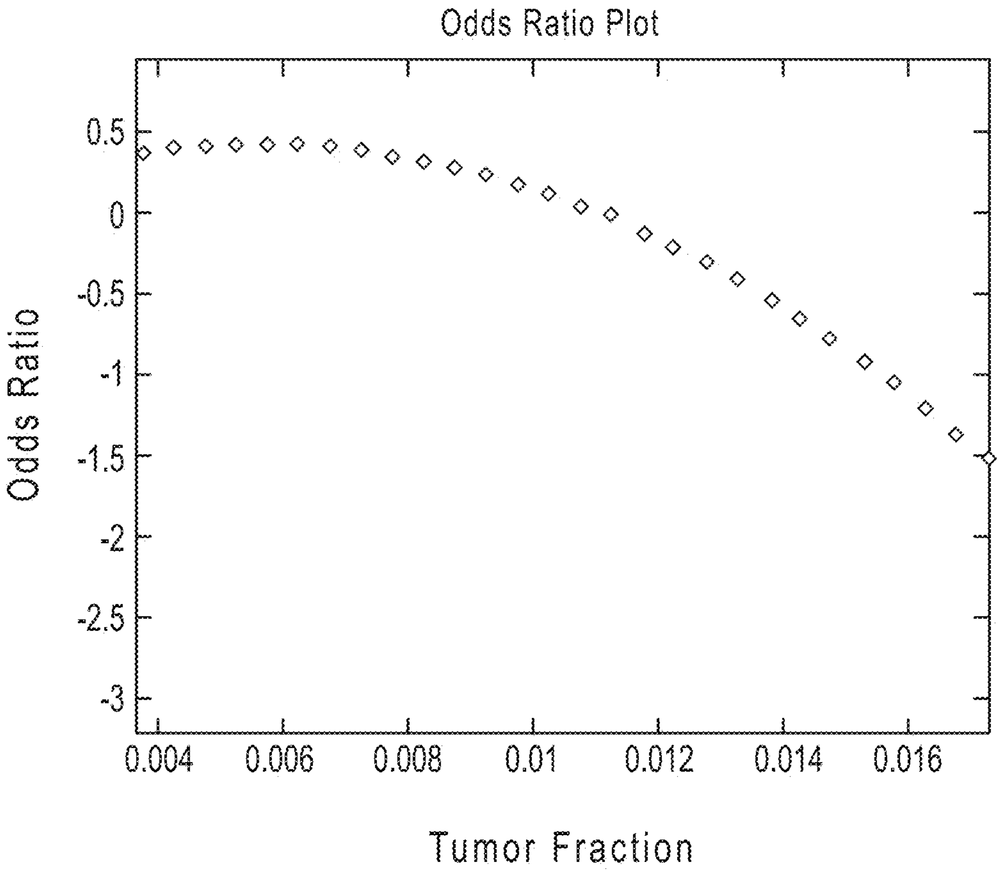
FIG. 33 is a graph of the log of the odds ratio for various possible tumor fractions for the low tumor fraction sample (0.58%).

This example describes an exemplary method for non-invasive cell-free tumor DNA-based detection of breast cancer-related copy number variations. Breast cancer screening involves mammography, which results in a high false positive rate and misses some cancers. Analysis of tumor-derived circulating cell-free DNA (ctDNA) for cancer-associated CNVs may allow for earlier, safer, and more accurate screening. A SNP-based massively multiplex PCR (mmPCR) approach was used to screen for CNVs in ctDNA isolated from the plasma of breast cancer patients. The mmPCR assay was designed to target 3,168 SNPs on chromosomes 1, 2, and 22, which often have CNVs in cancer (e.g., 49% of breast cancer samples have a 22q deletion). Six plasma samples from breast cancer patients—one stage IIa, four stage IIb, and one stage IIIb—were analyzed. Each sample had CNVs on one or more of the targeted chromosomes. The assay identified CNVs in all six plasma samples, including in one stage IIb sample that was correctly called at a ctDNA fraction of 0.58% (FIGS. 30, 31B, 32A, 32B, and 33); detection only required 86 heterozygous SNPs. A stage IIa sample was also corrected called at a ctDNA fraction of 4.33% using approximately 636 heterozygous SNPs (FIGS. 29, 31A, and 32A). This demonstrates that focal or whole chromosome arm CNVs, both common in cancer, can be readily detected.

Figure 28:
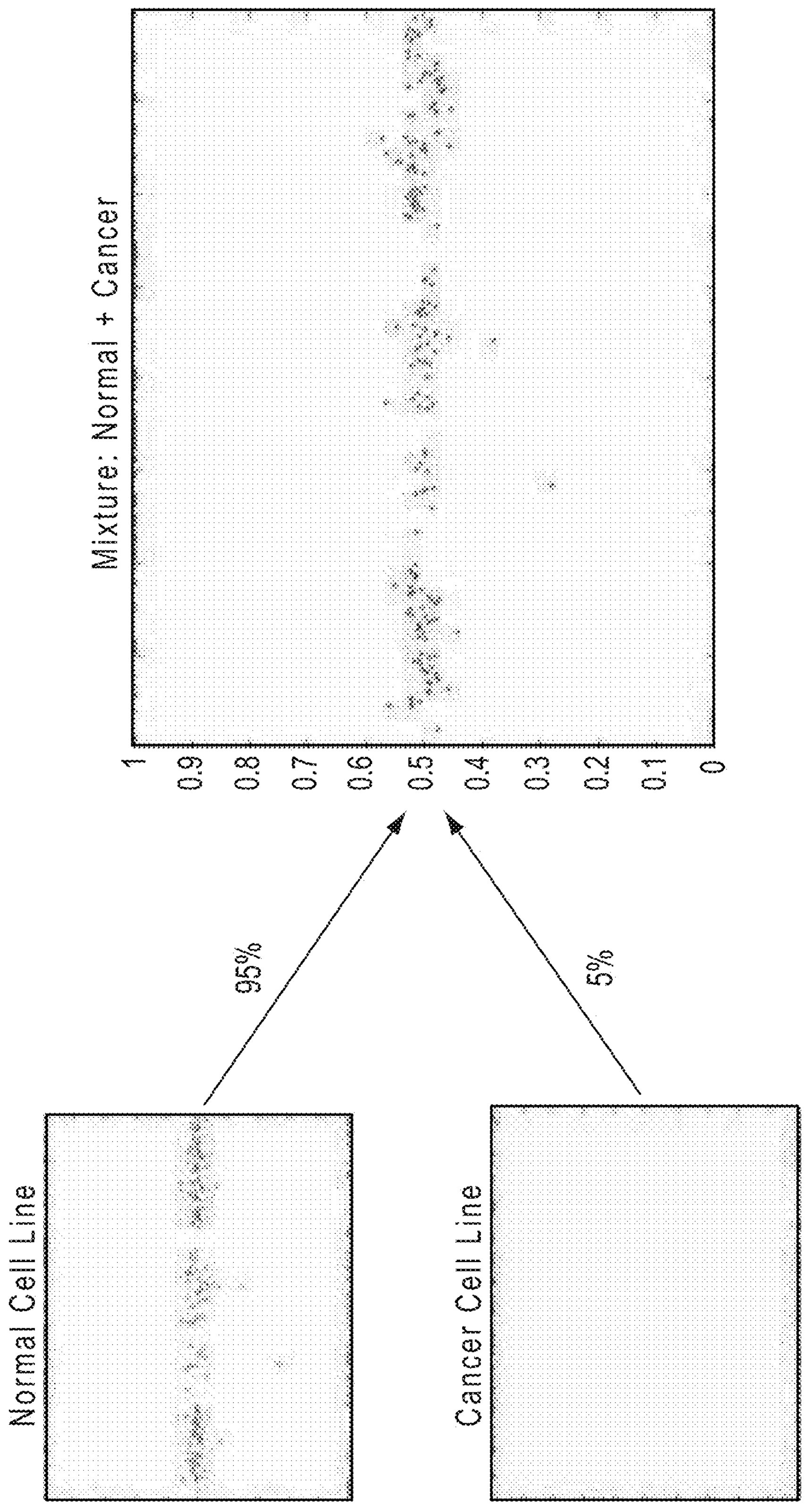
FIG. 28 contains a graph of reference counts (counts of one allele, such as the "A" allele) divided by total counts for that locus for a normal (noncancerous) cell line, a graph of reference counts divided by total counts for a cancer cell line with a deletion and a graph of reference counts divided by total counts for a mixture of DNA from the normal cell line (95%) and the cancer cell line (5%).

To further evaluate sensitivity, 22 artificial mixtures containing a 3 Mb 22q CNV from a cancer cell line were mixed with DNA from a normal cell line (5:95) to simulate a ctDNA fraction of between 0.43% and 7.35% (FIGS. 28A-28C). The method correctly detected CNVs in 100% of these samples. Thus, artificial cfDNA polynucleotide standards/controls can be made by spiking isolated polynucleotide samples that include fragmented polynucleotide mixtures generated by non-cfDNA sources known to exhibit CNV, such as tumor cell lines, into other DNA samples at concentrations similar to those observed for cfDNA in vivo, such as between, for example, 0.01% and 20%, 0.1 and 15%, or 0.4 and 10% of DNA in that fluid. These standards/controls can be used as controls for assay design, characterization, development, and/or validation, and as quality control standards during testing, such as cancer testing performed in a CLIA lab and/or as standards included in research use only or diagnostic test kits. Significantly, in numerous cancers-including breast and ovarian-CNVs are more prevalent relative to point mutations. Together, this supports that this SNP-based mmPCR approach offers a cost-effective, non-invasive method for detecting these cancers.

Example 5

This example describes an exemplary method for detection of copy number variations in breast cancer samples using SNP-targeted massively multiplexed PCR. Evaluation of CNV in tumor tissues typically involves SNP microarray or aCGH. These methods have high whole-genome resolution, but require large amounts of input material, have high fixed costs, and do not work well on formaldehyde fixed-paraffin embedded (FFPE) samples. For this example, 28,000-plex SNP-targeted PCR with next generation sequencing (NGS) was used to target 1p, 1q, 2p, 2q, 4p16, 5p15, 7q11, 15q, 17p, 22q11, 22q13 and chromosomes 13, 18, 21 and X for detection of CNVs in breast cancer samples. Accuracy was validated on 96 samples with aneuploidies or microdeletions. Single-molecule sensitivity was established by analyzing single cells. Of 17 breast cancer samples (15 fresh frozen and 2 FFPE tumor tissues, 5 pairs of matched tumor and normal cell lines) analyzed, 16 (including both FFPEs) were observed with full or partial CNVs in one to 15 targets (average: 7.8); evidence of tumor heterogeneity was observed. The three tissues with one CNV all had a 1q duplication, the most frequent cytogenetic abnormality in breast carcinoma. The most frequent regions with CNVs were 1q, 7p, and 22q1. Only one tumor tissue (with 9 CNVs) had a region with LOH; this LOH was also detected in adjacent putatively normal tissue that lacked the other 8 CNVs. By contrast, 5 or more regions with LOH and a high total CNV incidence (average: 12.8) was detected in cell lines. Thus, massively multiplexed PCR offers an economical high-throughput approach to investigate CNVs in a targeted manner, and is applicable to difficult-to-analyze samples, such as FFPE tissues.

Example 6

This example illustrates exemplary methods for calculating the limit of detection for any of the methods of the invention. These methods were used to calculate the limit of detection for single nucleotide variants (SNVs) in a tumor biopsy (FIG. 34) and a plasma sample (FIG. 35).

The first method (denoted "LOD-mr5" in FIGS. 34 and 35) calculates the limit of detection based on a minimum of 5 reads being chosen as the minimum number of times a SNV is observed in the sequencing data to have sufficient confidence the SNV is actually present. The limit of detection is based on whether the observed the depth of read (DOR) is above this minimum of 5. The gray lines in FIGS. 34 and 35 indicate SNVs for which the limit of detection is limited by the DOR. In these cases, not enough reads were measured to reach the error limit of the assay. If desired, the limit of detection can be improved (resulting in a lower numerical value) for these SNVs by increasing the DOR.

The second method (denoted "LOD-zs5.0" in FIGS. 34 and 35) calculates the limit of detection based on the z-score. The Z-score is the number of standard deviations an observed error percentage is away from the background mean error. If desired, outliers can be removed and the z-score can be recalculated and this process can be repeated. The final weighted mean and the standard deviation of the error rate are used to calculate the z-score. The mean is weighted by the DOR since the accuracy is higher when the DOR is higher.

For the exemplary z-score calculation used for this example, the background mean error and standard deviation were calculated from all the other samples of the same sequencing run weighted by their depth of read, for each genomic locus and substitution type. Samples were not considered in the background distribution if they were 5 standard deviations away from the background mean. The orange lines in FIGS. 34 and 35 indicate SNVs for which the limit of detection is limited by the error rate. For these SNV's enough reads were taken to reach the 5 read minimum, and the limit of detection was limited by the error rate. If desired, the limit of detection can be improved by optimizing the assay to reduce the error rate.

The third method (denoted "LOD-zs5.0-mr5" in FIGS. 34 and 35) calculates the limit of detection based on the maximum value of the above two metrics.

Figure 34:
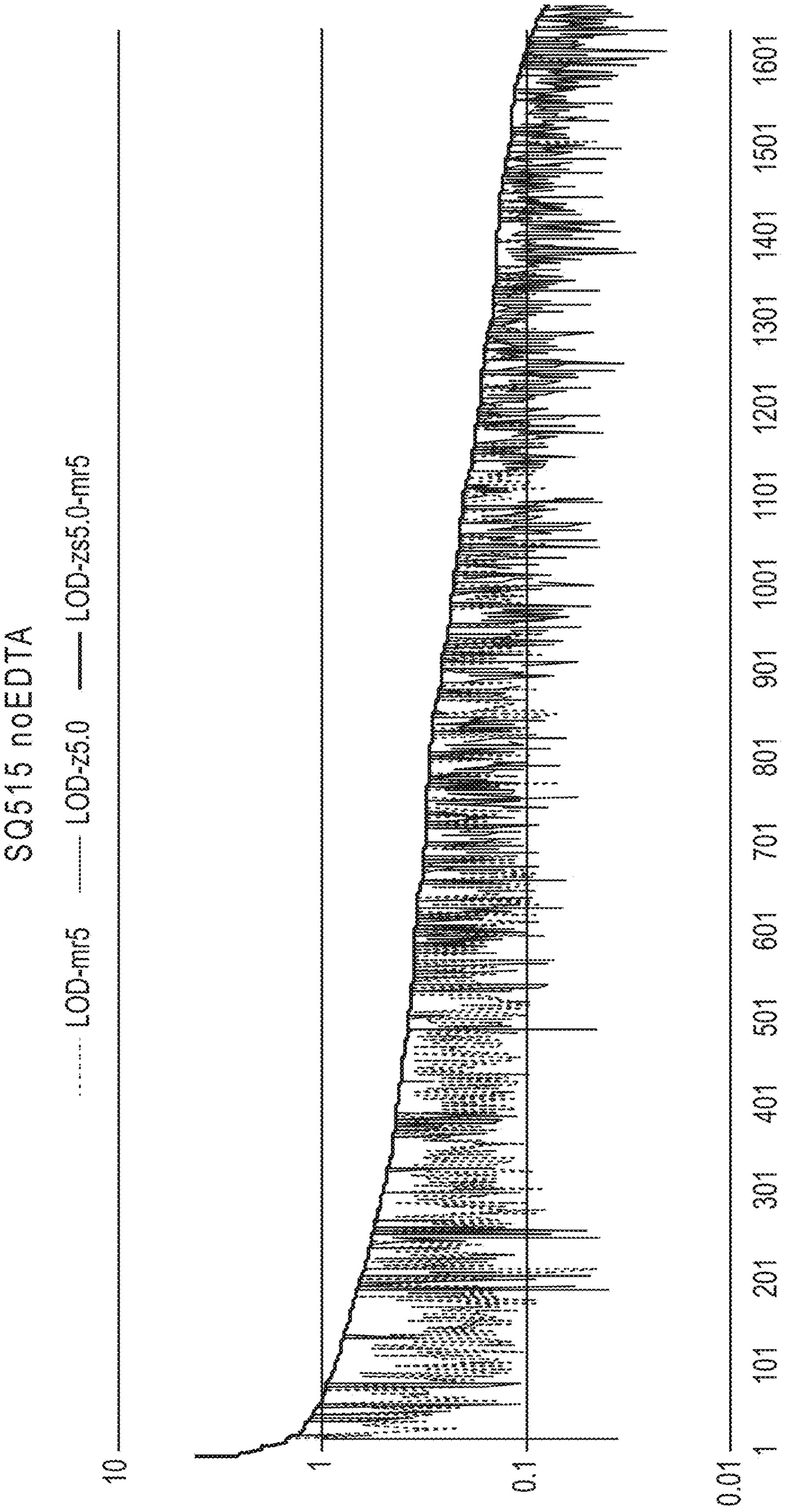
FIG. 34 is a graph showing the limit of detection for single nucleotide variants in a tumor biopsy using three different methods described in Example 6.
Figure 35:
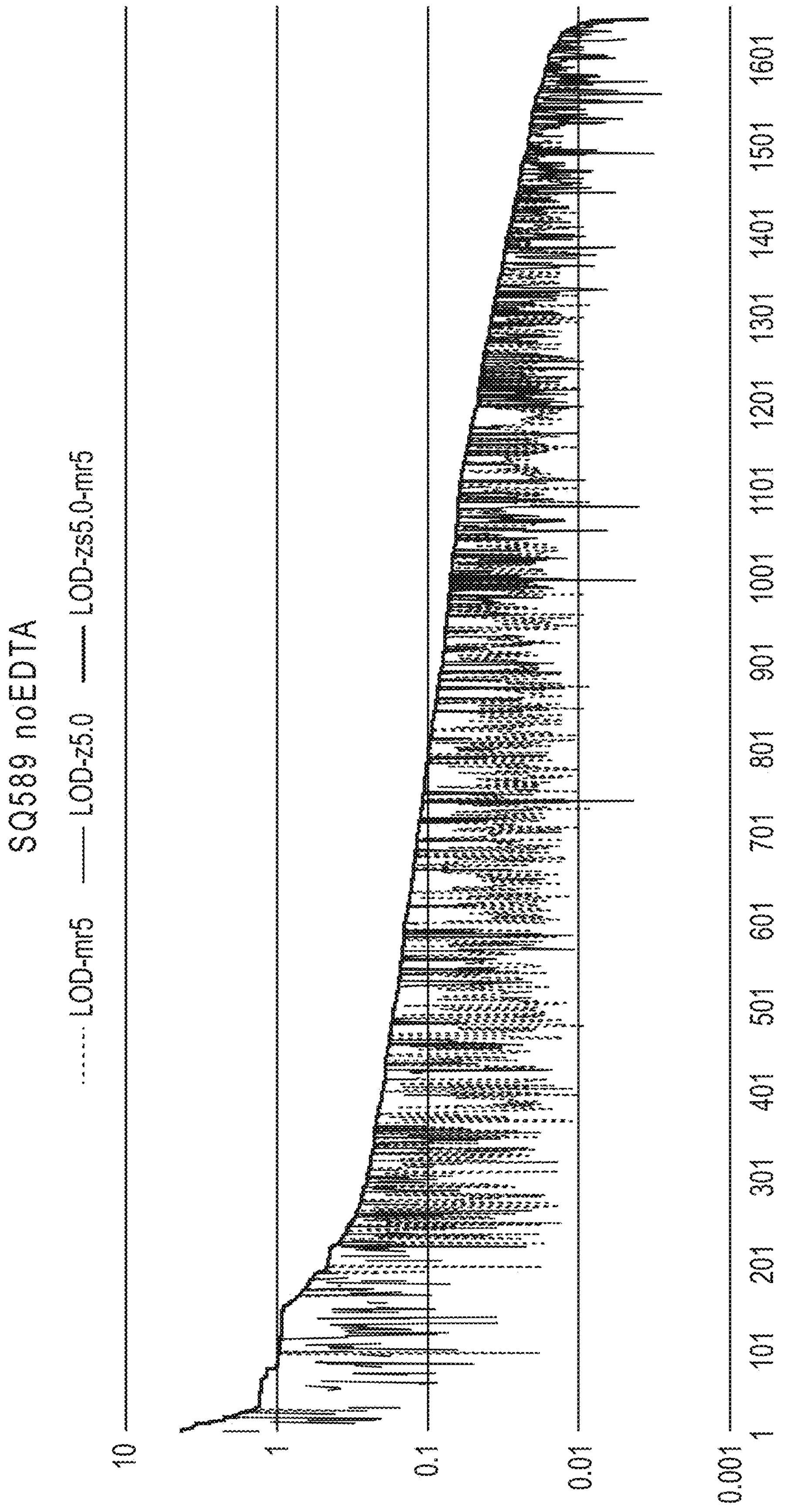
FIG. 35 is a graph showing the limit of detection for single nucleotide variants in a plasma sample using three different methods described in Example 6.

For the analysis of a tumor sample shown in FIG. 34, the mean limit of detection was 0.36%, and the median limit of detection was 0.28%. The number of DOR limited (gray lines) SNVs was 934. The number of error rate limited (orange lines) SNVs was 738.

For the analysis of cDNA in a plasma sample shown in FIG. 35, the mean limit of detection was 0.24%, and the median limit of detection was 0.09%. The number of DOR limited (gray lines) SNVs was 732. The number of error rate limited (orange lines) SNVs was 921.

Example 7

This example illustrates the detection of CNVs and SNVs from the same single cell. The following primer libraries were used: a library of ~28,000 primers for detecting CNVs, a library of ~3,000 primers for detecting CNVs, and library of primers for detecting SNVs. For analysis of a single cell, cells were serial diluted until there were 3 or 4 cells per droplet. An individual cell was pipetted and placed into a PCR tube. The cell was lysed using Protease K, salt, and DTT using the following conditions: 56° C. for 20 minutes, 95° C. for 10 minutes, and then a 4° C. hold. For analysis of genomic DNA, DNA from the same cell line as the analyzed single cell was either purchased or obtained by growing the cells and extracting the DNA.

For amplification with the library of ~28,000 primers, the following PCR conditions were used: a 40 uL reaction volume, 7.5 nM of each primer, and 2× master mix (MM). In some embodiments QIAGEN Multiplex PCR Kit is used for the master mix (QIAGEN catalog No. 206143; see, e.g., information available the at world wide web at qiagen.com/products/catalog/assay-technologies/end-point-pcr-and-rt-pcr-reagents/qiagen-multiplex-pcr-kit, is which is hereby incorporated by reference in its entirety). The kit includes 2×QIAGEN Multiplex PCR Master Mix (providing a final concentration of 3 mM $MgCl_2$, 3×0.85 ml), 5× Q-Solution (1×2.0 ml), and RNase-Free Water (2×1.7 ml). The QIAGEN Multiplex PCR Master Mix (MM) contains a combination of KCl and $(NH_4)_2SO_4$ as well as the PCR additive, Factor MP, which increases the local concentration of primers at the template. Factor MP stabilizes specifically bound primers, allowing efficient primer extension by, e.g., HotStarTaq DNA Polymerase. HotStarTaq DNA Polymerase is a modified form of Taq DNA polymerase and has no polymerase activity at ambient temperatures. The following thermocycling conditions were used for the first round of PCR: 95° C. for 10 minutes; 25 cycles of 96° C. for 30 seconds, 65° C. for 29 minutes, and 72° C. for 30 seconds; and then 72° C. for 2 minutes, and a 4° C. hold. For the second round of PCR a 10 ul reaction volume, 1×MM, and 5 nM of each primer was used. The following thermocycling conditions were used: 95° C. for 15 minutes; 25 cycles of 94° C. for 30 seconds, 65° C. for 1 minute, 60° C. for 5 minutes, 65° C. for 5 minutes, and 72° C. for 30 seconds; and then 72° C. for 2 minutes, and a 4° C. hold.

For the library of ~3,000 primers, exemplary reaction conditions include a 10 ul reaction volume, 2×MM, 70 mM TMAC, and 2 nM primer of each primer. For the library of primers for detecting SNVs, exemplary reaction conditions include a 10 ul reaction volume, 2×MM, 4 mM EDTA, and 7.5 nM primer of each primer. Exemplary thermocycling conditions include 95° C. for 15 minutes, 20 cycles of 94° C. for 30 seconds, 65° C. for 15 minutes, and 72° C. for 30 seconds; and then 72° C. for 2 minutes, and a 4° C. hold.

The amplified products were barcoded. One run of sequencing was performed with an approximately equal number of reads per sample.

Figure 36A:
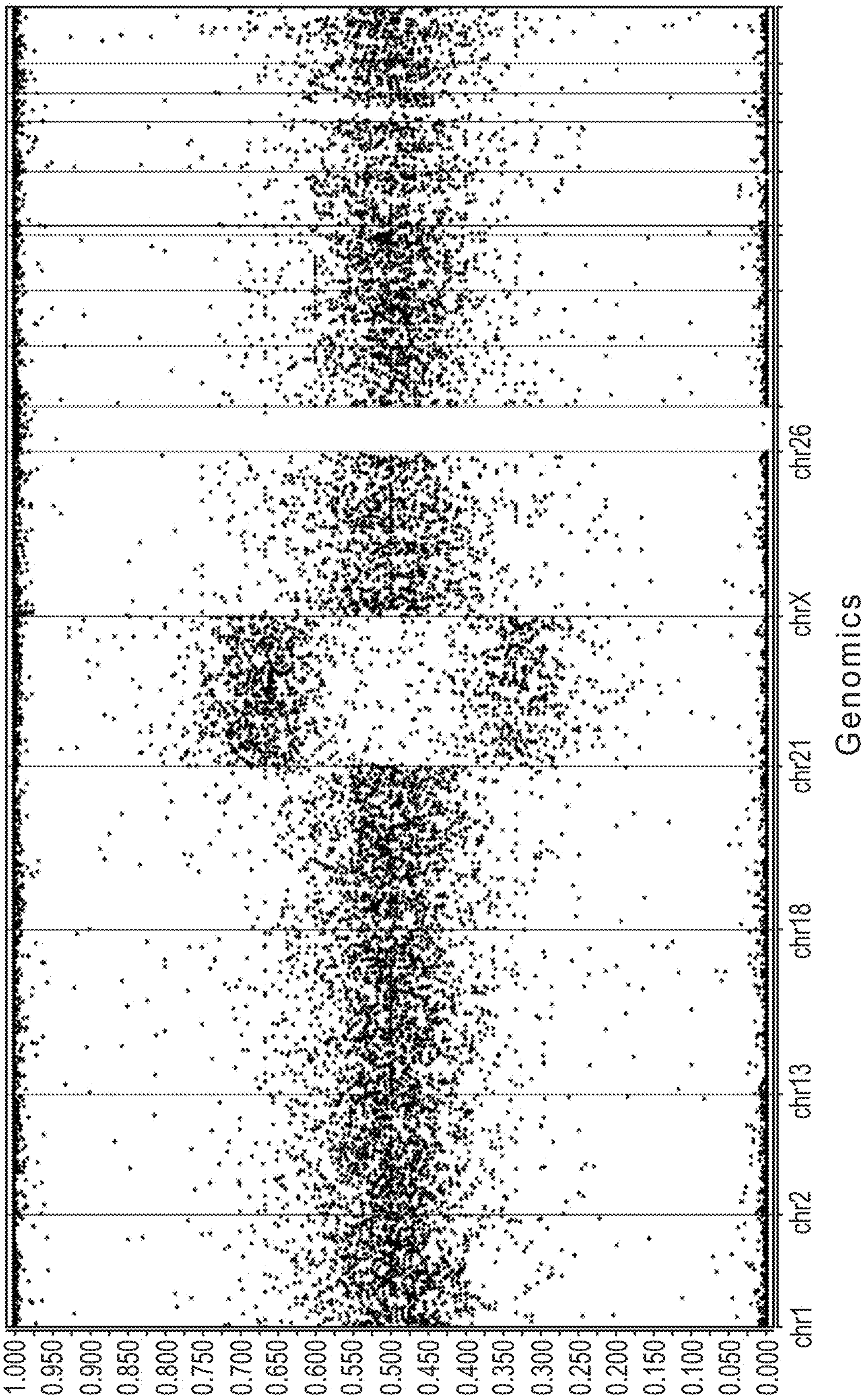
FIGS. 36A and 36B are graphs of the analysis of genomic DNA (FIG. 36A) or DNA from a single cell (FIG. 36B) using a library of approximately 28,000 primers designed to detect CNVs. The presence of two central bands instead of one central band indicates the presence of a CNV. The x-axis represents the linear position of the SNPs, and the y-axis indicates the fraction of A allele reads out of the total reads.
Figure 36B:
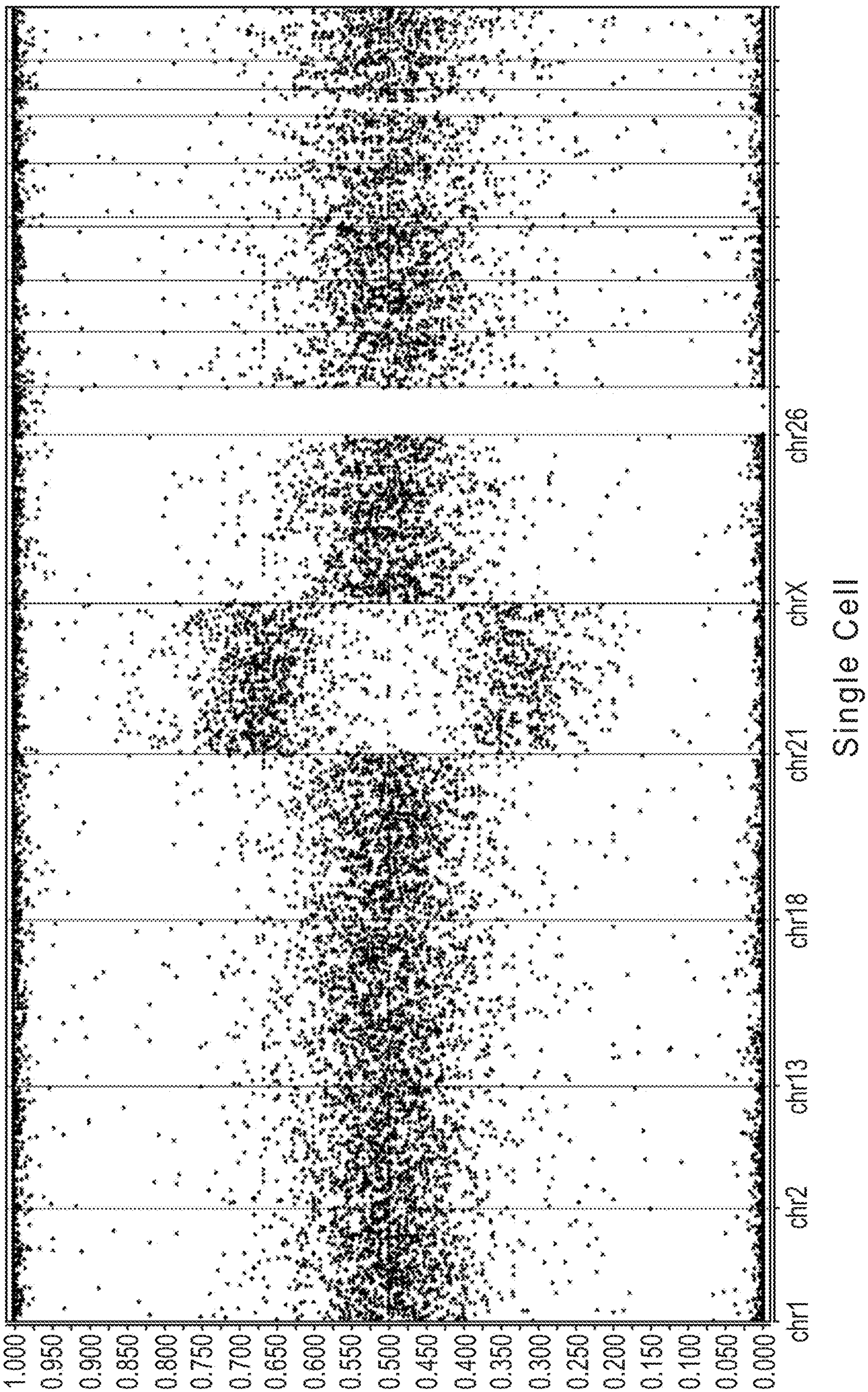

FIGS. 36A and 36B show results from analysis of genomic DNA (FIG. 36A) or DNA from a single cell (FIG. 36B) using a library of approximately 28,000 primers designed to detect CNVs. Approximately 4 million reads were measured per sample. The presence of two central bands instead of one central band indicates the presence of a CNV. For three samples of DNA from a single cell, the percent of mapped reads was 89.9%, 94.0%, and 93.4%, respectively. For two samples of genomic DNA the percent of mapped reads was 99.1% for each sample.

Figure 37A:
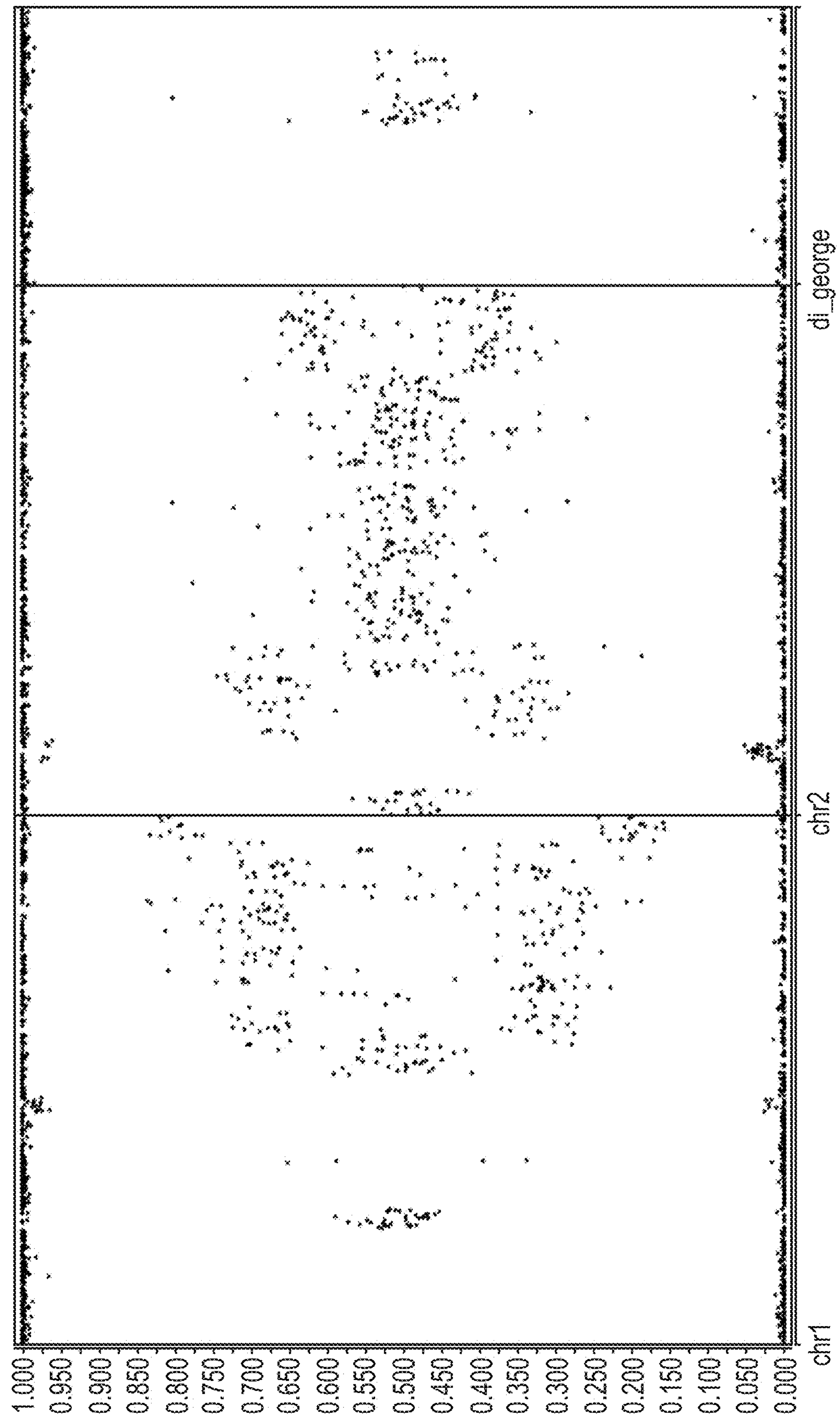
FIGS. 37A and 37B are graphs of the analysis of genomic DNA (FIG. 37A) or DNA from a single cell (FIG. 37B) using a library of approximately 3,000 primers designed to detect CNVs. The presence of two central bands instead of one central band indicates the presence of a CNV. The x-axis represents the linear position of the SNPs, and the y-axis indicates the fraction of A allele reads out of the total reads.
Figure 37B:
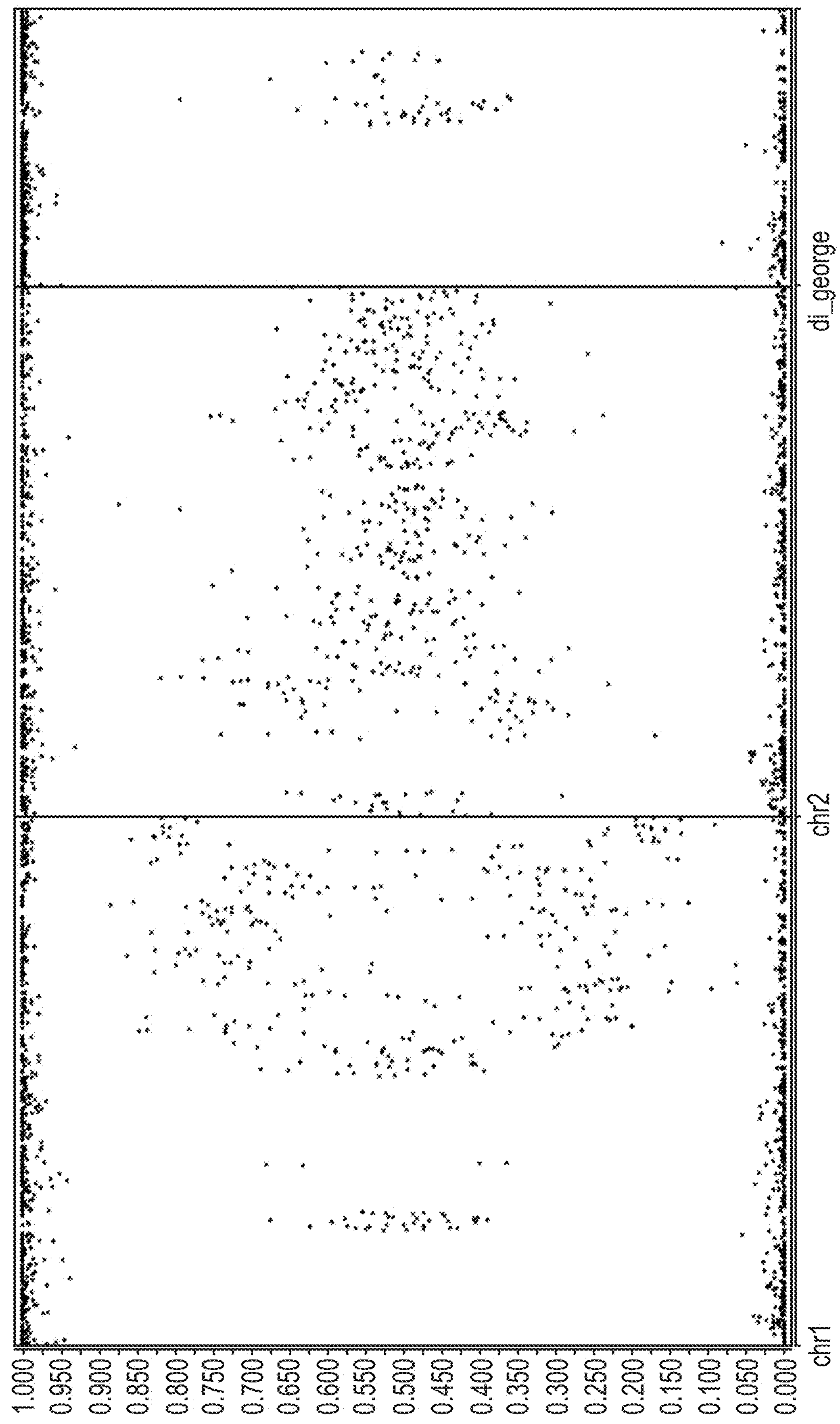
Figure 38:
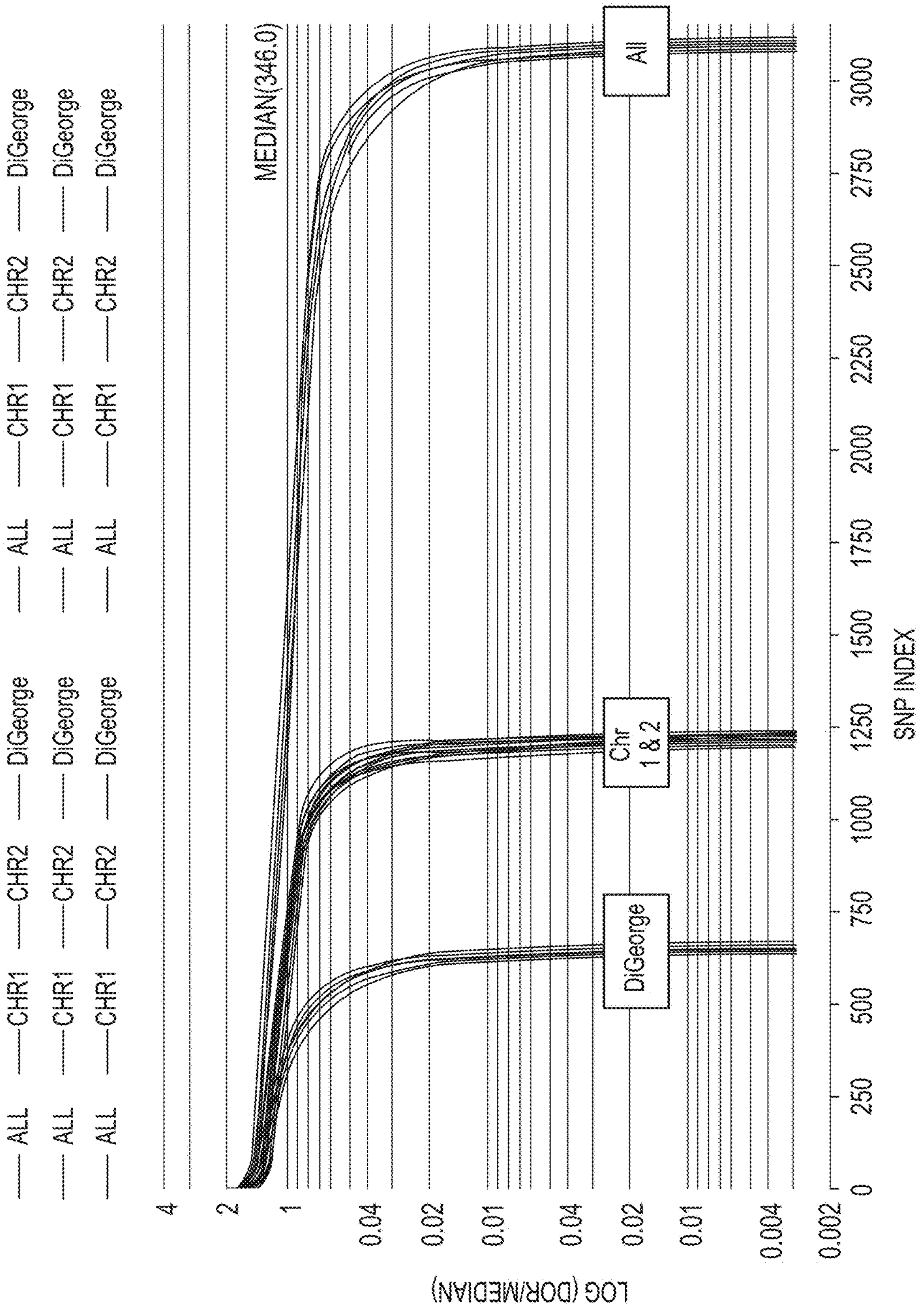
FIG. 38 is a graph illustrating the uniformity in DOR for these ~3,000 loci.

FIGS. 37A and 37B show results from analysis of genomic DNA (FIG. 37A) or DNA from a single cell (FIG. 37B) using a library of approximately 3,000 primers designed to detect CNVs. Approximately 1.2 million reads were measured per sample. The presence of two central bands instead of one central band indicates the presence of a CNV. For three samples of DNA from a single cell, the percent of mapped reads was 98.2%, 98.2%, and 97.9%, respectively. For two samples of genomic DNA the percent of mapped reads was 98.8% for each sample. FIG. 38 illustrates the uniformity in DOR for these ~3,000 loci.

Figures 39, 40:
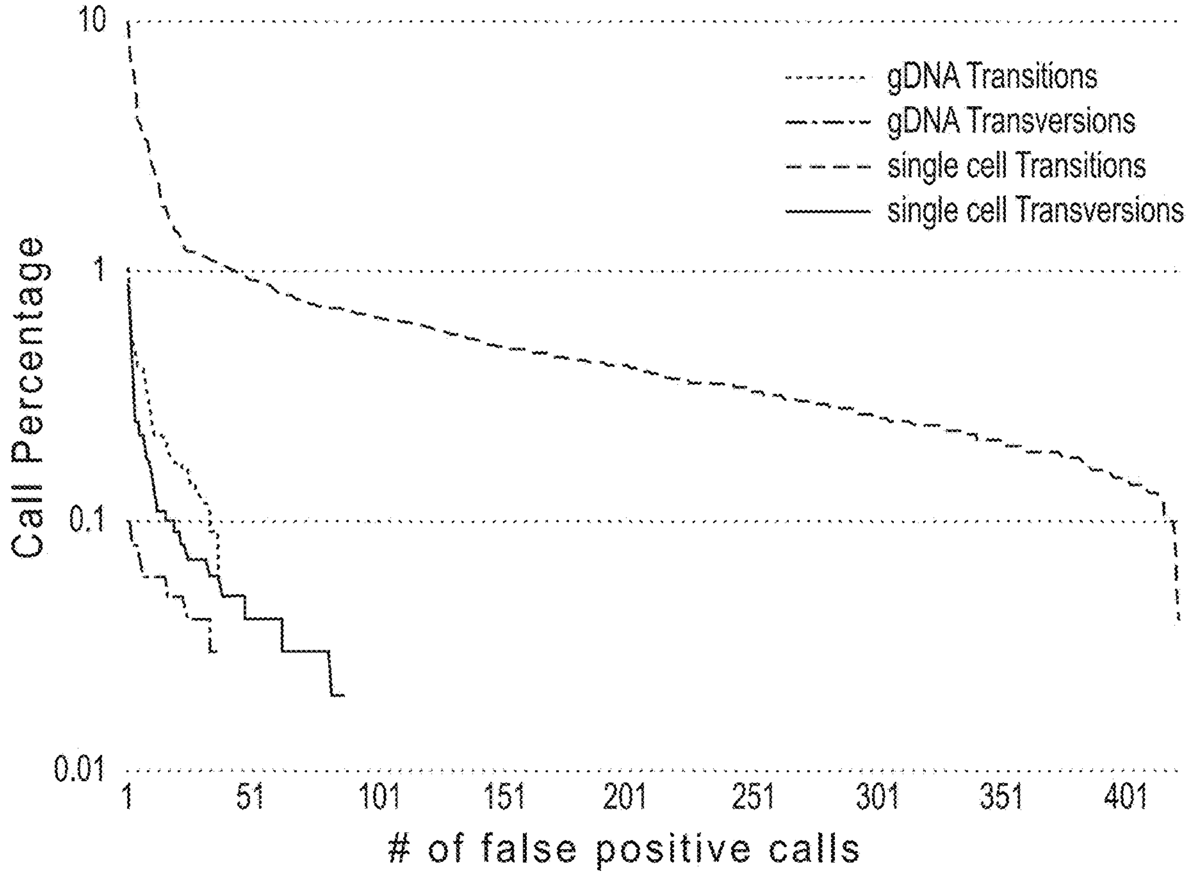
FIG. 39 is a table comparing error call metrics for genomic DNA and DNA from a single cell.
FIG. 40 is a graph of error rates for transition mutations and transversion mutations.

For calling SNVs, the call percent for true positive mutations was similar for DNA from a single cell and genomic DNA. A graph of call percent for true positive mutations for single cells on the y-axis versus that for genomic DNA on the x-axis yielded a curve fit of y=1.0076×−0.3088 with $R^2$=0.9834. FIG. 39 shows similar error call metrics for genomic DNA and DNA from a single cell. FIG. 40 shows that the error rate for detecting transition mutations was greater than for detecting transversion mutations, indicating it may be desirable to select transversion mutations for detection rather than transition mutations when possible.

Example 8

This example further validates a massively multiplexed PCR methodology for chromosomal aneuploidy and CNV determination disclosed herein, called CONVERGe (Copy Number Variant Events Revealed Genotypically), and further illustrates the development and use of "PlasmArt" standards for PCR of ctDNA samples. PlasmArt standards include polynucleotides having sequence identity to regions of the genome known to exhibit CNV and a size distribution that reflects that of cfDNA fragments naturally found in plasma.

Sample Collection

Human breast cancer cell lines (HCC38, HCC1143, HCC1395, HCC1937, HCC1954, and HCC2218) and matched normal cell lines (HCC38BL, HCC1143BL, HCC1395BL, HCC1937BL, HCC1954BL, and HCC2218BL) were obtained from the American Type Culture Collection (ATCC). Trisomy 21 B-lymphocyte (AG16777) and paired father/child DiGeorge Syndrome (DGS) cell lines (GM10383 and GM10382, respectively) were from the Coriell Cell Repository (Camden, NJ). GM10382 cells only have the paternal 22q11.2 region.

We procured tumour tissues from 16 breast cancer patients, including 11 fresh frozen (FF) samples from Geneticist (Glendale, CA) and five formalin-fixed paraffin-embedded (FFPE) samples from North Shore-LIJ (Manhasset, NY). We acquired matched buffy coat samples for eight patients and matched plasma samples for nine patients. FF tumour tissues and matched buffy coat and plasma samples from five ovarian cancer patients were from North Shore-LIJ. For eight breast tumour FF samples, tissue subsections were resected for analysis. Institutional review board approvals from Northshore/LIJ IRB and Kharkiv National Medical University Ethics Committee were obtained for sample collection and informed consent was obtained from all subjects.

Blood samples were collected into EDTA tubes. Circulating tumour DNA was isolated from 1 mL plasma using the QIAamp Circulating Nucleic Acid Kit (Qiagen, Valencia, CA).

To make the PlasmArt standards according to one exemplary method, first, 9 □106 cells were lysed with hypotonic lysis buffer (20 mM Tris-Cl (pH 7.5), 10 mM NaCl, and 3 mM $MgCl_2$) for 15 min on ice. Then, 10% IGEPAL CA-630 (Sigma, St. Louis, MO) was added to a final concentration of 0.5%. After centrifugation at 3,000 g for 10 min at 4° C., pelleted nuclei were resuspended in 1× micrococcal nuclease (MNase) Buffer (New England BioLabs, Ipswich, MA) before adding 1000 U of MNase (New England BioLabs), and then incubated for 5 min at 37° C. Reactions were stopped by adding EDTA to a final concentration of 15 mM. Undigested chromatin was removed by centrifugation at 2,000 g for 1 min. Fragmented DNA was purified with the DNA Clean & Concentrator™-500 kit (Zymo Research, Irvine, CA). Mononucleosomal DNA produced by MNase digestion was also purified and size-selected using AMPure XP magnetic beads (Beckman Coulter, Brea, CA). DNA fragments were sized and quantified with a Bioanalyzer DNA 1000 chip (Agilent, Santa Clara, CA).

To model ctDNA at different concentrations, different fractions of PlasmArts from HCC1954 and HCC2218 cancer cells were mixed with those from the corresponding matched normal cell line (HCC1954BL and HCC2218BL, respectively). Three samples at each concentration were analyzed. Similarly, to model allelic imbalances in plasma DNA in a focal 3.5 Mb region, we generated PlasmArts from DNA mixtures containing different ratios of DNA from a child with a maternal 22q11.2 deletion and DNA from the father. Samples containing only the father's DNA were used as negative controls. Eight samples at each concentration were analyzed.

Figure 41A:
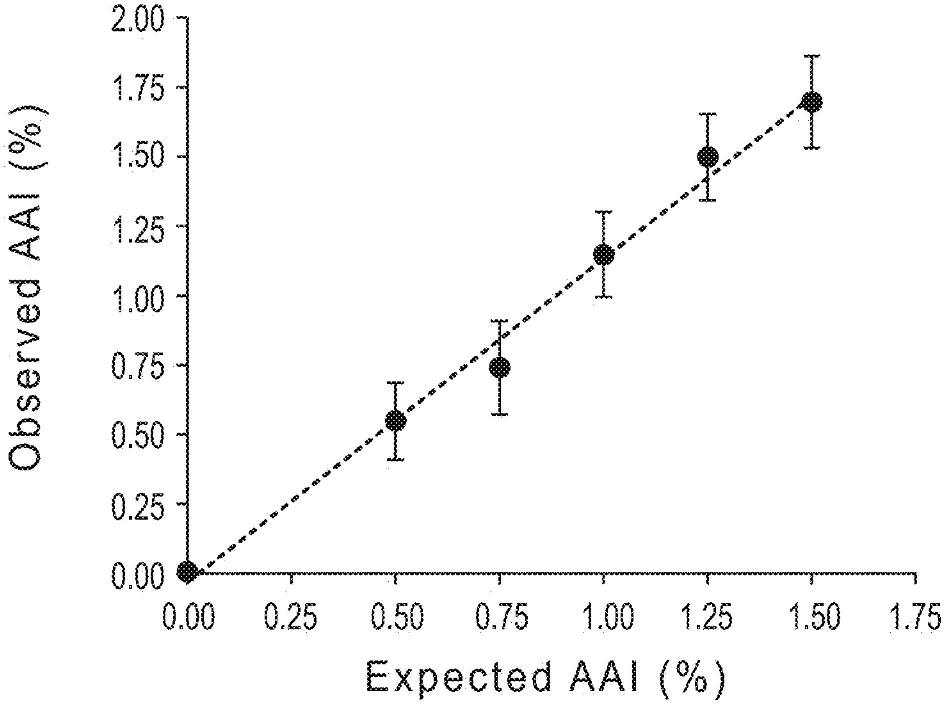
FIGS. 41A-D are graphs of Sensitivity of CONVERGe determined with PlasmArts.
Figure 42A:
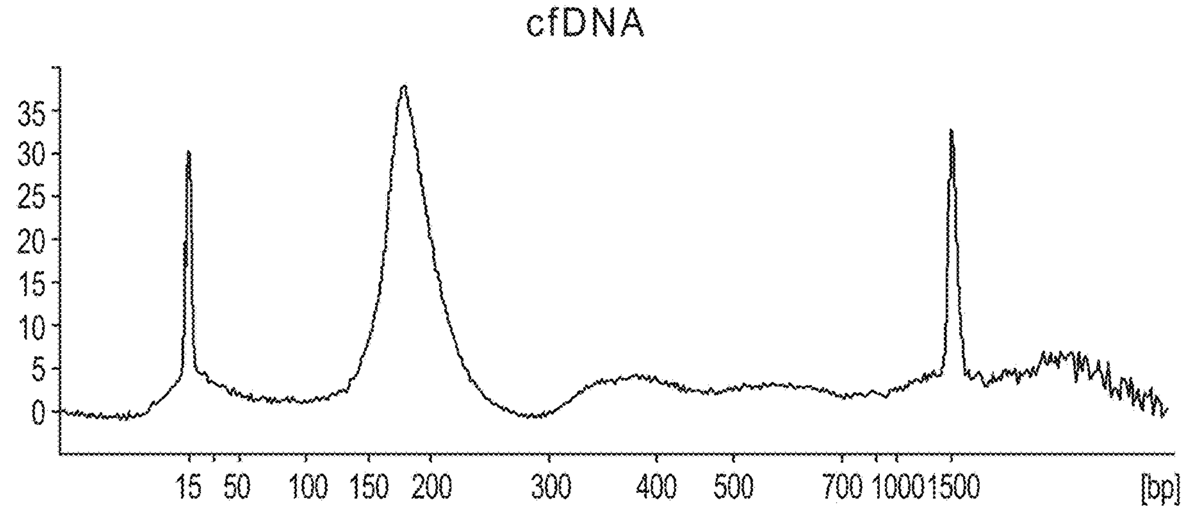
FIGS. 42A-B provide a model system for validation. Plasmart samples were made from cell lines with similar size profiles to plasma.
Figure 42B:
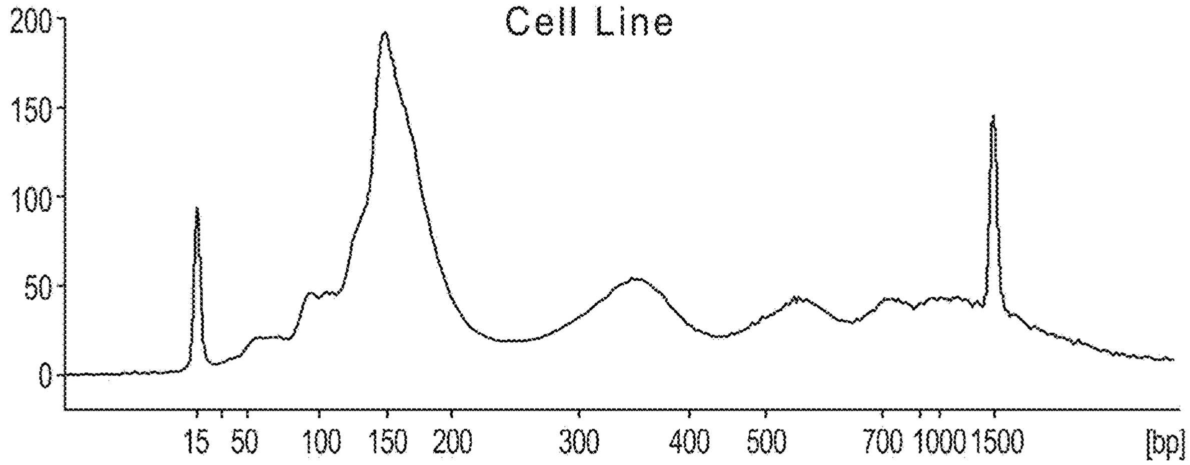
Figure 43A:
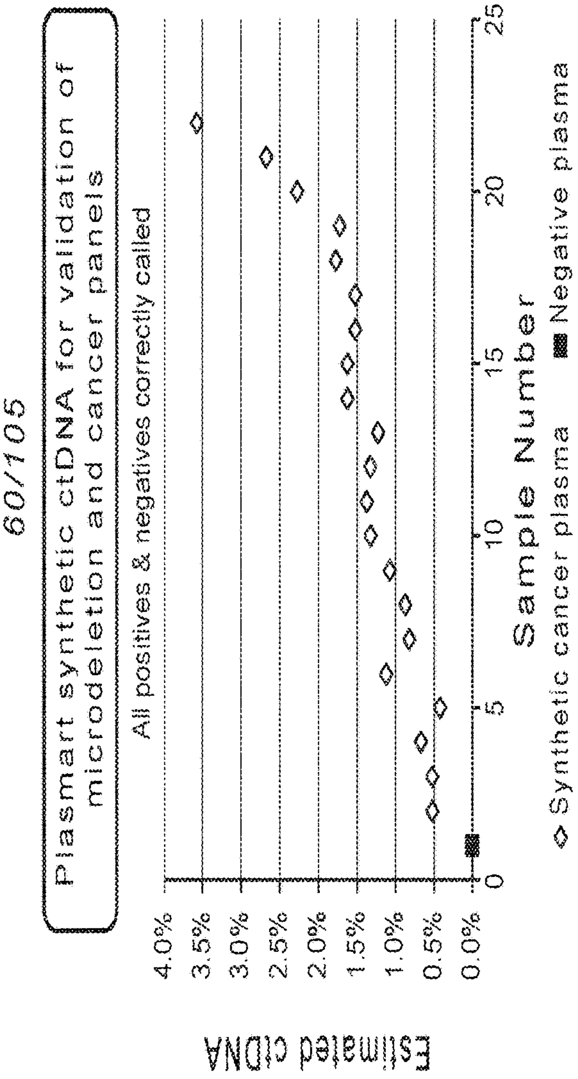
FIG. 43A, FIG. 43B, FIG. 43C, and FIG. 43D provide results from a dilution curve of Plasmart synthetic ctDNA standards for validation of microdeletion and cancer panels.
Figure 43B:
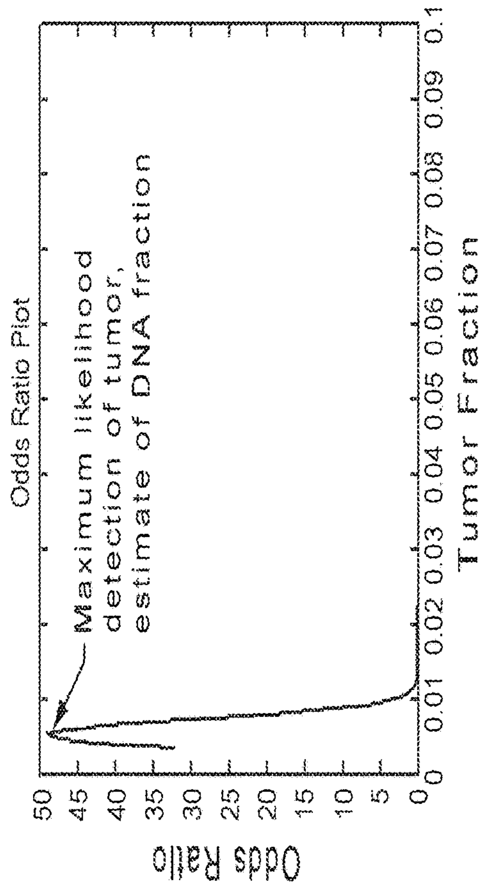
Figure 43C:
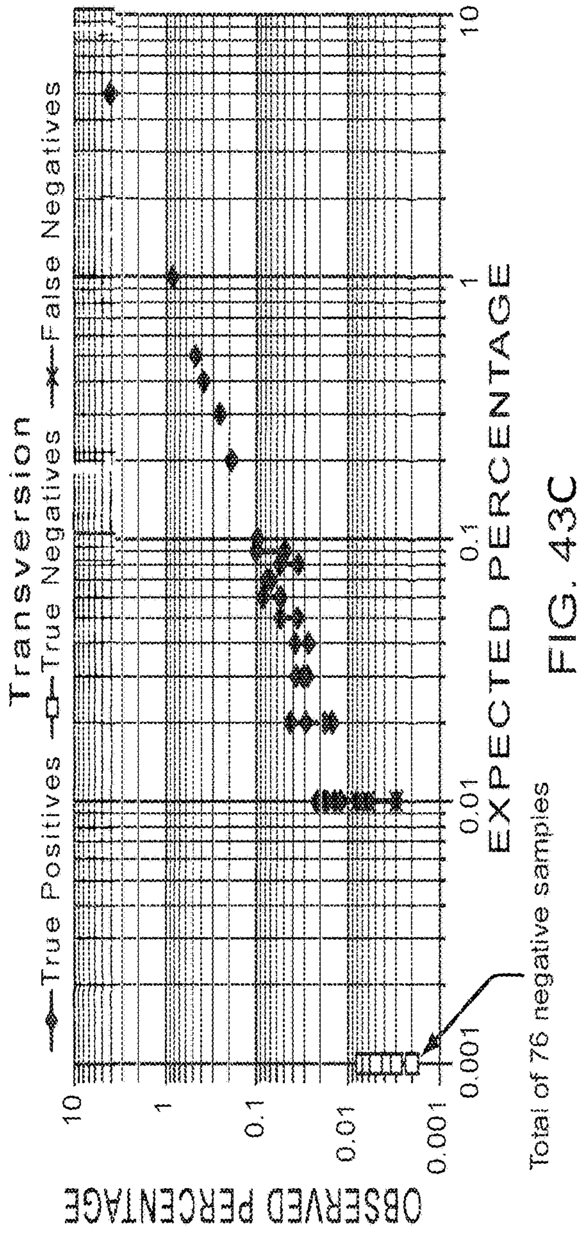
Figure 43D:
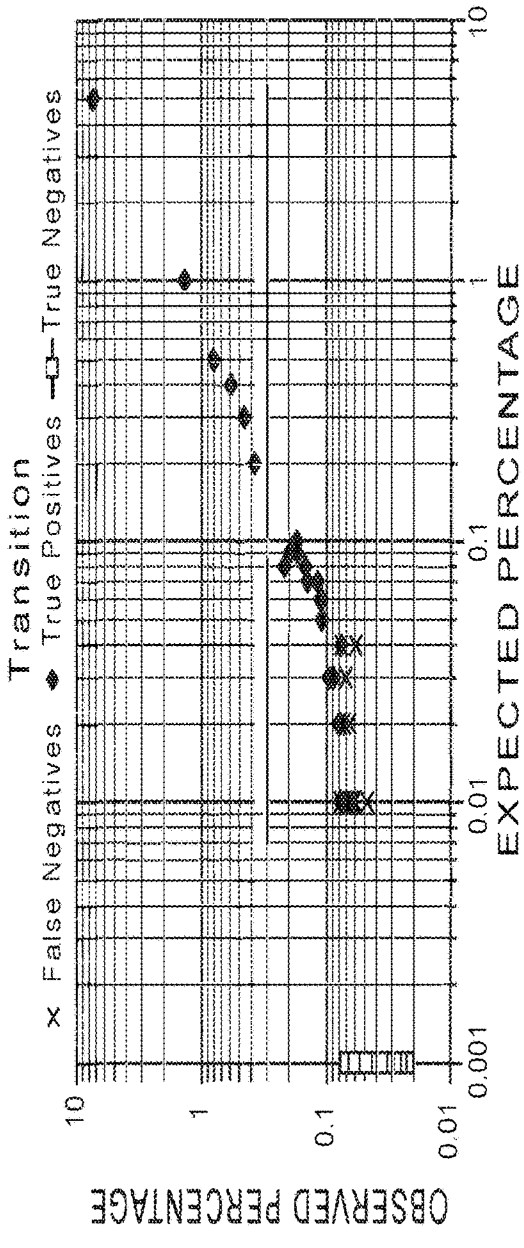

Accordingly, to evaluate the sensitivity and reproducibility of CONVERGe, especially when the proportion of abnormal DNA for a CNV, or average allelic imbalance (AAI), is low, we used it to detect CNVs in DNA mixtures comprised of a previously characterized abnormal sample titrated into a matched normal sample. The mixtures consisted of artificial cfDNA, termed "PlasmArt", with fragment size distribution approximating natural cfDNA (see above). FIG. 42 graphically displays the size distribution of an exemplary PlasmArt prepared from a cancer cell line compared to the size distribution of cfDNA, looking at CNVs on chromosome arms 1p, 1q, 2p, and 2q. In the first pair, a son's tumor DNA sample having a 3 Mb Focal CNV deletion of the 22q11.2 region was titrated into a matched normal sample from the father at between 0-1.5% total cfDNA (FIG. 41*a*). CONVERGe reproducibly identified CNVs corresponding to the known abnormality with estimated AAI of >0.35% in mixtures of ≥0.5%+/−0.2% AAI, failed to detect the CNV in 6/8 replicates at 0.25% abnormal DNA, and reported a value of ≤0.05% for all eight negative control samples. The AAI values estimated by CONVERGe showed high linearity (R2=0.940) and reproducibility (error variance=0.087). The assay was sensitive to different levels of amplification within the same sample. Based on these data a conservative detection threshold of 0.45% AAI could be used for subsequent analyses. Using this cutoff another experiment was performed in which Plasmart synthetic ctDNA was spiked at known concentrations to create synthetic cancer plasma at between around 0.5% and around 3.5%. Negative plasma was also included as a control. All of the synthetic cancer plasma yielded estimates above 0.45% and the reading for the negative plasma was well below 0.45% (FIG. 43A-D). FIG. 43A shows the maximum likelihood of tumor, and FIG. 43B shows an estimate of DNA fraction results as an odds ratio plot. FIG. 43C is a plot for the detection of transversion events. FIG. 43D is a plot for the detection of Transition events.

Figure 41B:
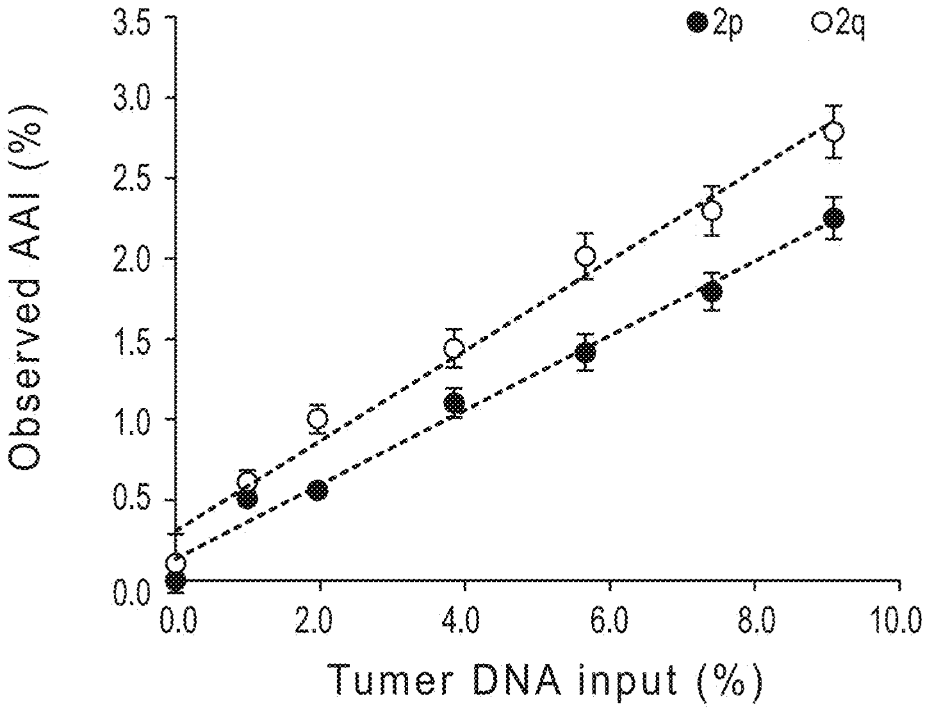
Figure 41C:
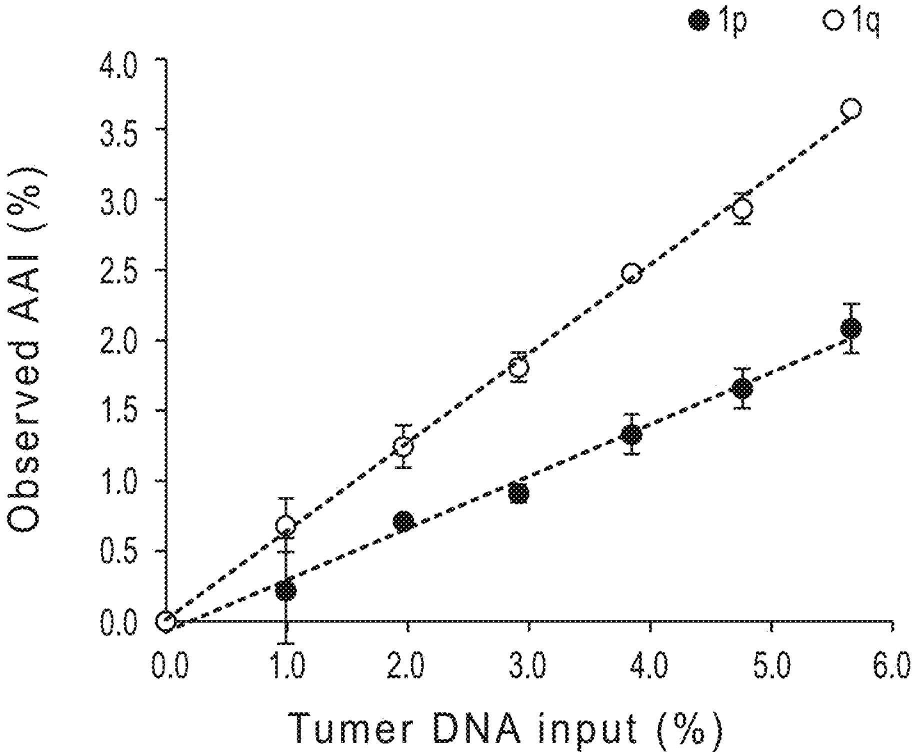
Figure 41D:
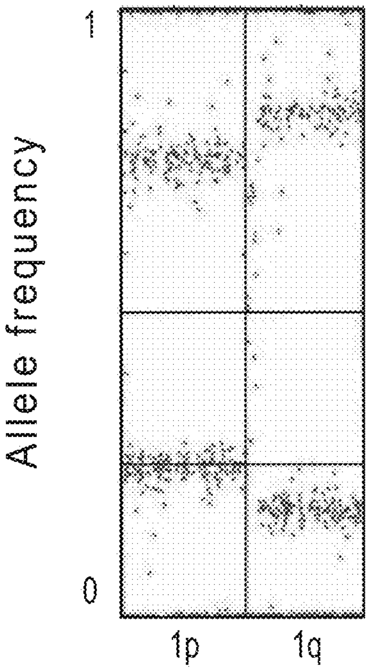

Two additional PlasmArt titrations, prepared from pairs of matched tumor and normal cell line samples and having CNVs on chromosome 1 or chromosome 2, were also evaluated (FIG. 41*b*, 41*c*). Among negative controls, all values were <0.45%, and high linearity (R2=0.952 for HCC1954 1p, R2=0.993 for HCC1954 1q, R2=0.977 for HCC2218 2p, R2=0.967 for HCC2218 2q) and reproducibility (error variance=0.190 for HCC1954 1p, 0.029 for HCC1954 1q, 0.250 for HCC2218 2p, and 0.350 for HCC2218 2q) were observed between the known input DNA amount and that calculated by CONVERGe. The difference in the slopes of the regressions for regions 1p and 1q of one sample pair correlates with the relative difference in copy number observed in the B-allelic frequencies (BAFs) of regions 1p and 1q of the same sample, demonstrating the relative precision of the AAI estimate calculated by CONVERGe (FIG. 41*c*, 41*d*).

The workflow for processing samples is illustrated in FIG. 63. CONVERge has application to a variety of sample sources including FFPE, Fresh Frozen, Single Cell, Germline control and cfDNA. We applied CONVERGe to six human breast cancer cell lines and matched normal cell lines to assess whether it can detect somatic CNVs. Arm-level and focal CNVs were present in all six tumour cell lines, but were absent from their matched normal cell lines, with the exception of chromosome 2 in HCC1143 in which the normal cell line exhibits a deviation from the 1:1 homolog ratio (FIG. 63*b*). To validate these results on a different platform, we performed CytoSNP-12 microarray analyses, which produced consistent results for all samples (FIG. 63*d*, 63*e*). Moreover, the maximum homolog ratios for CNVs identified by CONVERGe and CytoSNP-12 microarrays exhibited a strong linear correlation (R2=0.987, P<0.001) (FIG. 63*f*).

Figure 64A:
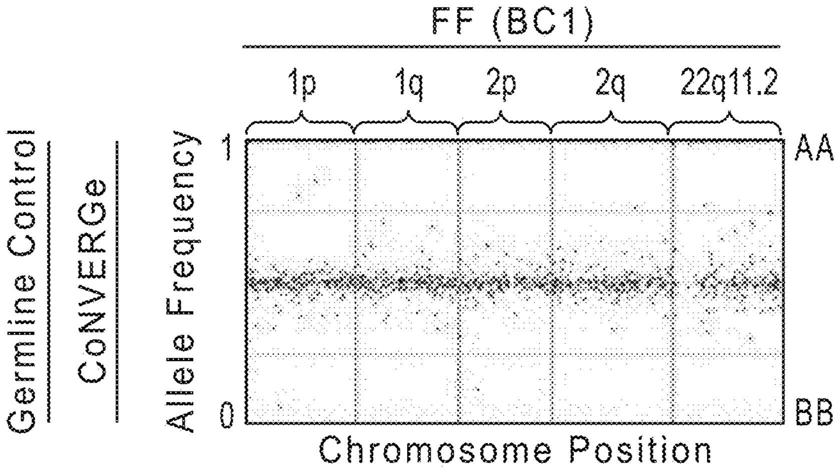
FIGS. 64A-H provide a comparison of Fresh Frozen (FF) and FFPE (formalin-fixed paraffin embedded) breast cancer samples to matched buffy coat gDNA control samples.
Figure 64B:
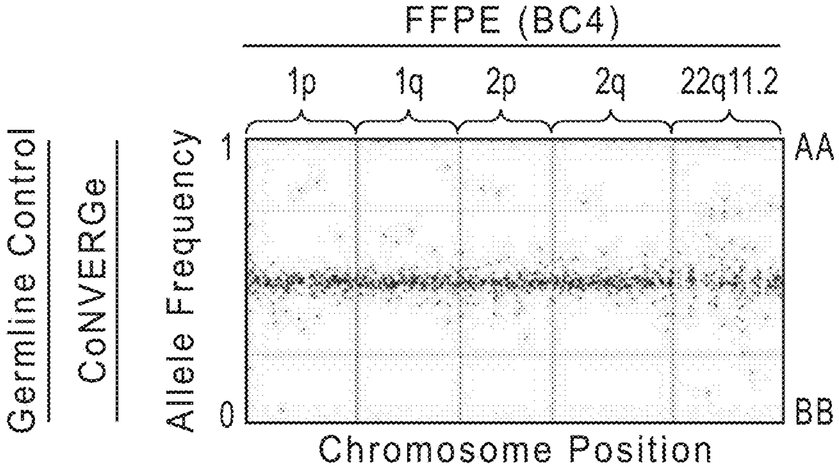
Figure 64C:
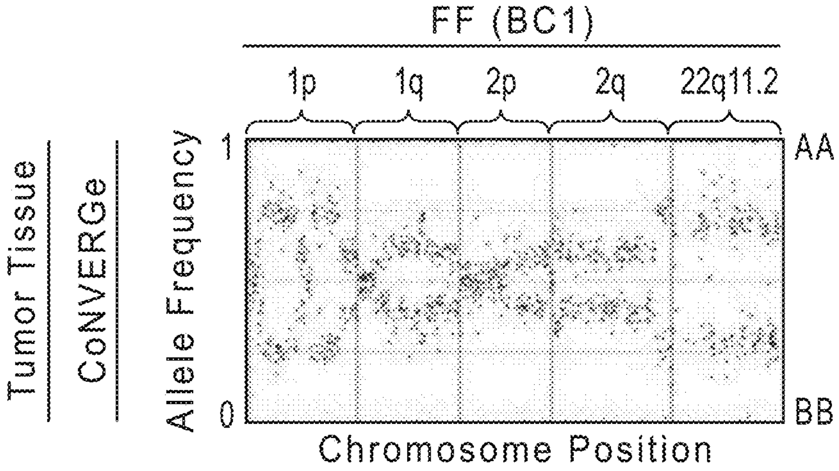
Figure 64D:
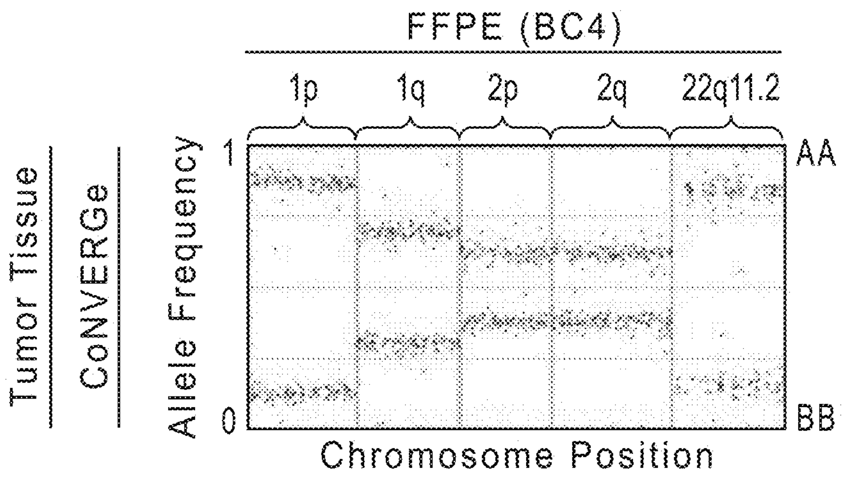
Figure 64E:
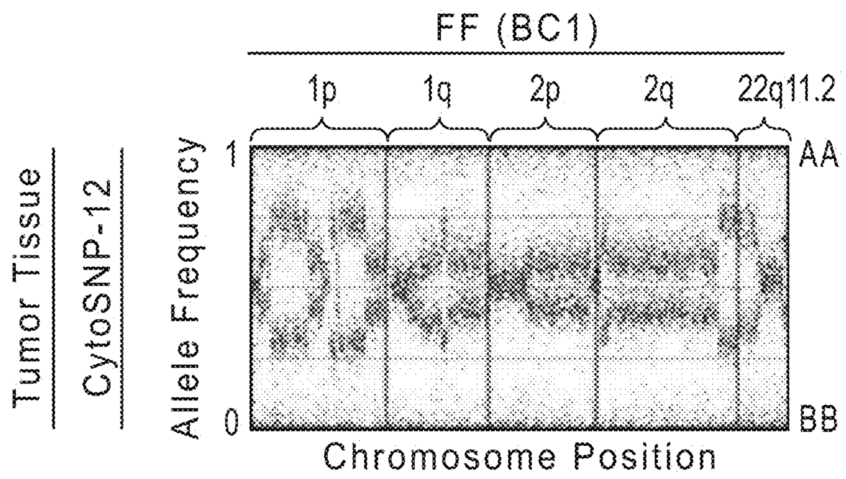
Figure 64F:
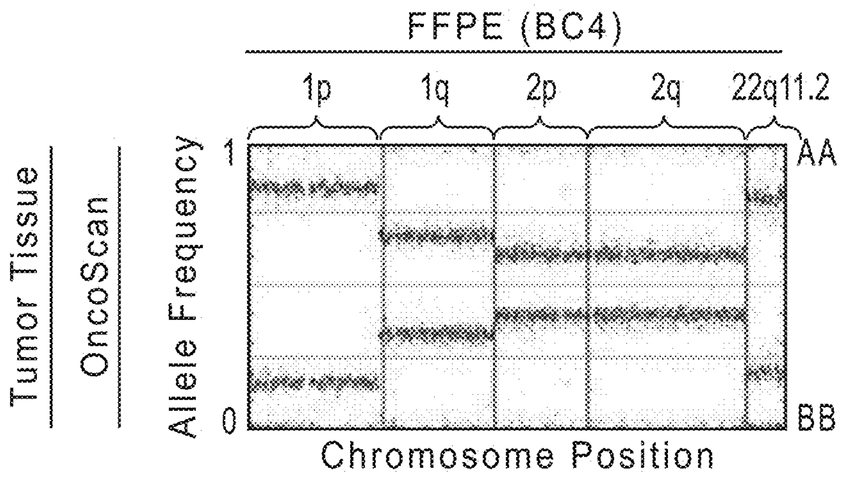
Figure 64G:
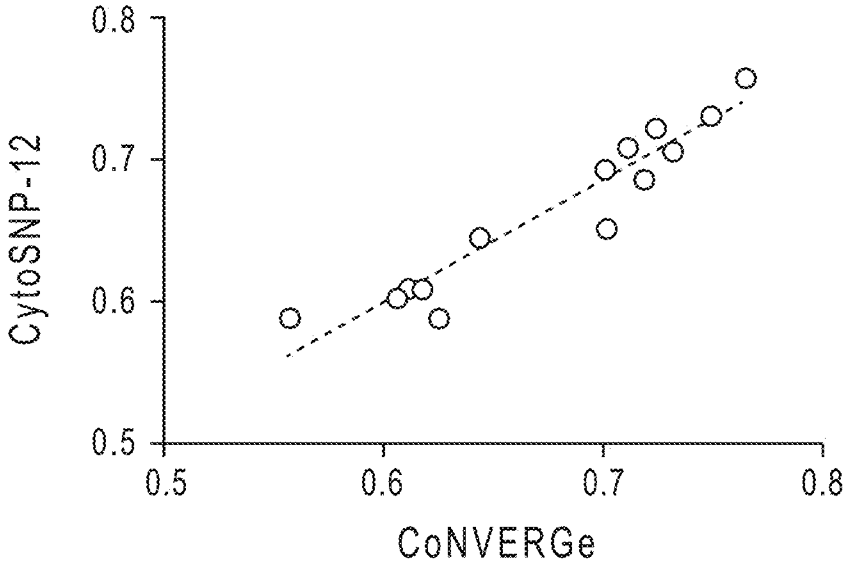
Figure 64H:
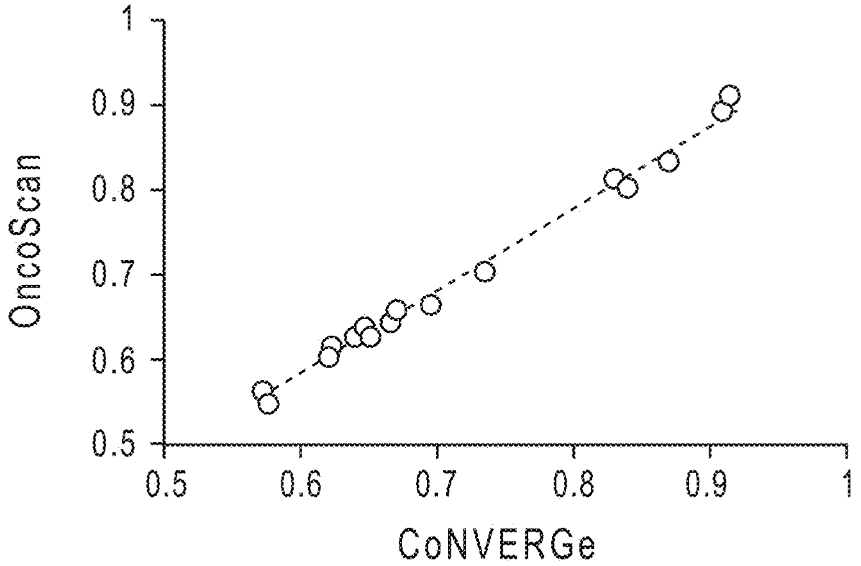
Figure 65A:
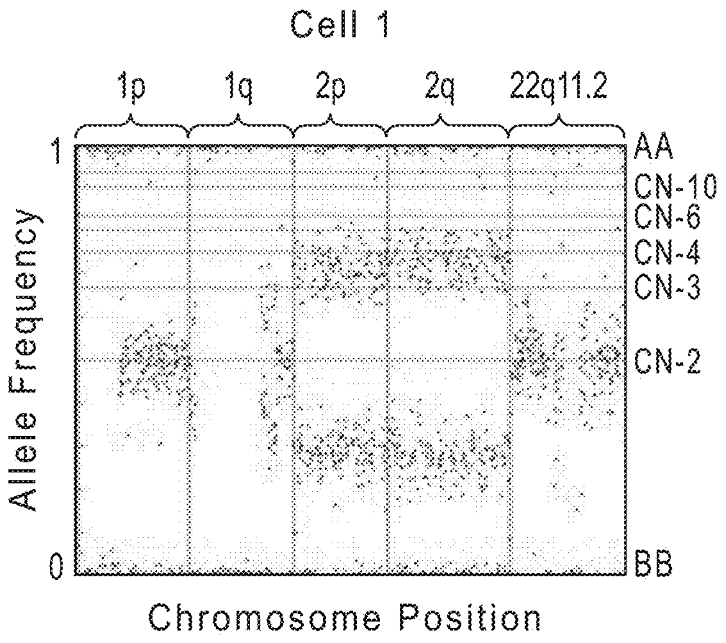
FIGS. 65A-D illustrate Allele frequency plots to reflect chromosome copy number using the CONVERGe assay to detect CNVs in single cells.
Figure 65B:
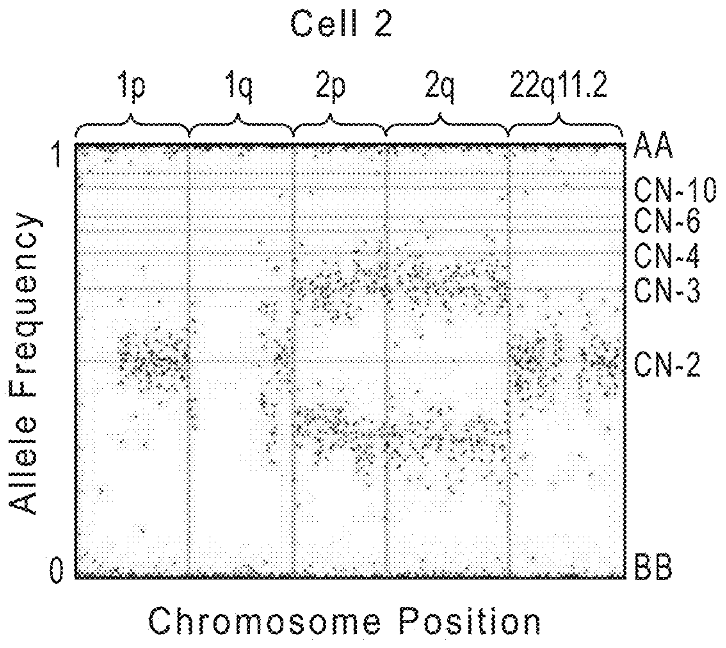
Figure 65C:
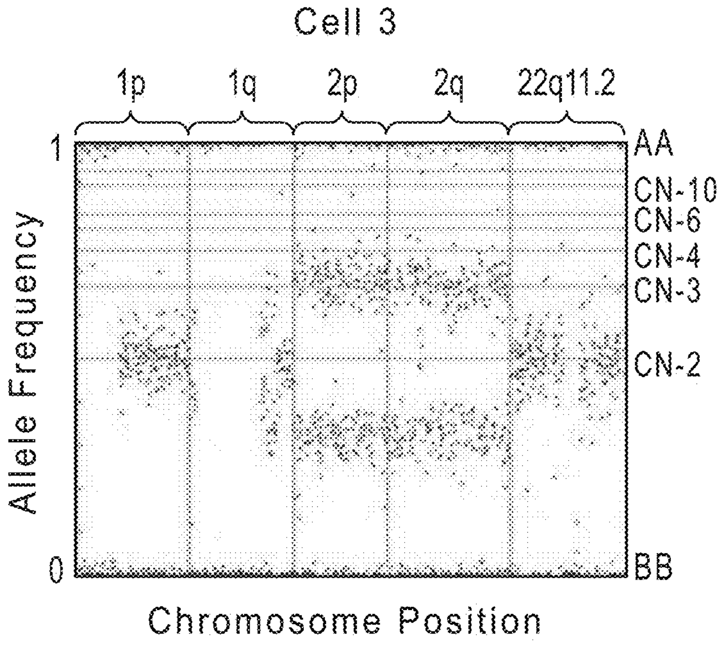
Figure 65D:
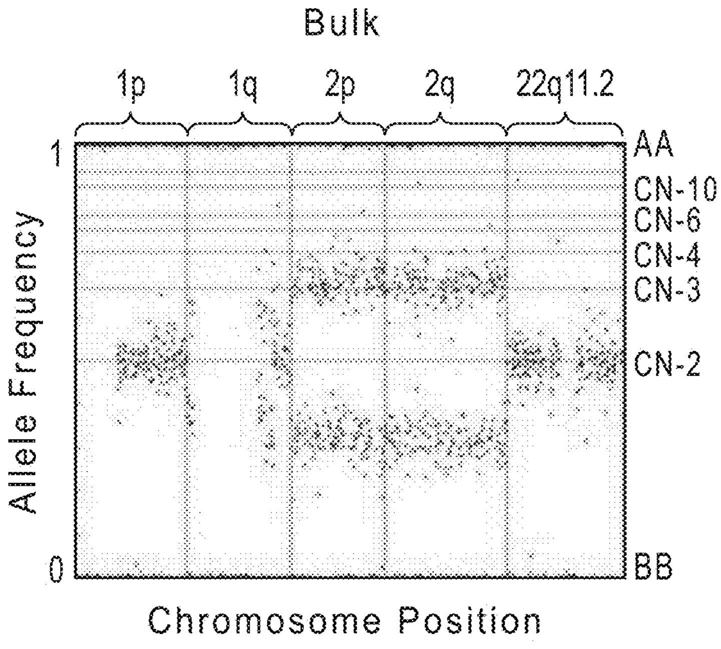

We next applied CONVERGe to fresh-frozen (FF) (FIG. 64*a*) and formalin-fixed, paraffin-embedded (FFPE) breast tumour tissue samples (FIG. 64*b*, 64*d*). In both sample types, several arm-level and focal CNVs were present; however, no CNVs were detected in DNA from matched buffy coat samples. CONVERGe results were highly correlated with those from microarray analyses of the same samples (FIG. 64*e-h*; R2=0.909, P<0.001 for CytoSNP-12 on FF; R2=0.992, P<0.001 for OncoScan on FFPE). CONVERGe also produces consistent results on small quantities of DNA extracted from laser capture microdissection (LCM) samples, for which microarray methods are not suitable.

Detection of CNVs in Single Cells with CONVERGe

To test the limits of the applicability of this mmPCR approach, we isolated single cells from the six aforementioned cancer cell lines and from a B-lymphocyte cell line that had no CNVs in the target regions. The CNV profiles from these single-cell experiments were consistent between three replicates and with those from genomic DNA (gDNA) extracted from a bulk sample of about 20,000 cells (FIG. 65). On the basis of the number of SNPs with no sequencing reads, the average assay drop-out rate for bulk samples was 0.48% (range: 0.41-0.60%), which is attributable to either synthesis or assay design failure. For single cells, the additional average assay drop-out rate observed was 0.39% (range: 0.19-0.67%). For single cell assays that did not fail (i.e. no assay drop-out occurred), the average single ADO rate calculated using heterozygous SNPs only was 0.05% (range: 0.00-0.43%). Additionally, the percentage of SNPs with high confidence genotypes (i.e. SNP genotypes determined with at least 98% confidence) was similar for both single cell and bulk samples and the genotype in the single cell samples matched those in the bulk sample (average 99.52%, range: 92.63-100.00%).

In single cells, allele frequencies are expected to directly reflect chromosome copy numbers, unlike in tumour samples where this may be confounded by TH and non-tumour cell contamination. BAFs of 1/n and (n−1)/n indicate n chromosome copies in a region. Chromosome copy numbers are indicated on the allele frequency plots for both single cells and matched gDNA samples (FIG. 65).

Application of CONVERGe to Plasma Samples

Figure 66B:
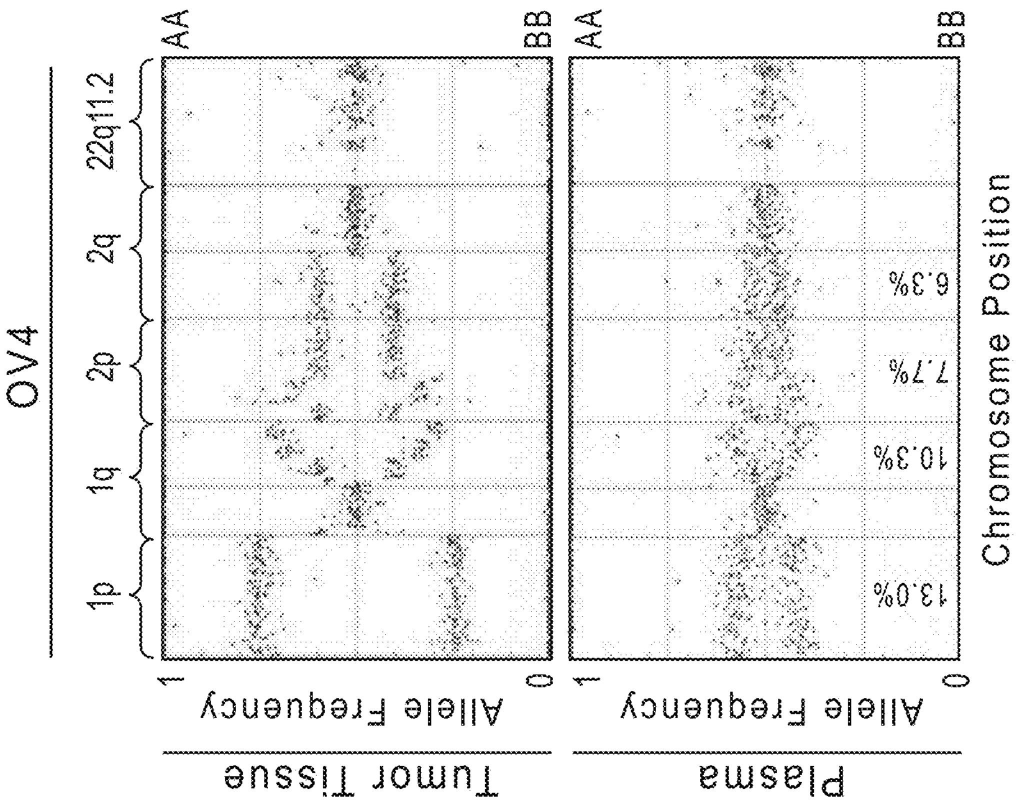
FIGS. 66A-C illustrate Allele frequency plots to reflect chromosome copy number using the CONVERGe assay to detect CNVs in real plasma samples.
Figure 66A:
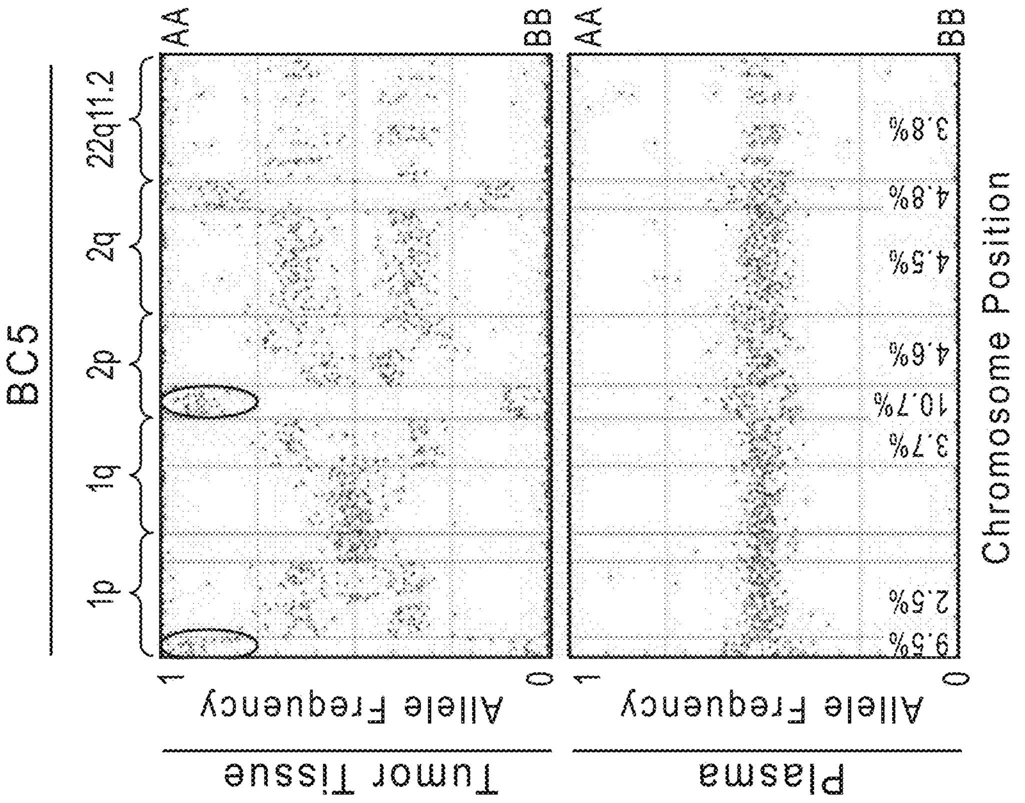
Figure 66C:
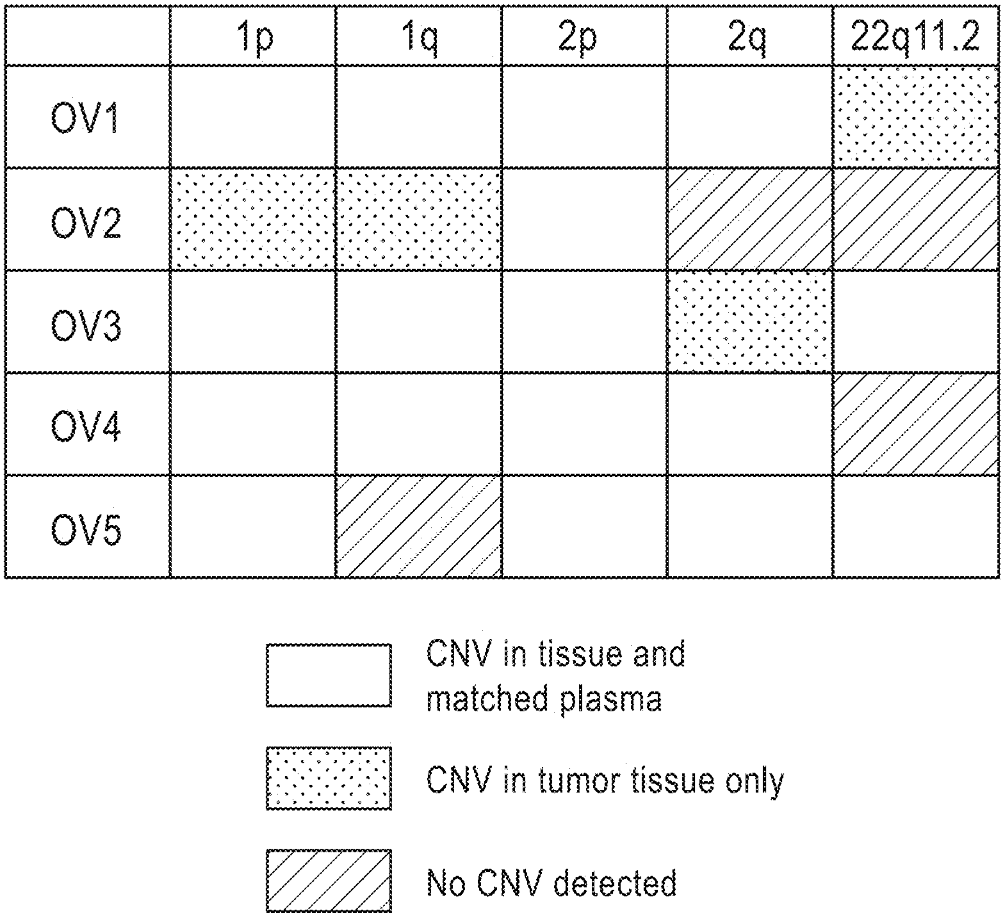

To investigate the ability of CONVERGe to detect CNVs in real plasma samples, we applied our approach to cfDNA paired with a matched tumour biopsy from each of two stage II breast cancer patients and five late-stage ovarian cancer. In all seven patients, CNVs were detected in both FF tumour tissues and in the corresponding plasma samples (FIG. 66). FIG. 67 provides a list of SNV breast cancer mutations. A total of 32 CNVs, at a level of ≥0.45% AAI, were detected in the seven plasma samples (range: 0.48-12.99% AAI) over the five regions assayed, which represent about 20% of the genome. Note that the presence of CNVs in plasma cannot be confirmed due to the lack of alternative orthogonal methods.

Although AAI estimates may appear correlated with BAFs in tumour, direct proportionality should not necessarily be expected due to tumour heterogeneity. For example, in sample BC5 (FIG. 66*a*), the ovals at the upper left area of FIG. 66*a* indicate regions that have BAFs compatible with N=11; combining this with the AAI calculation from the plasma sample leads to estimates for c of 2.33% and 2.67% for the two regions. Estimating c using the other regions in the sample give values between 4.46% and 9.53%, which clearly demonstrates the presence of tumor heterogeneity.

These data demonstrate that CNVs can be detected in plasma in a substantial fraction of samples, and suggest that the more prevalent a CNV is within a tumour, the more likely it is to be observed in cfDNA. Furthermore, CONVERGe detected CNVs from a liquid biopsy that may have otherwise unobserved in a traditional gone tumour biopsy.

Example 9

This example provides details regarding certain exemplary sample preparation methods used for CONVERGe analysis of different types of samples.

Single Cell CNV Protocol for 28,000-plex PCR

Multiplexed PCR allows simultaneous amplification of many targets in a single reaction. Target SNPs were identified in each genomic region with 10% minimum population minor allele frequency (1000 Genomes Project data; Apr. 30, 2012 release). For each SNP, multiple primers, semi-nested, were designed to have an amplicon length of a maximum length of 75 bp and a melting temperature between 54-60.5° C. Primer interaction scores for all possible combinations of primers were calculated; primers with high scores were eliminated to reduce the likelihood of primer dimer product formation. Candidate PCR assays were ranked and selected on the basis of target SNP minor allele frequency, observed heterozygosity rate (from dbSNP), presence in HapMap, and amplicon length.

In certain experiments, single cell samples were prepared and amplified using a mmPCR 28,000-plex protocol. The samples were prepared in the following way: For analysis of a single cell, cells were serial diluted until there were 3 or 4 cells per droplet. An individual cell was pipetted and placed into a PCR tube. The cell was lysed using Protease K, salt, and DTT using the following conditions: 56° C. for 20 minutes, 95° C. for 10 minutes, and then a 4° C. hold. For analysis of genomic DNA, DNA from the same cell line as the analyzed single cell was either purchased or obtained by growing the cells and extracting the DNA. The DNA was amplified in a 40 uL reaction volume containing Qiagen mp-PCR master mix (2×MM final conc), 7.5 nM primer conc. for 28K primer pairs having a hemi-nested Rev primers under the following conditions: 95C 10 min, 25× [96C 30 sec, 65C 29 min, 72C 30 sec], 72C 2 min, 4C hold. The amplification product was diluted 1:200 in water and 2 ul added to STAR 2 (10 ul reaction volume) 1λMM, 5 nM primer conc. and PCR was performed using hemi-nested inner Fwd primer and tag specific Rev primer: 95C 15 min, 25× [94C 30 sec, 65C 1 min, 60C 5 min, 65C 5 min, 72C 30 sec], 72C 2 min, 4C hold.

Full sequence tags and barcodes were attached to the amplification products and amplified for 9 cycles using adaptor specific primers. Prior to sequencing, the barcoded library product were pooled, purified with the QIAquick PCR Purification Kit (Qiagen), and quantified using the Qubit® dsDNA BR Assay Kit (Life Technologies). Amplicons were sequenced using an Illumina HiSeq 2500 sequencer.

Extraction of DNA from a Blood/Plasma Sample

Blood samples were collected into EDTA tubes. The whole blood sample was centrifuged and separated into three layers: the upper layer, 55% of the blood sample, was plasma and contains cell-free DNA (cfDNA); the buffy coat middle layer contained leucocytes having DNA, <1% of total; and the bottom layer, 45% of the collected blood sample, contained erythrocytes, no DNA was present in this fraction as erythrocytes are enucleated. Circulating tumor DNA was isolated from at least 1 mL plasma using the QIAamp Circulating Nucleic Acid Kit, Qia-Amp (Qiagen, Valencia, CA), according to the manufacture's protocol.

Plasma CNV Protocol for 3,168-plex for Chromosomes 1p, 1q, 2p, 2q, and 22q11

Plasma DNA libraries were prepared and amplified using a mmPCR 3,168-plex protocol. The samples were prepared in the following way: Up to 20 mL of blood was centrifuged to isolate the buffy coat and the plasma. Plasma extraction of cfDNA and library preparation was performed. DNA was eluted in 50 uL TE buffer. The input for mmPCR was 6.7 uL of amplified and purified Natera plasma library at an input amount of approximately 1200 ng. The plasma DNA was amplified in a 20 uL reaction volume containing Qiagen mp-PCR master mix (2×MM final conc), 2 nM tagged primer conc. (total 12.7 uM) in 3,168-plex primer pools and PCR amplified: 95C 10 min, 25× [96C 30 sec, 65C 20 min, 72C 30 sec], 72C 2 min, 4C hold. The amplification product was diluted 1:2,000 in water and 1 ul added to the Barcoding-PCR in a 10 uL reaction volume. The barcodes are attached to the amplification products via PCR amplification for 12 cycles using tag specific primers. Products of multiple samples are pooled and then purified with QIAquick PCR Purification Kit (Qiagen) and eluted in 50 ul DNA suspension buffer. Samples are sequenced by NGS as described for the Single Cell CNV Protocol for 28,000-plex PCR.

Figure 68A:
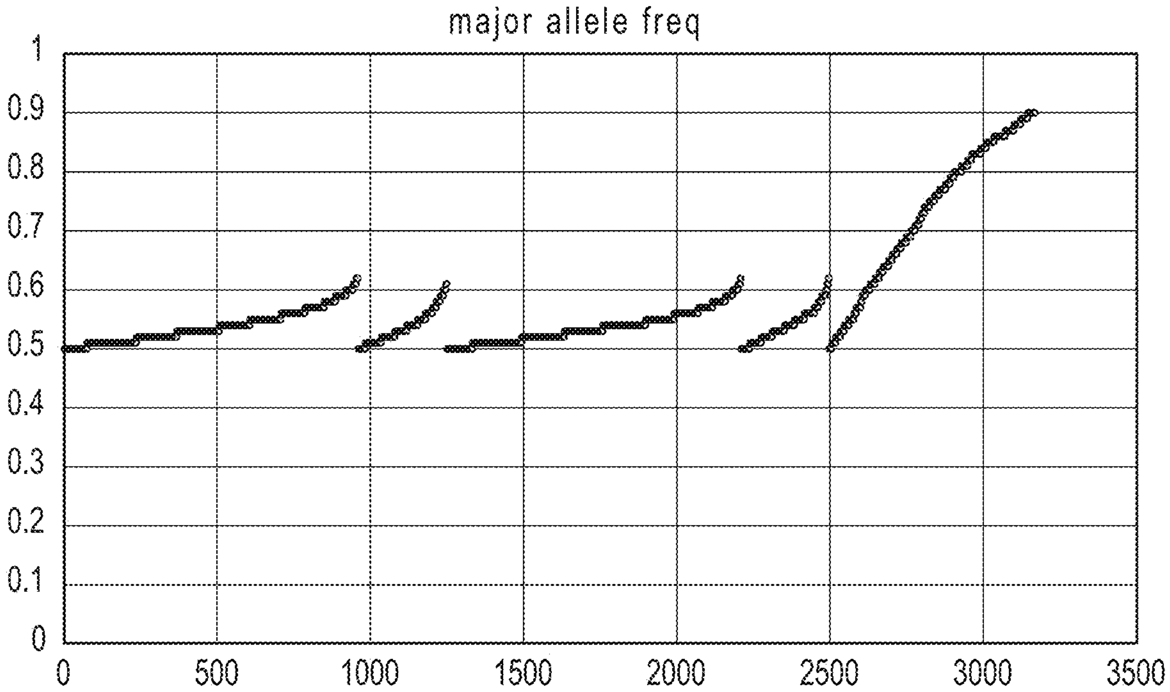
FIGS. 68A-B illustrate the major (FIG. 68A) and minor allele (FIG. 68B) frequencies of SNPs used in a 3168 mmPCR reaction.
Figure 68B:
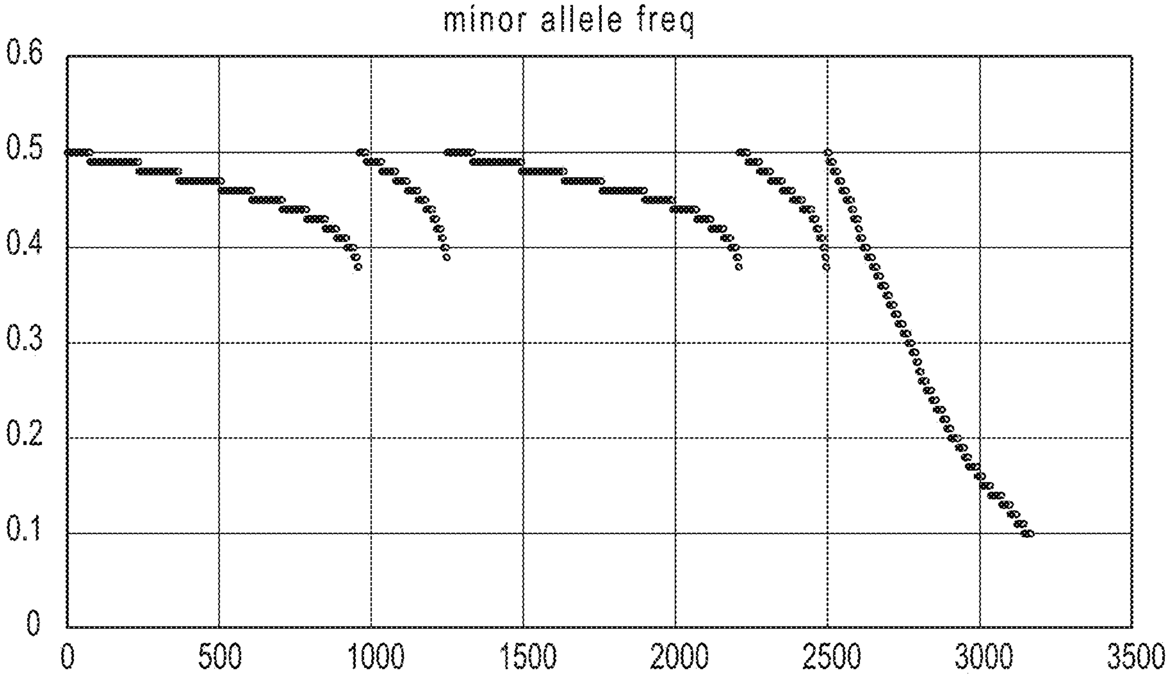

Breast Cancer Feasibility SNV Panel from Plasma cfDNA from breast cancer patient blood samples was prepared and amplified using 336 primer pairs that were distributed into four 84-plex pools. Natera plasma libraries were prepared as described for Plasma CNV Protocol for 3,168-plex for Chromosomes 1p, 1q, 2p, 2q, and 22q11. DNA was eluted in 50 uL TE buffer. The input for mPCR was 2.5 uL of amplified and purified Natera plasma library at an input amount of approximately 600 ng. FIG. 68A-B represents the major and minor allele frequencies of the SNPs used in a 3168 mmPCR reaction. The X-axis represents the number of SNPs, from left to right, for chromosome 1q, 1p, 2q, 2p and 22q. SNPs were selected from the 1000 Genomes map for Humans, Group 19 and dbSNP to pick targets, but only SNPs from the 1000 Genomes were used to screen for minor allele frequencies. The plasma DNA was amplified in four parallel reactions of 84-plex primer pools, a 10 uL reaction volume containing Qiagen mp-PCR master mix (2×MM final conc.), 4 mM EDTA, 7.5 nM primer concentration (total 1.26 uM) and PCR amplified: 95C 15 min, 25× [94C 30 sec, 65C 15 min, 72C 30 sec], 72C 2 min, 4C hold. The amplification product of the 4 subpools were each diluted 1:200 in water and 1 ul added to the Barcoding-PCR reaction in a 10 uL reaction volume containing Q5 HS HF master mix (1×final), and 1 μM each barcoding primer and each of the pools were amplified in the following reaction: 98C 1 min, 25× [98C 10 sec, 70C 10 sec, 60C 30 sec, 65C 15 sec, 72C 15 sec], 72C 2 min, 4C hold. Libraries were purified with QIAquick PCR Purification Kit (Qiagen) and eluted in 50 ul DNA suspension buffer. Samples were sequenced by paired end sequencing.

Example 10

This example provides details regarding certain exemplary methods for analyzing sequencing data to identify SNVs.

SNV METHOD 1: For this embodiment, a background error model was constructed using normal plasma samples, which were sequenced on the same sequencing run to account for run-specific artifacts. In certain embodiments, 5, 10, 15, 20, 25, 30, 40, 50, 100, 150, 200, 250, or more than 250 normal plasma samples were analyzed on the same sequencing run. In certain illustrative embodiments, 20, 25, 40, or 50 normal plasma samples are analyzed on the same sequencing run. Noisy positions with normal median variant allele frequency greater than a cutoff are removed. For example this cutoff in certain embodiments is >0.1%, 0.2%, 0.25%, 0.5%, 1%, 2%, 5%, or 10%. In certain illustrative embodiments noisy positions with normal medial variant allele frequency greater than 0.5% are removed. Outlier samples were iteratively removed from the model to account for noise and contamination. In certain embodiments, samples with a Z score of greater than 5, 6, 7, 8, 9, or 10 were removed from the data analysis. For each base substitution of every genomic loci, the depth of read weighted mean and standard deviation of the error were calculated. Tumor or cell-free plasma samples' positions with at least 5 variant reads and a Z-score of 10 against the background error model were called as a candidate mutation.

SNV METHOD 2: For this embodiment we aim to determine Single Nucleotide Variants (SNVs) using plasma ctDNA data. We model the PCR process as a stochastic process, estimate the parameters using a training set and make the final SNV calls using a separate testing set. The main idea is to determine the propagation of the error across multiple PCR cycles, calculate the mean and the variance of the background error, and differentiate the background error from real mutations.

The following parameters are estimated for each base:

p=efficiency (probability that each read is replicated in each cycle)

$p_e$=error rate per cycle for mutation type e (probability that an error of type e occurs)

$X_0$=initial number of molecules

As a read is replicated over the course of PCR process, the more errors occur. Hence, the error profile of the reads is determined by the degrees of separation from the original read. We refer to a read as $k^{th}$ generation if it has gone through k replications until it has been generated.

Let us define the following variables for each base:

$X_{ij}$=number of generation i reads generated in the PCR cycle j $Y_{ij}$=total number of generation i reads at the end of cycle j $X_{ij}^{e}$=number of generation i reads with mutation e generated in the PCR cycle j Moreover, in addition to normal molecules $X_0$, if there are additional $f_e X_0$ molecules with the mutation e at the beginning of the PCR process (hence fe/(1+fe) will be the fraction of mutated molecules in the initial mixture).

Given the total number of generation i-1 reads at cycle j-1, the number of generation i reads generated at cycle j has a binomial distribution with a sample size of $Y_{i-1,j-1}$ and probability parameter of p. Hence, $E(X_{ij}, Y_{i-1,j-1}, p)=p\ Y_{i-1,j-1}$ and $Var(X_{ij}, |Y_{i-1,j-1}, p)=p\ (1-p)\ Y_{i-1,j-1}$.

We also have $Y_{ij}=\Sigma_{k=i}^{j}X_{ik}$. Hence, by recursion, simulation or similar methods, we can determine $E(X_{ij},)$. Similarly, we can determine $Var(X_{ij})=E\ (Var(X_{ij}, |p))+Var(E(X_{ij}, |p))$ using the distribution of p.

finally, $E(X_{ij}^{e}|Y_{i-1,j-1}, p_e)=p_e\ Y_{i-1,j-1}$ and $Var(X_{ij}^{e}|Y_{i-1,j-1}, p)=p_e\ (1-p_e)\ Y_{i-1,j-1}$, and we can use these to compute $E(X_{ij}^{e})$ and $Var(X_{ij}^{e})$.

20.

6+0.2 Algorithm

The algorithm starts by estimating the efficiency and error rate per cycle using the training set. Let n denote the total number of PCR cycles.

The number of reads $R_b$ at each base b can be approximated by $(1+p_b)^n\ X_0$, where $p_b$ is the efficiency at base b. Then $(R_b/X_0)^{1/n}$ can be used to approximate $1+p_b$. Then, we can determine the mean and the standard variation of $p_b$ across all training samples, to estimate the parameters of the probability distribution (such as normal, beta, or similar distributions) for each base.

Similarly, the number of error e reads $R_b^{e}$ at each base b can be used to estimate $p_e$. After determining the mean and the standard deviation of the error rate across all training samples, we approximate its probability distribution (such as normal, beta, or similar distributions) whose parameters are estimated using this mean and standard deviation values.

Next, for the testing data, we estimate the initial starting copy at each base as $$\int_0^1 \frac{R_b}{(1+p_b)^n} f(p_b)dp_b$$

where f(·) is an estimated distribution from the training set.

$$\int_0^1 \frac{R_b}{(1+p_b)^n} f(p_b)dp_b$$

where f(·) is an estimated distribution from the training set.

Hence, we have estimated the parameters that will be used in the stochastic process. Then, by using these estimates, we can estimate the mean and the variance of the molecules created at each cycle (note that we do this separately for normal molecules, error molecules, and mutation molecules).

Finally, by using a probabilistic method (such as maximum likelihood or similar methods), we can determine the best $f_e$ value that fits the distribution of the error, mutation, and normal molecules the best. More specifically, we estimate the expected ratio of the error molecules to total molecules for various $f_e$ values in the final reads, and determine the likelihood of our data for each of these values, and then select the value with the highest likelihood.

In certain embodiments, Method 2 above is performed as follows:

a) Estimate a PCR efficiency and a per cycle error rate using a training data set;

b) Estimate a number of starting molecules for the testing data set at each base using the distribution of the efficiency estimated in step (a);

c) If needed, update the estimate of the efficiency for the testing data set using the starting number of molecules estimated in step (b);

d) Estimate the mean and variance for the total number of molecules, background error molecules and real mutation molecules (for a search space consisting of an initial percentage of real mutation molecules) using testing set data and parameters estimated in steps (a), (b) and (c);

e) Fit a distribution to the number of total error molecules (background error and real mutation) in the total molecules, and calculate the likelihood for each real mutation percentage in the search space; and f) Determine the most likely real mutation percentage and calculate the confidence using the data from in step (e).

Example 11

Figure 44:
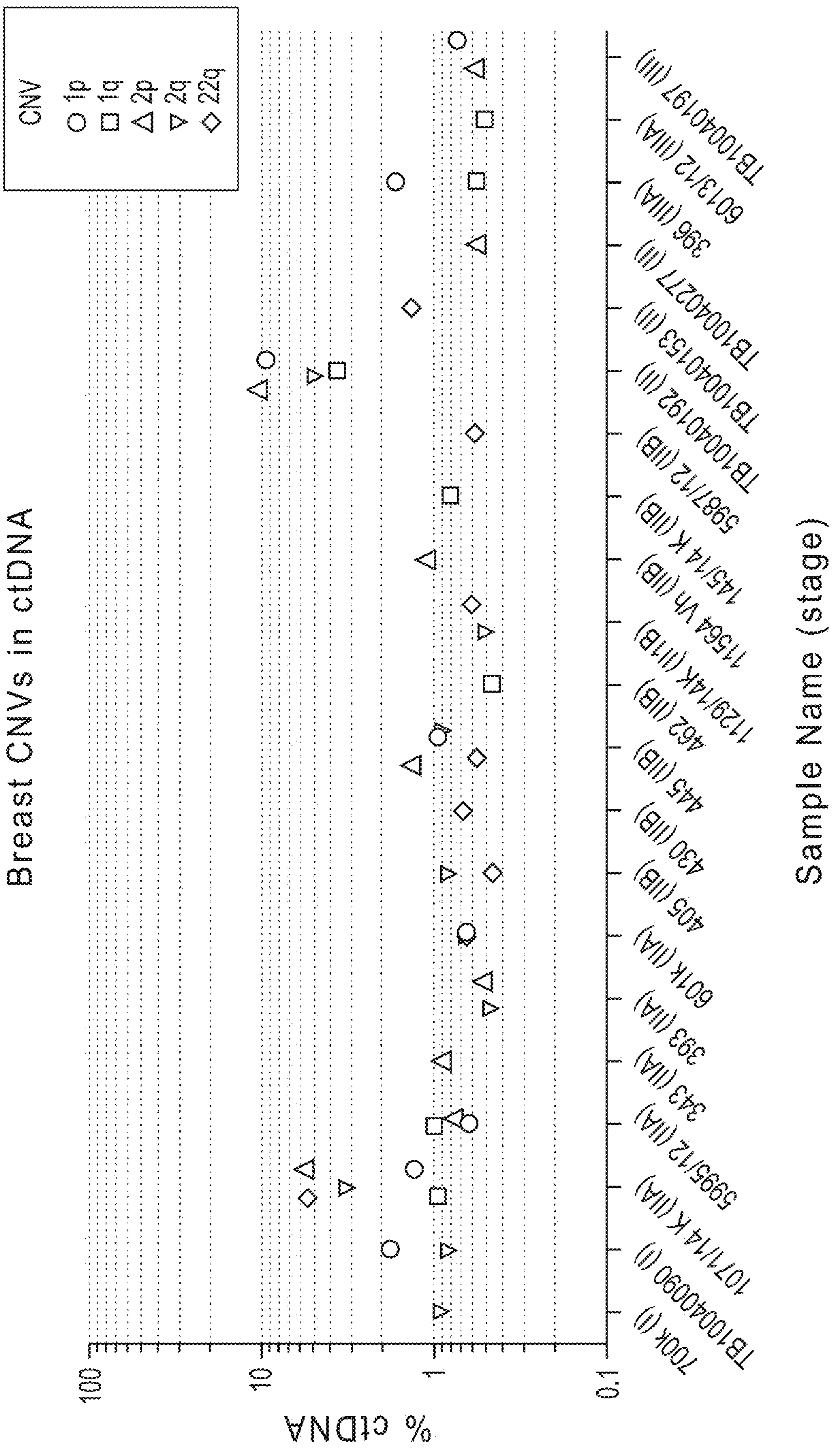
FIG. 44 is a plot showing CNVs for various chromosomal regions as indicated for various samples at different % ctDNAs. The plot depicts plasma from 21 breast cancer patients (stage 1-IIIB) and demonstrated that CNVs could be detected in ctDNA with an AAI ≥0.45% and required as few as 62 heterozygous SNPs.
Figure 45:
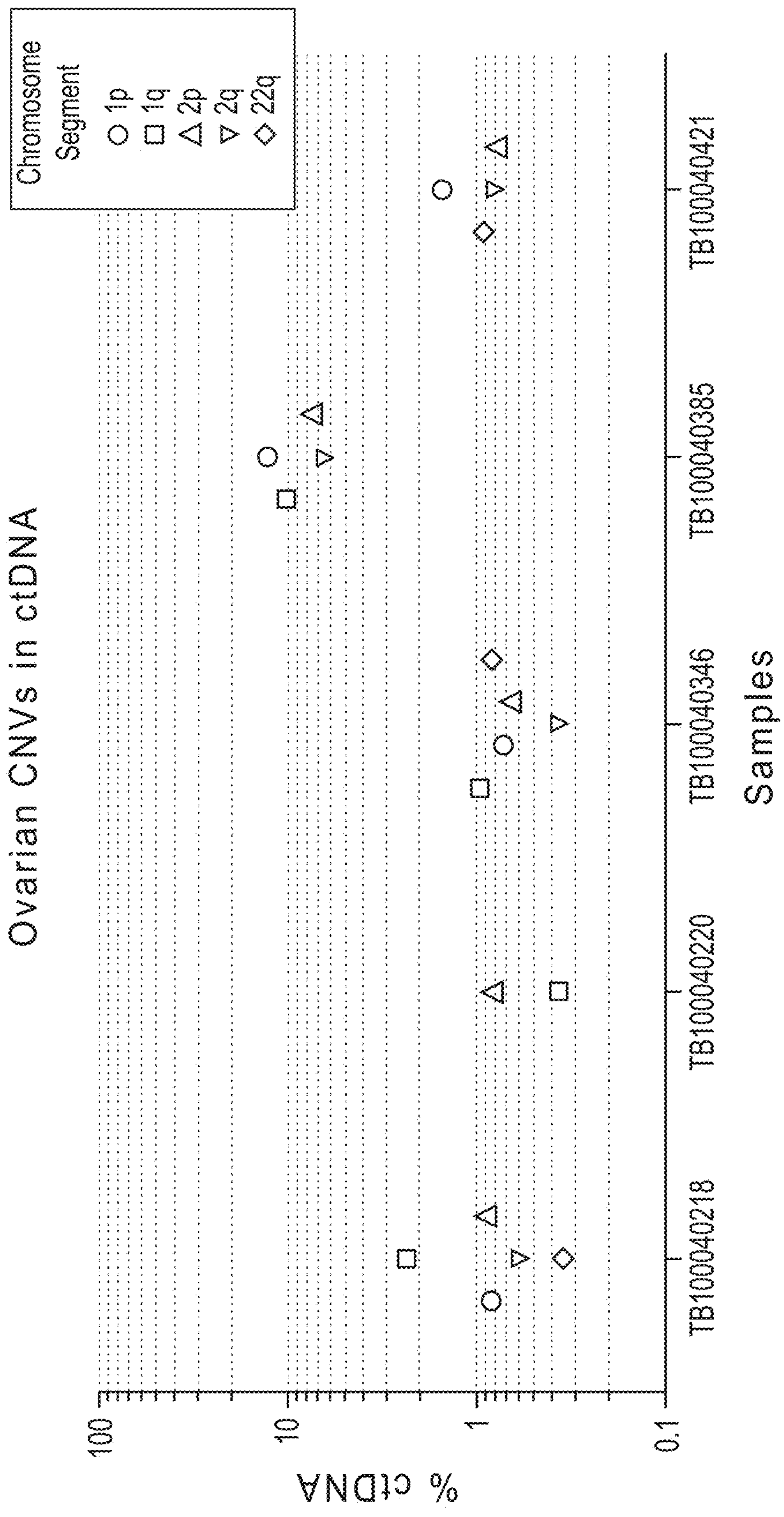
FIG. 45 is a plot showing CNVs for various chromosomal regions for various ovarian cancer samples with different % ctDNA levels. The plot indicates 100% detection rate at a 9.45% cutoff.

This example provides results using the multiplexed PCR CONVERGe methods provided herein, for the detection of cancer by detecting CNV in circulating DNA. The Plasma CNV Protocol for 3,168-plex for Chromosomes 1p, 1q, 2p, 2q, and 22q11 provided herein, was used. Plasma from 21 breast cancer patients (stage I-IIIB) was analyzed. The results shown in FIG. 44 demonstrate that CNVs were detected in all samples using an AAI >=0.45% and required as few as 62 heterozygous SNPs. A similar protocol was used to analyze plasma from ovarian cancer patients. Using a 0.45% cutoff, a 100% ovarian cancer detection rate was achieved, as shown in FIG. 45. Each of the five samples also had a matched tumor sample.

Example 12

Figures 46A, 46B:
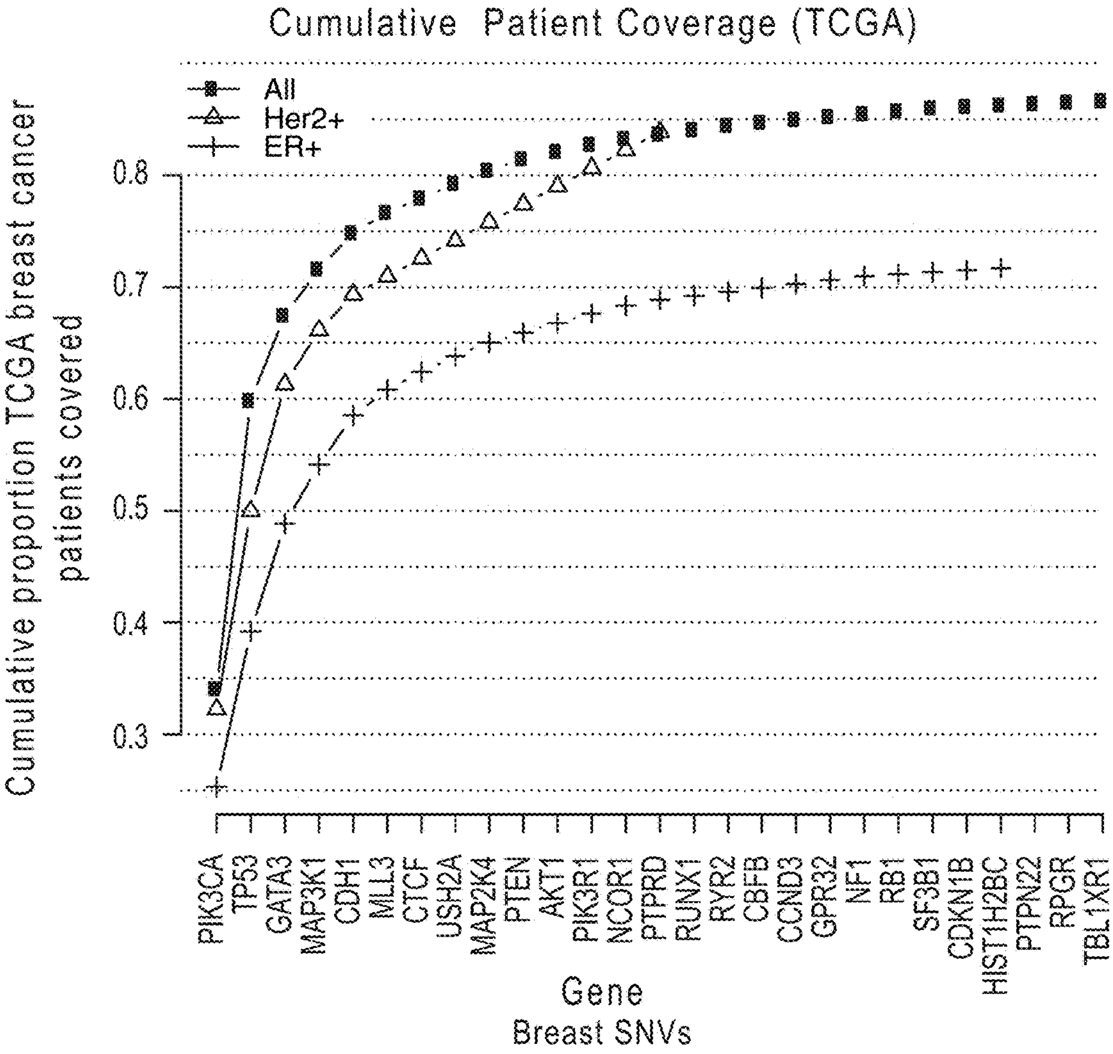
FIG. 46A is a table showing the percent of breast or lung cancer patients with an SNV or a combined SNV and/or CNV in ctDNA. The analysis was on ctDNA (plasma) from Stage I-III cancer patients and indicates that the ability to detect CNV in plasma dramatically improves detection rate vs. testing SNVs alone.
FIG. 46B plots cumulative proportion TCGA breast cancer patients covered vs. genes with breast SNVs.
Figure 46C:
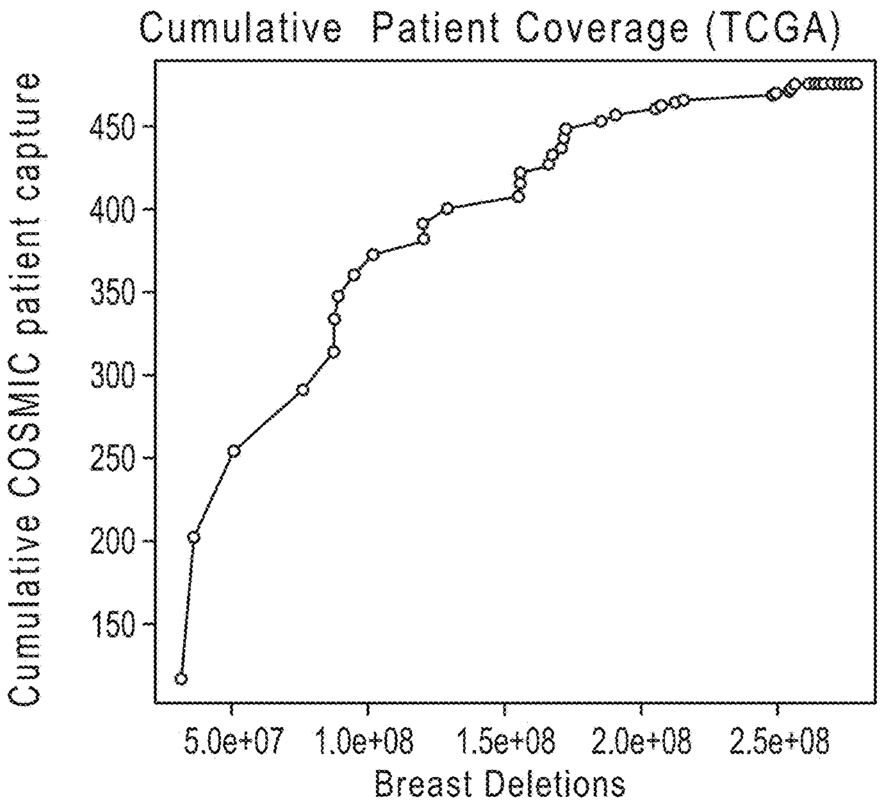
FIG. 46C plots cumulative COSMIC patient capture vs. cumulative patient coverage (TCGA) for breast deletions.
Figure 46D:
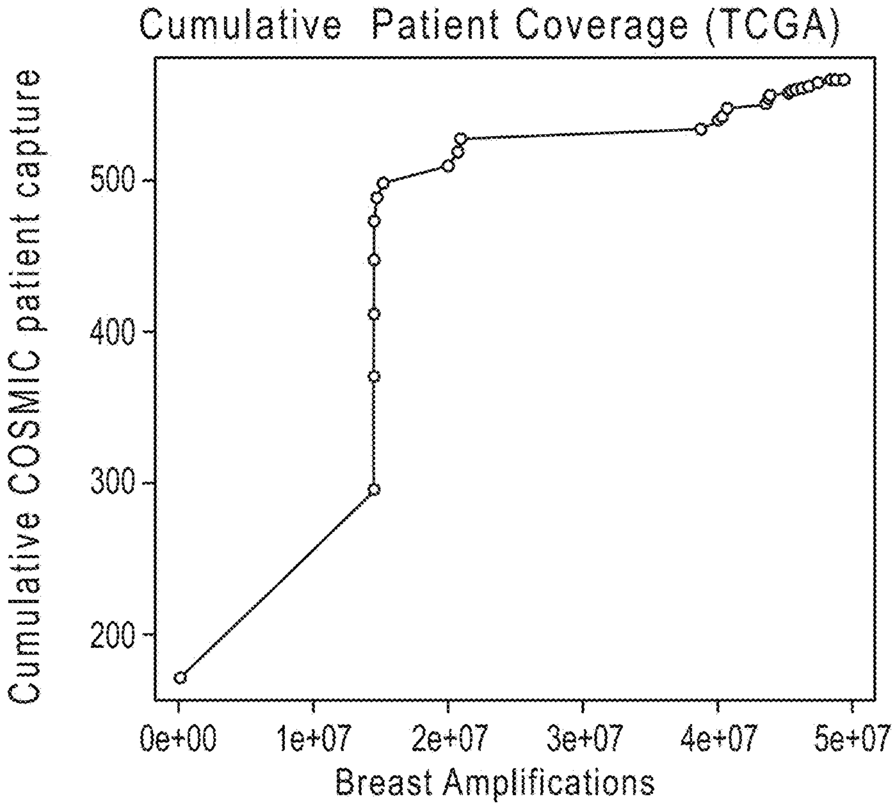
FIG. 46D plots cumulative COSMIC patient capture vs. cumulative patient coverage (TCGA) for breast amplifications.

This example demonstrates that a dramatic improvement in the ability to detect cancer is achieved by testing plasma for the presence of CNVs and SNVs. CNVs and SNVs were detected using the methods provided in the Examples above. Samples were prepared according to the appropriate protocols in Example 9. SNVs were identified using SNV Method 1 above. As shown in FIG. 46, the sensitivity of detecting breast and lung cancer are greatly improved by analyzing plasma from Stage I-III cancer patients for both CNVs and SNVs versus testing for SNVs alone. Analyzing SNVs only, 71% of cancers were detected in plasma samples. However by analyzing for the presence of SNVs and/or CNVs the detection rate goes up to 83% for breast and 92% for lung in the patient populations analyzed. If one considers all of the SNVs and CNVs that have been identified in the TCGA and COSMIC data sets, the expected diagnostic load would be greater than 97% for breast cancer and >98% for lung cancer.

Figures 47A, 47B:
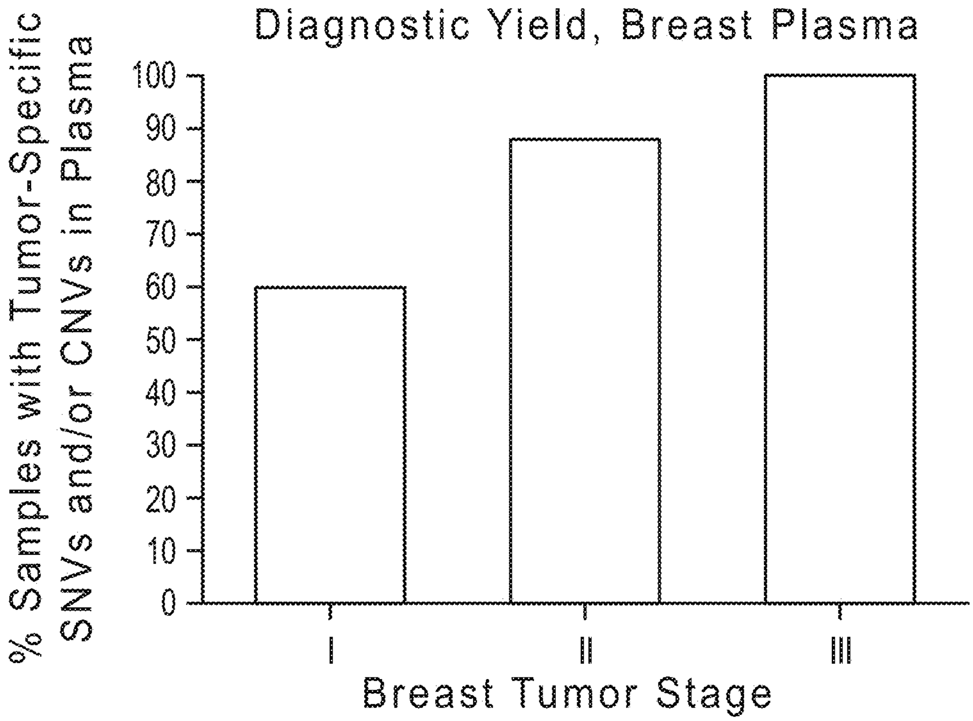
FIG. 47A is a graph of % samples at different breast cancer stages with tumor-specific SNVs and/or CNVs in plasma.
FIG. 47B is a table of percent detection of breast CNVs and SNVs by stage.
Figures 48A, 48B:
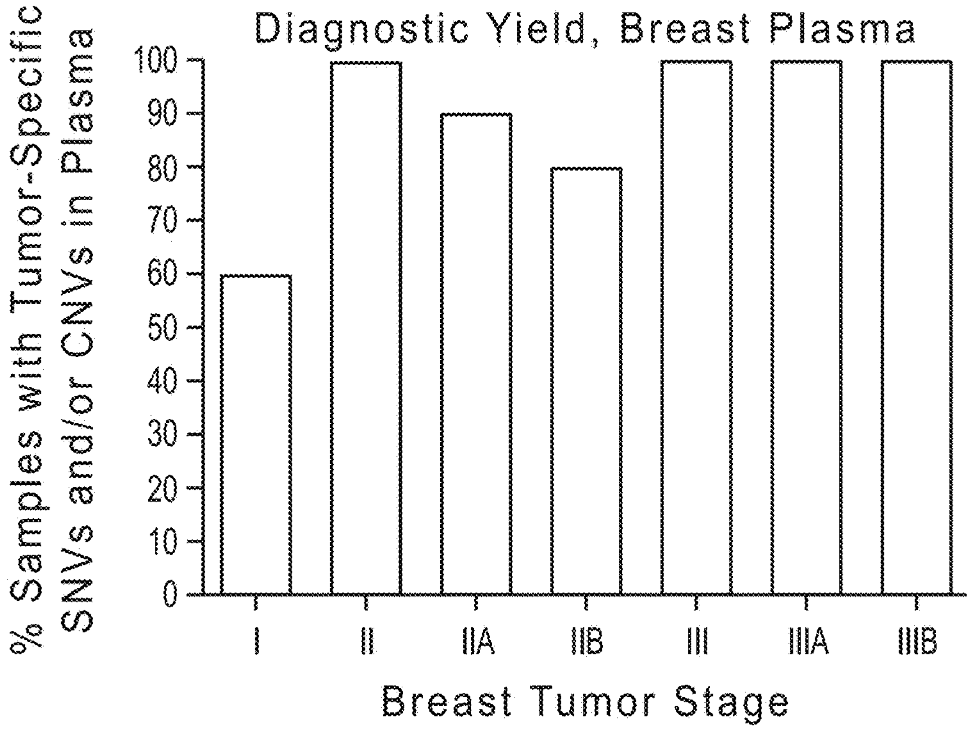
FIG. 48A is a graph of % samples at different breast cancer substages with tumor-specific SNVs and/or CNVs in plasma.
FIG. 48B is a table of percent detection of breast CNVs and SNVs by tumor substage.
Figures 49A, 49B:
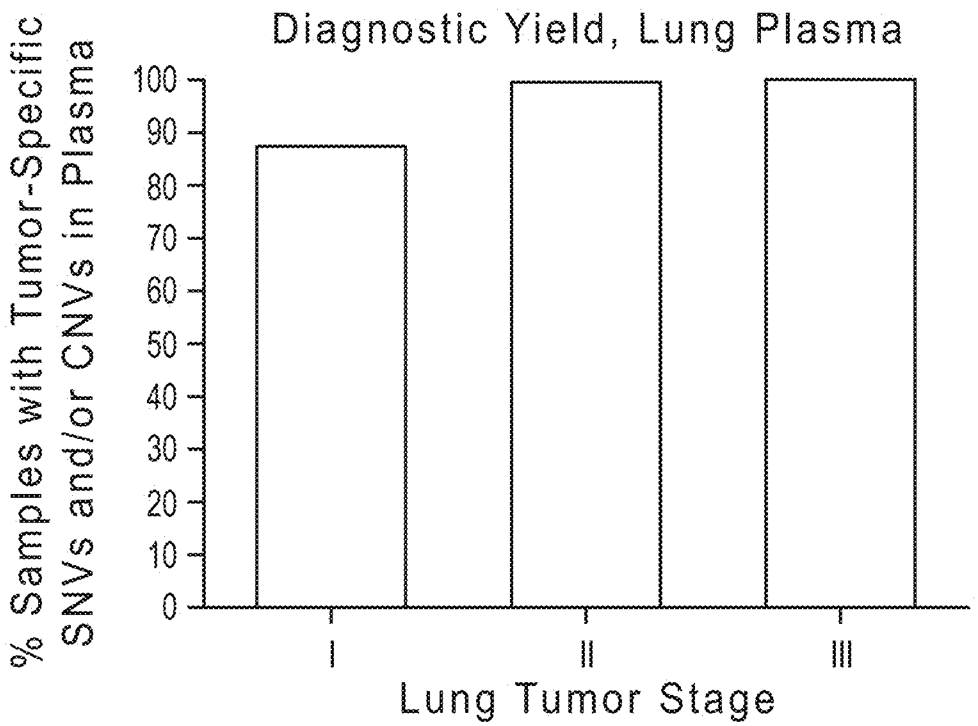
FIG. 49A is a graph of % samples at different lung cancer stages with tumor-specific SNVs and/or CNVs in plasma.
FIG. 49B is a table of lung plasma detection rate of lung SNVs and/or CNVs.
Figures 50A, 50B:
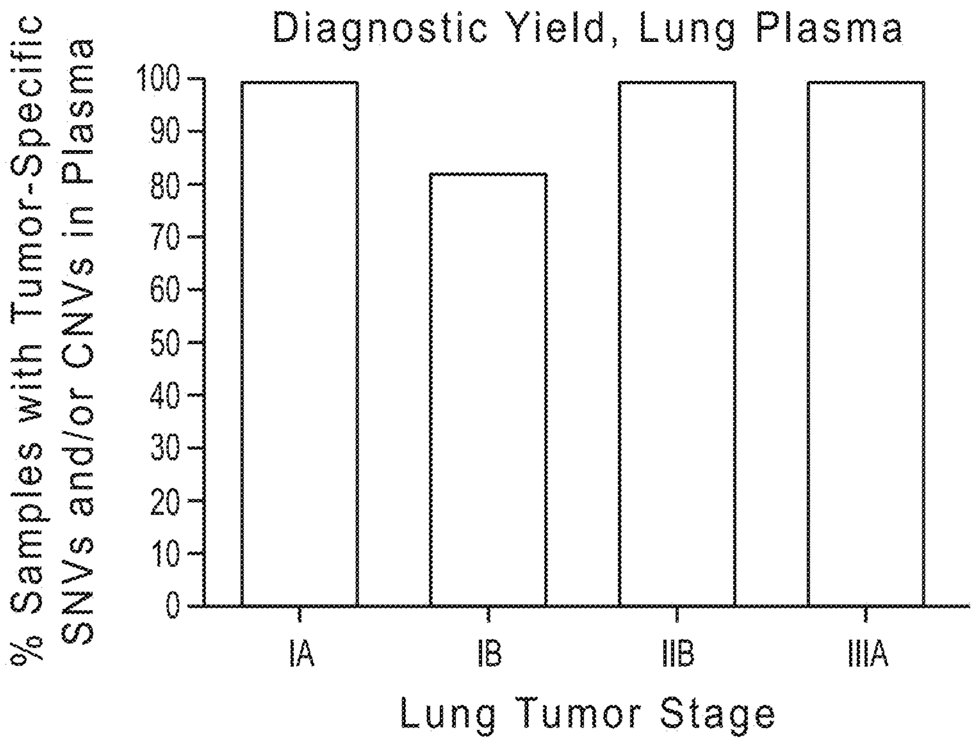
FIG. 50A is a graph of % samples at different lung cancer substages with tumor-specific SNVs and/or CNVs in plasma.
FIG. 50B is a table of lung plasma detection rate of lung SNVs and/or CNVs by tumor substage.

Further analysis was performed on samples from 41 patient samples with different stages of cancer using the plasma sample prep methods provided in Example 9 and SNV Method 1 provided above. As shown in FIG. 47, when assaying for CNVs and SNVs in circulating tumor DNA from breast cancer patients 60% of Stage I, 88% of Stage II and 100% of Stage III breast cancers were detected using a limit of quantification of 0.2% ctDNA for SNVs and 0.45% ctDNA for CNVs. As shown in FIG. 48, when assaying for CNVs and SNVs in ctDNA and looking at 41 patient samples with different substages of breast cancer, 60% of Stage I, 100% of Stage II, 90% of Stage IIA, 80% of Stage IIB, and 100% of Stage III, IIIA, and IIIB breast cancers were detected using a limit of quantification of 0.2% ctDNA for SNVs and 0.45% ctDNA for CNVs. As shown in FIG. 49, when assaying for CNVs and SNVs in 24 circulating tumor DNA from lung cancer patient samples 88% of Stage I, 100% of Stage II and 100% of Stage III lung cancers were detected using a limit of quantification of 0.2% ctDNA for SNVs and 0.45% ctDNA for CNVs. As shown in FIG. 50, when assaying for CNVs and SNVs in ctDNA and looking at 24 patient samples with different substages of lung cancer, 100% detection rate was achieved for all substages except that an 82% detection rate was achieved for the patients with stage IB lung cancer using a limit of quantification of 0.2% ctDNA for SNVs and 0.45% ctDNA for CNVs.

Example 13

This example demonstrates that detection of SNV in ctDNA overcomes the limitations in identifying variant alleles in biopsied samples due to tumor heterogeneity. TRACERx samples of three small cell lung cancer patient samples and one adenocarcinoma lung cancer patient sample for which tumor biopsies and corresponding pre-operative blood plasma samples had been collected were used for analysis of tumor heterogeneity. Samples were obtained from the Cancer Research UK Lung Cancer Centre of Excellence, University College London Cancer Institute, London WC1E 6BT, UK. Samples were primary lung cancer samples for analysis of SNV mutations. Two to three biopsies from various regions from the entire cancerous lung were taken from each patient (FIG. 51A). Each biopsied sample was assayed by whole exome sequencing (Illumina HiSeq200; Illumina, San Diego, CA), followed by AmpliSeq® sequencing (Ion Torrent, South San Francisco, CA) on a PGM® for identification of underlying clonal heterogeneity. Following sequencing and SNV analyses, the variant allele frequency (VAF) was determined for each biopsy sample (FIG. 51B).

Figure 52:
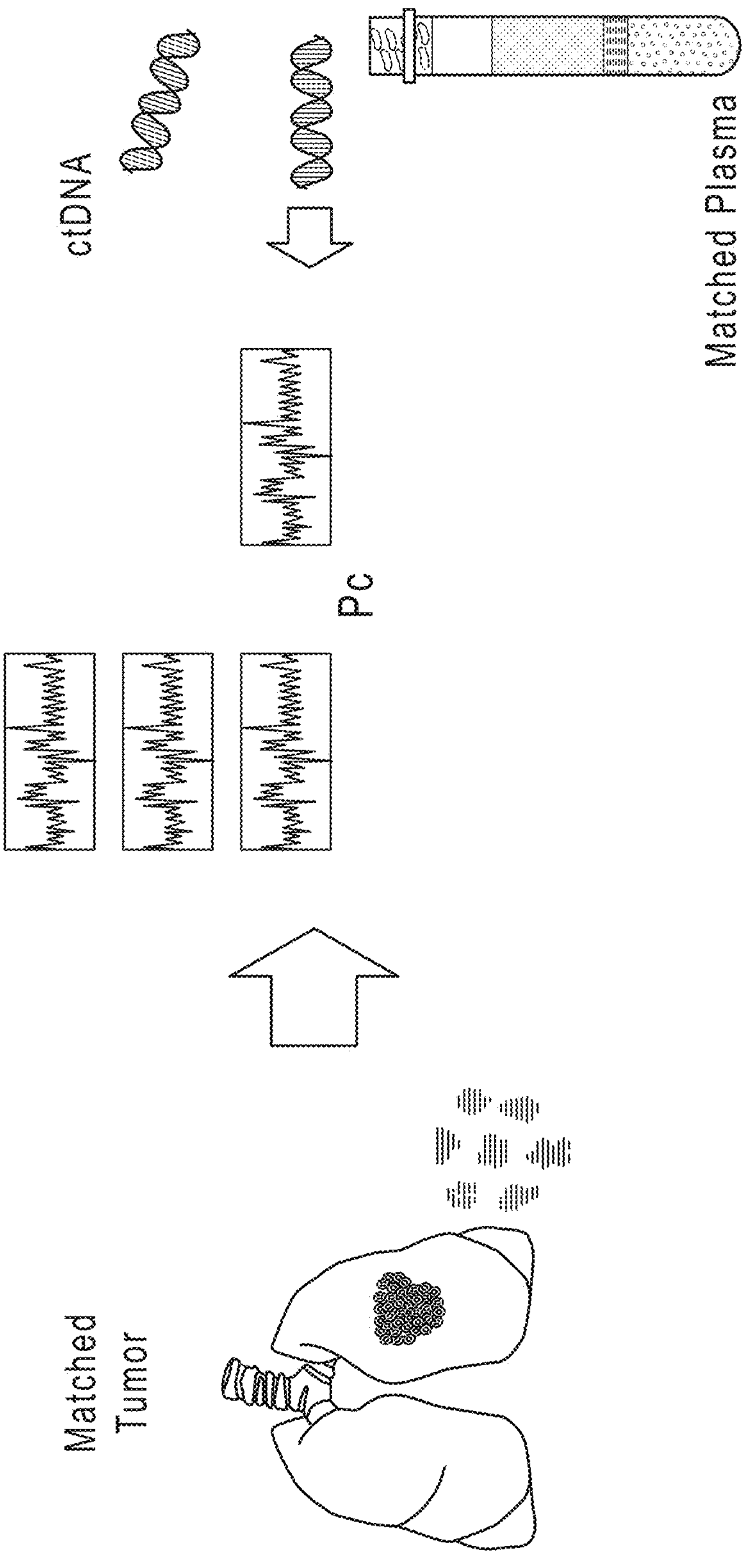
FIG. 52 illustrates the use of ctDNA from plasma to identify both clonal and subclonal SNV mutations to overcome tumor heterogeneity.

Plasma samples from each of the four patients were used to isolate ctDNA and identify both clonal and subclonal SNV mutations in plasma to overcome tumor heterogeneity (FIG. 52). Clonal populations had VAF allele calls in all biopsied samples assayed and in plasma while subclonal populations had VAF allele calls in at least one biopsy sample, but not all biopsy samples. The plasma was considered to be a cumulative representative of the SNV's found in the ctDNA of each patient. Not all SNV's identified by sequencing were able to have corresponding PCR assays designed.

Figure 54A:
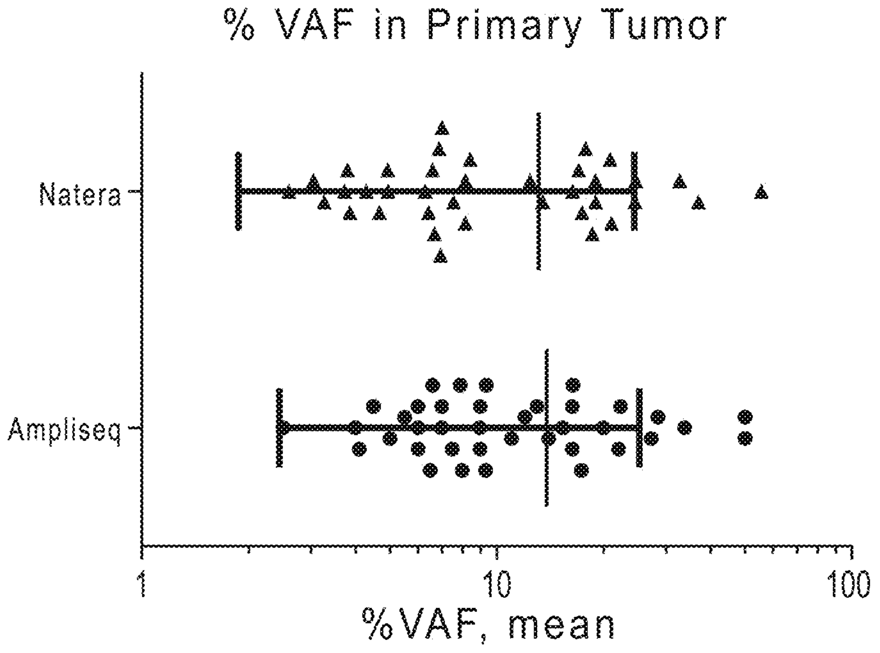
FIG. 54A is a plot of % VAF in Primary Lung Tumor.
Figure 54B:
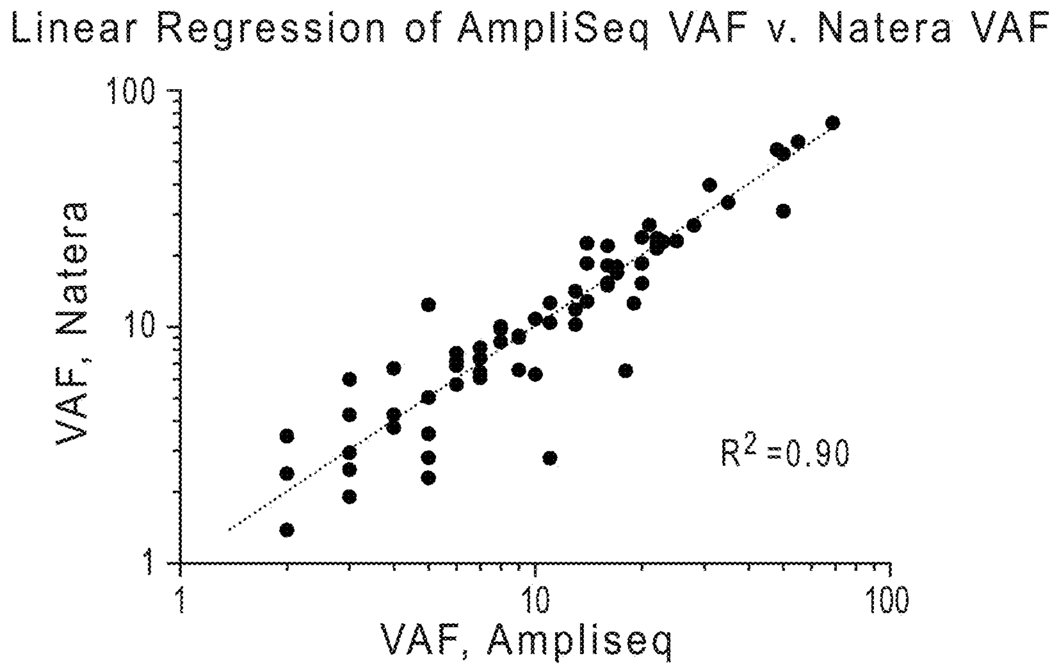
FIG. 54B is a linear regression plot of AmpliSeq VAF vs. Natera VAF.
Figure 55:
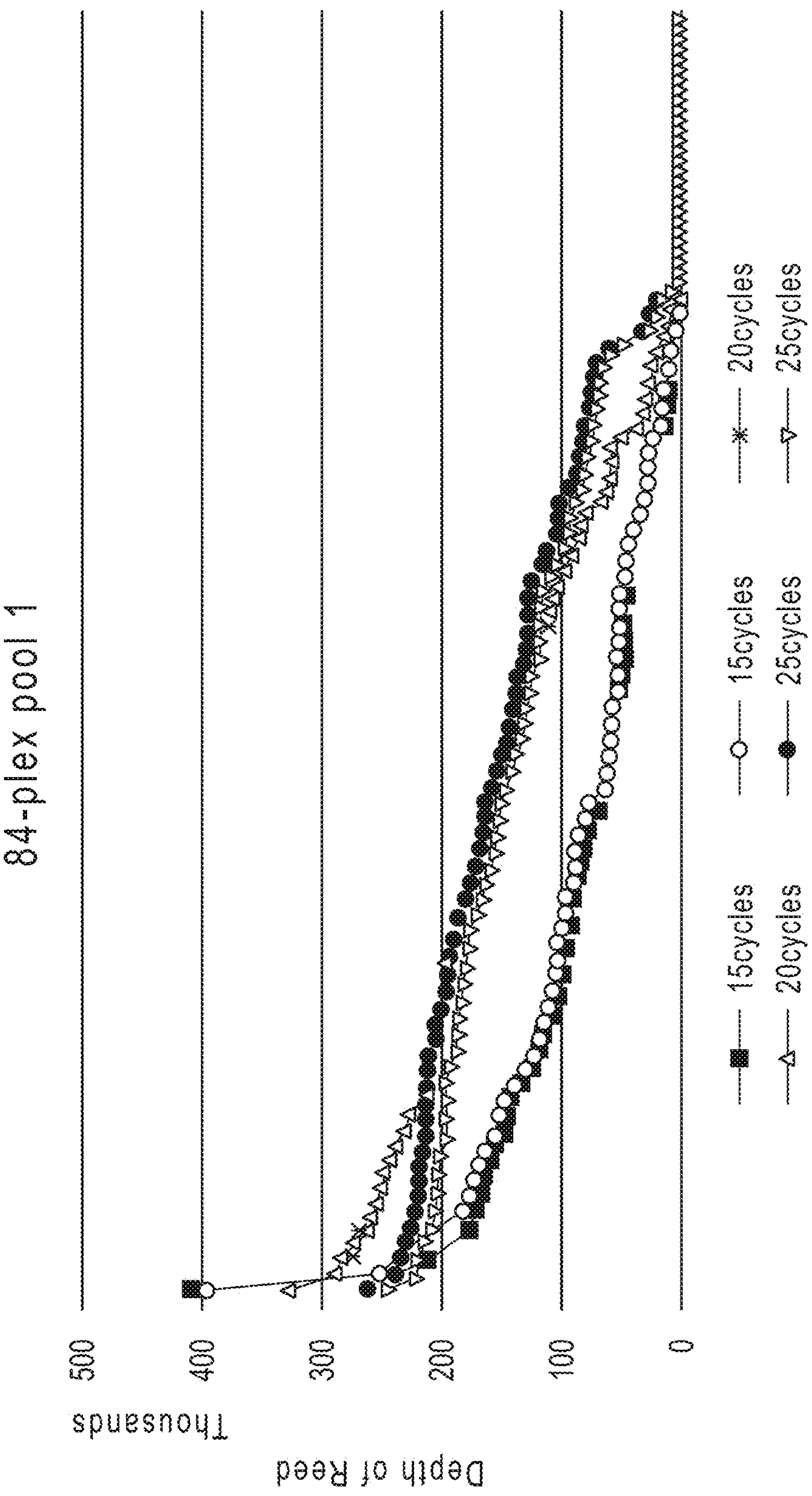
FIG. 55 is a graph of Pool 1/4 of an 84-plex SNV PCR primer reaction when primer concentration is limited.
Figure 56:
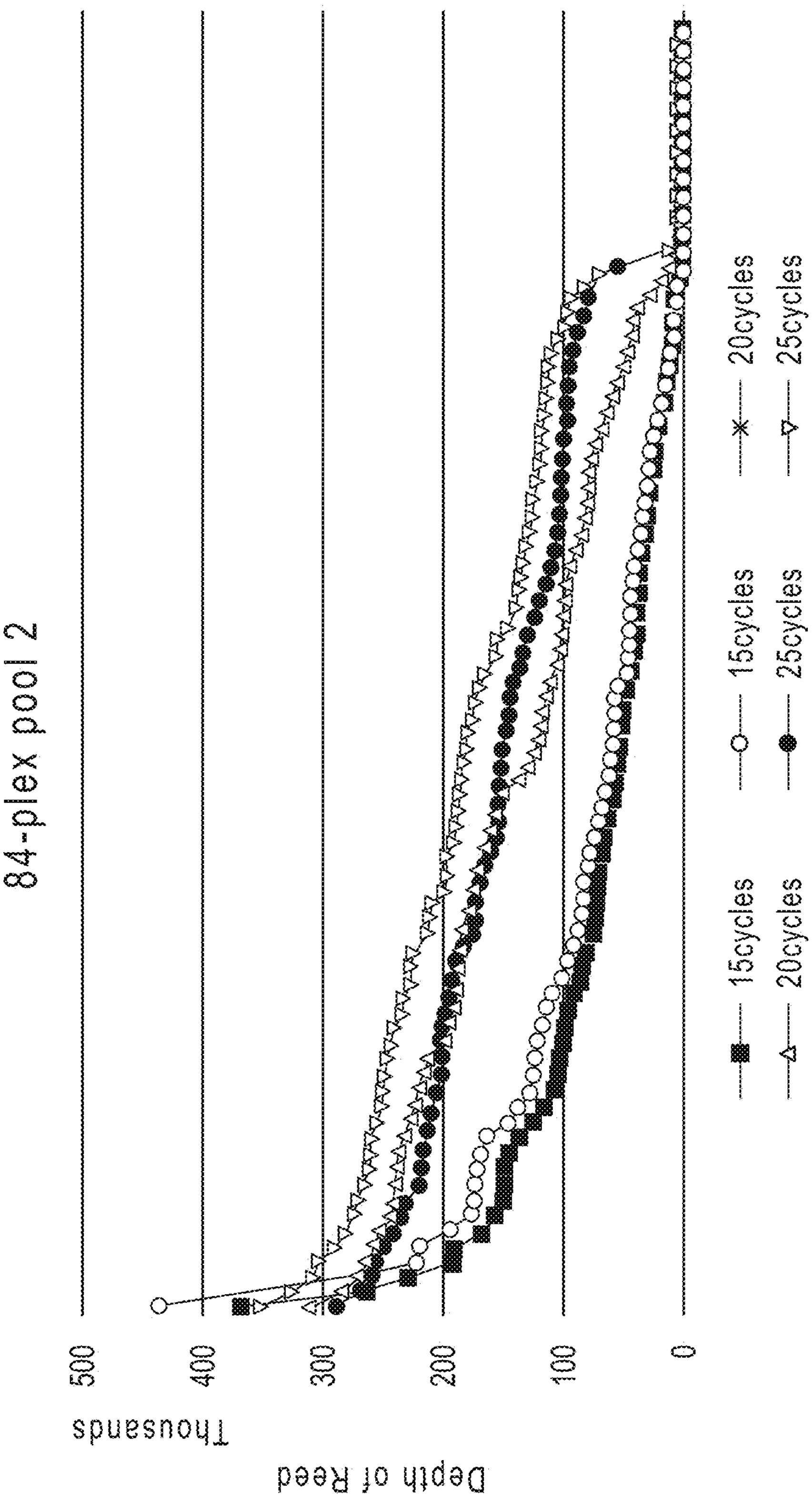
FIG. 56 is a graph of Pool 2/4 of an 84-plex SNV PCR primer reaction when primer concentration is limited.
Figure 57:
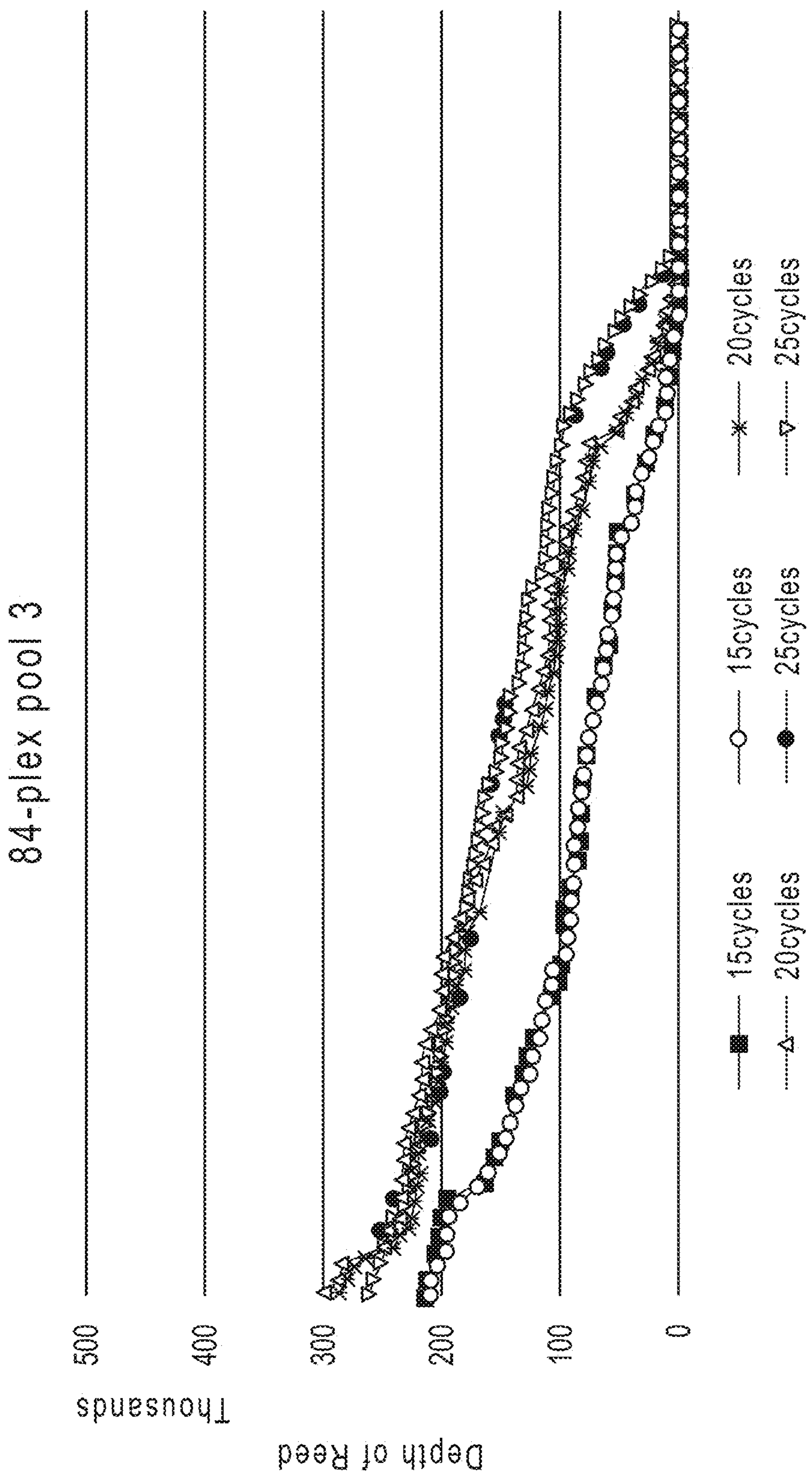
FIG. 57 is a graph of Pool 3/4 of an 84-plex SNV PCR primer reaction when primer concentration is limited.
Figure 58:
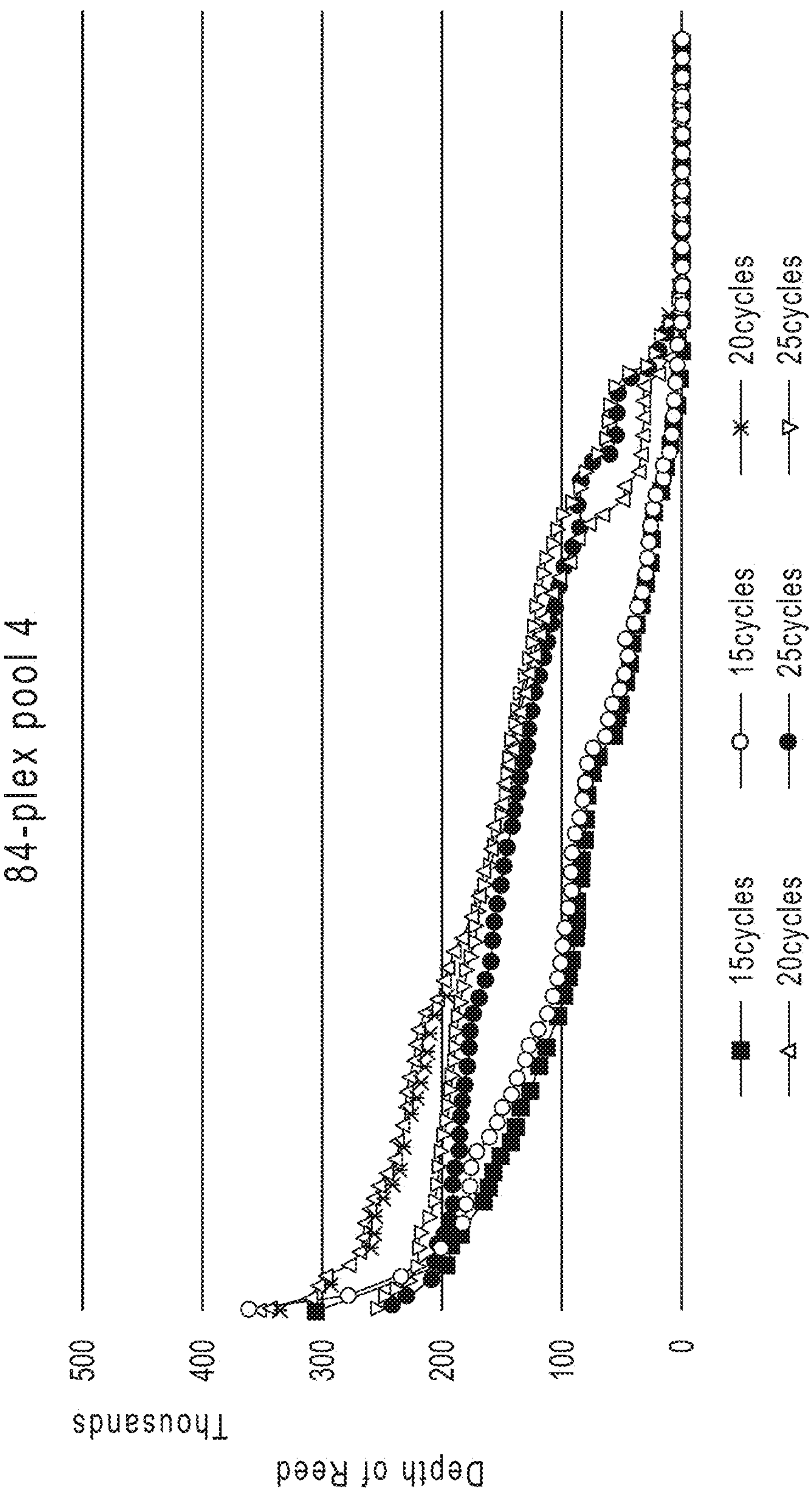
FIG. 58 is a graph of Pool 4/4 of an 84-plex SNV PCR primer reaction when primer concentration is limited.

To compare the AmpliSeq (Swanton) and mmPCR/NGS assay methods for identifying tumor heterogeneity, Natera designed PCR assays for each SNV mutation for VAF detection in both biopsied and corresponding ctDNA from plasma (FIG. 53). Blank cells represent no biopsy sample available and a zero value represents no VAF detected. The following 11 genes were initially identified as a negative (false VAF call) by the AmpliSeq FP or FN assays but were called correctly by the Natera TP or TN assays and mmPCR/NGS assay methods: L12: CYFIP1, FAT1, MLLT4, and RASA1; L13: HERC4, JAK2, MSH2, MTOR, and PLCG2; L15: GABRG1; L17: TRIM67. Surprisingly, when the AmpliSeq raw sequencing data was re-examined these results were verified. The raw AmpliSeq data sequencing files revealed that the data fell below the PGM or Illumina detectable threshold setting. The data identified 16/38 variants were detected in plasma and that there were several biopsy samples in the L12 patient samples that had predominant clonal SNV mutations: L12: BRIP1, CARS, FAT1, MLLT4, NFE2L2, TP53, TP53 as well as patients L13: EGFR, EGFR, TP53 and L15: KDM6A, ROS1. An additional two patients were found to have a total of four subclonal variant mutations in plasma: L12: CIC, KDM6A and L17; NF1, TRIM67. These results are summarized in FIG. 54A which is a whisker plot of the mean VAF for each sample listed in FIG. 53 by each assay method and FIG. 54B is a direct comparison represented by a linear regression plot of each assay's VAF sample mean.

Example 14

This example demonstrates that by using low primer concentrations such that primer amount is the limiting reactant in multiplex PCR in a workflow that is followed by next generation sequencing, uniformity of density of reads, and therefore limits of detection, across a pool of amplification reactions is improved. Some experiments were carried out for plasma CNV using the 3,168-plex panel according to Example 9 above except that the total reaction volume was 10 uL instead of 20 uL. Furthermore, PCR was carried out for 15, 20, or 25 cycles. Other experiments were carried out using the four 84-plex pools on breast cancer samples according to the protocol of Example 9 except that primer concentrations were 2 nM and PCR amplification was carried out for 15, 20, or 25 cycles.

Not to be limited by theory, it is believed that primer limited multiplex PCR provides improved depth of read uniformity for multiplex PCR before multi-read sequencing, such as sequencing on an Illumina HiSeq or MiSeq system or an Ion Torrent PGM or Proton system, based on the following considerations: If some of the amplifications in a multiplex PCR have lower efficiencies than others, then with normal multiplex PCR we will end up with a wide range of depth of read ("DOR") values. However, if the amount of primer is limited, and the multiplex PCR is cycled more times than what it takes to exhaust the primers, then the more efficient amplifications will stop doubling (because they have no more primers to use) and the less efficient ones will continue to double; this will result in a more similar amount of amplification product for all of the amplification products. This will translate into a much more uniform distribution of the DOR.

The following calculations are used to determine the number of cycles that would exact a given amount of primer and starting nucleic acid template:

- assume a given starting DNA input level: 100k copies of each target (10^5; this is easily achieved with using amplified library)
- assume we use 2 nM of each primer as an exemplary concentration, although other concentrations such as, for example, 0.2, 0.5, 1, 1.5, 2, 2.5, 5, or 10 nM could work too.
- calculate the number of primer molecules for each primer: 2*10^-9 (molar concentration, 2 nM)×10*10^-6 (reaction volume, 10 ul)×6*10^23 (number of molecules per mole, Avogadro's number)=12*10^9 calculate the amplification fold needed to consume all primers: 12*10^9 (number of primer molecules)/10^5 (number of copies of each target)=12*10^4 calculate the number of cycles needed to achieve this amplification fold, assuming 100% efficiency at each cycle: log 2 (12*10^4)=17 cycles. (this is log 2 because at each cycle, the number of copies doubles).

So for these conditions (100k copies input, 2 nM primers, 10 ul reaction volume, assuming 100% PCR efficiency at each cycle), the primers would be consumed after 17 PCR cycles.

However, the key assumption is that some of the products DO NOT have 100% efficiency, so without measuring their efficiencies (which is only practicable for a small number of them anyway), it would take more than 17 cycles to consume them.

Figure 59:
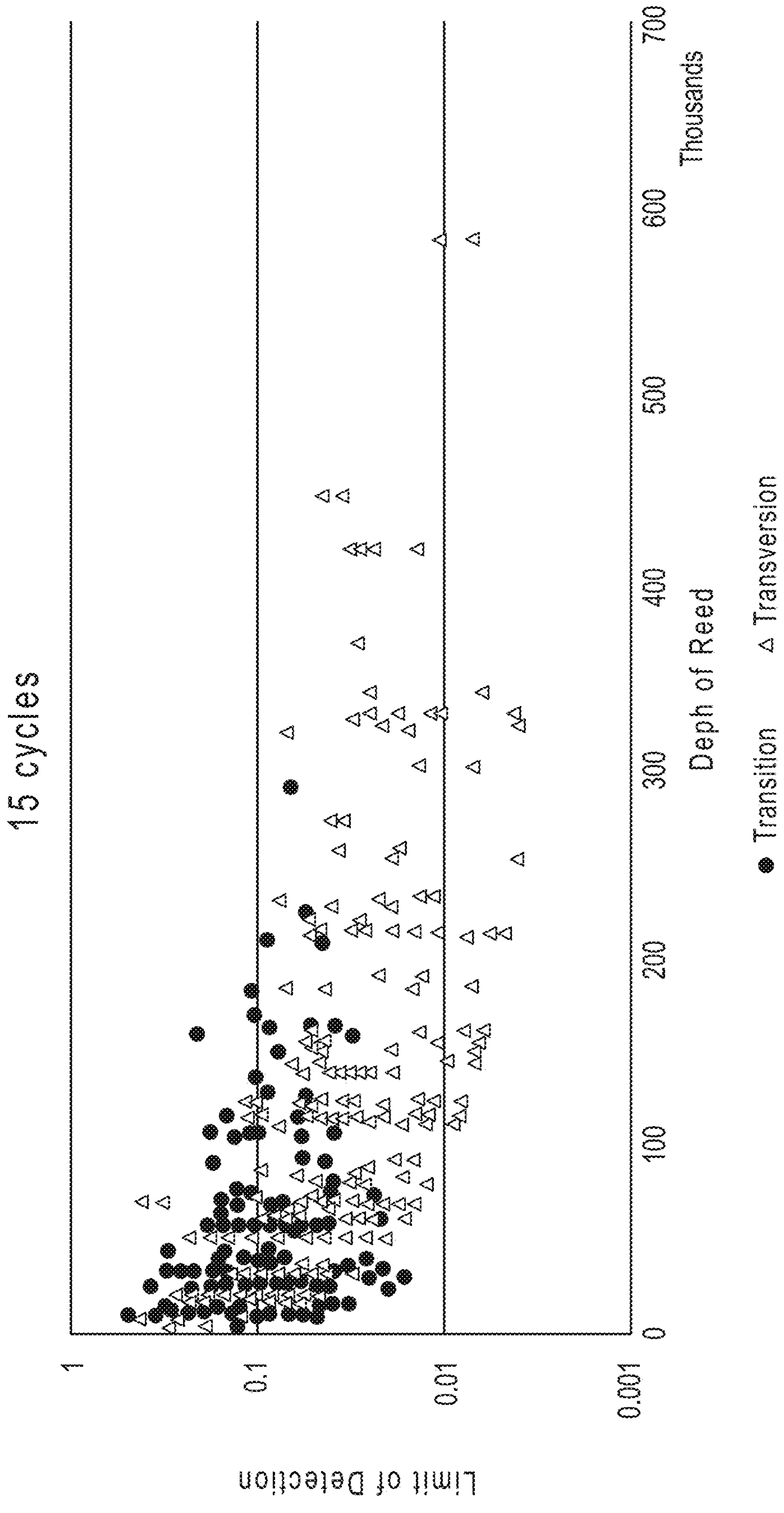
FIG. 59 illustrates a plot of Limit of Detection (LOD) vs. Depth of Read (DOR) for detection of SNV Transition and Transversion mutations in a 84-plex PCR reaction at 15 PCR cycles.
Figure 60:
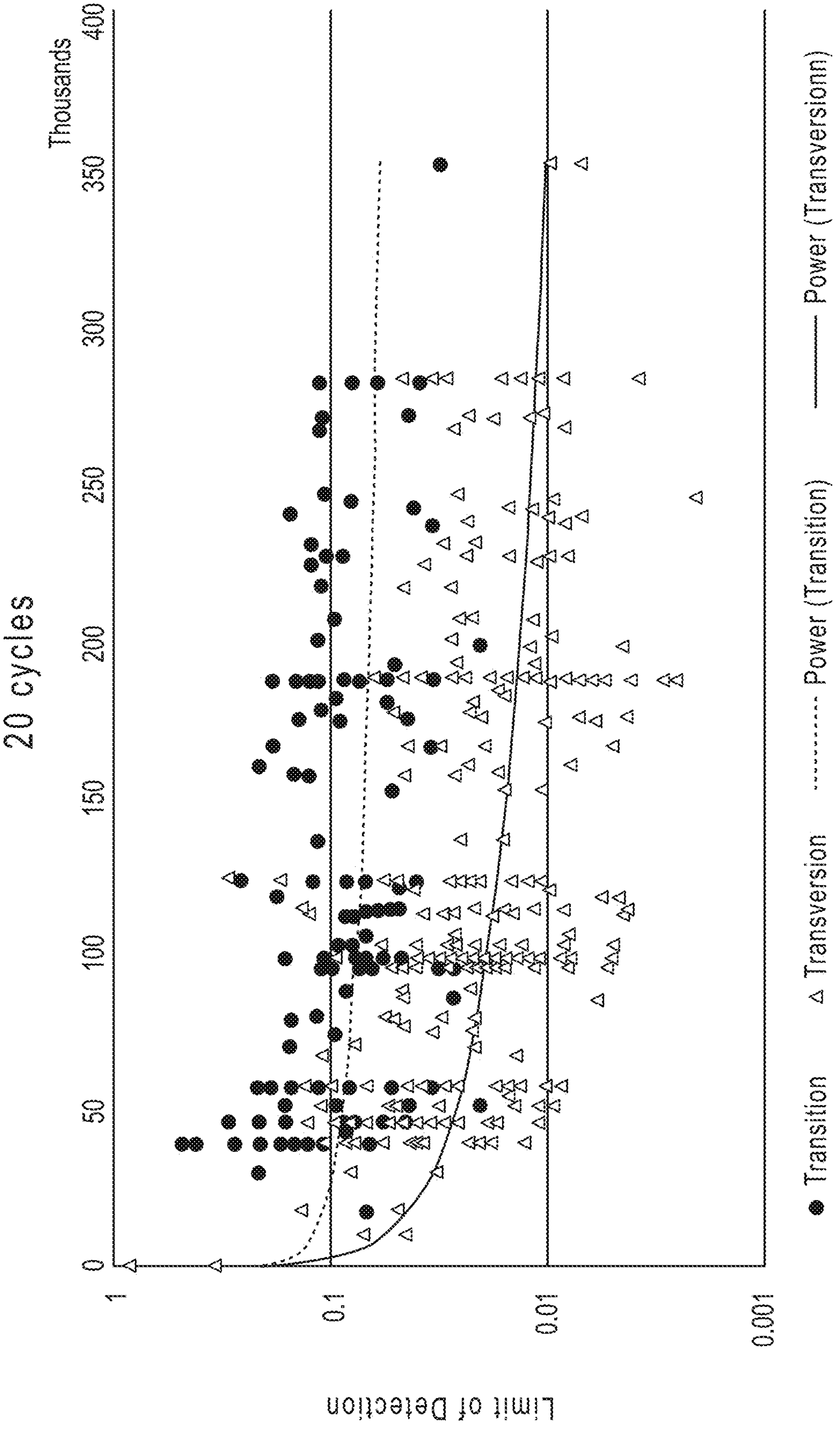
FIG. 60 illustrates a plot of Limit of Detection (LOD) vs. Depth of Read (DOR) for detection of SNV Transition and Transversion mutations in a 84-plex PCR reaction at 20 PCR cycles.
Figure 61:
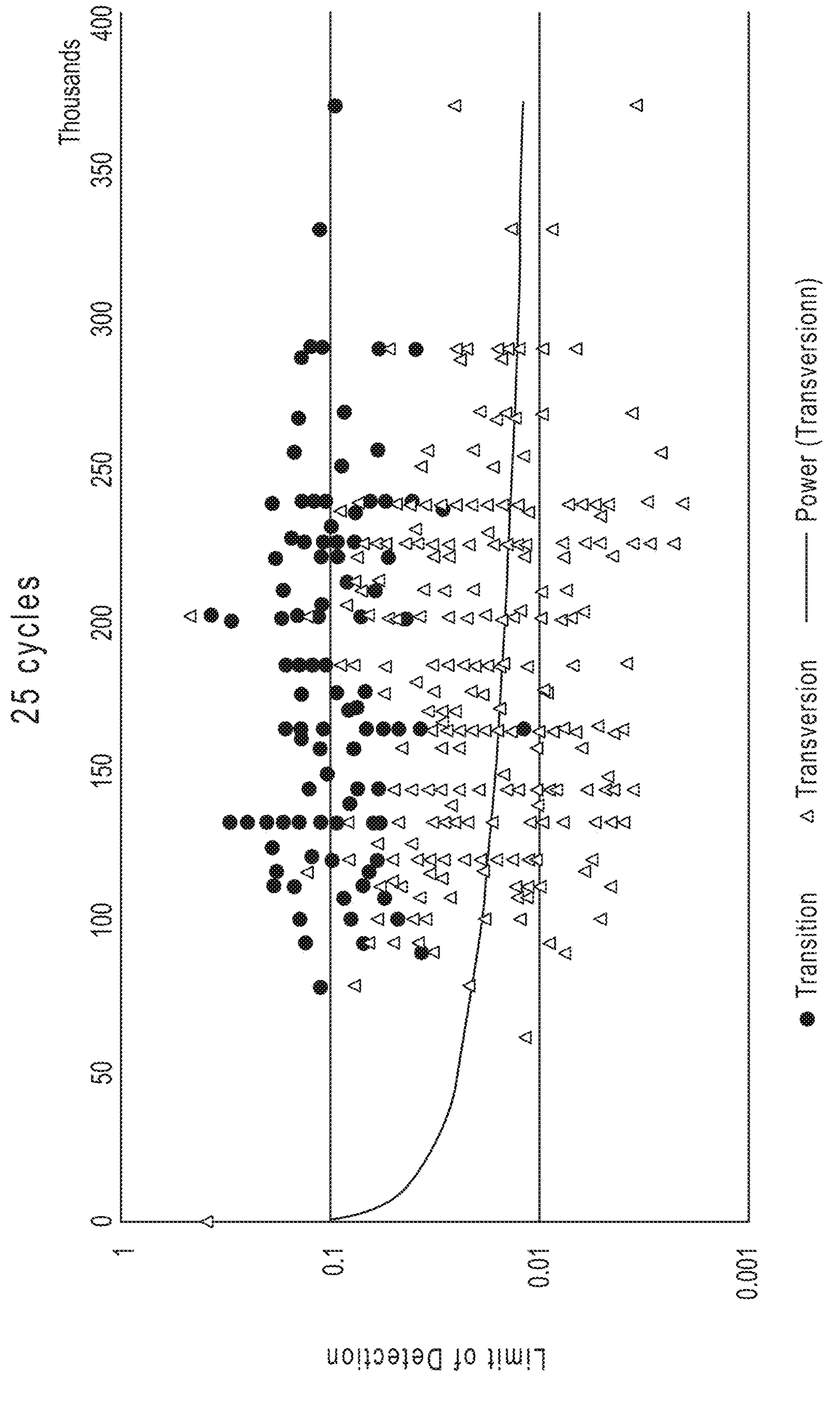
FIG. 61 illustrates a plot of Limit of Detection (LOD) vs. Depth of Read (DOR) for detection of SNV Transition and Transversion mutations in a 84-plex PCR reaction at 25 PCR cycles.
Figure 62A:
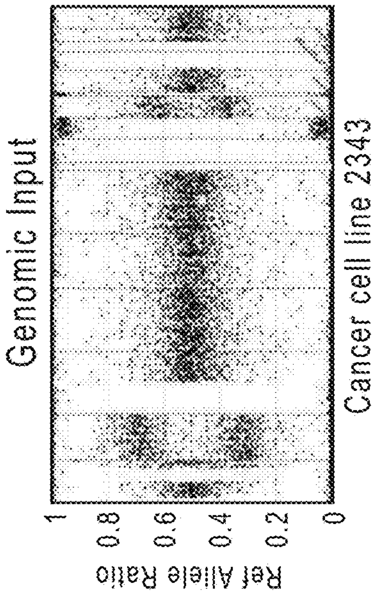
FIG. 62A is a plot illustrating sensitivity of detection of SNVs in tumor cell genomic DNA.
Figure 62B:
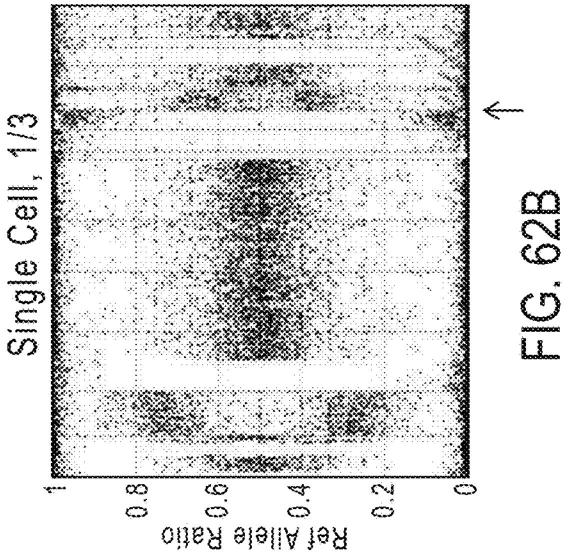
FIG. 62B illustrates sensitivity of detection of SNVs in 1/3 single cells.
Figure 62C:
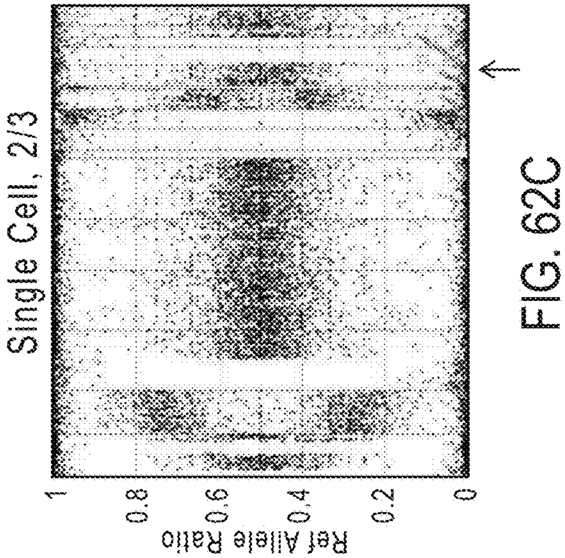
FIG. 62C illustrates sensitivity of detection of SNVs in 2/3 single cells.
Figure 62D:
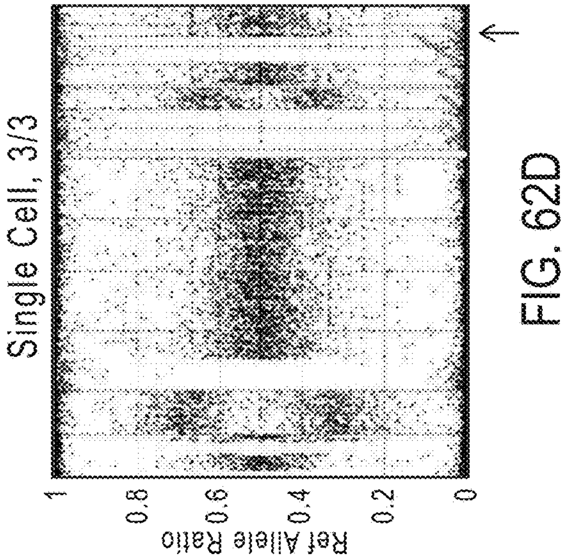
FIG. 62D illustrates sensitivity of detection of SNVs in 3/3 single cells. Comparable sensitivities are seen between tumor and single cell genomic DNA.
Figure 63A:
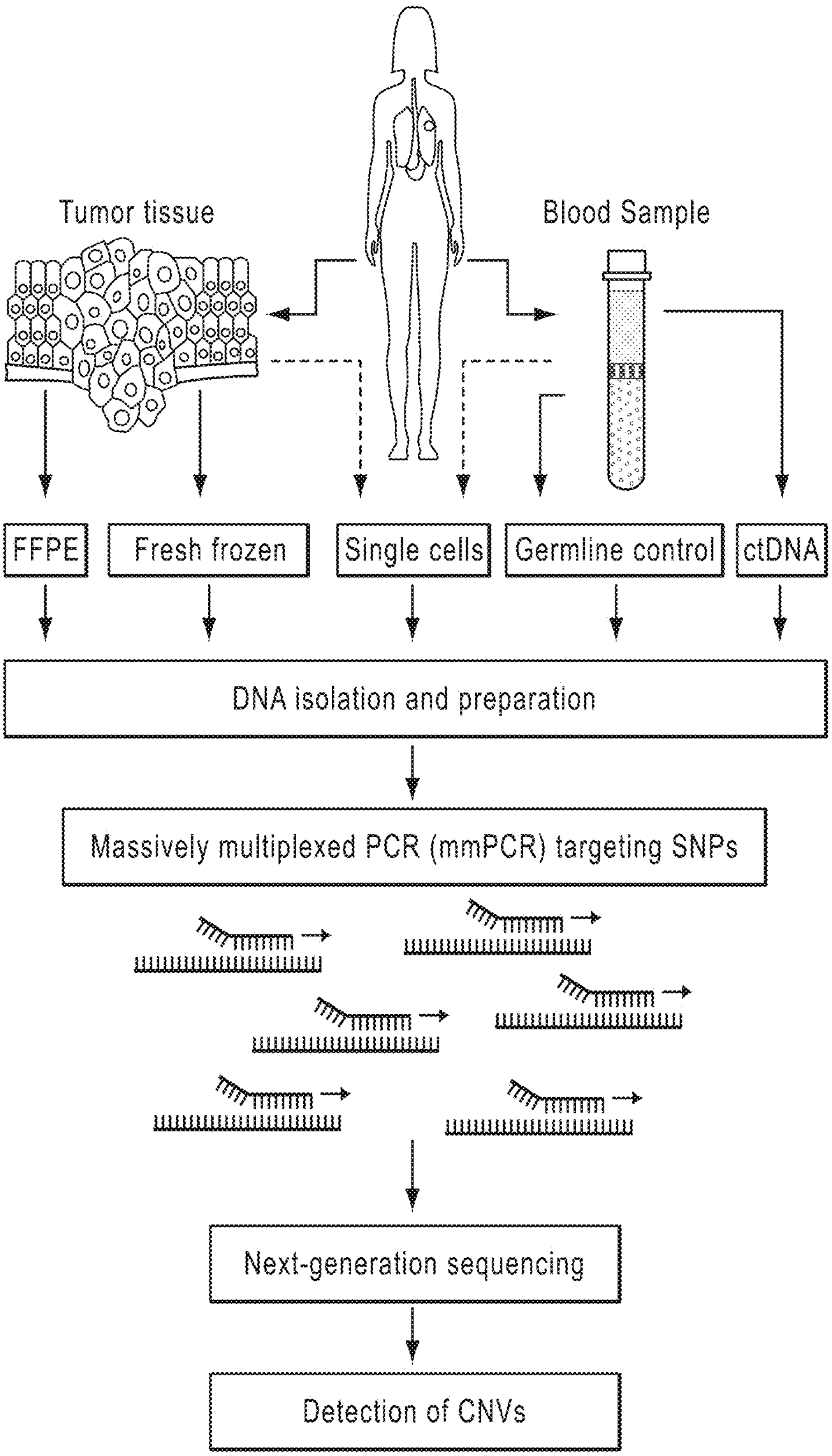
FIG. 63A illustrates the workflow for analysis of CNVs in a variety of cancer sample types in a massively multiplexed PCR (mmPCR) assay targeting SNPs.
Figure 63B:
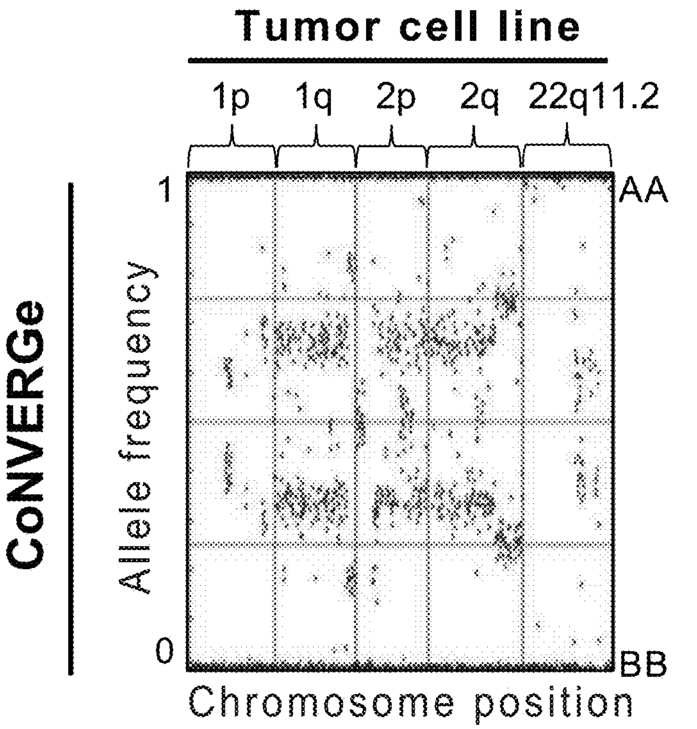
FIG. 63B illustrates detection of somatic CNVs in human breast cancer cell lines and matched normal cell lines (FIG. 63C) on the CONVERGe platform.
Figure 63C:
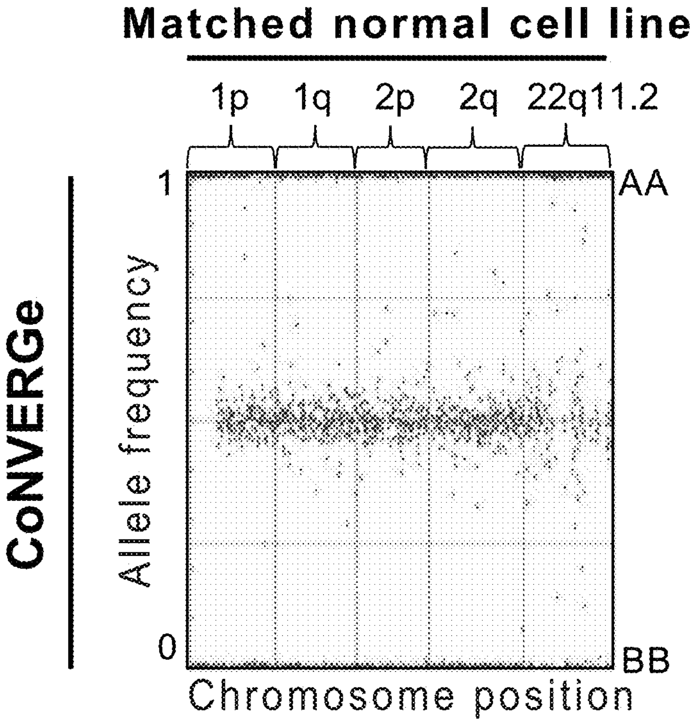
FIG. 63D illustrates detection of somatic CNVs in human breast cancer cell lines and matched normal cell lines (FIG. 63E) on the CytoSNP-12 microarray platform.
FIG. 63F is a plot of the maximum homolog ratios for CNVs identified by CONVERG3e or CytoSNP-12 showing a strong linear correlation of identified CNVs by either method.
Figure 63D:
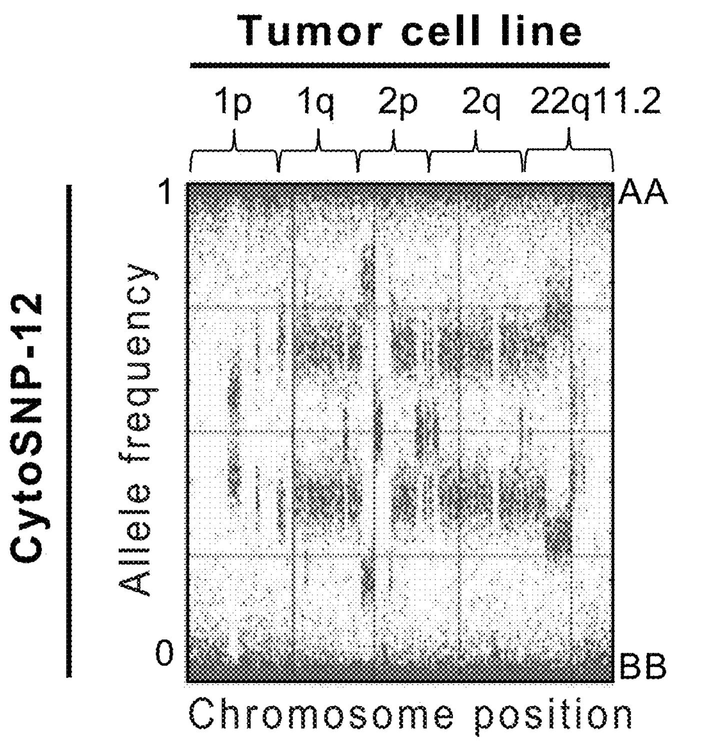
Figure 63E:
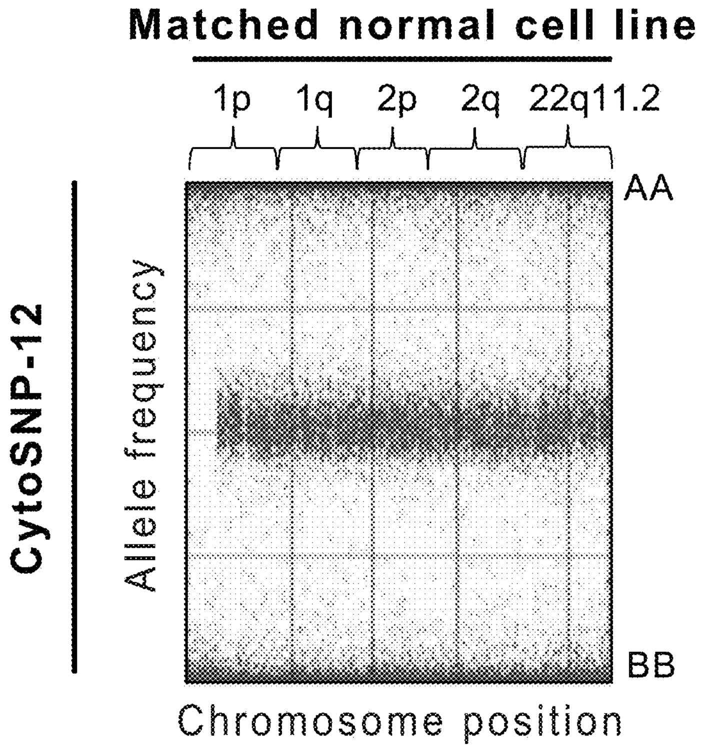
Figure 63F:
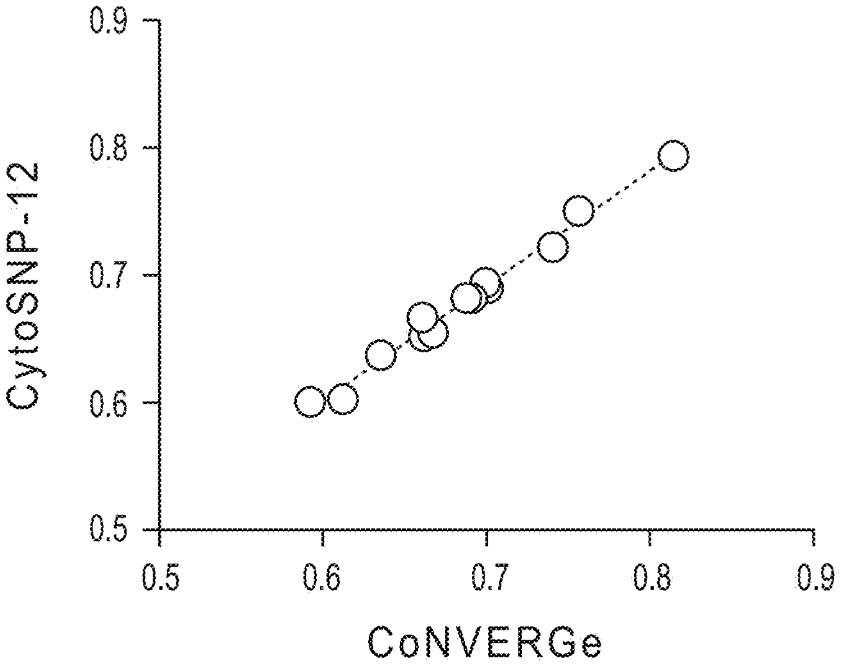

FIGS. 55-58 show results for the four 84-plex SNV PCR primer pools. For each of the pools we observed improved DOR efficiency with increasing cycles from 15 to 20 to 25. Similar results were obtained for experiments using the 3,168-plex panel (FIGS. 59-61). The limit of detection decreased (i.e. SNV sensitivity increased) with increasing depth of read. Furthermore, the sensitivity was consistently better when detecting transversion mutations than transition mutations. It is likely that additional increases in DOR efficiency can be obtained with additional cycles when using primer-limiting multiplex PCR before multi-read sequencing.

Accordingly, in one aspect provided herein is a method of amplifying a plurality of target loci in a nucleic acid sample that includes (i) contacting the nucleic acid sample with a library of primers and other primer extension reaction components to provide a reaction mixture, wherein the relative amount of each primer in the reaction mixture compared to the other primer extension reaction components creates a reaction wherein the primers are present at a limiting concentration, and wherein the primers hybridize to a plurality of different target loci; and (ii) subjecting the reaction mixture to primer extension reaction conditions for sufficient number of cycles to consume or exhaust the primers in the library of primers, to produce amplified products that include target amplicons. For example, the plurality of different target loci can include at least 2, 3, 5, 10, 25, 50, 100, 200, 250, 500, 1,000; 2,000; 5,000; 7,500; 10,000; 20,000; 25,000; 30,000; 40,000; 50,000; 75,000; or 100,000 different target loci, and at most, 50, 100, 200, 250, 500, 1,000; 2,000; 5,000; 7,500; 10,000; 20,000; 25,000; 30,000; 40,000; 50,000; 75,000; 100,000, 200,000, 250,000, 500, 000, and 1,000,000 different target loci to produce a reaction mixture.

The method in illustrative embodiments, includes determining an amount of primer that will be a rate limiting amount. This calculation typically includes estimating and/or determining the number of target molecules and involves analyzing and/or determining the number of amplification cycles performed. For example, in illustrative embodiments, the concentration of each primer is less than 100, 75, 50, 25, 10, 5, 2, 1, 0.5, 0.25, 0.2 or 0.1 nM. In various embodiments, the GC content of the primers is between 30 to 80%, such as between 40 to 70% or 50 to 60%, inclusive. In some embodiments, the range of GC content (e.g., the maximum GC content minus minimum GC content, such as 80%-60%=a range of 20%) of the primers is less than 30, 20, 10, or 5%. In some embodiments, the melting temperature (Tm) of the primers is between 40 to 80° C., such as 50 to 70° C., 55 to 65° C., or 57 to 60.5° C., inclusive. In some embodiments, the range of melting temperatures of the primers is less than 20, 15, 10, 5, 3, or 1° C. In some embodiments, the length of the primers is between 15 to 100 nucleotides, such as between 15 to 75 nucleotides, 15 to 40 nucleotides, 17 to 35 nucleotides, 18 to 30 nucleotides, 20 to 65 nucleotides, inclusive. In some embodiments, the primers include a tag that is not target specific, such as a tag that forms an internal loop structure. In some embodiments, the tag is between two DNA binding regions. In various embodiments, the primers include a 5' region that is specific for a target locus, an internal region that is not specific for the target locus and forms a loop structure, and a 3' region that is specific for the target locus. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the test primers include a 5' region that is not specific for a target locus (such as a tag or a universal primer binding site) followed by a region that is specific for a target locus, an internal region that is not specific for the target locus and forms a loop structure, and a 3' region that is specific for the target locus. In some embodiments, the range of the length of the primers is less than 50, 40, 30, 20, 10, or 5 nucleotides. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 100, 75, 50, 25, 15, 10, or 5 nucleotides.

In various embodiments of any of the aspects of the invention, the primer extension reaction conditions are polymerase chain reaction conditions (PCR). In various embodiments, the length of the annealing step is greater than 3, 5, 8, 10, or 15 minutes but less than 240, 120, 60, or 30 minutes. In various embodiments, the length of the extension step is greater than 3, 5, 8, 10, or 15 minutes but less than 240, 120, 60 or 30 minutes.

Example 15

This Example demonstrates the ability of the SNV detection methods of the present invention to identify mosaicism in single cell analysis also referred to as single molecule analysis. FIG. 62 shows multiplex PCR results from tumor cell genomic DNA and single cell/molecule inputs using the 28K-plex primer set according to the 28K single cell method provided in Example 9. Using this method, greater than 85% of reads were mapped-over 4.7M reads (about 167 reads per target). The lower portion of the figure shows that mosaicism was observed among cells.

What is claimed is:

1. A method for preparing a plasma sample of a subject having cancer or suspected of having cancer useful for detecting one or more genomic variants in the plasma sample, the method comprising:

performing whole exome sequencing or whole genome sequencing on a tumor sample of the subject to identify a plurality of genomic variants;

selectively enriching 10 to 500 target loci each encompassing one of the genomic variants identified in the tumor sample of the subject, from cell-free DNA isolated from a plasma sample of the subject or DNA derived therefrom, to obtain selectively enriched DNA, wherein the target loci are selectively enriched together in the same reaction volume using target-specific primers or probes, wherein at least one selectively enriched DNA molecule comprises two or more target loci that include two or more of the genomic variants identified in the tumor sample of the subject; and sequencing the selectively enriched DNA to obtain sequence reads, and detecting one or more of the genomic variants present in the cell-free DNA from the sequence reads, wherein the sequencing has a depth of read of at least 50,000 reads per target locus.

2. The method of claim 1, wherein the tumor sample of the subject is a tissue sample of a solid tumor.

3. The method of claim 1, wherein the cell-free DNA comprises circulating tumor DNA.

4. The method of claim 1, wherein the selectively enriching comprises selectively enriching 20 to 50 target loci each encompassing one of the genomic variants using target-specific primers or probes.

5. The method of claim 1, wherein the selectively enriching comprises selectively enriching 50 to 100 target loci each encompassing one of the genomic variants using target-specific primers or probes.

6. The method of claim 1, wherein the method further comprises designing target-specific primers or probes capable of hybridizing to the genomic variants identified in the tumor sample.

7. The method of claim 1, wherein the genomic variants encompassed by the two or more target loci are two or more nearby single nucleotide polymorphisms or variants.

8. The method of claim 1, wherein the method further comprises performing barcoding PCR prior to the sequencing.

9. The method of claim 1, wherein the method further comprises detecting recurrence and/or metastases of the cancer from the genomic variants detected in the cell-free DNA.

10. The method of claim 1, wherein the cancer is colorectal cancer, lung cancer, bladder cancer, or breast cancer.

11. A method for preparing a plasma sample of a subject having cancer or suspected of having cancer useful for detecting one or more genomic variants in the plasma sample, the method comprising:

performing whole exome sequencing or whole genome sequencing on a tumor sample of the subject to identify a plurality of genomic variants;

selectively enriching 10 to 500 target loci each encompassing one of the genomic variants identified in the tumor sample of the subject, from cell-free DNA isolated from a plasma sample of the subject or DNA derived therefrom, to obtain selectively enriched DNA, wherein the target loci are selectively enriched together in the same reaction volume using target-specific primers or probes, wherein at least one selectively enriched DNA molecule comprises two or more target loci that include two or more of the genomic variants identified in the tumor sample of the subject; and sequencing the selectively enriched DNA to obtain sequence reads, and detecting one or more of the genomic variants present in the cell-free DNA from the sequence reads, wherein the method is capable of detecting at least one genomic variant that is present in less than or equal to 0.015% of the cell-free DNA comprising the target locus encompassing said genomic variant.

12. The method of claim 11, wherein the tumor sample of the subject is a tissue sample of a solid tumor.

13. The method of claim 11, wherein the sequencing has a depth of read of at least 50,000 reads per target locus.

14. The method of claim 11, wherein the cell-free DNA comprises circulating tumor DNA.

15. The method of claim 11, wherein the selectively enriching comprises selectively enriching 20 to 50 target loci each encompassing one of the genomic variants using target-specific primers or probes.

16. The method of claim 11, wherein the selectively enriching comprises selectively enriching 50 to 100 target loci each encompassing one of the genomic variants using target-specific primers or probes.

17. The method of claim 11, wherein the method further comprises designing target-specific primers or probes capable of hybridizing to the genomic variants identified in the tumor sample.

18. The method of claim 11, wherein the genomic variants encompassed by the two or more target loci are two or more nearby single nucleotide polymorphisms or variants.

19. The method of claim 11, wherein the method further comprises performing barcoding PCR prior to the sequencing.

20. The method of claim 11, wherein the method further comprises detecting recurrence and/or metastases of the cancer from the genomic variants detected in the cell-free DNA.

21. The method of claim 11, wherein the cancer is colorectal cancer, lung cancer, bladder cancer, or breast cancer.

22. The method of claim 11, wherein the method is capable of detecting at least one genomic variant that is present in 0.005% to 0.015% of the cell-free DNA comprising the target locus encompassing genomic variant.

* * * * *